(12) United States Patent
Kim et al.

(10) Patent No.: US 11,997,923 B2
(45) Date of Patent: May 28, 2024

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si (KR)

(72) Inventors: Won Sam Kim, Cheonan-si (KR); Hyun Ji Oh, Cheonan-si (KR); Dae Hwan Oh, Cheonan-si (KR); Sun Hee Lee, Cheonan-si (KR); Soung Yun Mun, Cheonan-si (KR); Jeong Seok Kim, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 504 days.

(21) Appl. No.: 17/343,622

(22) Filed: Jun. 9, 2021

(65) Prior Publication Data
US 2022/0093869 A1    Mar. 24, 2022

Related U.S. Application Data

(63) Continuation-in-part of application No. 17/066,386, filed on Oct. 8, 2020, now Pat. No. 11,072,604.

(30) Foreign Application Priority Data

Nov. 19, 2019  (KR) .................. 10-2019-0148780
Aug. 24, 2020  (KR) .................. 10-2020-0106335

(51) Int. Cl.
H01L 51/00    (2006.01)
C07D 407/12   (2006.01)
C07D 409/12   (2006.01)
C07D 409/14   (2006.01)
H10K 85/60    (2023.01)
H10K 30/80    (2023.01)

(52) U.S. Cl.
CPC ......... *H10K 85/636* (2023.02); *C07D 407/12* (2013.01); *C07D 409/12* (2013.01); *C07D 409/14* (2013.01); *H10K 85/633* (2023.02); *H10K 30/865* (2023.02); *H10K 85/6574* (2023.02); *H10K 85/6576* (2023.02)

(58) Field of Classification Search
CPC .................. H10K 85/636; H10K 85/633
See application file for complete search history.

(56) References Cited

U.S. PATENT DOCUMENTS

2019/0088879 A1*  3/2019  Haketa ............... H10K 85/6574

* cited by examiner

*Primary Examiner* — Anthony Ho
(74) *Attorney, Agent, or Firm* — Vorys, Sater, Seymour and Pease LLP; Mih Suhn Koh

(57) ABSTRACT

Provided are a compound of Formula 7 improving the luminous efficiency, stability and life span of an organic electronic element employing the compound, the organic electronic element, and an electronic device thereof.

19 Claims, 2 Drawing Sheets

COMPOUND FOR ORGANIC ELECTRONIC ELEMENT, ORGANIC ELECTRONIC ELEMENT USING THE SAME, AND AN ELECTRONIC DEVICE THEREOF

CROSS-REFERENCE TO RELATED APPLICATION

This application is a continuation-in-part of U.S. patent application Ser. No. 17/066,386, filed Oct. 8, 2020, which claims the benefit of Korean Patent Application No. KR 10-2019-0148780, filed Nov. 19, 2019, and of Korean Patent Application No. KR 10-2020-0106335, filed Aug. 24, 2020, each of which is incorporated by reference herein in its entirety.

BACKGROUND

Technical Field

The present invention relates to a compound for organic electronic element, an organic electronic element using the same, and an electronic device thereof.

Background Art

In general, organic light emitting phenomenon refers to a phenomenon that converts electric energy into light energy by using an organic material. An organic electronic element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electronic element may be classified into a light emitting material and a charge transport material, such as a hole injection material, a hole transport material, an electron transport material, an electron injection material and the like depending on its function.

In the organic light emitting diode, the most problematic is the lifetime and the efficiency. As the display becomes large, the efficiency and the lifetime problem must be solved. Efficiency, life span, driving voltage and the like are related to each other. As the efficiency is increased, the driving voltage is relatively decreased, and as the driving voltage drops, the crystallization of the organic material due to joule heating generated during driving is reduced, and as a result, the life span tends to increase.

However, simply improving the organic material layer cannot maximize the efficiency. This is because, when the optimal combination of the energy level and T1 value between each organic material layer and the intrinsic properties (mobility, interface characteristics, etc.) of the material are achieved, long life and high efficiency can be achieved at the same time.

Further, recently, in organic electroluminescent devices, in order to solve the emission problem in the a hole transport layer, an emitting-auxiliary layer must be present between the hole transport layer and an emitting layer, and it is necessary to develop different emitting-auxiliary layers according to the respective emitting layers (R, G, B).

In general, electrons are transferred from the electron transport layer to the emitting layer, and holes are transferred from the hole transport layer to the emitting layer to generate excitons by recombination.

However, the material used for the hole transport layer has a low HOMO value and therefore has mostly low T1 value. As a result, the exciton generated in the emitting layer is transferred to the hole transport layer, resulting in charge unbalance in the emitting layer, and light is emitted at the interface of the hole transport layer.

When light is emitted at the interface of the hole transport layer, the color purity and efficiency of the organic electronic device are lowered and the life span is shortened. Therefore, it is urgently required to develop an emitting-auxiliary layer having a high T1 value and a HOMO level between the HOMO energy level of the hole transport layer and the HOMO energy level of the emitting layer.

Meanwhile, it is necessary to develop a hole injection layer material having stable characteristics, that is, a high glass transition temperature, against joule heating generated when the device is driven, while delaying penetration of the metal oxide from the anode electrode (ITO), which is one of the causes of shortening the lifetime of the organic electronic device, into the organic layer. The low glass transition temperature of the hole transport layer material has a characteristic that when the device is driven, the uniformity of the surface of the thin film is lowered, which has been reported to have a great influence on the lifetime of the device. In addition, OLED devices are mainly formed by a deposition method, and it is necessary to develop a material that can withstand long time in deposition, that is, a material having high heat resistance characteristics.

That is, in order to sufficiently exhibit the excellent characteristics of the organic electronic element, a material for forming an organic material layer in an element such as a hole injection material, a hole transport material, a light emitting material, an electron transport material, an electron injection material, an emitting-auxiliary layer material should be supported by stable and efficient materials. However, such a stable and efficient organic material layer material for an organic electronic element has not been sufficiently developed yet. Therefore, development of new materials is continuously required, and development of materials for the hole transport layer or the emitting-auxiliary layer is urgently required.

Prior technical literature:
Patent Literature: (Patent Document 0001) KR 1020130076842 A

BRIEF SUMMARY OF THE INVENTION

In order to solve the problems of the background art described above, the present invention has revealed a compound having a novel structure, and that when the compound is applied to an organic electronic element, the luminous efficiency, stability and lifetime of the element are greatly improved.

Accordingly, it is an object of the present invention to provide a novel compound, an organic electronic element using the same, and an electronic device.

Technical Solution

The present invention provides a compound represented by Formula 1:

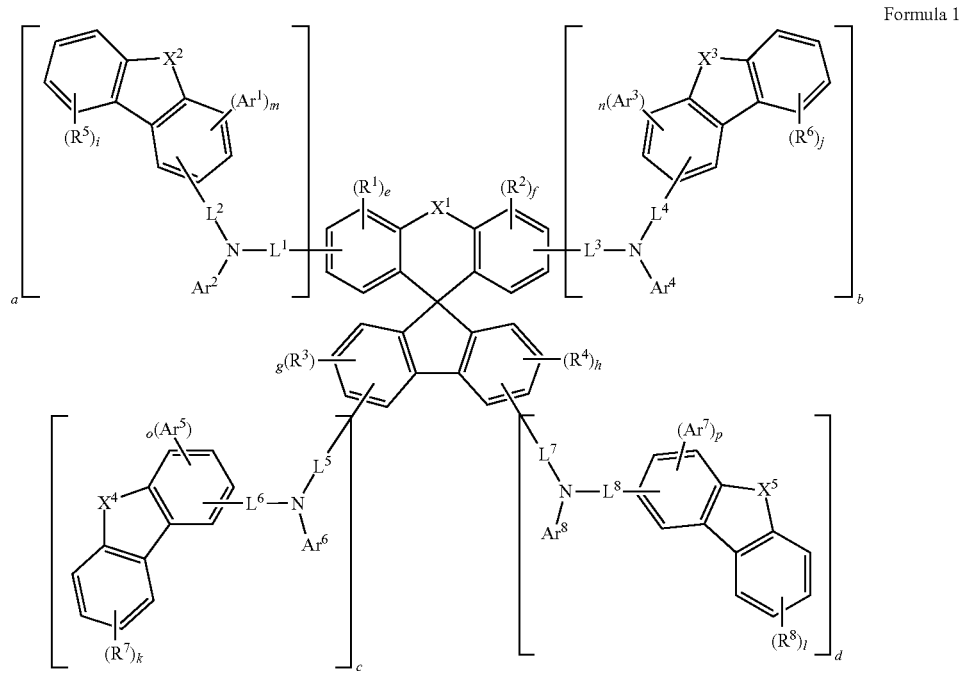

Formula 1

In another aspect, the present invention provides an organic electronic device including the compound represented by Formula 1 and an electronic device thereof.

Effects of the Invention

By using the compound according to the present invention, it is possible to achieve a high luminous efficiency, a low driving voltage, and a high heat resistance of the element, and can greatly improve the color purity and lifetime of the element.

DETAILED DESCRIPTION OF THE INVENTION

Figure 1:
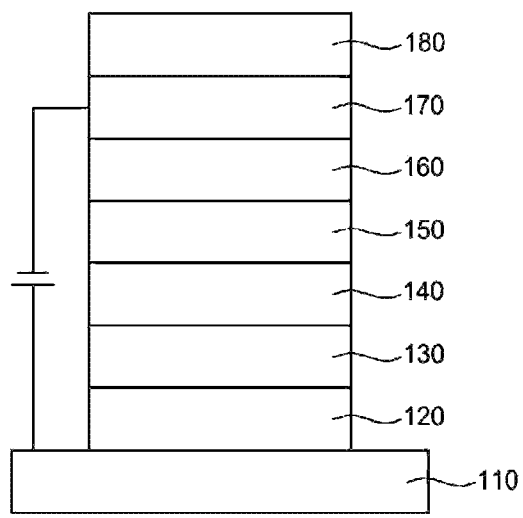
FIG. 1 to FIG. 3 each illustrate an example organic electronic element according to one aspect of the present invention.

Hereinafter, several embodiments of the present invention will be described in detail. In the following, a detailed description of known functions and configurations of an organic electric element or device which are incorporated herein will be omitted when it may make the subject matter of the present invention rather unclear. Terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected" "coupled" or "connected" between each component.

Unless otherwise stated, the following is the meaning of the terms used in the specification and the accompanying claims.

Unless otherwise stated, the term "halo" or "halogen", as used herein, includes fluorine, bromine, chlorine, or iodine.

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "alkenyl" or "alkynyl", as used herein, has double or triple bonds of 2 to 60 carbon atoms, but is not limited thereto, and includes a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxyl group", "alkoxy group" or "alkyloxy group", as used herein, means an oxygen radical attached to an alkyl group, but is not limited thereto, and has 1 to 60 carbon atoms.

Unless otherwise stated, the term "aryloxyl group" or "aryloxy group", as used herein, means an oxygen radical attached to an aryl group, but is not limited thereto, and has 6 to 60 carbon atoms.

Unless otherwise stated, the term "aryl group" or "arylene group", as used herein, has 6 to 60 carbon atoms, but is not limited thereto. Herein, the aryl group or arylene group means a monocyclic and polycyclic aromatic group, and may also be formed in conjunction with an adjacent group. Examples of "aryl group" may include a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heterocyclic group", as used herein, contains one or more heteroatoms, but is not limited thereto, has 2 to 60 carbon atoms, includes any one of monocyclic and polycyclic rings, and may include heteroaliphadic ring and/or heteroaromatic ring. Also, the heterocyclic group may also be formed in conjunction with an adjacent group.

Unless otherwise stated, the term "heteroatom", as used herein, represents at least one of N, O, S, P, or Si.

Also, the term "heterocyclic group" may include a ring including $SO_2$ instead of carbon consisting of cycle. For example, "heterocyclic group" includes compound below.

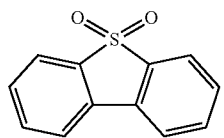 [SMILES: O=S1(=O)c2ccccc2-c2ccccc21]

Unless otherwise stated, the term "fluorenyl group" or "fluorenylene group", as used herein, means a monovalent or divalent functional group, in which R, R' and R" are all hydrogen in the following structures, and the term "substituted fluorenyl group" or "substituted fluorenylene group" means that at least one of the substituents R, R', R" is a substituent other than hydrogen, and include those in which R and R' are bonded to each other to form a spiro compound together with the carbon to which they are bonded.

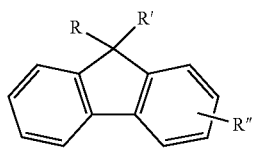

The term "spiro compound", as used herein, has a 'spiro union', and a spiro union means a connection in which two rings share only one atom. At this time, atoms shared in the two rings are called 'spiro atoms', and these compounds are called 'monospiro-', 'di-spiro-' and 'tri-spiro-', respectively, depending on the number of atoms in a compound.

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Other hetero compounds or hetero radicals other than the above-mentioned hetero compounds include, but are not limited thereto, one or more heteroatoms.

Unless otherwise stated, the term "substituted or unsubstituted", as used herein, means that substitution is substituted by at least one substituent selected from the group consisting of, but is not limited thereto, deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group.

Unless otherwise expressly stated, the Formula used in the present invention, as used herein, is applied in the same manner as the substituent definition according to the definition of the exponent of the following Formula.

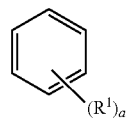

wherein, when a is an integer of zero, the substituent $R^1$ is absent, when a is an integer of 1, the sole substituent $R^1$ is linked to any one of the carbon constituting the benzene ring, when a is an integer of 2 or 3, each substituent $R^1$s may be the same and different, when a is an integer of 4 to 6, and is linked to the benzene ring in a similar manner, whereas the indication of hydrogen bound to the carbon forming the benzene ring is omitted.

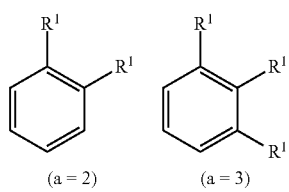

Hereinafter, a compound according to an aspect of the present invention and an organic electronic element comprising the same will be described.

One aspect of the present invention is to provide a compound represented by Formula 1:

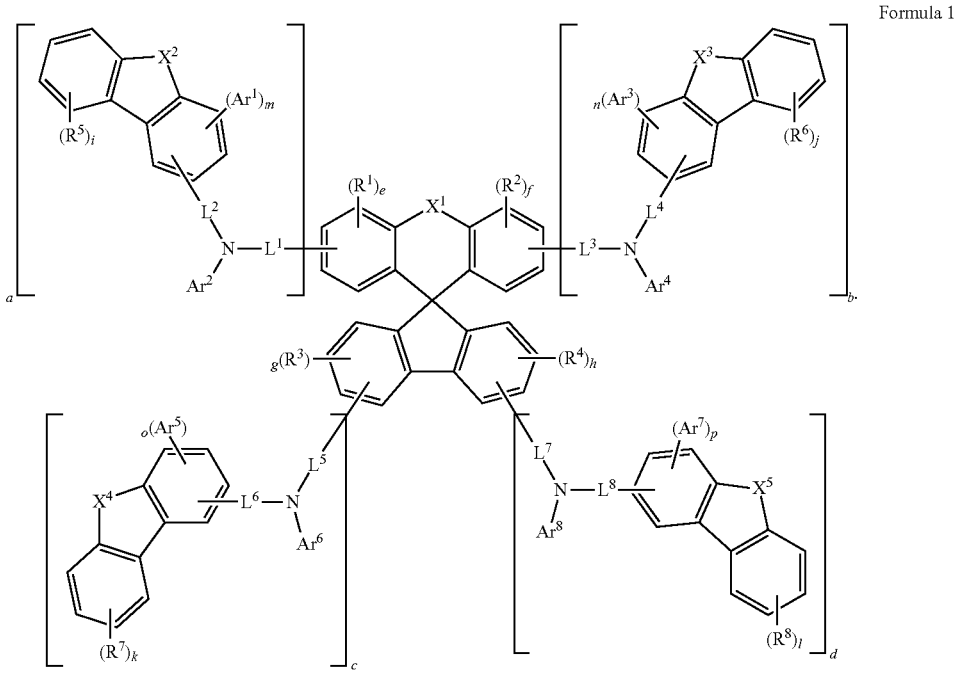

Formula 1

In Formula 1, each symbol may be defined as follows:
1) $X^1$, $X^2$, $X^3$, $X^4$ and $X^5$ are each independently O or S,
2) a, b, c and d are each independently an integer of 0 to 4, a+b+c+d is 1 or more,
3) e, f, g, h, i, j, k and l are each independently an integer of 0 to 4,
wherein in case e, f, g, h, i, j, k and l are 2 or more, $R^1$, $R^2$, $R^3$, $R^4$, $R^5$, $R^6$, $R^7$ and $R^8$ are each in plural being the same or different, and an adjacent plurality of $R^1$ or a plurality of $R^2$ or a plurality of $R^3$ or a plurality of $R^4$ or a plurality of $R^5$ or a plurality of $R^6$ or a plurality of $R^7$ or a plurality of $R^8$ may be bonded to each other to form a ring, 4) m, n, o and p are each independently an integer of 0 to 3, m+n+o+p is 1 or more,
5) $L^1$, $L^2$, $L^3$, $L^4$, $L^5$, $L^6$, $L^7$ and $L^8$ are the same or different from each other, and are each independently selected from the group consisting of single bond; a $C_6$-$C_{60}$ arylene group; a fluorenylene group; a fused ring group of a $C_3$-$C_{60}$ aliphatic ring and a $C_6$-$C_{60}$ aromatic ring; a $C_2$-$C_{60}$ heterocyclic group;
wherein in case $L^1$, $L^2$, $L^3$, $L^4$, $L^5$, $L^6$, $L^7$ and $L^8$ are an arylene group, it is preferably an $C_6$~$C_{36}$ arylene group, more preferably an $C_6$~$C_{24}$ arylene group, when $L^1$, $L^2$, $L^3$, $L^4$, $L^5$, $L^6$, $L^7$ and $L^8$ are a fused ring group, it is preferably a fused ring group of an $C_6$~$C_{36}$ aliphatic ring and an $C_6$~$C_{36}$ aromatic ring, and more preferably a fused ring group of an $C_6$~$C_{24}$ aliphatic ring and an $C_6$~$C_{24}$ aromatic ring, when $L^1$, $L^2$, $L^3$, $L^4$, $L^5$, $L^6$, $L^7$ and $L^8$ are a heterocyclic group, it is preferably a $C_2$~$C_{36}$ heterocyclic group, and more preferably a $C_2$~$C_{24}$ heterocyclic group.
6) $Ar^1$, $Ar^3$, $Ar^5$ and $Ar^7$ are the same or different from each other, and are each independently selected from the group consisting of hydrogen; deuterium; tritium; halogen; cyano group; nitro group; $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; $C_1$-$C_{50}$ alkyl group; $C_2$-$C_{20}$ alkenyl group; $C_2$-$C_{20}$ alkynyl group; $C_1$-$C_{30}$ alkoxyl group; $C_6$-$C_{30}$ aryloxy group; and -L'-N($R_a$)($R_b$);
wherein in case $Ar^1$, $Ar^3$, $Ar^5$ and $Ar^7$ are an aryl group, it is preferably an $C_6$~$C_{36}$ aryl group, more preferably an $C_6$~$C_{25}$ aryl group, in case $Ar^1$, $Ar^3$, $Ar^5$ and $Ar^7$ are an heterocyclic group, it is preferably a $C_2$~$C_{36}$ heterocyclic group, and more preferably a $C_2$~$C_{24}$ heterocyclic group, in case $Ar^1$, $Ar^3$, $Ar^5$ and $Ar^7$ are a fused ring group, it is preferably a fused ring group of an $C_6$~$C_{36}$ aliphatic ring and an $C_6$~$C_{36}$ aromatic ring, more preferably a fused ring group of an $C_6$~$C_{24}$ aliphatic ring and an $C_6$~$C_{24}$ aromatic ring, in case $Ar^1$, $Ar^3$, $Ar^5$ and $Ar^7$ are alkyl groups, it is preferably an $C_1$~$C_{36}$ alkyl group, more preferably an $C_1$~$C_{24}$ alkyl group,
7) $Ar^2$, $Ar^4$, $Ar^6$ and $Ar^8$ are each independently selected from the group consisting of a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; -$L^9$-Ar';
wherein in case $Ar^2$, $Ar^4$, $Ar^6$ and $Ar^8$ are an aryl group, it is preferably an $C_6$~$C_{36}$ aryl group, more preferably an $C_6$~$C_{25}$ aryl group, in case $Ar^2$, $Ar^4$, $Ar^6$ and $Ar^8$ are heterocyclic groups, it is preferably a $C_2$~$C_{36}$ heterocyclic group, and more preferably a $C_2$~$C_{24}$ heterocyclic group, in case $Ar^2$, $Ar^4$, $Ar^6$ and $Ar^8$ are a fused ring group, it is preferably a fused ring group of an $C_6$~$C_{36}$ aliphatic ring and an $C_6$~$C_{36}$ aromatic ring, more preferably a fused ring group of an $C_6$~$C_{24}$ aliphatic ring and an $C_6$~$C_{24}$ aromatic ring.
8) wherein $L^9$ is selected from the group consisting of single bond; a $C_6$-$C_{60}$ arylene group; a fluorenylene group; a fused ring group of a $C_3$~$C_{60}$ aliphatic ring and a $C_6$-$C_{60}$ aromatic ring; a $C_2$-$C_{60}$ heterocyclic group; Ar' is selected from a $C_6$-$C_{60}$ aryl group; a fluorenylene group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring;

wherein in case $L^9$ is arylene group, it is preferably an $C_6$~$C_{36}$ arylene group, more preferably an $C_6$~$C_{24}$ arylene group, when $L^9$ is a fused ring group, it is preferably a fused ring group of an $C_6$~$C_{36}$ aliphatic ring and an $C_6$~$C_{36}$ aromatic ring, and more preferably a fused ring group of an $C_6$~$C_{24}$ aliphatic ring and an $C_6$~$C_{24}$ aromatic ring, when $L^9$ is a heterocyclic group, it is preferably a $C_2$~$C_{36}$ heterocyclic group, and more preferably a $C_2$~$C_{24}$ heterocyclic group.

wherein in case Ar' is an aryl group, it is preferably an $C_6$~$C_{36}$ aryl group, more preferably an $C_6$~$C_{25}$ aryl group, in case Ar' is a heterocyclic group, it is preferably $C_2$~$C_{36}$ heterocyclic groups, and more preferably $C_2$~$C_{24}$ heterocyclic groups, in case Ar' is a fused ring group, it is preferably a fused ring group of an $C_6$~$C_{36}$ aliphatic ring and an $C_6$~$C_{36}$ aromatic ring, more preferably a fused ring group of an $C_6$~$C_{24}$ aliphatic ring and an $C_6$~$C_{24}$ aromatic ring.

9) $R^1$, $R^2$, $R^3$, $R^4$, $R^5$, $R^6$, $R^7$ and $R^8$ are the same or different from each other, and are each independently selected from the group consisting of hydrogen; deuterium; tritium; halogen; cyano group; nitro group; $C_6$-$C_{60}$ aryl group; a fluorenyl group; a $C_2$-$C_6$ heterocyclic group including at least one heteroatom of O, N, S, Si or P; a fused ring group of a $C_3$-$C_{60}$ aliphatic ring and a $C_6$-$C_{60}$ aromatic ring; $C_1$-$C_{50}$ alkyl group; $C_2$-$C_{20}$ alkenyl group; $C_2$-$C_{20}$ alkynyl group; $C_1$-$C_{30}$ alkoxyl group; $C_6$-$C_{30}$ aryloxy group; and -L'-N($R_a$)($R_b$);

wherein in case $R^1$, $R^2$, $R^3$, $R^4$, $R^5$, $R^6$, $R^7$ and $R^8$ are an aryl group, it is preferably an $C_6$~$C_{36}$ aryl group, more preferably an $C_6$~$C_{25}$ aryl group, in case $R^1$, $R^2$, $R^3$, $R^4$, $R^5$, $R^6$, $R^7$ and $R^8$ are an heterocyclic group, it is preferably a $C_2$~$C_{36}$ heterocyclic group including at least one heteroatom of O, N, S, Si or P; in case $R^1$, $R^2$, $R^3$, $R^4$, $R^5$, $R^6$, $R^7$ and $R^8$ are a fused ring group, it is preferably a fused ring group of an $C_6$~$C_{36}$ aliphatic ring and an $C_6$~$C_{36}$ aromatic ring, more preferably a fused ring group of an $C_6$~$C_{24}$ aliphatic ring and an $C_6$~$C_{24}$ aromatic ring.

10) wherein L' is selected from the group consisting of a single bond; a $C_6$-$C_{60}$ arylene group; a fluorenylene group; $C_3$-$C_{60}$ aliphatic ring; a $C_2$-$C_{60}$ heterocyclic group including at least one heteroatom of O, N, S, Si or P; a combination thereof; wherein $R_a$ and $R_b$ are each independently selected from the group consisting of a $C_6$-$C_{60}$ aryl group; a fluorenyl group; $C_3$-$C_{60}$ aliphatic ring; a $C_2$-$C_{60}$ heterocyclic group including at least one heteroatom of O, N, S, Si or P;

wherein in case L' is an arylene group, it is preferably an $C_6$~$C_{36}$ arylene group, more preferably an $C_6$~$C_{24}$ arylene group, in case L' is an aliphatic ring, it is preferably a $C_3$~$C_{36}$ aliphatic ring, more preferably $C_6$~$C_{24}$ aliphatic ring, when L' is a heterocyclic group, it is preferably a $C_2$~$C_{36}$ heterocyclic group including at least one heteroatom of O, N, S, Si or P; and more preferably a $C_2$~$C_{24}$ heterocyclic group, wherein in case $R_a$ and $R_b$ are an aryl group, it is preferably an $C_6$~$C_{36}$ aryl group, more preferably an $C_6$~$C_{25}$ aryl group, in case $R_a$ and $R_b$ are an aliphatic ring, it is preferably a $C_3$~$C_{36}$ aliphatic ring, more preferably $C_3$~$C_{24}$ aliphatic ring, in case $R_a$ and $R_b$ are a heterocyclic group, it is preferably a $C_2$~$C_{36}$ heterocyclic group including at least one heteroatom of O, N, S, Si or P; and more preferably a $C_2$~$C_{24}$ heterocyclic group including at least one heteroatom of O, N, S, Si or P;

11) wherein, the aryl group, arylene group, heterocyclic group, fluorenyl group, fluorenylene group, fused ring group, alkyl group, alkenyl group, alkoxy group and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{25}$ aryl group; $C_6$-$C_{25}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group; $C_8$-$C_{20}$ arylalkenyl group; and -L'-N($R_a$)($R_b$); the substituents may combine each other to form a saturated or unsaturated ring selected from the group consisting of a $C_3$-$C_{60}$ aliphatic ring, a $C_6$-$C_{60}$ aromatic ring, a $C_2$-$C_{60}$ heterocyclic group, a fused ring formed by combination thereof.

In one embodiment, Formula 1 includes a compound represented by any one of Formulas 1-1 to 1-9:

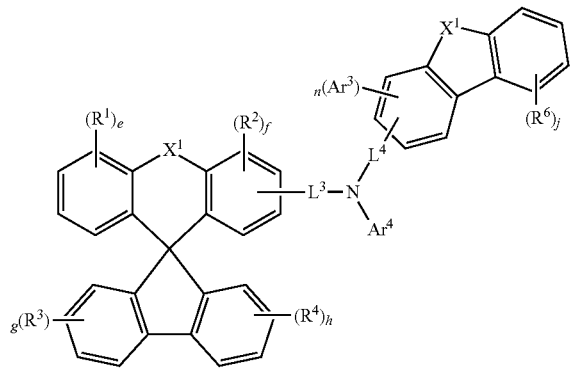

<Formula 1-1>

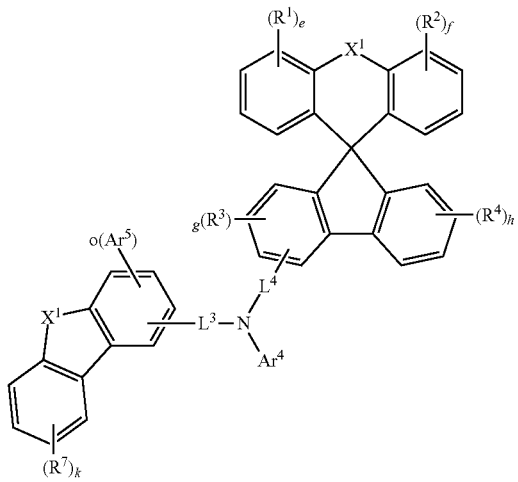

<Formula 1-2>

<Formula 1-3>
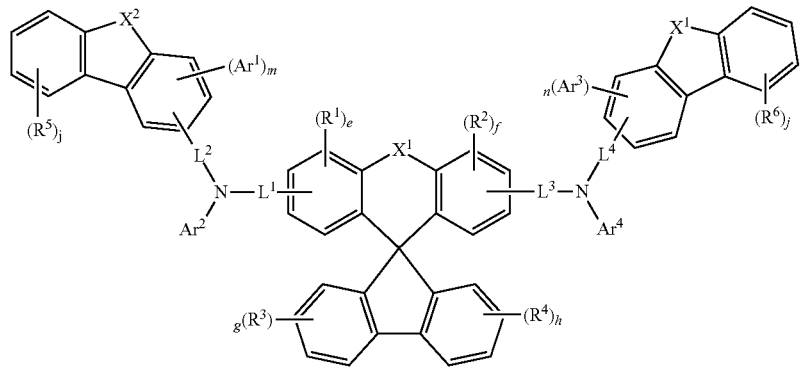
<Formula 1-4>
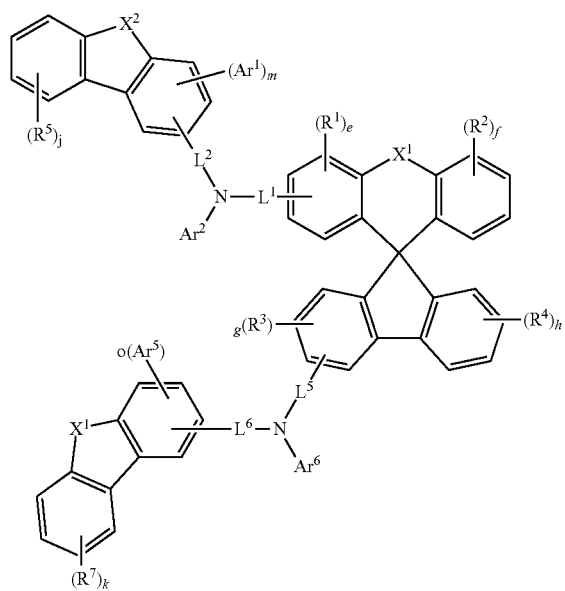
<Formula 1-5>
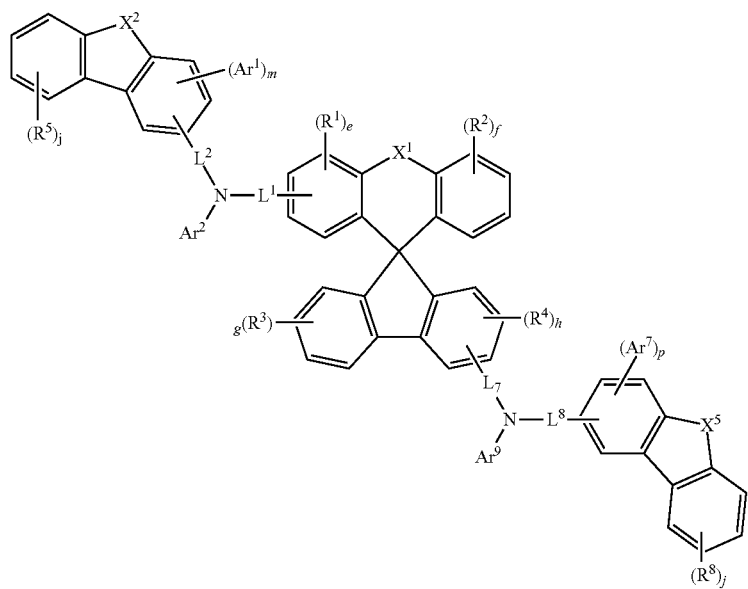

<Formula 1-6>
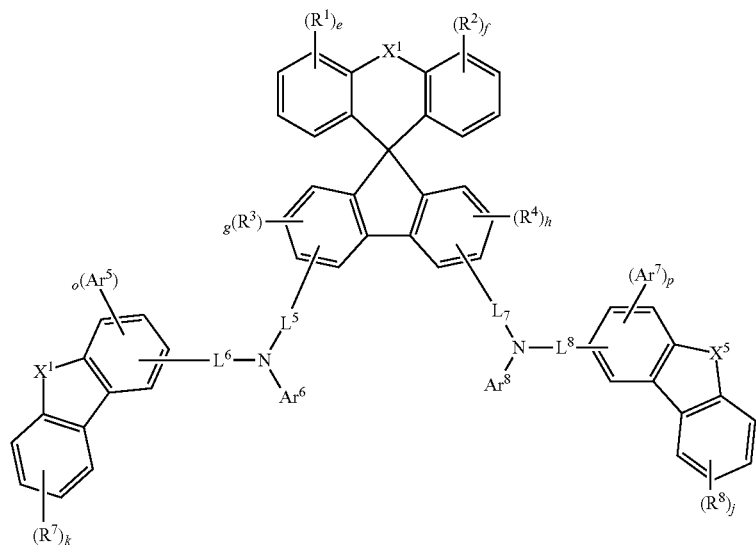
<Formula 1-7>
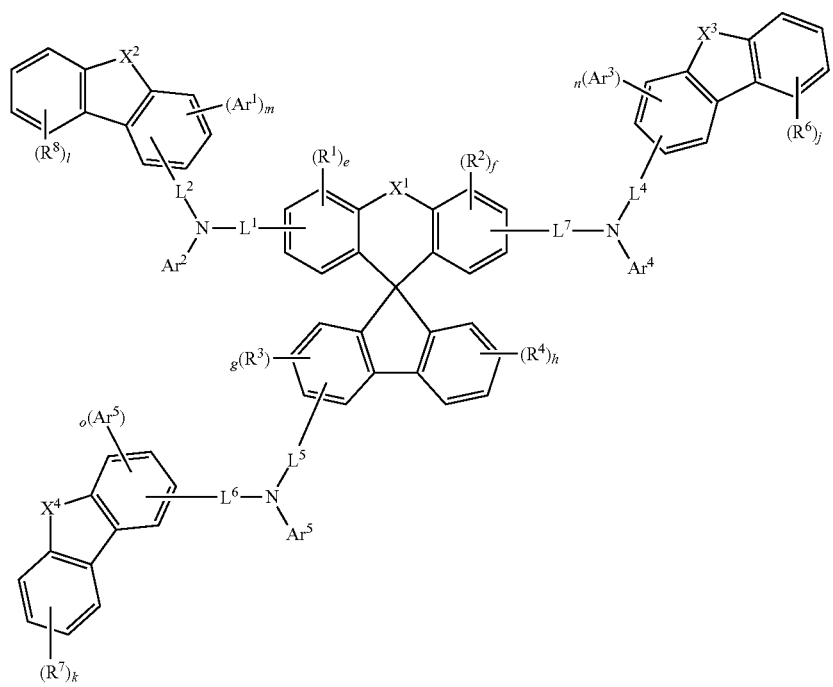

<Formula 1-8>
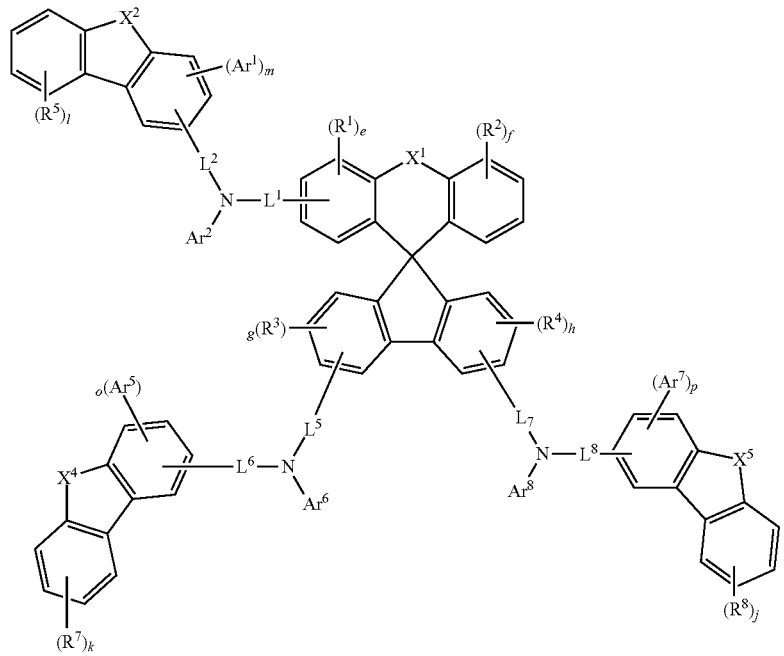
<Formula 1-9>
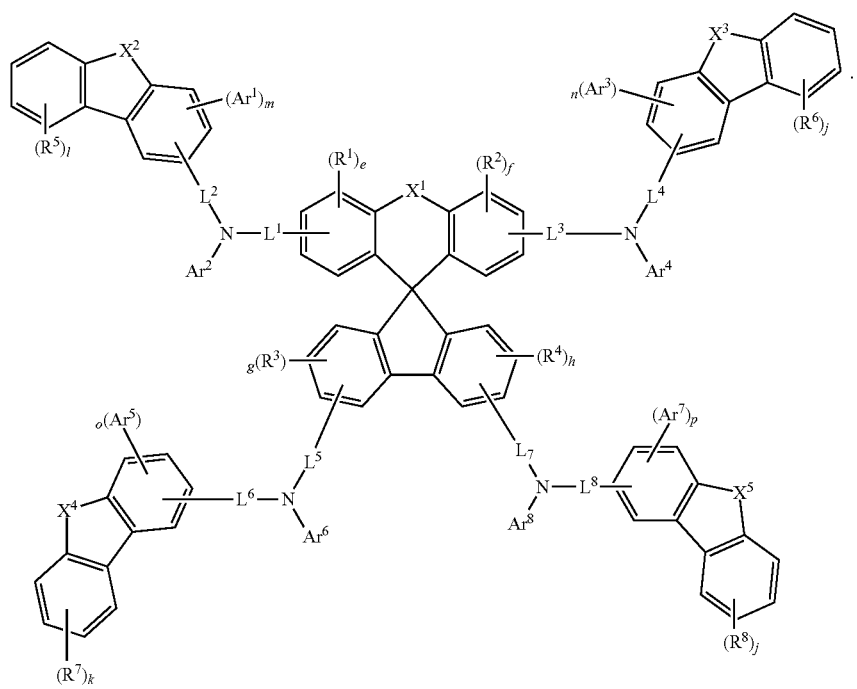
In Formulas 1-1 to 1-9,
$X^1, X^2, X^3, X^4, X^5$ and $R^1, R^2, R^3, R^4, R^5, R^6, R^7, R^8$ and $sL^1, L^2, L^3, L^4, L^5, L^6, L^7, L^8$ and e, f, g, h, i, j, k, l, m, n, o and p are the same as defined for those in Formula 1.
In another embodiment, Formula 1 includes a compound represented by Formula 2:

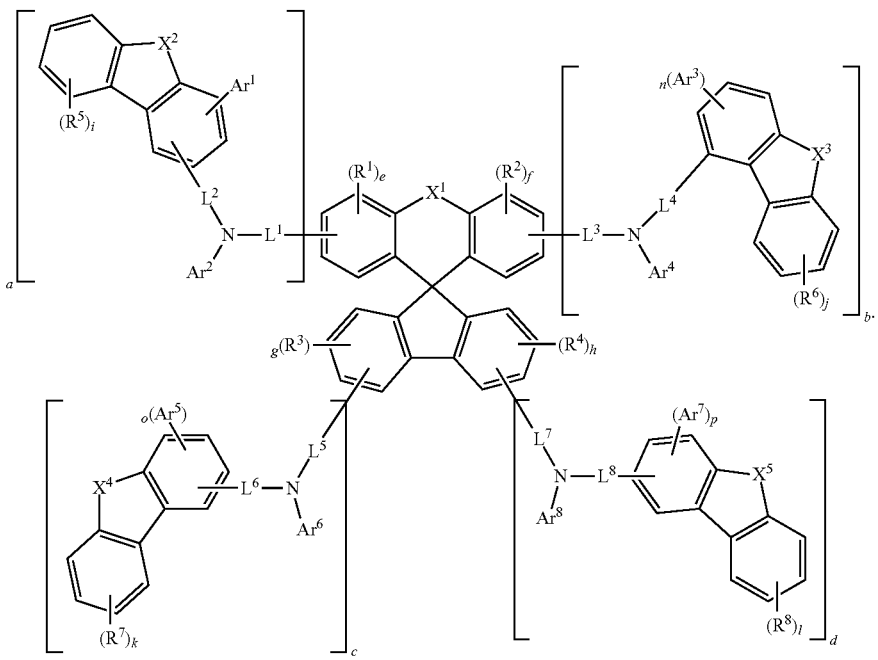

<Formula 2>

In Formula 2,
$X^1$, $X^2$, $X^3$, $X^4$, $X^5$ and $R^1$, $R^2$, $R^3$, $R^4$, $R^5$, $R^6$, $R^7$, $R^8$ and $L^1$, $L^2$, $L^3$, $L^4$, $L^5$, $L^6$, $L^7$, $L^8$ and $Ar^1$, $Ar^2$, $Ar^3$, $Ar^4$, $Ar^5$, $Ar^6$, $Ar^7$, and $Ar^8$, and a, b, c, d, e, f, g, h, i, j, k, l and n are the same as defined for those in Formula 1.

In another embodiment, Formula 1 includes a compound represented by any one of Formulas 2-1 to 2-4:

<Formula 2-1>

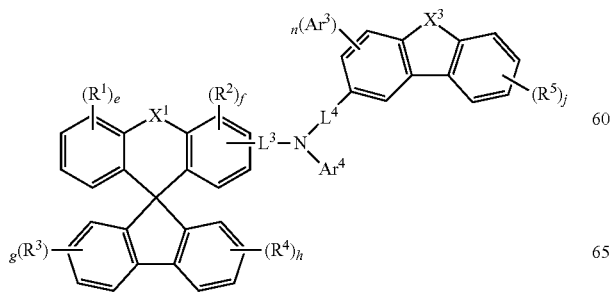

<Formula 2-2>

<Formula 2-3>

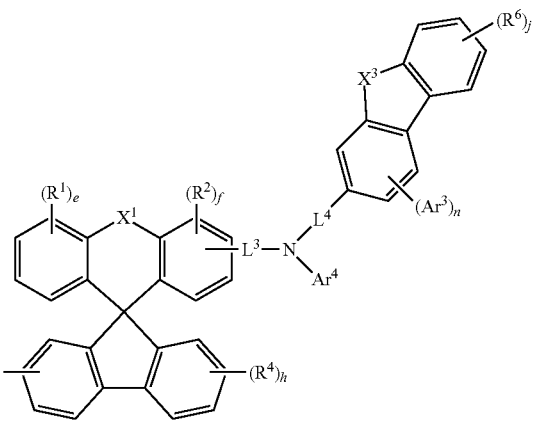

<Formula 2-4>

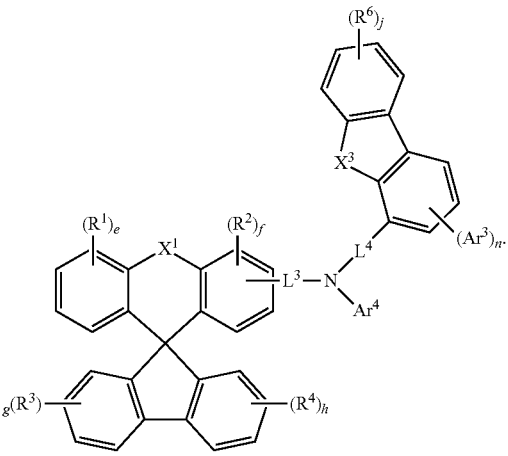

In Formulas 2-1 to 2-4,
$X^1$, $X^3$, $R^1$, $R^2$, $R^3$, $R^4$, $R^6$, $L^3$, $L^4$, $Ar^3$, $Ar^4$, e, f, g, h, j and n are the same as defined in Formula 1.

In another embodiment, Formula 1 includes a compound represented by Formula 3:

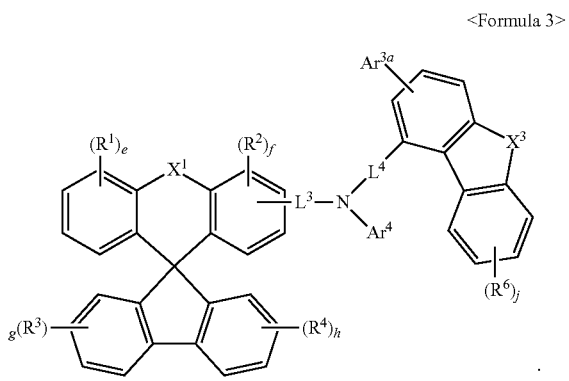

<Formula 3>

In Formula 3,
1) $X^1$, $X^3$, $R^1$, $R^2$, $R^3$, $R^4$, $R^6$, $L^3$, $L^4$, $Ar^4$, e, f, g, h 및 j are the same as defined in Formula 1,
2) $Ar^{3a}$ is selected from the group consisting of deuterium; tritium; halogen; cyano group; nitro group; $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; $C_1$-$C_{60}$ alkyl group; $C_2$-$C_{20}$ alkenyl group; $C_2$-$C_{20}$ alkynyl group; $C_1$-$C_{30}$ alkoxyl group; $C_6$-$C_{30}$ aryloxy group; and -L'-N($R_a$)($R_b$).

In another embodiment, Formula 1 includes a compound represented by Formula 4:

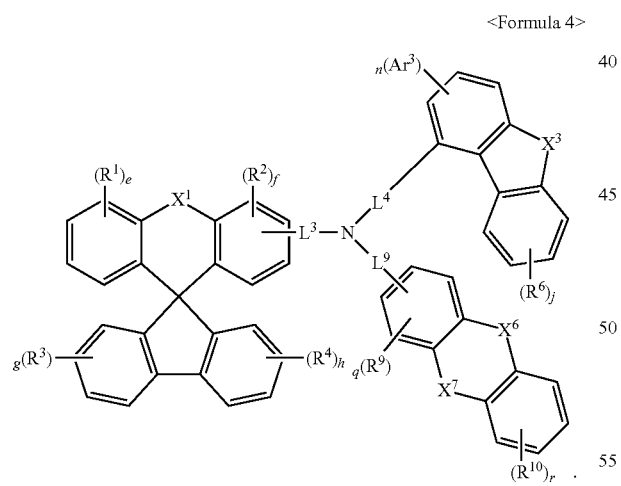

<Formula 4>

In Formula 4,
1) $X^1$, $X^3$, $R^1$, $R^2$, $R^3$, $R^4$, $R^6$, $L^3$, $L^4$, $L^9$, $Ar^3$, e, f, g, h, j and n are the same as defined in Formula 1,
2) $X^6$ and $X^7$ are each independently a single bone, CR'R", O or S, except that $X^6$ and $X^7$ are a single bond at the same time,
3) R' and R" are each independently a hydrogen; $C_6$-$C_{60}$ aryl group; a fluorenyl group; a $C_3$-$C_{60}$ heterocyclic group; $C_1$-$C_{50}$ alkyl group; $C_2$-$C_{60}$ alkenyl group; or $C_6$-$C_{60}$ aryloxy group; R' and R" are bonded to each other to form a $C_6$-$C_{60}$ aromatic ring; fluorenyl group; a $C_2$-$C_{60}$ heterocyclic group including at least one heteroatom of O, N, S, Si or P; $C_3$-$C_{60}$ aliphatic ring; or a fused ring group of a $C_3$-$C_{60}$ aliphatic ring and a $C_6$-$C_{60}$ aromatic ring,
wherein in case R' and R" are an aryl group, it is preferably an $C_6$~$C_{36}$ aryl group, more preferably an $C_6$~$C_{25}$ aryl group, in case R' and R" are a heterocyclic group, it is preferably $C_2$~$C_{36}$ heterocyclic groups, and more preferably $C_2$~$C_{24}$ heterocyclic groups, in case R' and R" are an alkyl group, it is preferably $C_1$-$C_{36}$ alkyl group, and more preferably $C_1$-$C_{24}$ alkyl group, in case R' and R" are an alkenyl group, it is preferably a $C_2$-$C_{36}$ alkenyl group, and more preferably a $C_2$-$C_{24}$ alkenyl group, in case R' and R" are an aryloxy group, it is preferably $C_6$-$C_{36}$ aryloxy group, and more $C_6$-$C_{24}$ aryloxy group.
4) $R^9$ and $R^{10}$ are the same as the definition of $R^1$ in Formula 1,
5) q is an integer of 0 to 3, r is an integer of 0 to 4.

In another embodiment, Formula 1 includes a compound represented by Formula 4-1:

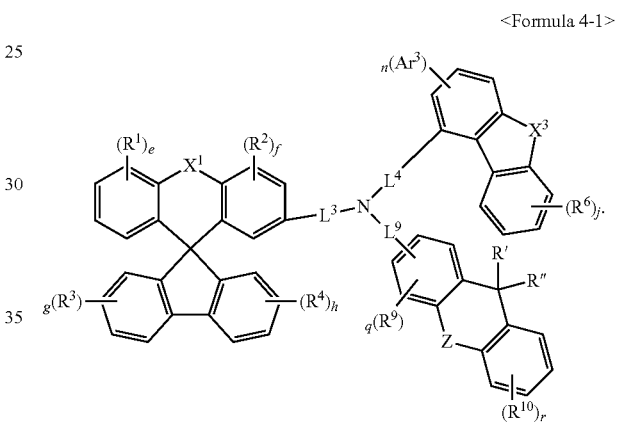

<Formula 4-1>

In Formula 4-1,
1) $X^1$, $X^3$, $R^1$, $R^2$, $R^3$, $R^4$, $R^6$, $L^3$, $L^4$, $L^9$, $Ar^3$, e, f, g, h, j and n are the same as defined in Formula 1,
2) $R^9$, $R^{10}$, R', R", q and r are the same as defined in Formula 4,
3) Z is a single bond, O or S.

In another embodiment, Formula 1 includes a compound represented by Formula 4-2:

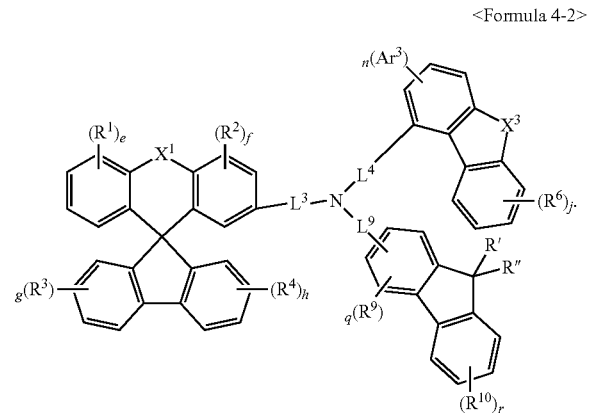

<Formula 4-2>

In Formula 4-2,
1) $X^1$, $X^3$, $R^1$, $R^2$, $R^3$, $R^4$, $R^6$, $L^3$, $L^4$, $L^9$, $Ar^3$, e, f, g, h, j and n are the same as defined in Formula 1,
2) $R^9$, $R^{10}$, R', R", q and r are the same as defined in Formula 4.

In another embodiment, Formula 1 includes a compound represented by any one of Formulas 5-1 to 5-4:

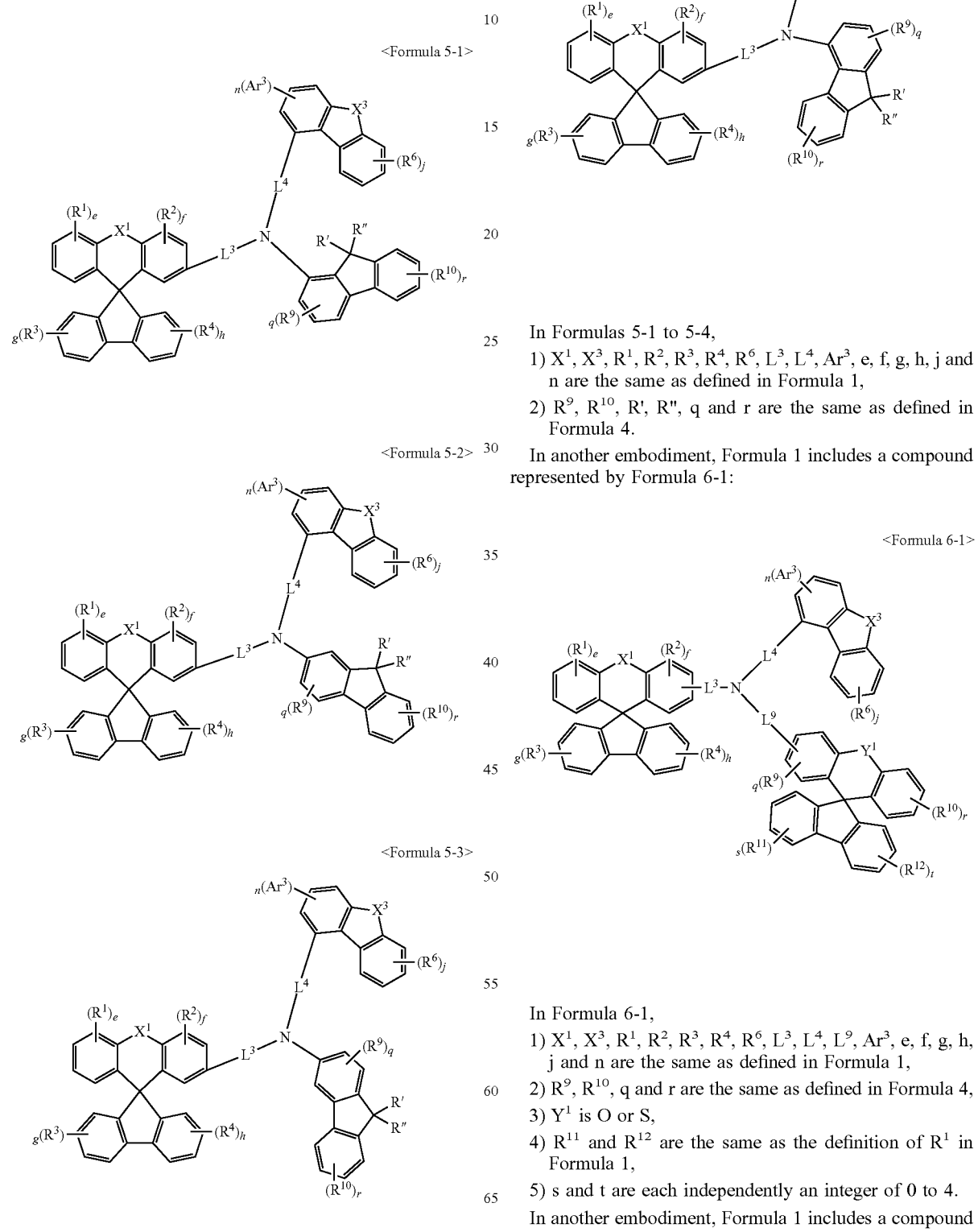

<Formula 5-1>

<Formula 5-2>

<Formula 5-3>

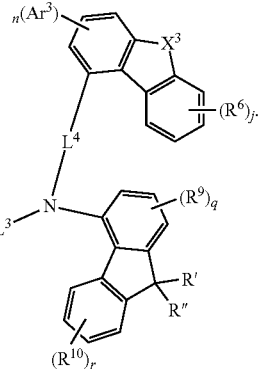

<Formula 5-4>

In Formulas 5-1 to 5-4,
1) $X^1$, $X^3$, $R^1$, $R^2$, $R^3$, $R^4$, $R^6$, $L^3$, $L^4$, $Ar^3$, e, f, g, h, j and n are the same as defined in Formula 1,
2) $R^9$, $R^{10}$, R', R", q and r are the same as defined in Formula 4.

In another embodiment, Formula 1 includes a compound represented by Formula 6-1:

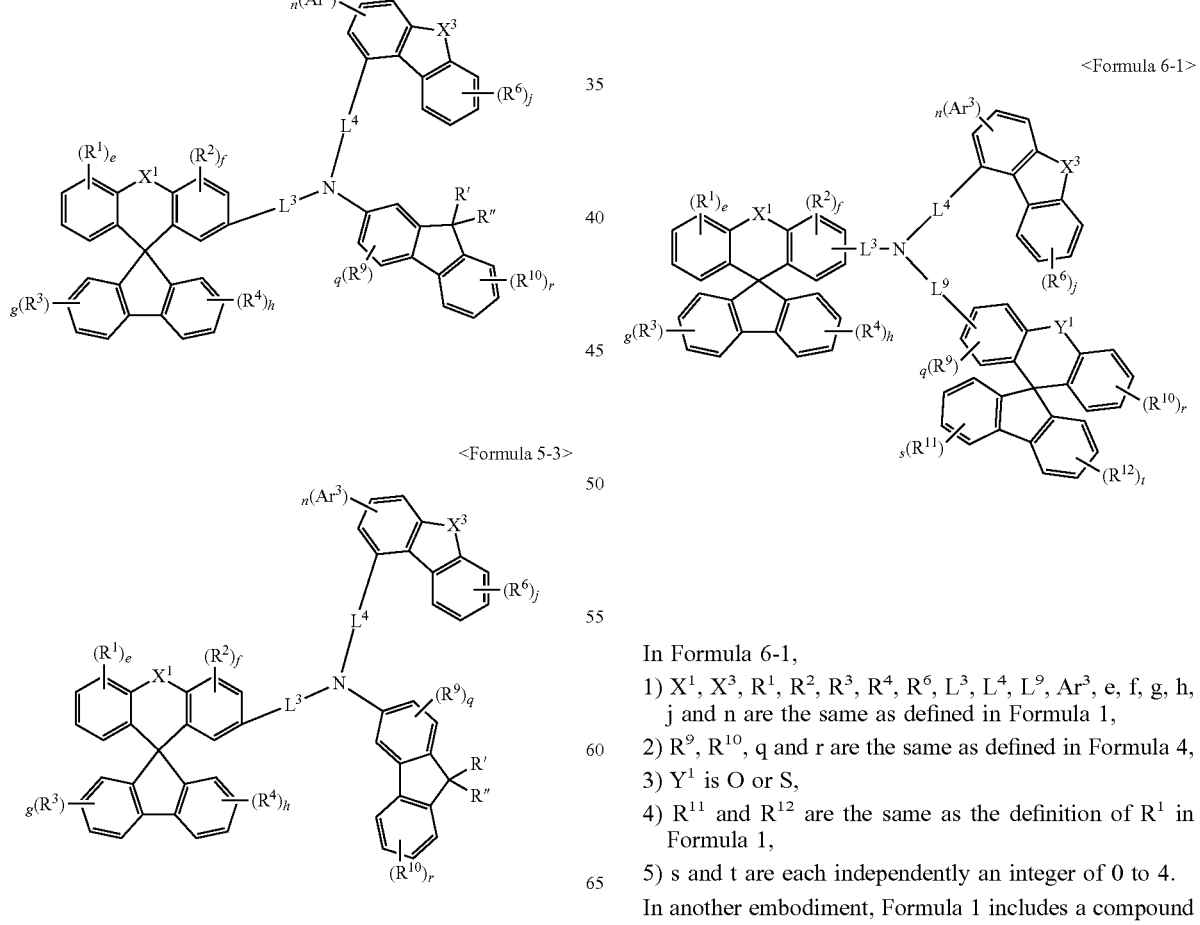

<Formula 6-1>

In Formula 6-1,
1) $X^1$, $X^3$, $R^1$, $R^2$, $R^3$, $R^4$, $R^6$, $L^3$, $L^4$, $L^9$, $Ar^3$, e, f, g, h, j and n are the same as defined in Formula 1,
2) $R^9$, $R^{10}$, q and r are the same as defined in Formula 4,
3) $Y^1$ is O or S,
4) $R^{11}$ and $R^{12}$ are the same as the definition of $R^1$ in Formula 1,
5) s and t are each independently an integer of 0 to 4.

In another embodiment, Formula 1 includes a compound represented by Formula 6-2:

<Formula 6-2>

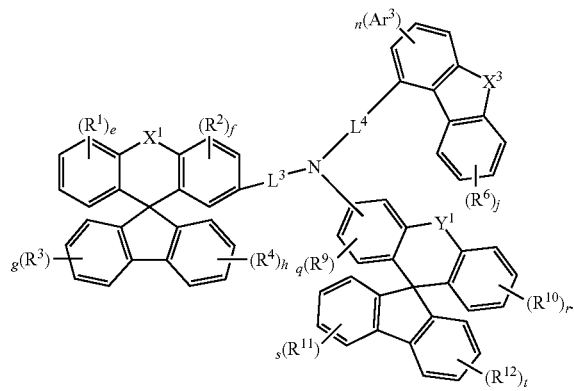

<Formula 6-3>

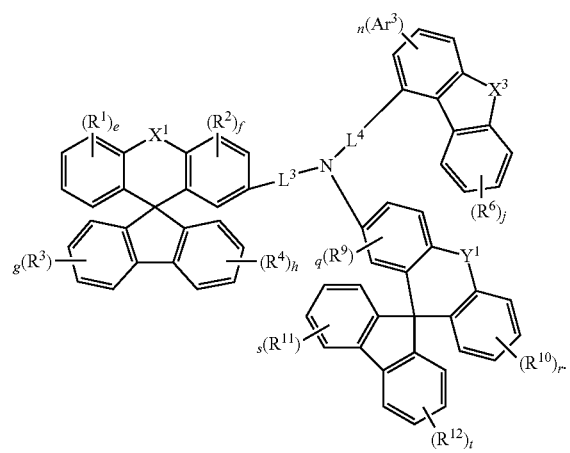

In Formula 6-2,
1) $X^1$, $X^3$, $R^1$, $R^2$, $R^3$, $R^4$, $R^6$, $L^3$, $L^4$, $Ar^3$, e, f, g, h, j and n are the same as defined in Formula 1,
2) $R^9$, $R^{10}$, q and r are the same as defined in Formula 4,
3) $Y^1$, $R^{11}$, $R^{12}$, s and t are the same as defined in Formula 6-1.

In another embodiment, Formula 1 includes a compound represented by Formula 6-3:

In Formula 6-3,
1) $X^1$, $X^3$, $R^1$, $R^2$, $R^3$, $R^4$, $R^6$, $L^3$, $L^4$, $Ar^3$, e, f, g, h, j and n are the same as defined in Formula 1,
2) $R^9$, $R^{10}$, q and r are the same as defined in Formula 4,
3) $Y^1$, $R^{11}$, $R^{12}$, s and t are the same as defined in Formula 6-1.

Specifically, the compound represented by Formula 1 may be a compound represented by any one of Compounds P-1 to P-139, but it is not limited thereto:

P-1

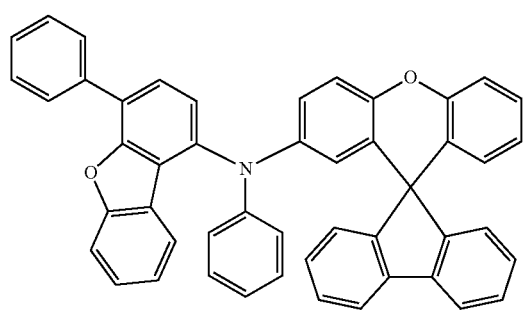

P-2

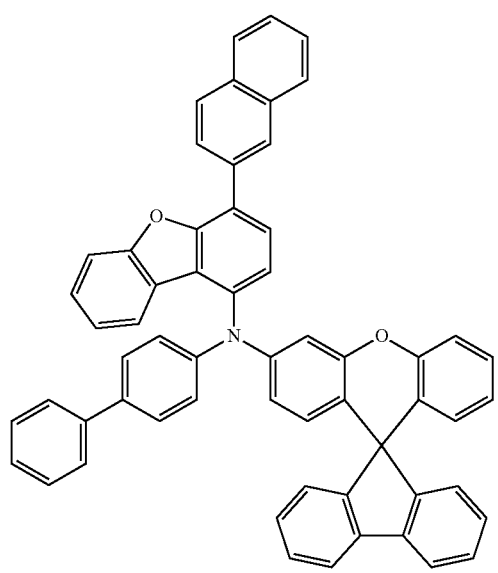

-continued
P-3
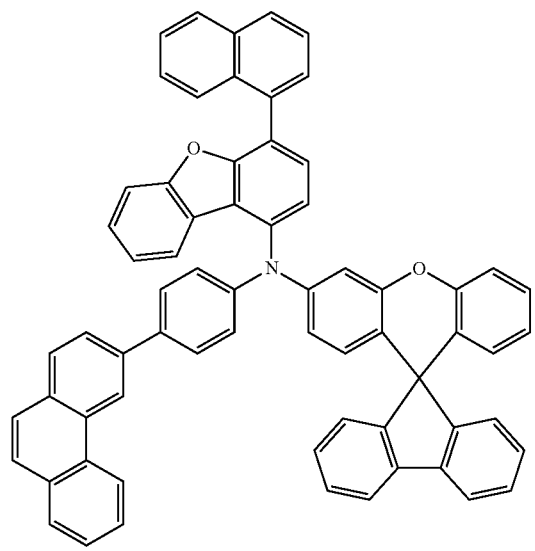
P-4
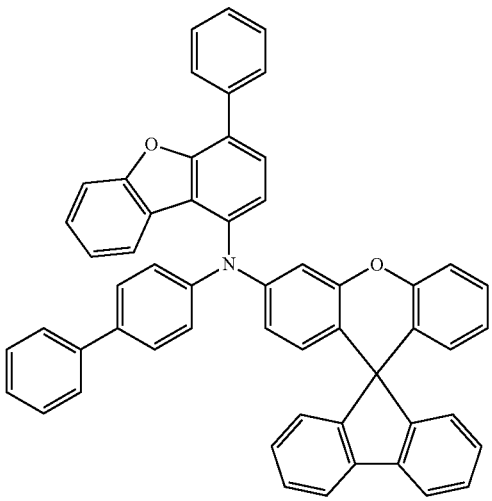
P-5
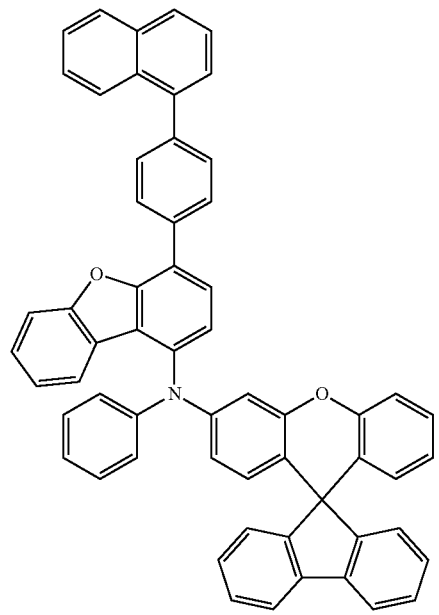
P-6
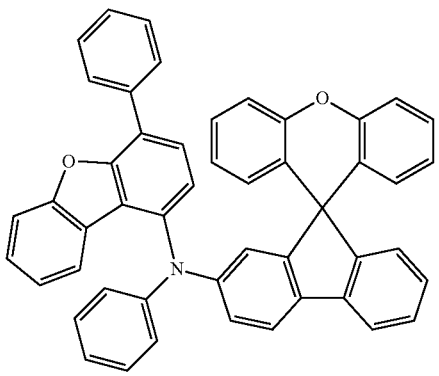
P-7
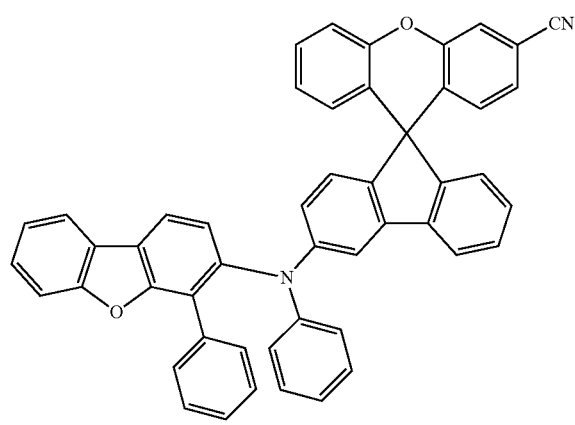
P-8
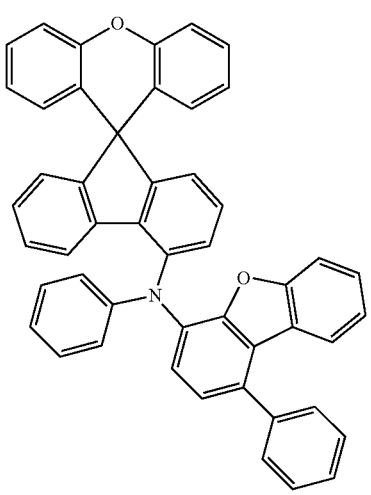

-continued
P-9
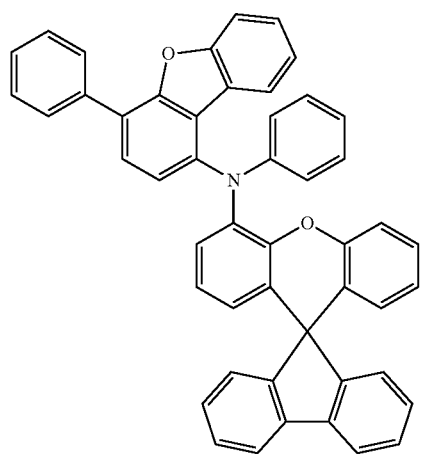
P-10
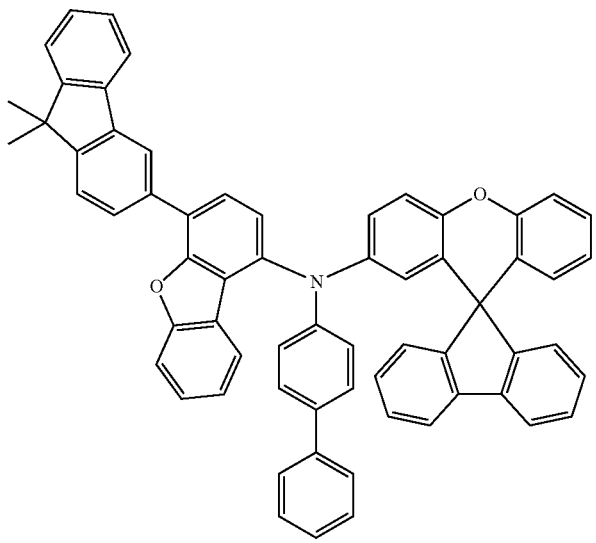
P-11
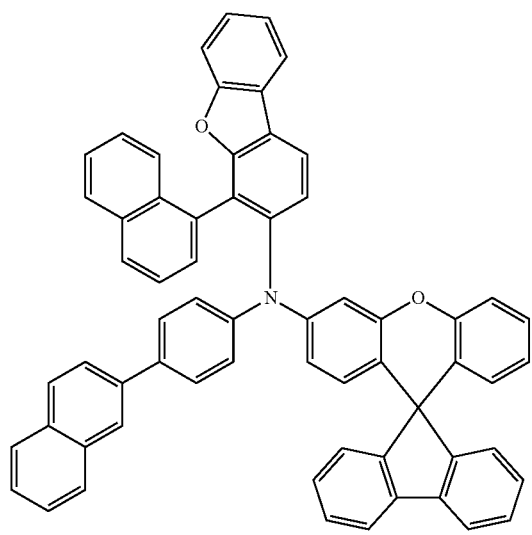
P-12
P-13
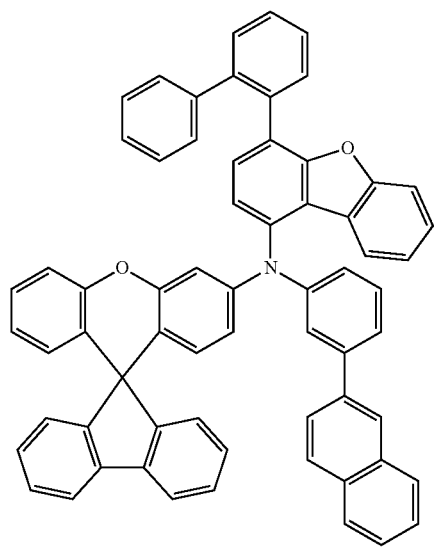
P-14
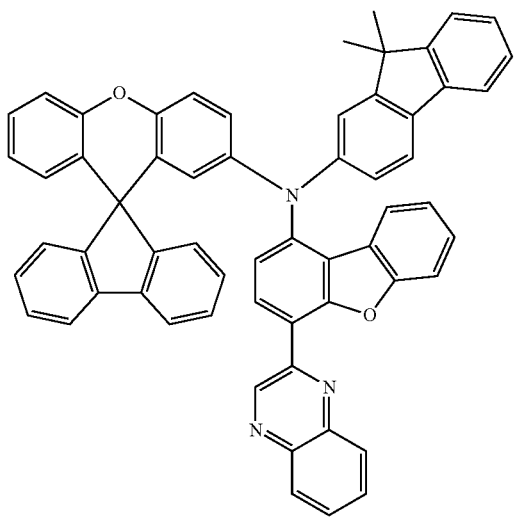

-continued
P-15
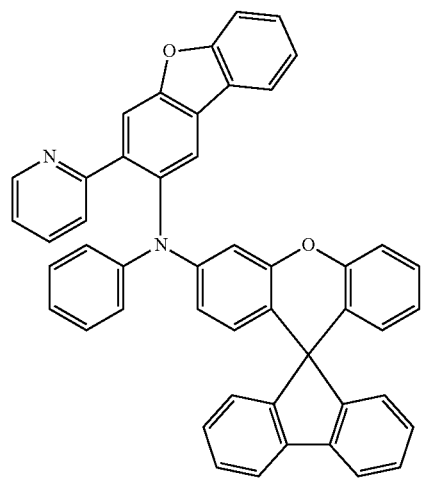
P-16
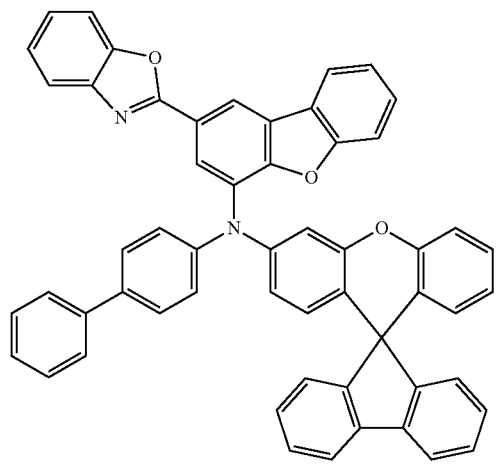
P-17
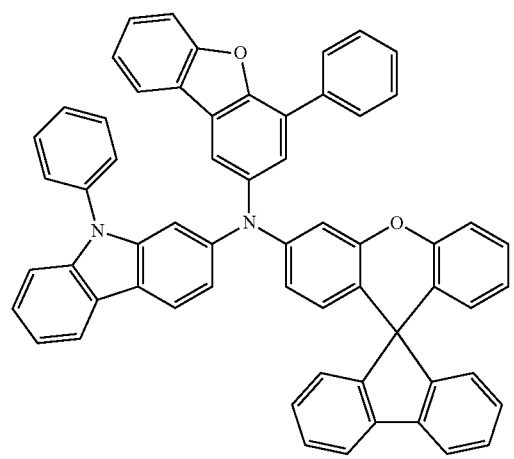
P-18
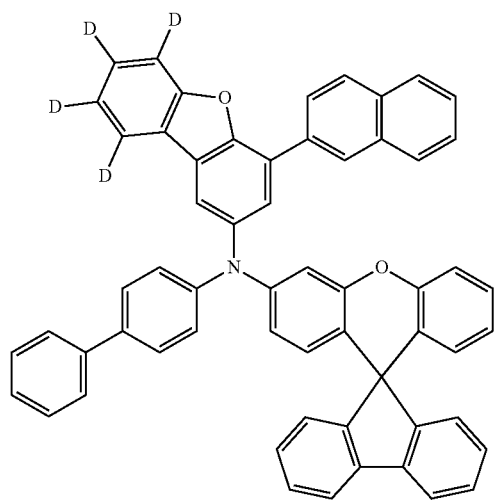
P-19
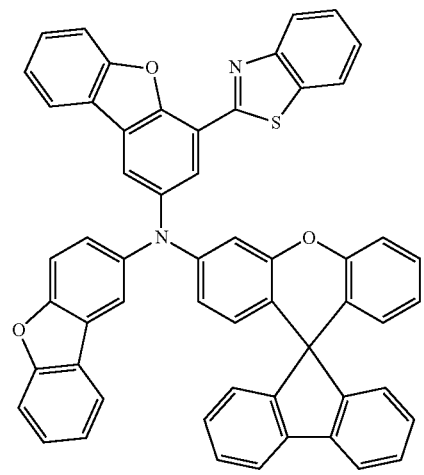
P-20
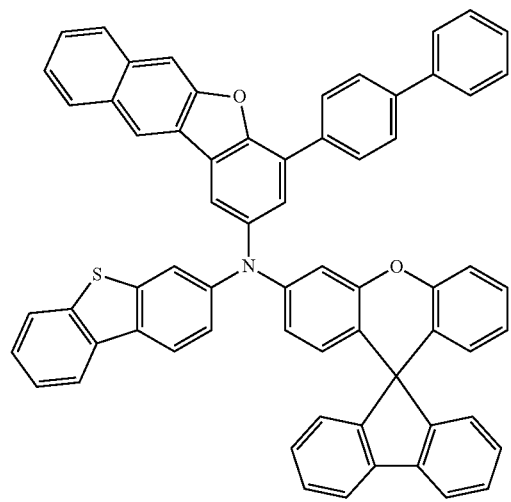

-continued
P-21
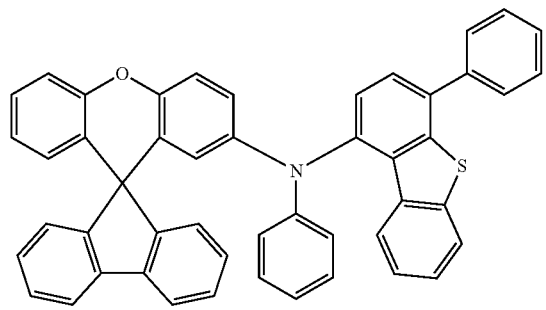
P-22
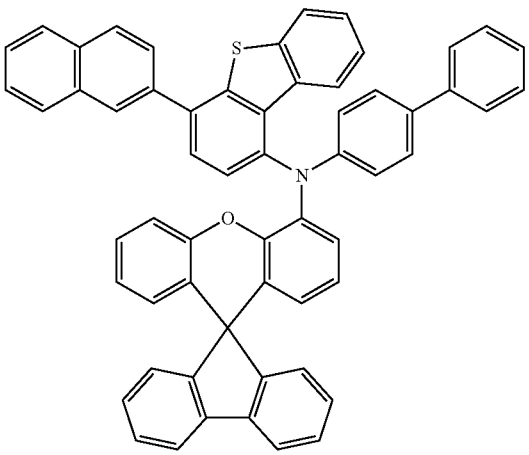
P-23
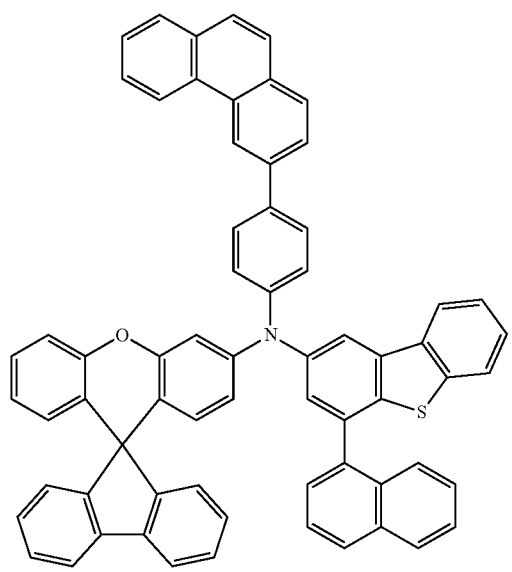
P-24
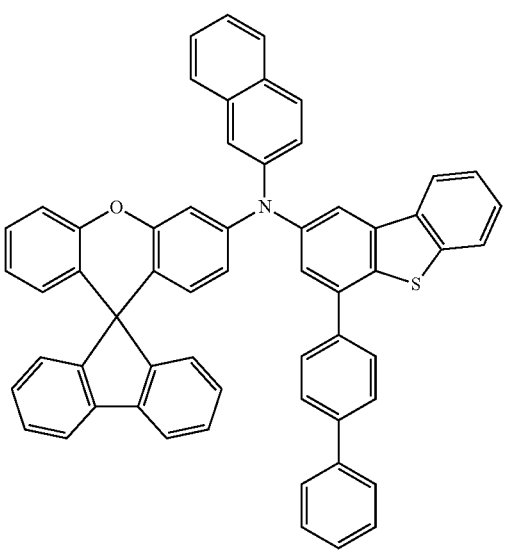
P-25
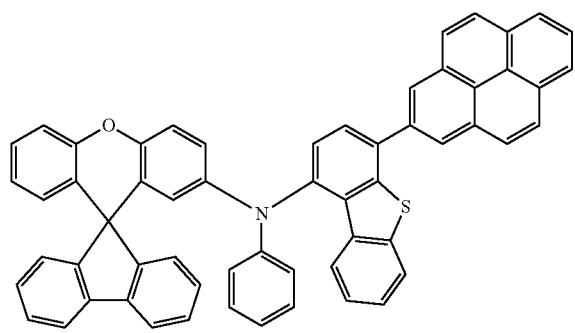
P-26
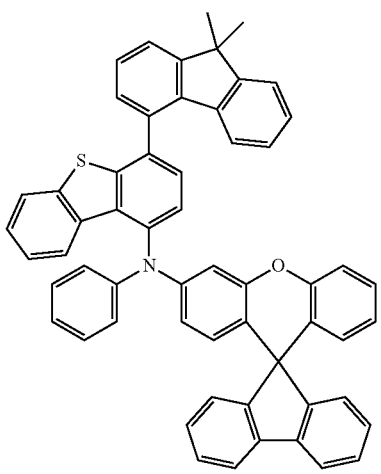

-continued
P-27
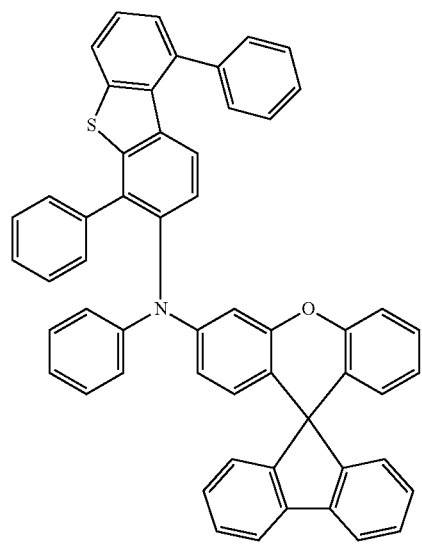
P-28
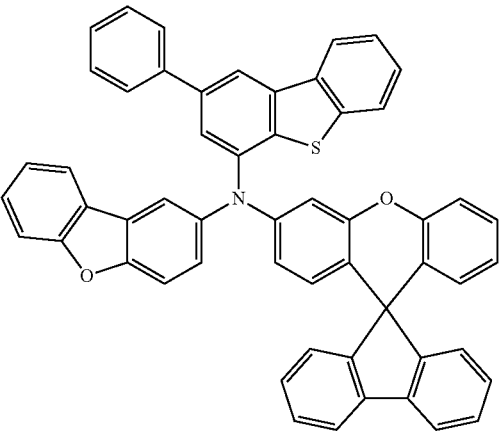
P-29
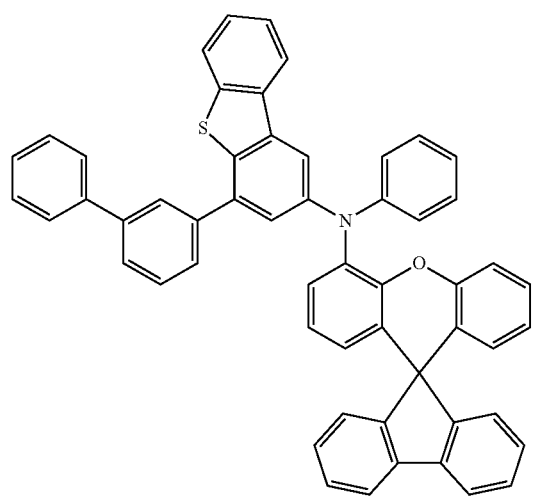
P-30
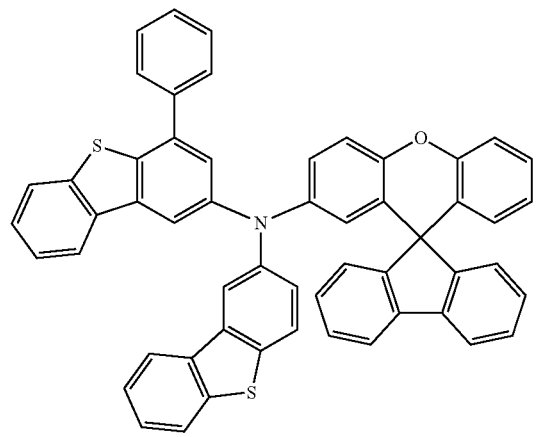
P-31
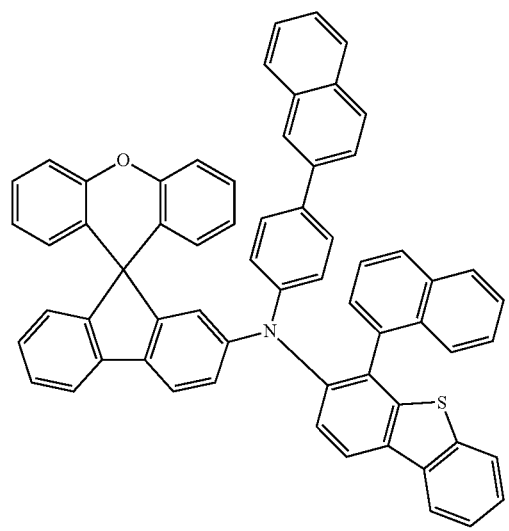
P-32
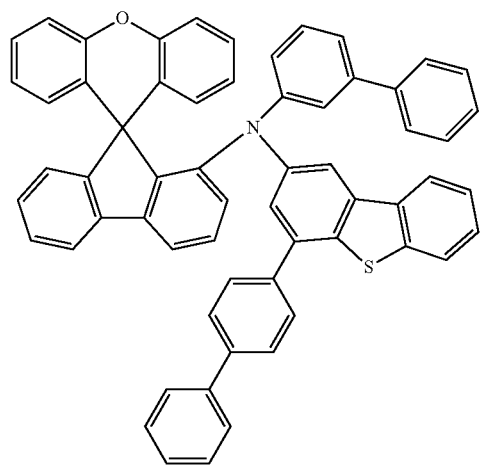

-continued
P-33
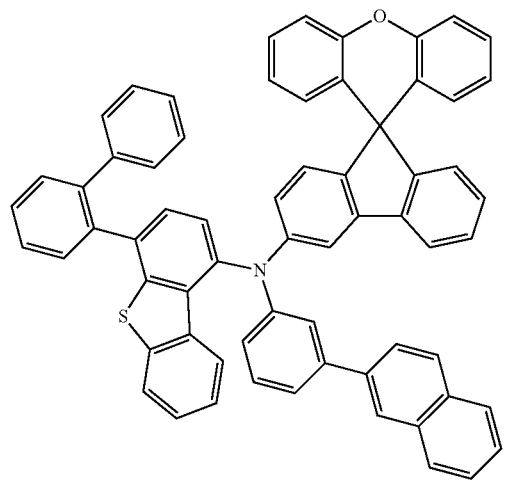
P-34
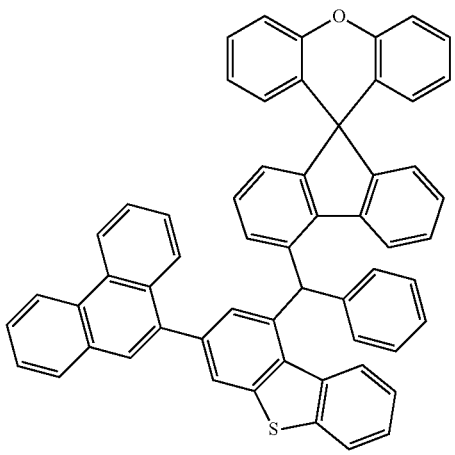
P-35
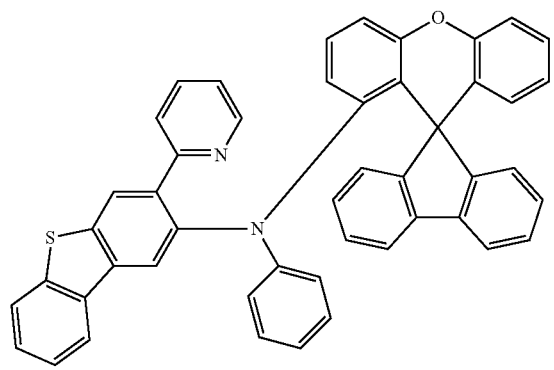
P-36
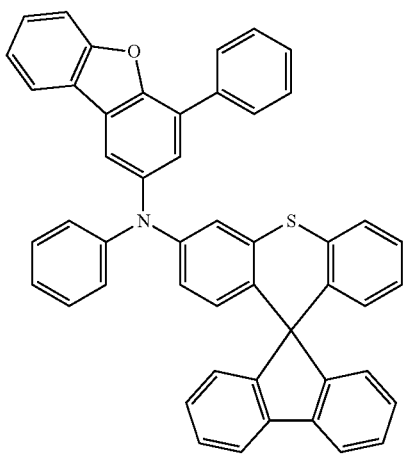
P-37
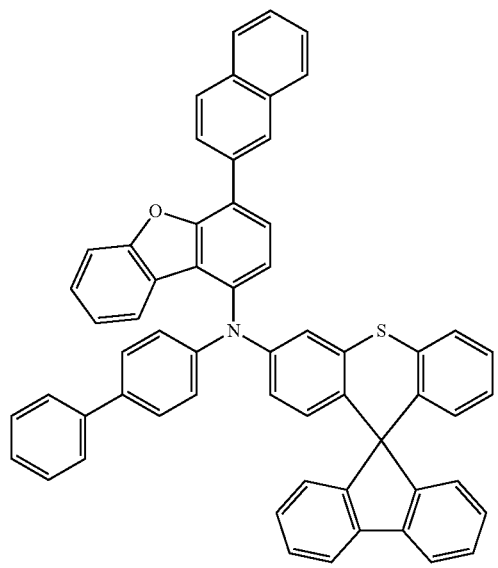
P-38
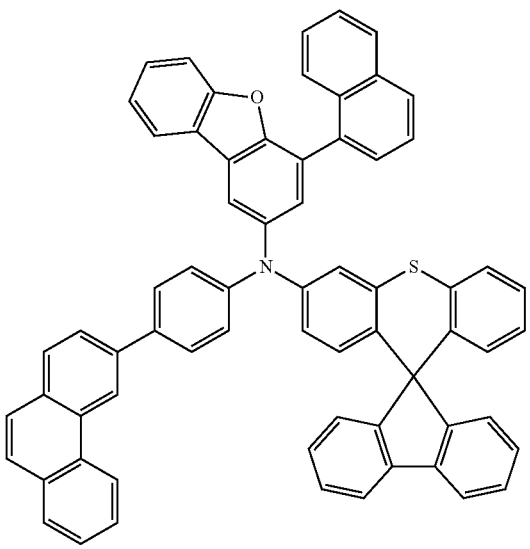

-continued
P-39
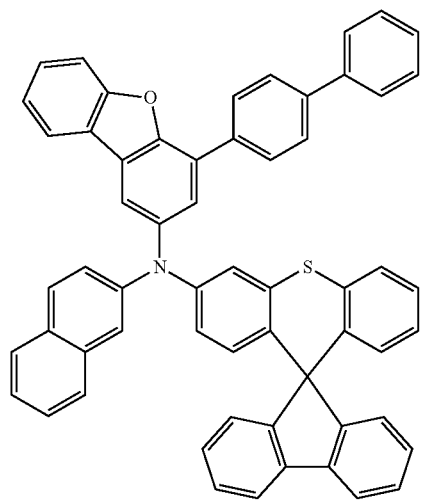
P-40
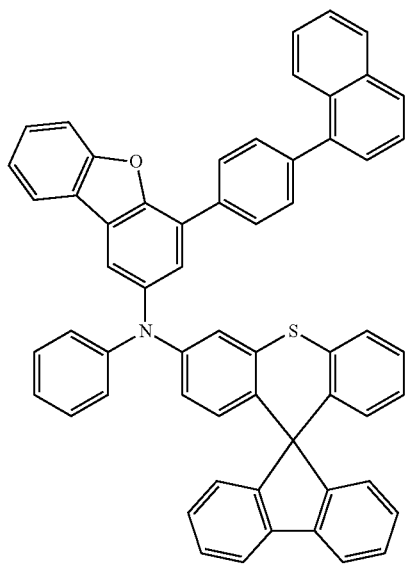
P-41
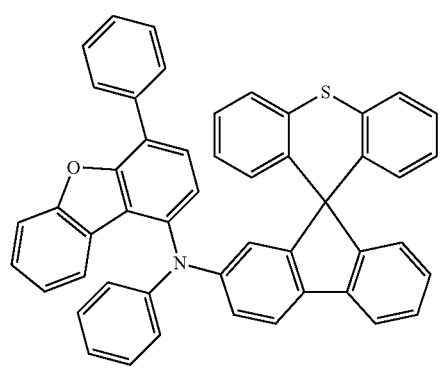
P-42
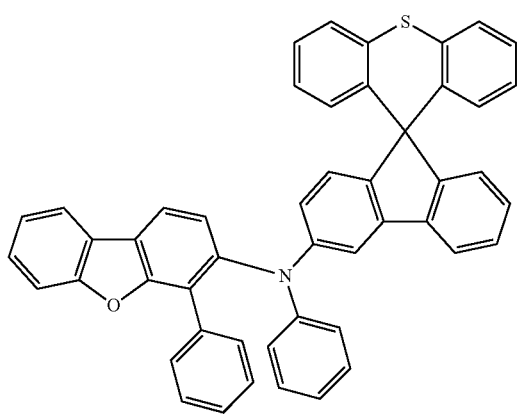
P-43
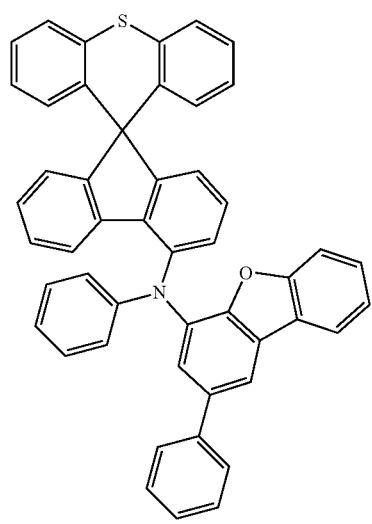
P-44
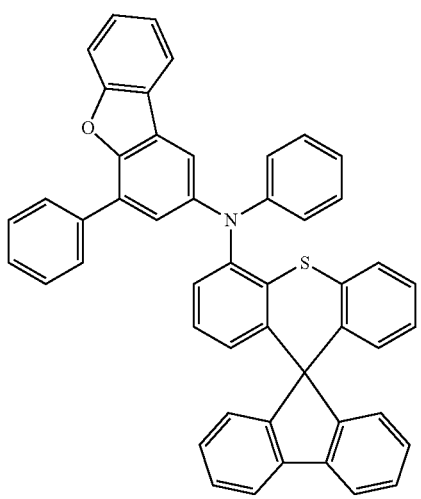

-continued
P-45
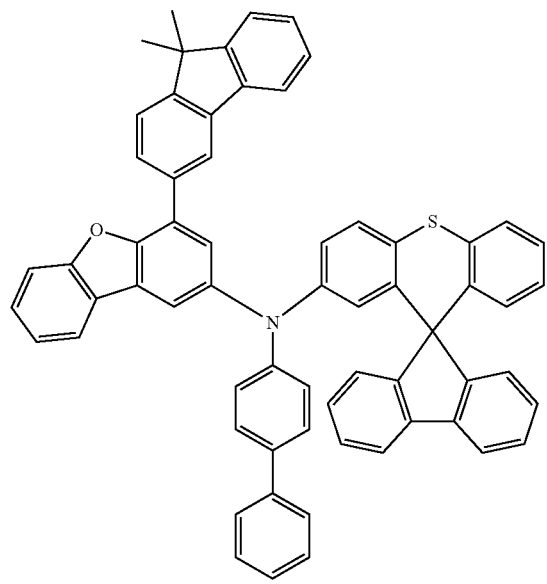
P-46
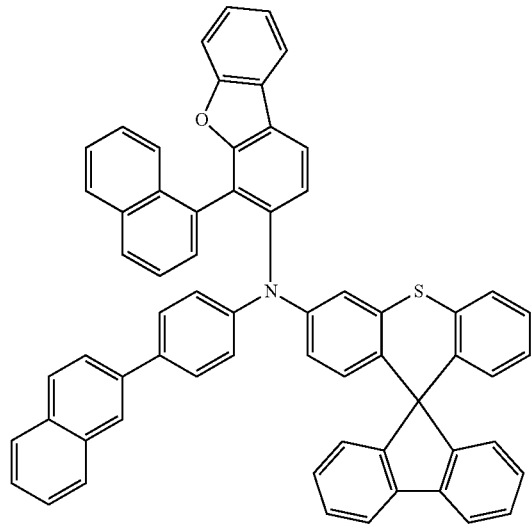
P-47
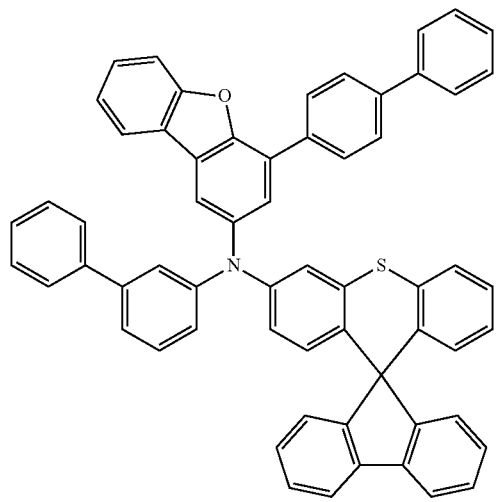
P-48
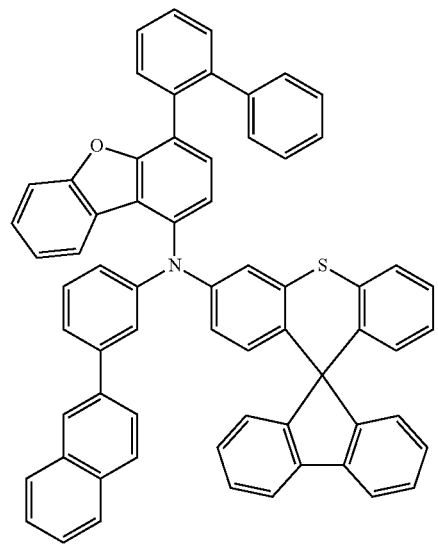

-continued
P-49
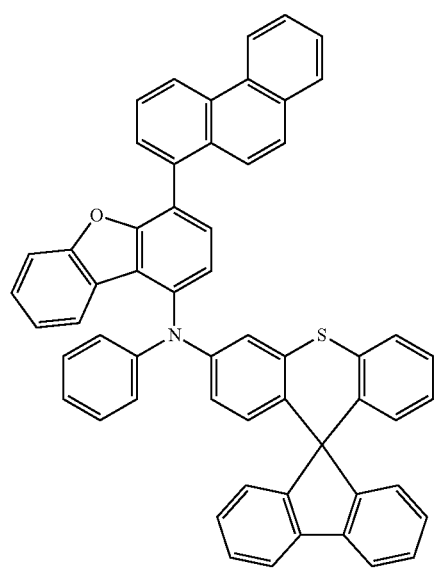
P-50
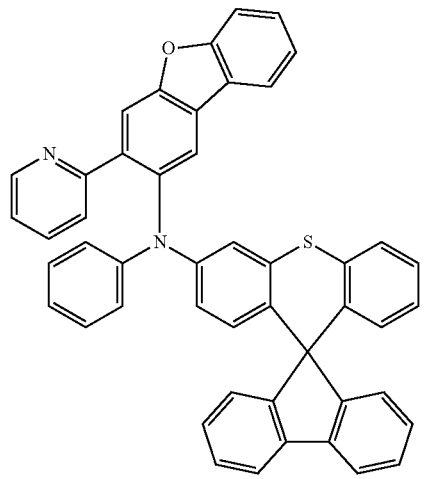
P-51
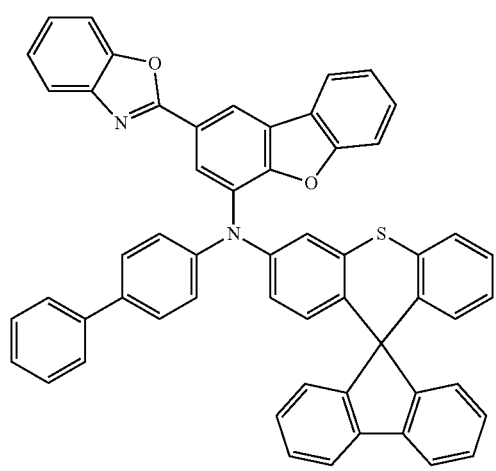
P-52
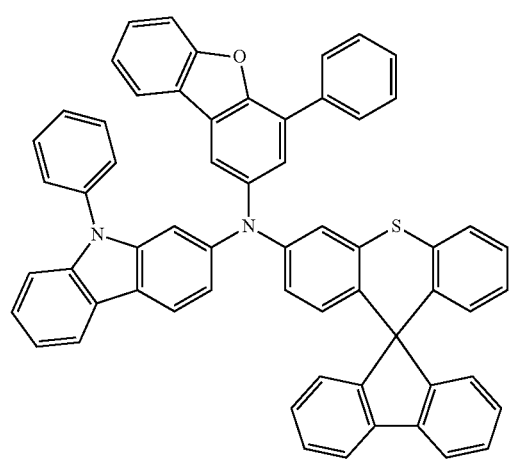
P-53
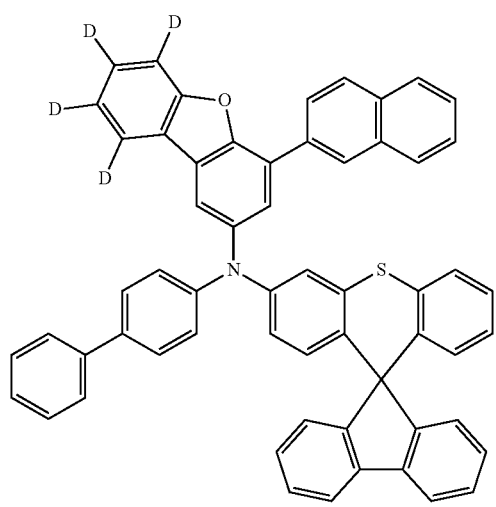
P-54
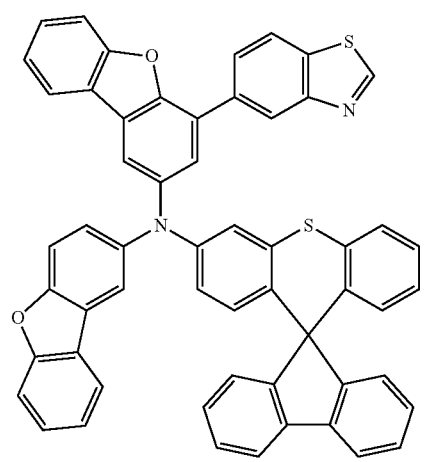

-continued
P-55
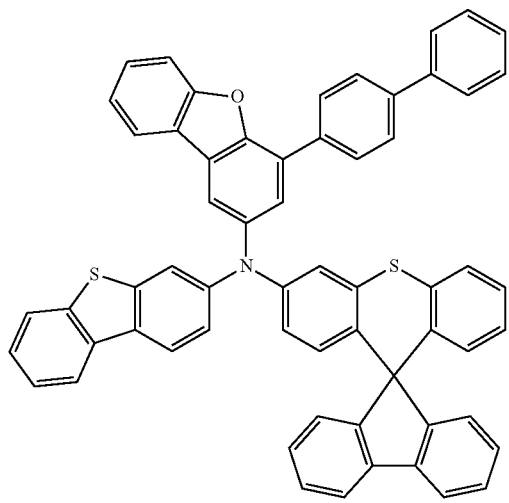
P-56
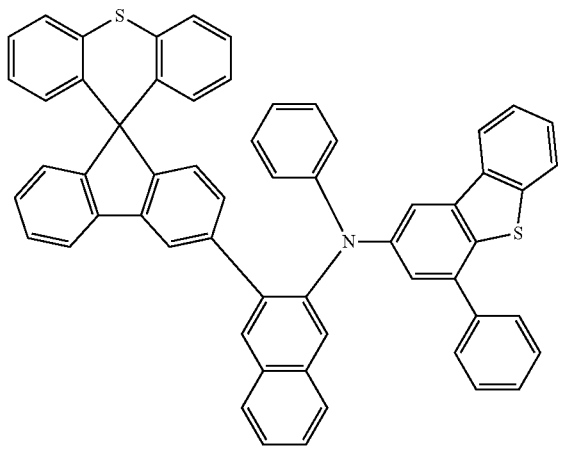
P-57
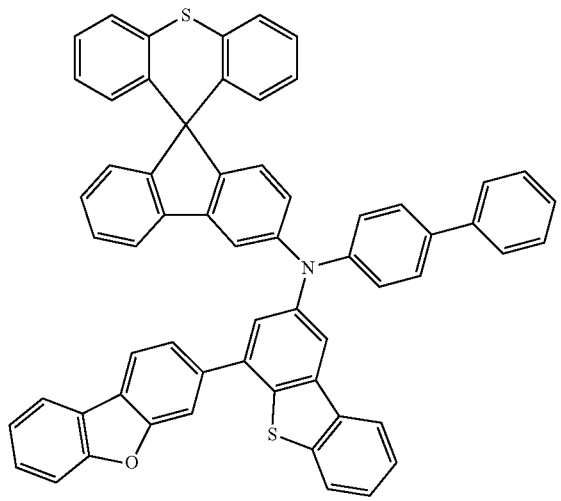
P-58
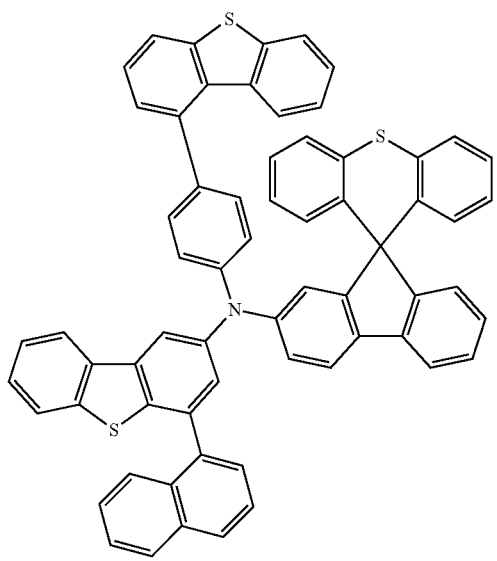
P-59
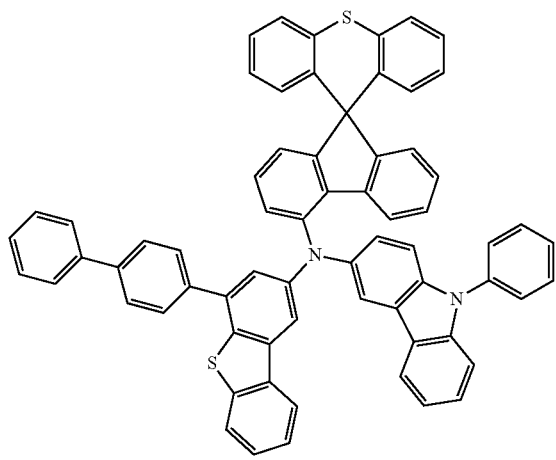
P-60
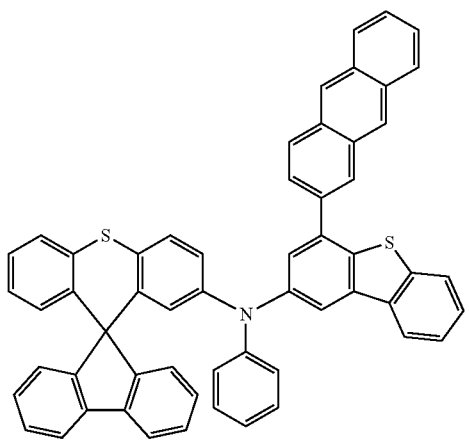

-continued
P-61
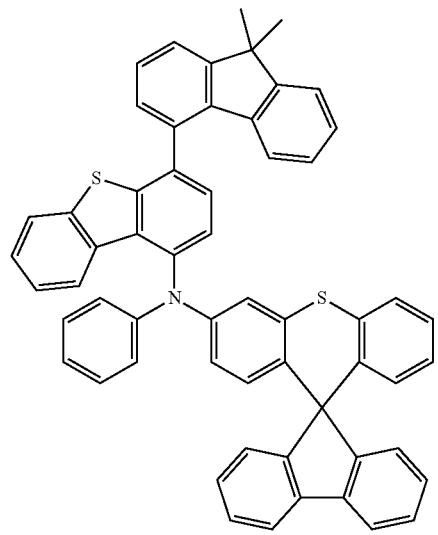
P-62
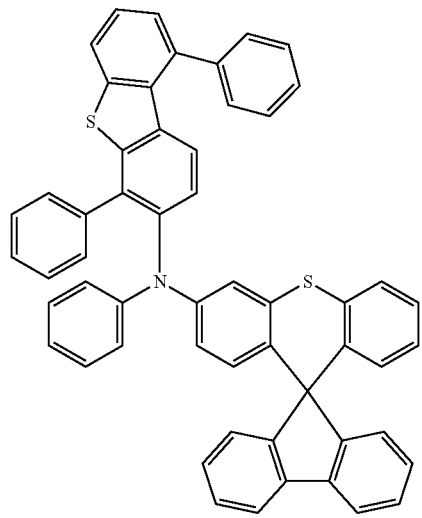
P-63
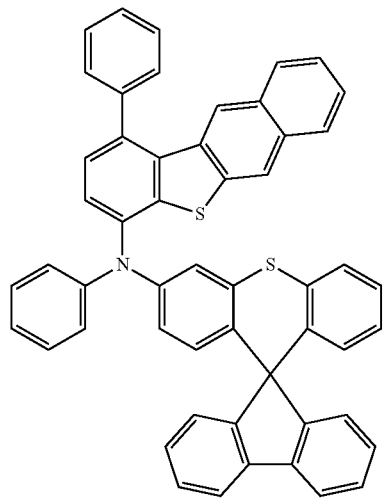
P-64
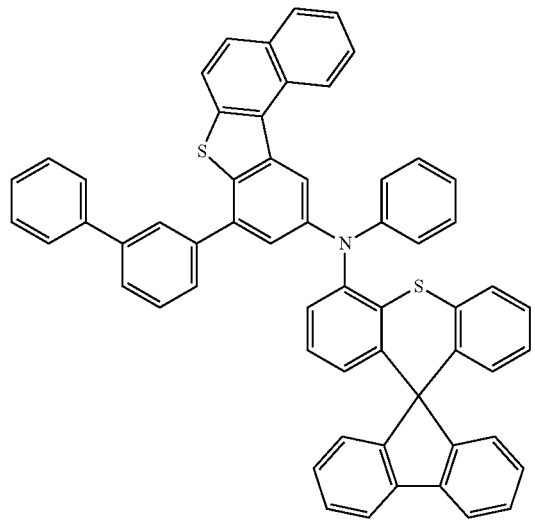
P-65
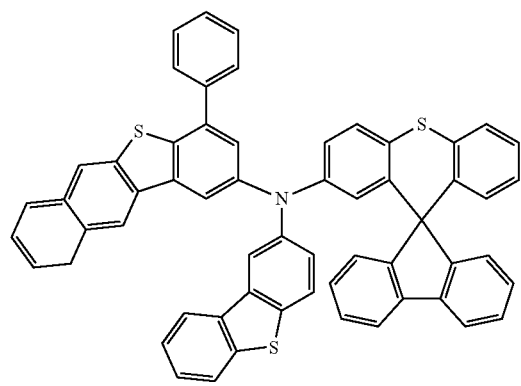
P-66
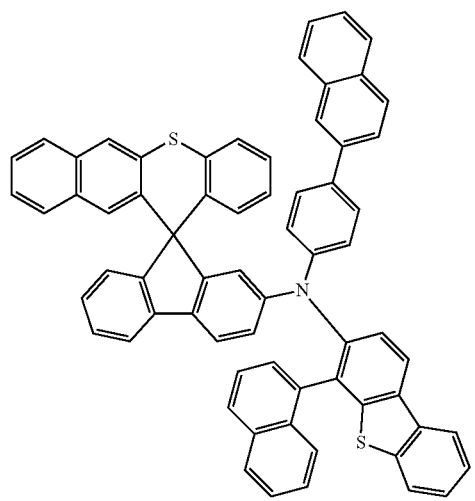

-continued
P-67
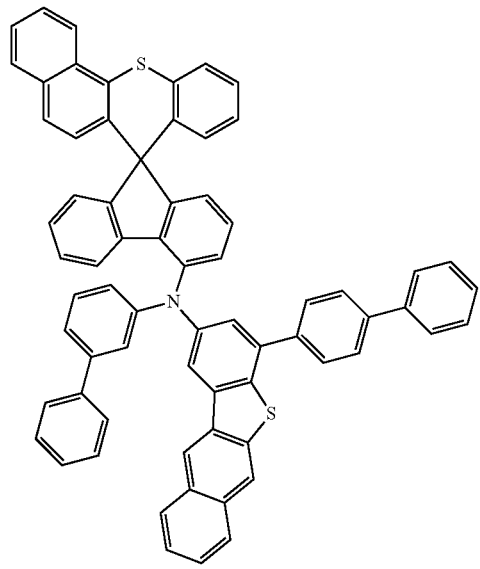
P-68
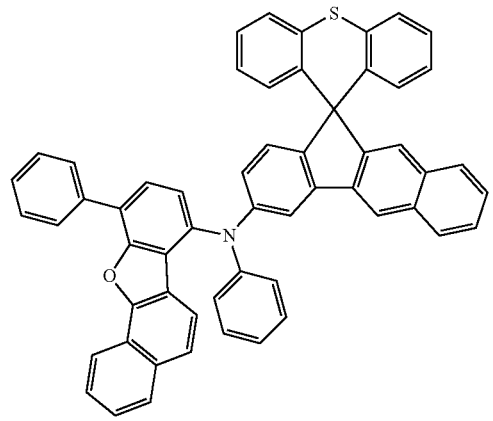
P-69
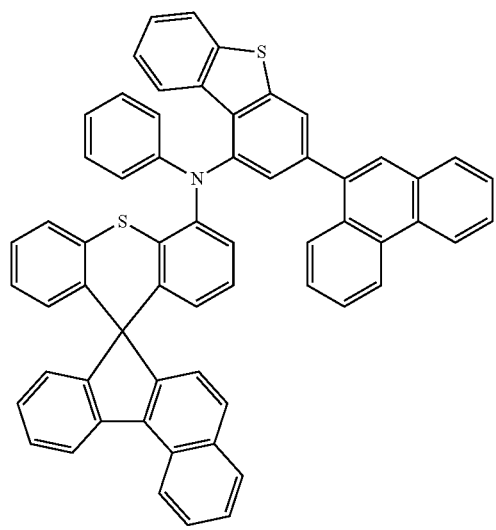
P-70
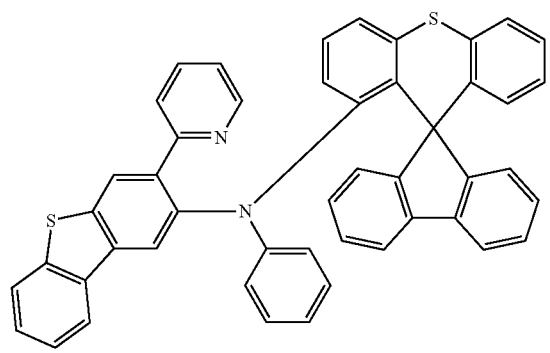
P-71
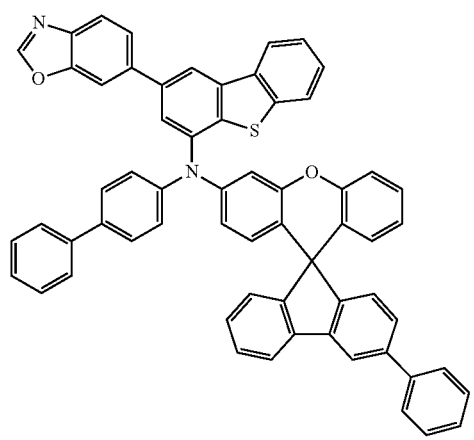
P-72
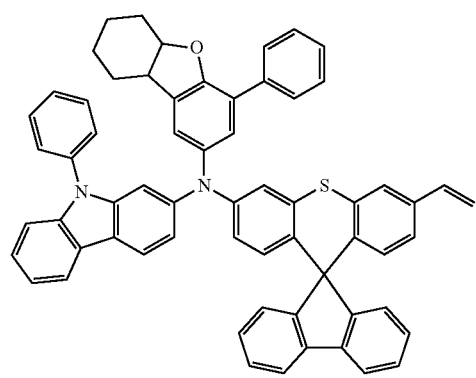

-continued
P-73
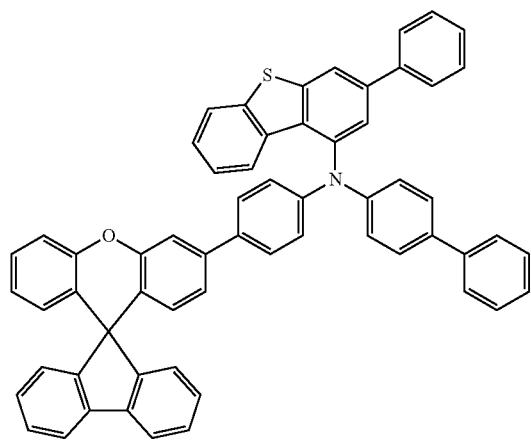
P-74
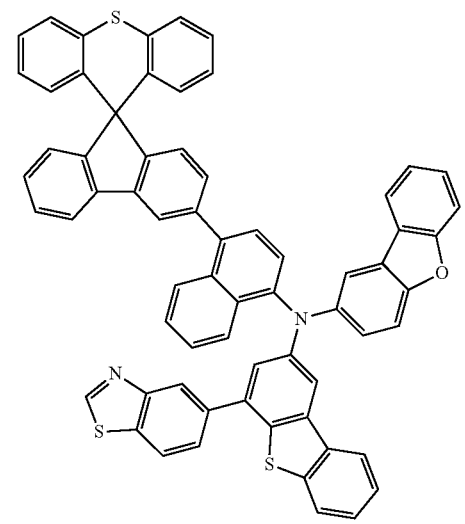
P-75
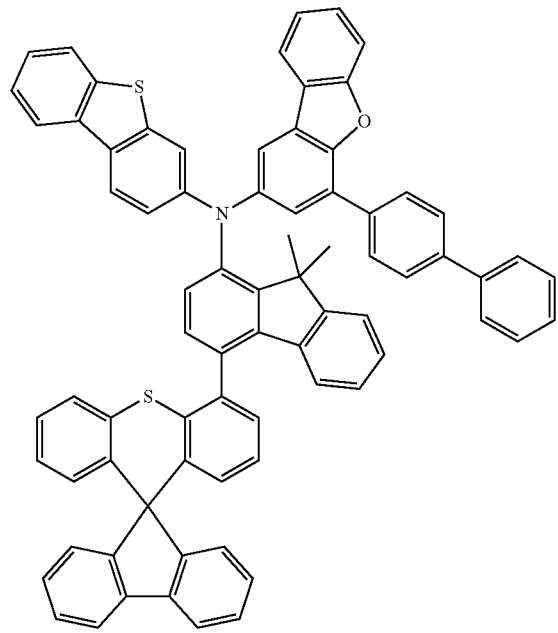
P-76
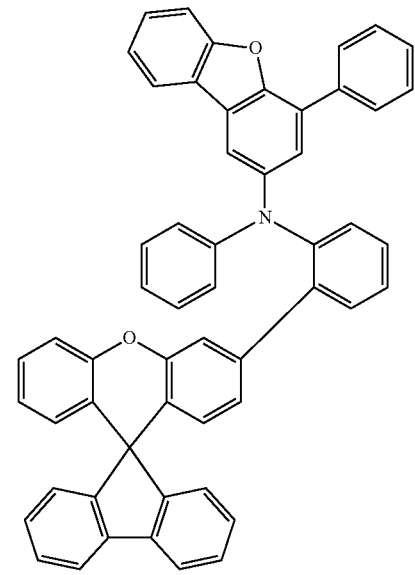
P-77
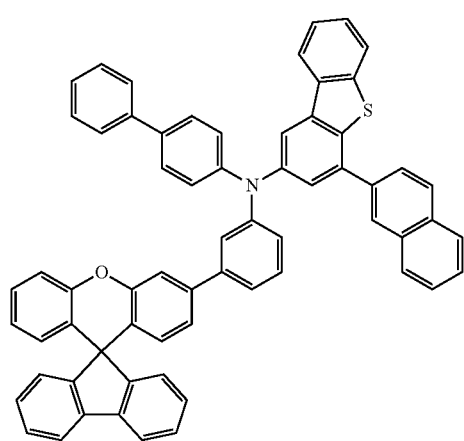
P-78
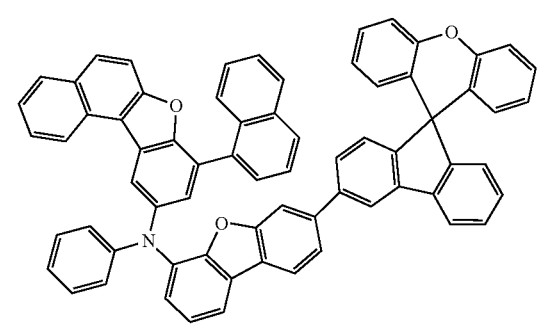

-continued
P-79
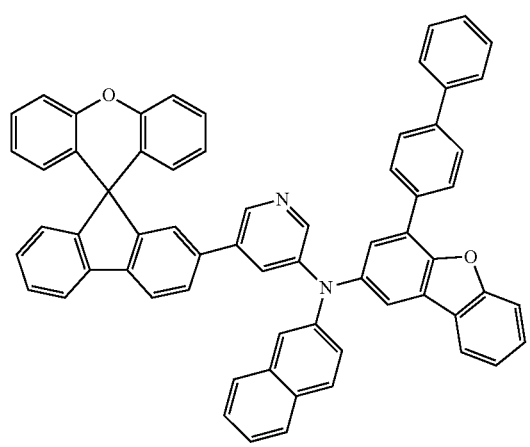
P-80
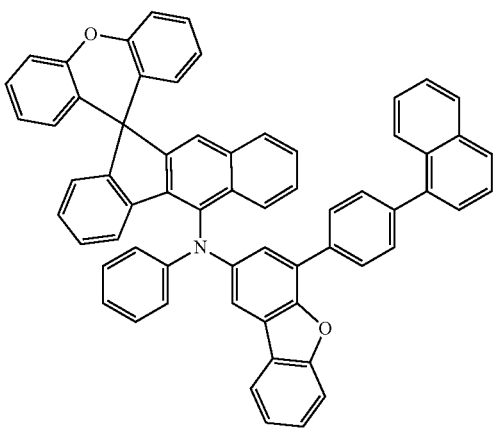
P-81
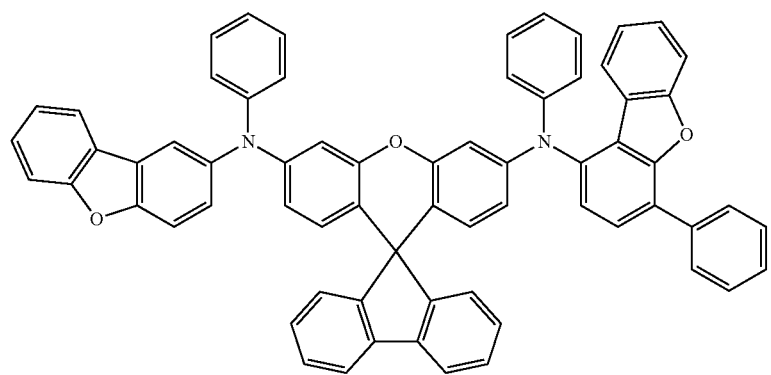
P-82
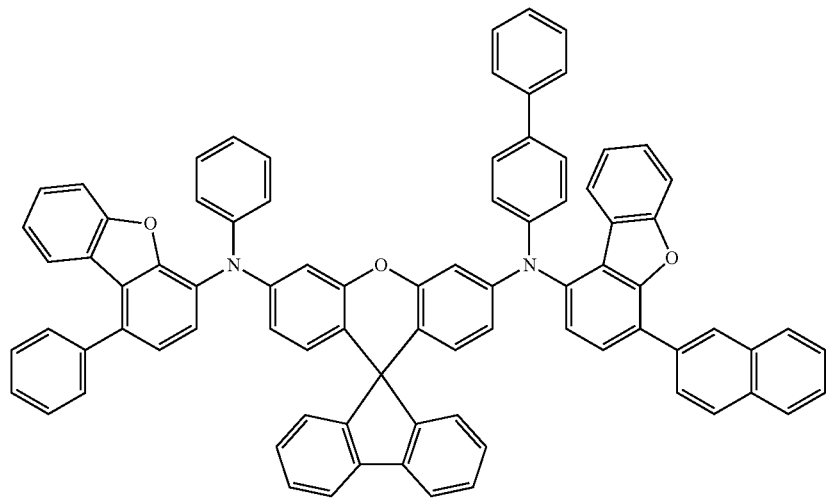

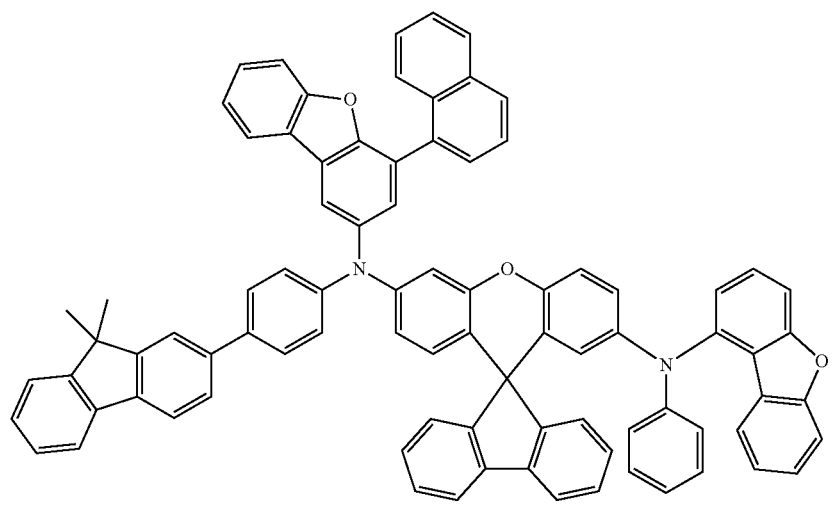
P-83
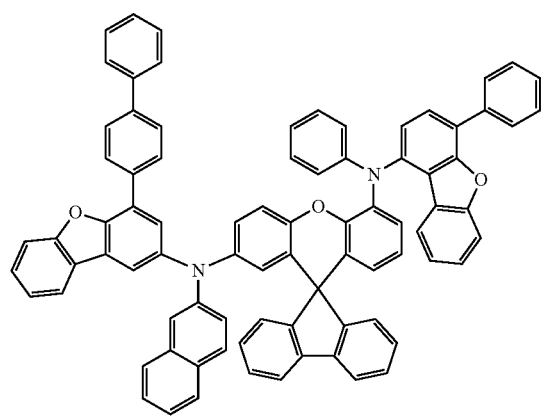
P-84
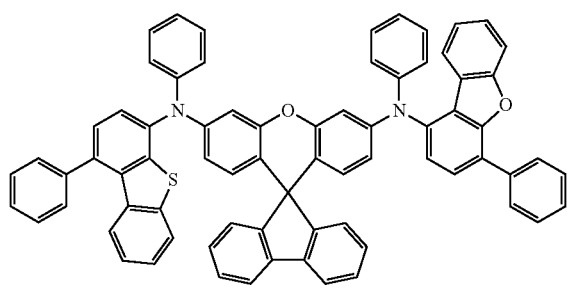
P-85
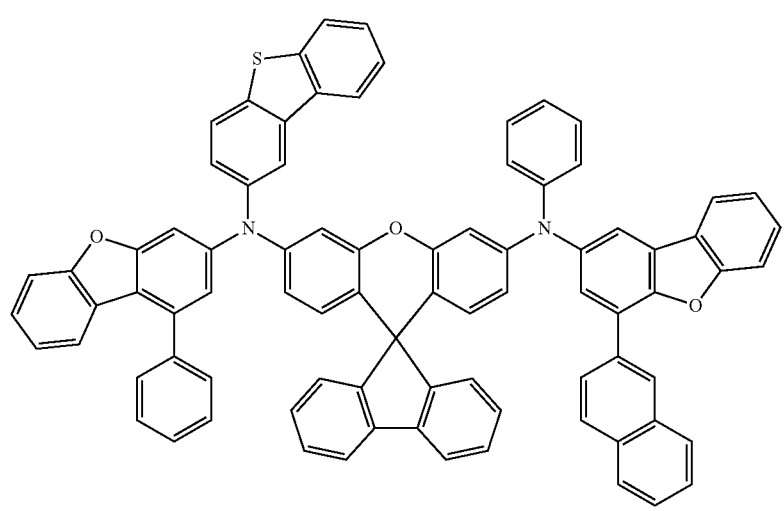
P-86

P-87
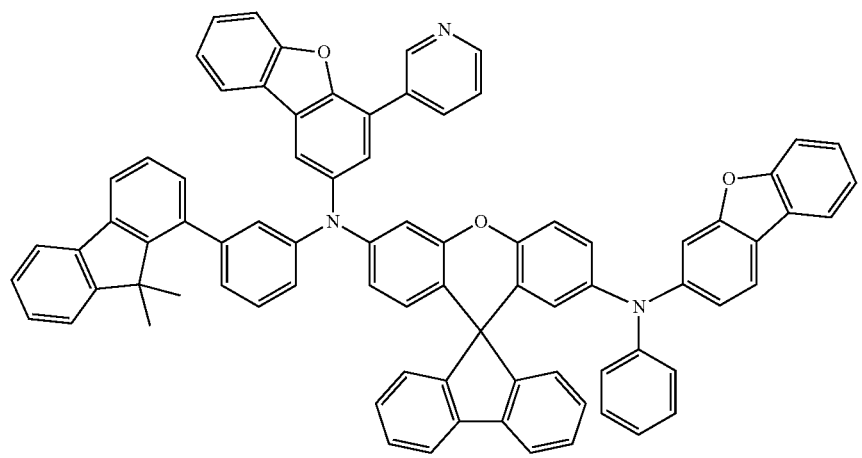
P-88
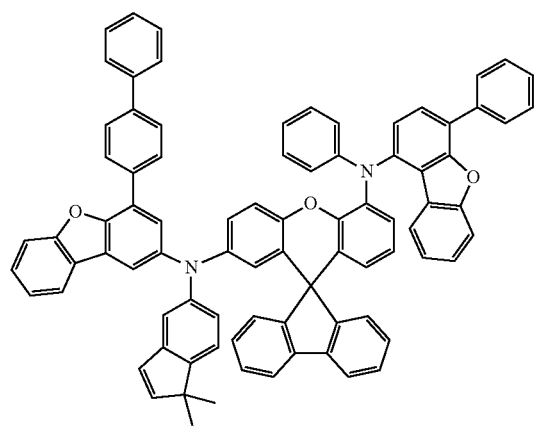
P-89
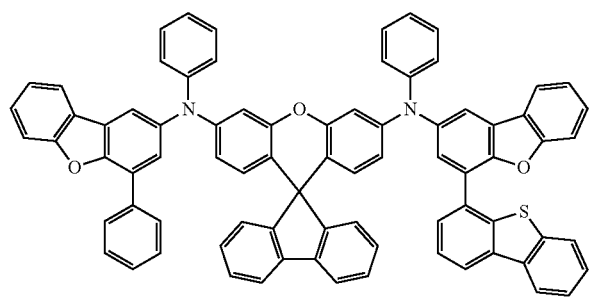
P-90
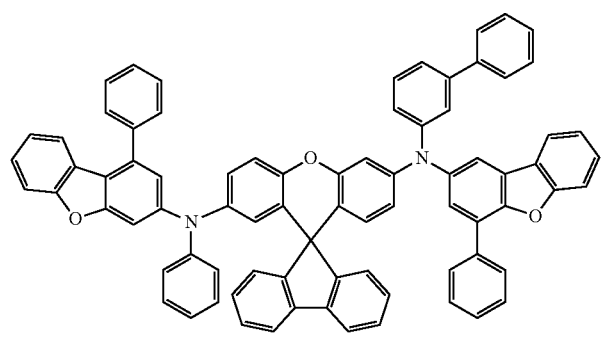
P-91
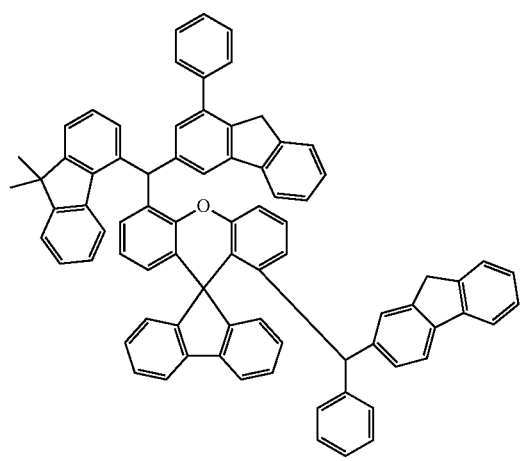

-continued
P-92
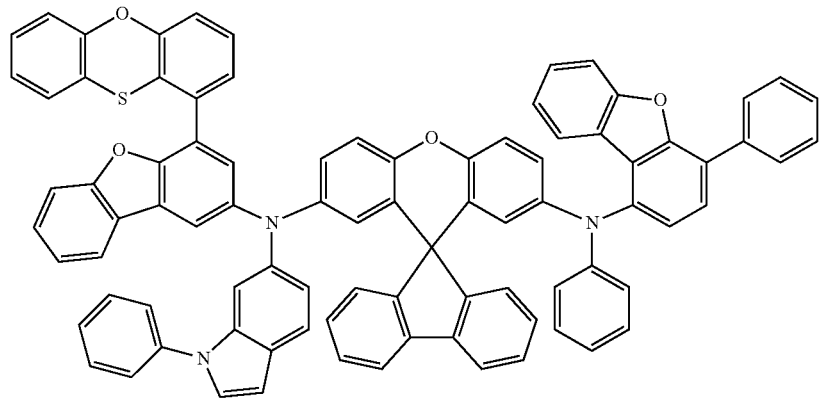
P-93
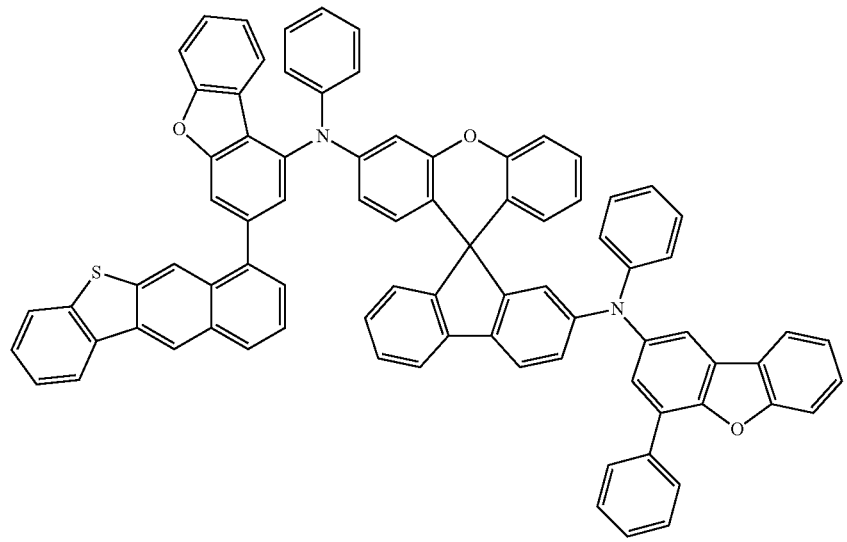
P-94
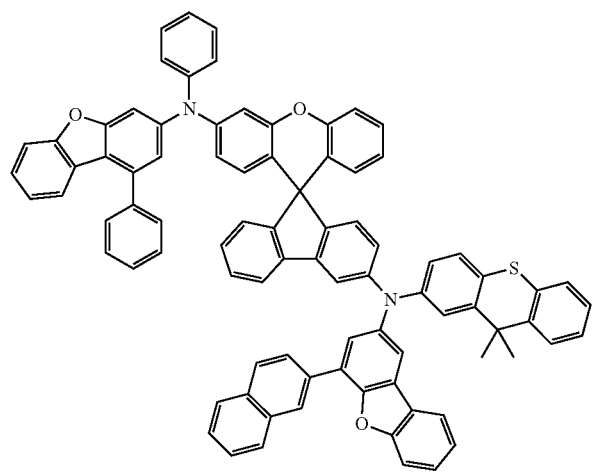
P-95
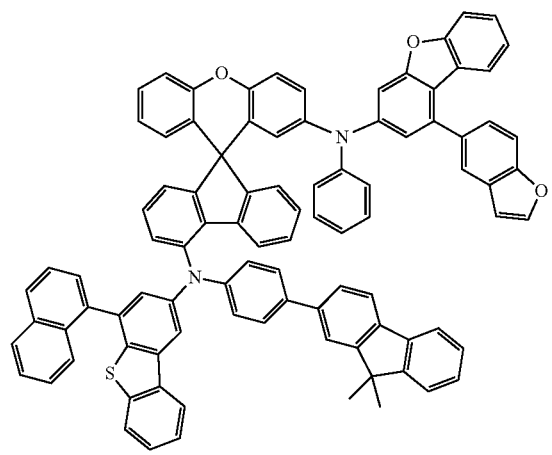

-continued
P-96
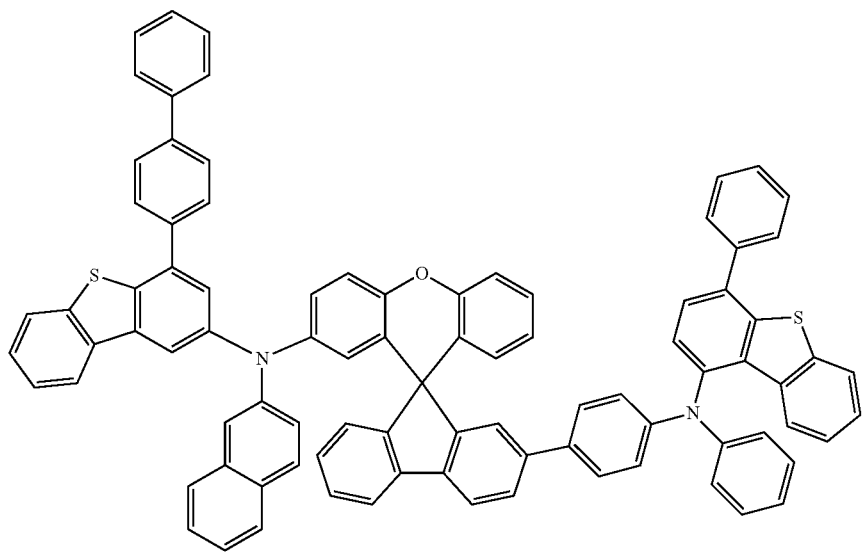
P-97
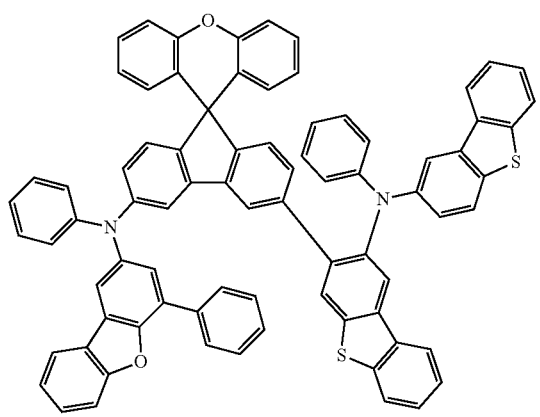
P-98
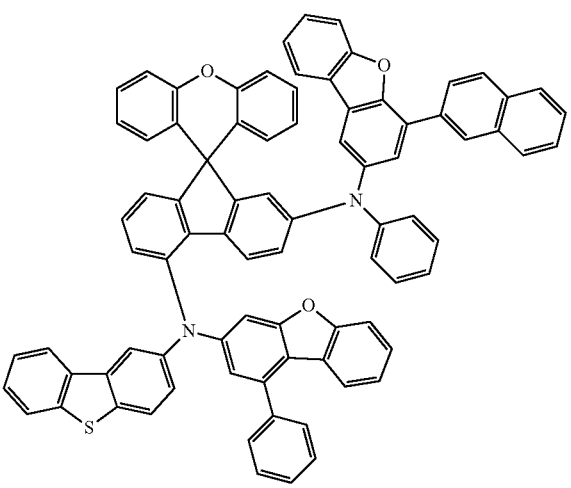
P-99
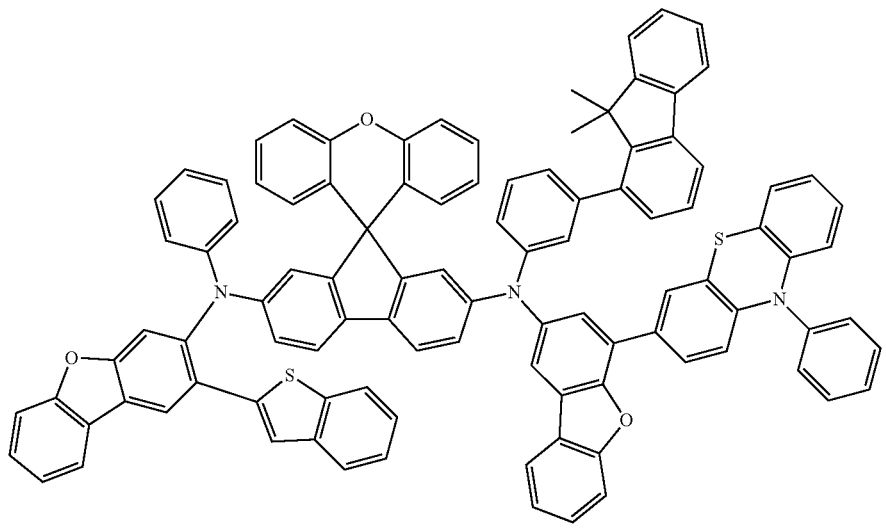

-continued
P-100
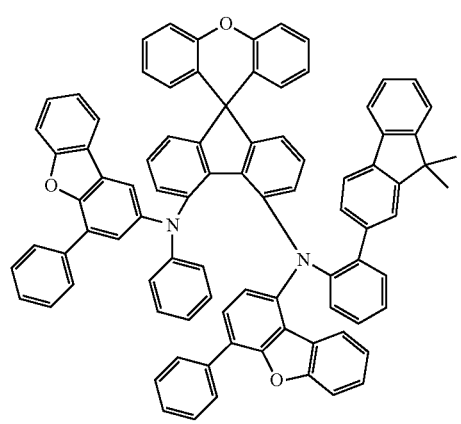
P-101
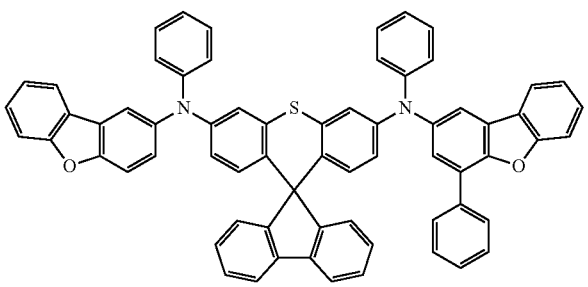
P-102
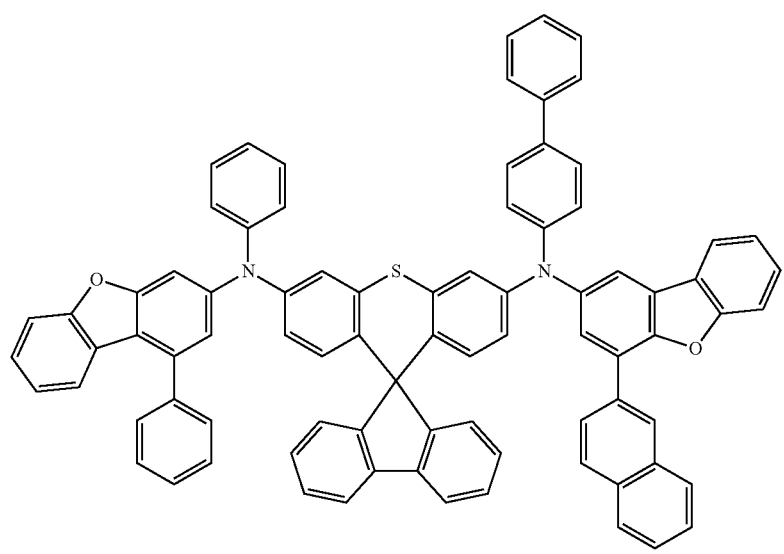
P-103
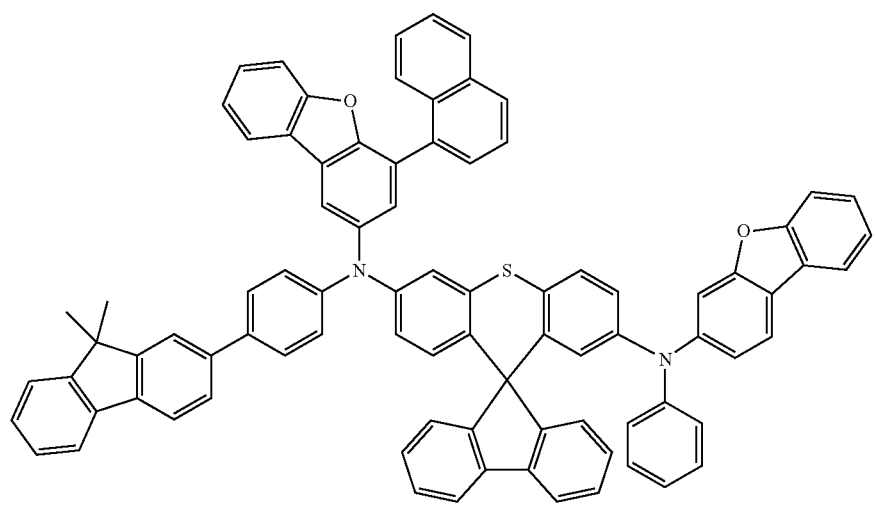

-continued
P-104
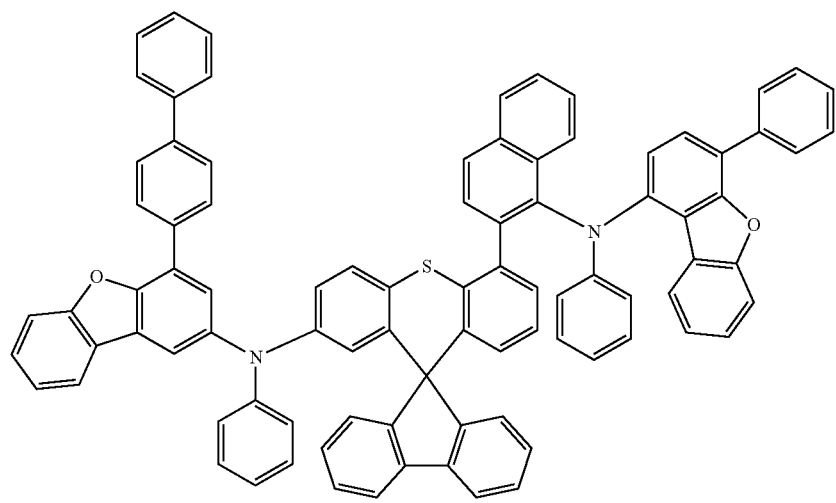
P-105
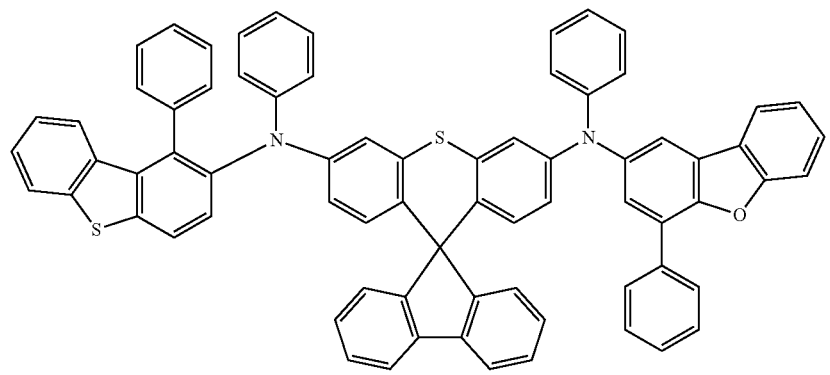
P-106
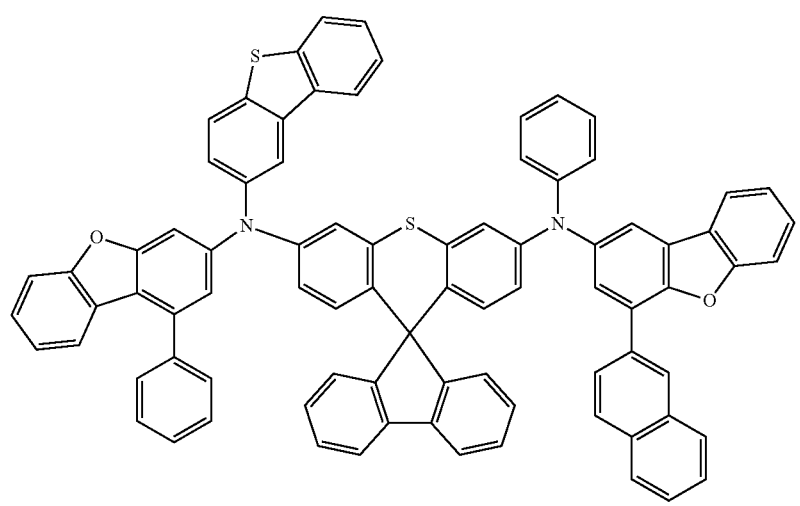

P-107
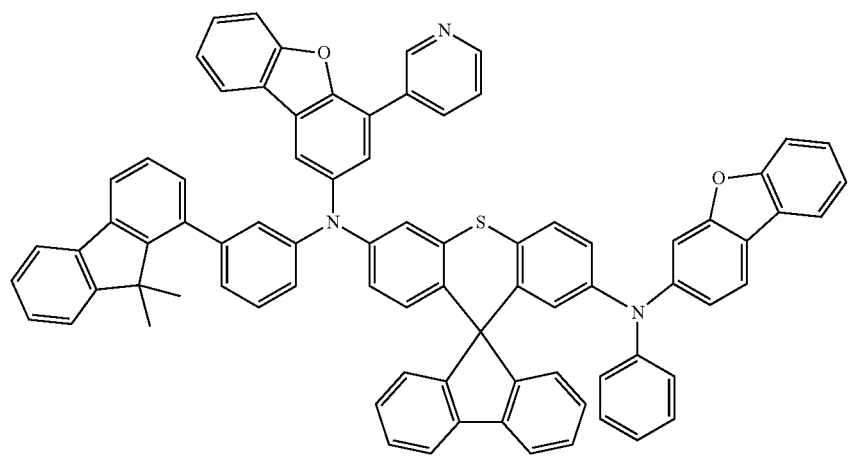
P-108
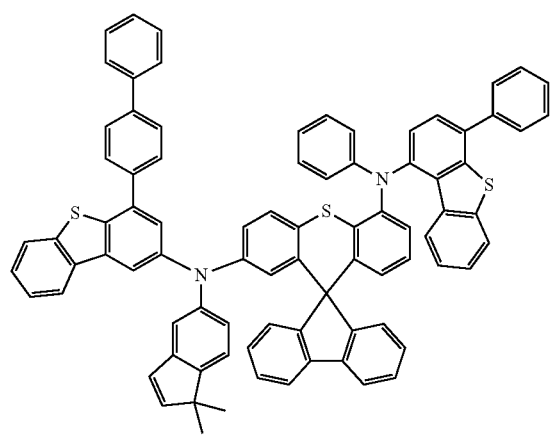
P-109
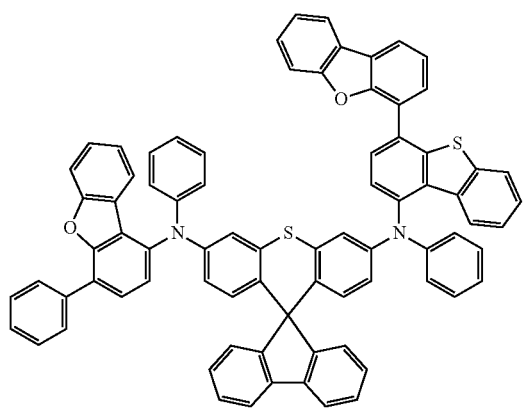
P-110
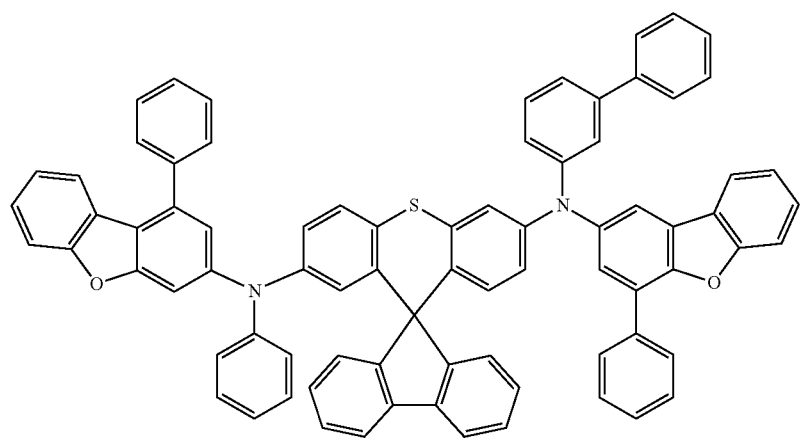

P-111
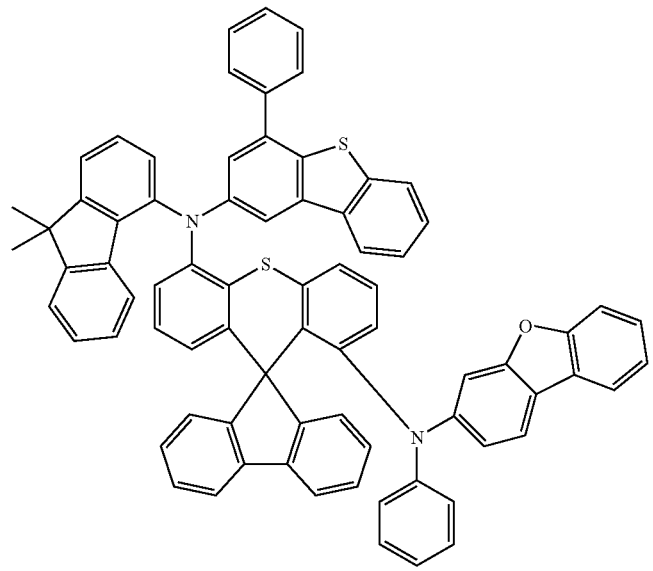
P-112
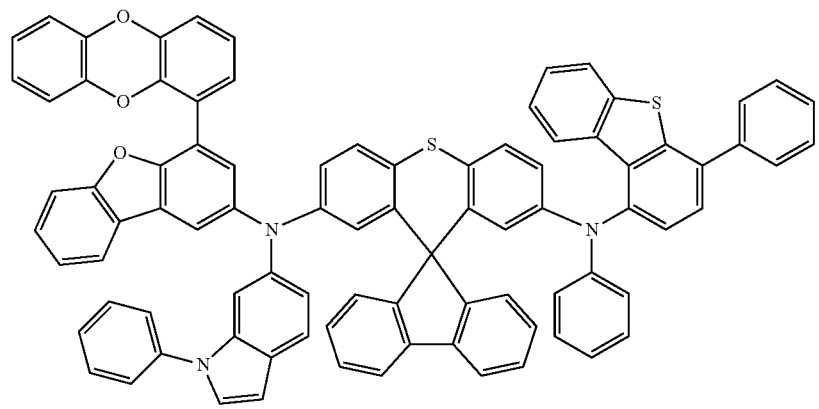
P-113
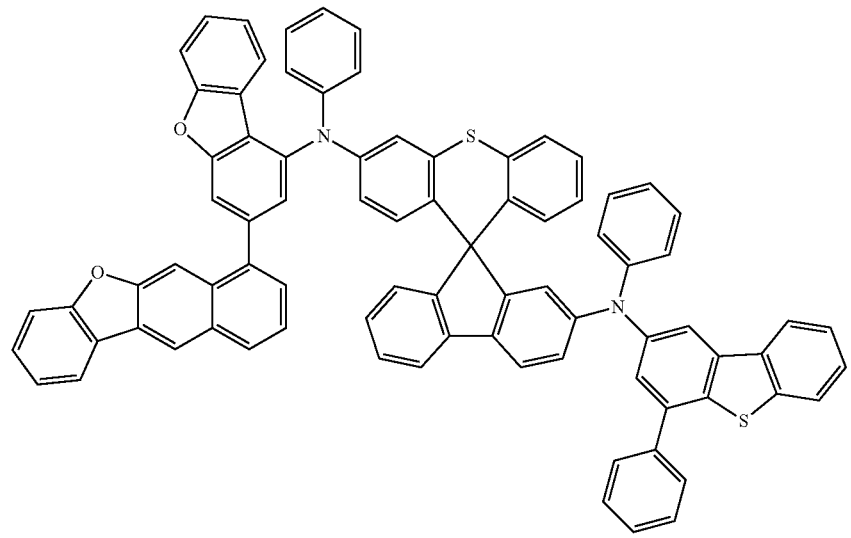

P-114
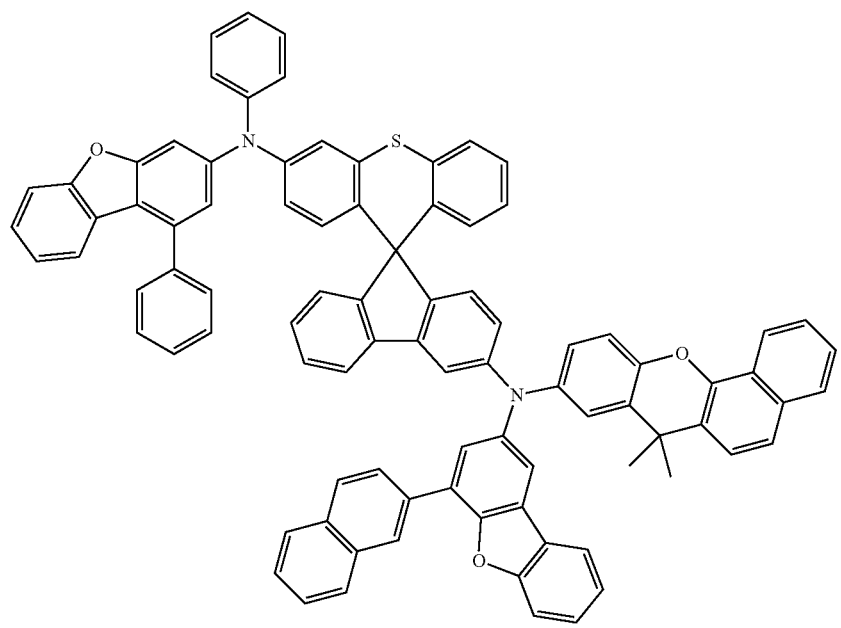
P-115
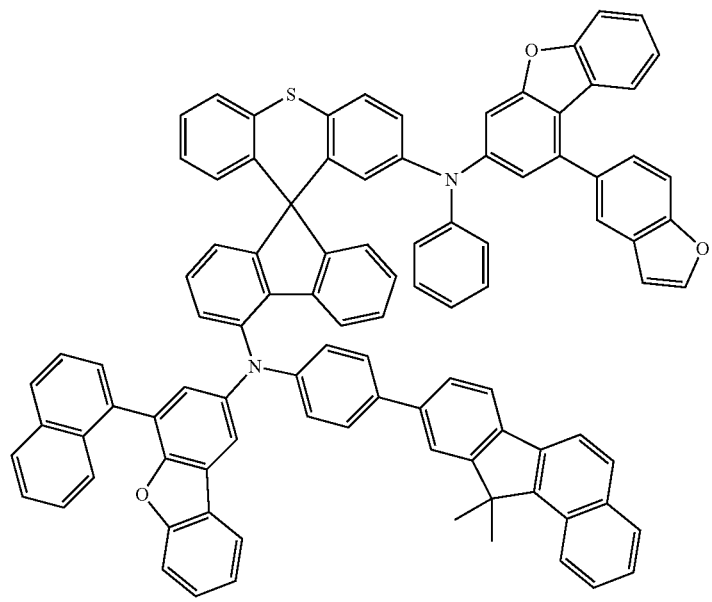
P-116
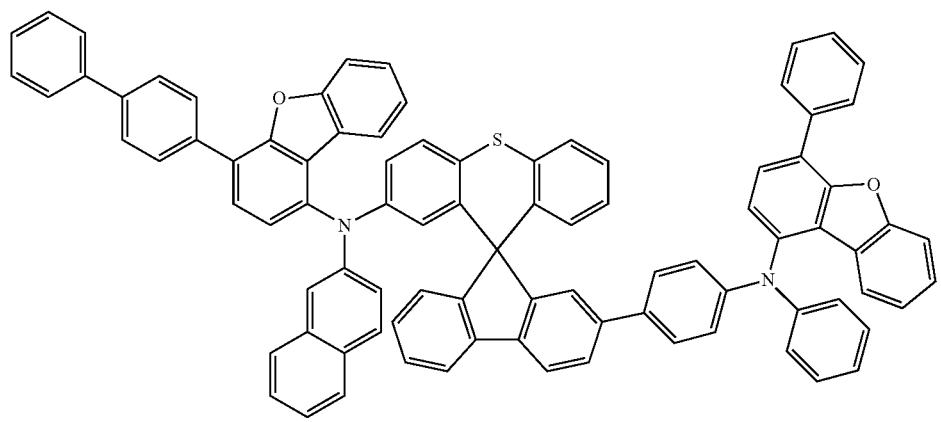

-continued
P-117
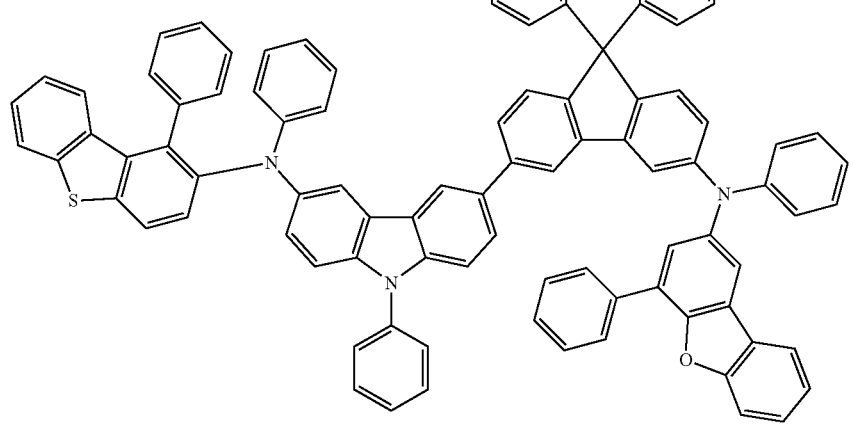
P-118
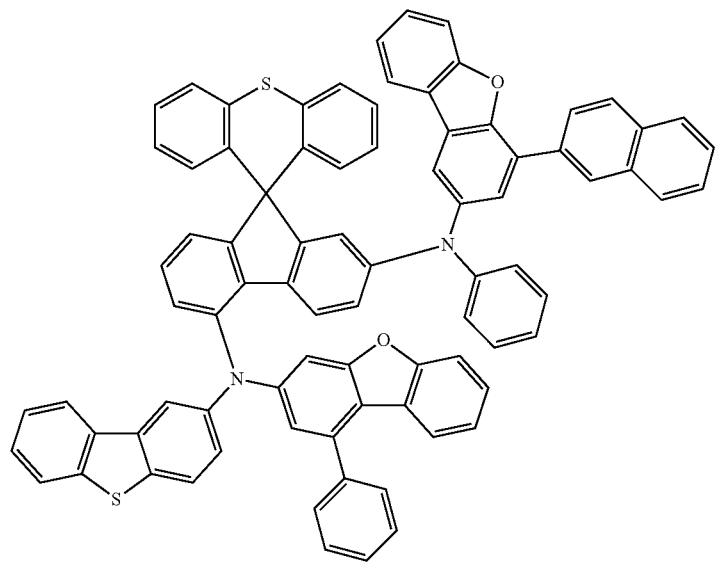
P-119
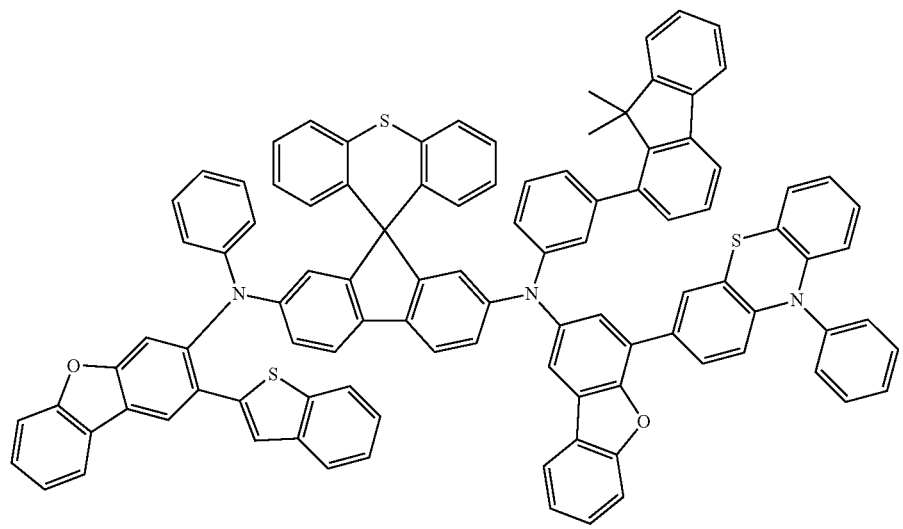

-continued
P-120
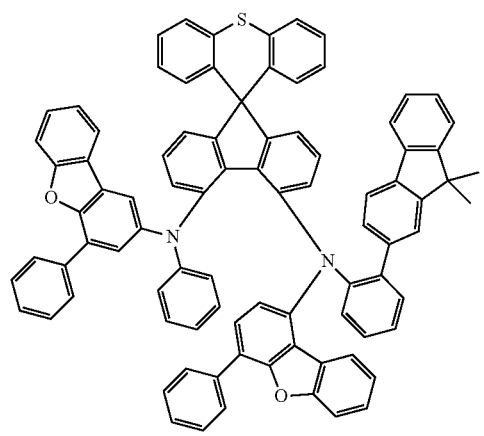
P-121
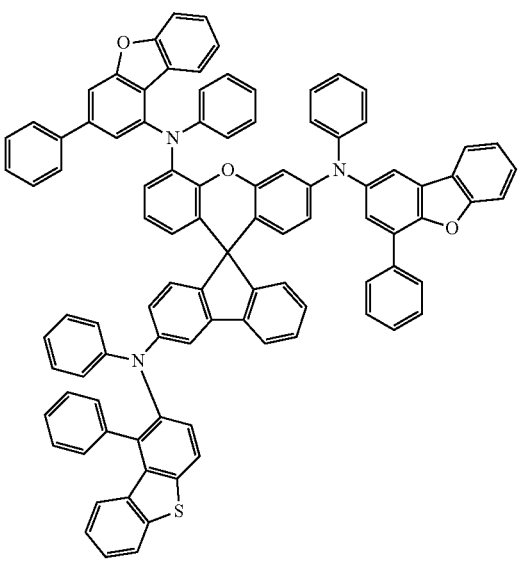
P-122
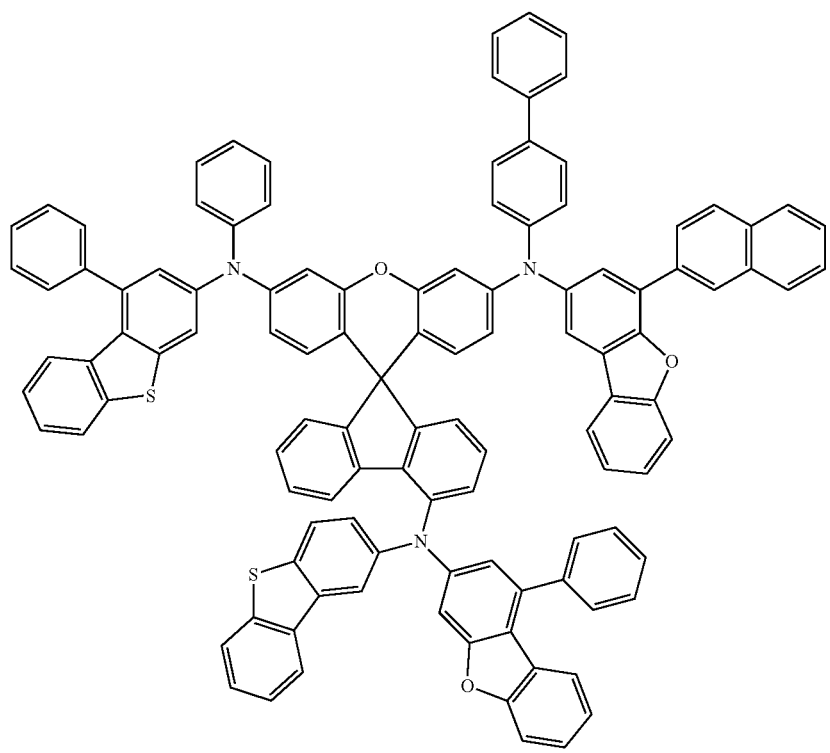

-continued
P-123
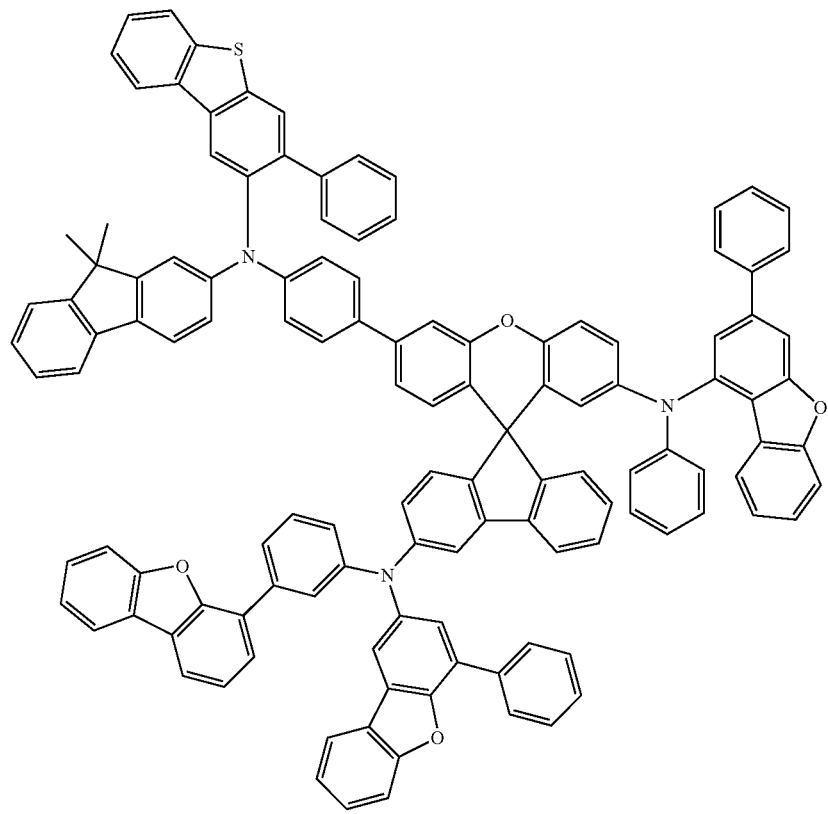
P-124
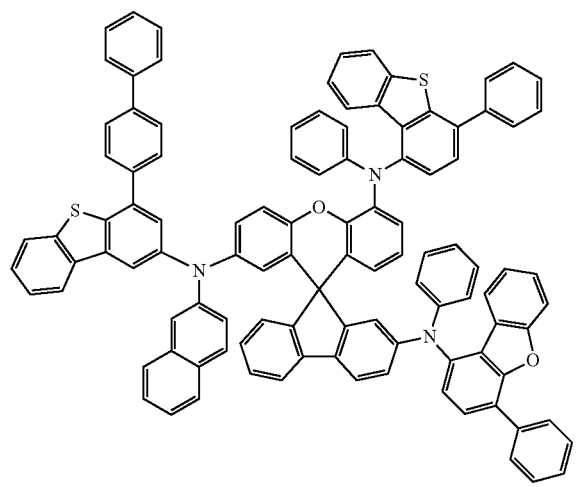
P-125
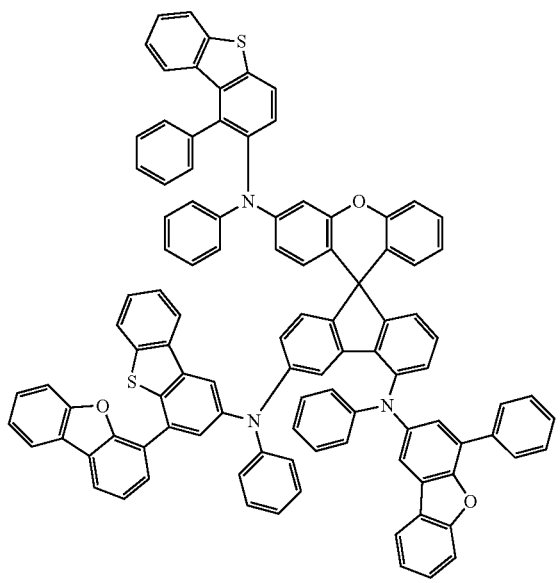

-continued
P-126
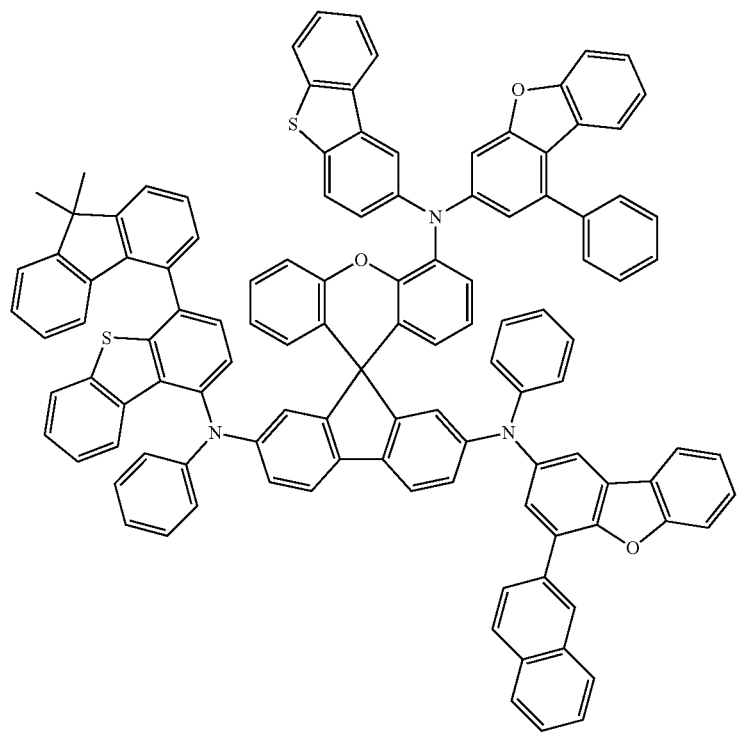
P-127
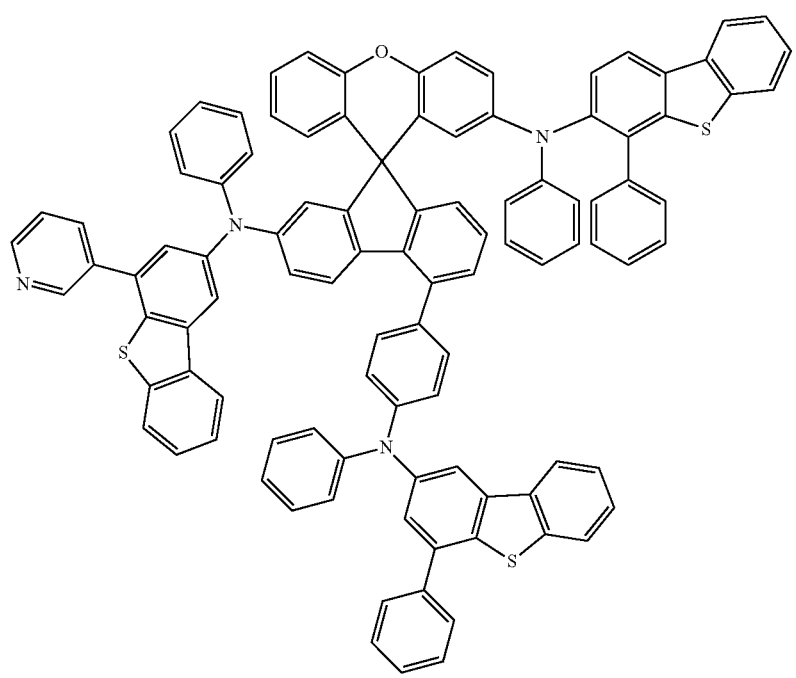

P-128
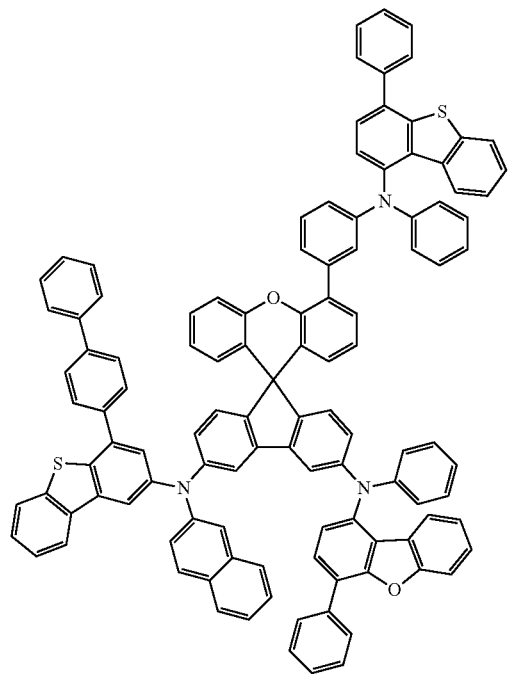
P-129
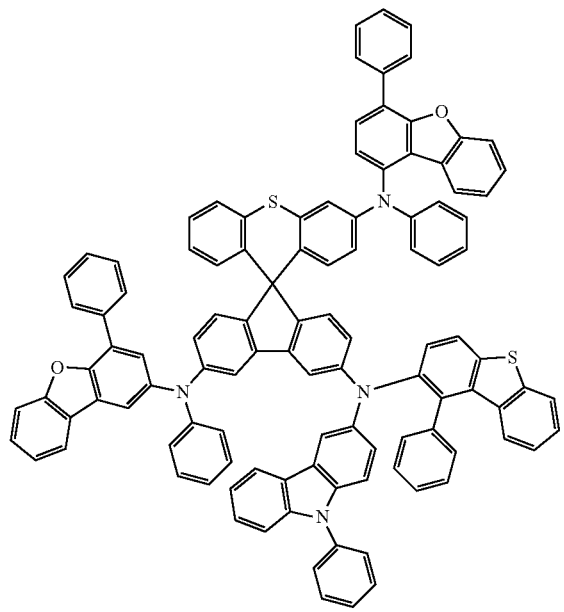
P-130
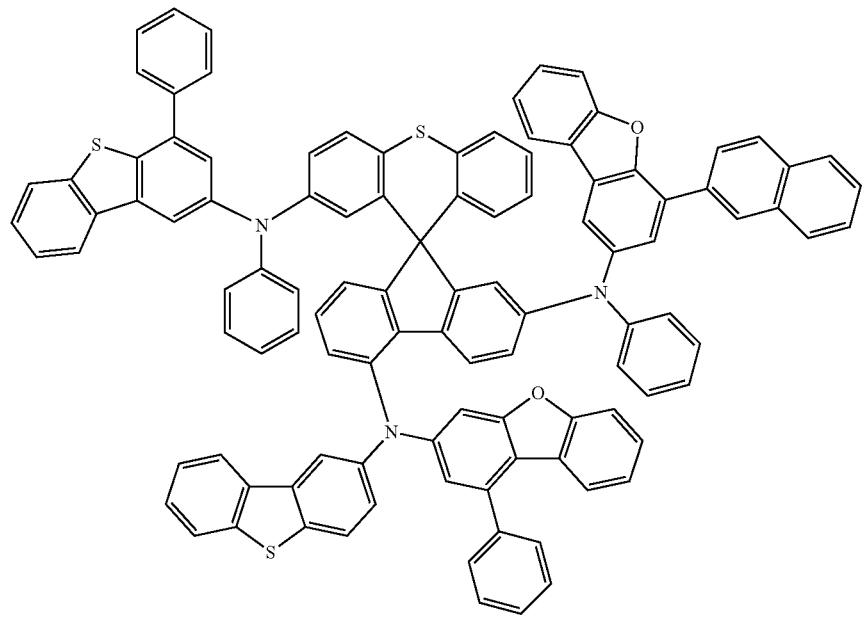

-continued
P-131
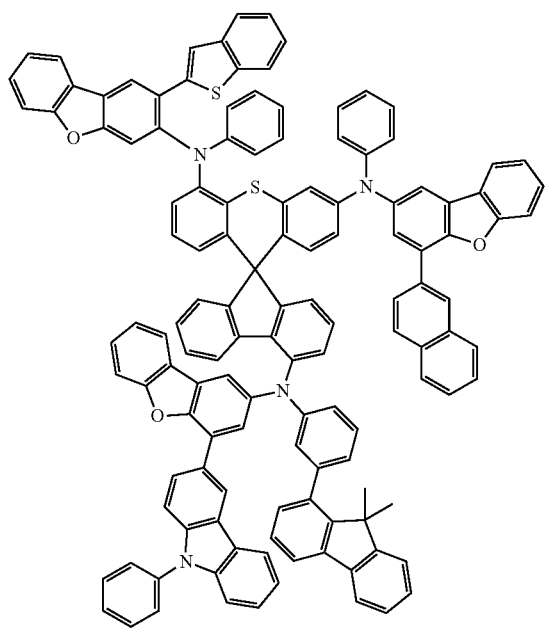
P-132
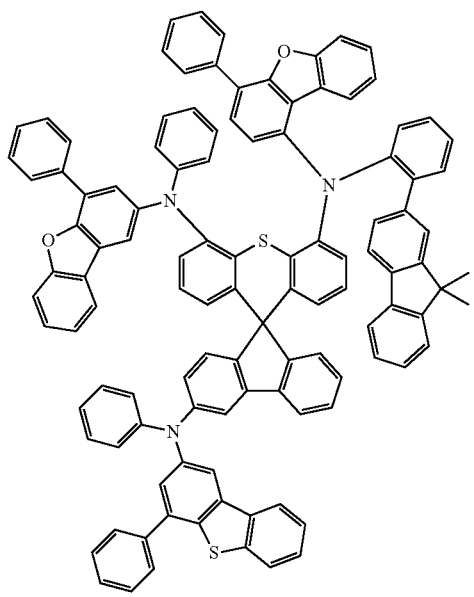
P-133
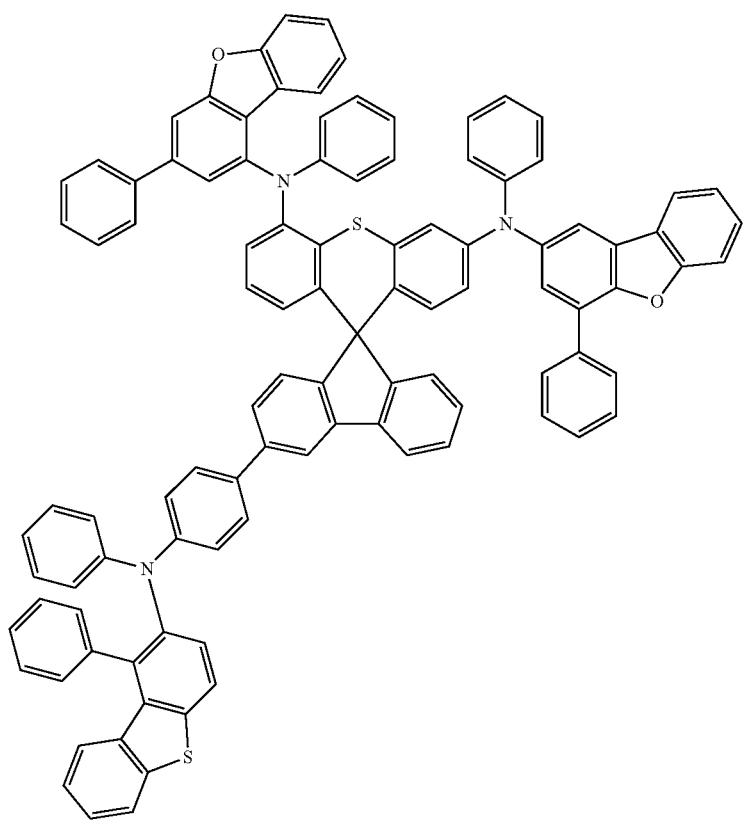

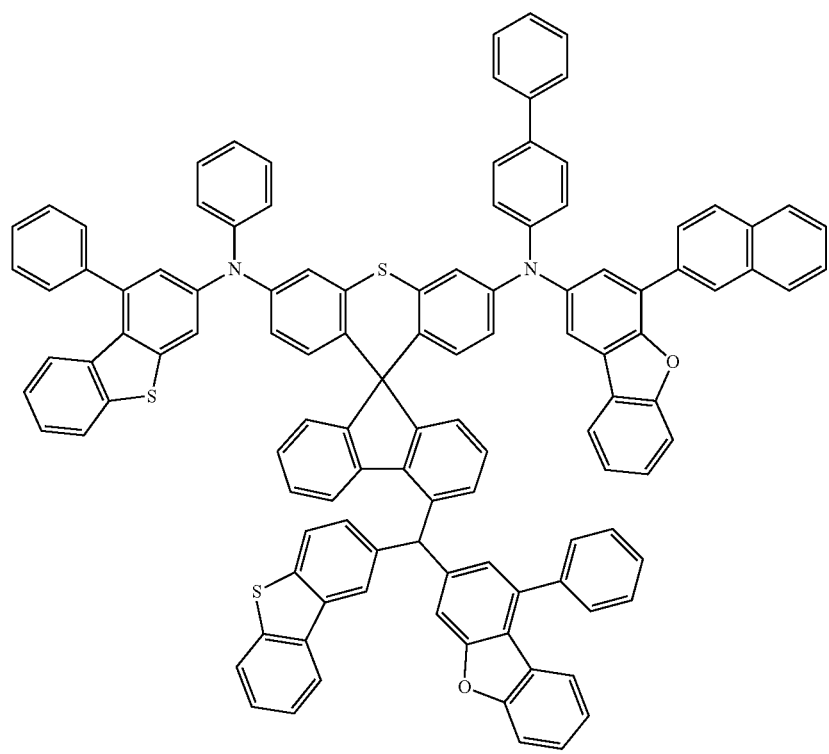
P-134
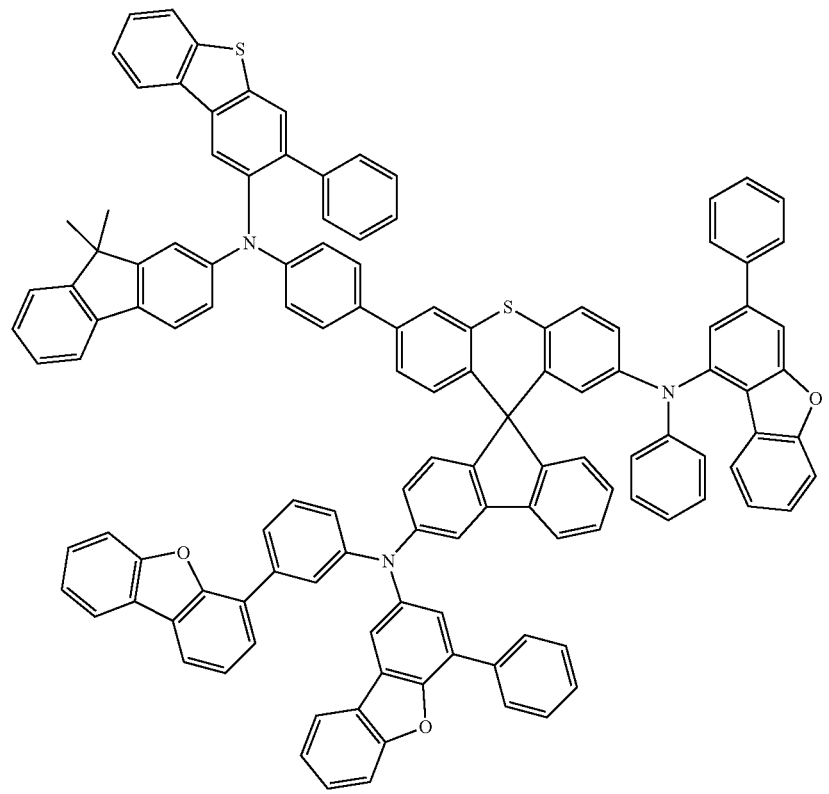
P-135

-continued
P-136
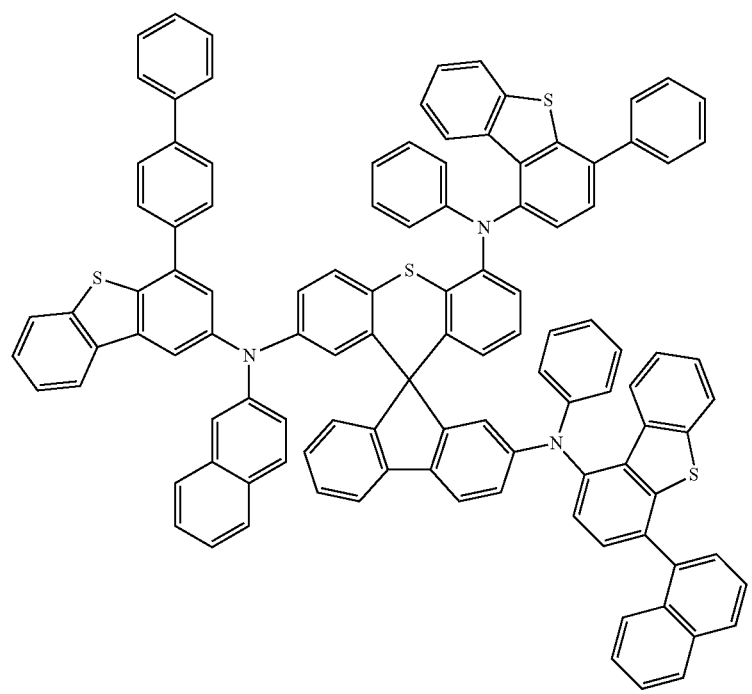
P-137
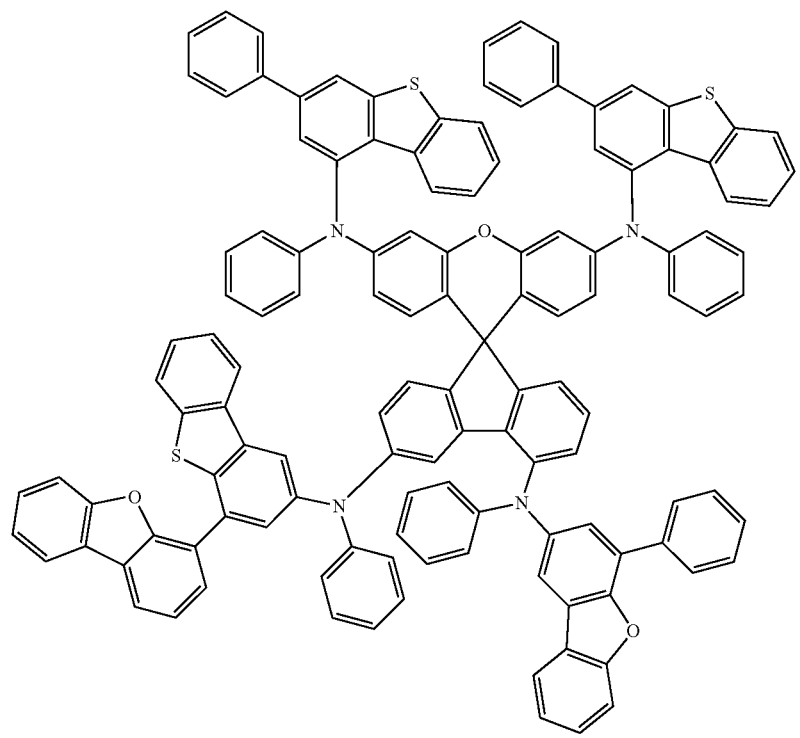

P-138
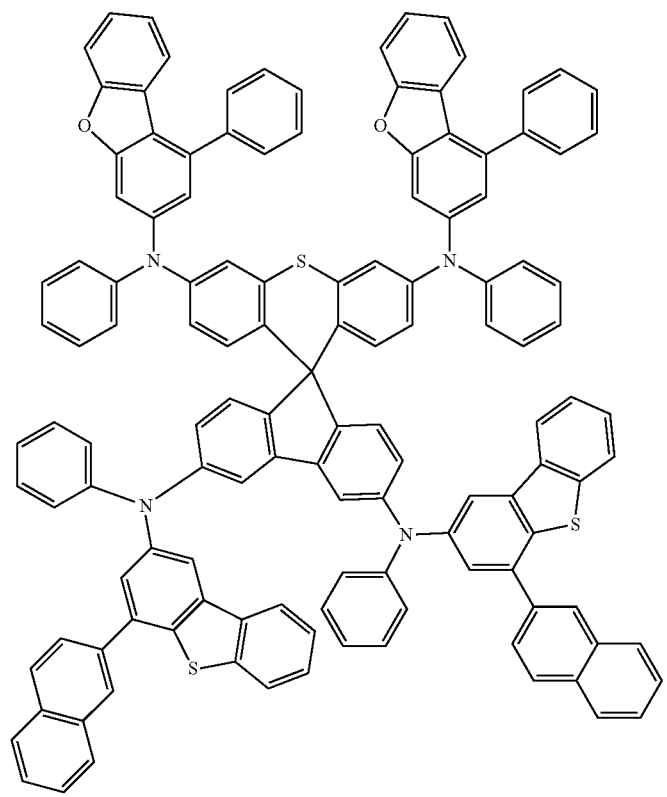
P-139
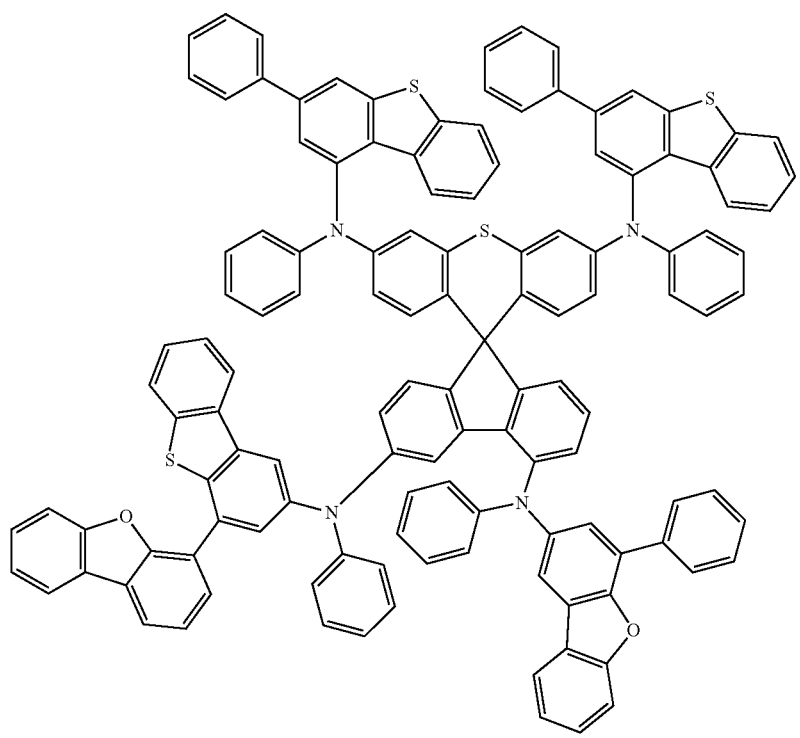

More specifically, the compound represented by Formula 1 may be a compound represented by any one of the following compounds P1-1 to P1-86, but is not limited thereto:
P1-1
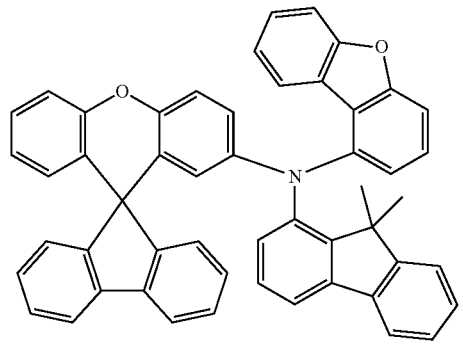
P1-2
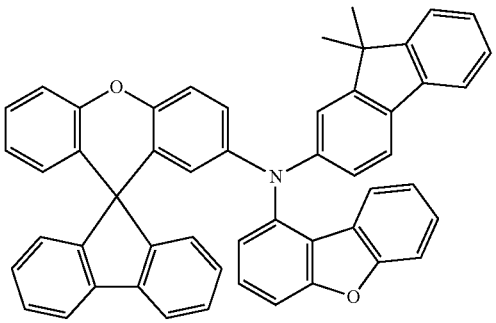
P1-3
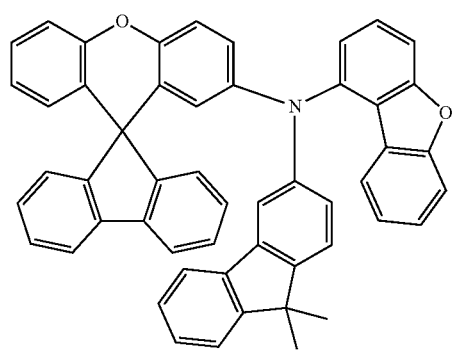
P1-4
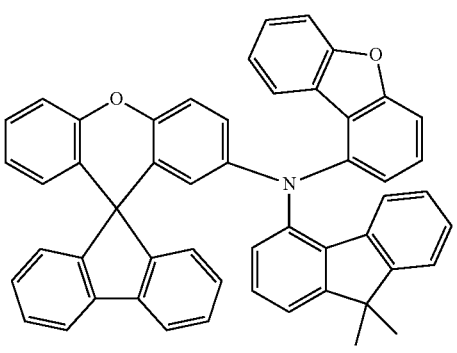
P1-5
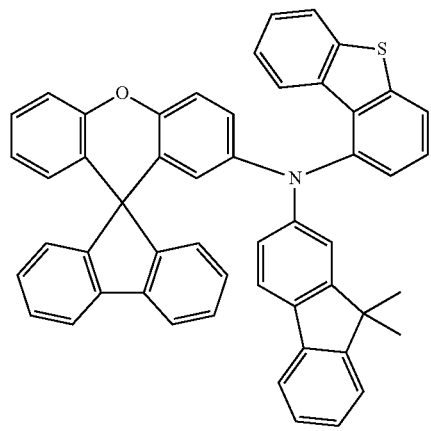
P1-6
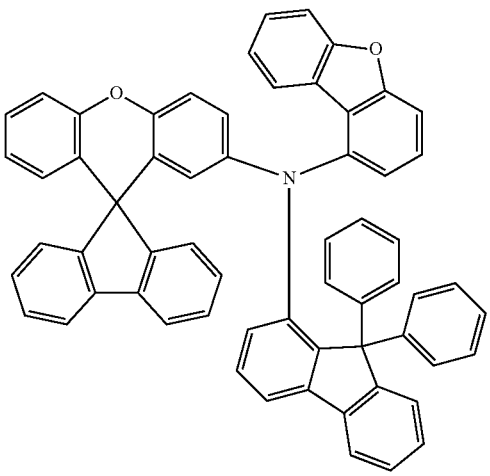

-continued
P1-7
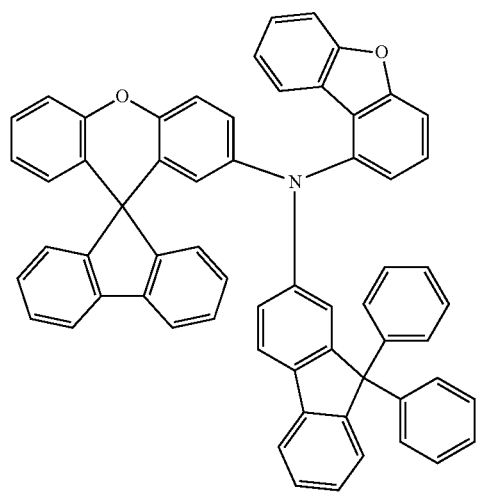
P1-8
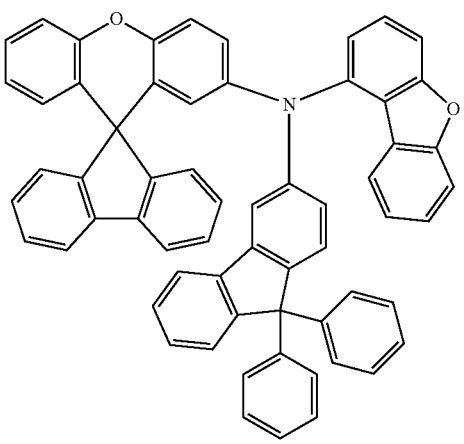
P1-9
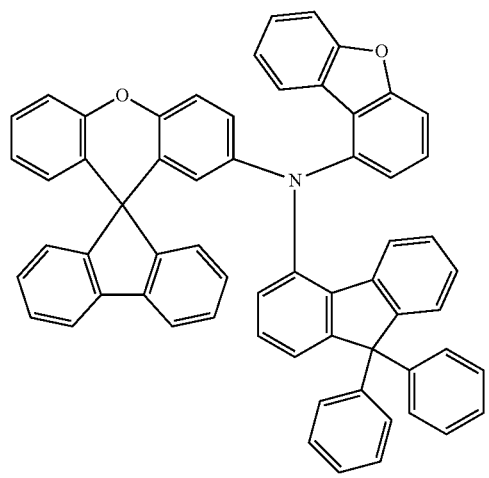
P1-10
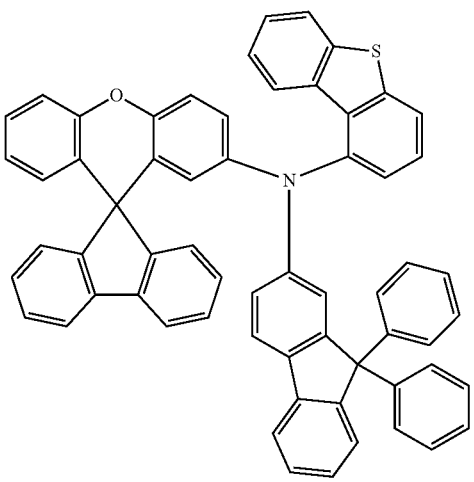
P1-11
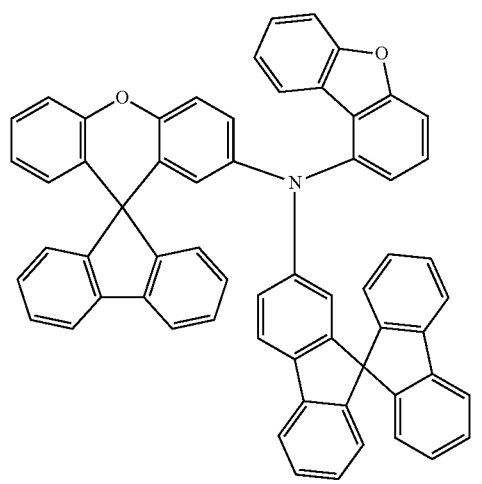
P1-12
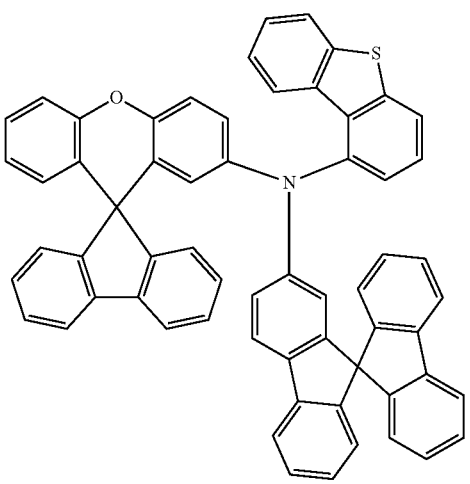

P1-13
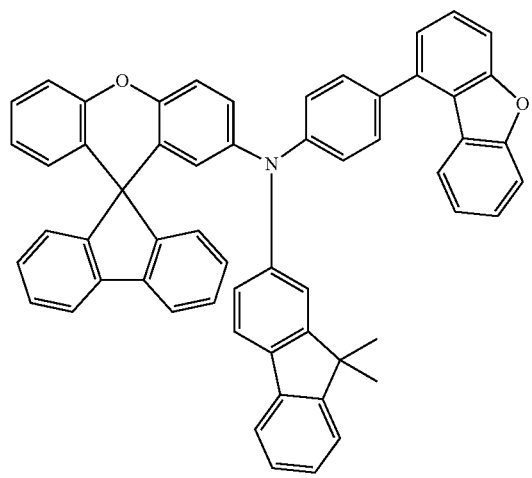
P1-14
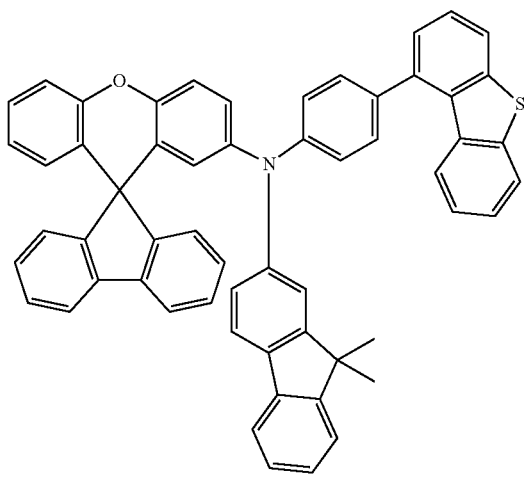
P1-15
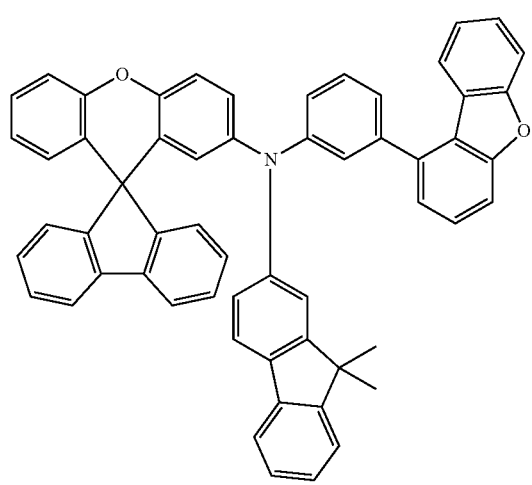
P1-16
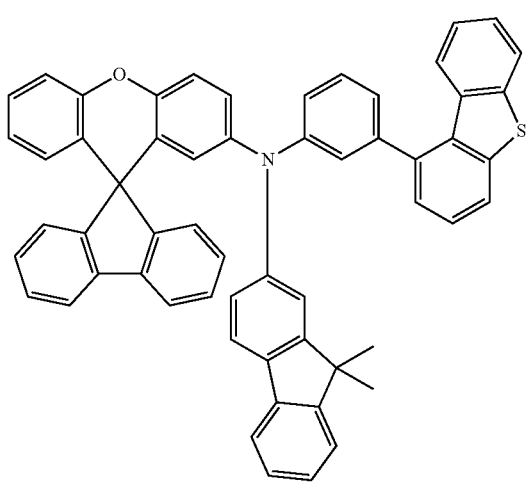
P1-17
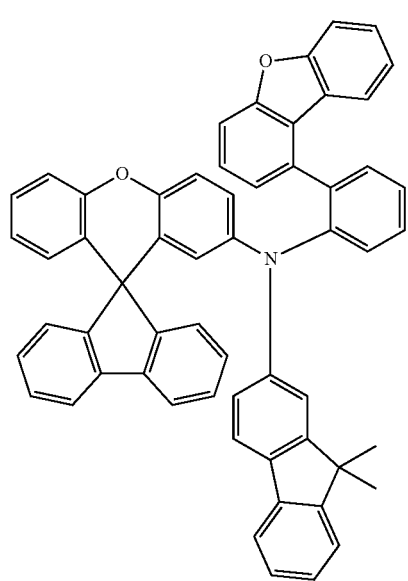
P1-18
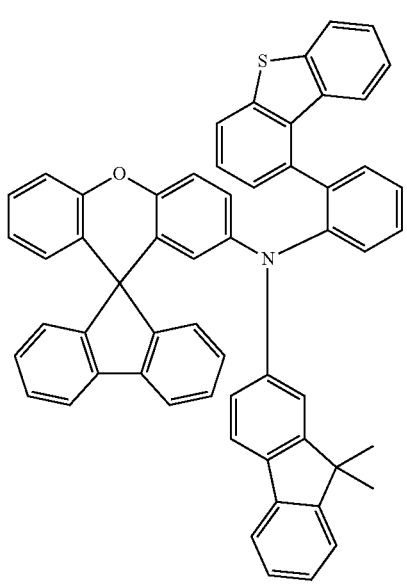

-continued
P1-19
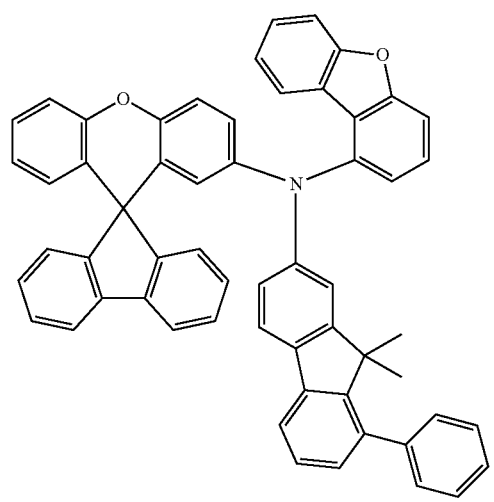
P1-20
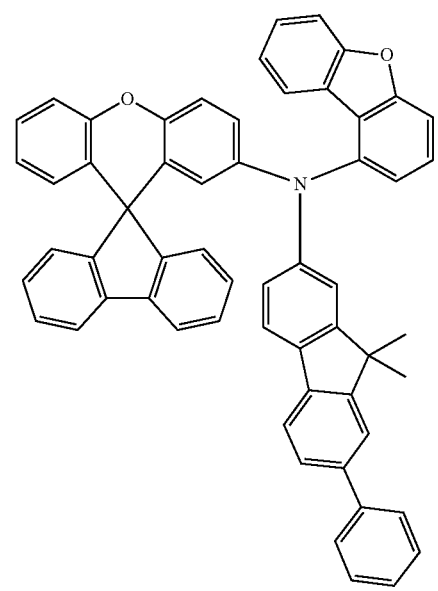
P1-21
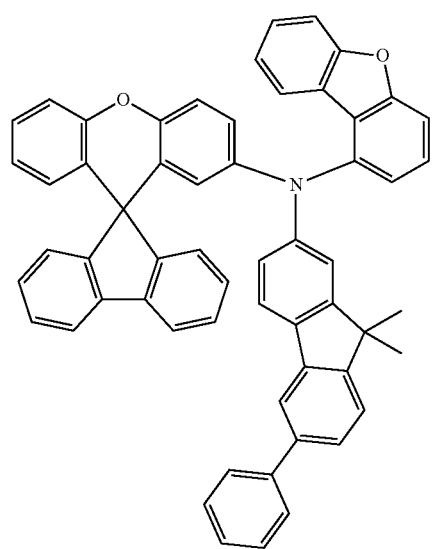
P1-22
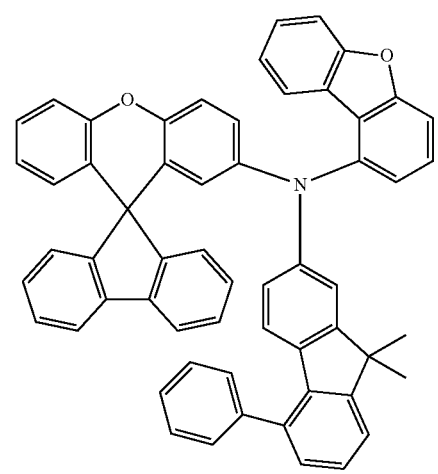

-continued
P1-23
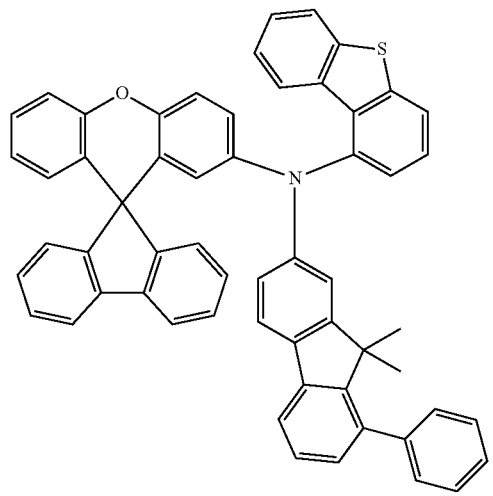
P1-24
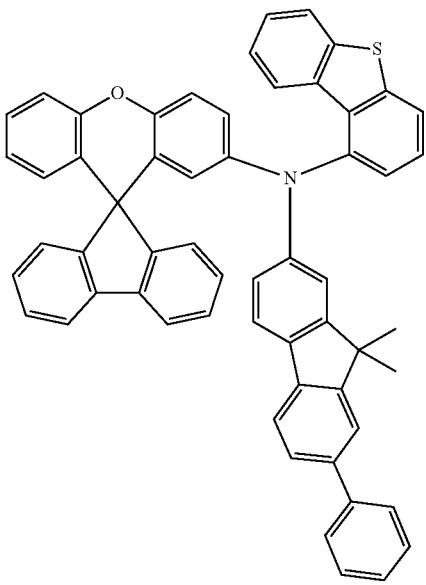
P1-25
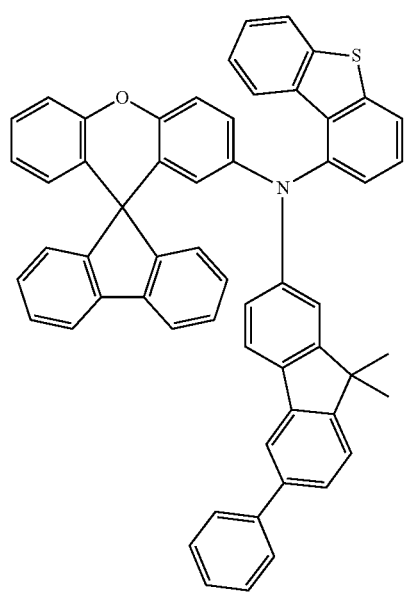
P1-26
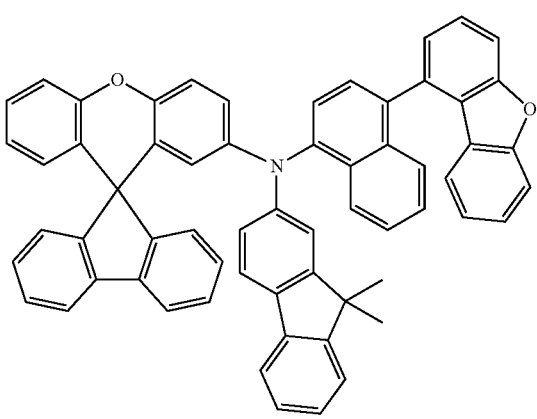
P1-27
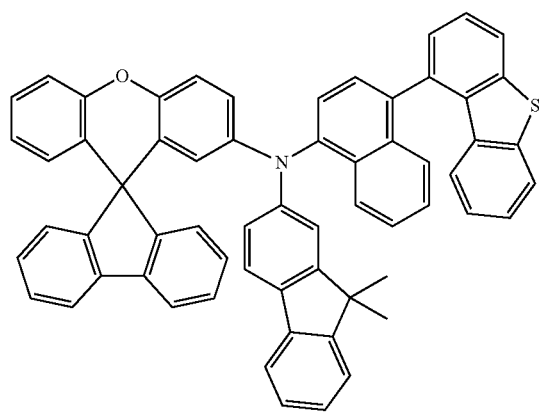
P1-28
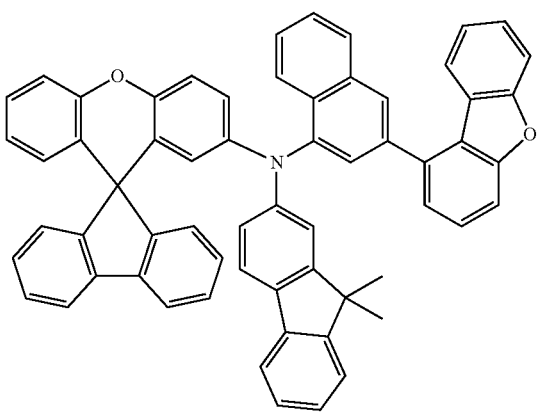

-continued
P1-29
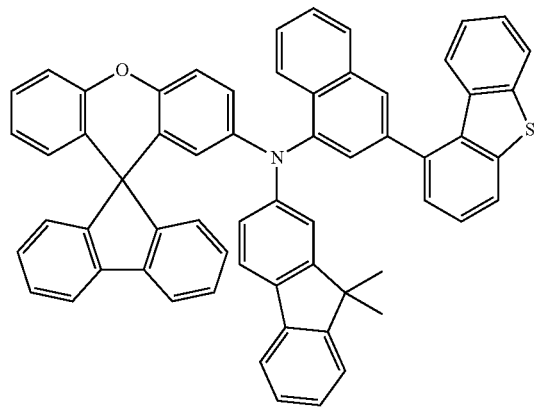
P1-30
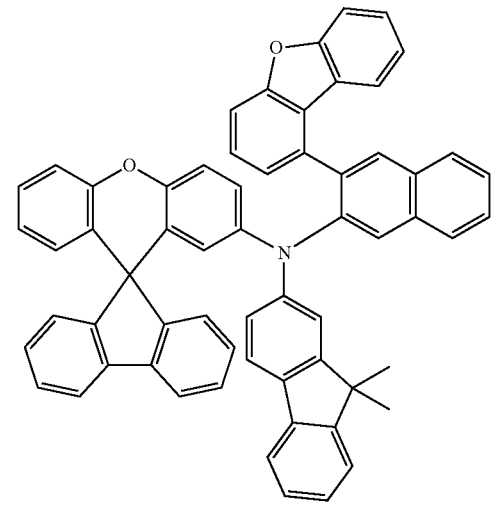
P1-31
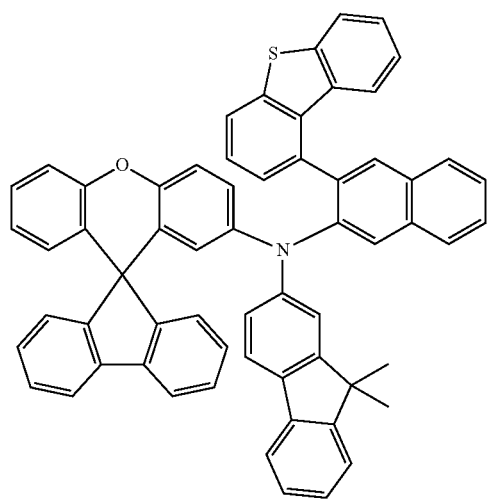
P1-32
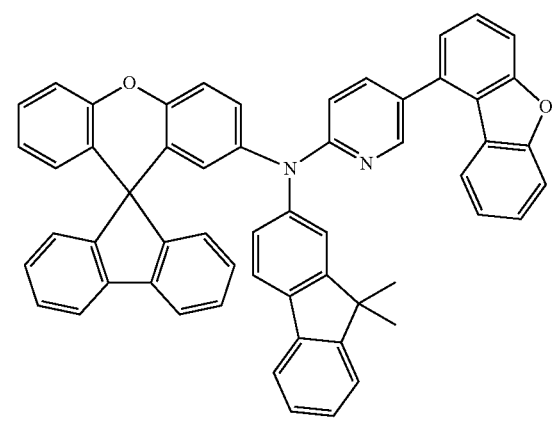
P1-33
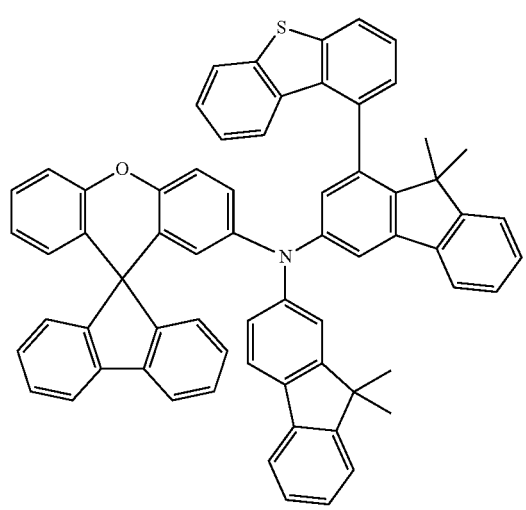
P1-34
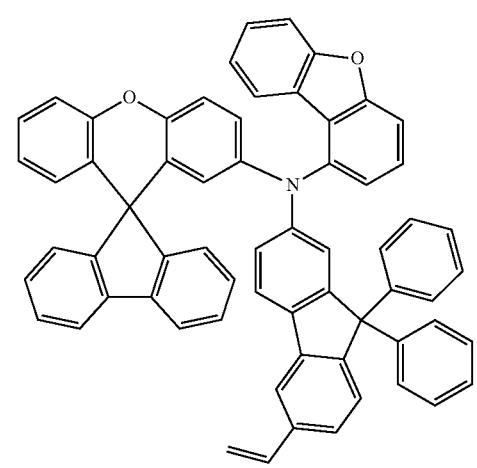

-continued
P1-35
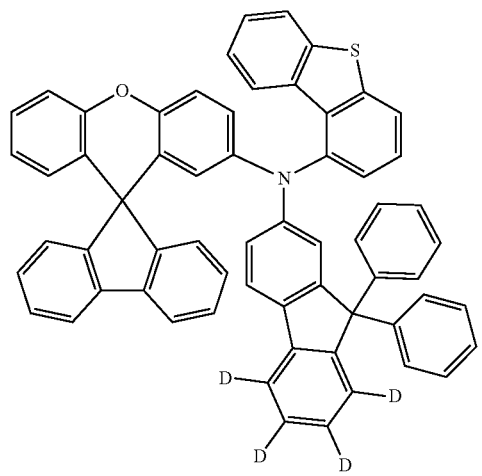
P1-36
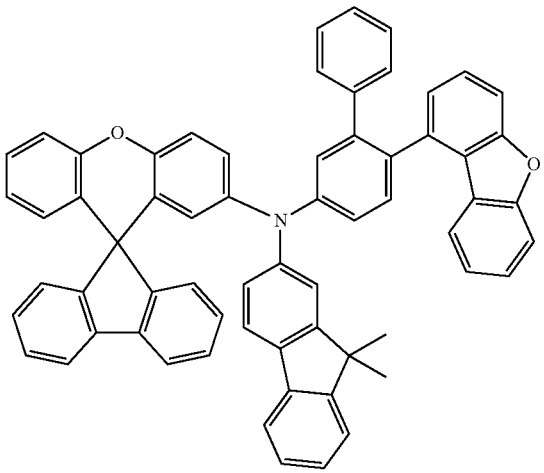
P1-37
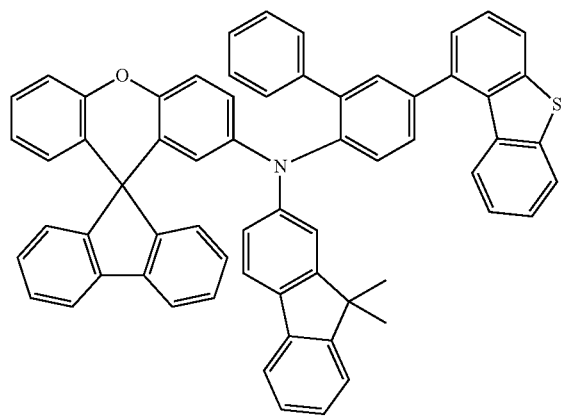
P1-38
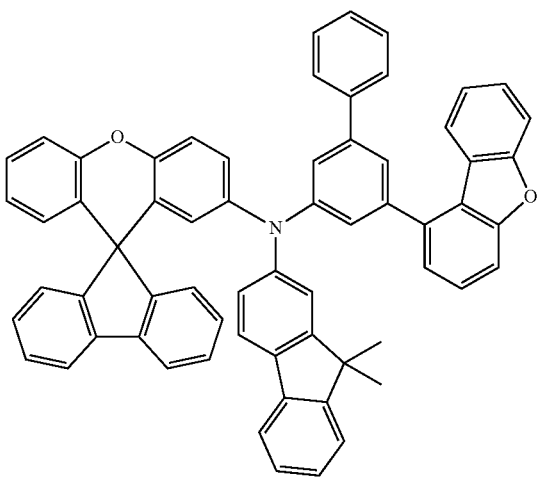
P1-39
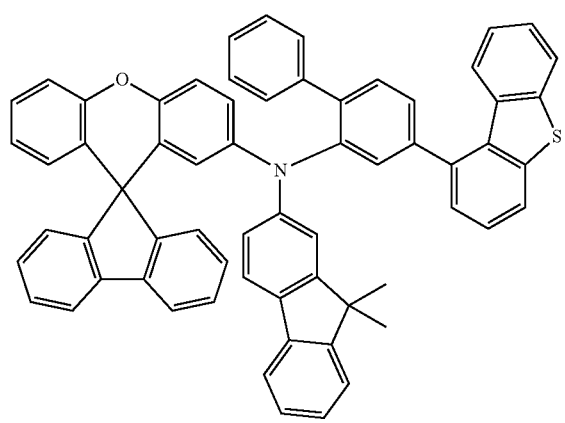
P1-40
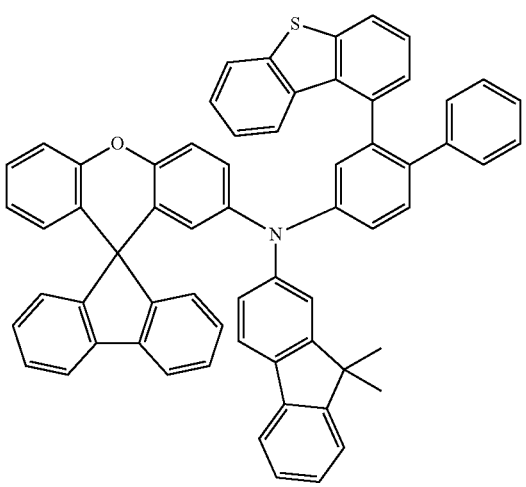

-continued
P1-41
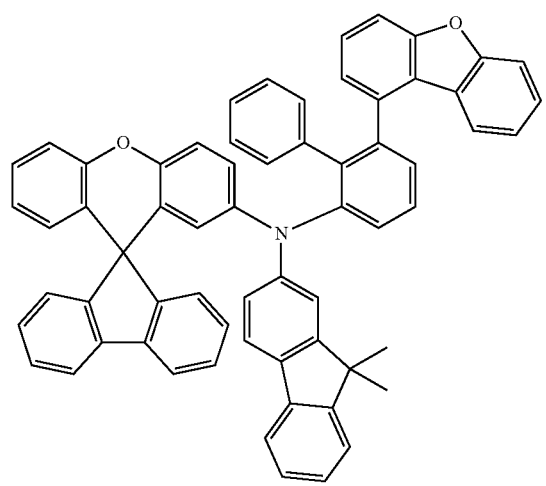
P1-42
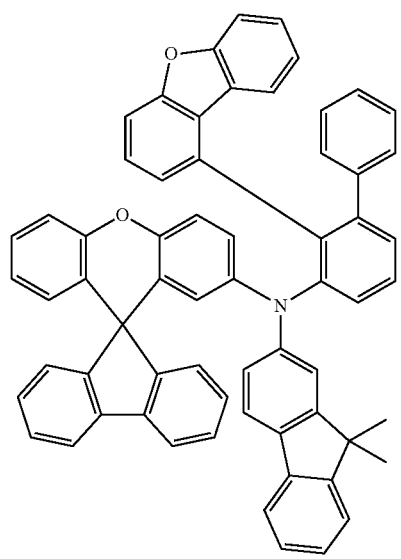
P1-43
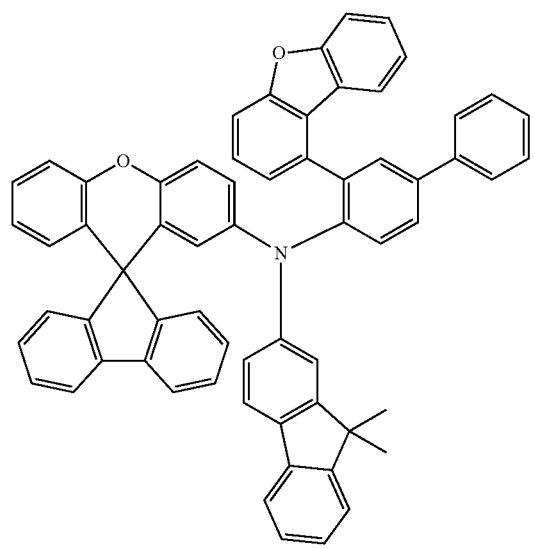
P1-44
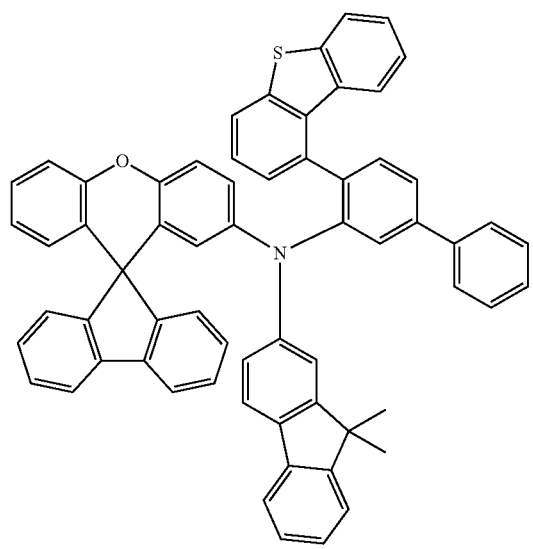

-continued
P1-45
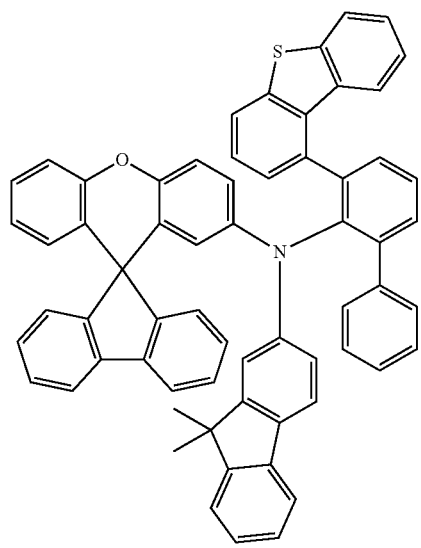
P1-46
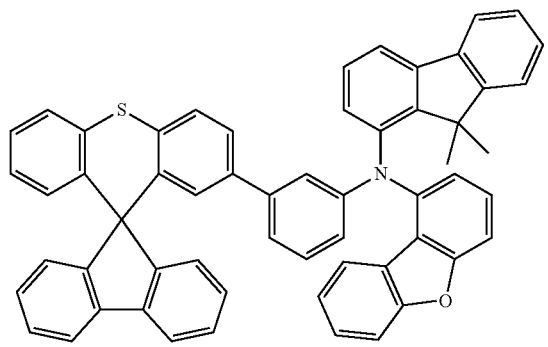
P1-47
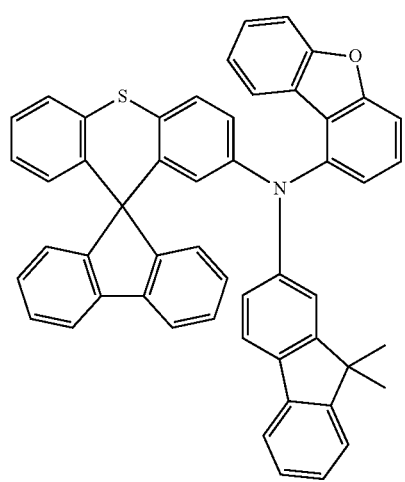
P1-48
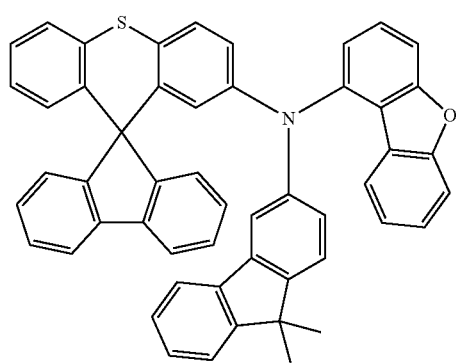
P1-49
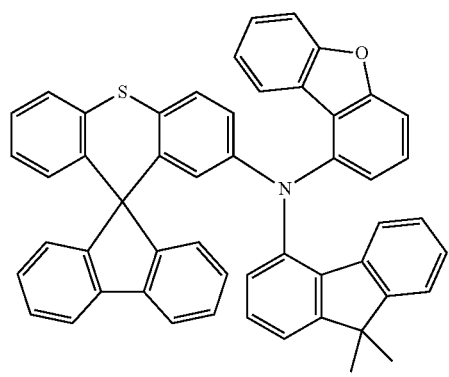
P1-50
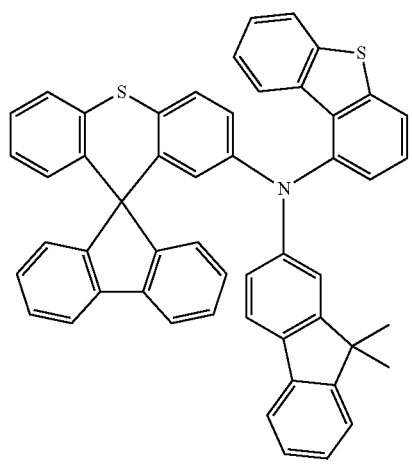

-continued
P1-51
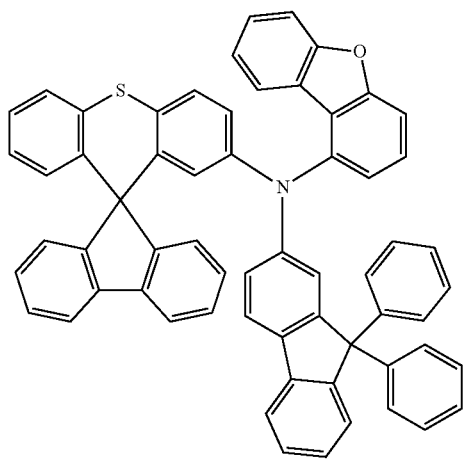
P1-52
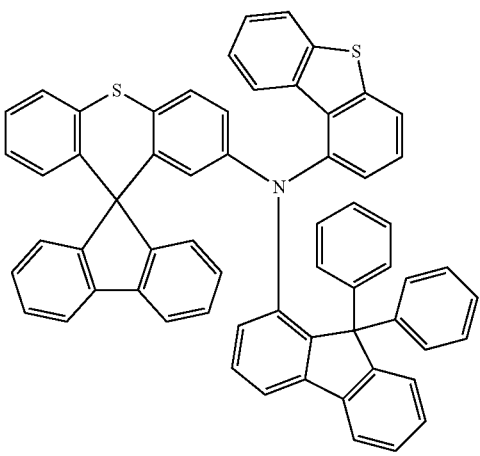
P1-53
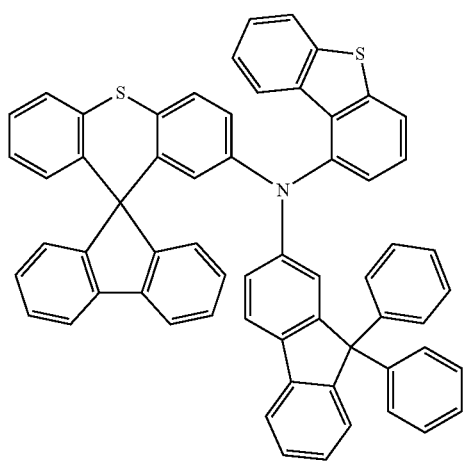
P1-54
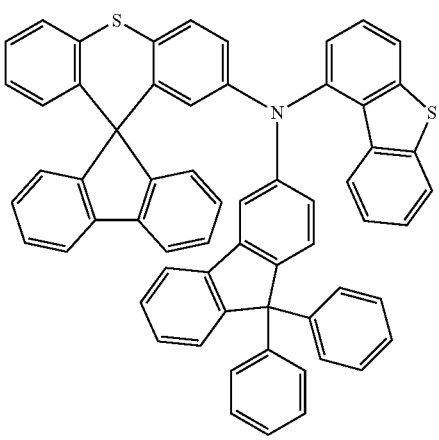
P1-55
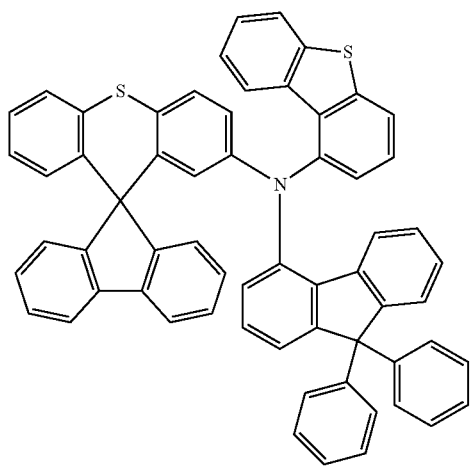
P1-56
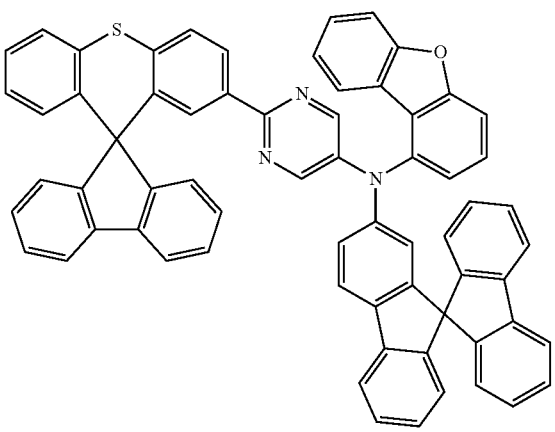

-continued
P1-57
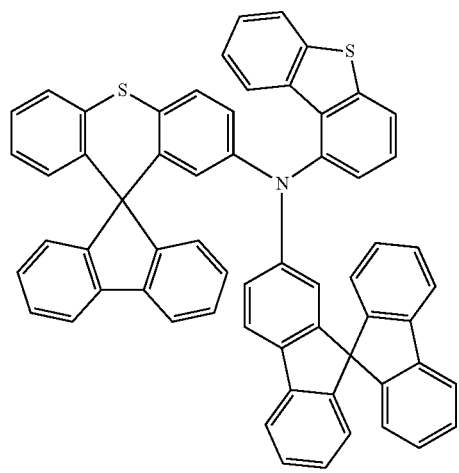
P1-58
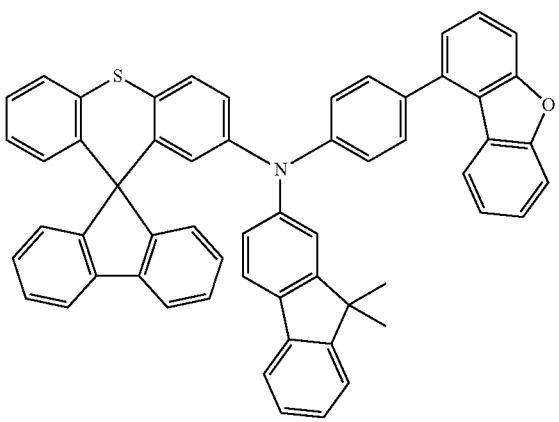
P1-59
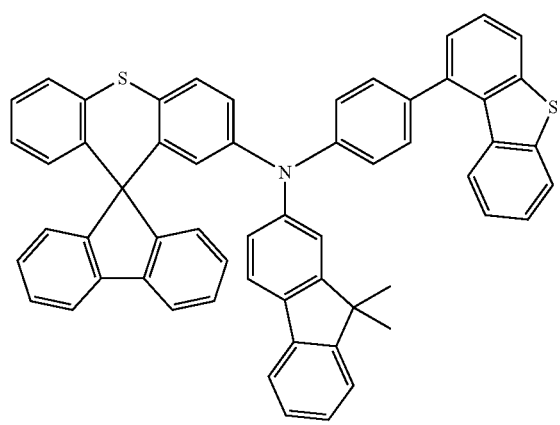
P1-60
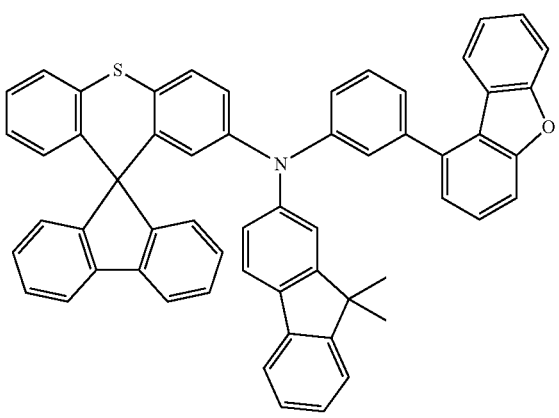
P1-61
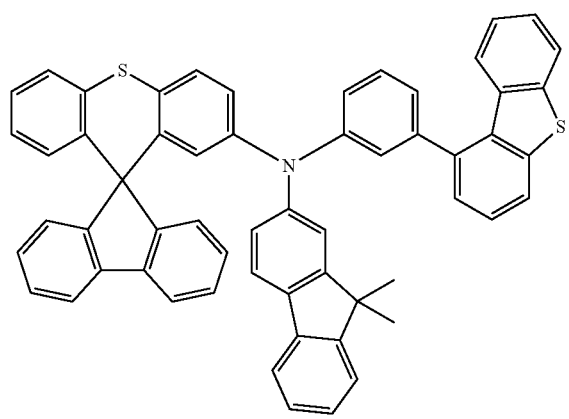
P1-62
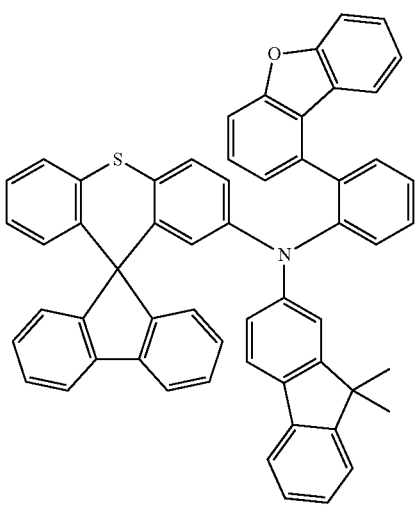

-continued
P1-63
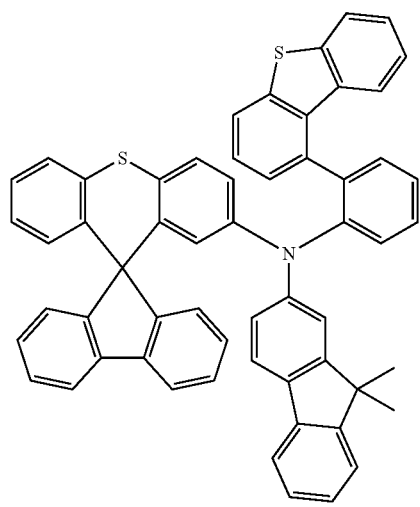
P1-64
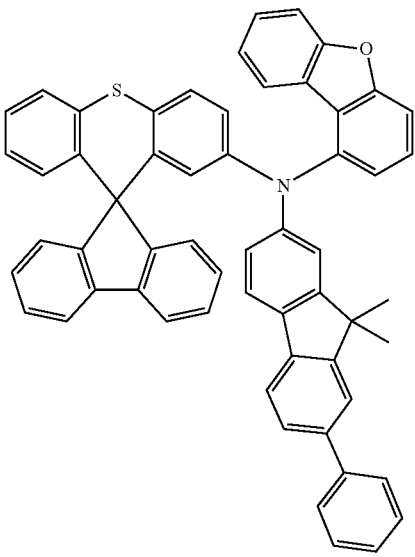
P1-65
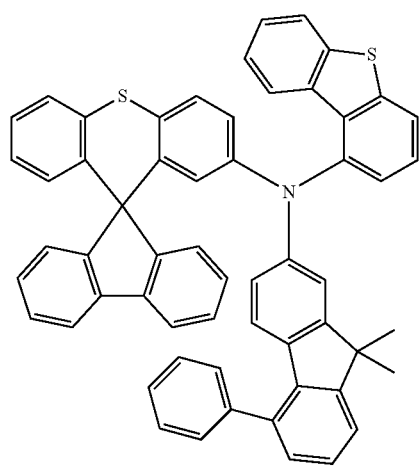
P1-66
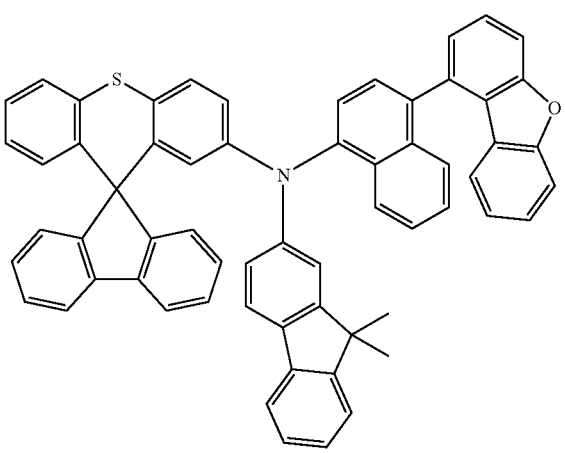
P1-67
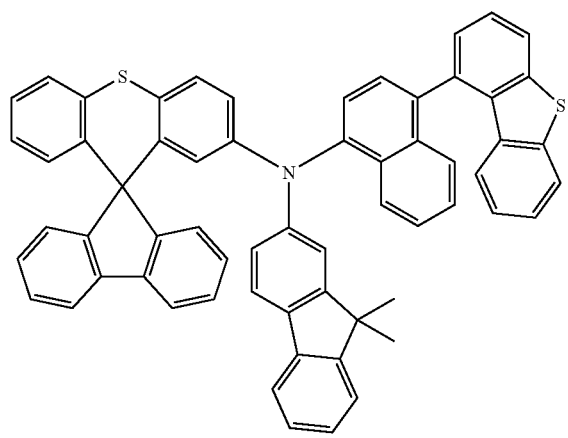
P1-68
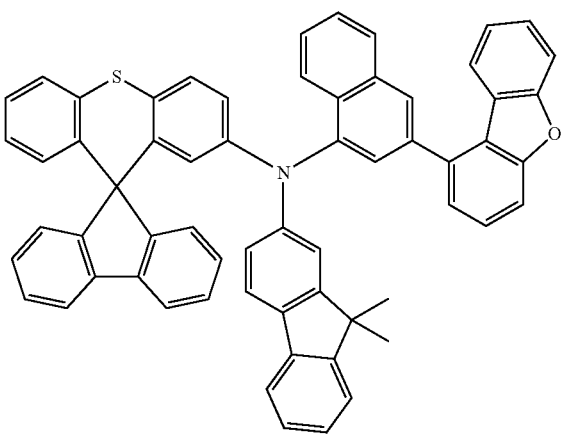

-continued
P1-69
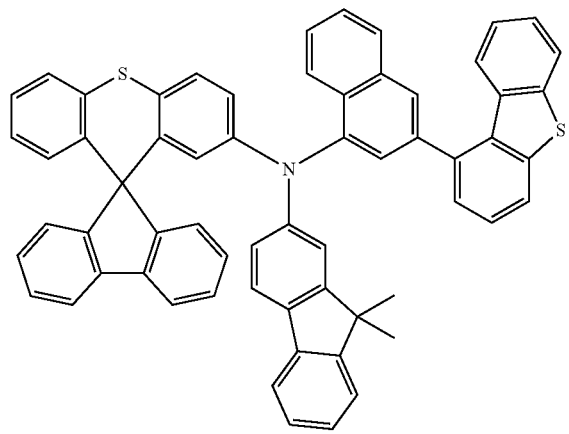
P1-70
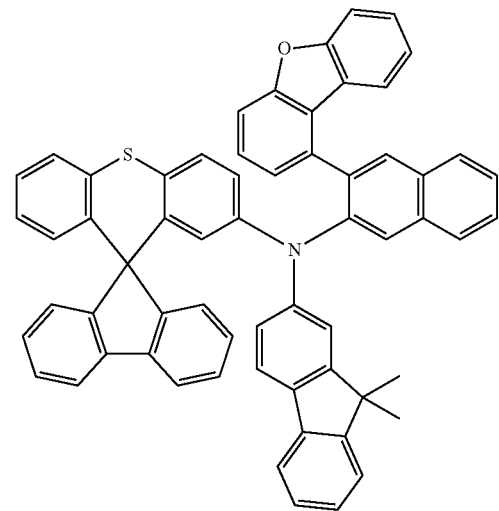
P1-71
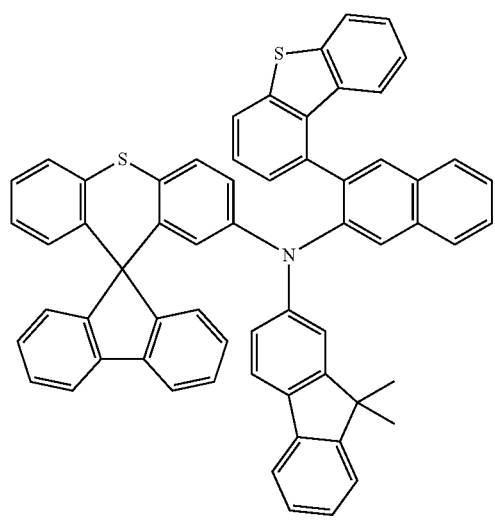
P1-72
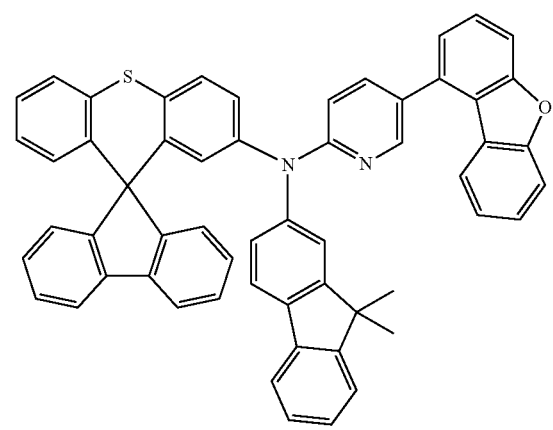
P1-73
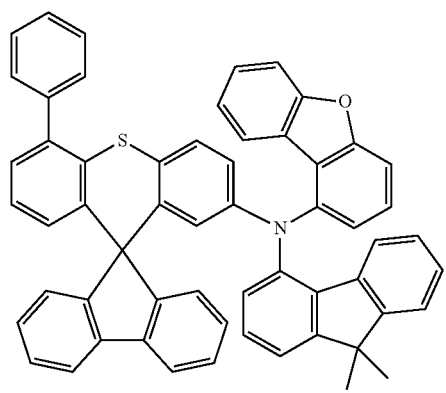
P1-74
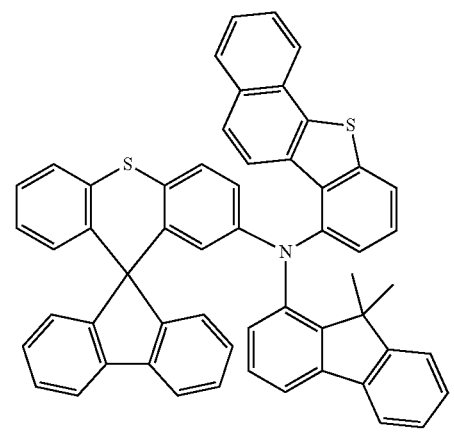

-continued
P1-75
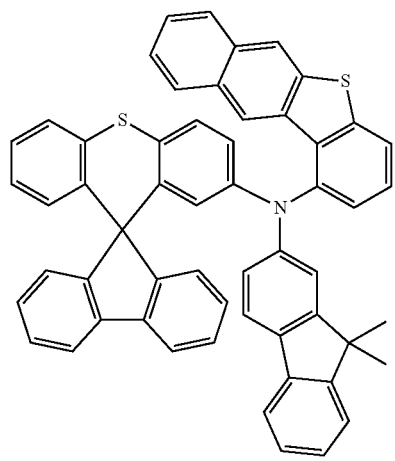
P1-76
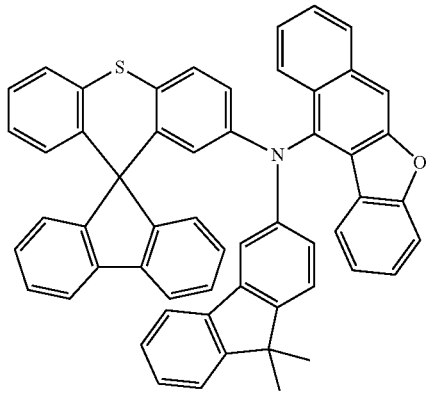
P1-77
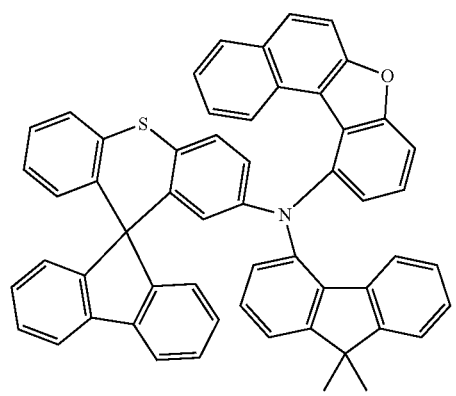
P1-78
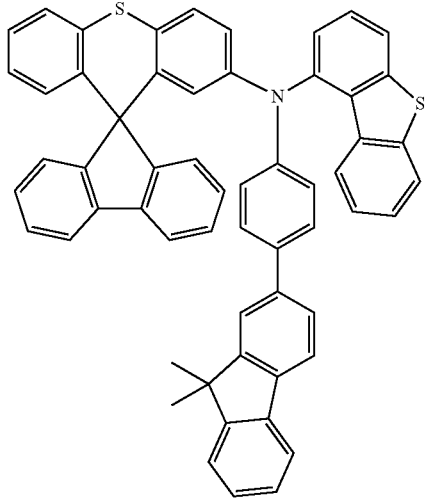
P1-79
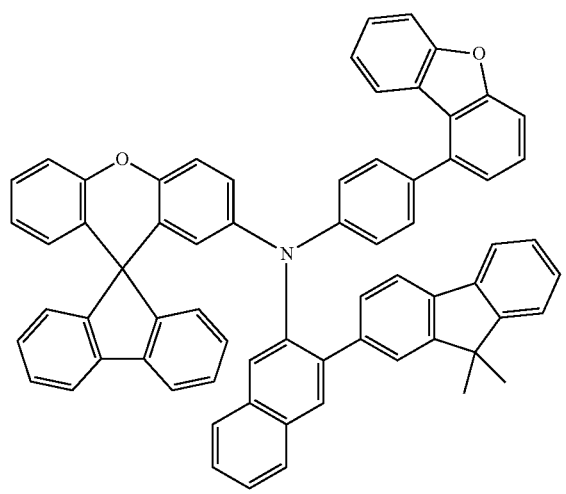
P1-80
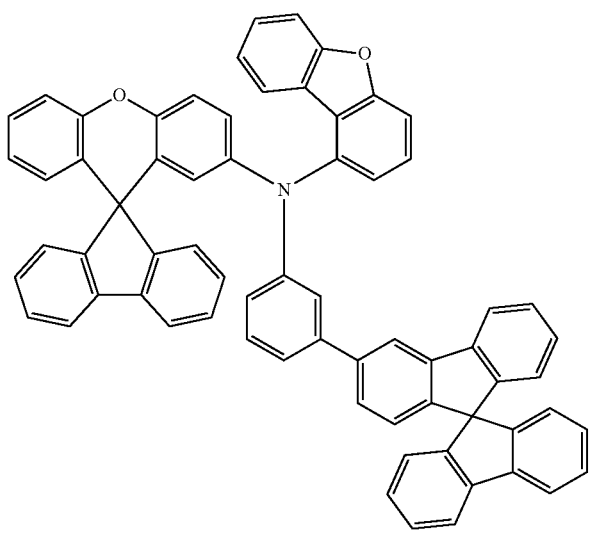

-continued
P1-81
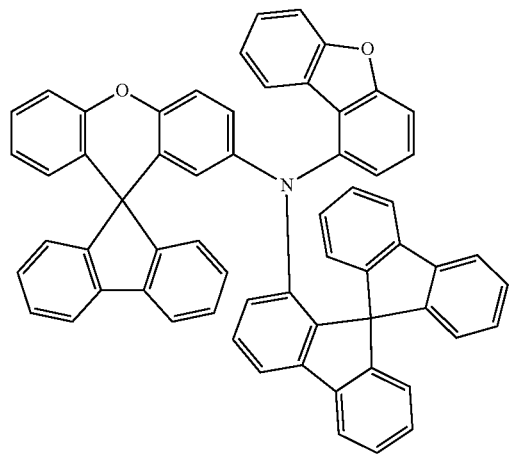
P1-82
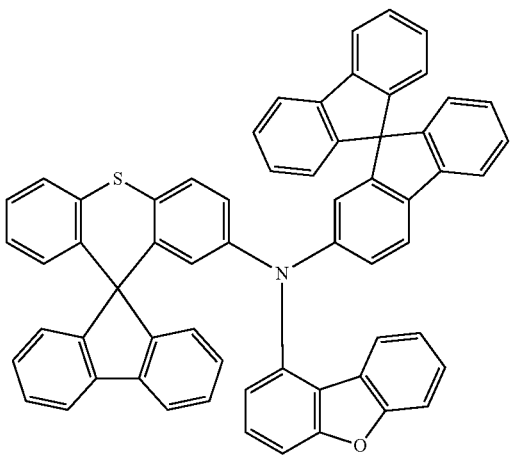
P1-83
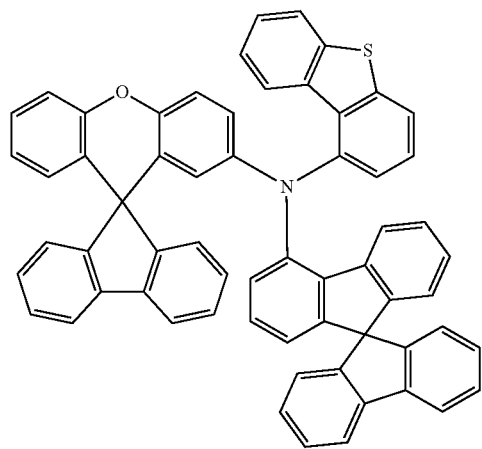
P1-84
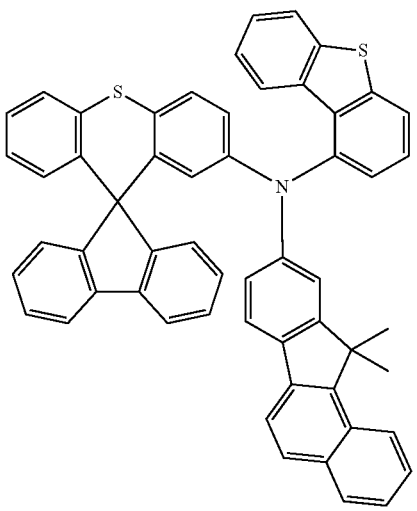
P1-85
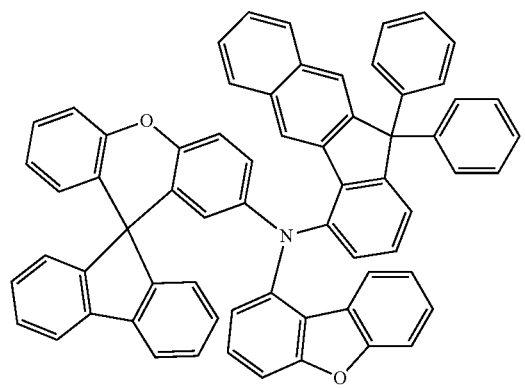
P1-86
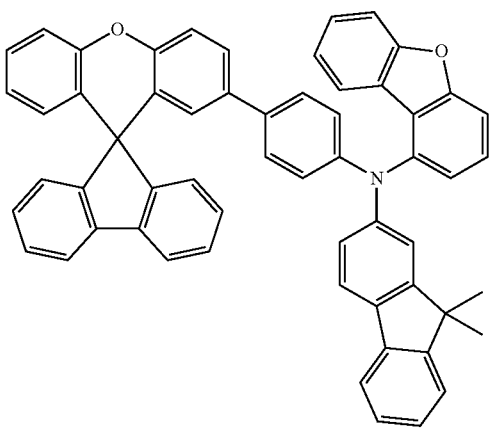

Also, the compound represented by Formula 1 may be a compound represented by any one of the following compounds P2-1 to P2-55, but is not limited thereto:
P2-1
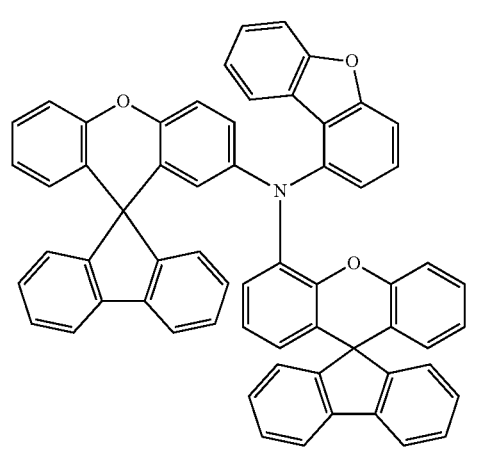
P2-2
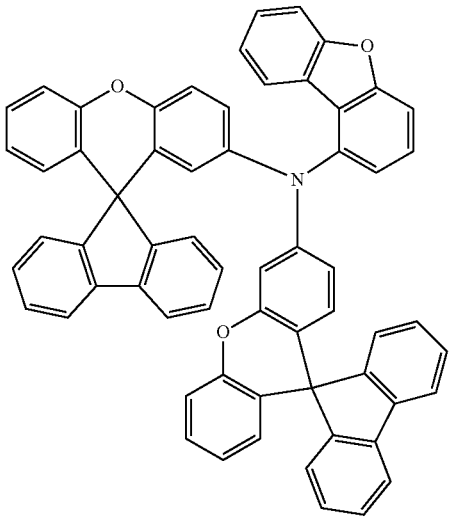
P2-3
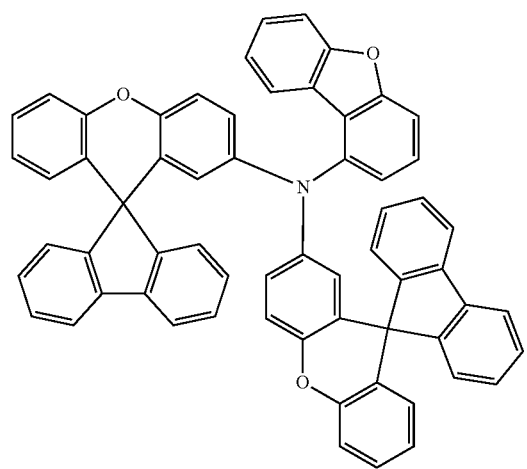
P2-4
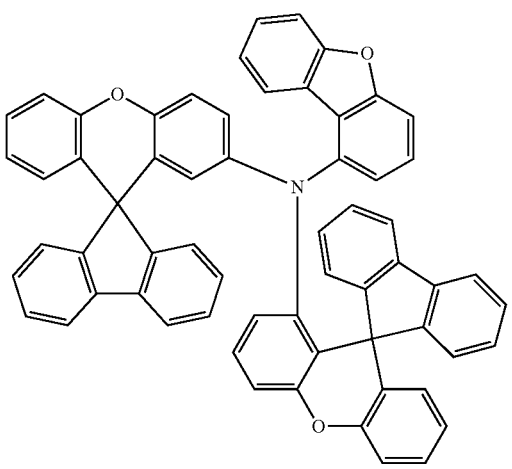
P2-5
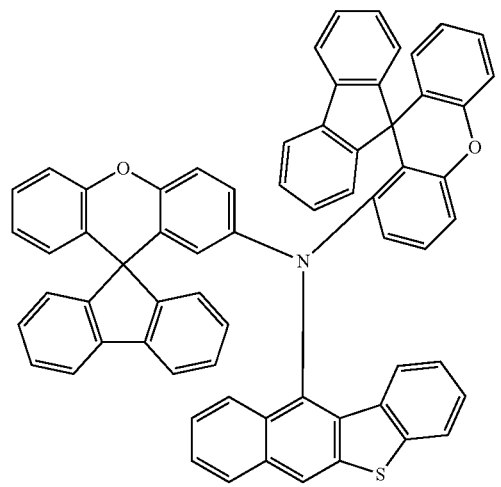
P2-6
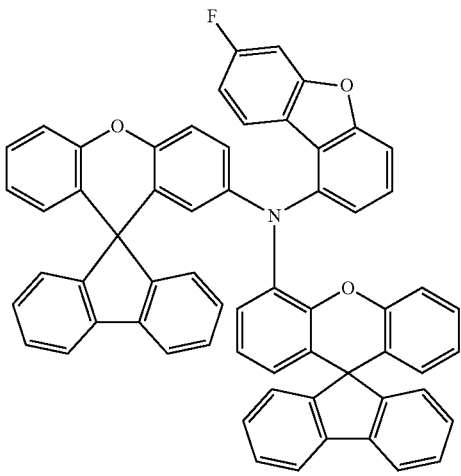

-continued
P2-7
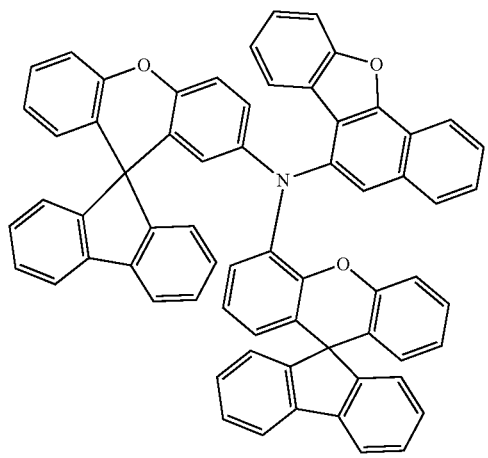
P2-8
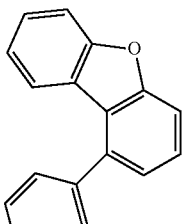
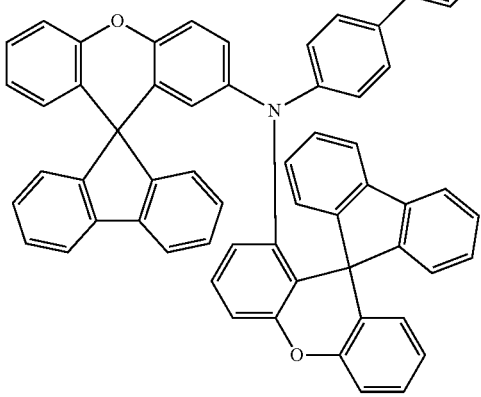
P2-9
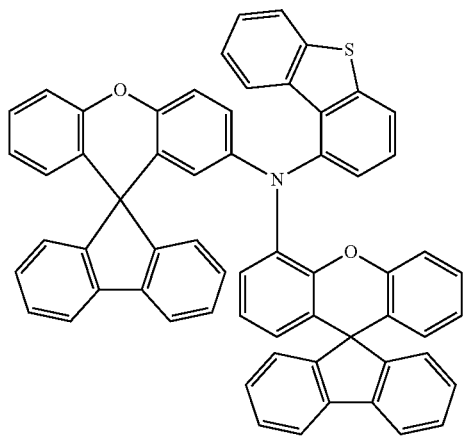
P2-10
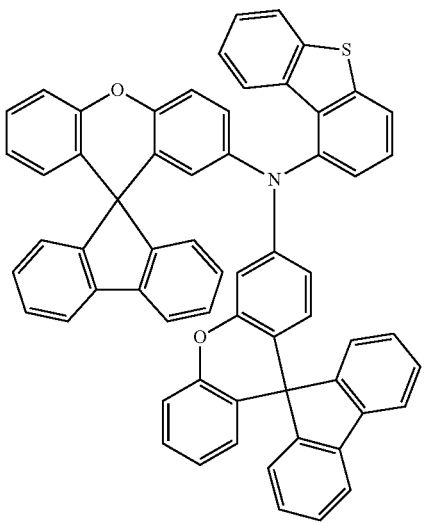
P2-11
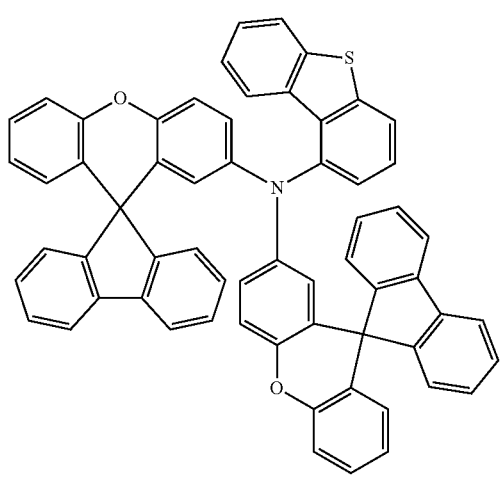
P2-12
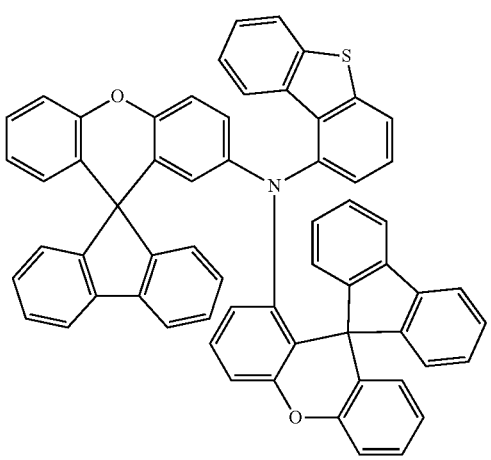

-continued
P2-13
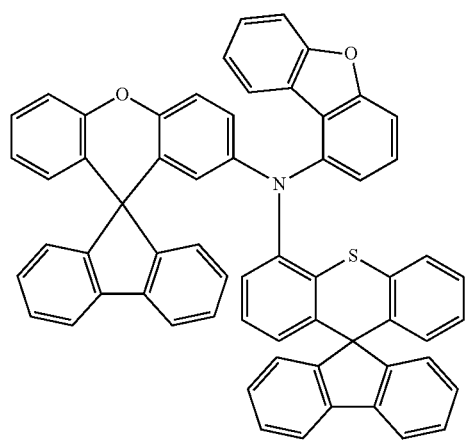
P2-14
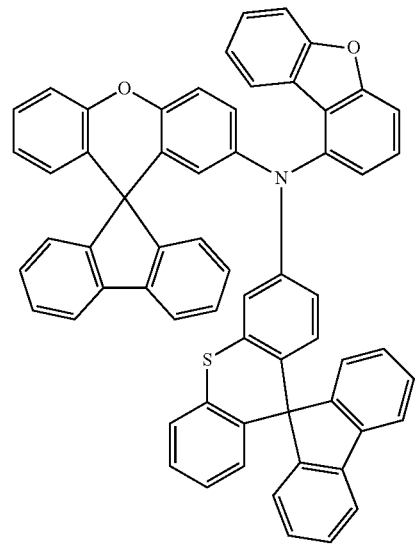
P2-15
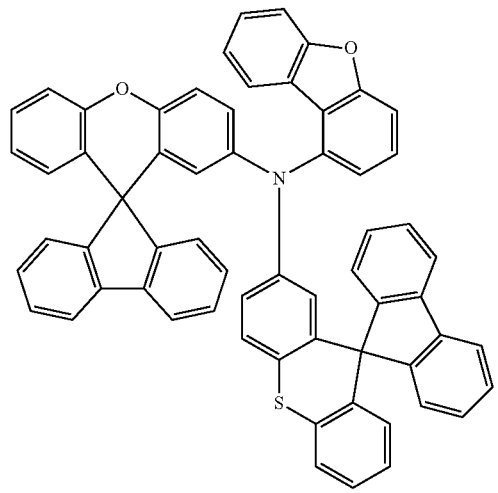
P2-16
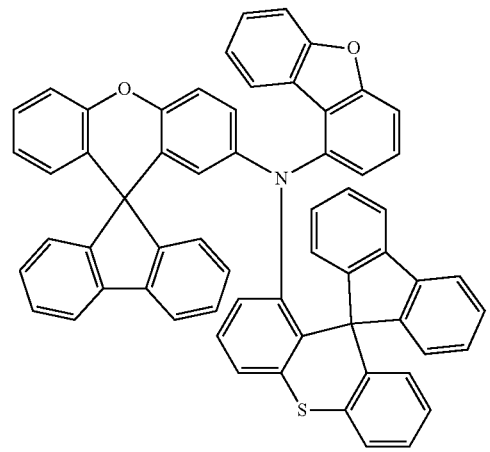
P2-17
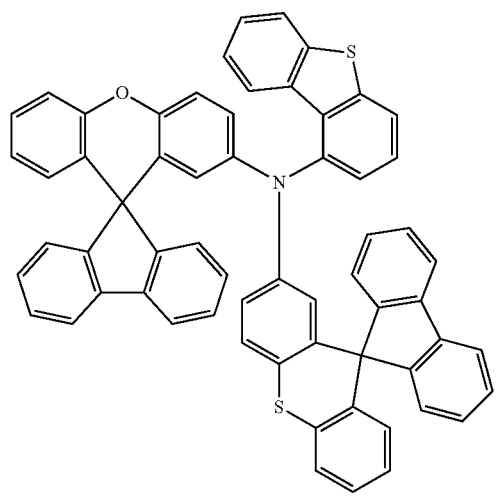
P2-18
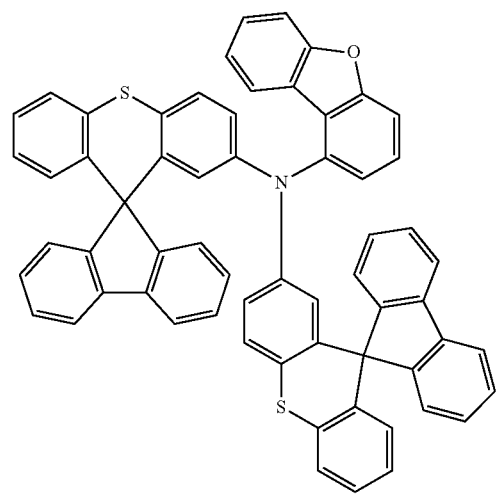

-continued
P2-19
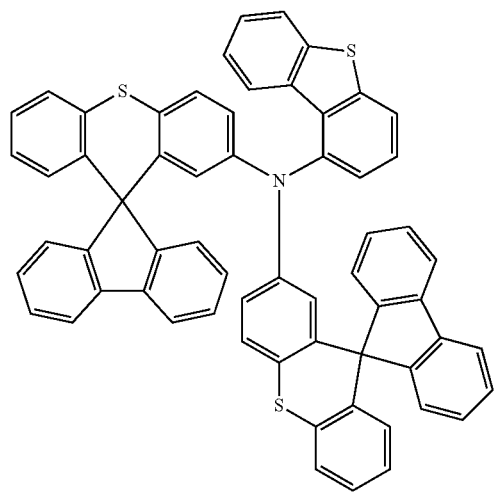
P2-20
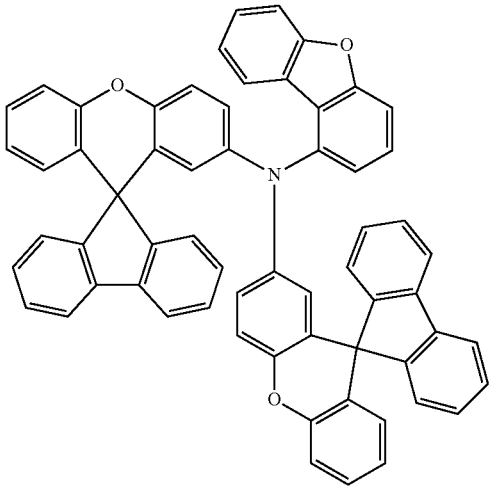
P2-21
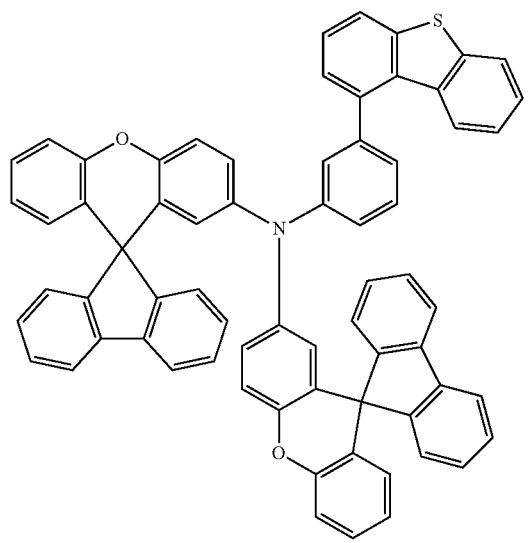
P2-22
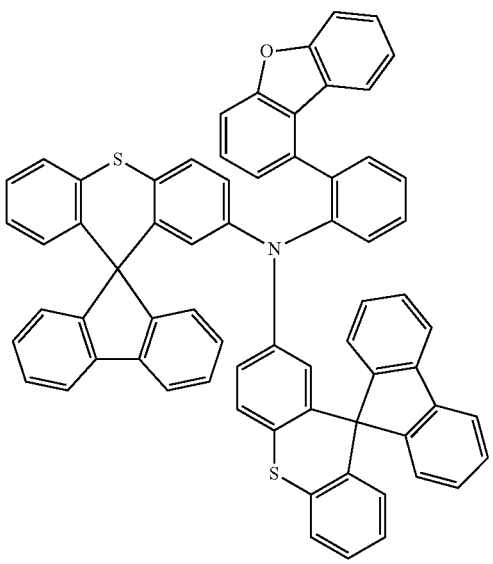
P2-23
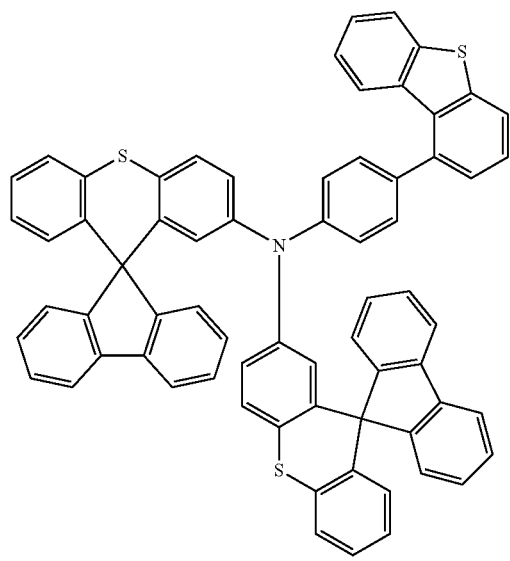
P2-24
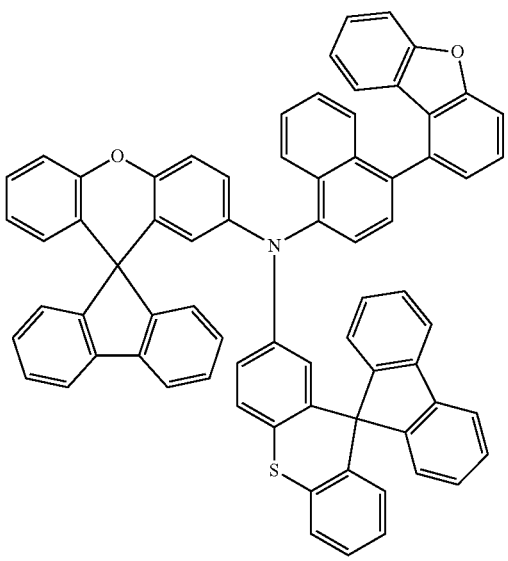

-continued
P2-25
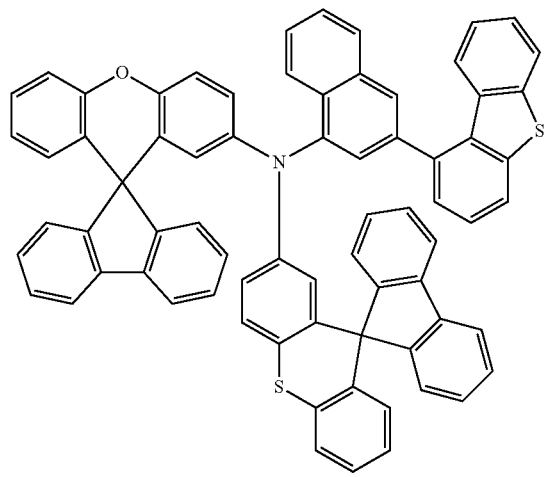
P2-26
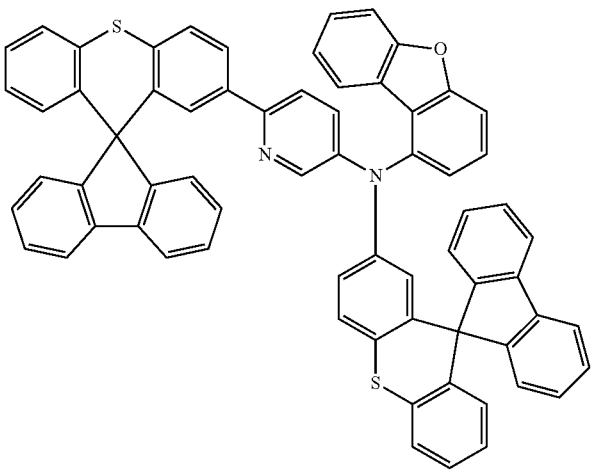
P2-27
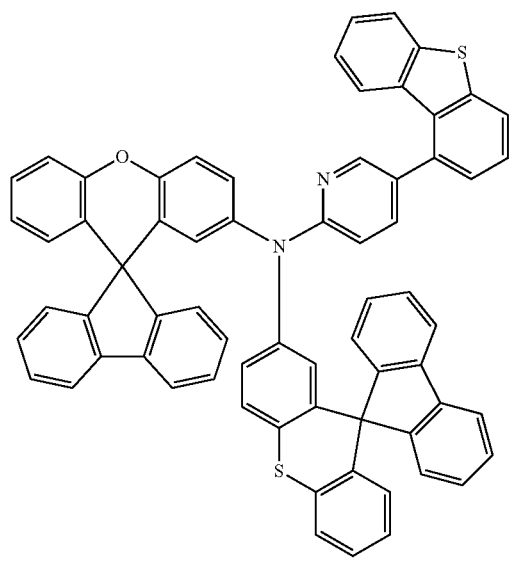
P2-28
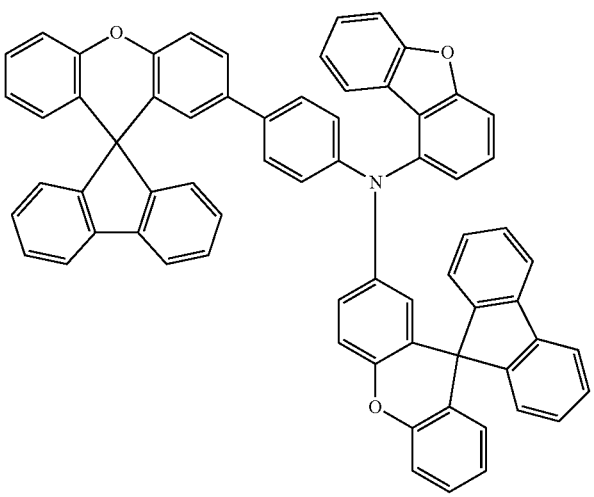
P2-29
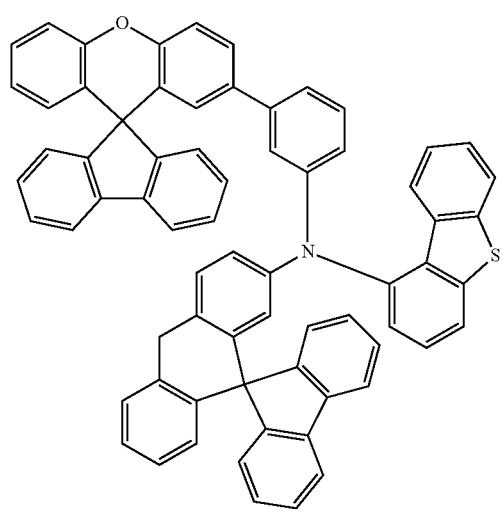
P2-30
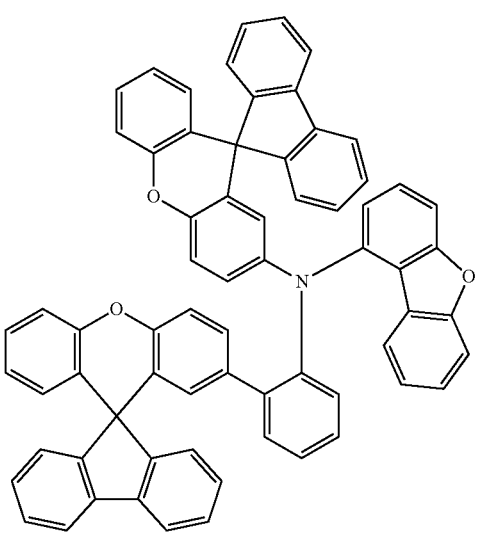

-continued
P2-31
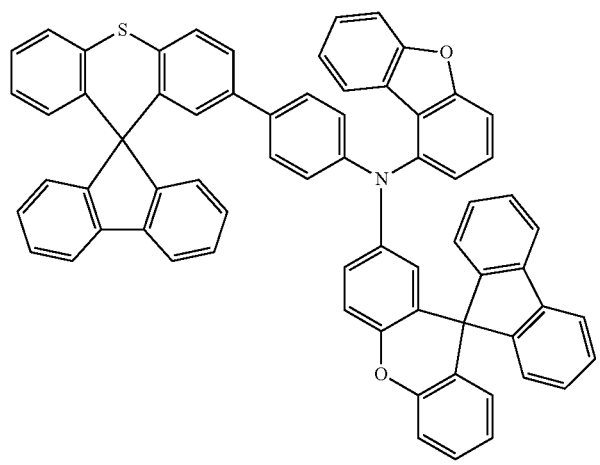
P2-32
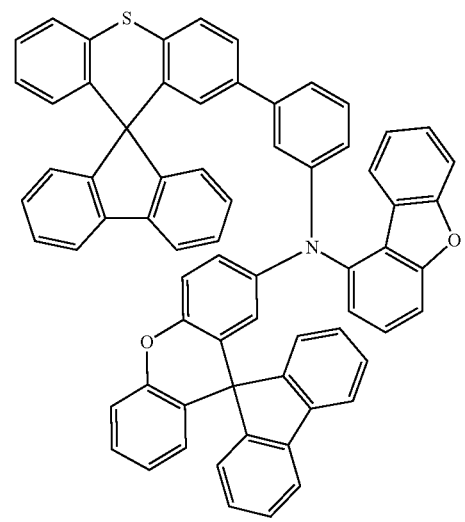
P2-33
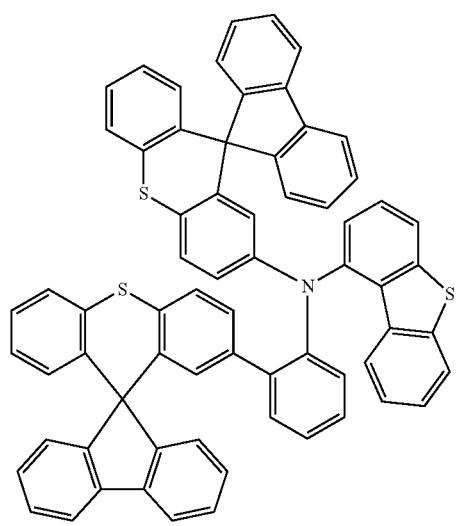
P2-34
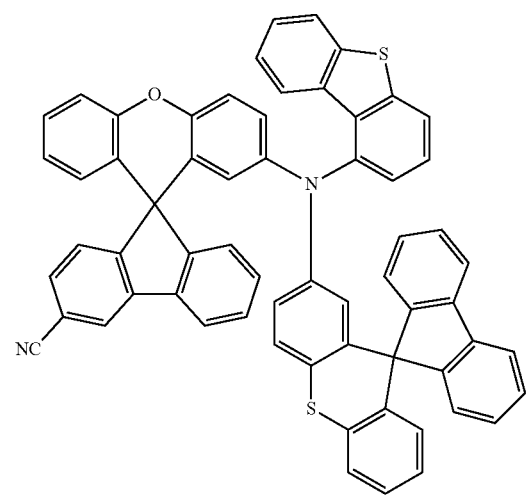
P2-35
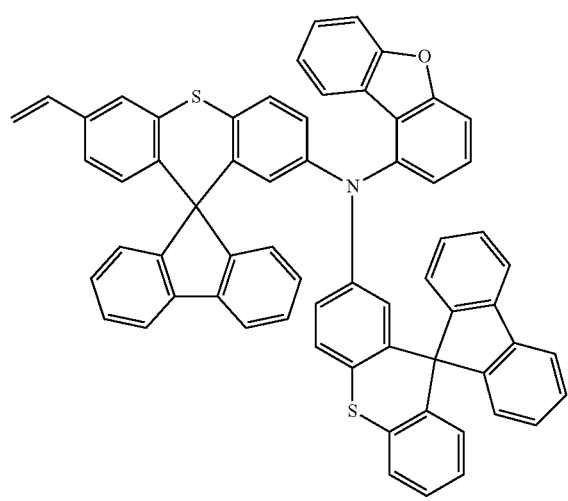
P2-36
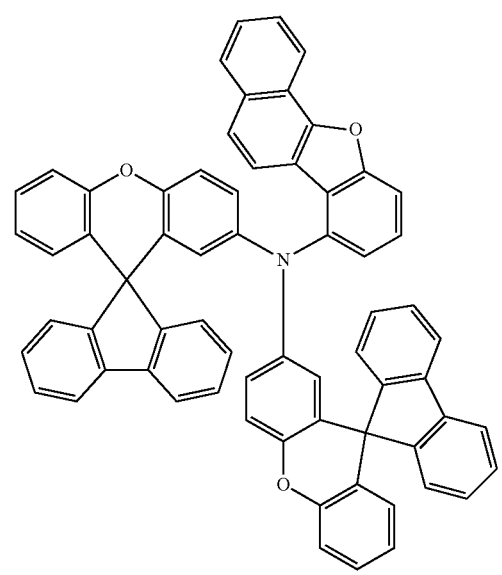

-continued
P2-37
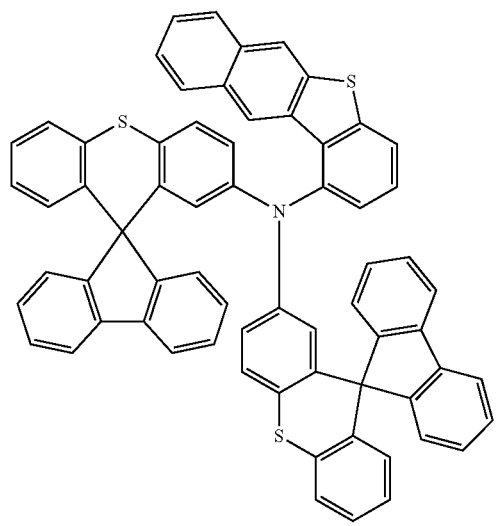
P2-38
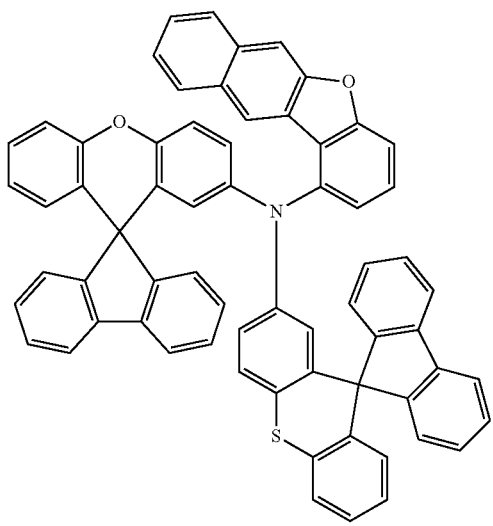
P2-39
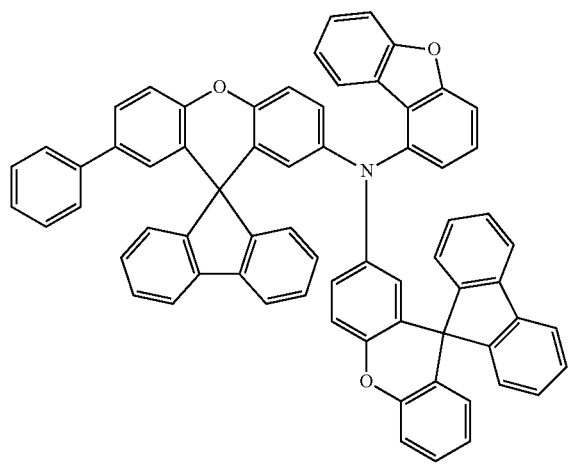
P2-40
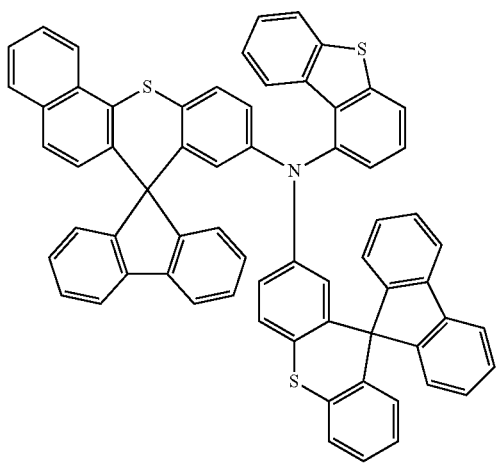
P2-41
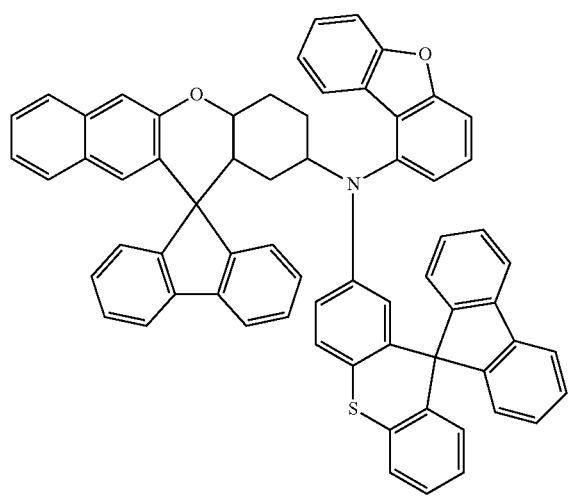
P2-42
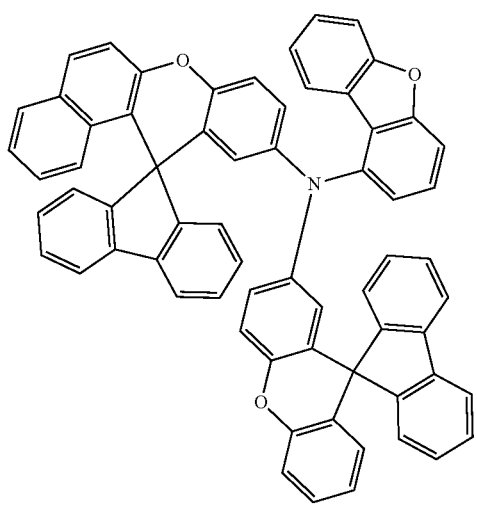

-continued
P2-43
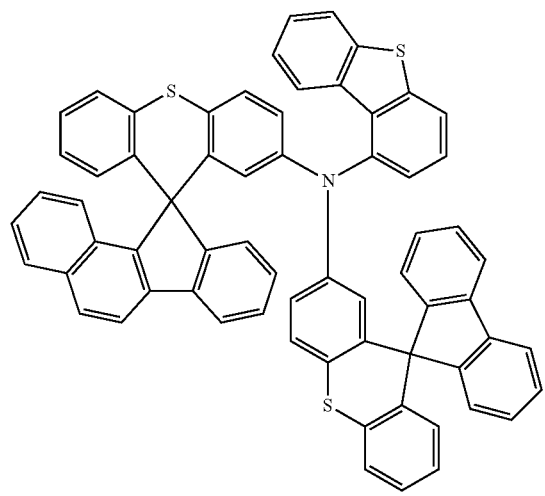
P2-44
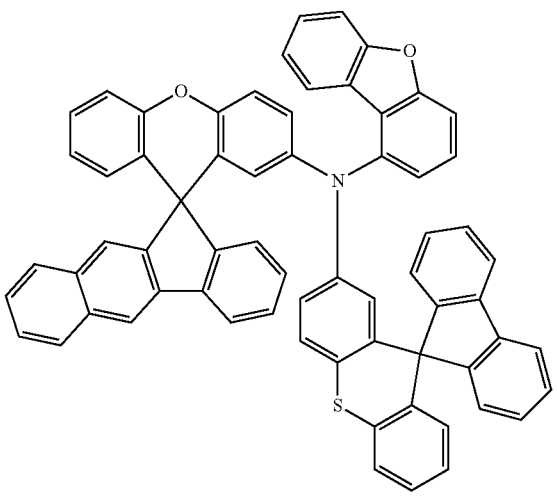
P2-45
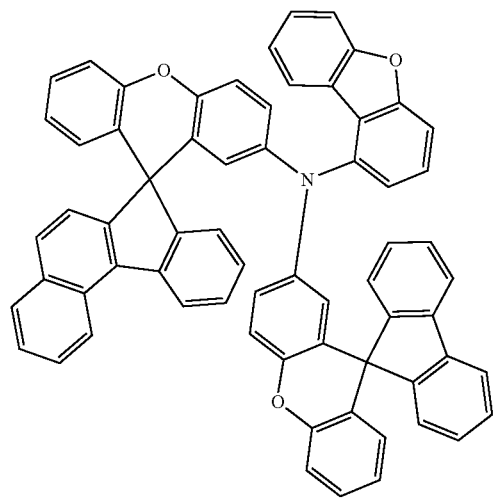
P2-46
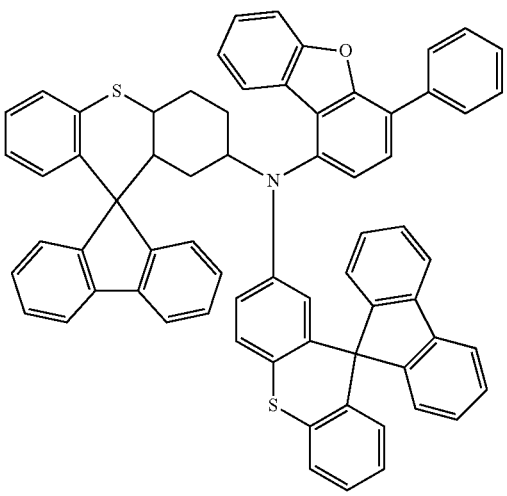
P2-47
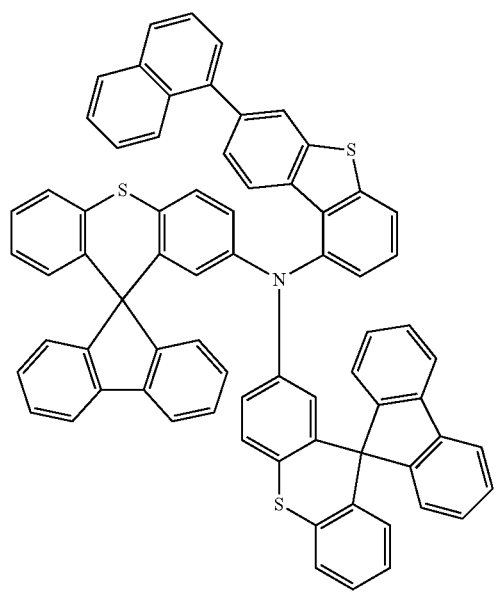
P2-48
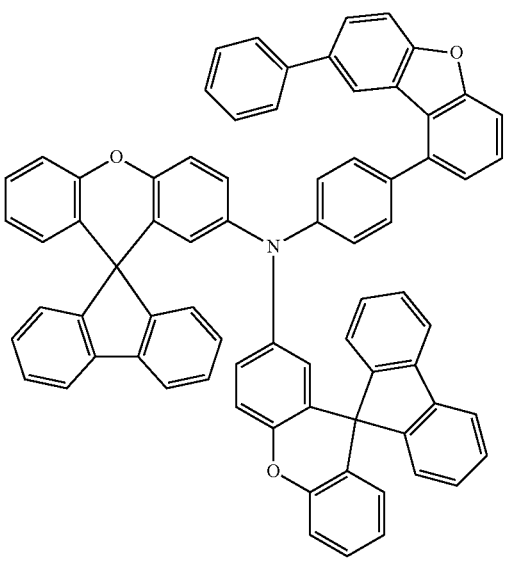

-continued
P2-49
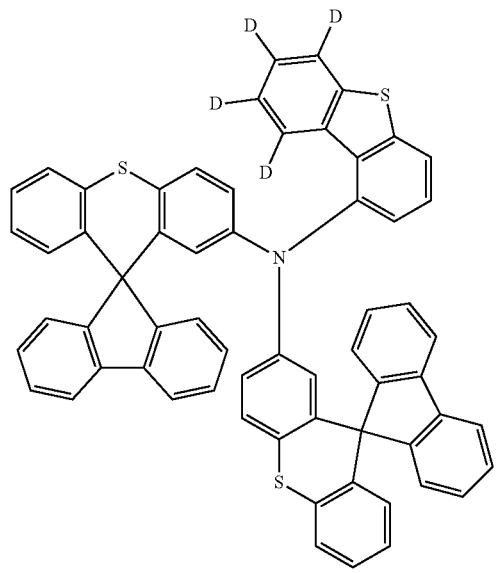
P2-50
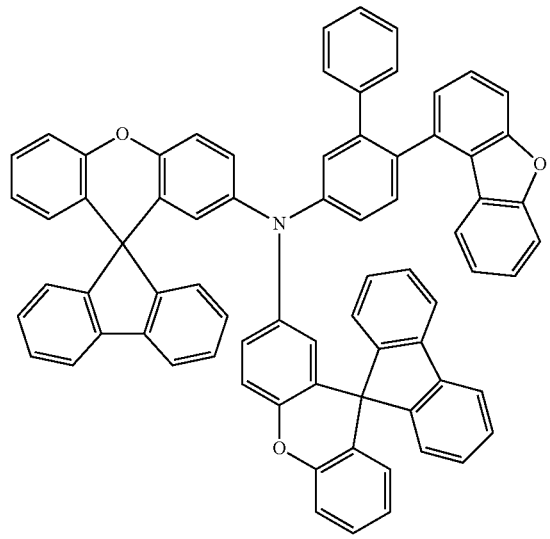
P2-51
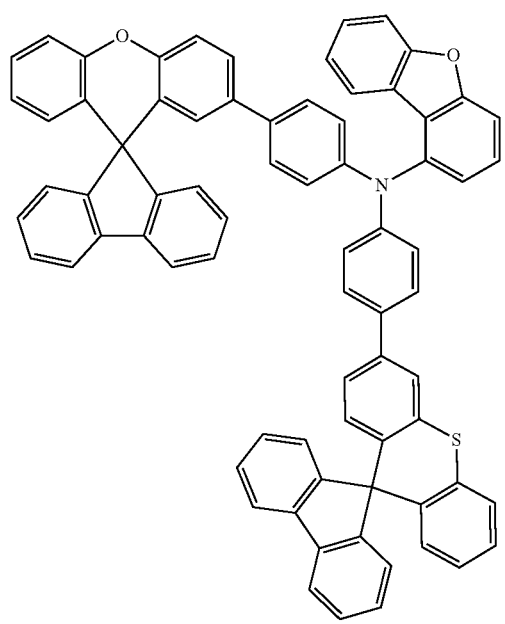
P2-52
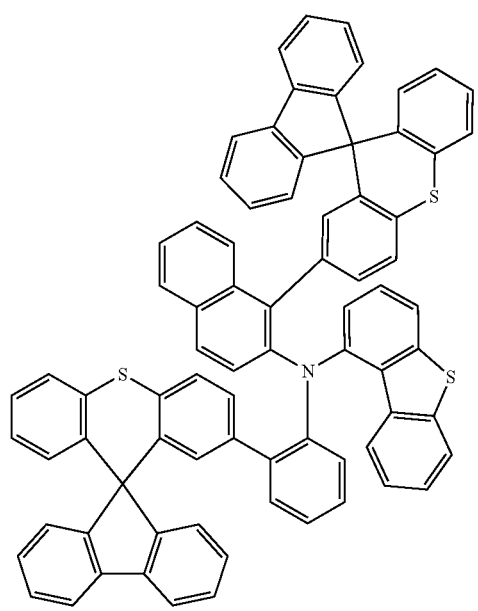

-continued

P2-53

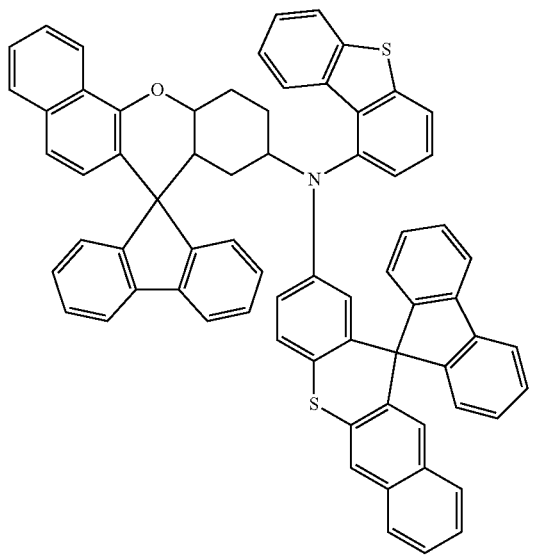

P2-54

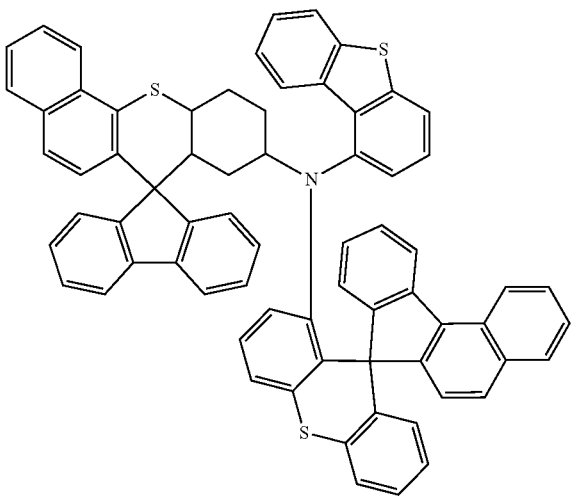

P2-55

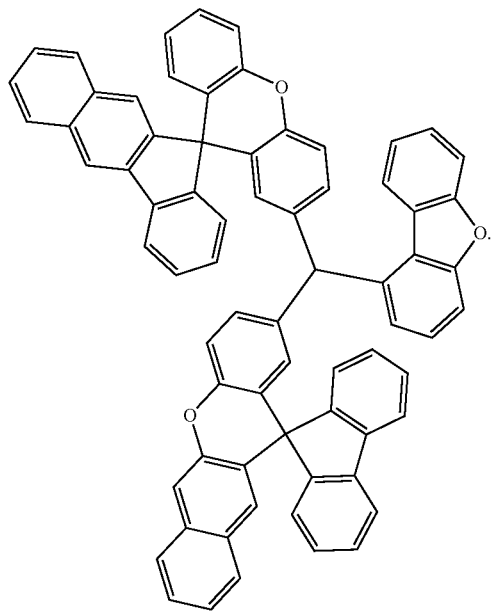

The present invention also provides a compound represented by Formula 7:

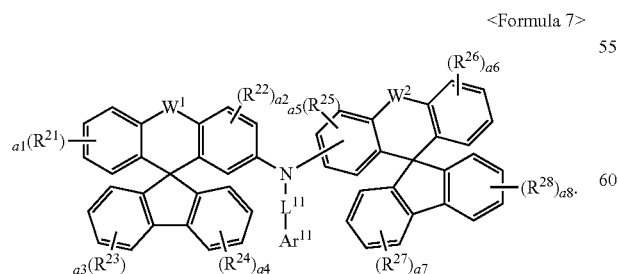

<Formula 7>

In Formula 7,
1) $R^{21}$, $R^{22}$, $R^{23}$, $R^{24}$, $R^{25}$, $R^{26}$, $R^{27}$ and $R^{28}$ are the same as or different each other and are each independently selected from the group consisting of hydrogen; deuterium; halogen; cyano group; nitro group; $C_6$-$C_{60}$ aryl group; a fluorenyl group; a $C_2$-$C_{60}$ heterocyclic group including at least one heteroatom selected from the group consisting of O, N, S, Si or P; a fused ring group of a $C_3$-$C_{60}$ aliphatic ring and a $C_6$-$C_{60}$ aromatic ring; a $C_1$-$C_{60}$ alkyl group; a $C_2$-$C_{60}$ alkenyl group; a $C_2$-$C_{60}$ alkynyl group; a $C_1$-$C_{60}$ alkoxy group; and a $C_6$-$C_{60}$ aryloxy group; or a plurality of adjacent $R^{21}$s, or a plurality of $R^{22}$s, or a plurality of $R^{23}$s, or a plurality of $R^{24}$s, or a plurality of $R^{25}$s, or a plurality of $R^{26}$s, or a plurality of $R^{27}$s, or a plurality of $R^{28}$s can be bonded to each other to form a ring,
2) $W^1$ and $W^2$ are each independently O or S,
3) $L^{11}$ is a single bond; a $C_6$-$C_{60}$ arylene group; a fluorenylene group; a $C_2$-$C_{60}$ heterocyclic group containing at least one hetero atom of O, N, S, Si or P; a fused ring group of a $C_3$-$C_{60}$ aliphatic ring and a $C_6$-$C_{60}$ aromatic ring;

4) $Ar^{11}$ is a $C_6$-$C_{60}$ aryl group;
5) a1, a3, a4, a6, a7 and a8 are each independently an integer of 0 to 4, a2 and a5 are each independently an integer of 0 to 3,
6) wherein, the aryl group, arylene group, heterocyclic group, fluorenyl group, fluorenylene group, aliphatic ring group, fused ring group, alkyl group, alkenyl group, alkynyl group, alkoxyl group and aryloxy group may be substituted with one or more substituents selected from the group consisting of deuterium; halogen; a silane group; siloxane group; boron group; germanium group; cyano group; nitro group; a $C_1$-$C_{20}$ alkylthio group; $C_1$-$C_{20}$ alkoxy group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group and $C_8$-$C_{20}$ arylalkenyl group, wherein the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

In one embodiment, Formula 7 is represented by one of Formulas 7-1 to 7-3:

<Formula 7-1>

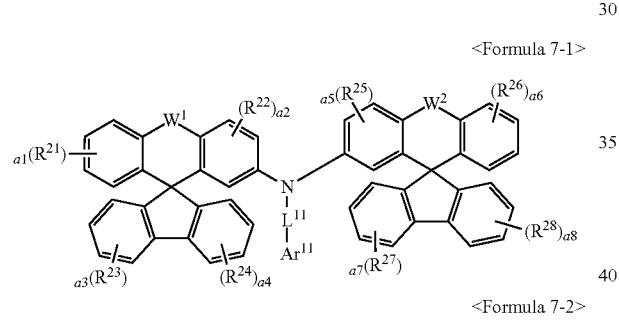

<Formula 7-2>

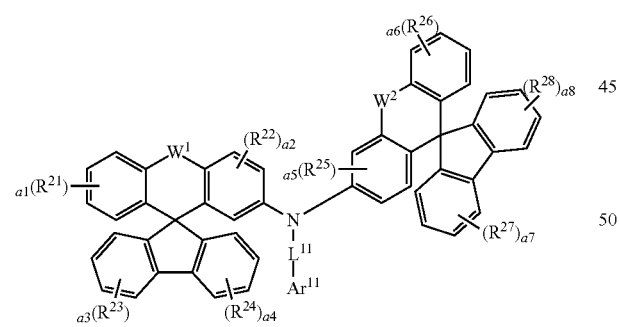

<Formula 7-3>

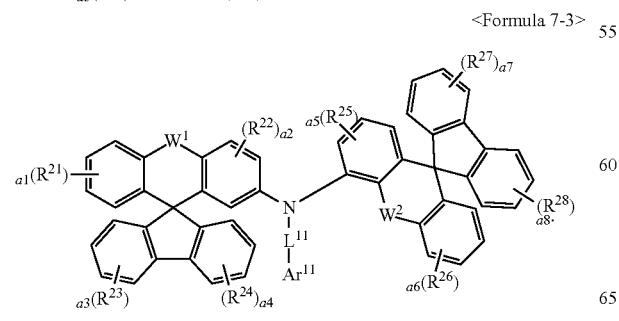

In Formulas 7-1 to 7-3, $R^{21}$, $R^{22}$, $R^{23}$, $R^{24}$, $R^{25}$, $R^{26}$, $R^{27}$ and $R^{28}$, $W^1$, $W^2$, $L^{11}$, $Ar^{11}$, and $a^1$, $a^2$, $a^3$, $a^4$, $a^5$, $a^6$, $a^7$ and $a^8$ are the same as defined for those in Formula 7.

In one embodiment, $L^{11}$ of Formula 7 is represented by one of Formulas a-1 to a-5:

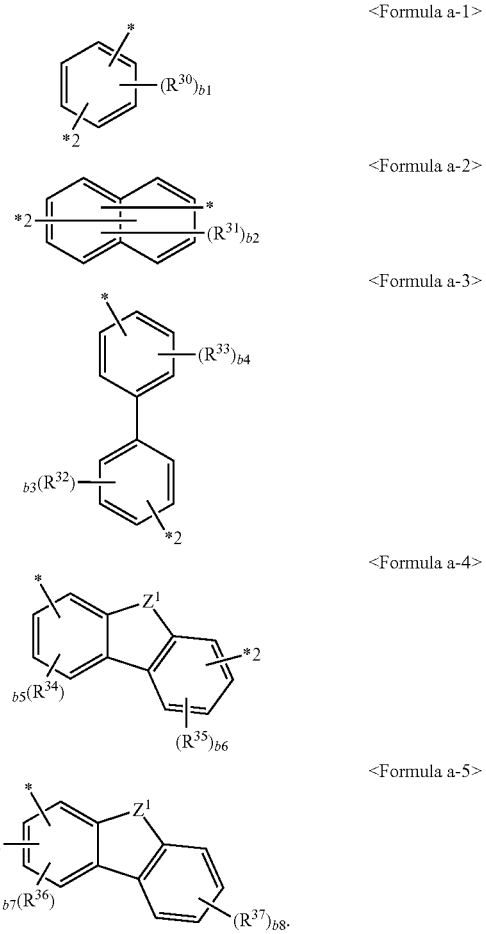

In Formulas a-1 to a-5,
1) $R^{30}$, $R^{31}$, $R^{32}$, $R^{33}$, $R^{34}$, $R^3$, $R^{36}$ and $R^{37}$ are the same as the definition of $R^{21}$,
2) b1, b3, b4 and b8 are each independently an integer of 0 to 4, b2 is an integer of 0 to 6, b5 and b6 are each independently an integer of 0 to 3, and b7 is an integer of 0 to 2,
3) $Z^1$ is O or S,
4) * means a position bonded to N (nitrogen) in Formula 7, and *2 means a position bonded to $Ar^{11}$ in Formula 7.

In another embodiment, $L^{11}$ is represented by one of Formulas a-6 to a-46:

<Formula a-6>

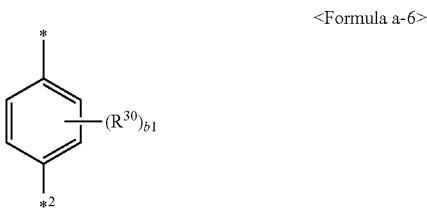

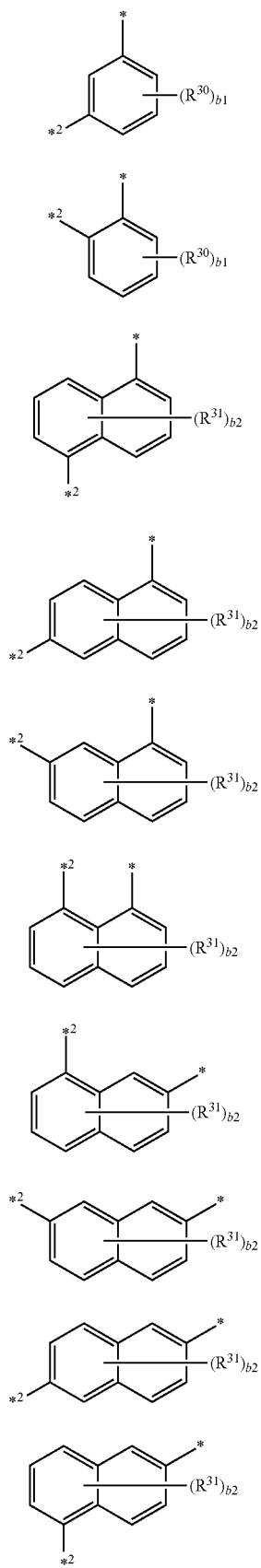
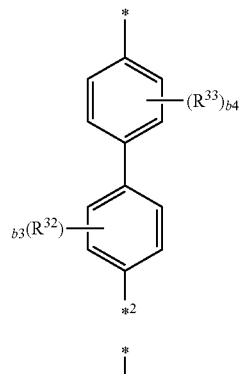
<Formula a-17>
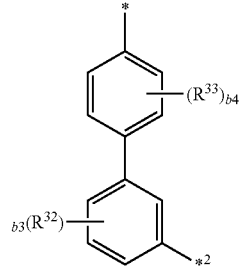
<Formula a-18>
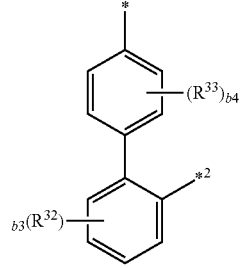
<Formula a-19>
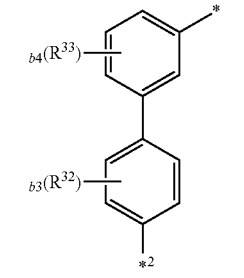
<Formula a-20>
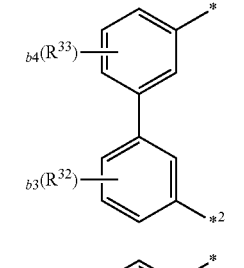
<Formula a-21>
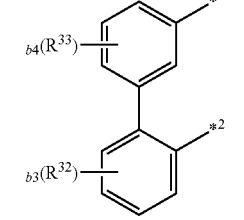
<Formula a-22>

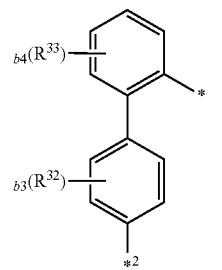
<Formula a-23>

<Formula a-24>
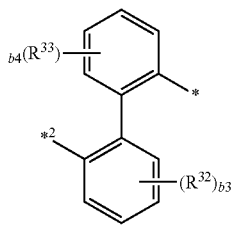
<Formula a-25>
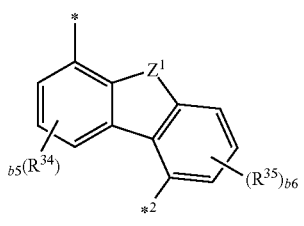
<Formula a-26>

<Formula a-27>

<Formula a-28>
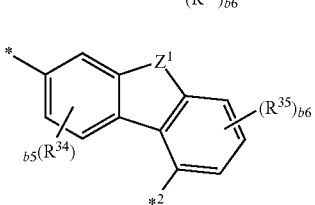
<Formula a-29>
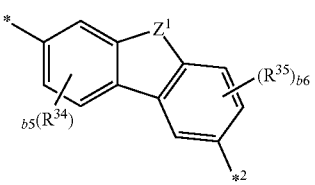
<Formula a-30>
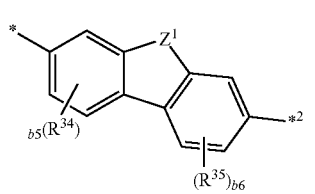
<Formula a-31>
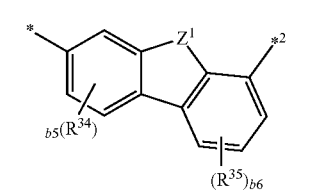
<Formula a-32>
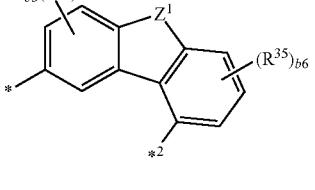
<Formula a-33>
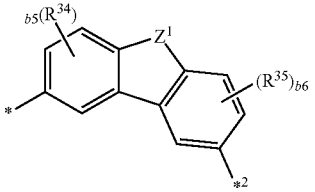
<Formula a-34>
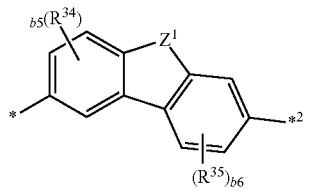
<Formula a-35>
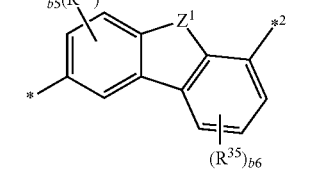
<Formula a-36>
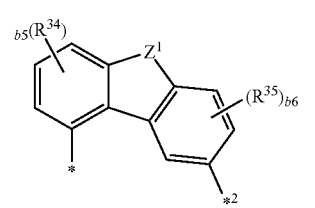
<Formula a-37>

<Formula a-38>
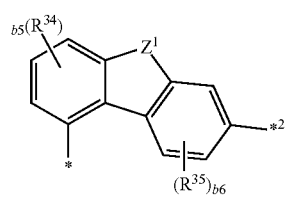
<Formula a-39>
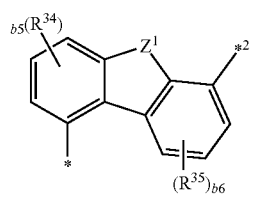
<Formula a-40>
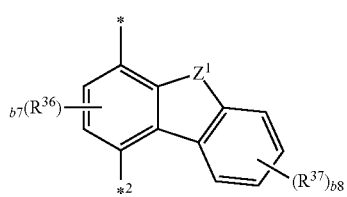
<Formula a-41>
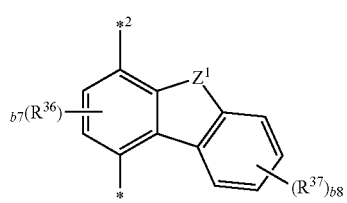
<Formula a-42>
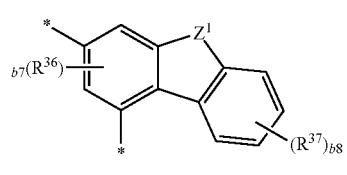
<Formula a-43>
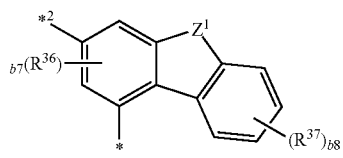
<Formula a-44>
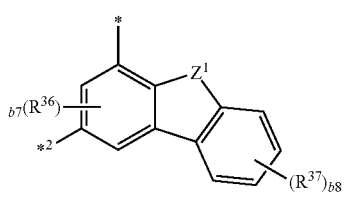
<Formula a-45>
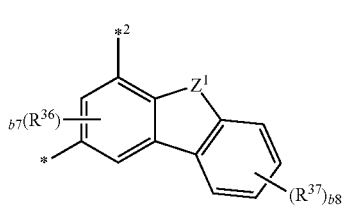
<Formula a-46>
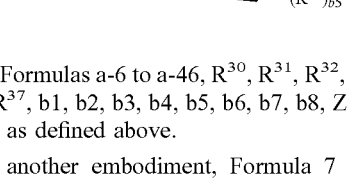
In Formulas a-6 to a-46, $R^{30}$, $R^{31}$, $R^{32}$, $R^{33}$, $R^{34}$, $R^{35}$, $R^{36}$ and $R^{37}$, b1, b2, b3, b4, b5, b6, b7, b8, $Z^1$, * and *2 are the same as defined above.
In another embodiment, Formula 7 is represented by Formula 7-4 or Formula 7-5:
<Formula 7-4>
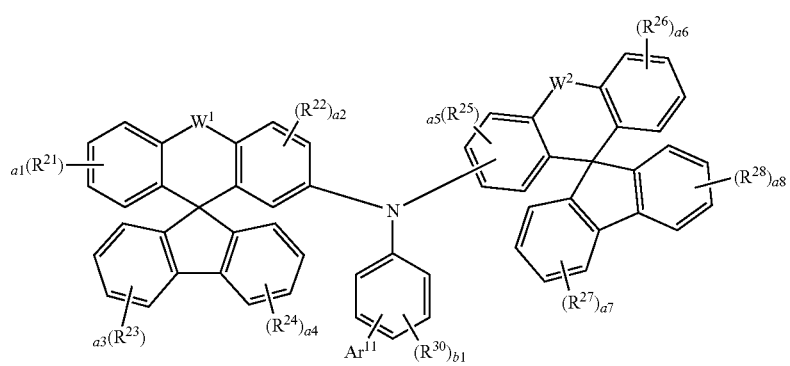

-continued

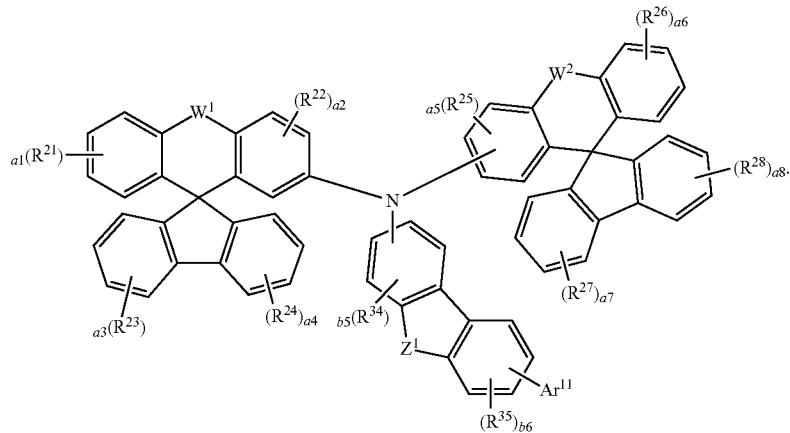

<Formula 7-5>

In Formula 7-4 and Formula 7-5,
1) $R^{21}$, $R^{22}$, $R^{23}$, $R^{24}$, $R^{25}$, $R^{26}$, $R^{27}$ and $R^{28}$ are the same as defined above,
2) $R^{30}$, $R^{34}$, $R^{35}$, b1, b5, b6 and $Z^1$ are the same as defined above.

In another embodiment, Formula 7 is represented by Formula 7-6:

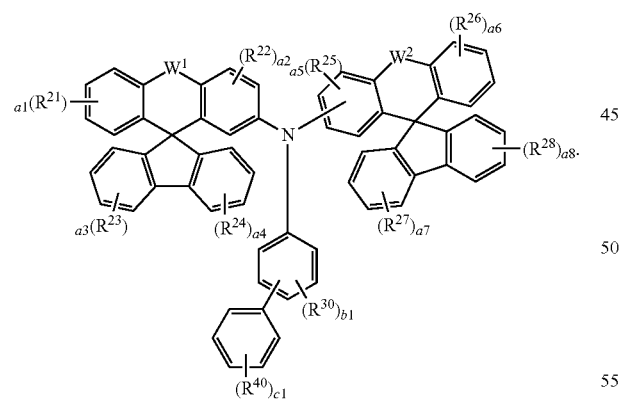

<Formula 7-6>

In Formula 7-6,
1) $R^{21}$, $R^{22}$, $R^{23}$, $R^{24}$, $R^{25}$, $R^{26}$, $R^{27}$ and $R^{28}$, a1, a2, a3, a4, a5, a6, a7 and a8, $W^1$ and $W^2$ are the same as defined above,
2) $R^{30}$ and b1 are the same as the defined above,
3) $R^{41}$ is the same as the definition of $R^{21}$,
4) c1 is an integer of 0 to 5.

In another embodiment, Formula 7 is represented by Formula 7-7:

<Formula 7-7>

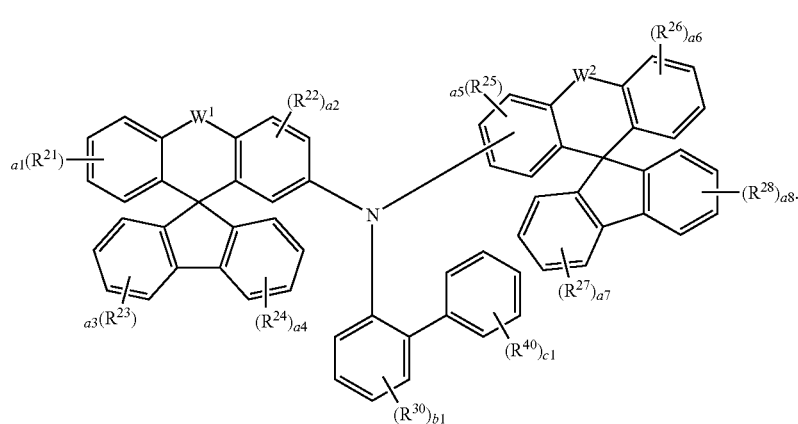

In Formula 7-7,
1) $R^{21}$, $R^{22}$, $R^{23}$, $R^{24}$, $R^{25}$, $R^{26}$, $R^{27}$ and $R^{28}$, a1, a2, a3, a4, a5, a6, a7 and a8, $W^1$ and $W^2$ are the same as defined above,
2) $R^{30}$ and b1 are the same as defined above,
3) $R^{40}$ is the same as the definition of $R^{21}$,
4) c1 is an integer of 0 to 5.

In another embodiment, Formula 7 is preferably represented by Formula 7-8:

<Formula 7-8>

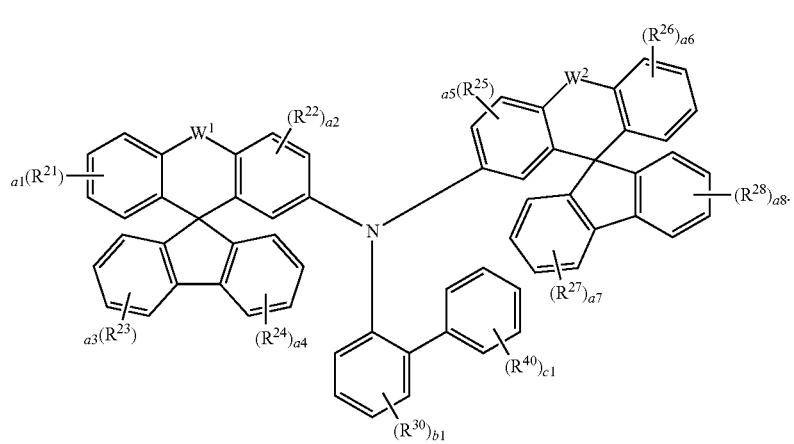

In Formula 7-8, $R^{21}$, $R^{22}$, $R^{23}$, $R^{24}$, $R^{25}$, $R^{26}$, $R^{27}$, $R^{28}$, $R^{30}$ and $R^{40}$, a1, a2, a3, a4, a5, a6, a7 and a8, b1, c1, $W^1$ and $W^2$ are the same as defined above.

In another embodiment, Formula 7 is preferably represented by one of Formulas 7-9 to 7-11:

<Formula 7-9>

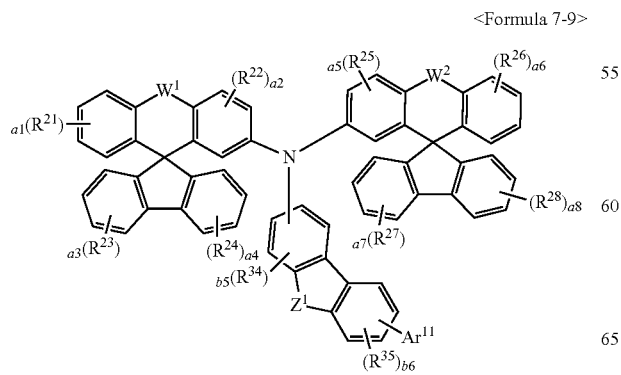

-continued

<Formula 7-10>

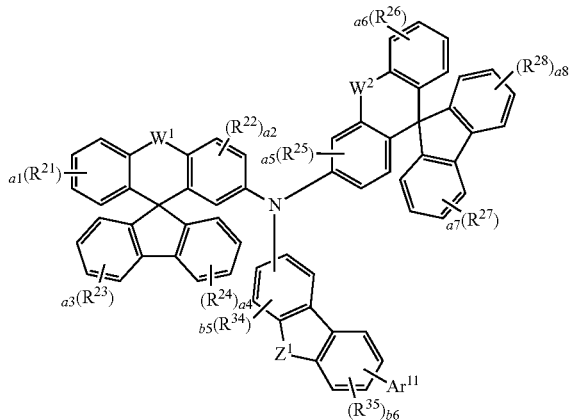

<Formula 7-11>

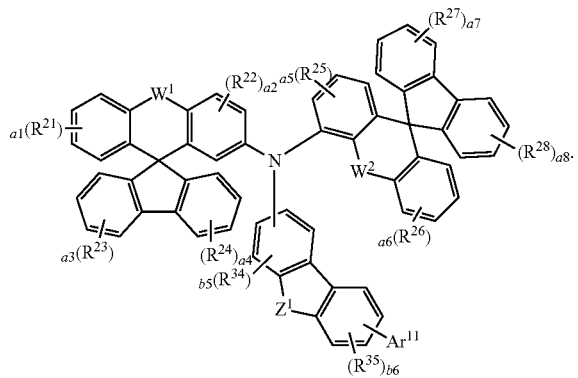

In Formulas 7-9 to 7-11, $R^{21}$, $R^{22}$, $R^{23}$, $R^{24}$, $R^{25}$, $R^{26}$, $R^{27}$, $R^{28}$, $R^{34}$ and $R^{35}$, a1, a2, a3, a4, a5, a6, a7 and a8, b5, b6, $W^1$, $W^2$, $Ar^{11}$ and $Z^1$ are defined the same as above.

In another embodiment, Formula 7 is preferably represented by Formula 7-12:

<Formula 7-12>

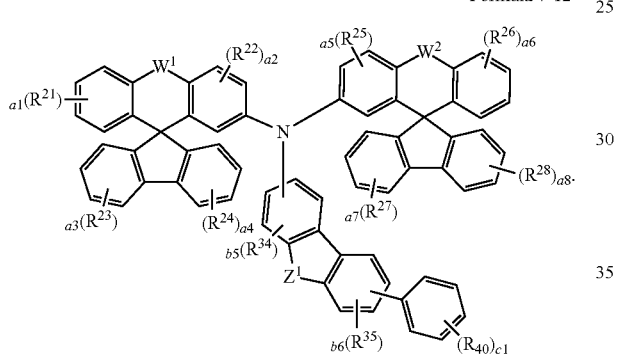

In Formula 7-12, $R^{21}$, $R^{22}$, $R^{23}$, $R^{24}$, $R^{25}$, $R^{26}$, $R^{27}$, $R^{28}$, $R^{34}$, $R^{35}$ and $R^{40}$, a1, a2, a3, a4, a5, a6, a7 and a8, b5, b6, c1, $W^1$, $W^2$, $Ar^{11}$ and $Z^1$ are the same as defined above.

A non-limiting example of the compound of Formula 7 includes Compounds P2-46, P2-47, and P3-1 to P3-40:

P2-46

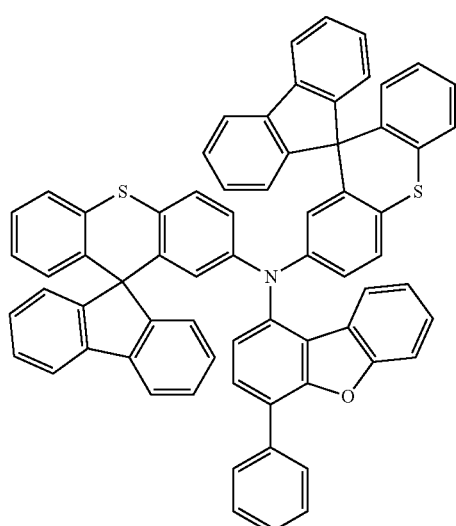

P2-47

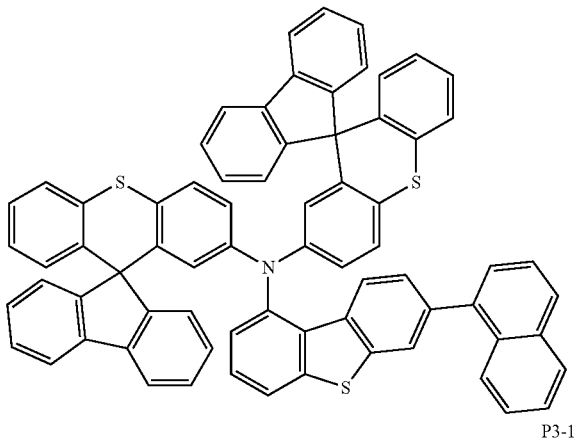

P3-1

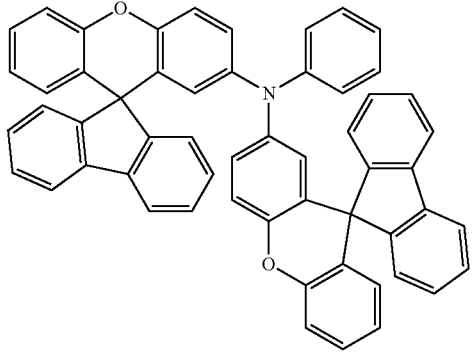

P3-2

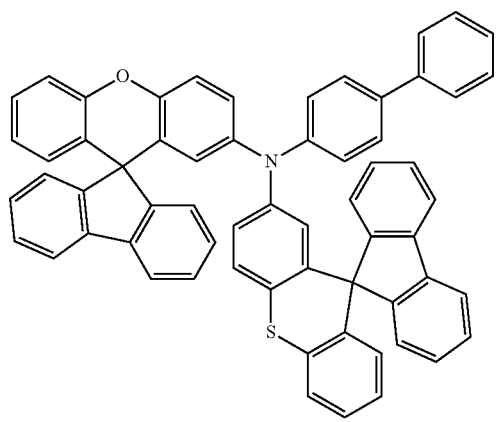

P3-3

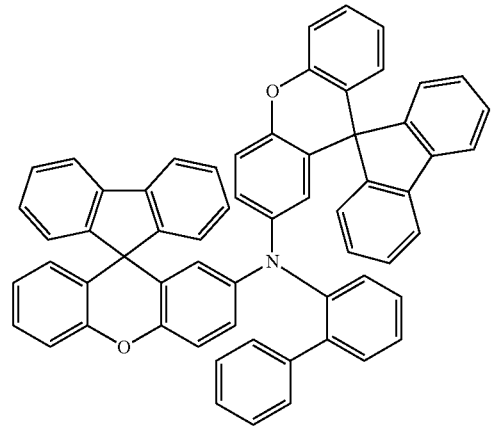

P3-4
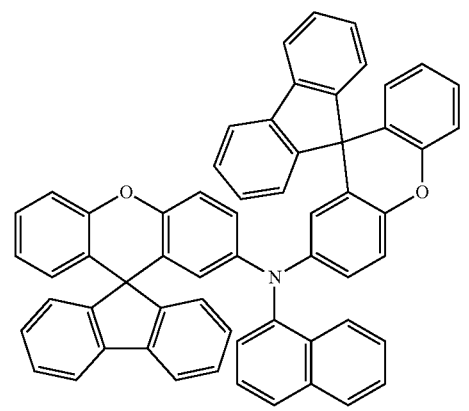
P3-5
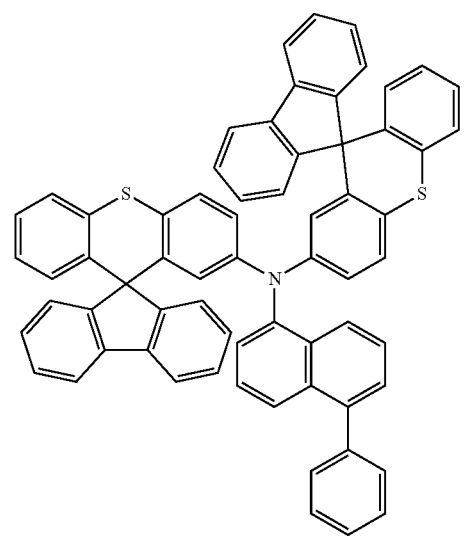
P3-6
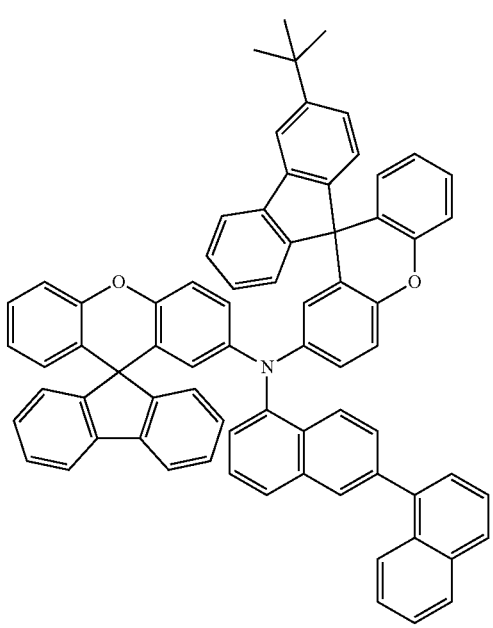
P3-7
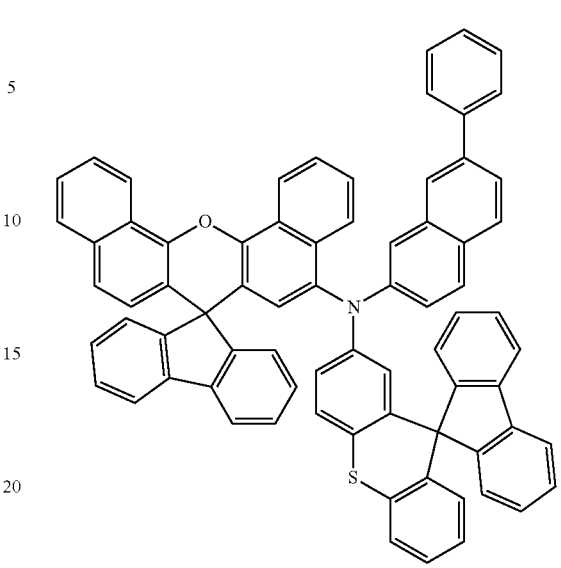
P3-8
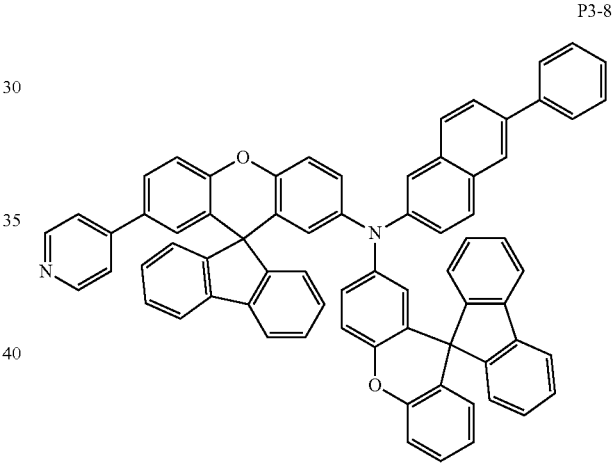
P3-9
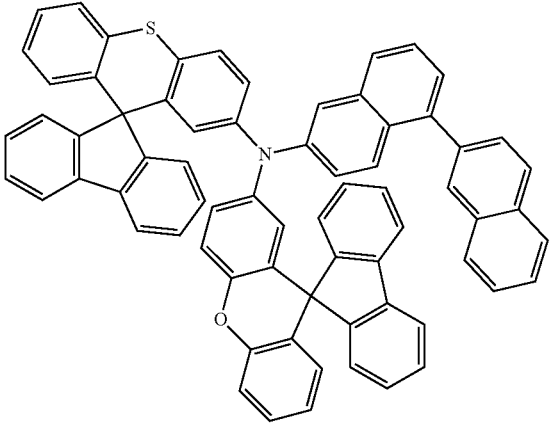

-continued
P3-10
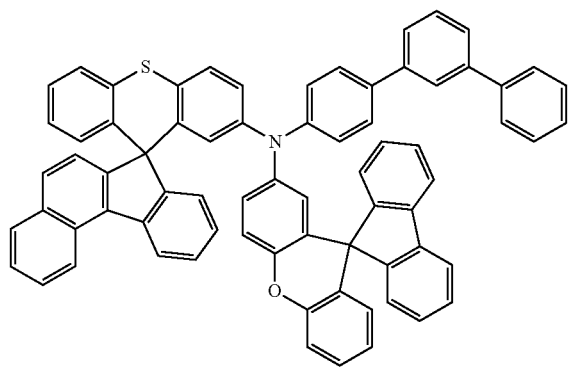
P3-11
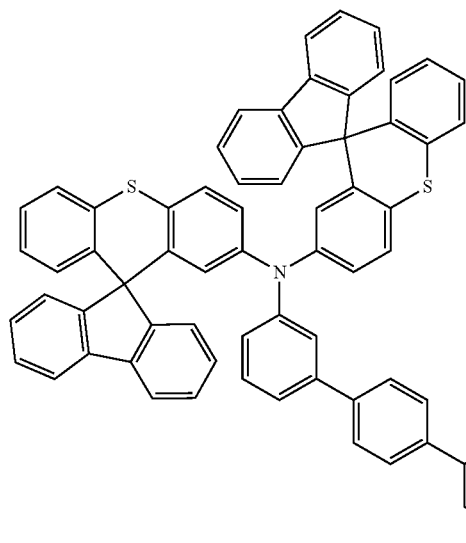
P3-12
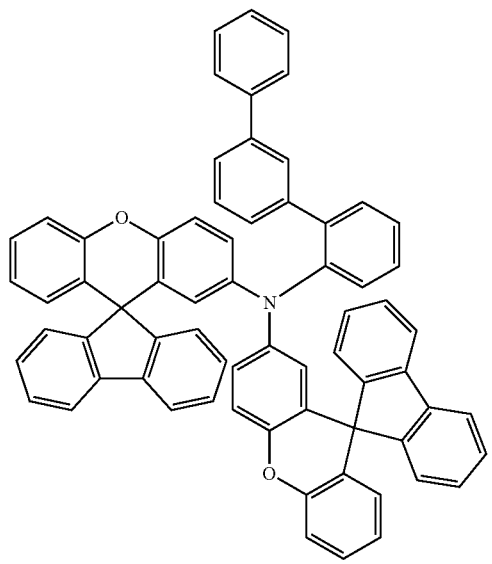
-continued
P3-13
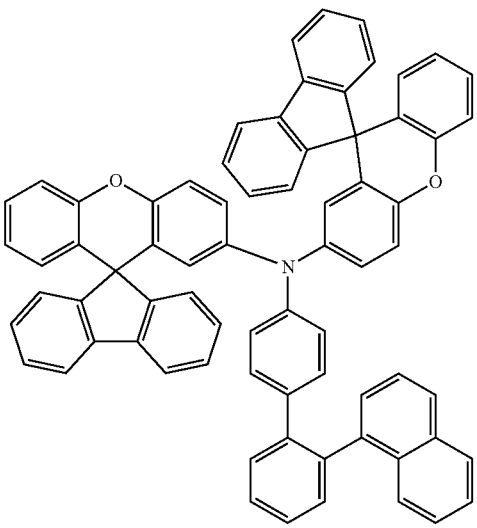
P3-14
P3-15
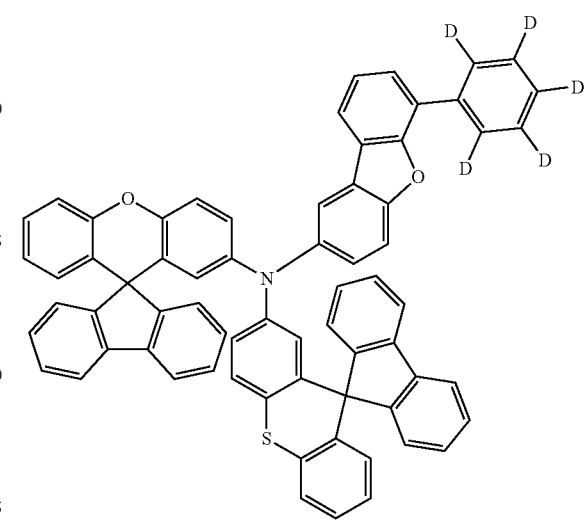

P3-16
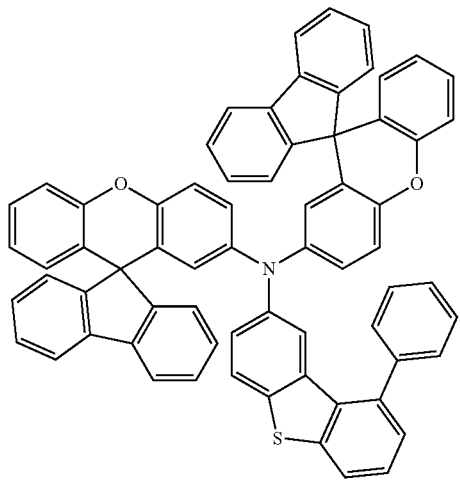
P3-17
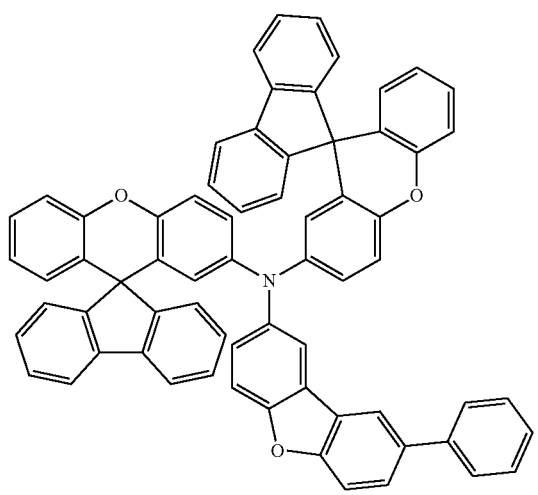
P3-18
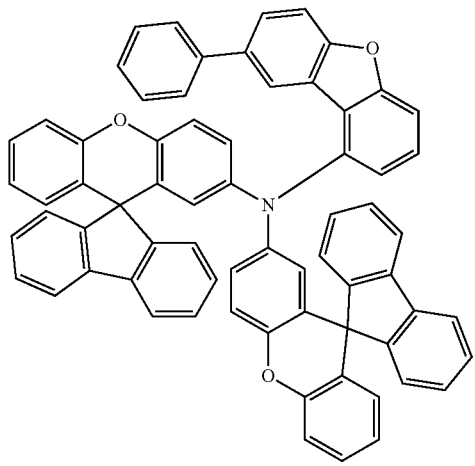
P3-19
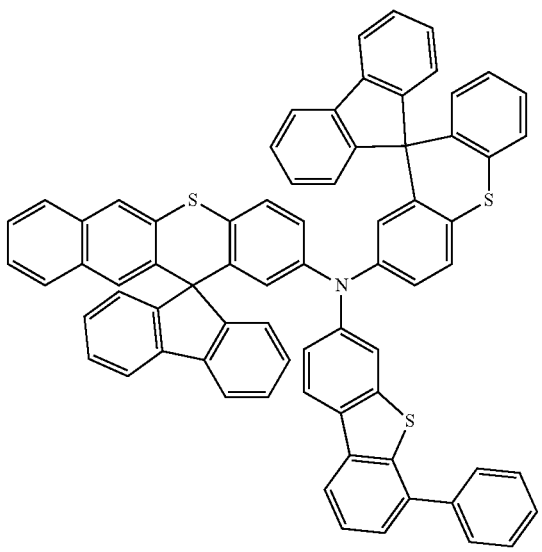
P3-20
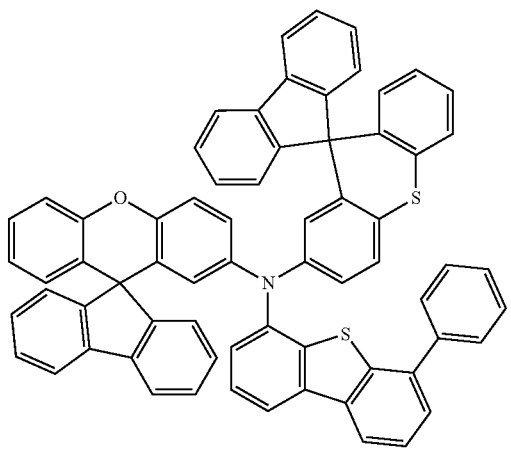
P3-21
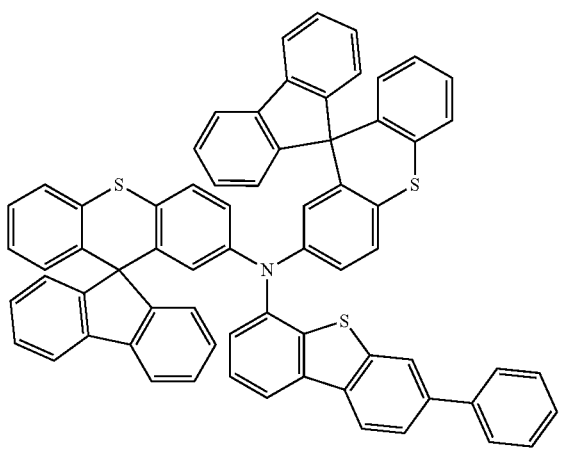

P3-22
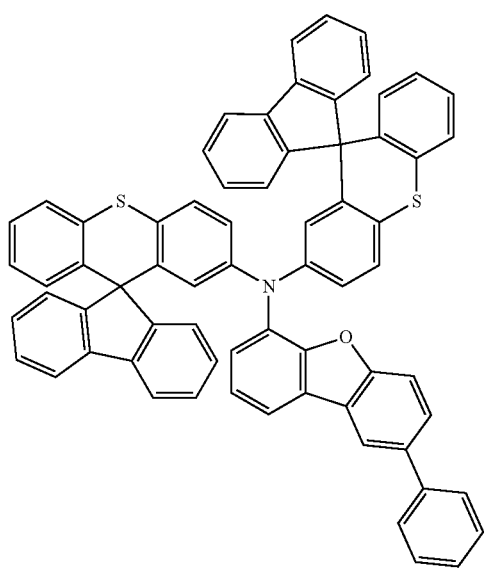
P3-25
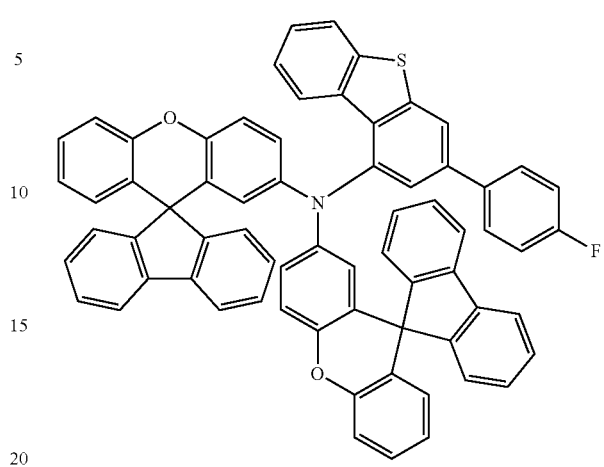
P3-23
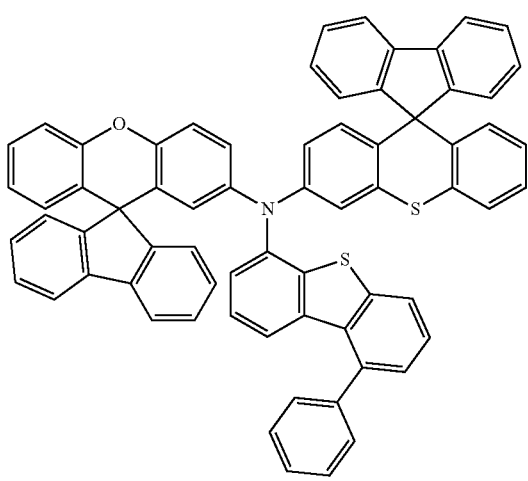
P3-26
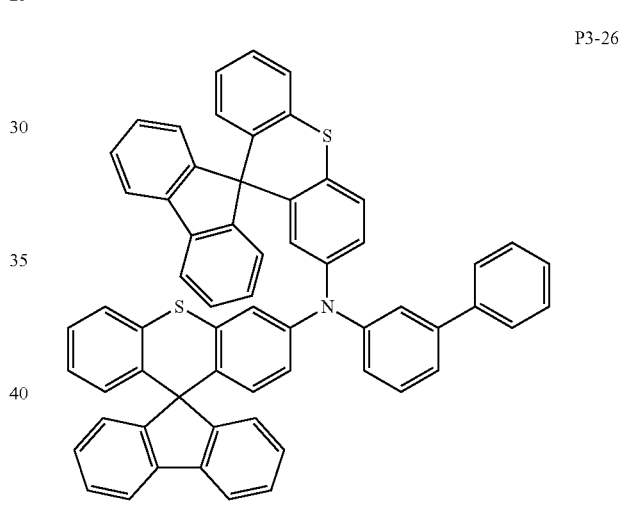
P3-24
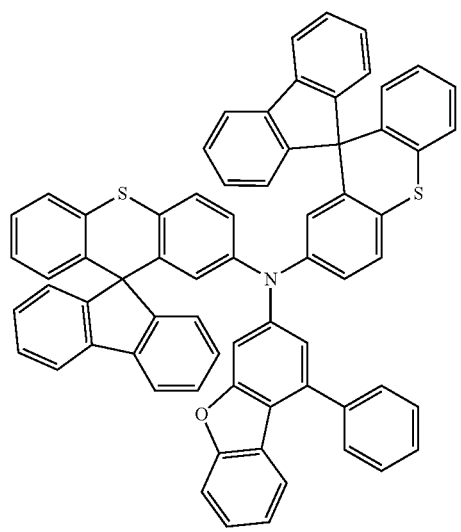
P3-27
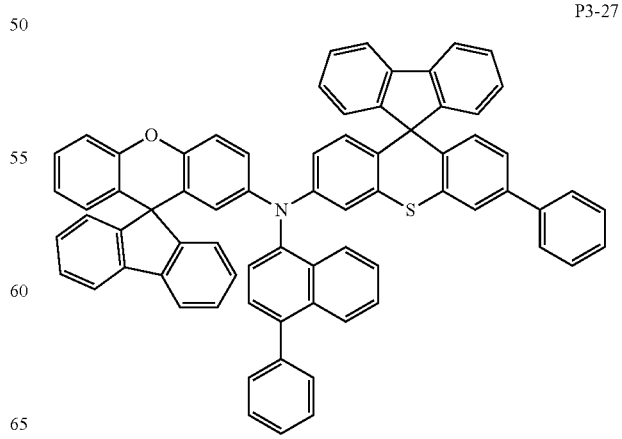

P3-28
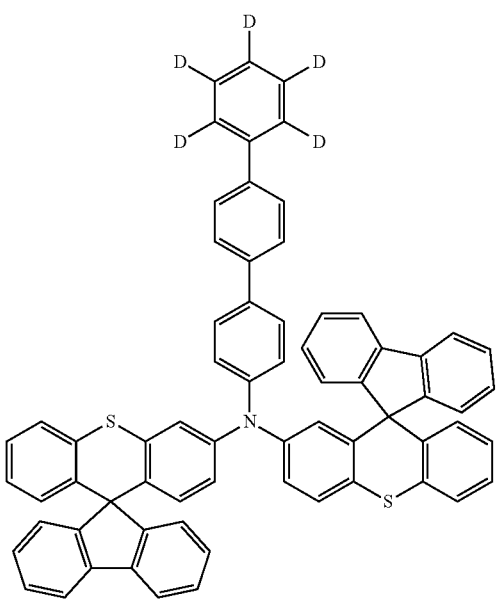
P3-30
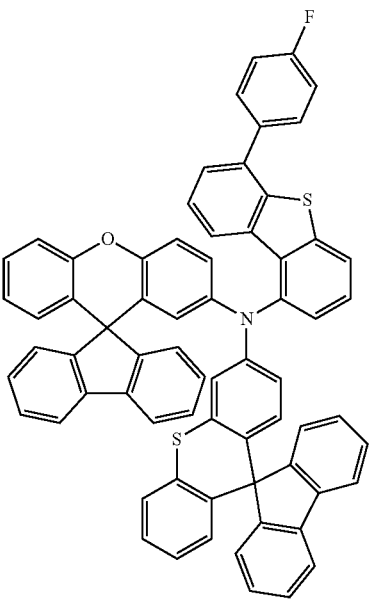
P3-29
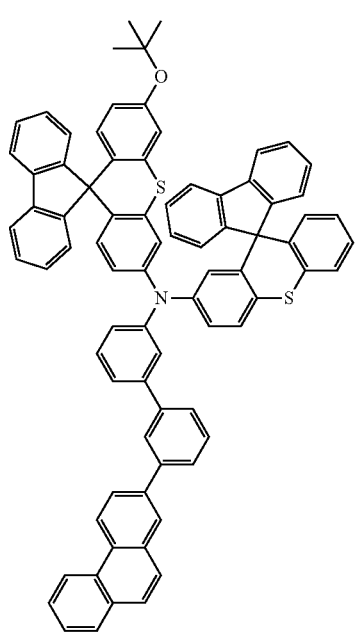
P3-31
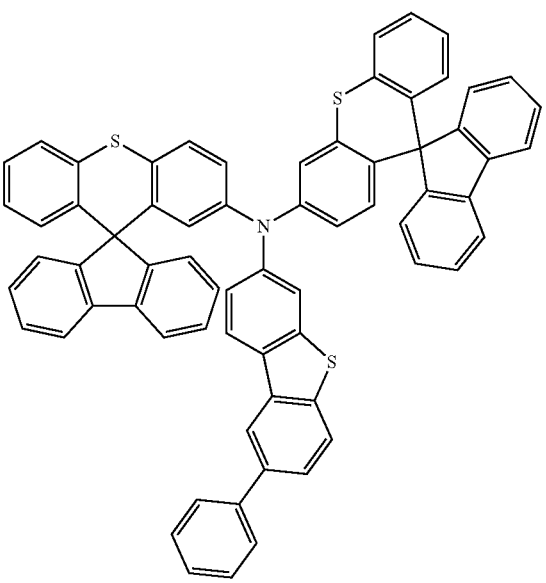

-continued
P3-32
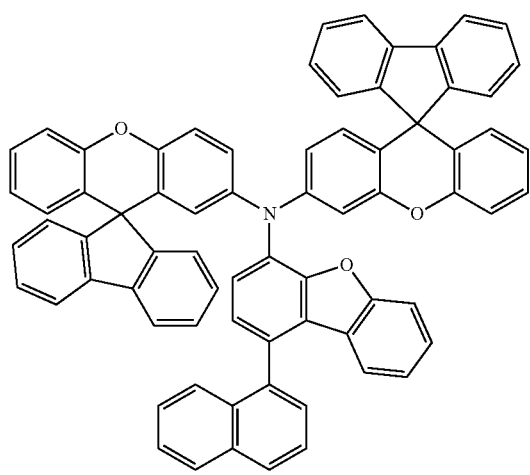
P3-35
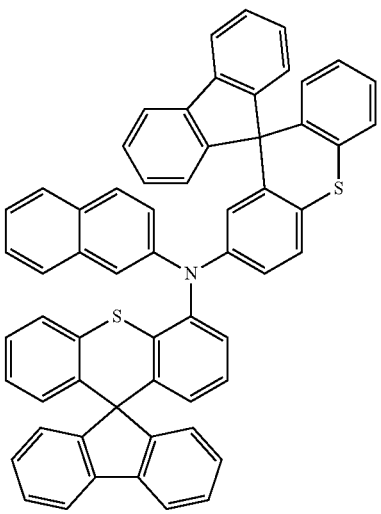
P3-33
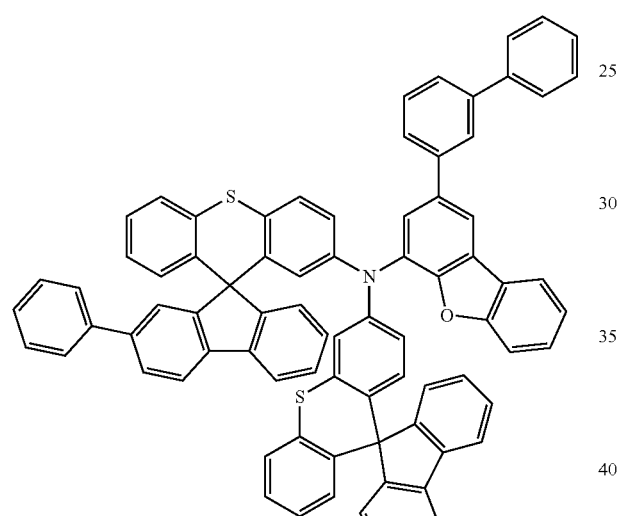
P3-36
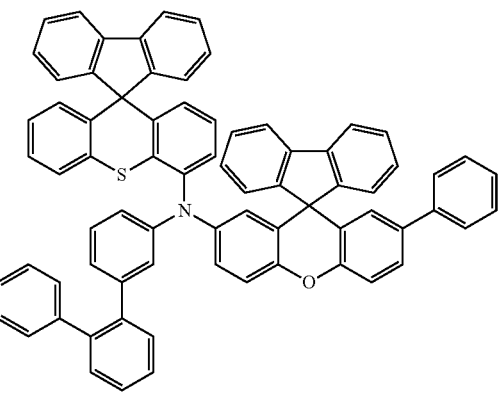
P3-34
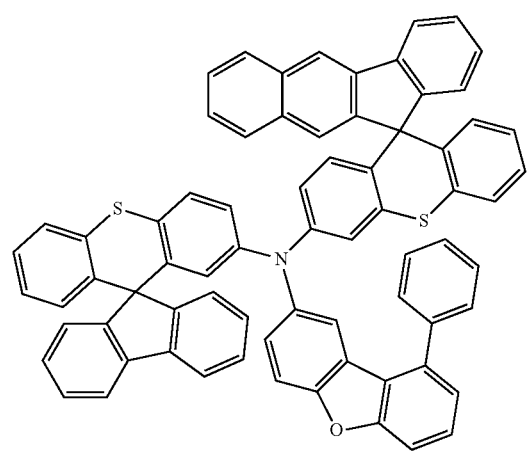
P3-37
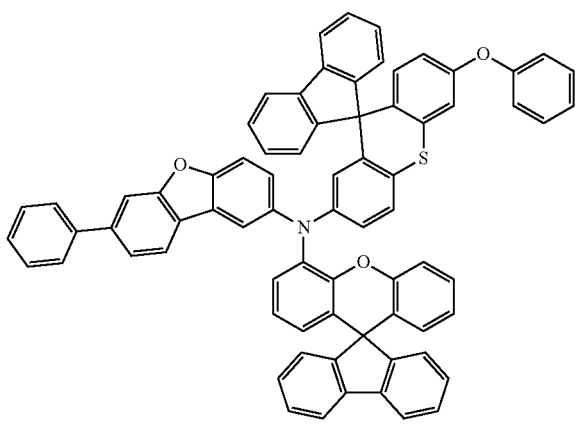

-continued

P3-38
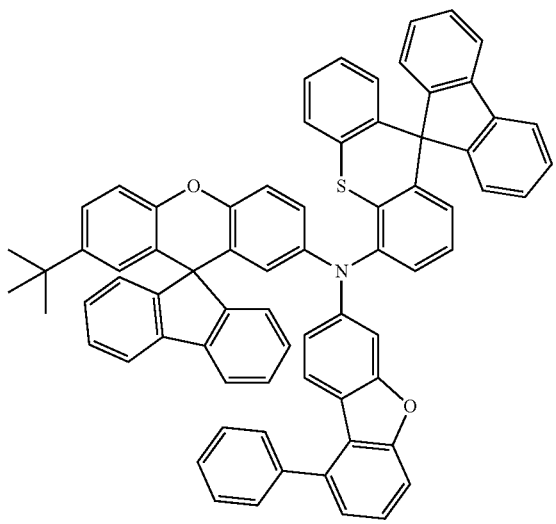

P3-39
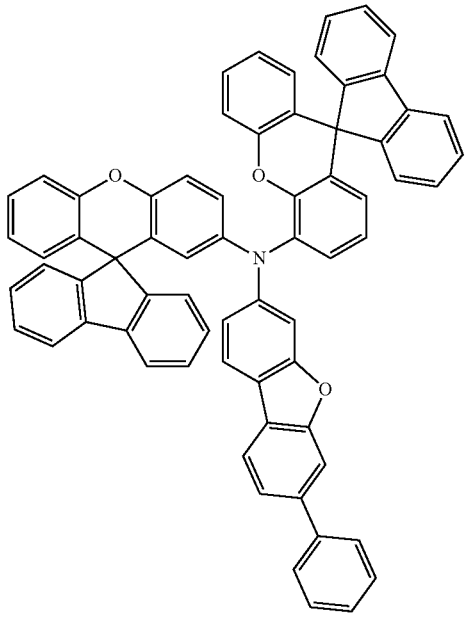

P3-40
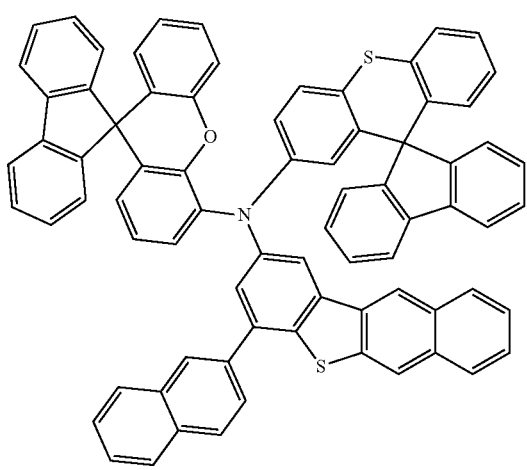

Referring to FIG. 1, the organic electronic element (100) according to the present invention includes a first electrode (110), a second electrode (170), an organic material layer comprising one or more compounds represented by Formula 1 or 2 or 7 between the first electrode (110) and the second electrode (170). Here, the first electrode (110) may be an anode or a positive electrode, and the second electrode (170) may be a cathode or a negative electrode. In the case of an inverted organic electronic element, the first electrode may be a cathode, and the second electrode may be an anode.

Figure 2:
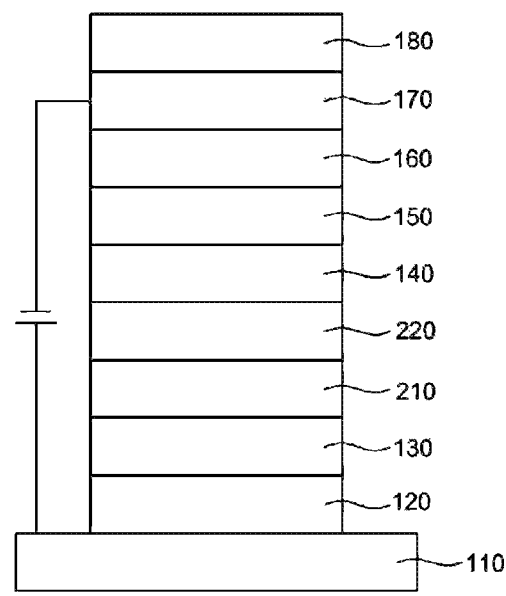

The organic material layer may sequentially include a hole injection layer(120), a hole transport layer (130), an emitting layer(140), an electron transport layer(150), and an electron injection layer(160) formed in sequence on the first electrode(110). Here, the remaining layers except the emitting layer (140) may not be formed. The organic material layer may further include a hole blocking layer, an electron blocking layer, an emitting-auxiliary layer(220), a buffer layer(210), etc., and the electron transport layer(150) and the like may serve as a hole blocking layer. (see FIG. 2)

Also, the organic electronic element according to an embodiment of the present invention may further include a protective layer or a light efficiency enhancing layer (180). The light efficiency enhancing layer may be formed on a surface not in contact with the organic material layer among both surfaces of the first electrode or on a surface not in contact with the organic material layer among both surfaces of the second electrode. The compound according to an embodiment of the present invention applied to the organic material layer may be used as a material for a hole injection layer(120), a hole transport layer (130), an emitting-auxiliary layer(220), an electron transport auxiliary layer, an electron transport layer(150), an electron injection layer (160), a host or dopant of an emitting layer(140) or the light efficiency enhancing layer. Preferably, for example, the compound according to Formula 1 or 7 of the present invention may be used as a material for the emitting-auxiliary layer. Another aspect of the present invention is to provide an organic electronic element comprising a first electrode (e.g., anode), a second electrode (e.g., cathode), and an organic material layer formed between the first and second electrodes, wherein the organic material layer comprises a compound represented by Formula 7.

Particularly, the organic material layer may comprise at least one of a hole injection layer, a hole transport layer, an emitting auxiliary layer, an emitting layer, an electron transport auxiliary layer, an electron transport layer, and an electron injection layer.

Figure 3:
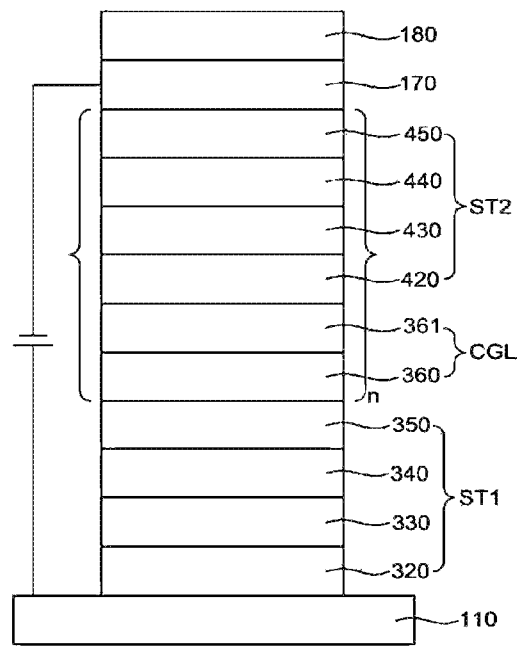
Figure 4:
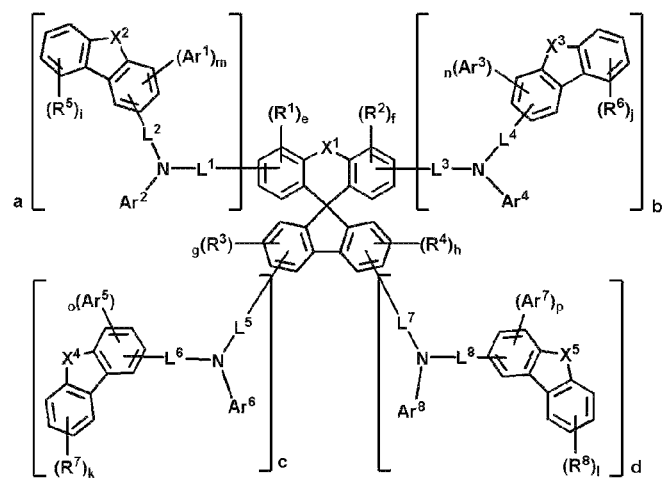
FIG. 4 shows the formula of a compound according to one aspect of the present invention.

In one embodiment, the organic material layer may be preferably an emitting auxiliary layer. In another embodiment, the organic material layer may comprise an emitting layer, a hole transport layer which may be formed between the first electrode and the emitting layer, and a plurality of emitting auxiliary layers which may be formed between the hole transport layer and the emitting layer. At least one of the plural emitting auxiliary layers may comprise a compound represented by Formula 7. In one embodiment, the plural emitting auxiliary layers may comprise a first emitting auxiliary layer which is formed adjacent to the hole transport layer, and a second emitting auxiliary layer which is formed adjacent to the emitting layer. The compound of Formula 7 according to one aspect of the present invention may be comprised in the first emitting auxiliary layer, and/or the second emitting auxiliary layer. The organic material layer may include 2 or more stacks including a hole transport layer, an emitting layer, and an electron transport layer sequentially formed on the anode, and may further include a charge generation layer formed between the 2 or more stacks (see FIG. 3). In one embodiment, the organic material layer further comprises a charge generation layer formed between the 2 or more stacks of layers.

Otherwise, even if the same core is used, the band gap, the electrical characteristics, the interface characteristics, and the like may vary depending on which substituent is bonded at which position, therefore the choice of core and the combination of sub-substituents associated therewith is also very important, and in particular, when the optimal combination of energy levels and T1 values and unique properties of materials(mobility, interfacial characteristics, etc.) of each organic material layer is achieved, a long life span and high efficiency can be achieved at the same time.

The organic electroluminescent device according to an embodiment of the present invention may be manufactured using a PVD (physical vapor deposition) method. For example, a metal or a metal oxide having conductivity or an alloy thereof is deposited on a substrate to form a cathode, and the organic material layer including the hole injection layer(120), the hole transport layer(130), the emitting layer (140), the electron transport layer(150), and the electron injection layer(160) is formed thereon, and then depositing a material usable as a cathode thereon can manufacture an organic electroluminescent device according to an embodiment of the present invention.

Also, the present invention provides the organic electronic element wherein the organic material layer is formed by one of a spin coating process, a nozzle printing process, an inkjet printing process, a slot coating process, a dip coating process or a roll-to-roll process, and the organic material layer provides an organic electronic element comprising the compound as an electron transport material.

As another specific example, the present invention provides an organic electronic element that is used by mixing the same or different compounds of the compound represented by Formula 1 or 7 to the organic material layer.

In another aspect, the present invention provides an emitting-auxiliary layer composition comprising a compound represented by Formula 1 or 7, and provides an organic electronic element comprising the emitting-auxiliary layer.

The present invention also provides an electronic device comprising a display device including the organic electronic element; and a control unit for driving the display device.

According to another aspect, the present invention provides an display device wherein the organic electronic element is at least one of an OLED, an organic solar cell, an organic photo conductor, an organic transistor(organic TFT) and an element for monochromic or white illumination. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, Synthesis Examples of the compound represented by Formula 1 or 7 of the present invention and preparation examples of the organic electronic element of the present invention will be described in detail by way of example, but are not limited to the following examples.

Synthesis Example 1

The compound (Final product) represented by Formula 1 according to the present invention may be prepared by reacting as in Scheme 1 below, but is not limited thereto.

<Reaction Scheme 1>

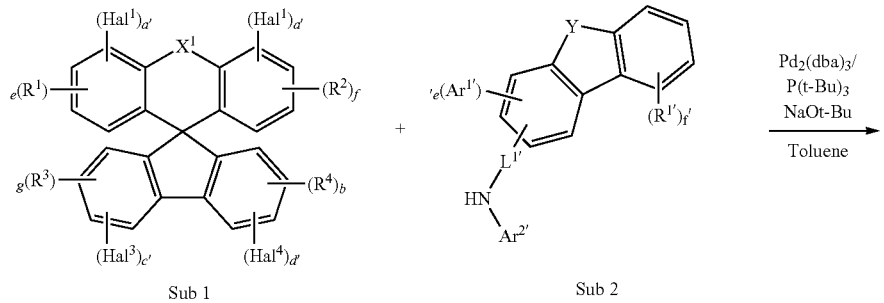

-continued

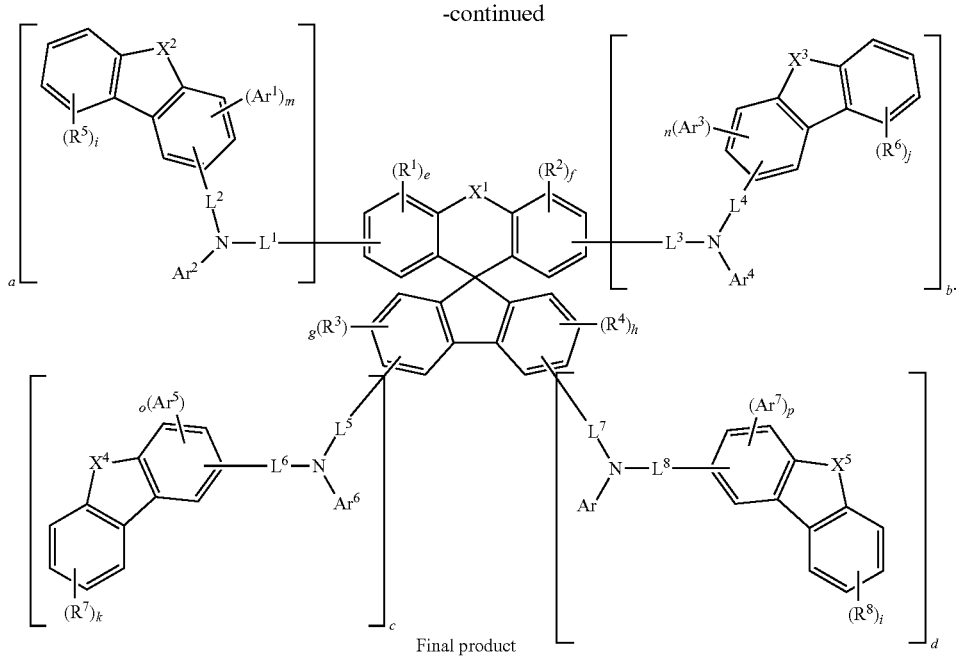

Final product

In Reaction Scheme 1,
1) $X^1$, $X^2$, $X^3$, $X^4$, $X^5$, $R^1$, $R^2$, $R^3$, $R^4$, $R^5$, $R^6$, $R^7$ and $R^8$, $L^1$, $L^2$, $L^3$, $L^4$, $L^5$, $L^6$, $L^7$ and $L^8$, $Ar^1$, $Ar^2$, $Ar^3$, $Ar^4$, $Ar^5$, $Ar^6$, $Ar^7$, and $Ar^8$, and a to P are the same as defined above,
2) $Hal^1$ to $Hal^4$ are each independently Br or $C_1$,
3) a' to d' are each independently 0 or 1, at least one of a' to d' is 1,
4) Y is the same as the definition of $X^1$, $X^2$, $X^3$, $X^4$, $X^5$,
5) $Ar^{1'}$ is the same as the definition of $Ar^1$, $Ar^3$, $Ar^5$ or $Ar^7$,
6) $Ar^{2'}$ is the same as the definition of $Ar^2$, $Ar^4$, $Ar^6$ or $Ar^8$,
7) $R^{1'}$ is the same as the definition of $R^5$, $R^6$, $R^7$, $R^8$,
8) $L^{1'}$ is the same as the definition of $L^2$, $L^4$, $L^6$ or $L^8$,
9) e' is an integer of 0 to 3, f' is an integer of 0 to 4.

The compound represented by Formula 7 according to the present invention (Final product 2) may be prepared by reacting the compounds as shown in Scheme 1-1, but it is not limited thereto.

<Reaction Scheme 1-1>

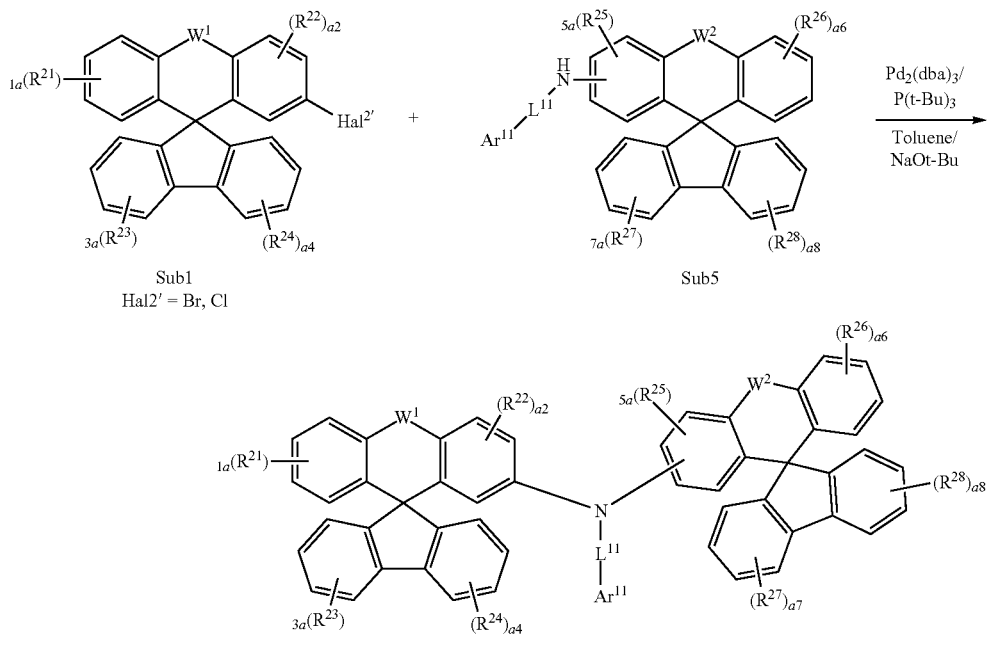

Final product 2

I. Synthesis of Sub 1

Sub 1 of Reaction Scheme 1 may be synthesized by the reaction path of Scheme 2 below, but is not limited thereto. When $X^1$ is —OH, the synthesis path of (1) of Reaction Scheme 2 is followed, and when $X^1$ is —SH, the synthesis path of (2) of Reaction Scheme 2 is followed.

<Reaction Scheme 2>

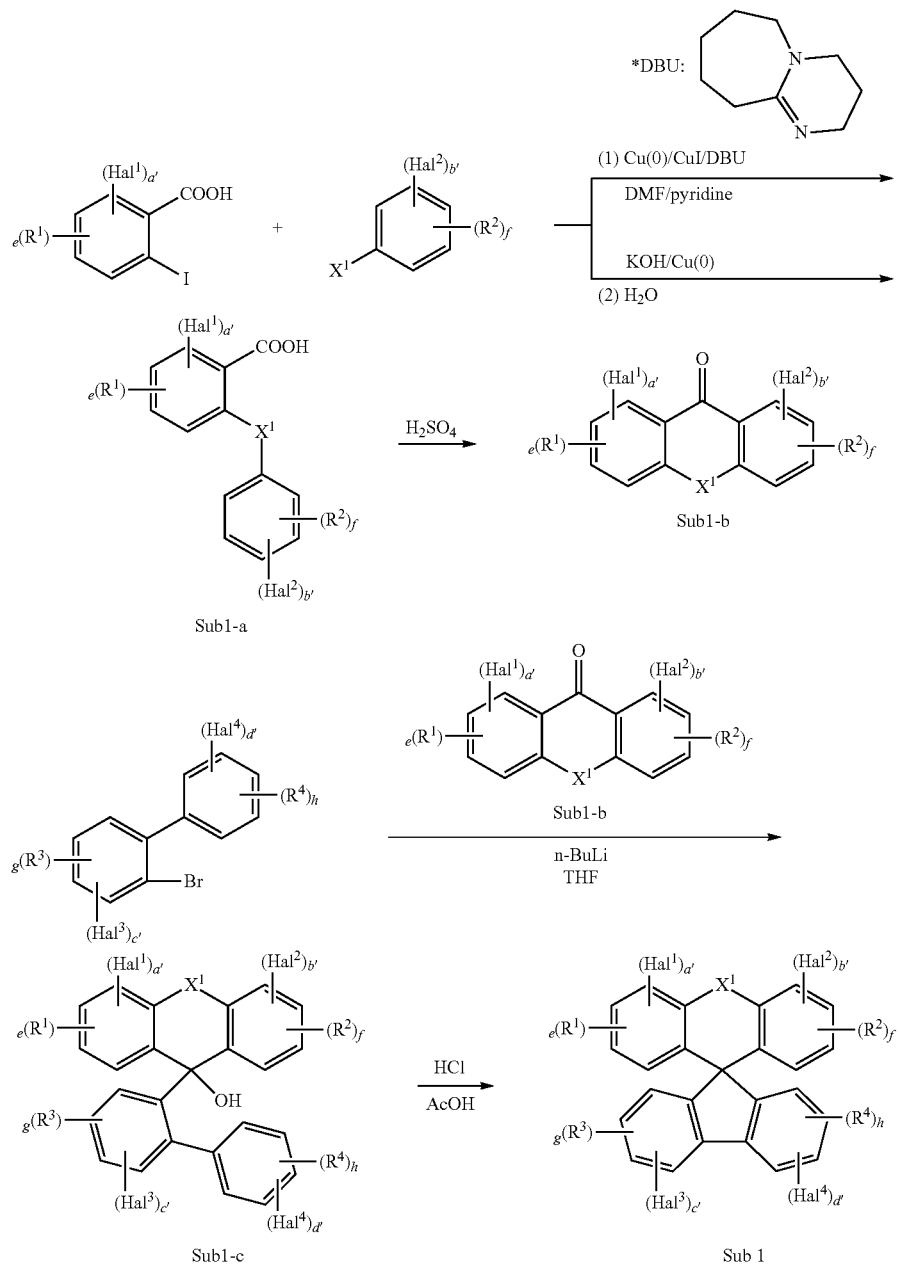

In Reaction Scheme 2,
$X^1$, $R^1$, $R^2$, $R^3$, $R^4$, e, f, g, h, $Hal^1$, $Hal^2$, $Hal^3$, $Hal^4$, and a', b', c', d' are the same as defined in Formula 1.

Synthesis Examples of Specific Compounds Belonging to Sub 1 are as Follows

1. Synthesis Example of Sub 1-1

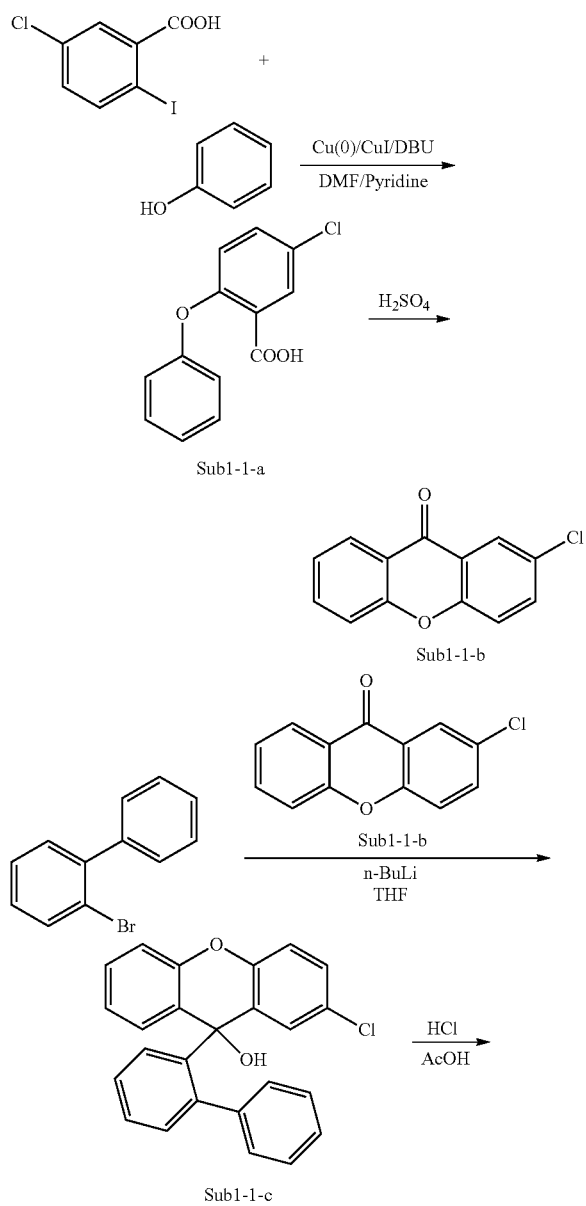

(1) Synthesis Example of Sub 1-1-a 5-chloro-2-iodobenzoic acid (50.0 g, 177 mmol), Phenol (33.3 g, 354 mmol), 1,8-diazabicyclo[5.4.0]undec-7-ene (DBU) (80.9 g, 531 mmol), pyridine (2.9 mL), Copper powder (1.5 g, 23 mmol), CuI (1.5 g, 7.97 mmol) were placed in a round bottom flask, and DMF (1.2 L) was added, followed by refluxing for 3 hours. When the reaction is complete, cool to room temperature and add 3M HCl until precipitation is complete. Thereafter, the precipitate was washed with water and dried to obtain 38.3 g (yield 87%) of the product.

(2) Synthesis Example of Sub 1-1-b

Sub 1-1-a (38.3 g, 154 mmol) obtained in the above synthesis was added to a round bottom flask, and $H_2SO_4$ (1.1 mL, 21.5 mmol) was added, followed by refluxing until all the starting materials were dissolved. When all the starting materials are dissolved, cool to room temperature and add ice water to precipitate. Thereafter, the precipitate was washed with water, dried, dissolved in $CH_2Cl_2$, and recrystallized with a Silicagel column to obtain 23.09 g (yield 65%) of the product.

(3) Synthesis Example of Sub 1-1-c 2-bromo-1,1'-biphenyl (23.3 g, 99.7 mmol) was dissolved in THF (270 mL) in a round bottom flask under a nitrogen atmosphere, and then cooled to −78° C.

Then, n-BuLi (40 mL) was slowly titrated and the mixture was stirred for 30 minutes. Subsequently, Sub1-1-b (23 g, 99.7 mmol) obtained in the above synthesis was dissolved in THF (140 mL), and then slowly titrated into a reaction round bottom flask. After stirring for an additional 1 hour at −78° C., it is gradually raised to room temperature. When the reaction was completed, the product was extracted with Ethyl acetate and water, and the organic layer was dried over $MgSO_4$ and concentrated, and the resulting compound was recrystallized in a silica gel column to obtain 32.6 g (yield 85%) of the product.

(4) Synthesis Example of Sub 1-1

Sub 1-1-c (32 g, 84.7 mmol) obtained in the above synthesis, acetic acid (208 mL), and concentrated hydrochloric acid (34.6 mL) were added to a round bottom flask, followed by stirring at 60 to 80° C. for 3 hours under a nitrogen atmosphere. When the reaction was completed, the product was extracted with $CH_2Cl_2$ and water, and the organic layer was dried over $MgSO_4$ and concentrated, and the resulting compound was recrystallized with a silica gel column to obtain 27.7 g (91% yield) of the product.

2. Synthesis Example of Sub 1-11

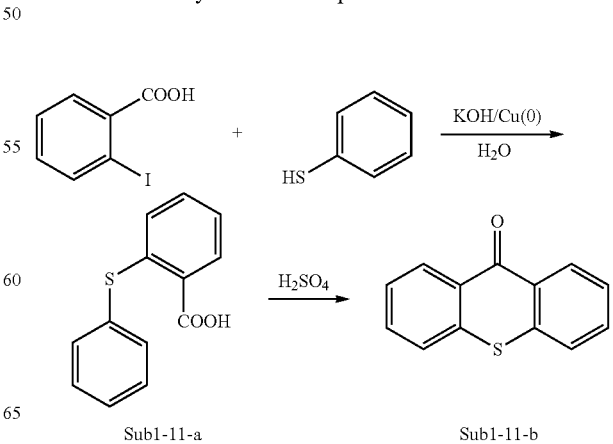

175

-continued

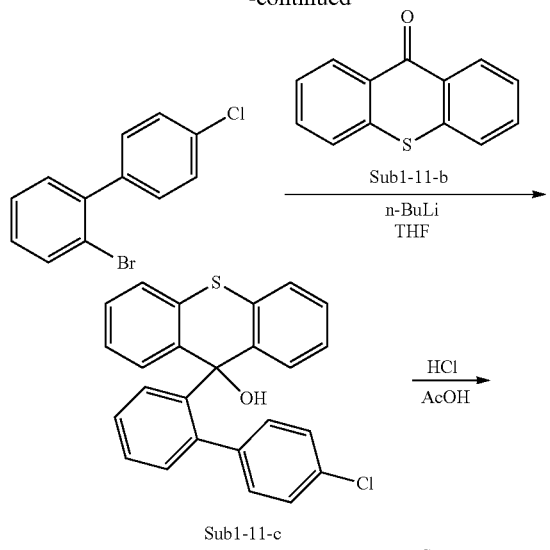

Sub1-11-c

Sub1-11

(1) Synthesis Example of Sub 1-11-a 2-iodobenzoic acid (50.0 g, 202 mmol), Thiophenol (22.2 g, 202 mmol), Potassium hydroxide (56.6 g, 1008 mmol), Copper powder (1.3 g, 20.2 mmol) were placed in a round bottom flask and water (1.3 L) was added, followed by refluxing for 12 hours. When the reaction is complete, cool to room temperature and add 3M HCl until precipitation is complete. Thereafter, the precipitate was washed with water and dried to obtain 41.3 g (yield 89%) of the product.

(2) Synthesis Example of Sub 1-11-b

Sub 1-11-a (41.3 g, 179 mmol) and $H_2SO_4$ (1.3 mL) obtained in the above synthesis was used for the synthesis of Sub 1-1-b to obtain 25.9 g (68% yield) of a product.

(3) Synthesis Example of Sub 1-11-c 2-bromo-4'-chloro-1,1'-biphenyl (32.6 g, 122 mmol), n-BuLi (49 mL), Sub 1-11-b (25.9 g, 122 mmol) obtained in the above synthesis was used for the synthesis of Sub 1-1-c to obtain 40.1 g (82% yield) of a product.

(4) Synthesis Example of Sub 1-11

Sub 1-11-c (40.1 g, 100 mmol) obtained in the above synthesis, acetic acid (250 mL), and concentrated hydrochloric acid (40 mL) were obtained by using the synthesis method of Sub 1-1 above to obtain 31.8 g (yield 83%) of the product.

176

3. Synthesis Example of Sub 1-20

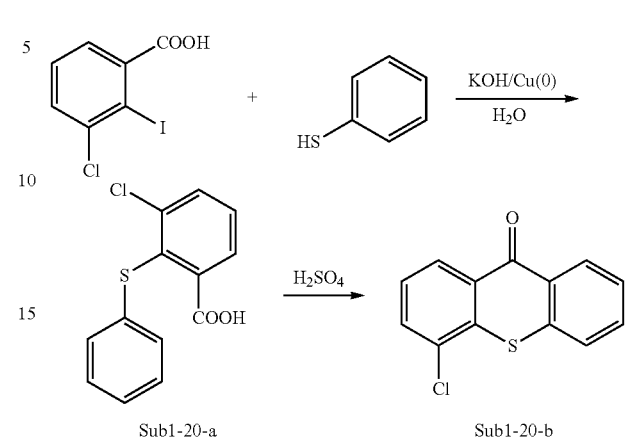

Sub1-20-a     Sub1-20-b

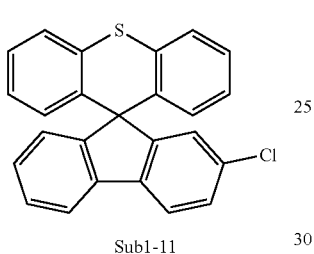

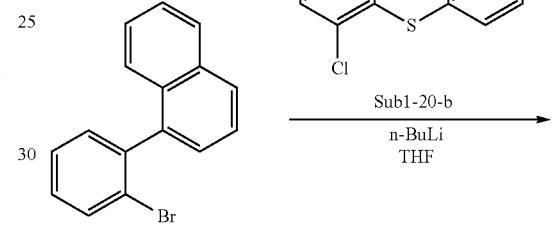

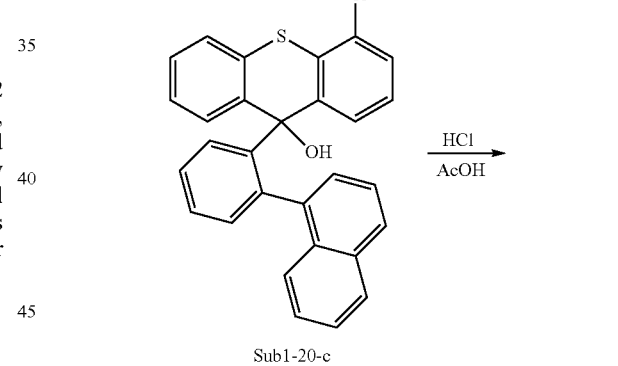

Sub1-20-c

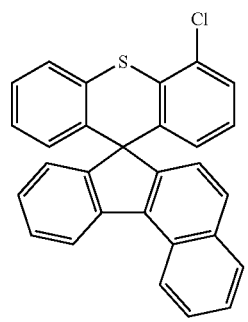

Sub1-20

(1) Synthesis Example of Sub 1-20-a 3-chloro-2-iodobenzoic acid (30.0 g, 106.2 mmol), Thiophenol (11.7 g, 106.2 mmol), Potassium hydroxide (29.8 g, 531 mmol), Copper powder (0.67 g, 10.6 mmol) were used to obtain 23.6 g of a product (84% yield) using the synthesis method of Sub 1-11-a.

(2) Synthesis Example of Sub 1-20-b

Sub 1-20-a (23.6 g, 89.2 mmol) and H₂SO₄ (0.67 mL) obtained in the above synthesis was used for the synthesis of Sub 1-1-b to obtain 14.5 g (66% yield) of a product.

(3) Synthesis Example of Sub 1-20-c 1-(2-bromophenyl)naphthalene (16.6 g, 58.8 mmol), n-BuLi (24 mL), Sub1-20-b (14.5 g, 58.8 mmol) obtained in the above synthesis was used for the synthesis of Sub 1-1-c to obtain 21.5 g (81% yield) of a product.

(4) Synthesis Example of Sub 1-20

Sub 1-20-c (21 g, 46.6 mmol) obtained in the above synthesis, acetic acid (116 mL), and concentrated hydrochloric acid (19 mL) were obtained by using the synthesis method of Sub 1-1 above to obtain 15.9 g (yield 79%) of the product.

4. Synthesis Example of Sub 1-55

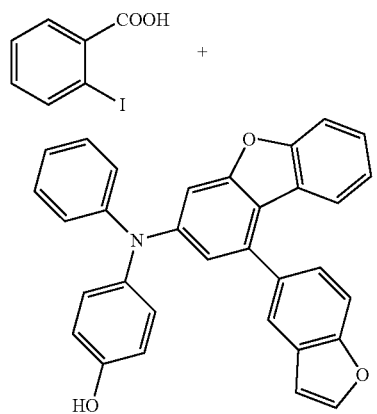

Sub1'-55

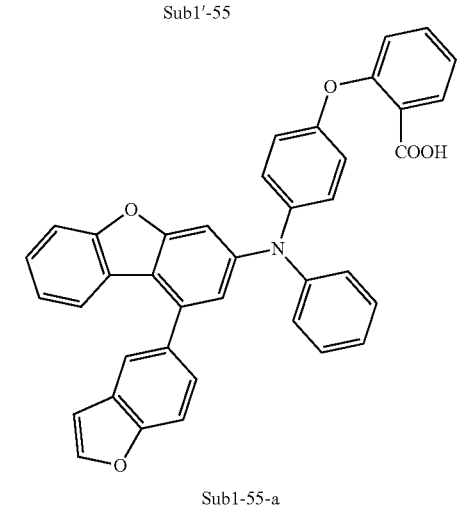

Sub1-55-a

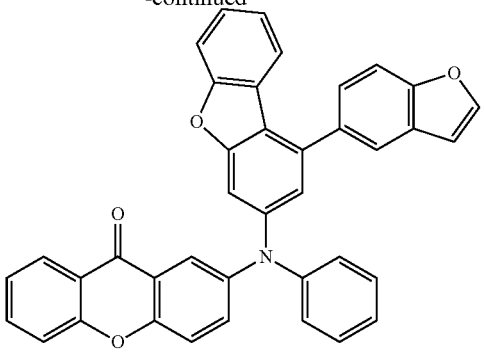

Sub1-55-b

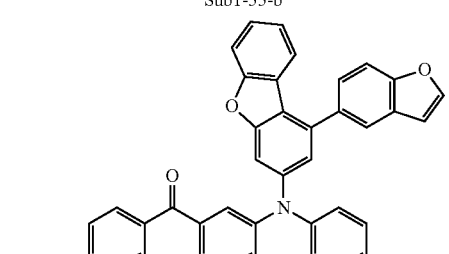

Sub1-55-b

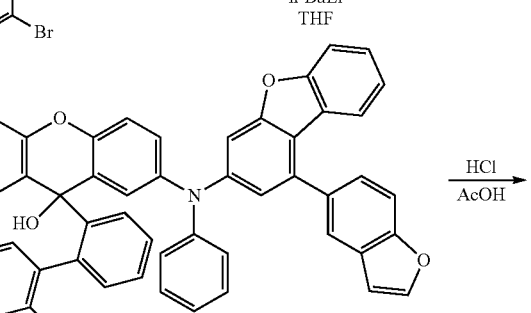

Sub1-55-c

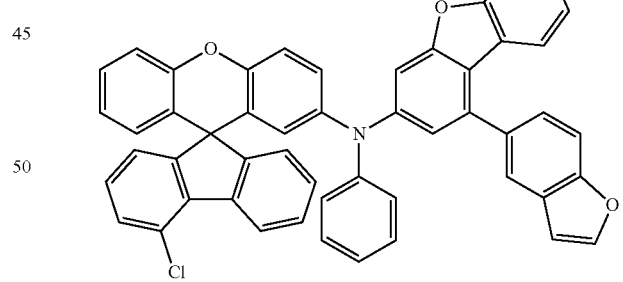

Sub1-55

(1) Synthesis Example of Sub 1-55-a 2-iodobenzoic acid (15 g, 60.5 mmol), Sub1'-55 (37.9 g, 120.1 mmol), 1,8-diazabicyclo[5.4.0]undec-7-ene (DBU) (27.6 g, 181.4 mmol), pyridine (0.98 mL), Copper powder (0.5 g, 7.9 mmol), CuI (0.5 g, 2.7 mmol) were used to obtain 27.7 g of a product (78% yield) using the synthesis method of Sub 1-1-a.

(2) Synthesis Example of Sub 1-55-b

Sub 1-55-a (27.7 g, 47.1 mmol) and H₂SO₄ (0.35 mL) obtained in the above synthesis was used for the synthesis of Sub 1-1-b to obtain 17.7 g (64% yield) of a product.

(3) Synthesis Example of Sub 1-55-c 2-bromo-2'-chloro-1,1'-biphenyl (7.8 g, 29 mmol), n-BuLi (11.7 mL), Sub 1-55-b (17 g, 29 mmol) obtained in the above synthesis was used for the synthesis of Sub 1-1-c to obtain 17.3 g (77% yield) of a product.

(4) Synthesis Example of Sub 1-55

Sub 1-55-c (17.3 g, 22.3 mmol) obtained in the above synthesis, acetic acid (56 mL), and concentrated hydrochloric acid (9.3 mL) were obtained by using the synthesis method of Sub 1-1 above to obtain 13.5 g (yield 80%) of the product.

5. Synthesis Example of Sub 1-140

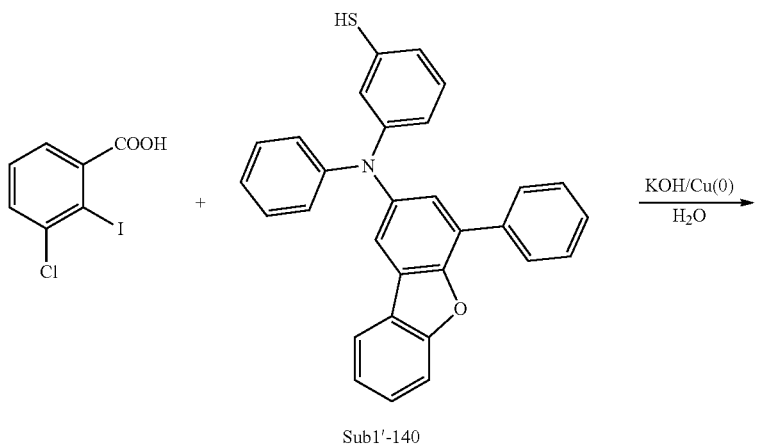

Sub1'-140

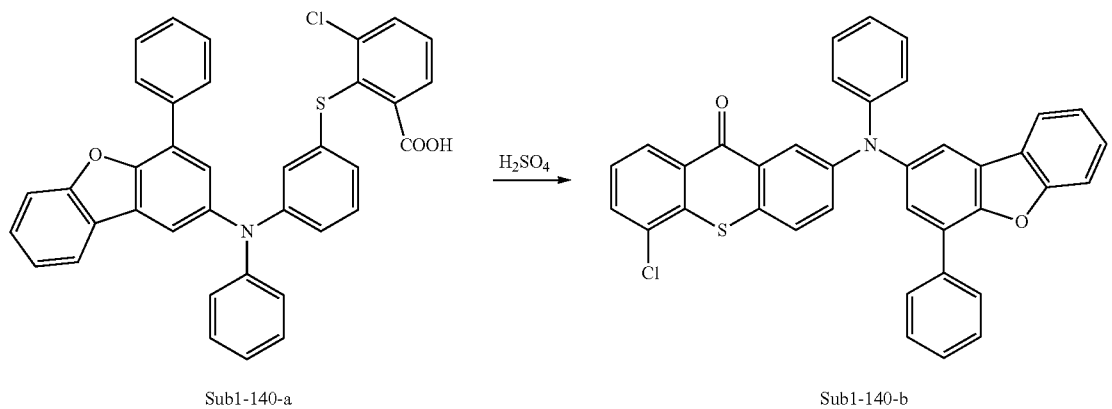

Sub1-140-a        Sub1-140-b

-continued
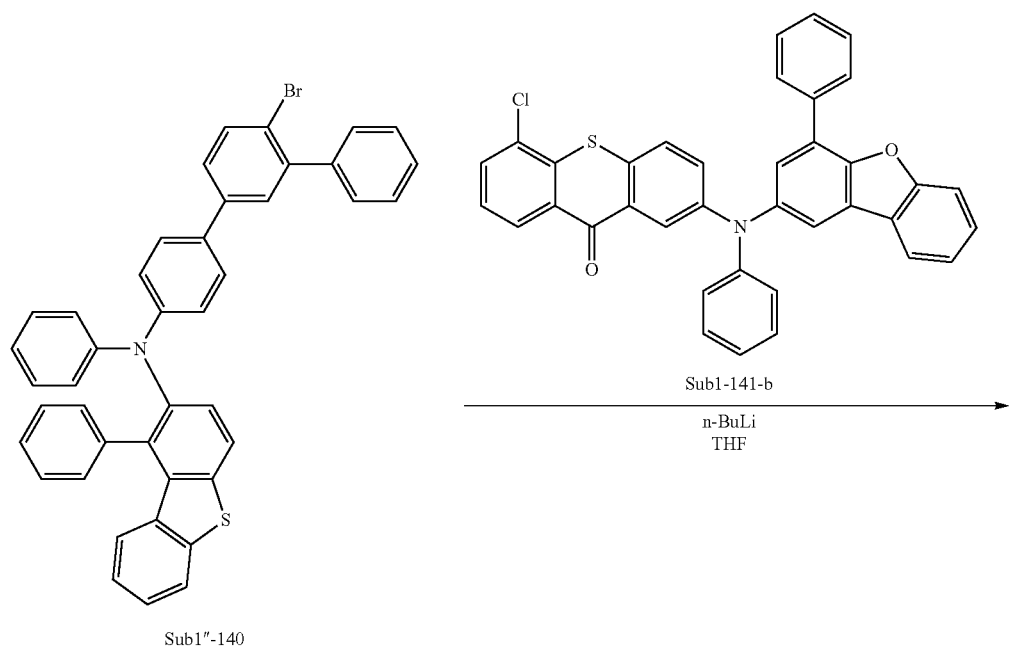
Sub1″-140    Sub1-141-b
n-BuLi
THF
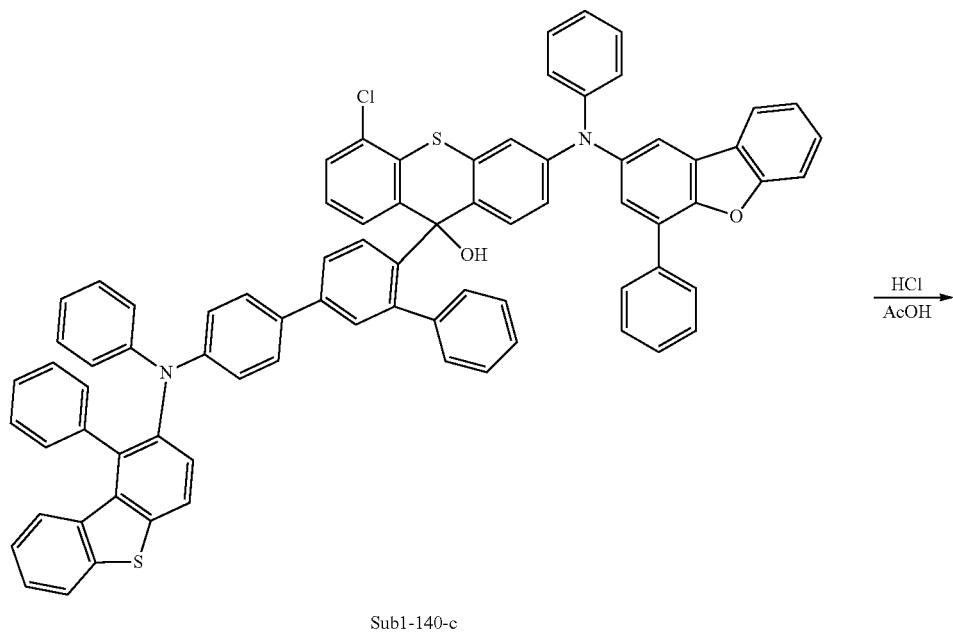
Sub1-140-c
HCl
AcOH

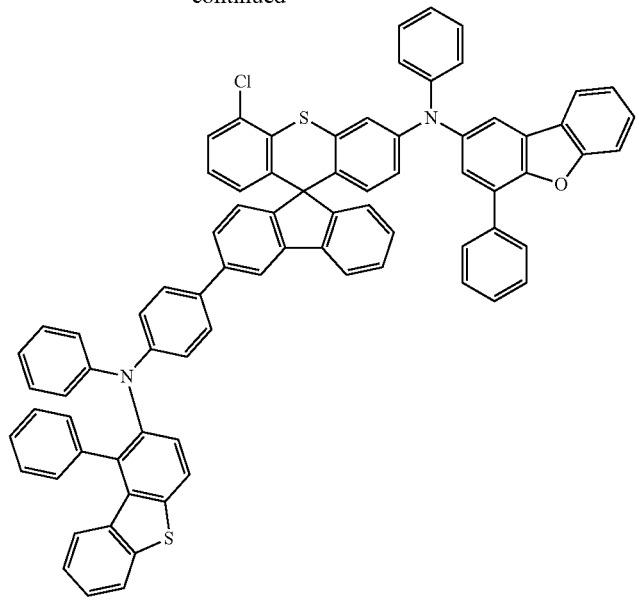

Sub1-140

(1) Synthesis Example of Sub 1-140-a 3-chloro-2-iodobenzoic acid (18 g, 63.7 mmol), Sub1'-140 (28.3 g, 63.7 mmol), Potassium hydroxide (17.9 g, 318.6 mmol), Copper powder (0.4 g, 6.4 mmol) were used to obtain 30.1 g of a product (79% yield) using the synthesis method of Sub 1-11-a.

(2) Synthesis Example of Sub 1-140-b

Sub 1-140-a (30.1 g, 46.3 mmol) and $H_2SO_4$ (0.35 mL) obtained in the above synthesis was used for the synthesis of Sub 1-1-b to obtain 18.1 g (62% yield) of a product.

(3) Synthesis Example of Sub 1-140-c

Sub1"-140 (19.9 g, 30.3 mmol), n-BuLi (12.2 mL), Sub1-141-b (18.1 g, 30.3 mmol) obtained in the above synthesis were used for the synthesis of Sub 1-1-c to obtain 24.5 g (70% yield) of a product.

(4) Synthesis Example of Sub 1-140

Sub 1-140-c (24.5 g, 21.1 mmol) obtained in the above synthesis, acetic acid (53 mL), and concentrated hydrochloric acid (8.8 mL) were obtained by using the synthesis method of Sub 1-1 above to obtain 18.1 g (yield 75%) of the product.

6. Synthesis Example of Sub 1-152

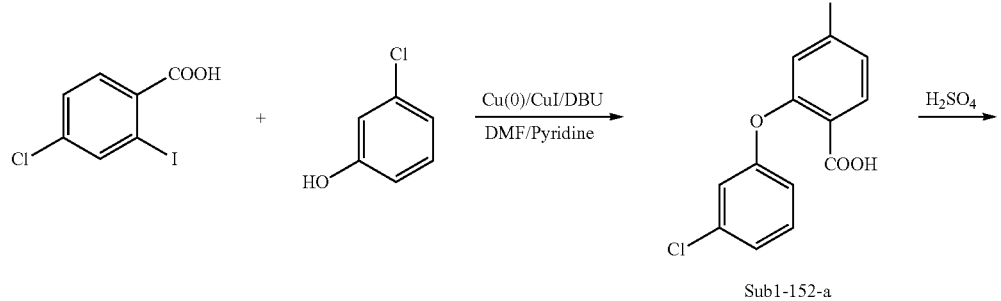

Sub1-152-a

-continued
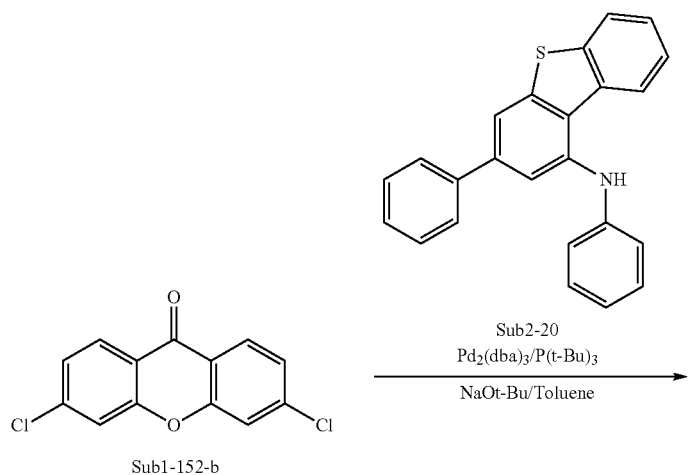
Sub2-20
Pd₂(dba)₃/P(t-Bu)₃
NaOt-Bu/Toluene
Sub1-152-b
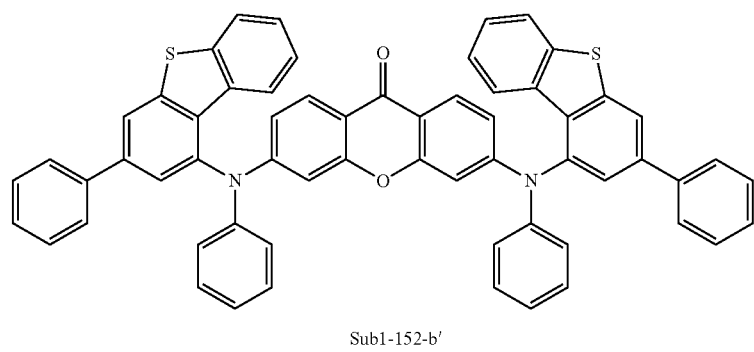
Sub1-152-b'
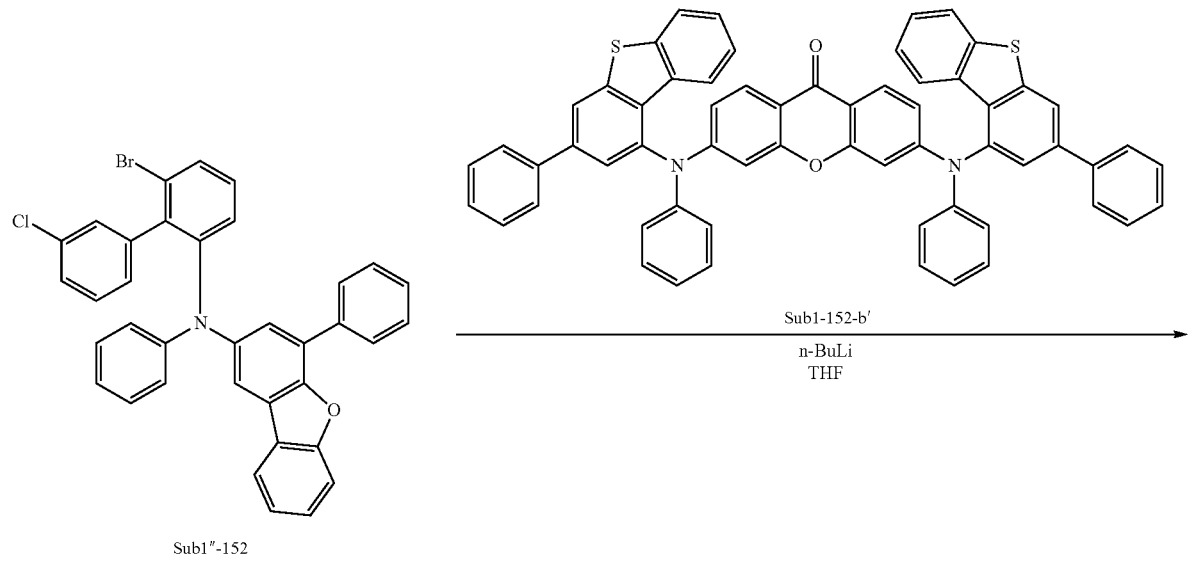
Sub1''-152
Sub1-152-b'
n-BuLi
THF -continued

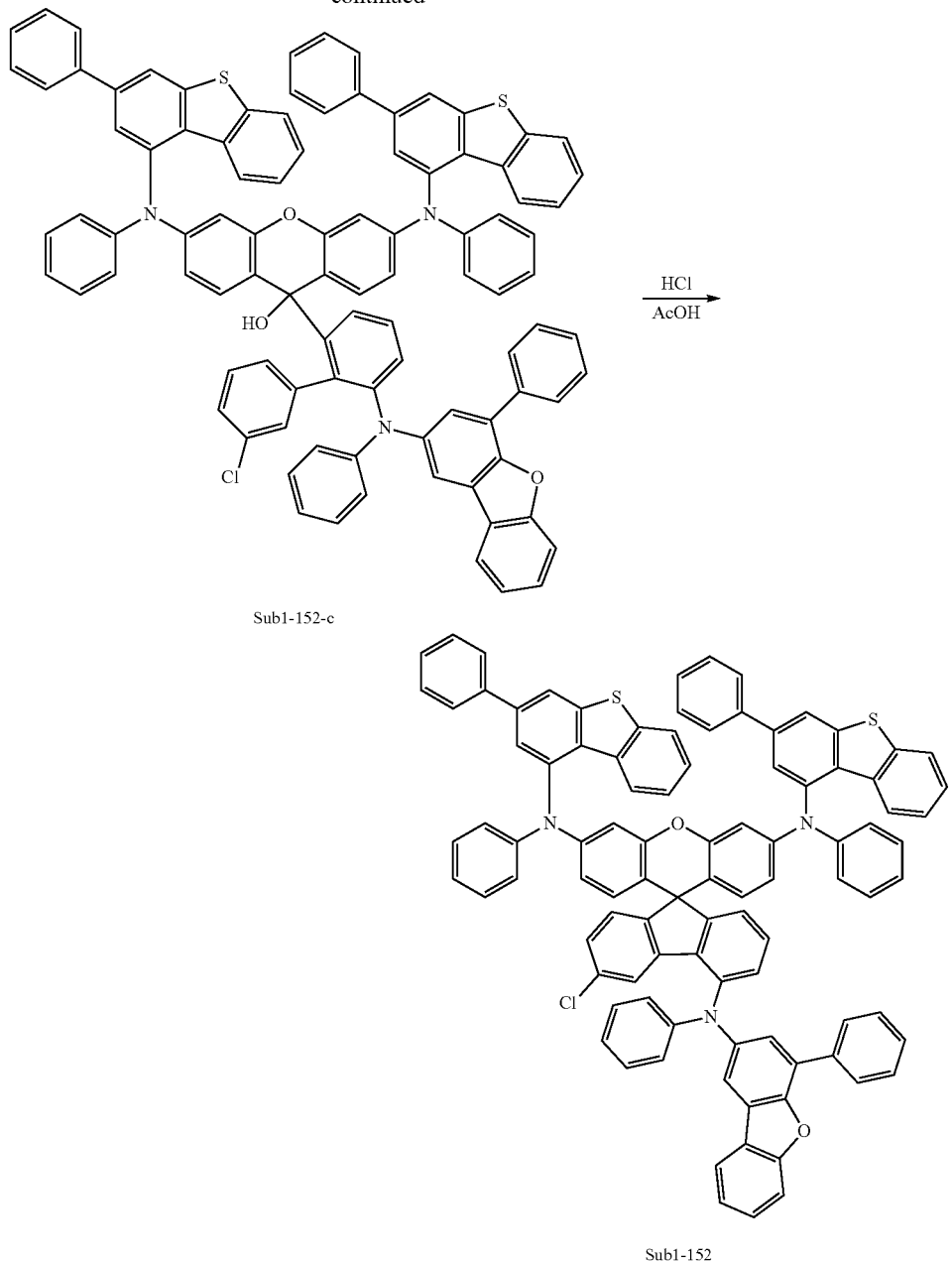

Sub1-152-c

Sub1-152

(1) Synthesis Example of Sub 1-152-a 4-chloro-2-iodobenzoic acid (12 g, 42.5 mmol), 3-chlorophenol (10.9 g, 84.97 mmol), 1,8-diazabicyclo[5.4.0]undec-7-ene (DBU) (19.4 g, 127.5 mmol), pyridine (0.69 mL), Copper powder (0.35 g, 5.5 mmol), CuI (0.36 g, 1.9 mmol) were used to obtain 9.7 g of a product (81% yield) using the synthesis method of Sub 1-1-a.

(2) Synthesis Example of Sub 1-152-b

Sub 1-152-a (9.7 g, 34.3 mmol) and $H_2SO_4$ (0.26 mL) obtained in the above synthesis was used for the synthesis of Sub 1-1-b to obtain 6.6 g (73% yield) of a product.

(3) Synthesis Example of Sub 1-152-b'

The obtained Sub 1-152-b (6.6 g, 24.9 mmol), Sub 2-20 (17.5 g, 49.8 mmol), $Pd_2(dba)_3$ (0.68 g, 0.75 mmol), P(t-Bu)$_3$ (50 wt % Sol.) (0.6 mL, 1.5 mmol), t-BuONa (7.18 g, 74.7 mmol) were added to anhydrous Toluene (150 mL) and reacted for 3 hours. After confirming the completion of the reaction, extraction was performed with $CH_2Cl_2$ and water, and the organic layer was dried over $MgSO_4$ and concentrated. The resulting compound was silica gel column and recrystallized to give a product 14.8 g (yield 60%).

(4) Synthesis Example of Sub 1-152-c

Sub 1″-152 (8.97 g, 14.9 mmol), n-BuLi (6 mL), Sub 1-152-b' (14.8 g, 14.9 mmol) obtained in the above synthesis was used to obtain a product 14.0 g (62% yield) using the synthesis method of Sub 1-1-c.

(5) Synthesis Example of Sub 1-152

Sub 1-152-c (14 g, 9.3 mmol) obtained in the above synthesis, acetic acid (23 mL), and concentrated hydrochloric acid (3.8 mL) were used to obtain 8.7 g (63% yield) of the product using the synthesis method of Sub 1-1.

Meanwhile, the compound belonging to Sub 1 may be the following compound, but is not limited thereto, and Table 1 shows FD-MS (Field Desorption-Mass Spectrometry) values of the compound belonging to Sub 1.

Sub1-1
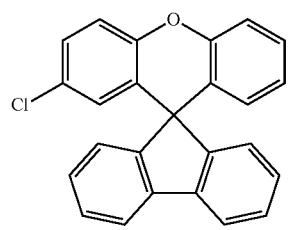

Sub1-2
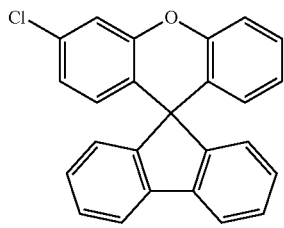

Sub1-3
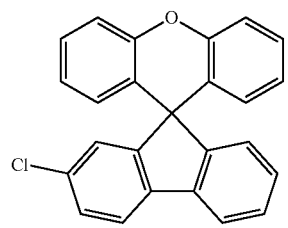

Sub1-4
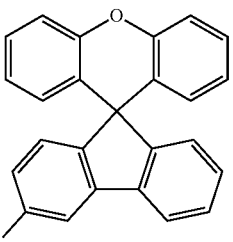

Sub1-5
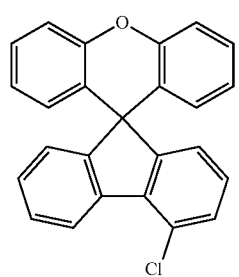

Sub1-6
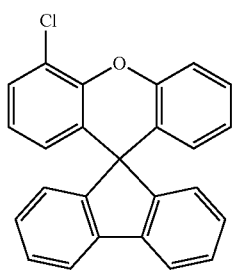

Sub1-7
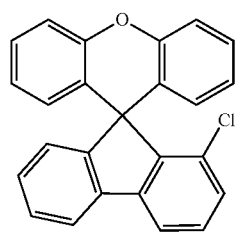

Sub1-8
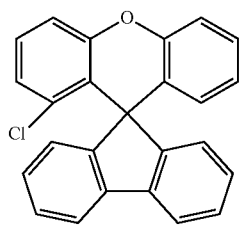

Sub1-9
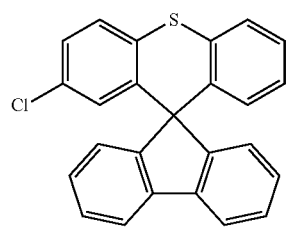

Sub1-10
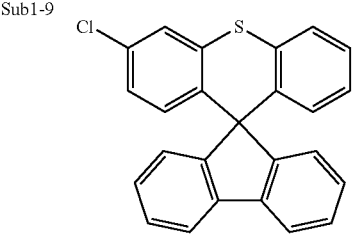

Sub1-11
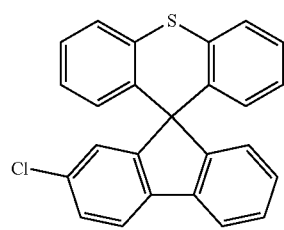
Sub1-12
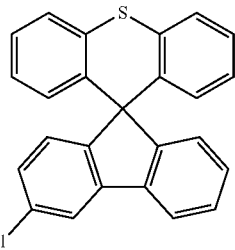
Sub1-13
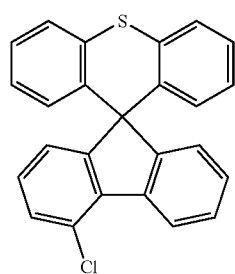
Sub1-14
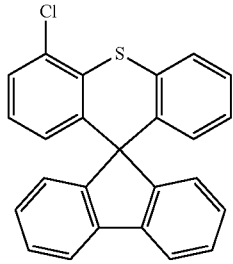
Sub1-15
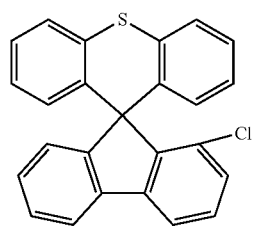
Sub1-16
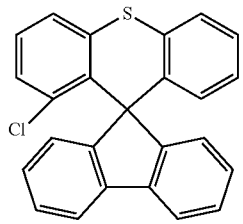
Sub1-17
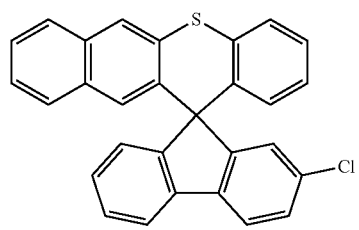
Sub1-18
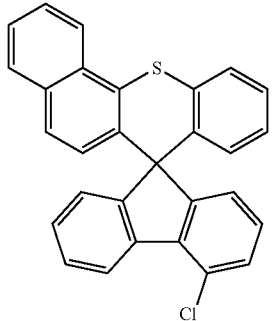
Sub1-19
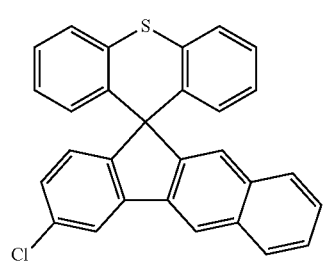
Sub1-20
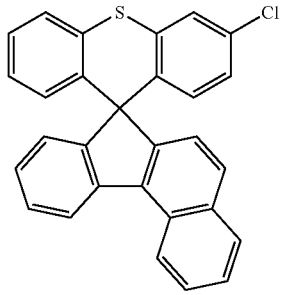

-continued
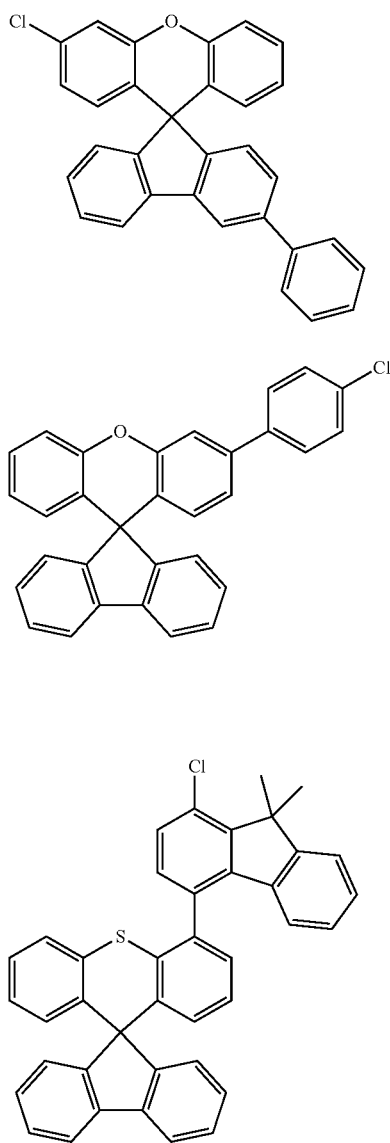
Sub1-21
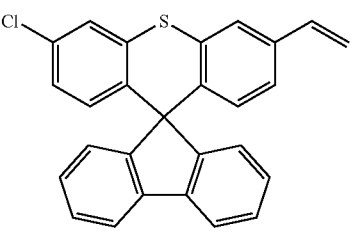
Sub1-22
Sub1-23
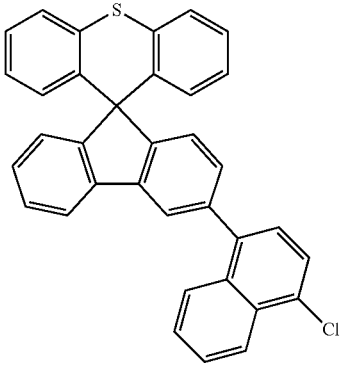
Sub1-24
Sub1-25
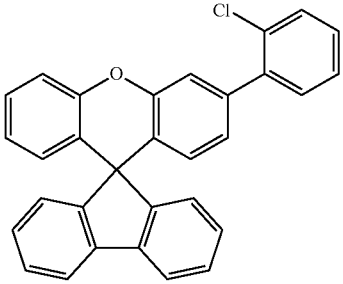
Sub1-26
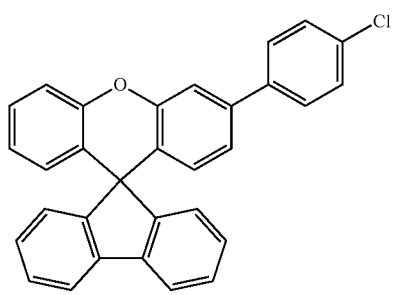
Sub1-27
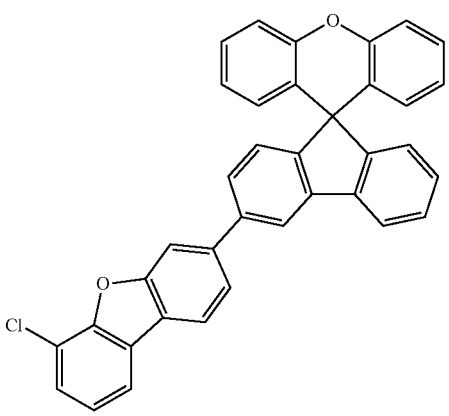
Sub1-28

-continued
Sub1-29
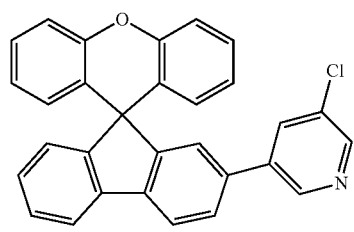
Sub1-30
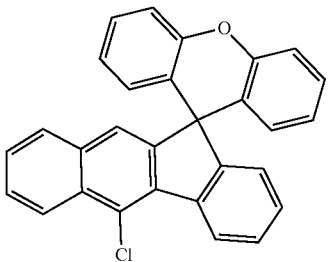
Sub1-31
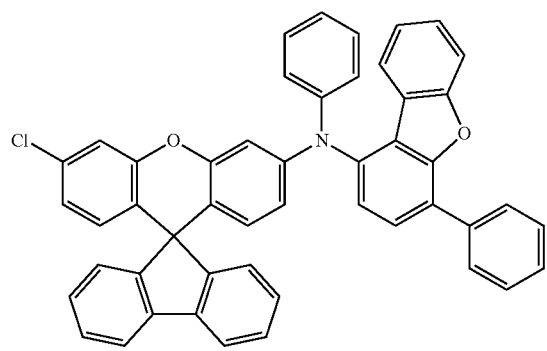
Sub1-32
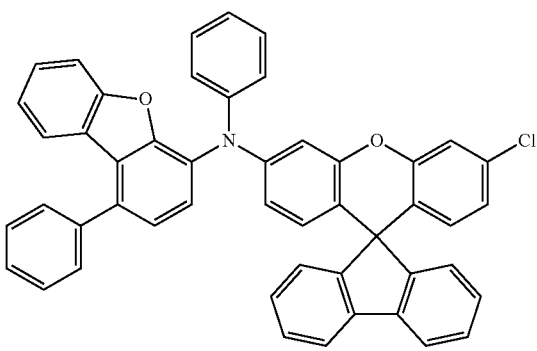
Sub1-33
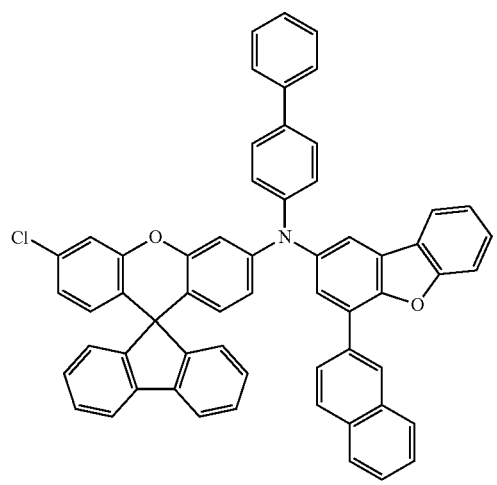
Sub1-34
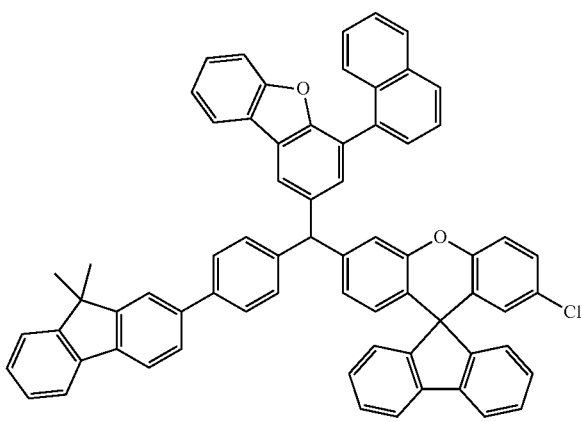

-continued
Sub1-35
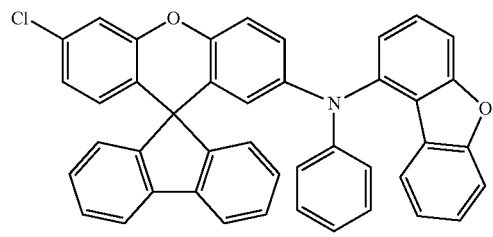
Sub1-36
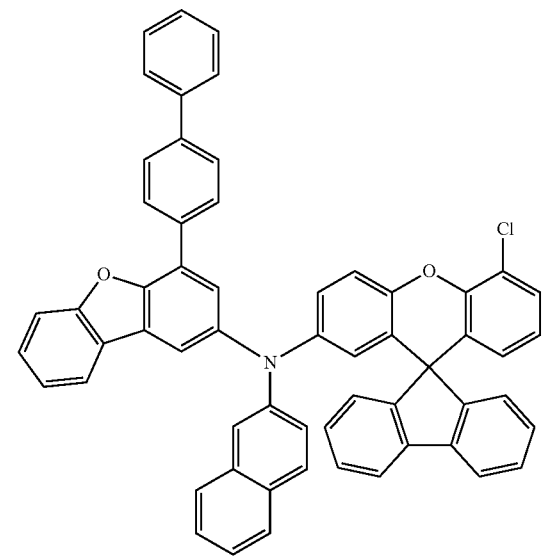
Sub1-37
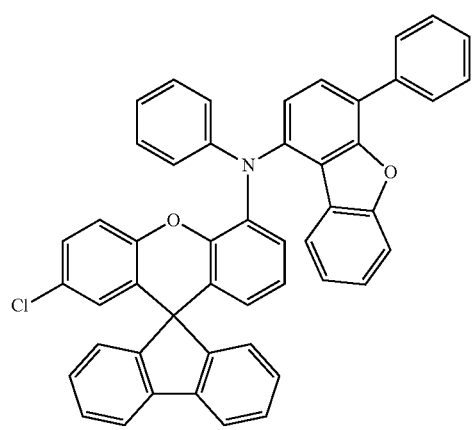
Sub1-38
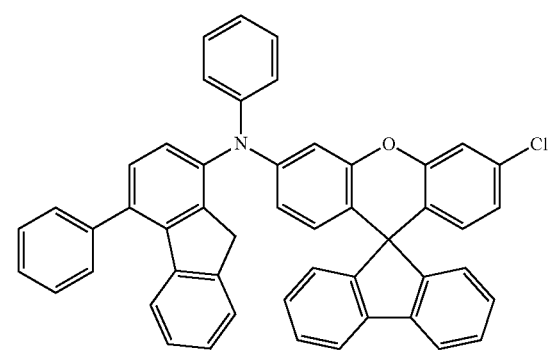
Sub1-39
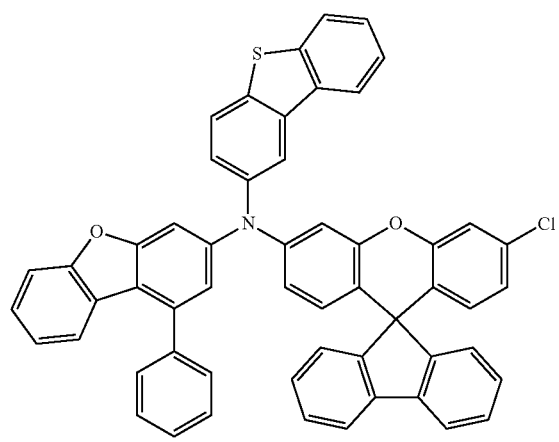
Sub1-40
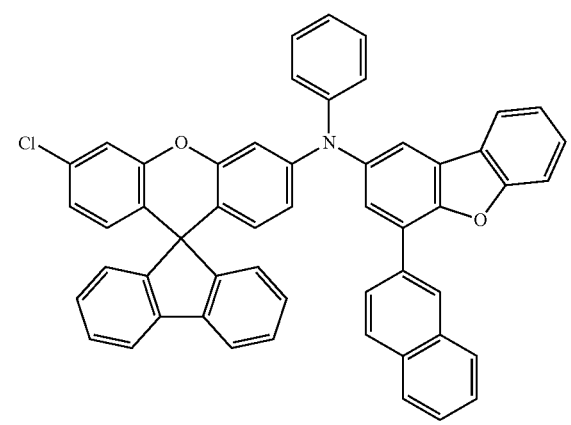

Sub1-41
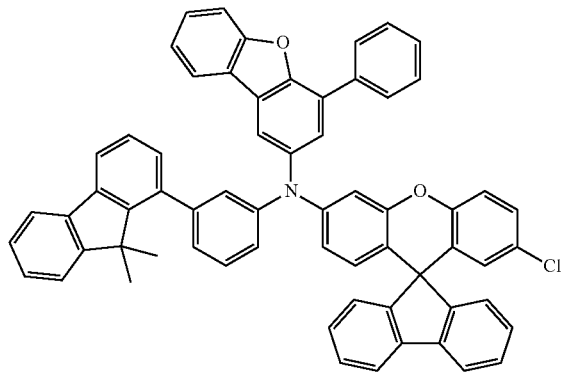
Sub1-42
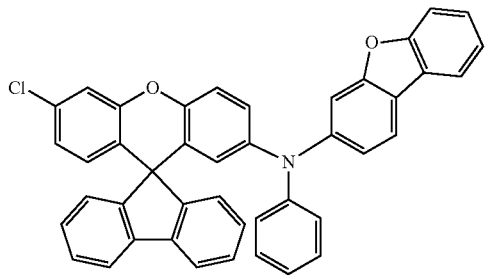
Sub1-43
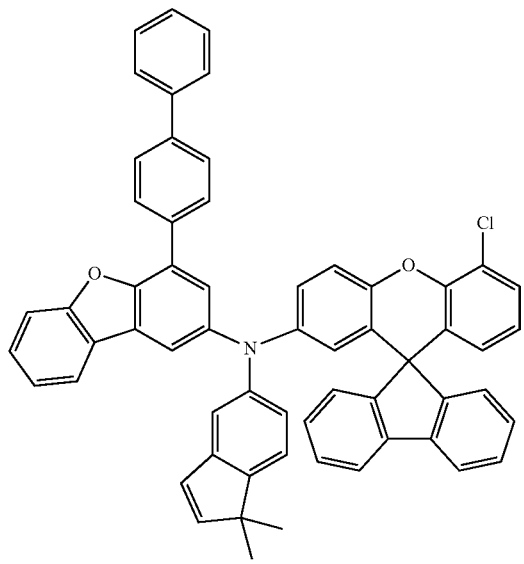
Sub1-44
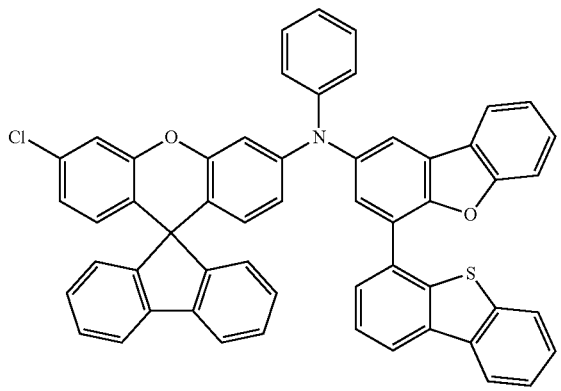
Sub1-45
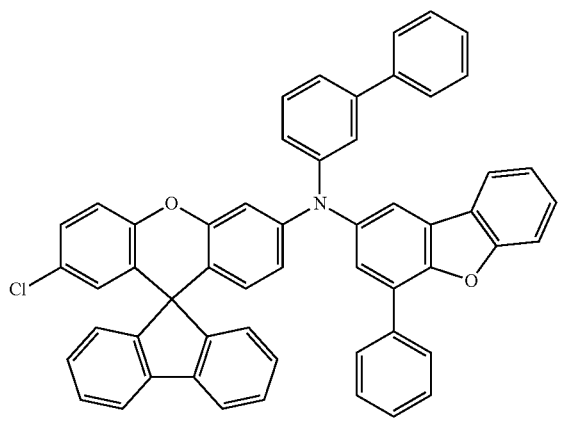
Sub1-46
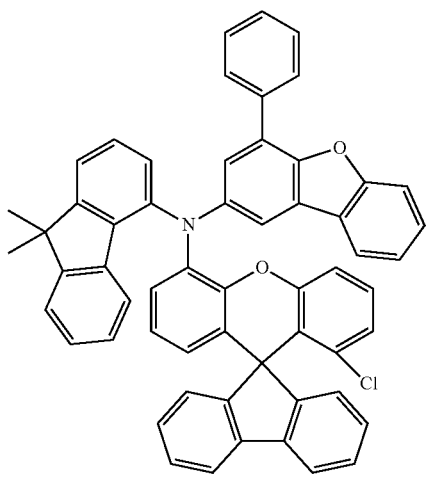

-continued
Sub1-47
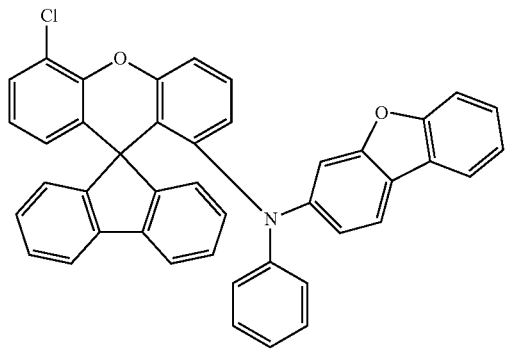
Sub1-48
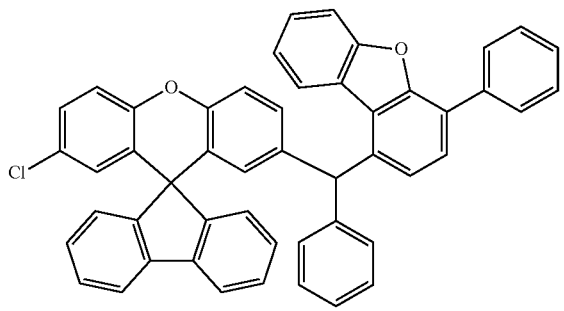
Sub1-49
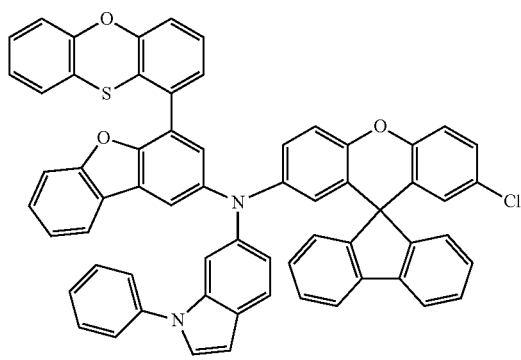
Sub1-50
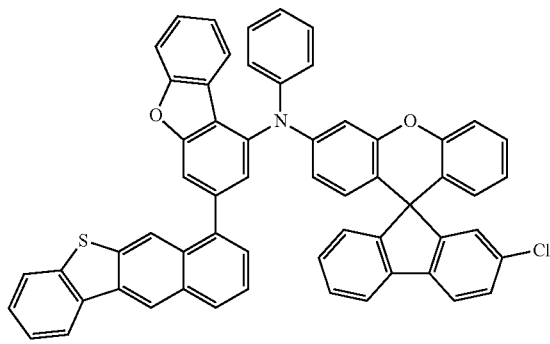
Sub1-51
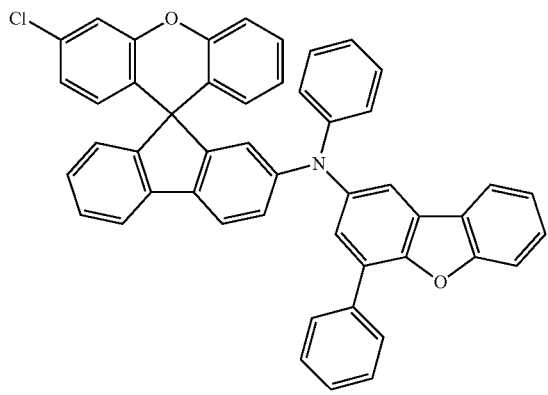
Sub1-52
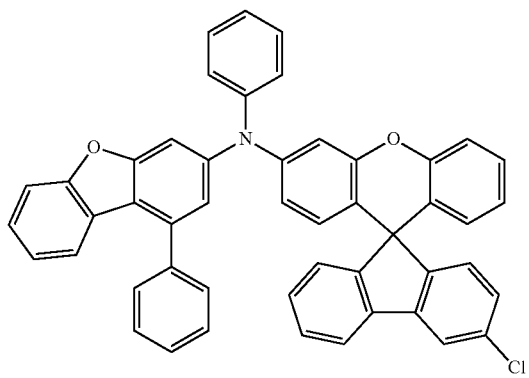
Sub1-53
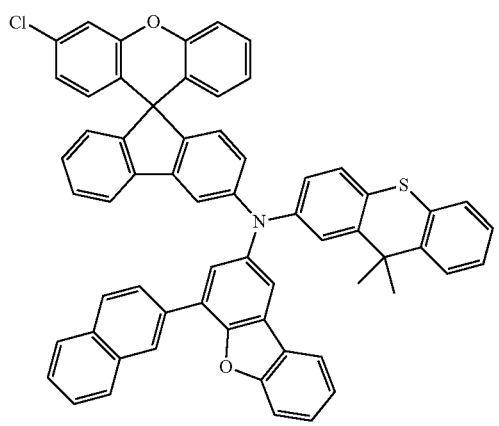
Sub1-54
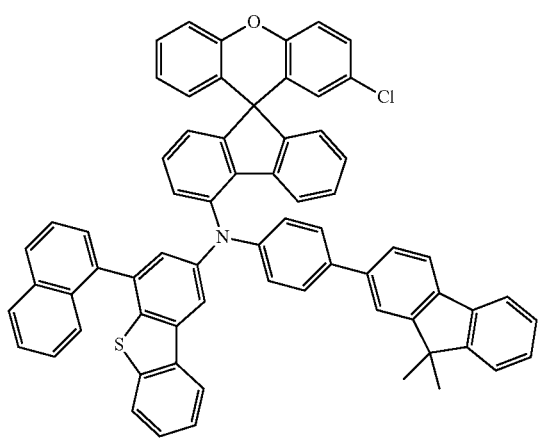

-continued
Sub1-55
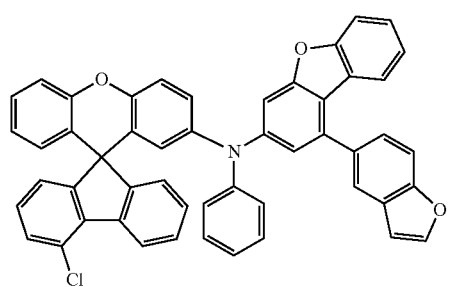
Sub1-56
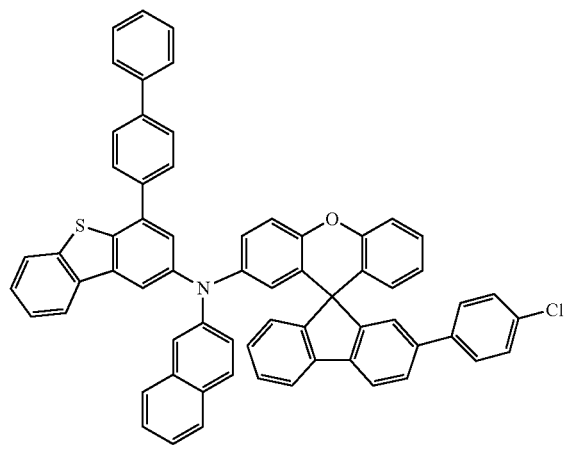
Sub1-57
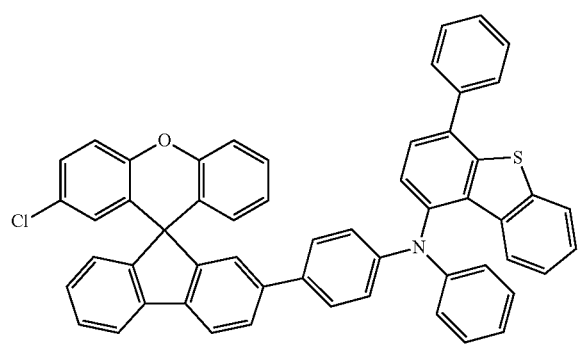
Sub1-58
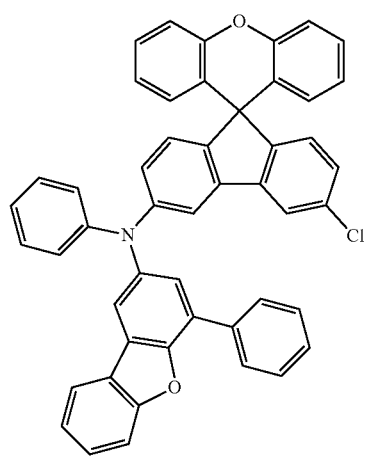
Sub1-59
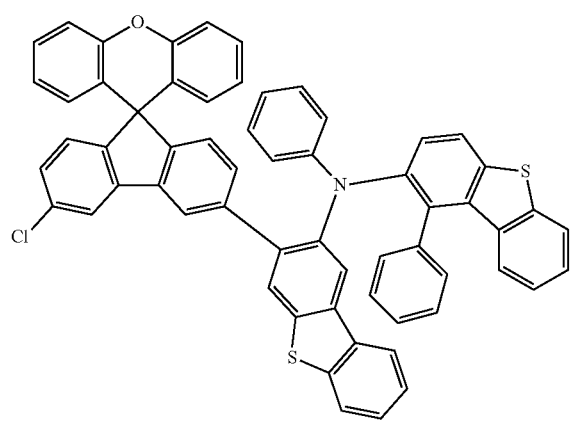
Sub1-60
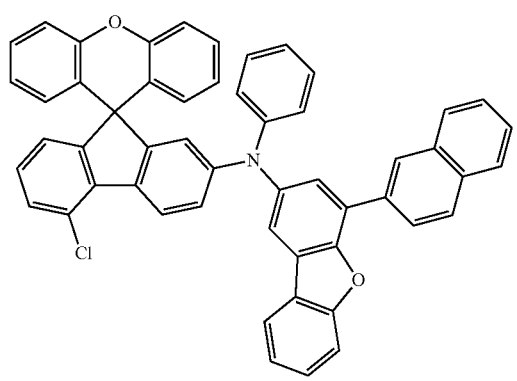

Sub1-61
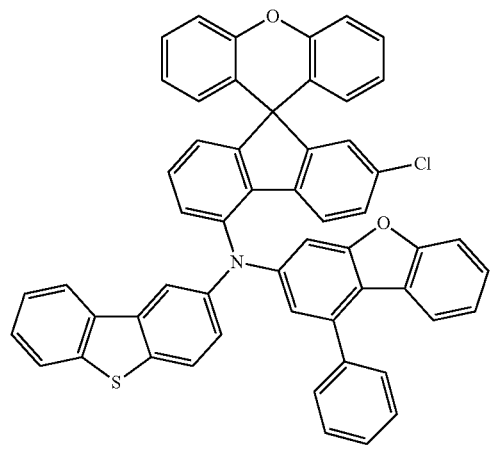
Sub1-62
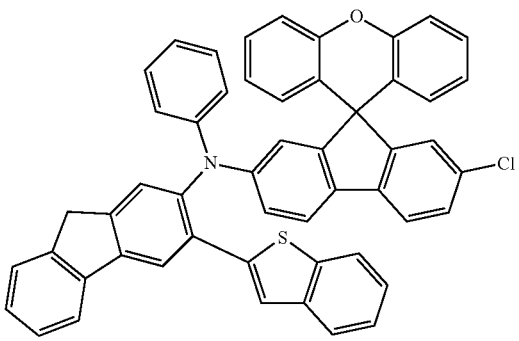
Sub1-63
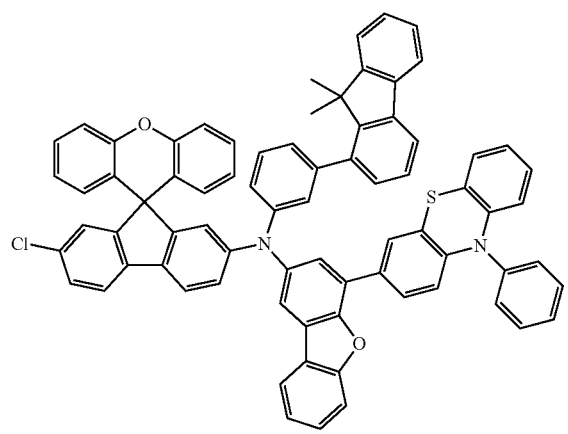
Sub1-64
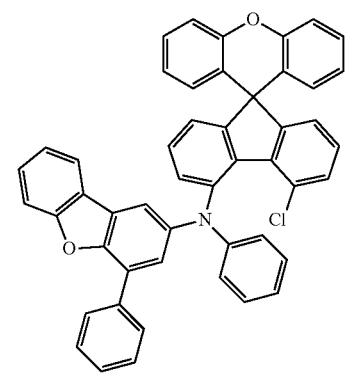
Sub1-65
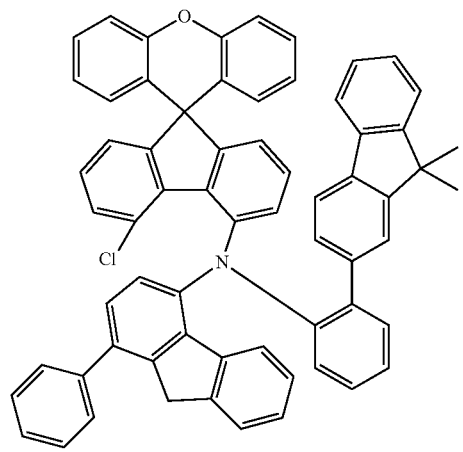
Sub1-66
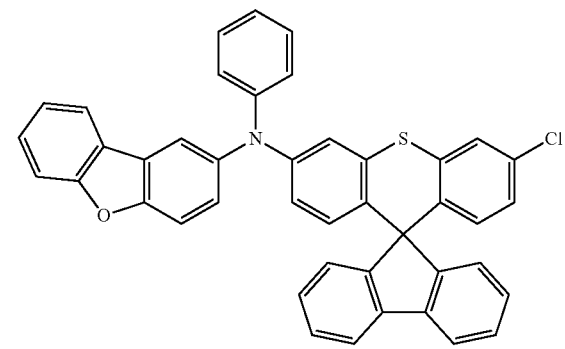

-continued
Sub1-67
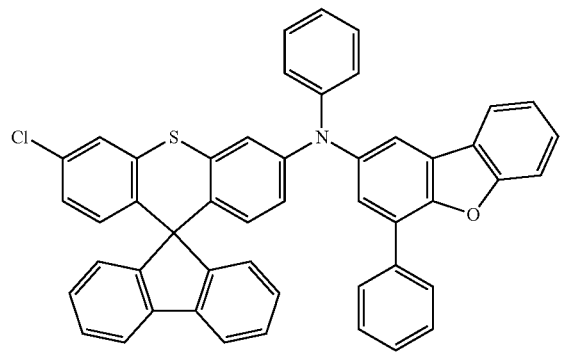
Sub1-68
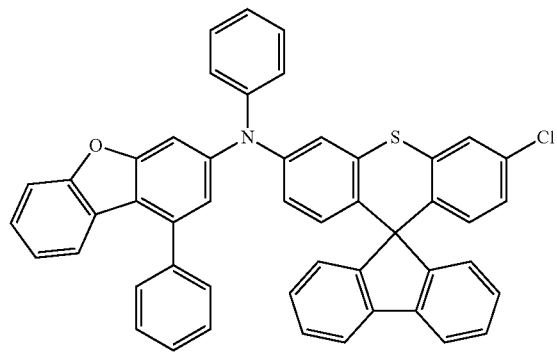
Sub1-69
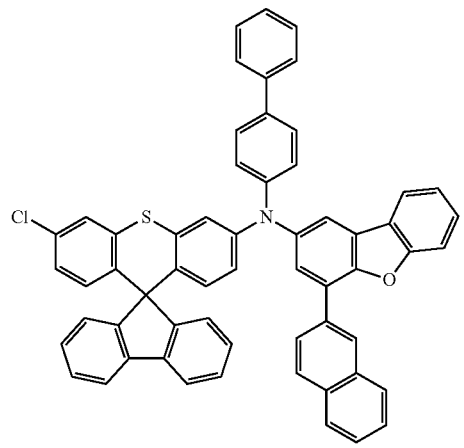
Sub1-70
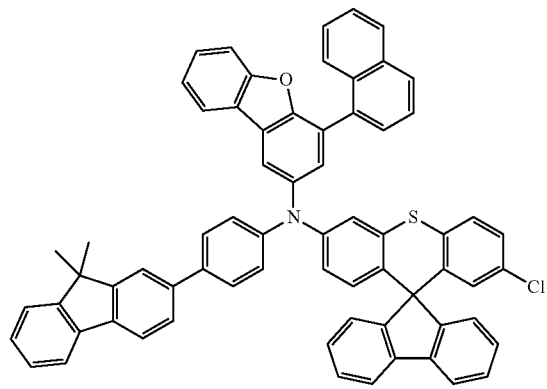
Sub1-71
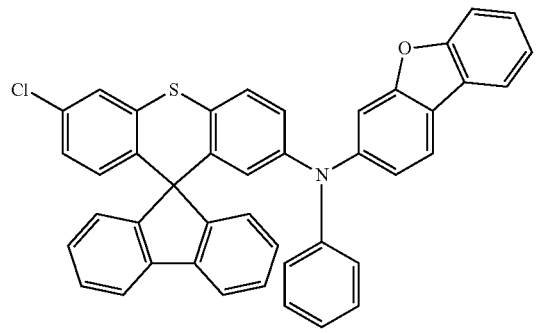
Sub1-72
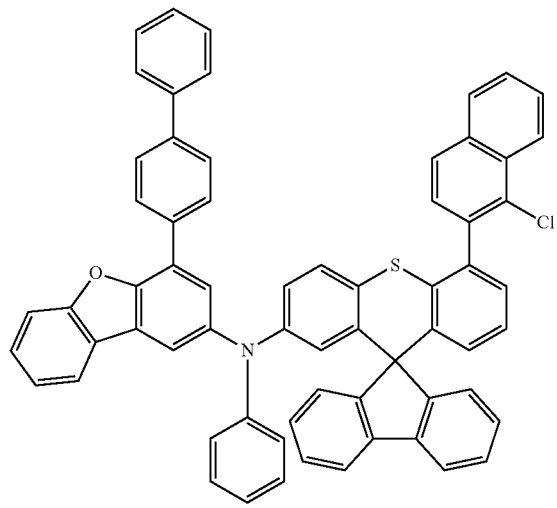

-continued
Sub1-73
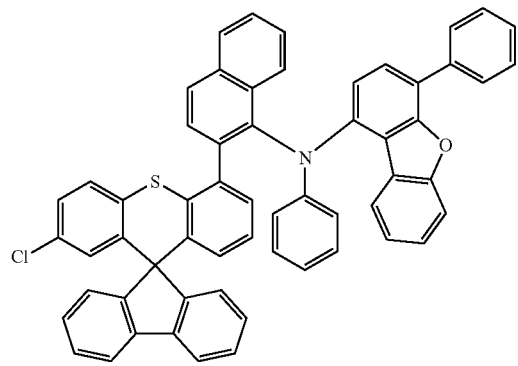
Sub1-74
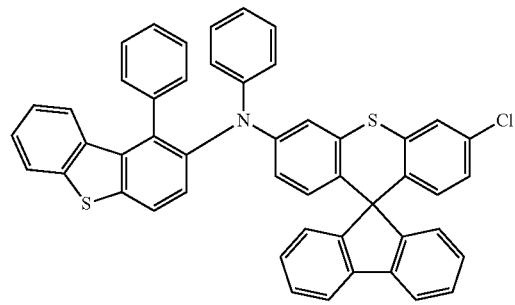
Sub1-75
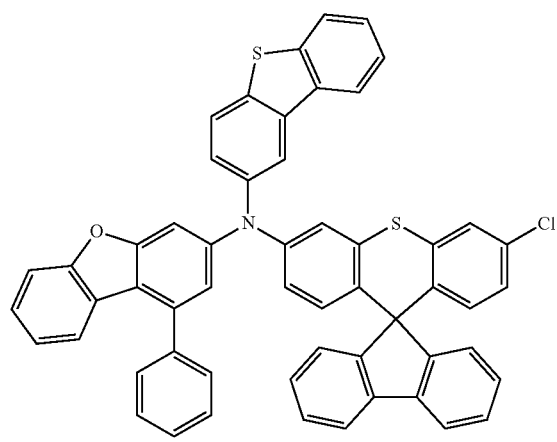
Sub1-76
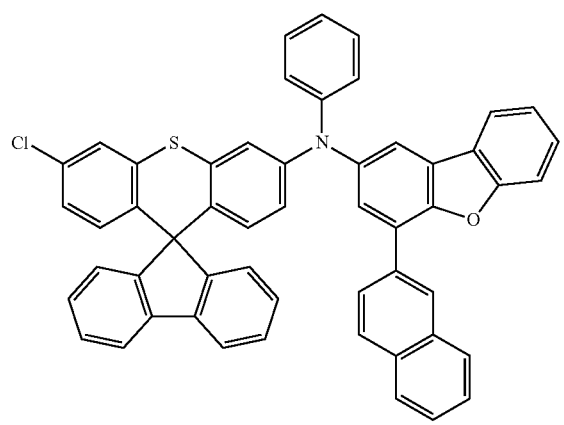
Sub1-77
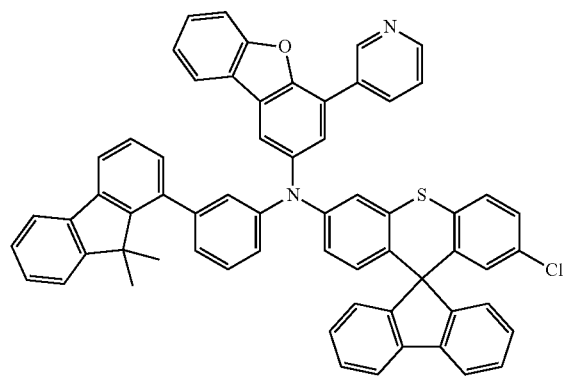
Sub1-78
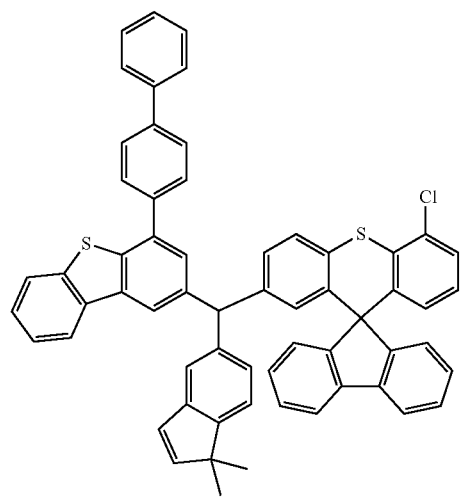

-continued
Sub1-79
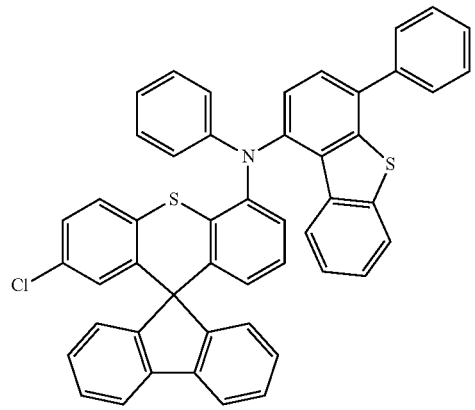
Sub1-80
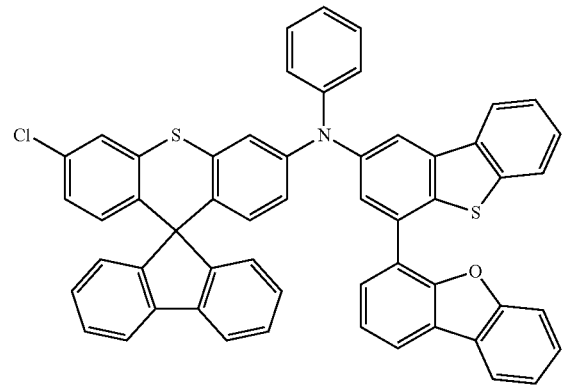
Sub1-81
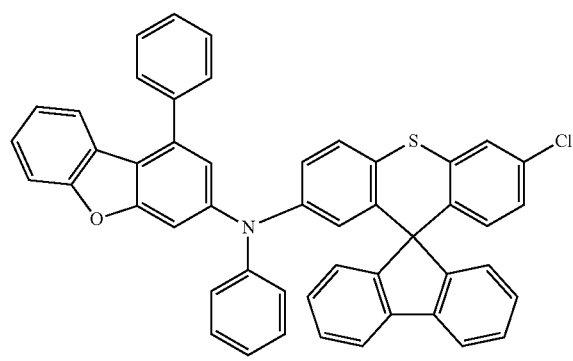
Sub1-82
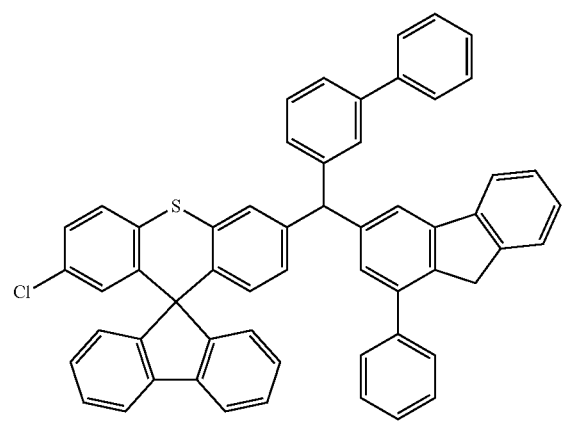
Sub1-83
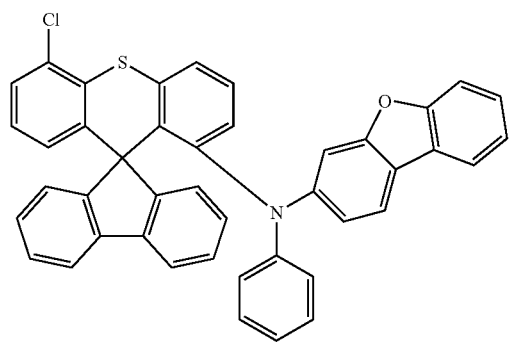
Sub1-84
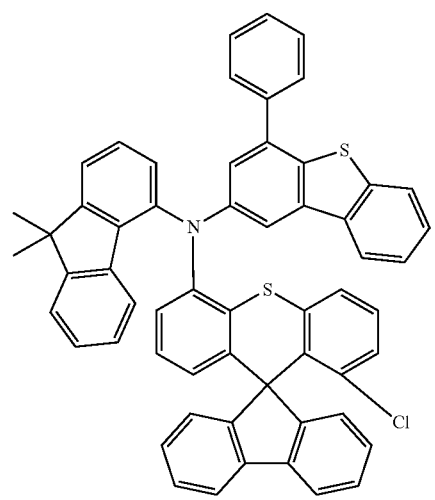

Sub1-85
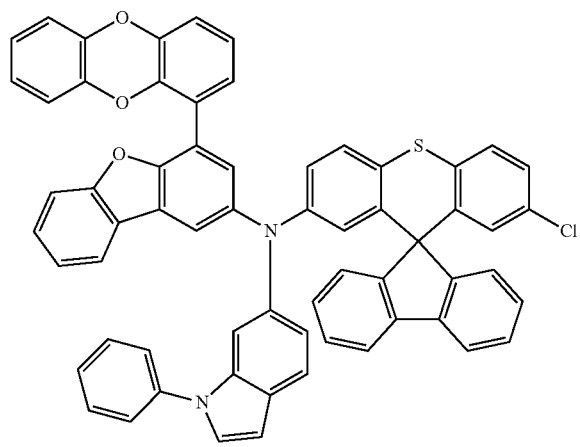
Sub1-86
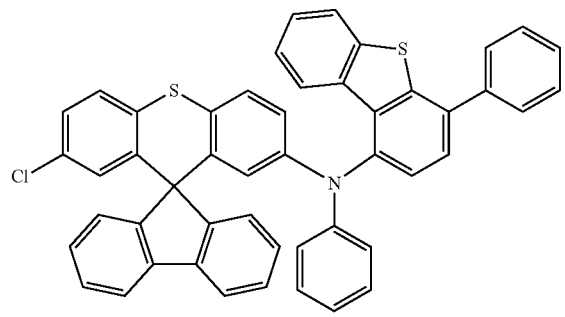
Sub1-87
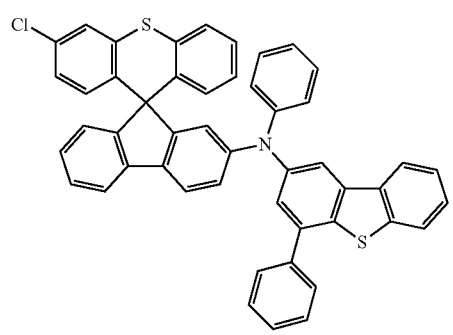
Sub1-88
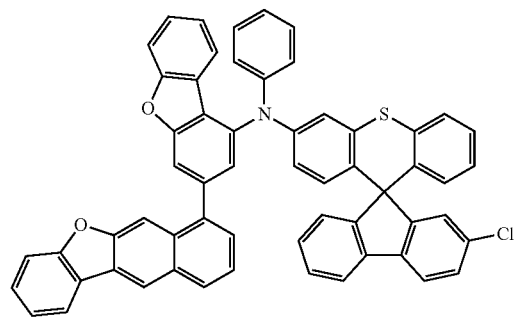
Sub1-89
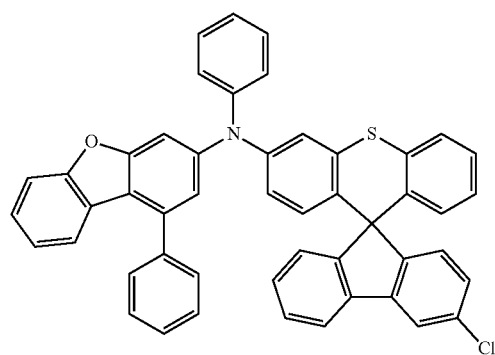
Sub1-90
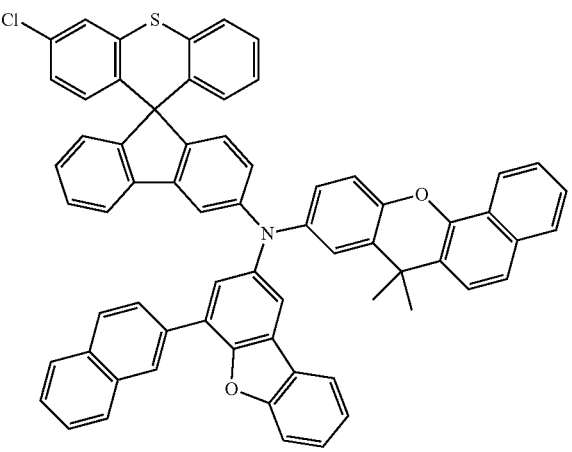

-continued
Sub1-91
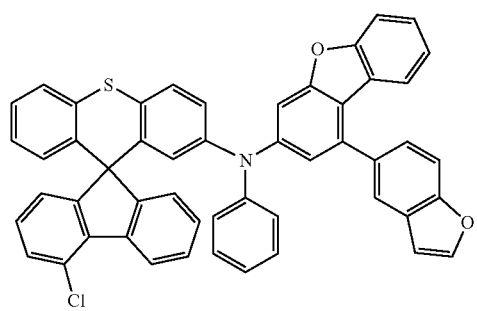
Sub1-92
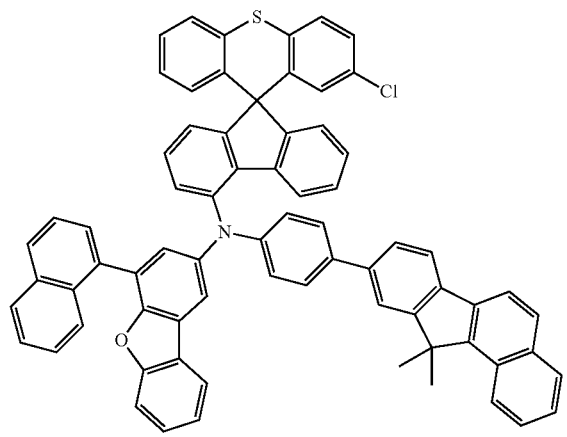
Sub1-93
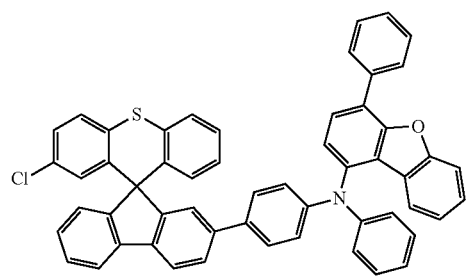
Sub1-94
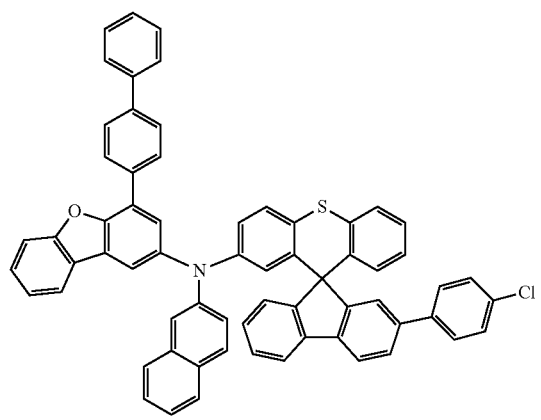
Sub1-95
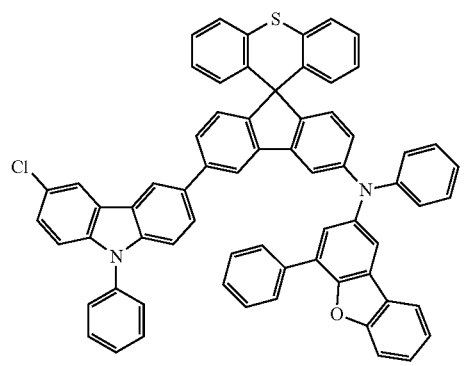
Sub1-96
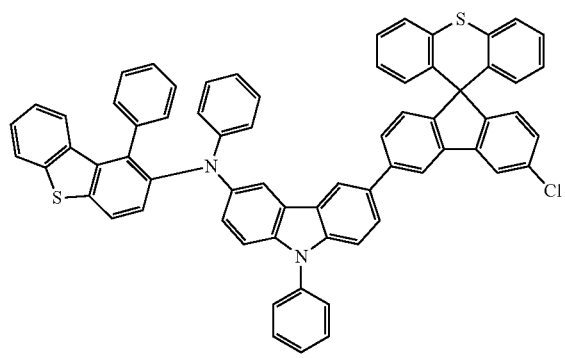

-continued
Sub1-97
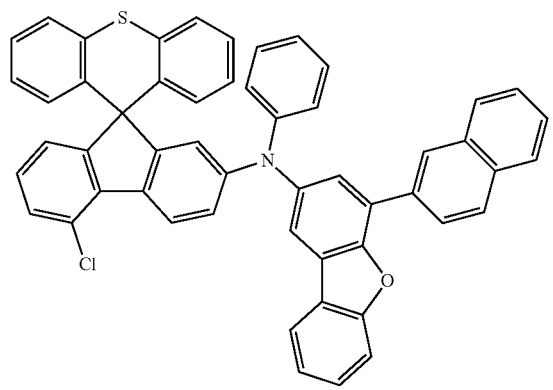
Sub1-98
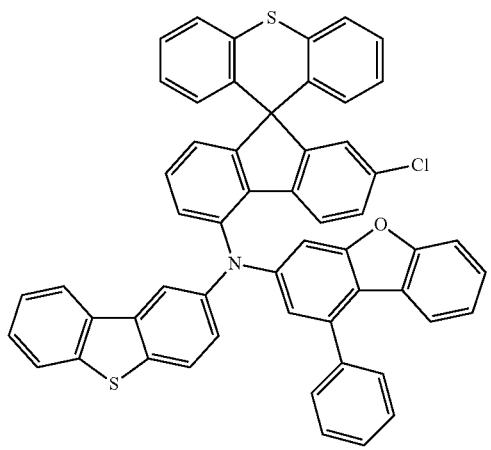
Sub1-99
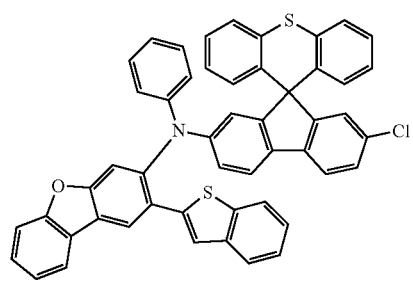
Sub1-100
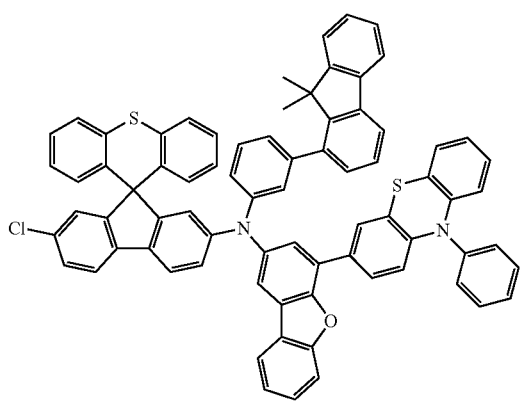
Sub1-101
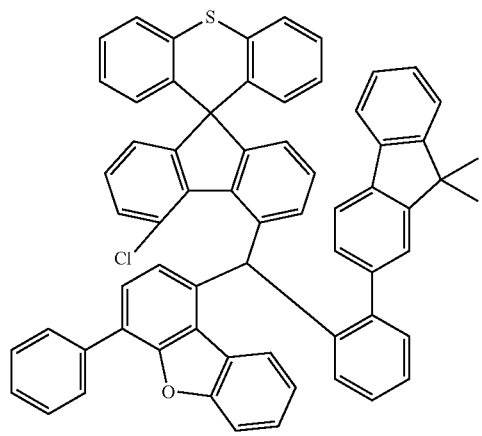
Sub1-102
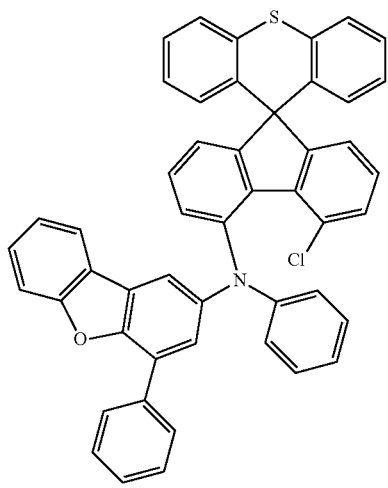

Sub1-103 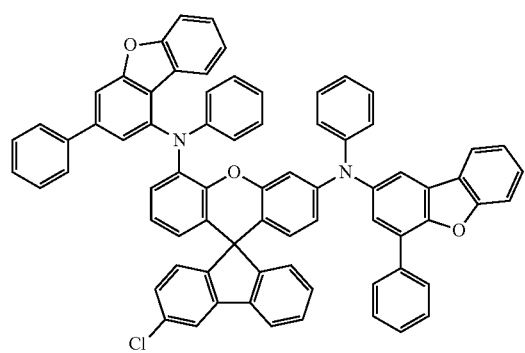
Sub1-104 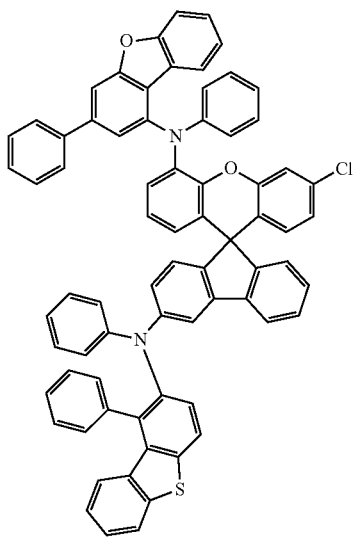
Sub1-105 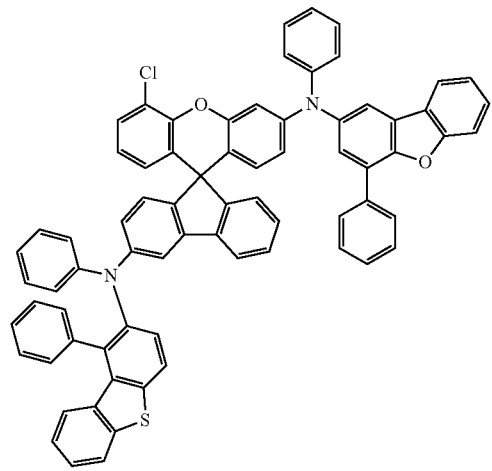
Sub1-106 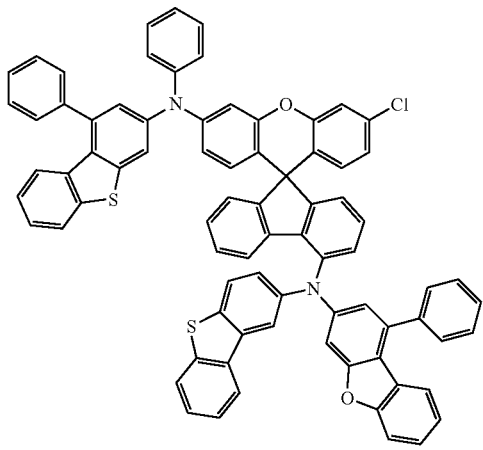

Sub1-107
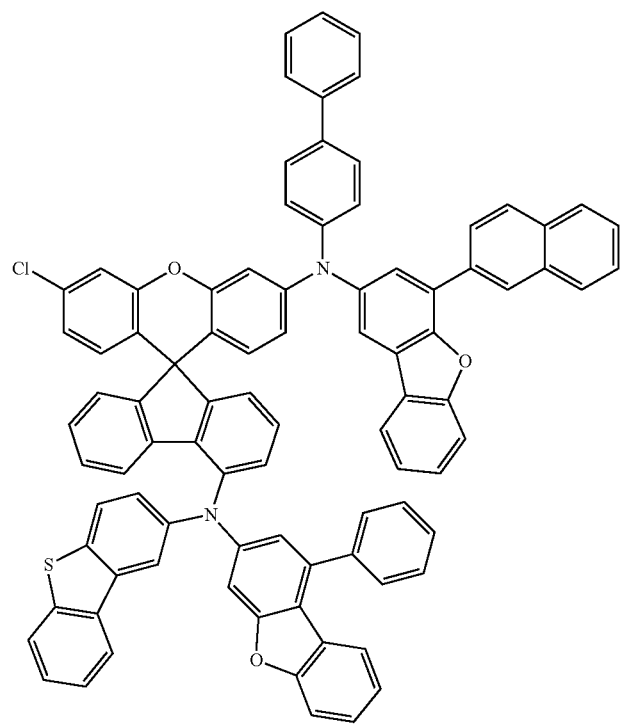
Sub1-108
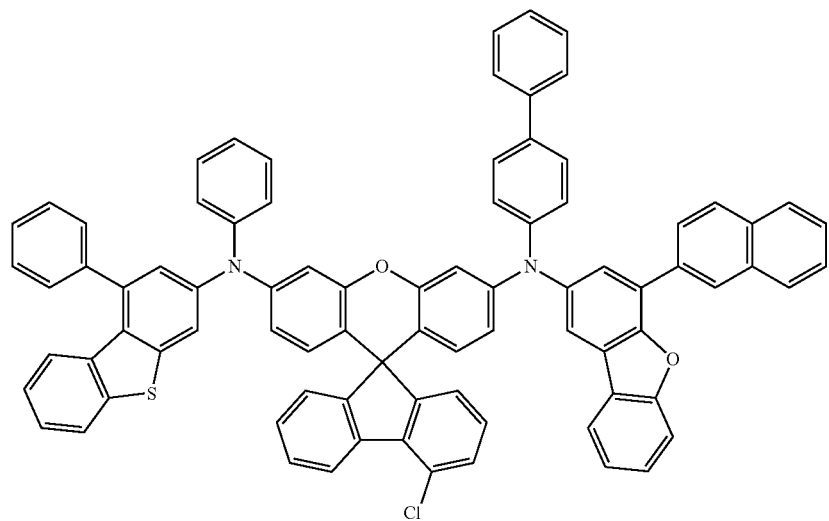

-continued
Sub1-109
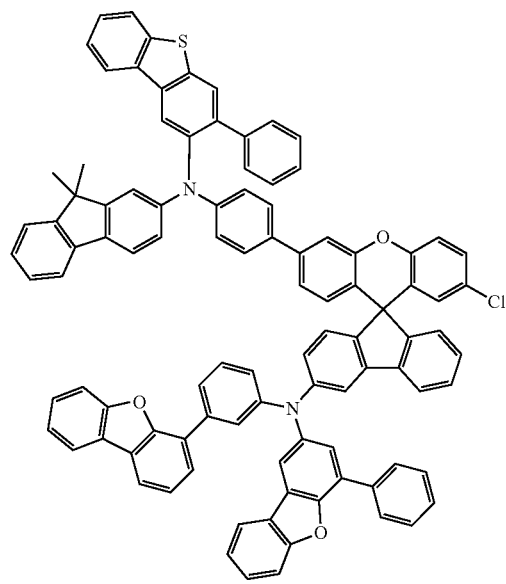
Sub1-110
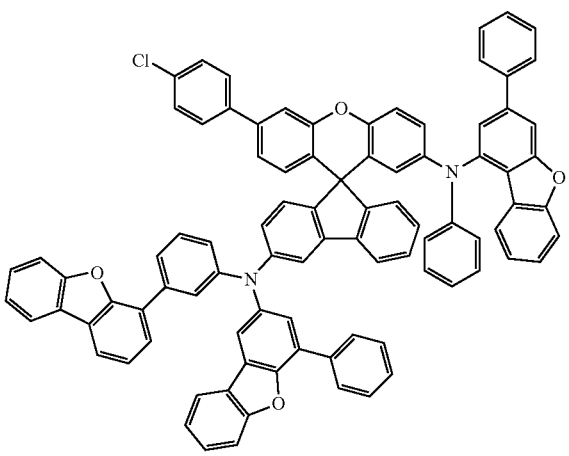
Sub1-111
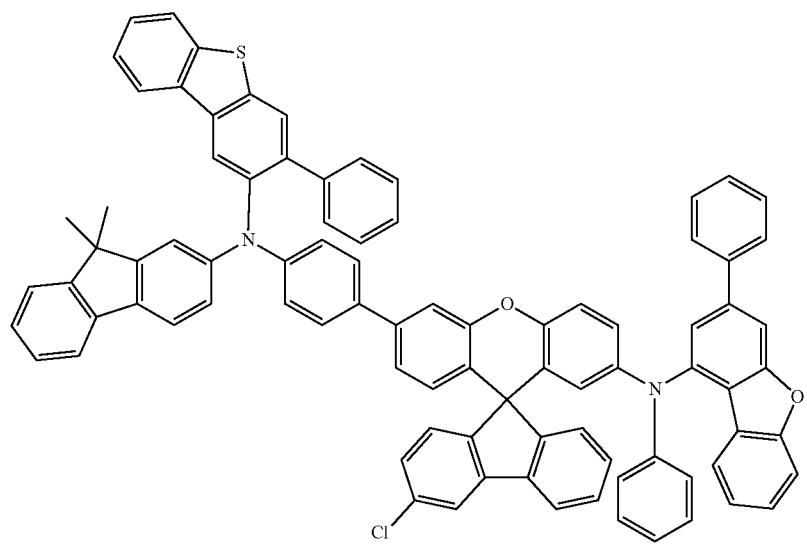
Sub1-112
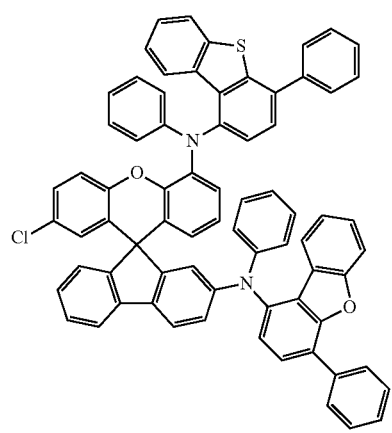
Sub1-113
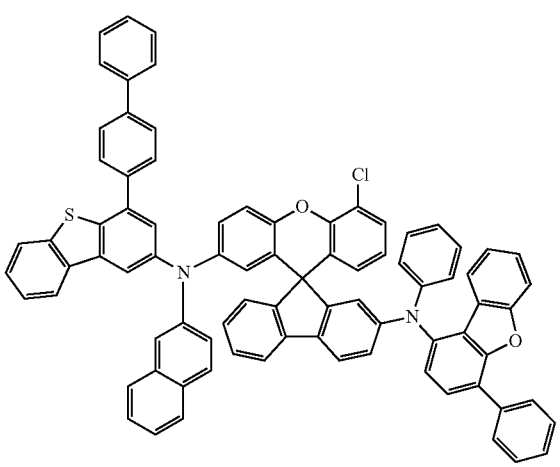

-continued
Sub1-114
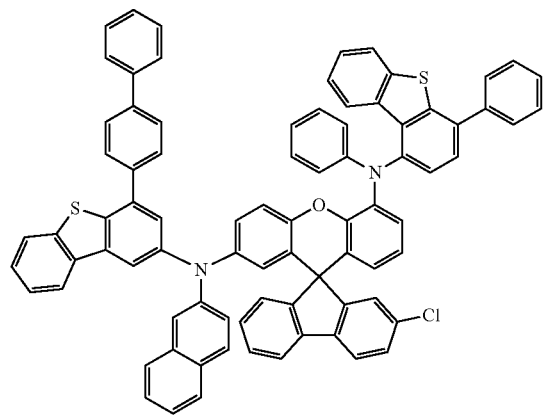
Sub1-115
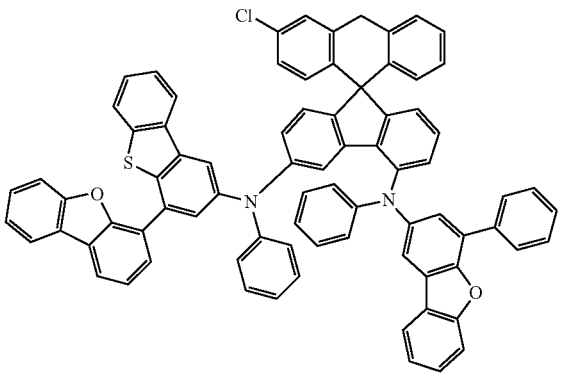
Sub1-116
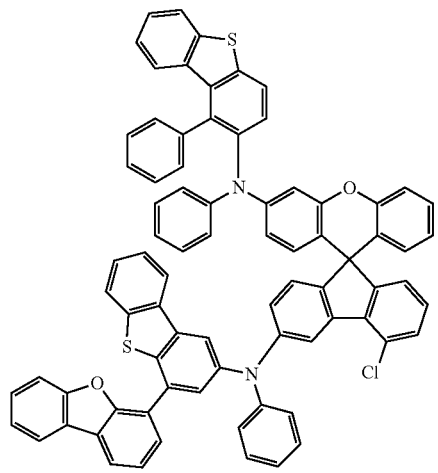
Sub1-117
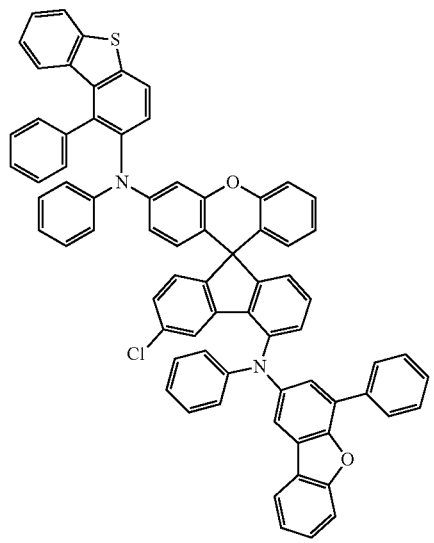
Sub1-118
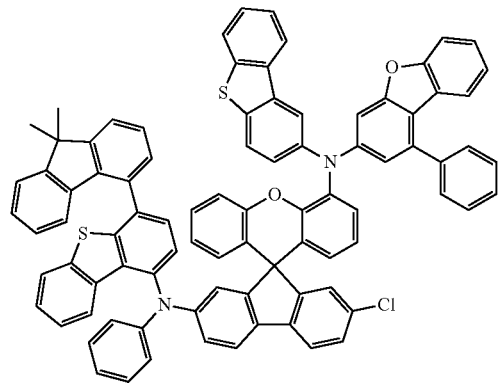
Sub1-119
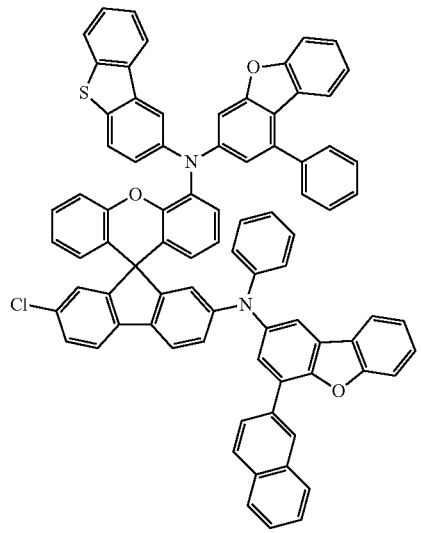

-continued
Sub1-120
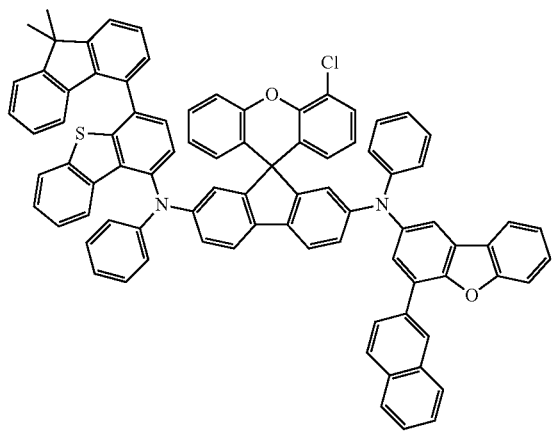
Sub1-121
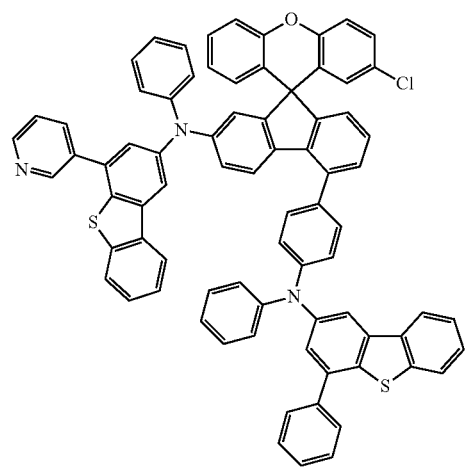
Sub1-122
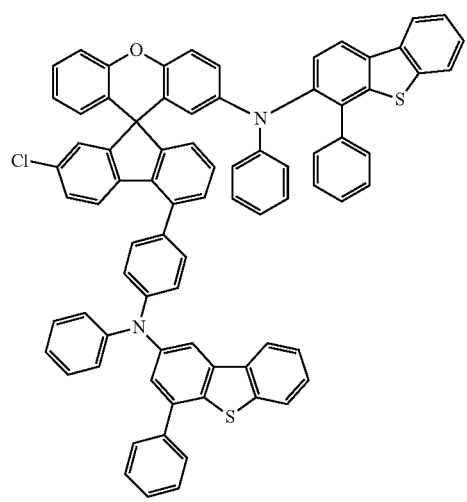
Sub1-123
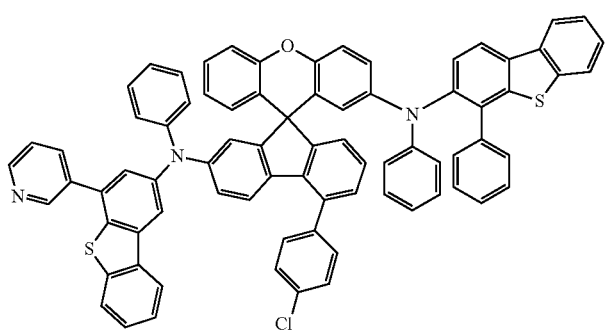

Sub1-124
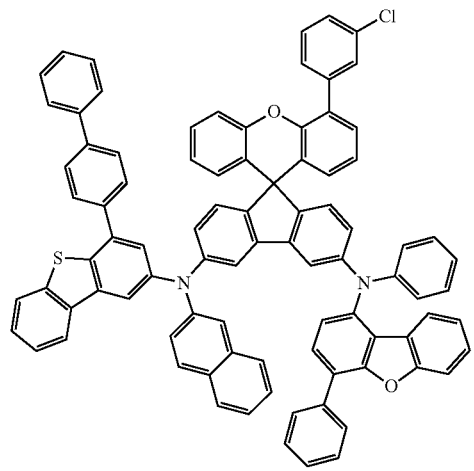
Sub1-125
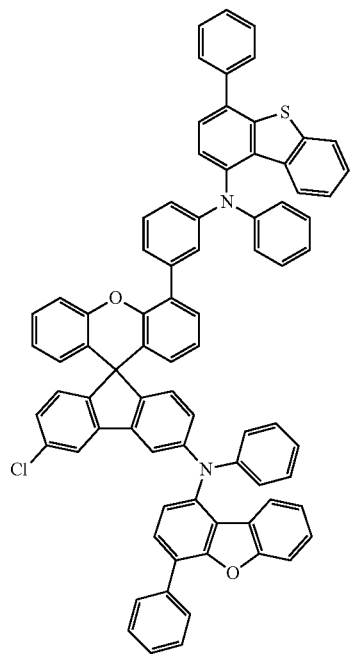
Sub1-126
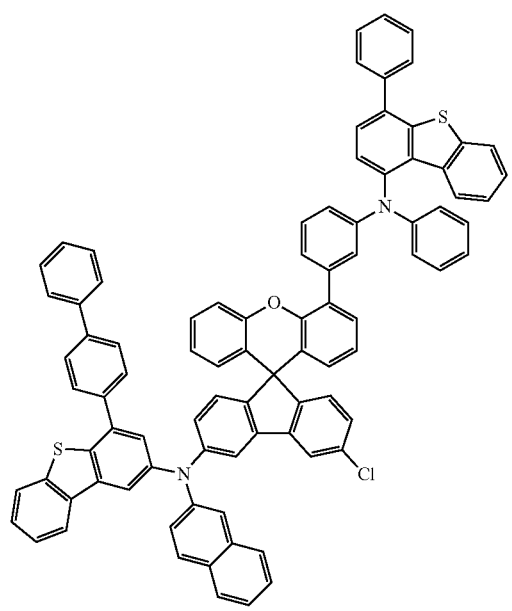
Sub1-127
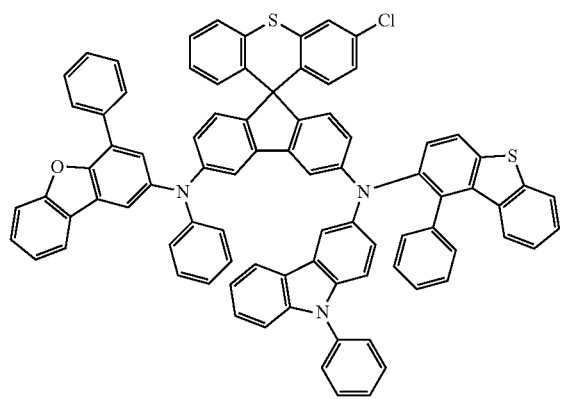

-continued
Sub1-128
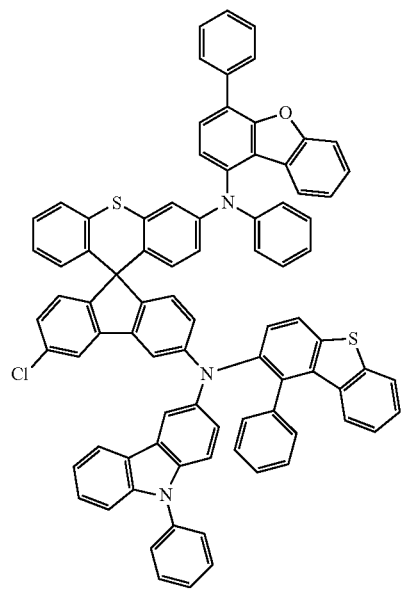
Sub1-129
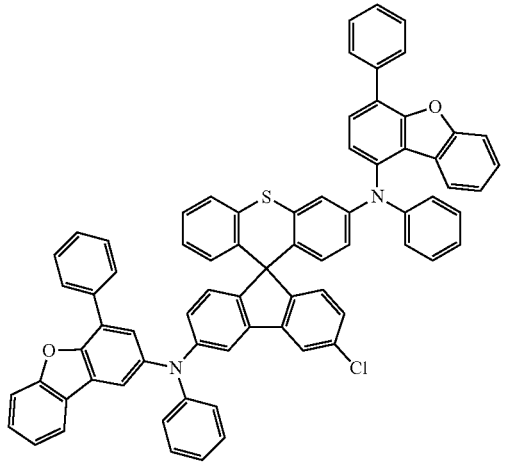
Sub1-130
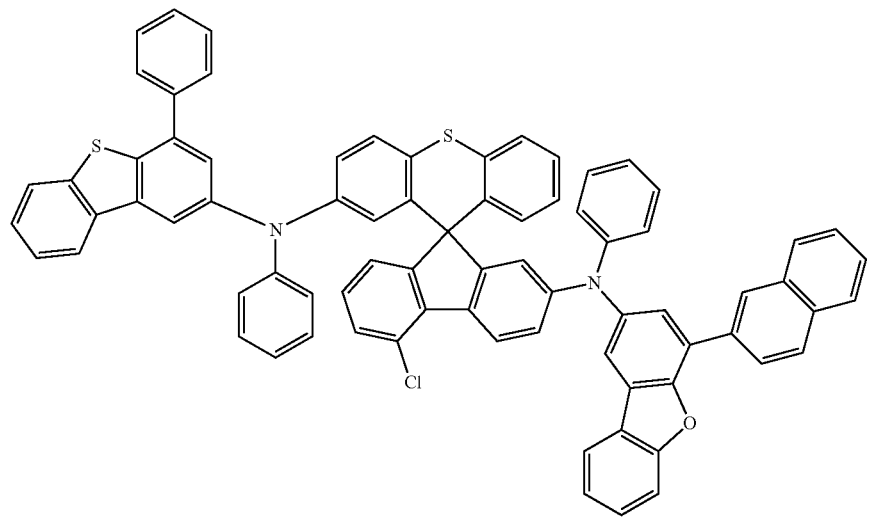
Sub1-131
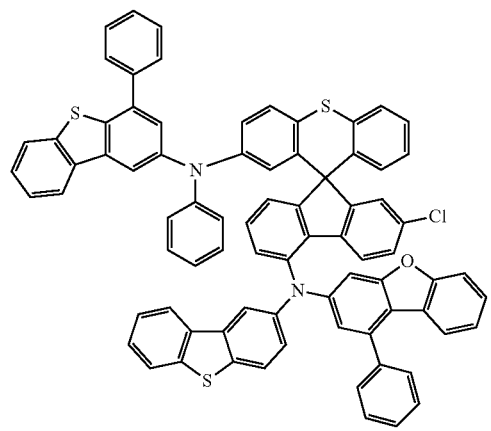
Sub1-132
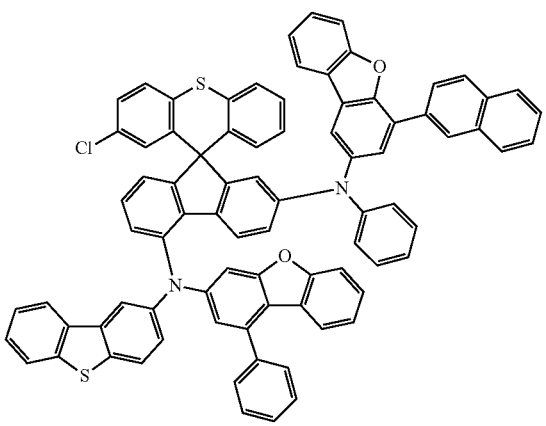

Sub1-133
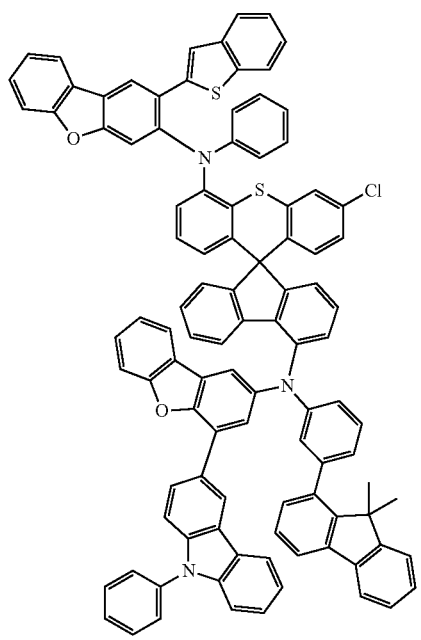
Sub1-134
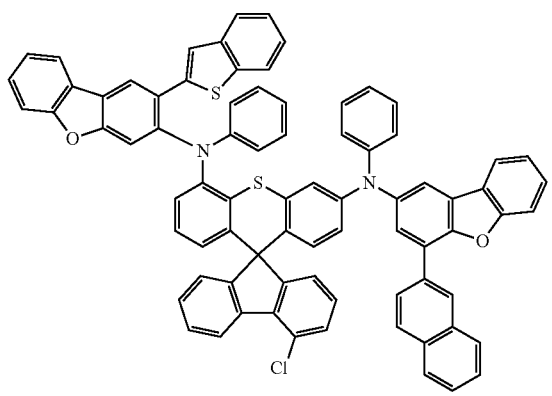
Sub1-135
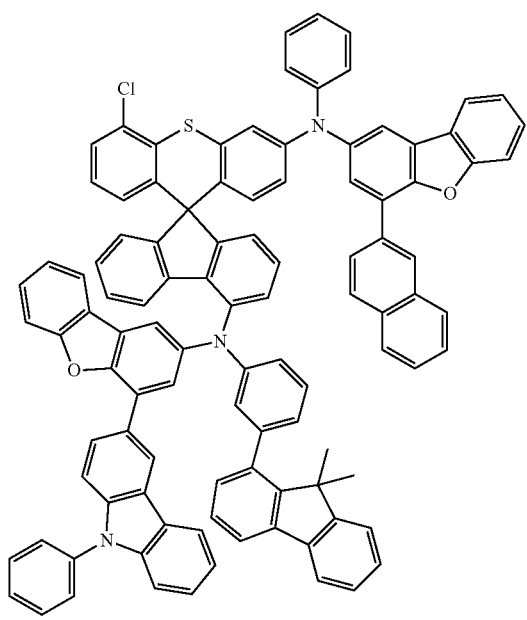
Sub1-136
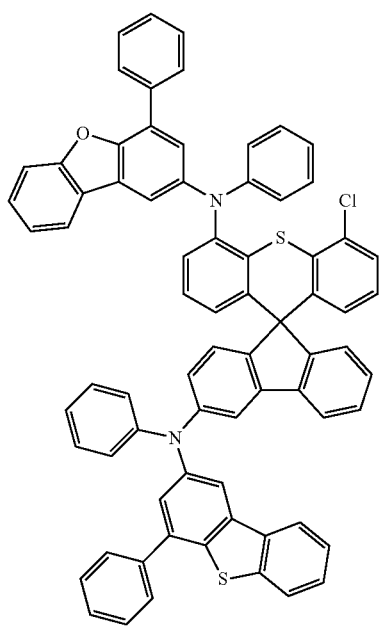

-continued
Sub1-137
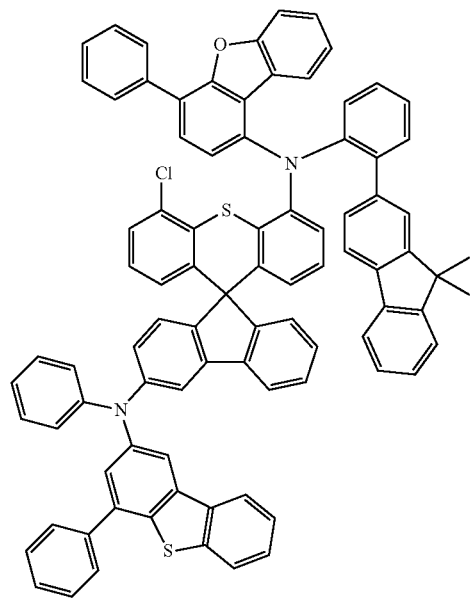
Sub1-138
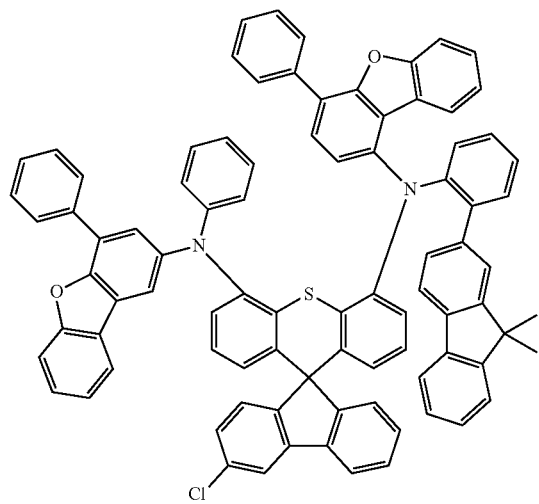
Sub1-139
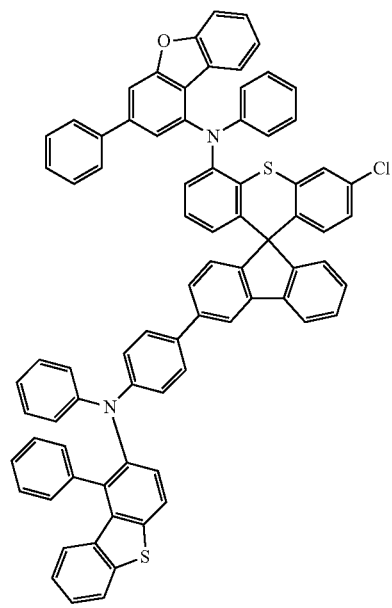
Sub1-140
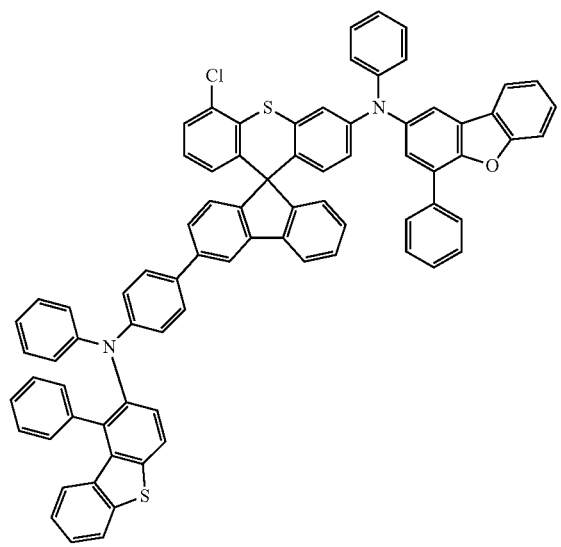

-continued
Sub1-141
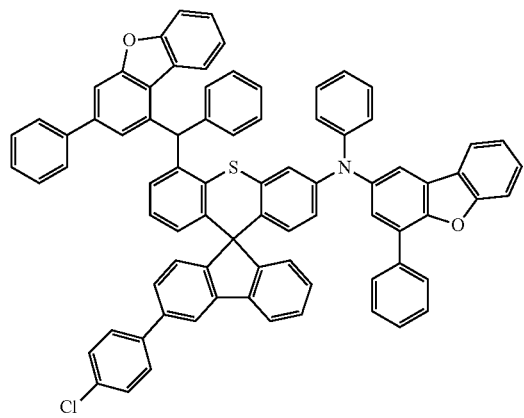
Sub1-142
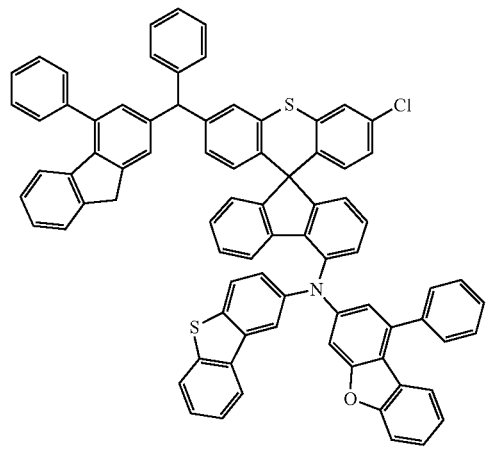
Sub1-143
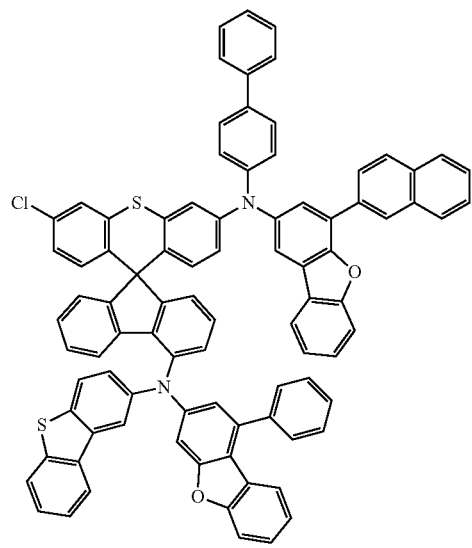
Sub1-144
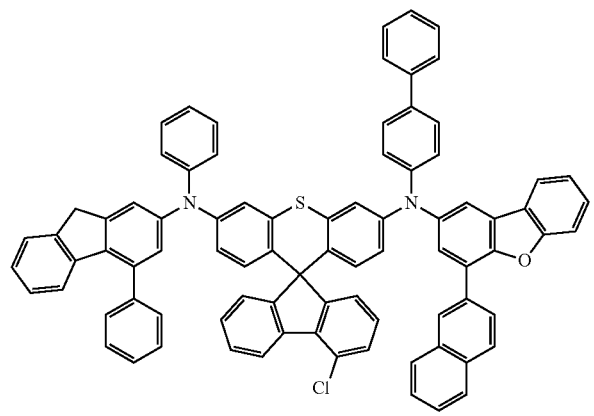
Sub1-145
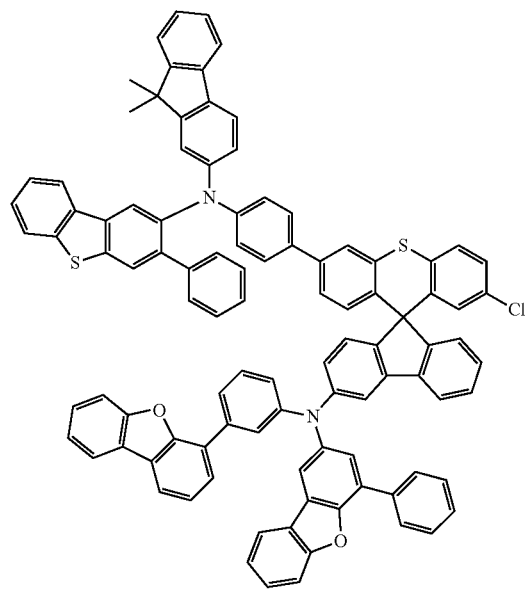
Sub1-146
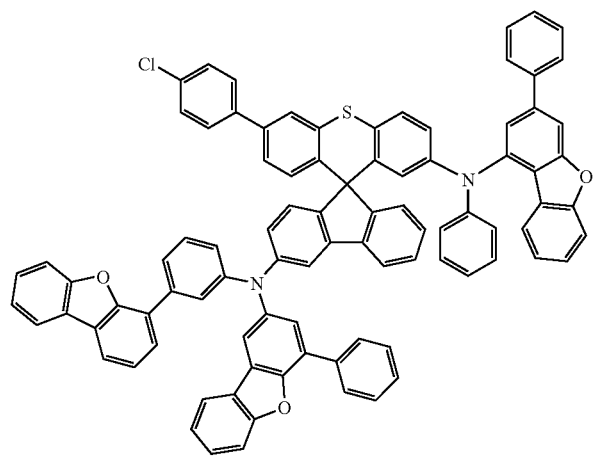

-continued
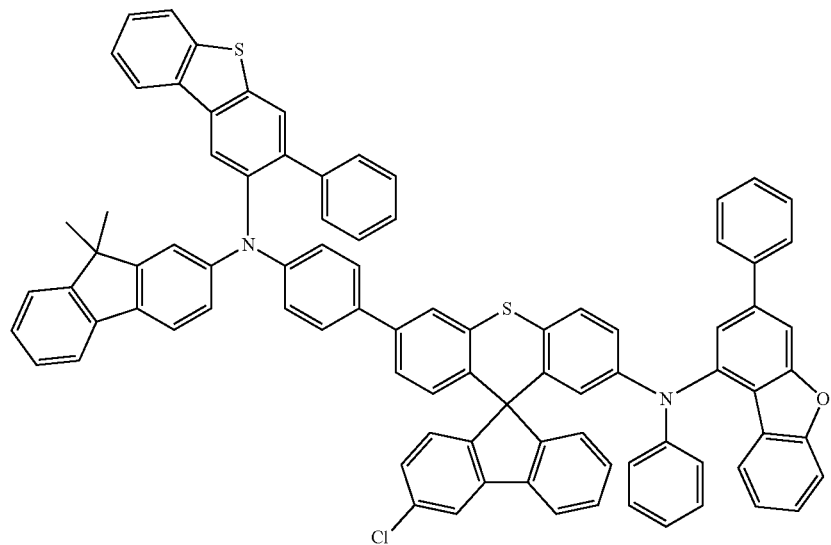
Sub1-147
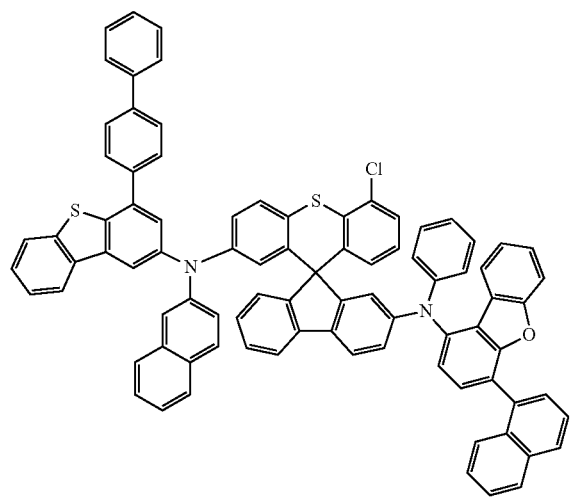
Sub1-148
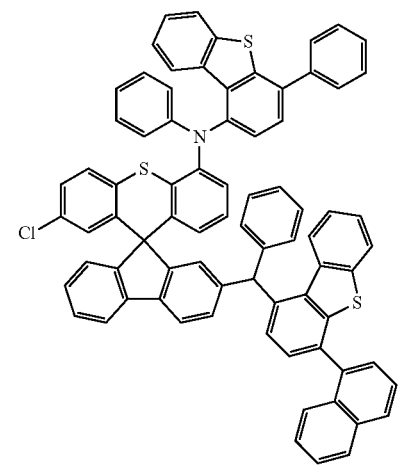
Sub1-149
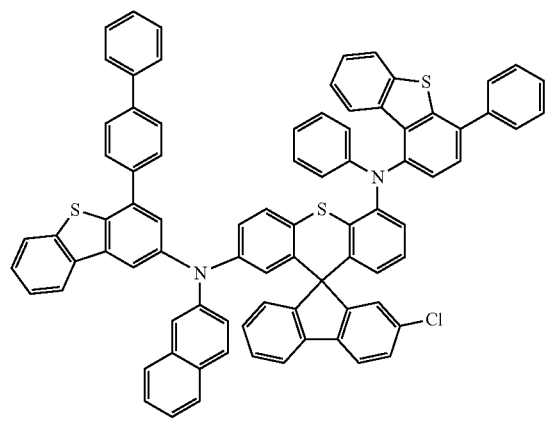
Sub1-150
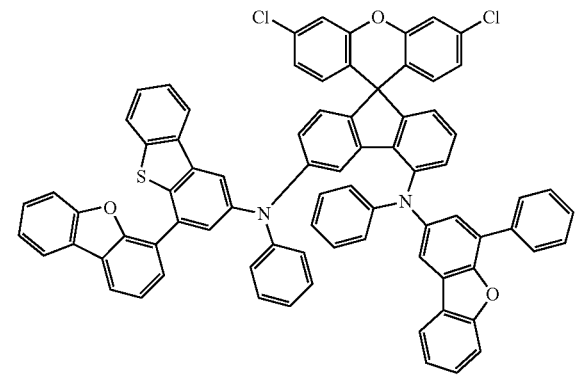
Sub1-151

-continued
Sub1-152
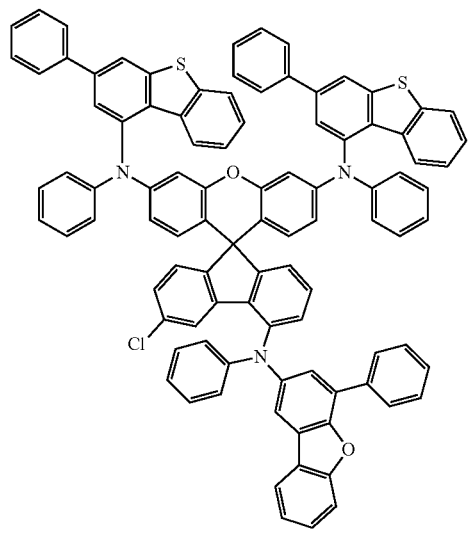
Sub1-153
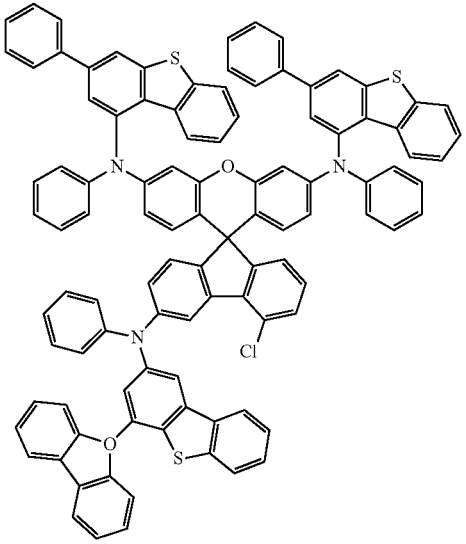
Sub1-154
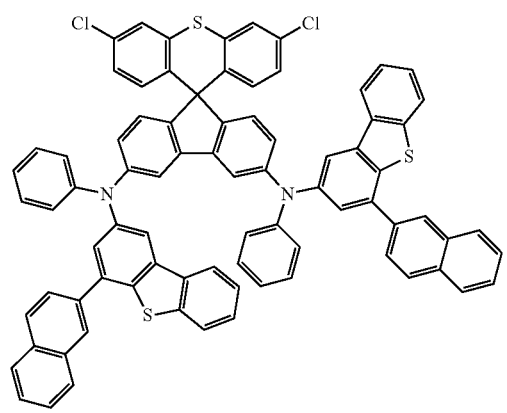
Sub1-154
Sub1-156
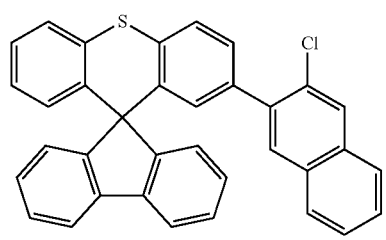
Sub1-157
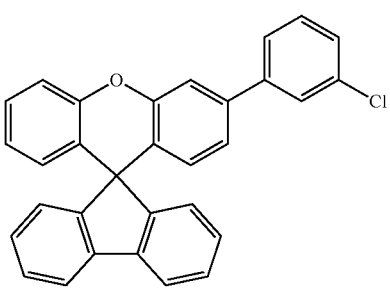

-continued
Sub1-158
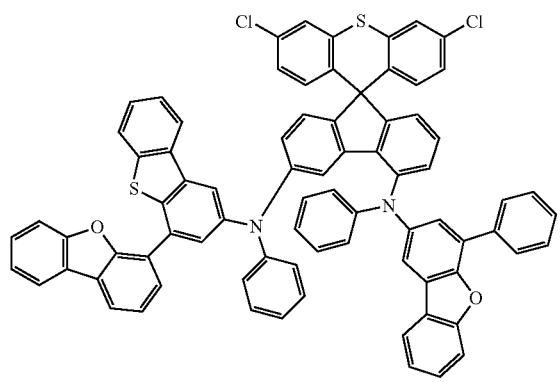
Sub1-159
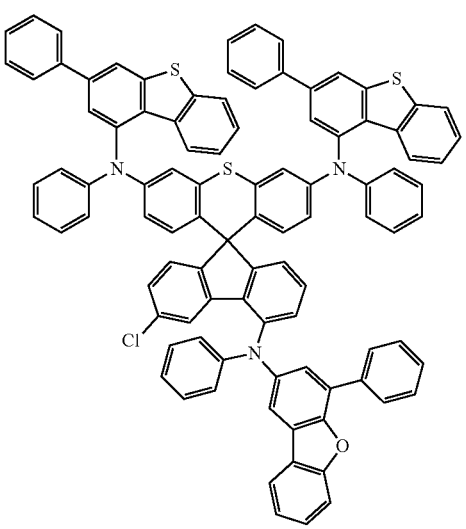
Sub1-160
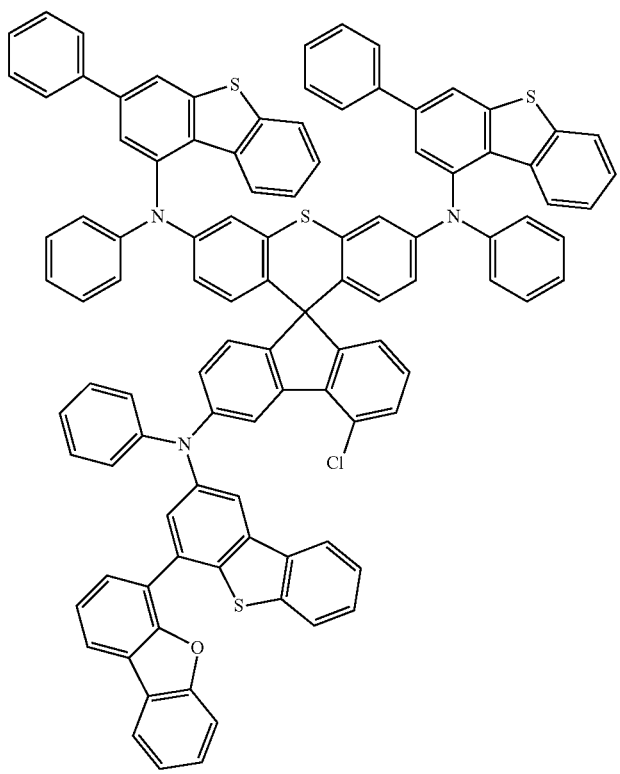
Sub1-161
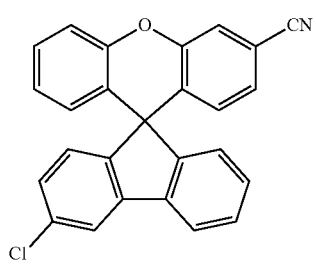
Sub1-162
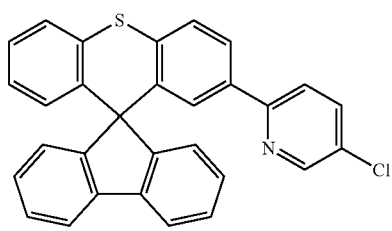
Sub1-163
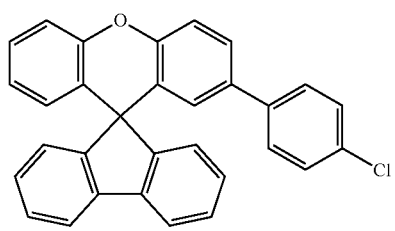

-continued
| Sub1-164 | Sub1-165 |
|---|---|
| 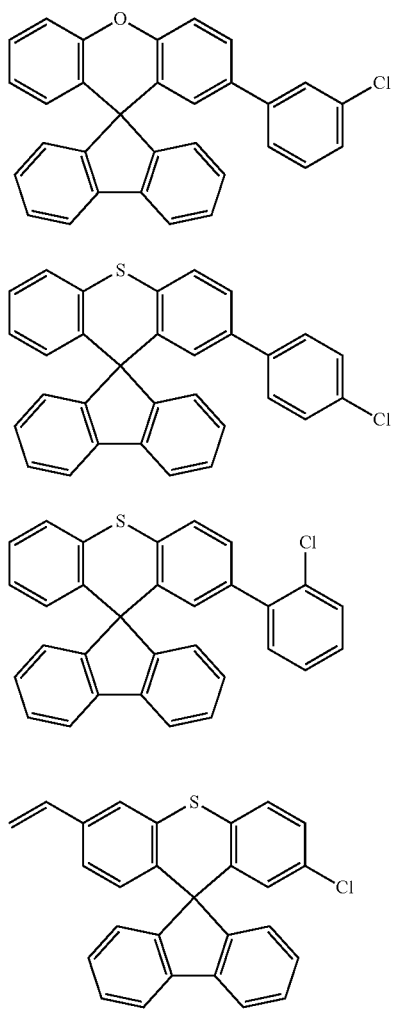 | 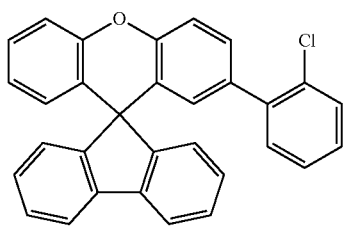 |
| Sub1-166 | Sub1-167 |
| | 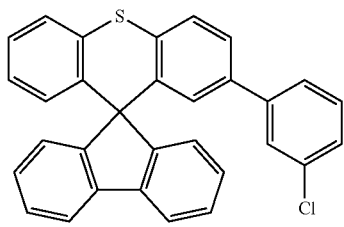 |
| Sub1-168 | Sub1-169 |
| | 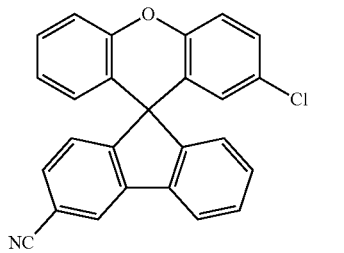 |
| Sub1-170 | Sub1-171 |
| | 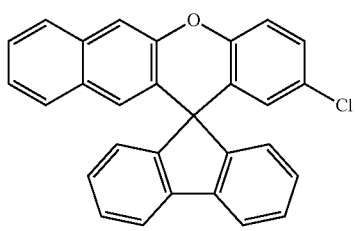 |
| Sub1-172 | Sub1-173 |
| | 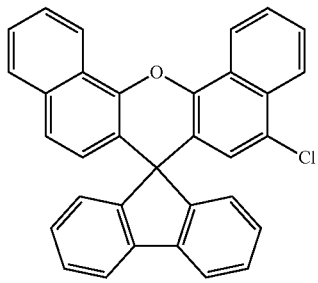 |
| Sub1-174 | Sub1-175 |
| | 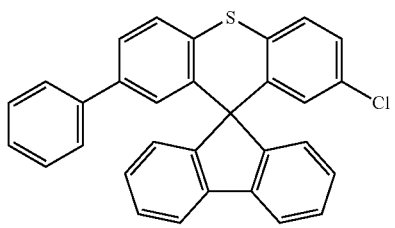 |

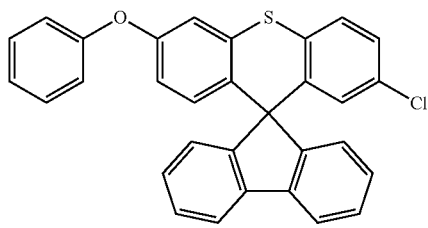

Sub1-176

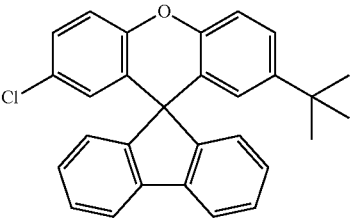

Sub1-177

TABLE 1

| compound | FD-MS | compound | FD-MS |
|---|---|---|---|
| Sub1-1 | m/z = 366.08($C_{25}H_{15}ClO$ = 366.84) | Sub1-2 | m/z = 366.08($C_{25}H_{15}ClO$ = 366.84) |
| Sub1-3 | m/z = 366.08($C_{25}H_{15}ClO$ = 366.84) | Sub1-4 | m/z = 366.08($C_{25}H_{15}ClO$ = 366.84) |
| Sub1-5 | m/z = 366.08($C_{25}H_{15}ClO$ = 366.84) | Sub1-6 | m/z = 366.08($C_{25}H_{15}ClO$ = 366.84) |
| Sub1-7 | m/z = 366.08($C_{25}H_{15}ClO$ = 366.84) | Sub1-8 | m/z = 366.08($C_{25}H_{15}ClO$ = 366.84) |
| Sub1-9 | m/z = 382.06($C_{25}H_{15}ClS$ = 382.91) | Sub1-10 | m/z = 382.06($C_{25}H_{15}ClS$ = 382.91) |
| Sub1-11 | m/z = 382.06($C_{25}H_{15}ClS$ = 382.91) | Sub1-12 | m/z = 382.06($C_{25}H_{15}ClS$ = 382.91) |
| Sub1-13 | m/z = 382.06($C_{25}H_{15}ClS$ = 382.91) | Sub1-14 | m/z = 382.06($C_{25}H_{15}ClS$ = 382.91) |
| Sub1-15 | m/z = 382.06($C_{25}H_{15}ClS$ = 382.91) | Sub1-16 | m/z = 382.06($C_{25}H_{15}ClS$ = 382.91) |
| Sub1-17 | m/z = 432.07($C_{29}H_{17}ClS$ = 432.97) | Sub1-18 | m/z = 432.07($C_{29}H_{17}ClS$ = 432.97) |
| Sub1-19 | m/z = 432.07($C_{29}H_{17}ClS$ = 432.97) | Sub1-20 | m/z = 432.07($C_{29}H_{17}ClS$ = 432.97) |
| Sub1-21 | m/z = 442.11($C_{31}H_{19}ClO$ = 442.94) | Sub1-22 | m/z = 408.07($C_{27}H_{17}ClS$ = 408.94) |
| Sub1-23 | m/z = 442.11($C_{31}H_{19}ClO$ = 442.94) | Sub1-24 | m/z = 508.11($C_{35}H_{21}ClS$ = 509.06) |
| Sub1-25 | m/z = 574.15($C_{40}H_{27}ClS$ = 575.17) | Sub1-26 | m/z = 442.11($C_{31}H_{19}ClO$ = 442.94) |
| Sub1-27 | m/z = 442.11($C_{31}H_{19}ClO$ = 442.94) | Sub1-28 | m/z = 532.12($C_{37}H_{21}ClO_2$ = 533.02) |
| Sub1-29 | m/z = 443.11($C_{30}H_{18}ClNO$ = 443.93) | Sub1-30 | m/z = 416.10($C_{29}H_{17}ClO$ = 416.90) |
| Sub1-31 | m/z = 699.20($C_{49}H_{30}ClNO_2$ = 700.23) | Sub1-32 | m/z = 699.20($C_{49}H_{30}ClNO_2$ = 700.23) |
| Sub1-33 | m/z = 825.24($C_{59}H_{36}ClNO_2$ = 826.39) | Sub1-34 | m/z = 941.31($C_{68}H_{44}ClNO_2$ = 942.56) |
| Sub1-35 | m/z = 623.17($C_{43}H_{26}ClNO_2$ = 624.14) | Sub1-36 | m/z = 825.24($C_{59}H_{36}ClNO_2$ = 826.39) |
| Sub1-37 | m/z = 699.20($C_{49}H_{30}ClNO_2$ = 700.23) | Sub1-38 | m/z = 715.17($C_{49}H_{30}ClNOS$ = 716.3) |
| Sub1-39 | m/z = 805.18($C_{55}H_{32}ClNO_2S$ = 806.38) | Sub1-40 | m/z = 749.21($C_{53}H_{32}ClNO_2$ = 750.29) |
| Sub1-41 | m/z = 892.29($C_{63}H_{41}ClN_2O_2$ = 893.48) | Sub1-42 | m/z = 623.17($C_{43}H_{26}ClNO_2$ = 624.14) |
| Sub1-43 | m/z = 841.27($C_{60}H_{40}ClNO_2$ = 842.44) | Sub1-44 | m/z = 805.18($C_{55}H_{32}ClNO_2S$ = 806.38) |
| Sub1-45 | m/z = 775.23($C_{55}H_{34}ClNO_2$ = 776.33) | Sub1-46 | m/z = 815.26($C_{58}H_{38}ClNO_2$ = 816.40) |
| Sub1-47 | m/z = 623.17($C_{43}H_{26}ClNO_2$ = 624.14) | Sub1-48 | m/z = 699.20($C_{49}H_{30}ClNO_2$ = 700.23) |
| Sub1-49 | m/z = 936.22($C_{63}H_{37}ClN_2O_3S$ = 937.51) | Sub1-50 | m/z = 855.20($C_{59}H_{34}ClNO_2S$ = 856.44) |
| Sub1-51 | m/z = 699.20($C_{49}H_{30}ClNO_2$ = 700.23) | Sub1-52 | m/z = 699.20($C_{49}H_{30}ClNO_2$ = 700.23) |
| Sub1-53 | m/z = 897.25($C_{62}H_{40}ClNO_2S$ = 898.52) | Sub1-54 | m/z = 957.28($C_{68}H_{44}ClNOS$ = 958.62) |
| Sub1-55 | m/z = 739.19($C_{51}H_{30}ClNO_3$ = 740.26) | Sub1-56 | m/z = 917.25($C_{65}H_{40}ClNO_2$ = 918.55) |
| Sub1-57 | m/z = 791.20($C_{55}H_{34}ClNOS$ = 792.39) | Sub1-58 | m/z = 699.20($C_{49}H_{30}ClNO_2$ = 700.23) |
| Sub1-59 | m/z = 897.19($C_{61}H_{36}ClNOS_2$ = 898.54) | Sub1-60 | m/z = 749.21($C_{53}H_{32}ClNO_2$ = 750.29) |
| Sub1-61 | m/z = 805.18($C_{55}H_{32}ClNO_2S$ = 806.38) | Sub1-62 | m/z = 755.17($C_{51}H_{30}ClNO_2S$ = 756.32) |
| Sub1-63 | m/z = 1088.32($C_{76}H_{49}ClN_2O_2S$ = 1089.75) | Sub1-64 | m/z = 699.20($C_{49}H_{30}ClNO_2$ = 700.23) |
| Sub1-65 | m/z = 891.29($C_{64}H_{42}ClNO_2$ = 892.50) | Sub1-66 | m/z = 639.14($C_{43}H_{26}ClNOS$ = 640.20) |
| Sub1-67 | m/z = 715.17($C_{49}H_{30}ClNOS$ = 716.30) | Sub1-68 | m/z = 715.17($C_{49}H_{30}ClNOS$ = 716.3) |
| Sub1-69 | m/z = 841.22($C_{59}H_{36}ClNOS$ = 842.45) | Sub1-70 | m/z = 957.28($C_{68}H_{44}ClNOS$ = 958.62) |
| Sub1-71 | m/z = 639.14($C_{43}H_{26}ClNOS$ = 640.20) | Sub1-72 | m/z = 917.25($C_{65}H_{40}ClNOS$ = 918.55) |
| Sub1-73 | m/z = 841.22($C_{59}H_{36}ClNOS$ = 842.45) | Sub1-74 | m/z = 731.15($C_{49}H_{30}ClNS_2$ = 732.36) |
| Sub1-75 | m/z = 821.16($C_{55}H_{32}ClNOS_2$ = 822.44) | Sub1-76 | m/z = 765.19($C_{53}H_{32}ClNOS$ = 766.36) |
| Sub1-77 | m/z = 908.26($C_{63}H_{41}ClN_2OS$ = 909.54) | Sub1-78 | m/z = 873.23($C_{60}H_{40}ClNS_2$ = 874.56) |
| Sub1-79 | m/z = 731.15($C_{49}H_{30}ClNS_2$ = 732.36) | Sub1-80 | m/z = 821.16($C_{55}H_{32}ClNOS_2$ = 822.44) |
| Sub1-81 | m/z = 715.17($C_{49}H_{30}ClNOS$ = 716.30) | Sub1-82 | m/z = 791.20($C_{55}H_{34}ClNOS$ = 792.39) |
| Sub1-83 | m/z = 639.14($C_{43}H_{26}ClNOS$ = 640.20) | Sub1-84 | m/z = 847.21($C_{58}H_{38}ClNS_2$ = 848.52) |
| Sub1-85 | m/z = 936.22($C_{63}H_{37}ClN_2O_3S$ = 937.51) | Sub1-86 | m/z = 731.15($C_{49}H_{30}ClNS_2$ = 732.36) |
| Sub1-87 | m/z = 731.15($C_{49}H_{30}ClNS_2$ = 732.36) | Sub1-88 | m/z = 855.20($C_{59}H_{34}ClNO_2S$ = 856.44) |
| Sub1-89 | m/z = 715.17($C_{49}H_{30}ClNOS$ = 716.30) | Sub1-90 | m/z = 947.26($C_{66}H_{42}ClNOS$ = 948.58) |
| Sub1-91 | m/z = 755.17($C_{51}H_{30}ClNO_2S$ = 756.32) | Sub1-92 | m/z = 1007.30($C_{72}H_{46}ClNOS$ = 1008.68) |
| Sub1-93 | m/z = 791.20($C_{55}H_{34}ClNOS$ = 792.39) | Sub1-94 | m/z = 917.25($C_{65}H_{40}ClNOS$ = 918.55) |
| Sub1-95 | m/z = 956.26($C_{67}H_{41}ClN_2OS$ = 957.59) | Sub1-96 | m/z = 972.24($C_{67}H_{41}ClN_2S_2$ = 973.65) |
| Sub1-97 | m/z = 765.19($C_{53}H_{32}ClNOS$ = 766.36) | Sub1-98 | m/z = 821.16($C_{55}H_{32}ClNOS_2$ = 822.44) |
| Sub1-99 | m/z = 771.15($C_{51}H_{30}ClNOS_2$ = 772.38) | Sub1-100 | m/z = 1104.30($C_{76}H_{49}ClN_2OS_2$ = 1105.81) |
| Sub1-101 | m/z = 907.27($C_{64}H_{42}ClNOS$ = 908.56) | Sub1-102 | m/z = 715.17($C_{49}H_{30}ClNOS$ = 716.03) |
| Sub1-103 | m/z = 1032.31($C_{73}H_{45}ClN_2O_3$ = 1033.62) | Sub1-104 | m/z = 1048.29($C_{73}H_{45}ClN_2O_2S$ = 1049.69) |
| Sub1-105 | m/z = 1048.29($C_{73}H_{45}ClN_2O_2S$ = 1049.69) | Sub1-106 | m/z = 1154.28($C_{79}H_{47}ClN_2O_2S_2$ = 1155.83) |
| Sub1-107 | m/z = 1264.35($C_{89}H_{53}ClN_2O_3S$ = 1265.92) | Sub1-108 | m/z = 1174.34($C_{83}H_{51}ClN_2O_2S$ = 1175.84) |
| Sub1-109 | m/z = 1406.42($C_{100}H_{63}ClN_2O_3S$ = 1408.13) | Sub1-110 | m/z = 1274.39($C_{91}H_{55}ClNO_4$ = 1275.90) |
| Sub1-111 | m/z = 1240.38($C_{88}H_{57}ClN_2O_2S$ = 1241.95) | Sub1-112 | m/z = 1048.29($C_{73}H_{45}ClN_2O_2S$ = 1049.69) |
| Sub1-113 | m/z = 1174.34($C_{83}H_{51}ClN_2O_2S$ = 1175.84) | Sub1-114 | m/z = 1190.31($C_{83}H_{51}ClN_2O_2S$ = 1191.90) |
| Sub1-115 | m/z = 1138.30($C_{79}H_{47}ClN_2O_3S$ = 1139.77) | Sub1-116 | m/z = 1154.28($C_{79}H_{47}ClN_2O_2S_2$ = 1155.83) |
| Sub1-117 | m/z = 1048.29($C_{73}H_{45}ClN_2O_2S$ = 1049.69) | Sub1-118 | m/z = 1270.34($C_{88}H_{55}ClN_2O_2S_2$ = 1271.99) |
| Sub1-119 | m/z = 1188.32($C_{83}H_{49}ClN_2O_3S$ = 1189.83) | Sub1-120 | m/z = 1214.37($C_{86}H_{55}ClN_2O_2S$ = 1215.91) |
| Sub1-121 | m/z = 1141.29($C_{78}H_{48}ClN_3OS_2$ = 1142.83) | Sub1-122 | m/z = 1140.30($C_{79}H_{49}ClN_2OS_2$ = 1141.84) |
| Sub1-123 | m/z = 1141.29($C_{78}H_{48}ClN_3OS_2$ = 1142.83) | Sub1-124 | m/z = 1250.37($C_{89}H_{55}ClN_2O_2S$ = 1251.94) |

TABLE 1-continued

| compound | FD-MS | compound | FD-MS |
|---|---|---|---|
| Sub1-125 | m/z = 1124.32($C_{79}H_{49}ClN_2O_2S$ = 1125.78) | Sub1-126 | m/z = 1266.34($C_{89}H_{55}ClN_2OS_2$ = 1268.00) |
| Sub1-127 | m/z = 1229.32($C_{85}H_{52}ClN_3OS_2$ = 1230.94) | Sub1-128 | m/z = 1229.32($C_{85}H_{52}ClN_3OS_2$ = 1230.94) |
| Sub1-129 | m/z = 1048.29($C_{73}H_{45}ClN_2O_2S$ = 1049.69) | Sub1-130 | m/z = 1114.28($C_{77}H_{47}ClN_2OS_2$ = 1115.81) |
| Sub1-131 | m/z = 1170.25($C_{79}H_{47}ClN_2OS_3$ = 1171.89) | Sub1-132 | m/z = 1204.29($C_{83}H_{49}ClN_2O_2S_2$ = 1205.89) |
| Sub1-133 | m/z = 1477.44($C_{103}H_{68}ClN_3O_2S_2$ = 1479.27) | Sub1-134 | m/z = 1154.28($C_{79}H_{47}ClN_2O_2S_2$ = 1155.83) |
| Sub1-135 | m/z = 1471.49($C_{105}H_{70}ClN_3O_2S$ = 1473.24) | Sub1-136 | m/z = 1064.27($C_{73}H_{43}ClN_2OS_2$ = 1065.75) |
| Sub1-137 | m/z = 1256.36($C_{88}H_{57}ClN_2OS_2$ = 1258.01) | Sub1-138 | m/z = 1240.38($C_{88}H_{57}ClN_2O_2S$ = 1241.95) |
| Sub1-139 | m/z = 1140.30($C_{79}H_{49}ClN_2OS_2$ = 1141.84) | Sub1-140 | m/z = 1140.30($C_{79}H_{49}ClN_2OS_2$ = 1141.84) |
| Sub1-141 | m/z = 1124.32($C_{79}H_{49}ClN_2O_2S$ = 1125.78) | Sub1-142 | m/z = 1170.25($C_{79}H_{47}ClN_2OS_3$ = 1171.89) |
| Sub1-143 | m/z = 1280.32($C_{89}H_{53}ClN_2O_2S_2$ = 1281.99) | Sub1-144 | m/z = 1190.31($C_{83}H_{51}ClN_2OS_2$ = 1191.90) |
| Sub1-145 | m/z = 1422.40($C_{100}H_{63}ClN_2O_2S_2$ = 1424.19) | Sub1-146 | m/z = 1290.36($C_{91}H_{55}ClN_2O_3S$ = 1291.96) |
| Sub1-147 | m/z = 1256.36($C_{88}H_{57}ClN_2OS_2$ = 1258.01) | Sub1-148 | m/z = 1256.31($C_{87}H_{53}ClN_2S_3$ = 1258.03) |
| Sub1-149 | m/z = 1130.26($C_{77}H_{47}ClN_2S_3$ = 1131.87) | Sub1-150 | m/z = 1206.29($C_{83}H_{51}ClN_2S_3$ = 1207.97) |
| Sub1-151 | m/z = 1236.39($C_{83}H_{62}Cl_2N_2O_3S$ = 1238.38) | Sub1-152 | m/z = 1493.57($C_{103}H_{84}ClN_3O_2S_2$ = 1495.39) |
| Sub1-153 | m/z = 1599.56($C_{109}H_{86}ClN_3OS_3$ = 1601.54) | Sub1-154 | m/z = 1214.24($C_{81}H_{48}Cl_2N_2S_3$ = 1216.37) |
| Sub1-155 | m/z = 1082.25($C_{73}H_{44}Cl_2N_2O_2S$ = 1084.13) | Sub1-156 | m/z = 508.11($C_{35}H_{21}ClS$ = 509.06) |
| Sub1-157 | m/z = 442.11($C_{31}H_{19}ClO$ = 442.94) | Sub1-158 | m/z = 1252.36($C_{83}H_{62}Cl_2N_2O_2S_2$ = 1254.44) |
| Sub1-159 | m/z = 1509.55($C_{103}H_{84}ClN_3OS_3$ = 1511.46) | Sub1-160 | m/z = 1615.53($C_{109}H_{86}ClN_3OS_4$ = 1617.60) |
| Sub1-161 | m/z = 391.08($C_{26}H_{14}ClNO$ = 391.85) | Sub1-162 | m/z = 459.08($C_{30}H_{18}ClNS$ = 459.99) |
| Sub1-163 | m/z = 442.11($C_{31}H_{19}ClO$ = 442.94) | Sub1-164 | m/z = 442.11($C_{31}H_{19}ClO$ = 442.94) |
| Sub1-165 | m/z = 442.11($C_{31}H_{19}ClO$ = 442.94) | Sub1-166 | m/z = 458.09($C_{31}H_{19}ClS$ = 459.00) |
| Sub1-167 | m/z = 458.09($C_{31}H_{19}ClS$ = 459.00) | Sub1-168 | m/z = 458.09($C_{31}H_{19}ClS$ = 459.00) |
| Sub1-169 | m/z = 391.08($C_{26}H_{14}ClNO$ = 391.85) | Sub1-170 | m/z = 408.07($C_{27}H_{17}ClS$ = 408.94) |
| Sub1-171 | m/z = 416.10($C_{29}H_{17}ClO$ = 416.90) | Sub1-172 | m/z = 460.08($C_{29}H_{17}ClN_2S$ = 460.98) |
| Sub1-173 | m/z = 466.11($C_{33}H_{19}ClO$ = 466.96) | Sub1-174 | m/z = 458.09($C_{31}H_{19}ClS$ = 459) |
| Sub1-175 | m/z = 458.09($C_{31}H_{19}ClS$ = 459) | Sub1-176 | m/z = 474.08($C_{31}H_{19}ClOS$ = 475) |
| Sub1-177 | m/z = 422.14($C_{29}H_{23}C_{10}$ = 422.95) | | |

II. Synthesis of Sub 2

Sub 2 of Reaction Scheme 1 may be synthesized by the reaction route of Scheme 3 below, but is not limited thereto. Sub 3 and Sub 4 are also included in Sub 2.

1. Synthesis Example of Sub 2-8

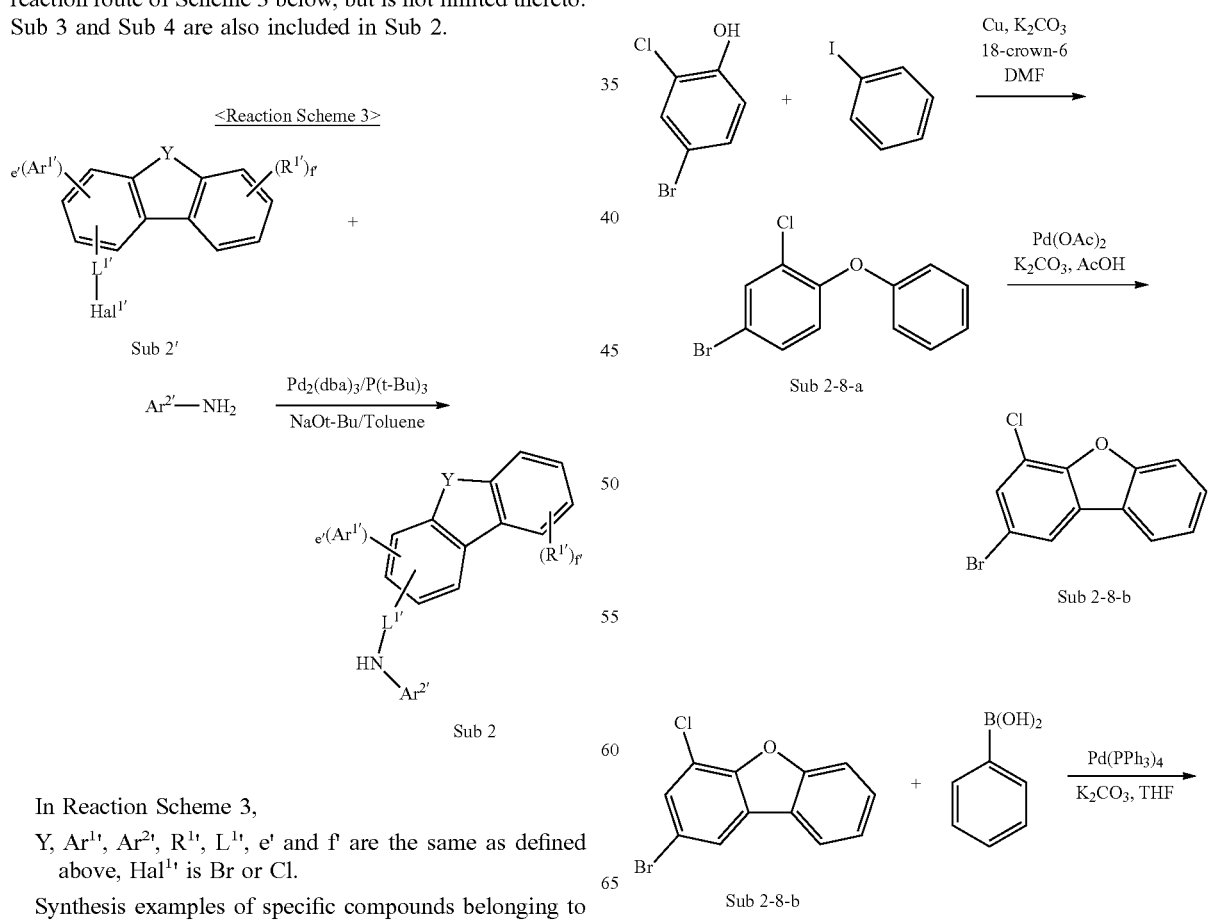

In Reaction Scheme 3,

Y, $Ar^{1'}$, $Ar^{2'}$, $R^{1'}$, $L^{1'}$, e' and f' are the same as defined above, $Hal^{1'}$ is Br or Cl.

Synthesis examples of specific compounds belonging to Sub 2 are as follows.

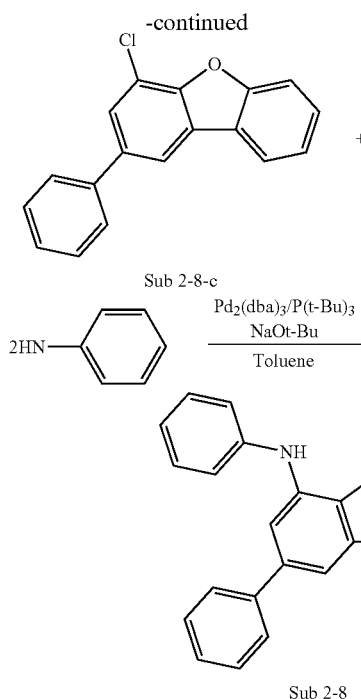

Sub 2-8

(1) Synthesis Example of Sub 2-8-a 4-bromo-2-chlorophenol (15 g, 73.5 mmole) was dissolved in a round bottom flask with DMF (400 mL) and iodobenzene (16.8 g, 80.9 mmol), $K_2CO_3$ (20.3 g 147.1 mmol), Cu (2.3 g, 36.8 mmol), Dibenzo-18-crown-6 (1.6 g, 4.4 mmole) were added and stirred at 120° C. When the reaction was completed, the solvent was removed, extracted with $CH_2Cl_2$ and water, the organic layer was dried over $MgSO_4$, concentrated, and the resulting compound was silica gel column to obtain 16.5 g (yield 79%) of the product.

(2) Synthesis Example of Sub 2-8-b

Acetic acid (400 mL) was added to 4-bromo-2-chloro-1-phenoxybenzene (16 g, 56.4 mmol)$^O$|| Pd(OAc)$_2$ (0.63 g, 2.8 mol), $K_2CO_3$ (7.8 g, 56.4 mol) and stirred at 120° C. for 48 hours. When the reaction was completed, the solvent was removed, extracted with Ethyl Acetate and water, the organic layer was dried over $MgSO_4$, concentrated, and the resulting compound was silica gel column to obtain 6.7 g (yield 42%) of the product.

(3) Synthesis Example of Sub 2-8-c

Sub 2-8-b (6.7 g, 23.8 mmol) obtained in the above synthesis, phenylboronic acid (2.9 g, 23.8 mmol) was added, dissolved in THF (100 mL), and Pd(PPh$_3$)$_4$ (1.4 g, 1.2 mmol) and $K_2CO_3$ (19.9 g, 71.4 mmol) were added, respectively, and then refluxed for 24 hours. When the reaction was completed, the solvent was removed, extracted with $CH_2Cl_2$ and water, the organic layer was dried over $MgSO_4$, concentrated, and the resulting compound was silica gel column to obtain 4.98 g (yield 75%) of the product.

(4) Synthesis Example of Sub 2-8

After dissolving Sub 2-8-c (4.98 g, 17.9 mmol) obtained in the above synthesis with Toluene (100 ml) in a round bottom flask, Aniline (1.83 g, 19.7 mmol), Pd$_2$(dba)$_3$ (0.49 g, 0.54 mmol), P(t-Bu)$_3$ (50 wt % Sol.) (0.43 mL, 1.07 mmol), NaOt-Bu (5.2 g, 53.6 mmol) were added and stirred at 80° C. When the reaction was completed, the solvent was removed, extracted with $CH_2Cl_2$ and water, the organic layer was dried over $MgSO_4$, concentrated, and the resulting compound was silica gel column to obtain 4.8 g (yield 80%) of the product.

2. Synthesis Example of Sub 2-43

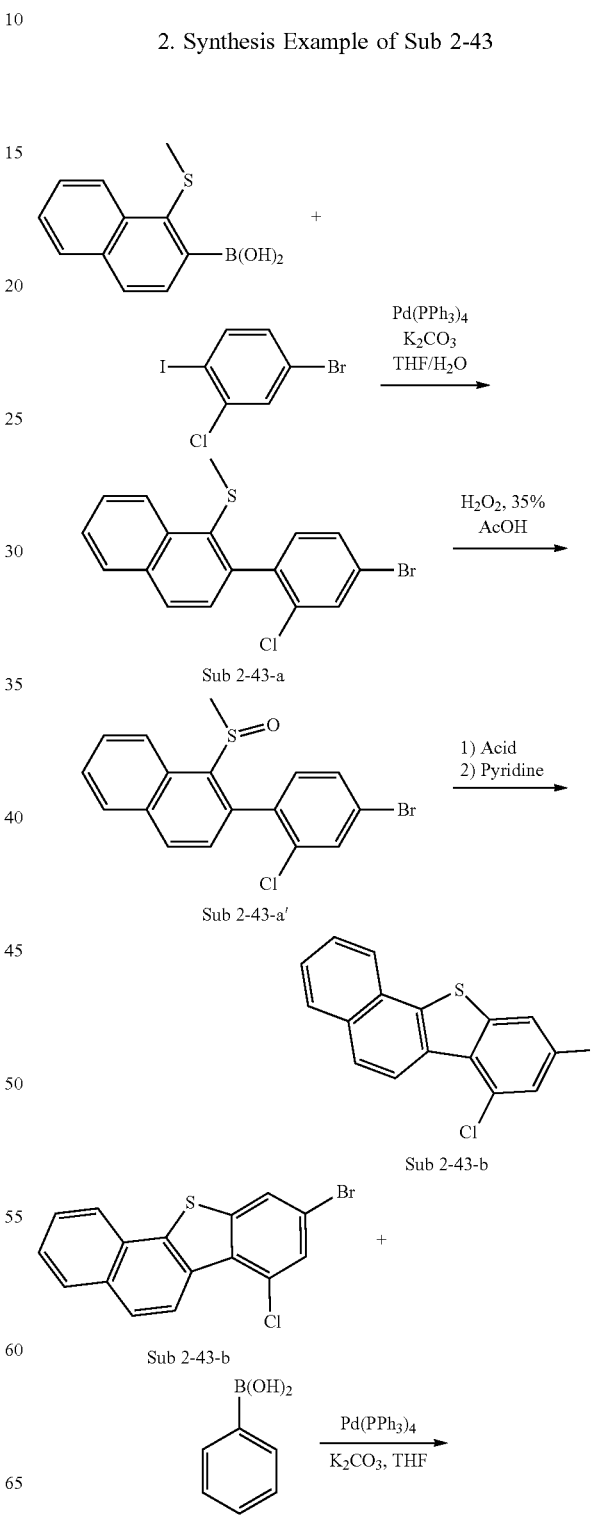

-continued

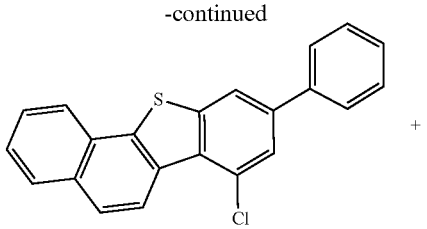

Sub 2-43-c

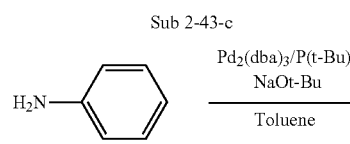

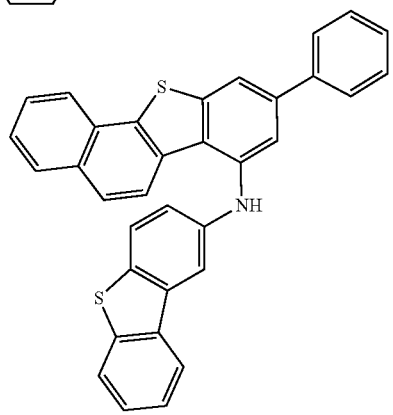

Sub 2-43

(1) Synthesis Example of Sub 2-43-a (2-(methylthio)phenyl)boronic acid (30 g, 137.6 mmol) was dissolved in a round bottom flask with THE (300 mL) and 4-bromo-2-chloroiodobenzene (43.7 g, 137.6 mmol), Pd(PPh$_3$)$_4$ (4.8 g, 4.1 mmol), K$_2$CO$_3$ (57 g, 412.7 mmol), and water (100 mL) were added and stirred at 80° C. When the reaction was completed, the solvent was removed, extracted with CH$_2$Cl$_2$ and water, the organic layer was dried over MgSO$_4$, concentrated, and the resulting compound was silica gel column to obtain 37.5 g (yield 75%) of the product.

(2) Synthesis Example of Sub 2-43-a'

Sub 2-43-a (37 g, 101.7 mmol) obtained in the above synthesis was dissolved in AcOH (300 mL) in a round bottom flask, H$_2$O$_2$ (8.7 mL, 101.7 mmol) was added and stirred at room temperature. When the reaction was completed, the solvent was removed, neutralized with 1 M NaOH, extracted with Ethyl acetate, and recrystallized to obtain 35.5 g (92% yield) of the product.

(3) Synthesis Example of Sub 2-43-b

Sub 2-43-a' (35 g, 92.2 mmol) obtained in the above synthesis was added to 300 g of Trifluloromethanesulfonic acid and stirred at 65° C. When the reaction was completed, pyridine was added and refluxed for 30 minutes, and the resulting compound was recrystallized in a silica gel column to obtain 26 g (yield 81%) of the product.

(4) Synthesis Example of Sub 2-43-c

Sub 2-43-b (26 g, 74.8 mmol) obtained in the above synthesis, phenylboronic acid (9.12 g, 74.8 mmol), Pd(PPh$_3$)$_4$ (4.32 g, 3.7 mmol), K$_2$CO$_3$ (62.54 g, 224.4 mmol) was added to THE (180 mL), and by using the synthesis method of Sub 2-8-c, the product 20.1 g (78% yield) was obtained.

(5) Synthesis Example of Sub 2-43

Sub 2-43-c (20.1 g, 58.3 mmol) obtained in the above synthesis was dissolved in a round bottom flask with Toluene (400 ml), and Aniline (6 g, 64.1 mmol), Pd$_2$(dba)$_3$ (1.6 g, 1.75 mmol), P(t-Bu)$_3$ (50 wt % Sol.) (1.42 mL, 3.5 mmol), NaOt-Bu (16.8 g, 174.85 mmol) were added, and product 23.4 g (yield 79%) was obtained using the synthesis method of Sub 2-8.

Sub 5 of Scheme 1-1 may be synthesized by the reaction route of Scheme 3-1, but is not limited thereto.

<Scheme 3-1>

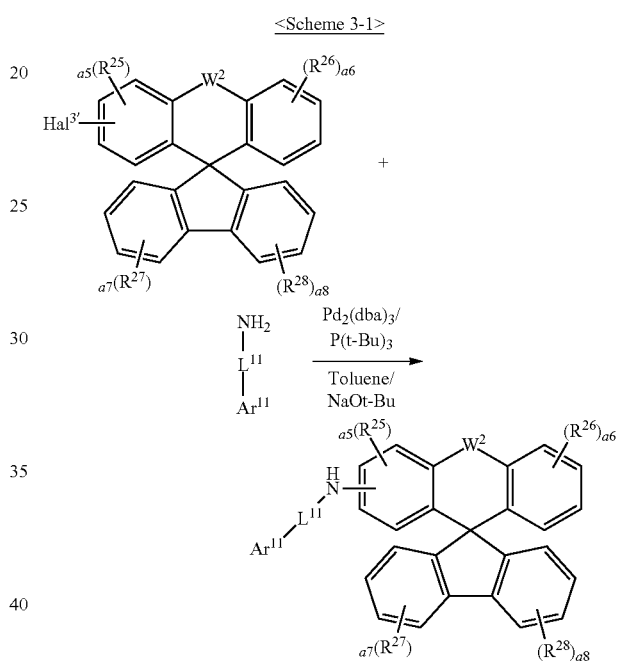

Hal$^{3'}$ in Scheme 3-1 is C$_1$ or Br.

1. Synthesis Example of Sub 5-2

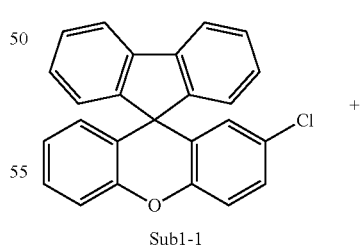

Sub1-1

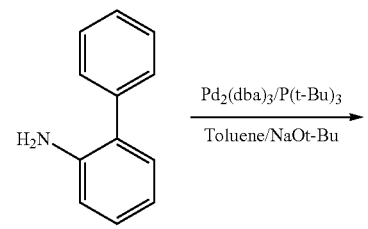

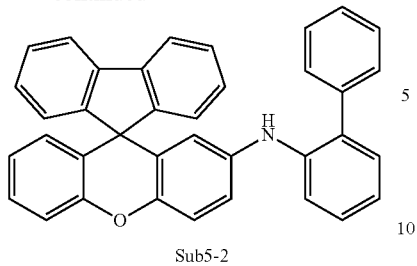
Sub5-2

Sub1-1 (13.5 g, 36.8 mmol) was added in a round bottom flask and dissolved in Toluene (270 mL), and [1,1'-biphenyl]-2-amine (6.23 g, 36.8 mmol), Pd$_2$(dba)$_3$ (1.68 g, 1.84 mmol), P(t-Bu)$_3$ (50 wt % Sol.) (1.49 mL, 3.68 mmol), NaOt-Bu (10.61 g, 110 mmol) were added and stirred at 80° C. After the reaction was completed, the reaction mixture was extracted with CH$_2$Cl$_2$ and water. The organic layer was dried over MgSO$_4$ and concentrated. The resulting compound was separated by silica gel column chromatography and recrystallized to obtain 14.9 g of the product. (yield: 81%).

2. Synthesis Example of Sub 5-12

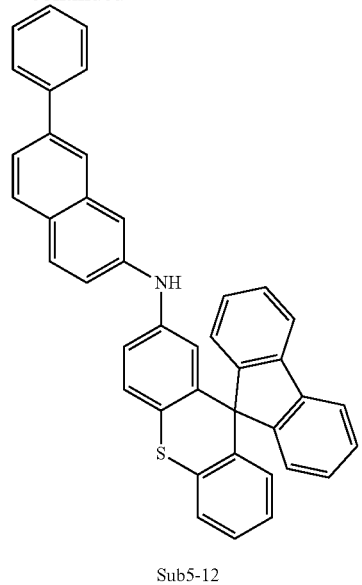
Sub5-12

Sub 1-9 (12.2 g, 31.9 mmol) was added in a round bottom flask and dissolved in Toluene (244 mL), 7-phenylnaphthalen-2-amine (6.99 g, 31.9 mmol), Pd$_2$(dba)$_3$ (1.46 g, 1.59 mmol), P(t-Bu)$_3$ (50 wt % Sol.) (1.29 mL, 3.19 mmol), NaOt-Bu (9.19 g, 95.6 mmol) were added thereto, and 15.0 g of a product (yield 83%) was obtained using the synthesis method of Sub 5-2.

3. Synthesis Example of Sub 5-19

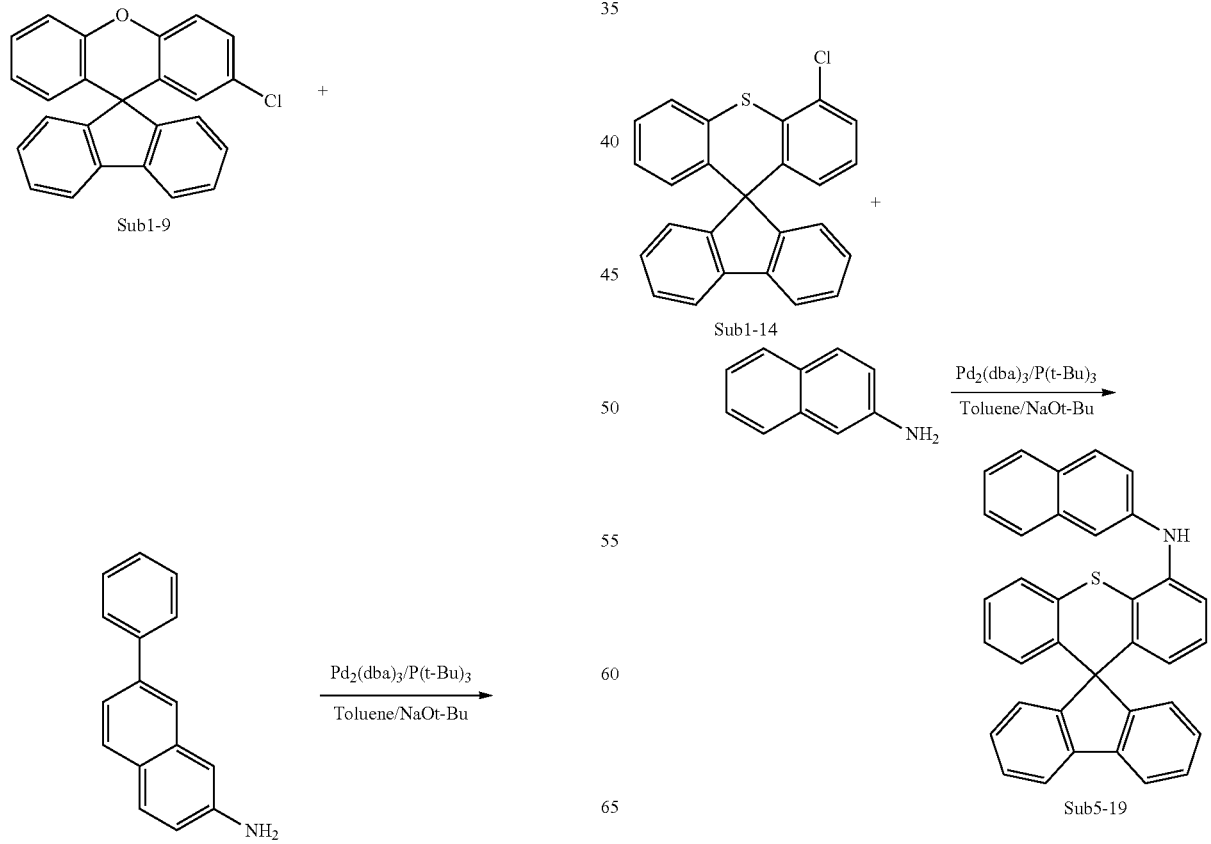
Sub5-19

Sub1-14 (10.5 g, 27.4 mmol) was added in a round bottom flask and dissolved in Toluene (210 mL), naphthalen-2-amine (3.93 g, 27.4 mmol), Pd$_2$(dba)$_3$ (1.26 g, 1.37 mmol), P(t-Bu)$_3$ (50 wt % Sol.) (1.11 mL, 2.74 mmol), NaOt-Bu (7.91 g, 82.3 mmol) were added thereto, and 10.1 g of a product (yield 75%) was obtained using the synthesis method of Sub 5-2.

Meanwhile, the compound belonging to Sub 2 and Sub 5 may be the following compound, but it is not limited thereto. Sub 3 and Sub 4 are also compounds belonging to Sub 2, and Table 2 below shows the FD-MS values of the compounds belonging to Sub 2 and Sub 5.

Sub2-1

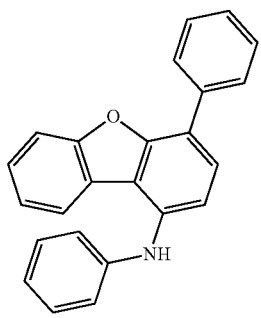

Sub2-2

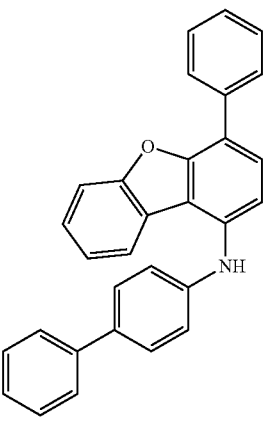

Sub2-3

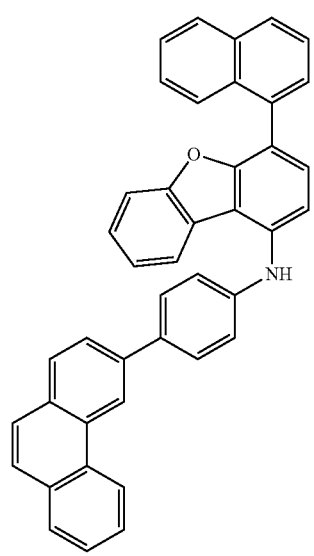

-continued

Sub2-4

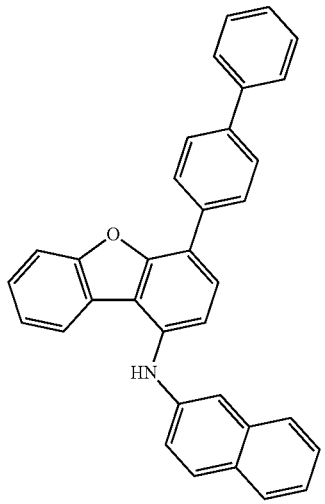

Sub2-5

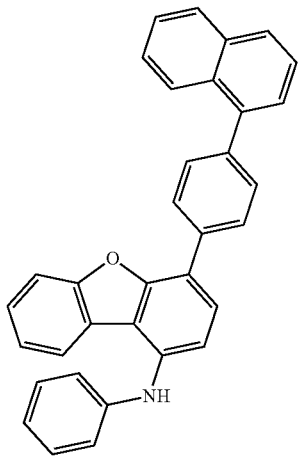

Sub2-6

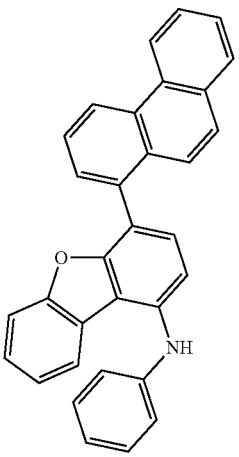

Sub2-7
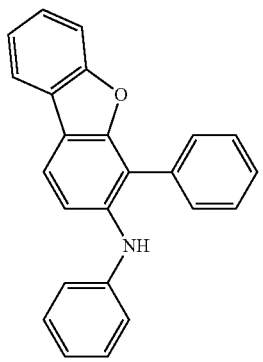
Sub2-8
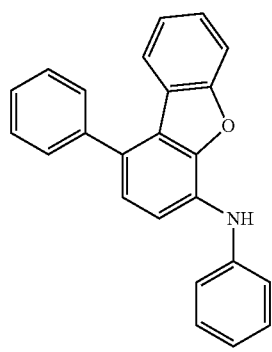
Sub2-9
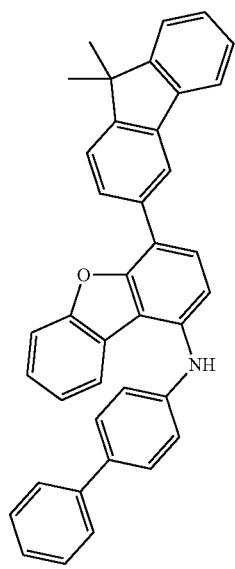
Sub2-10
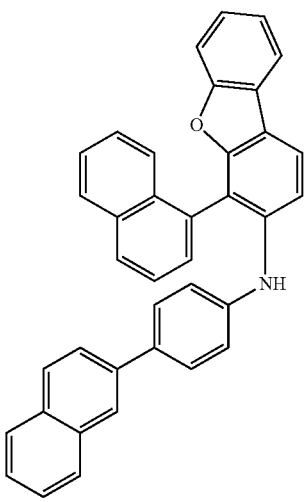
Sub2-11
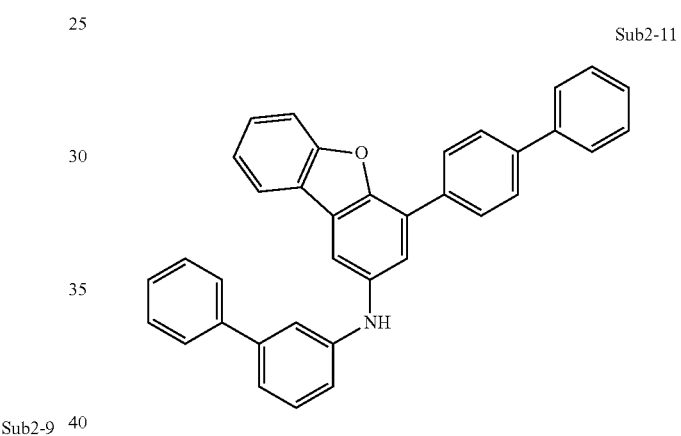
Sub2-12
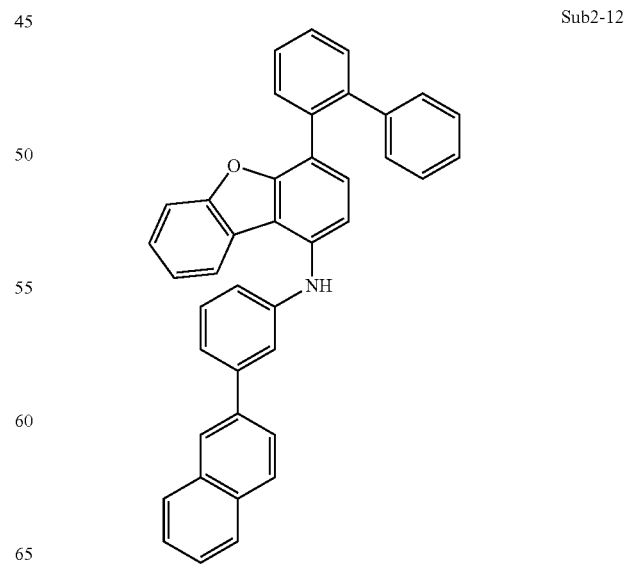

-continued
Sub2-13
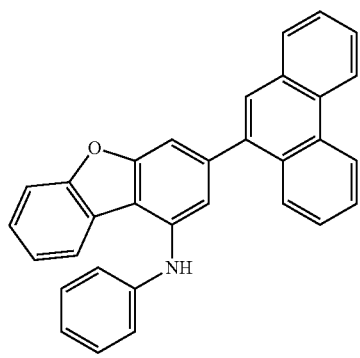
Sub2-14
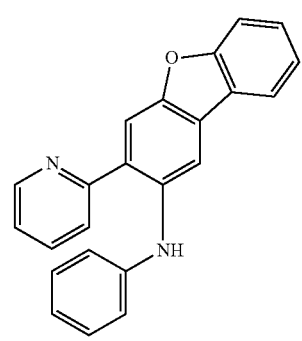
Sub2-15
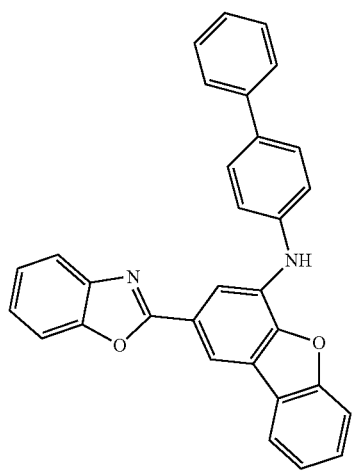
Sub2-16
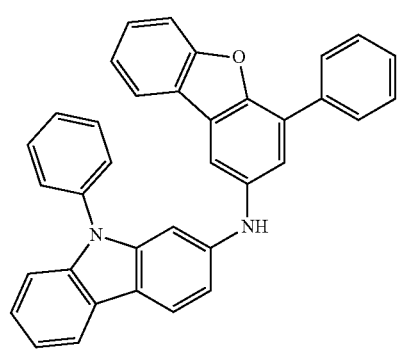
Sub2-17
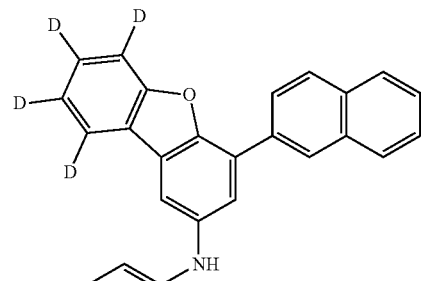
Sub2-18
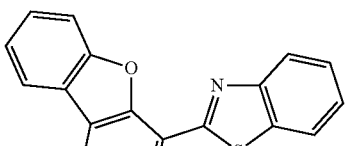
Sub2-19
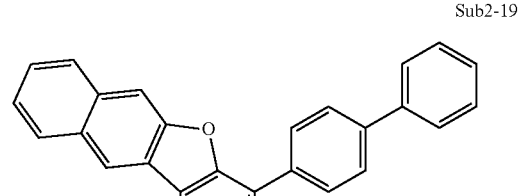
Sub2-20
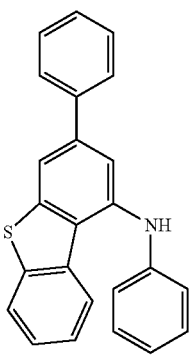

-continued
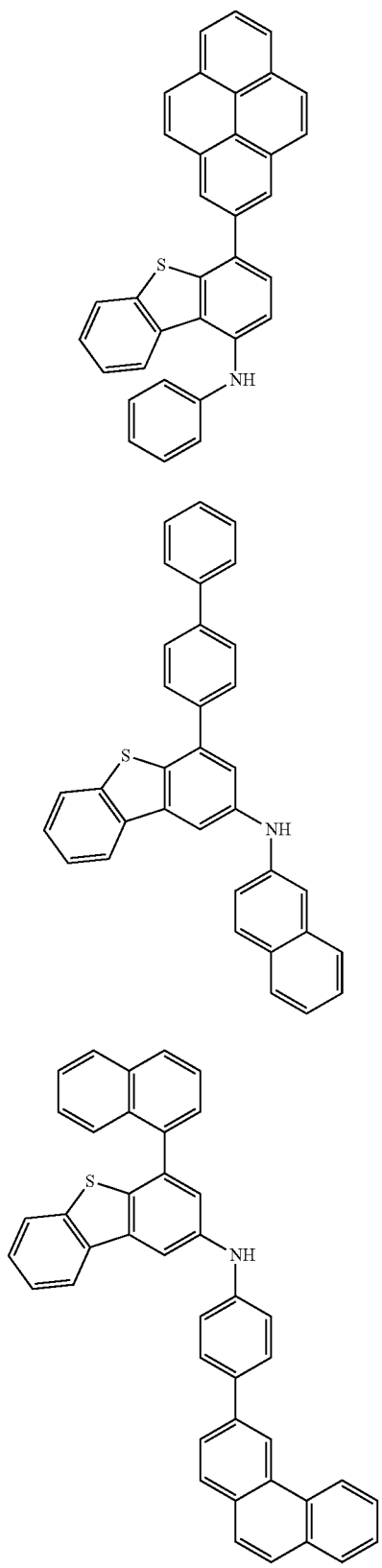
Sub2-21
Sub2-22
Sub2-23
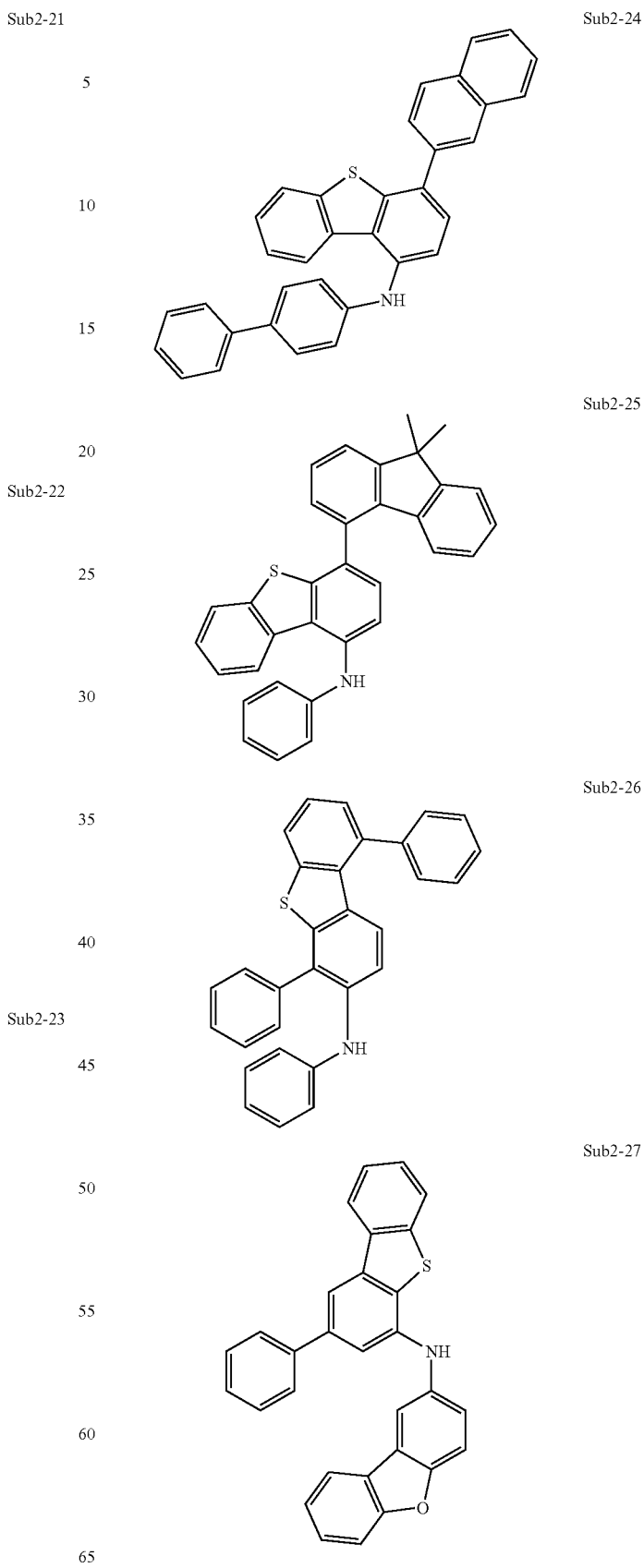
Sub2-24
Sub2-25
Sub2-26
Sub2-27

Sub2-28
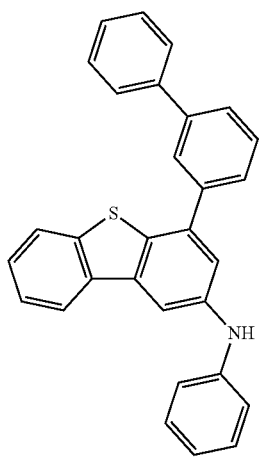
Sub2-29
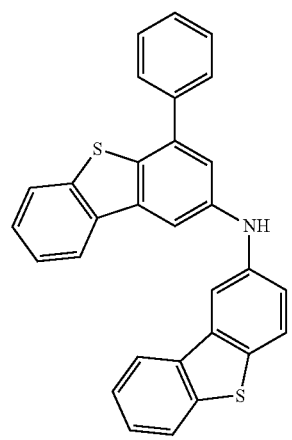
Sub2-30
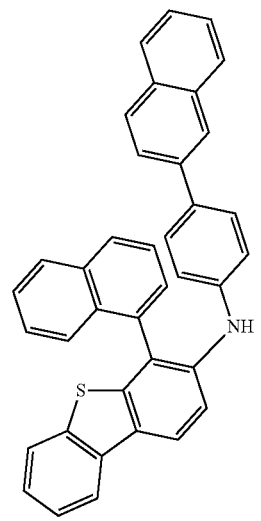
Sub2-31
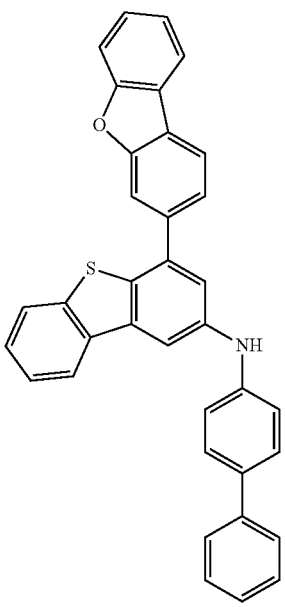
Sub2-32
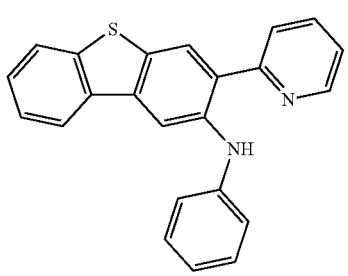
Sub2-33
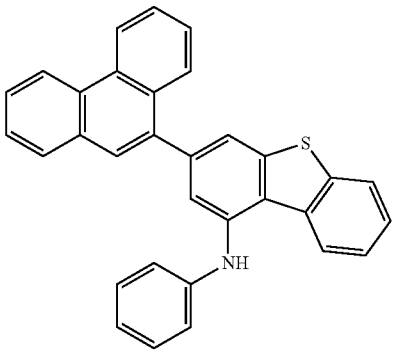
Sub2-34
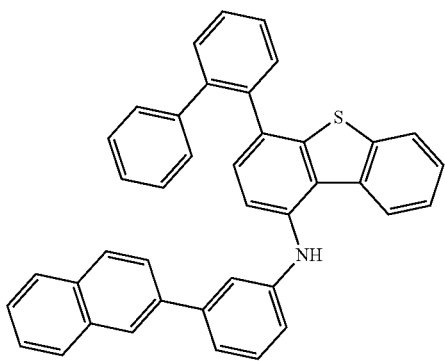

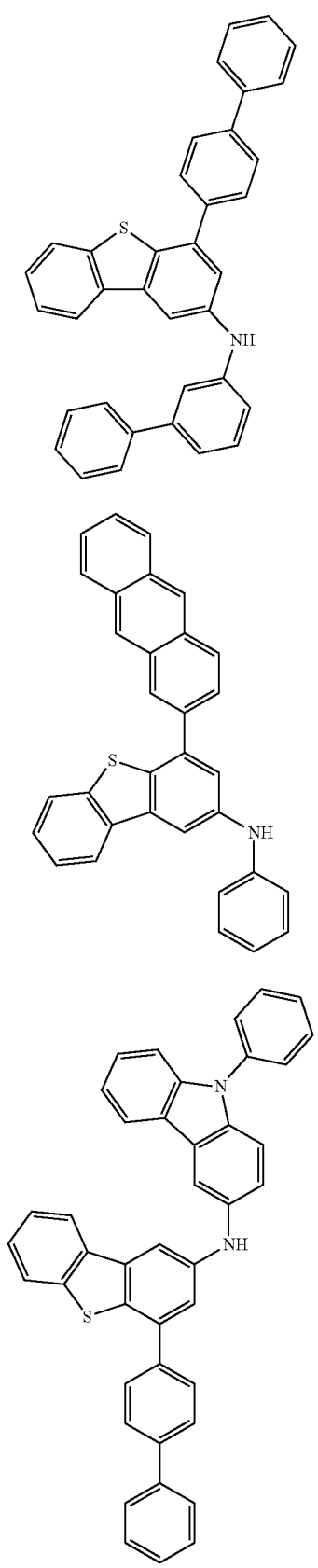
Sub2-35
Sub2-36
Sub2-37
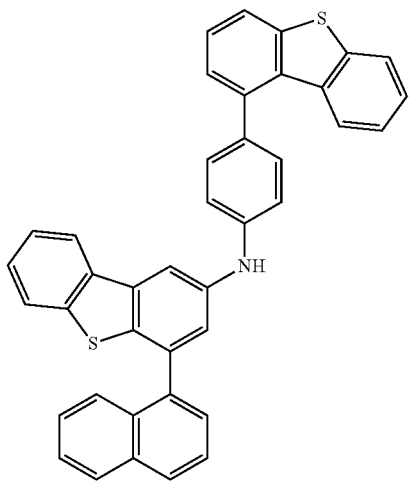
Sub2-38
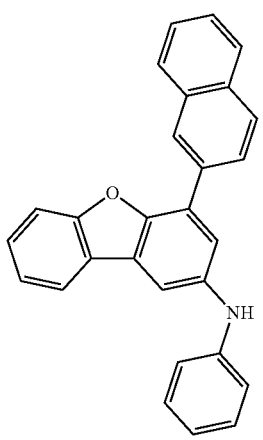
Sub2-39
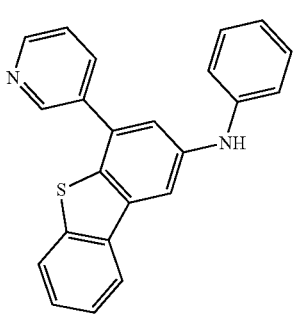
Sub2-40
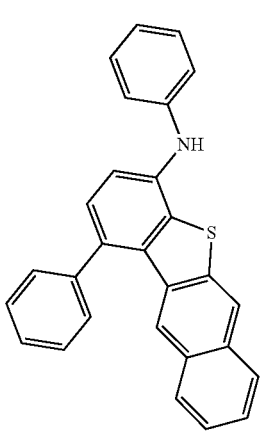
Sub2-41

Sub2-42
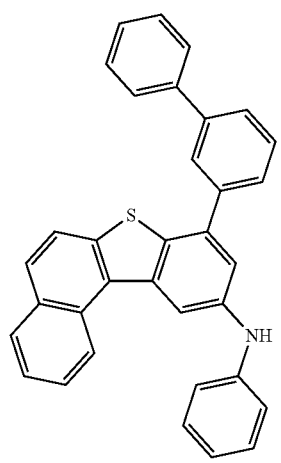
Sub2-43
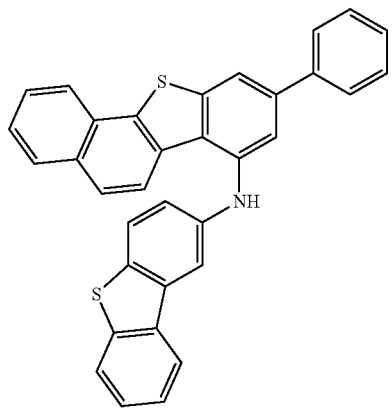
Sub2-44
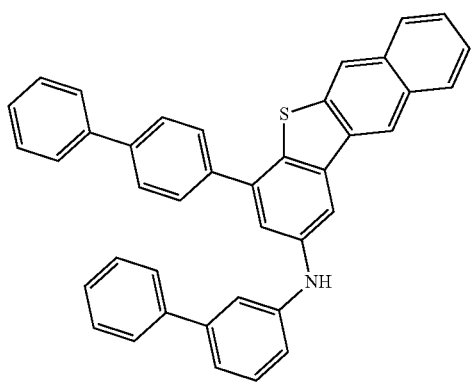
Sub2-45
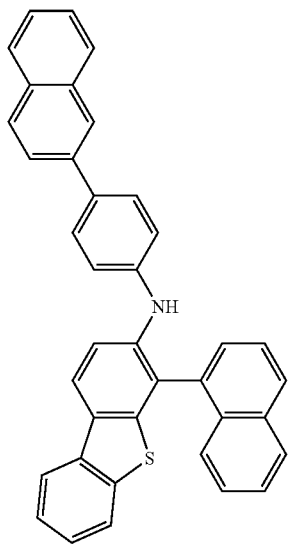
Sub2-46
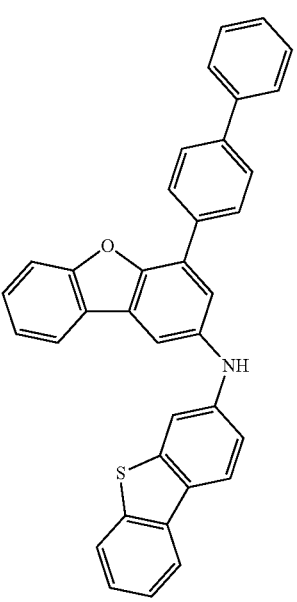
Sub2-47
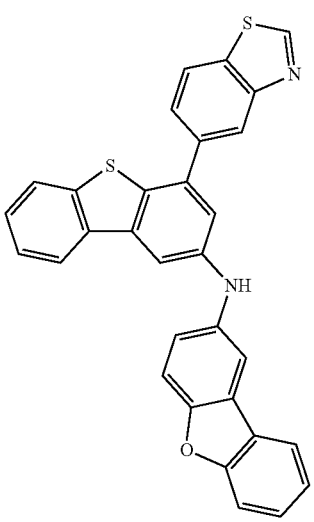

-continued
Sub2-48
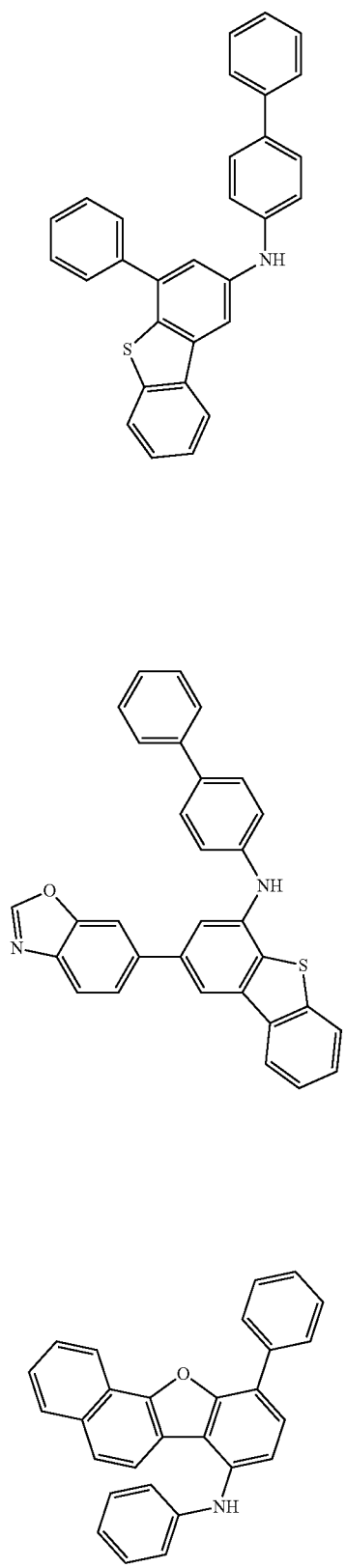
Sub2-49
Sub2-50
Sub2-51
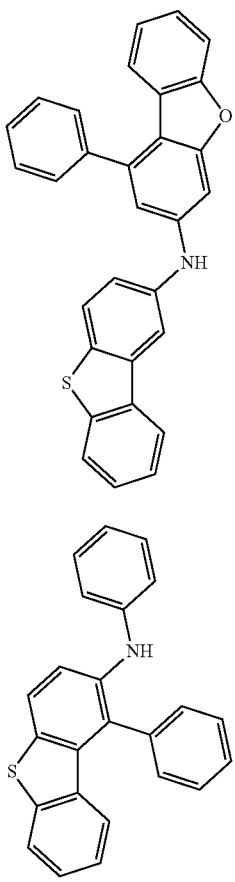
Sub2-52
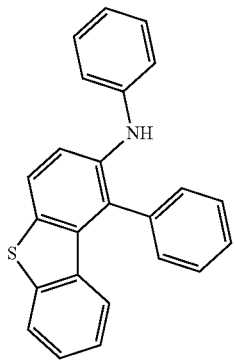
Sub2-53
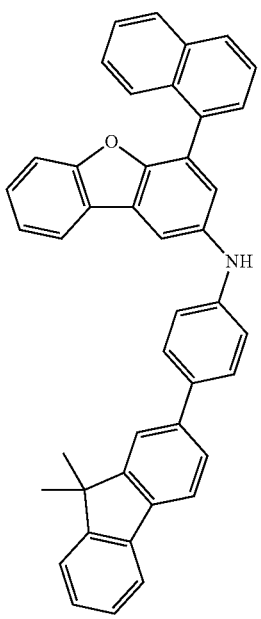

Sub2-54
Sub2-55
Sub2-56
Sub2-57
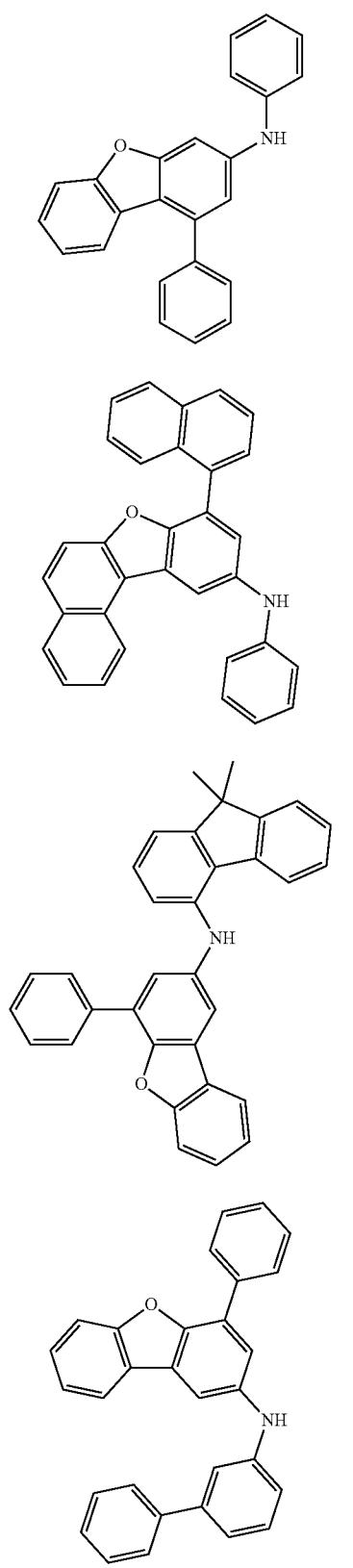
Sub2-58
Sub2-59
Sub2-60
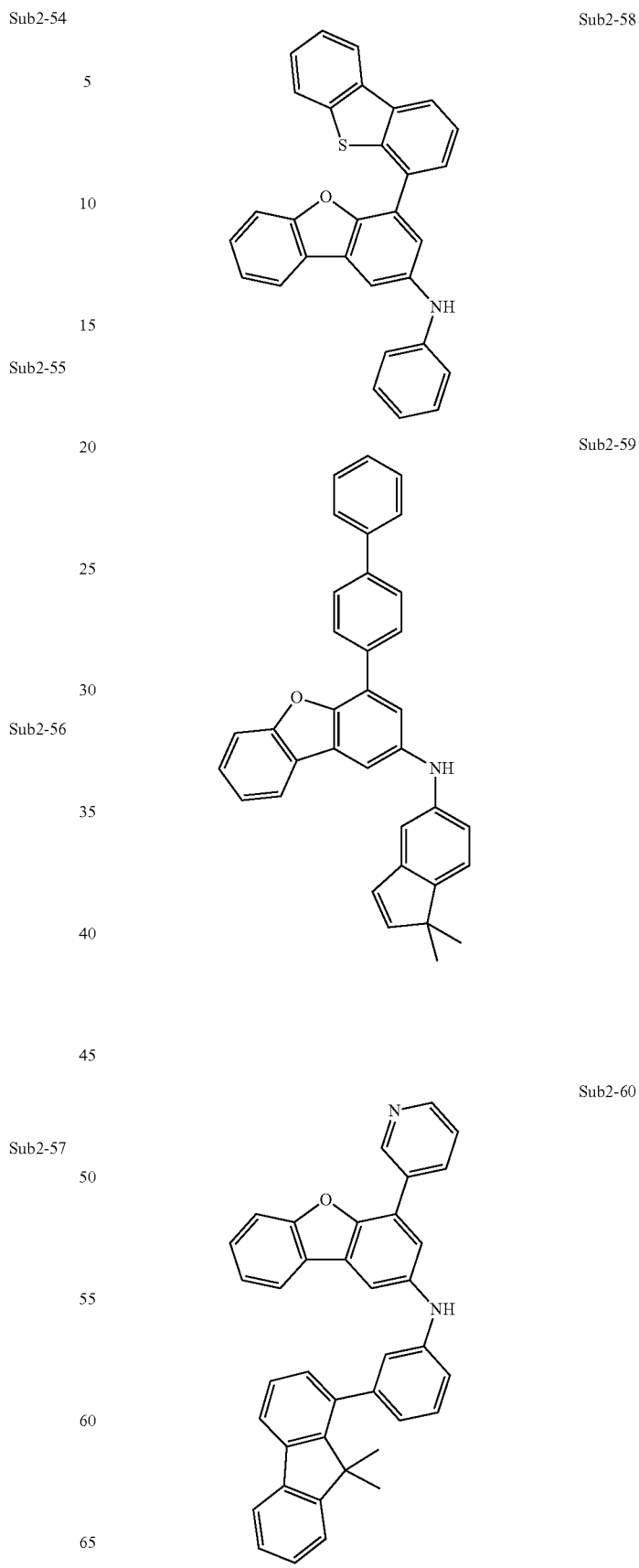

Sub2-61
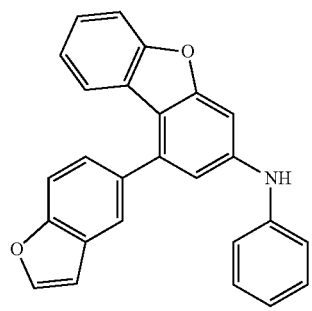
Sub2-64
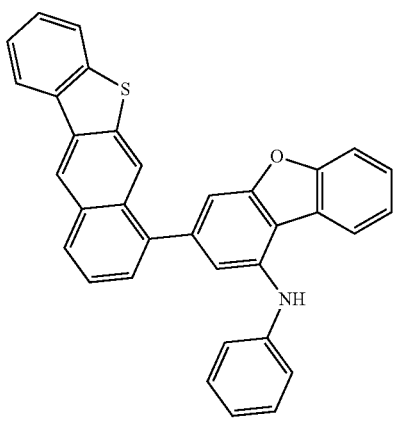
Sub2-62
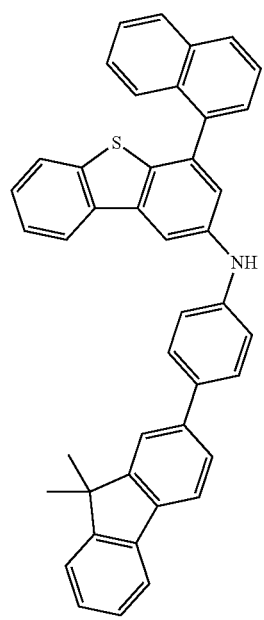
Sub2-65
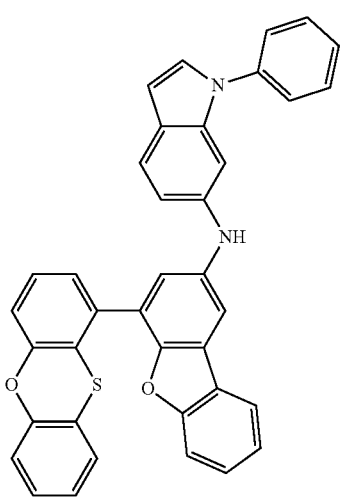
Sub2-63
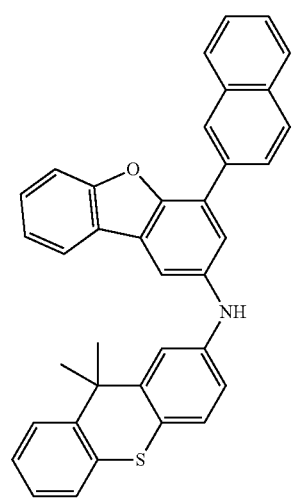
Sub2-66
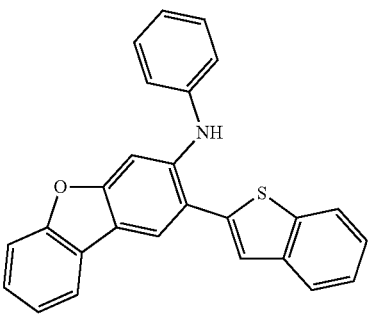

Sub2-67
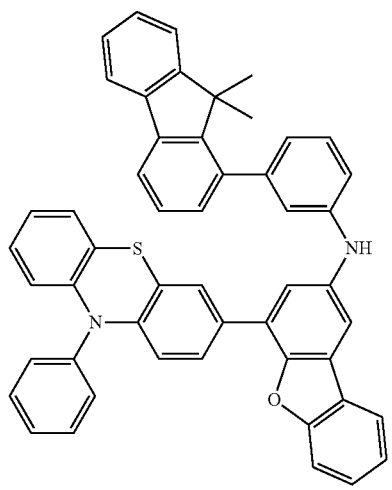
Sub2-70
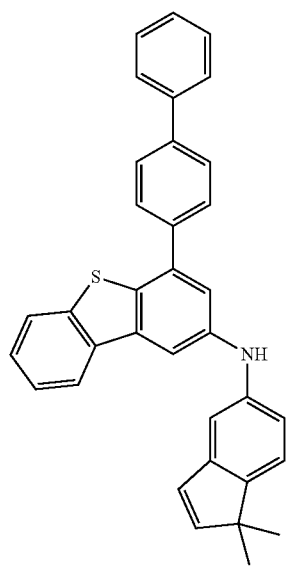
Sub2-68
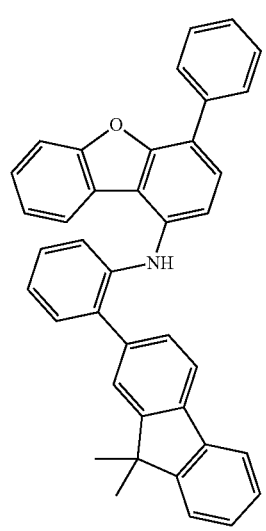
Sub2-71
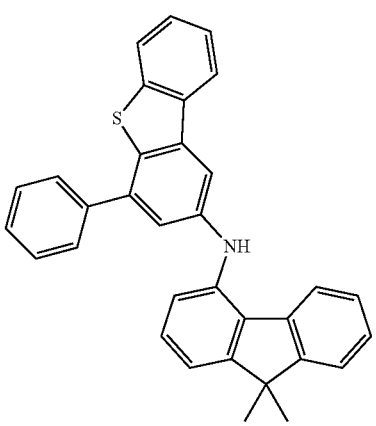
Sub2-69
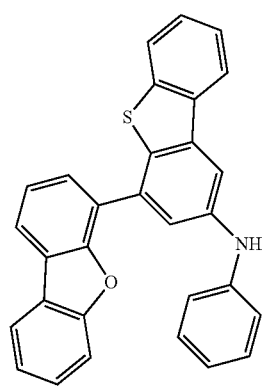
Sub2-72
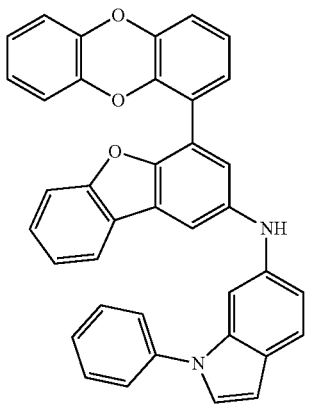

-continued
Sub2-73
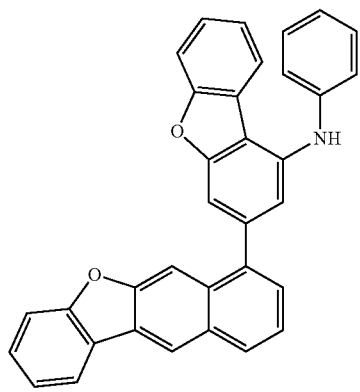
Sub2-74
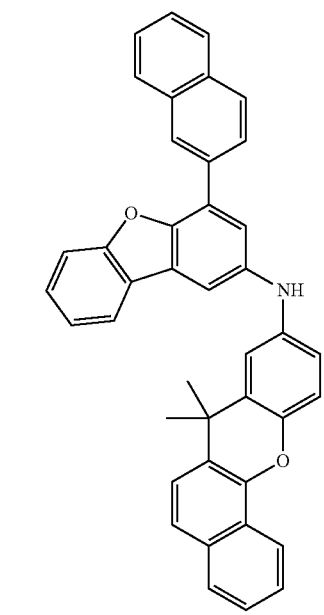
Sub2-75
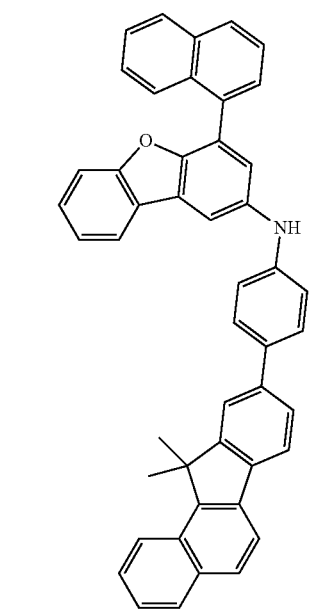
-continued
Sub2-76
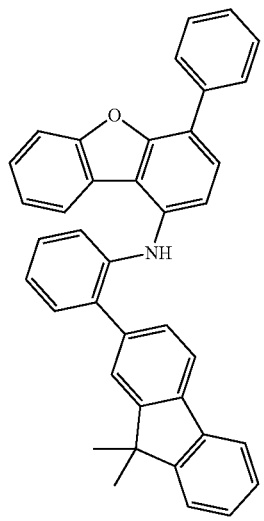
Sub2-77
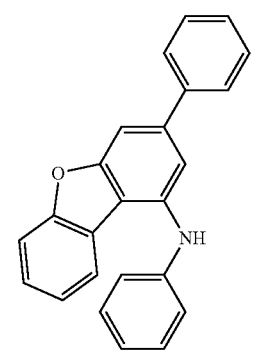
Sub2-78
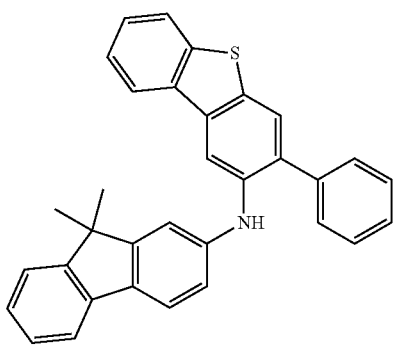

Sub2-79
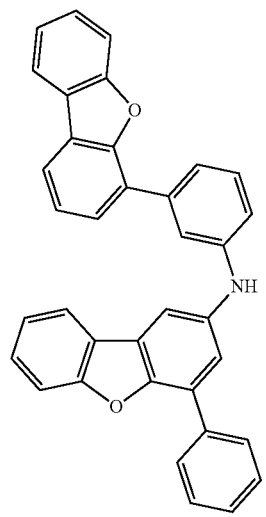
Sub2-80
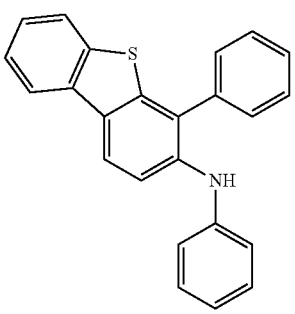
Sub2-81
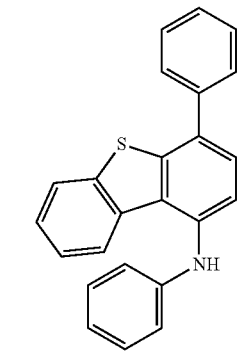
Sub2-82
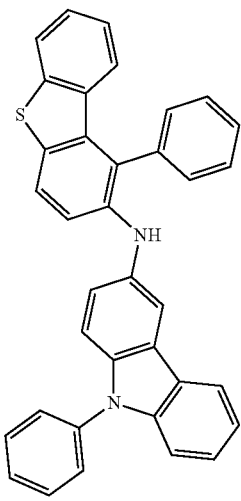
Sub2-83
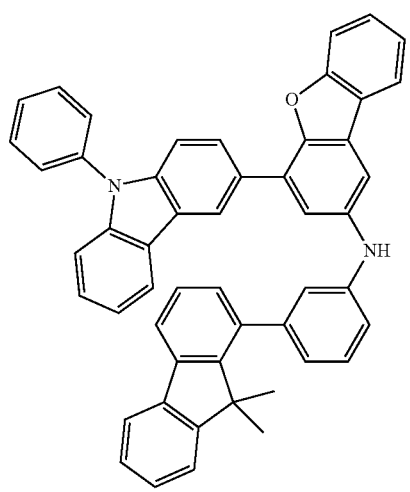
Sub2-84
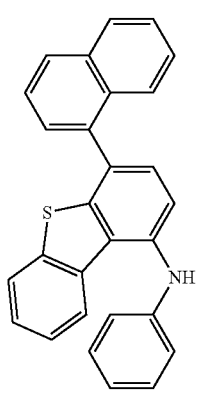

Sub2-85
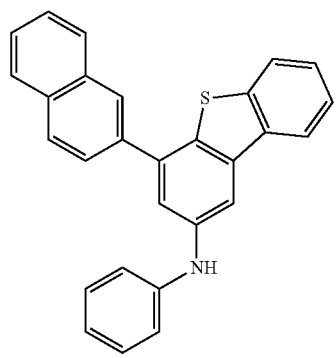
Sub2-86
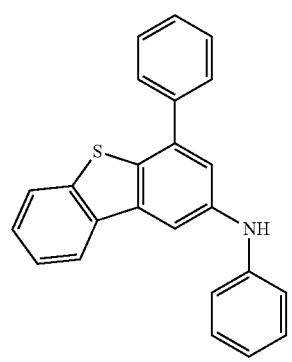
Sub2-87
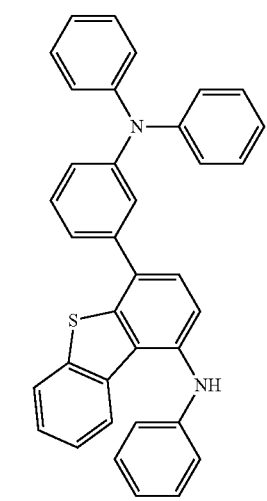
Sub2-88
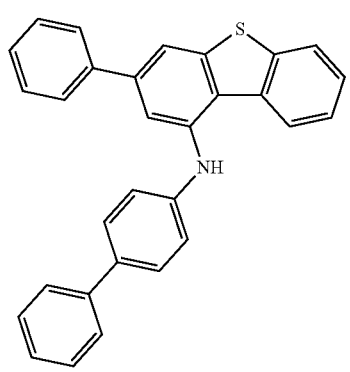
Sub2-89
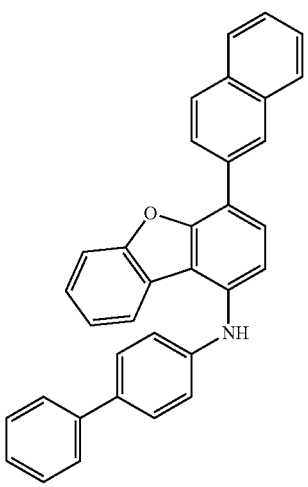
Sub2-90
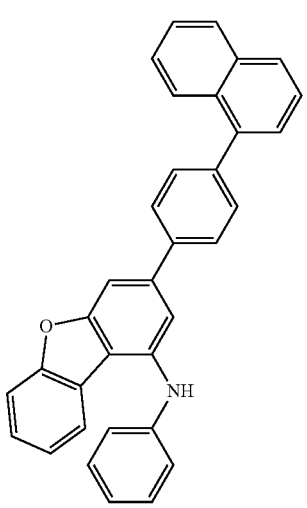
Sub2-91
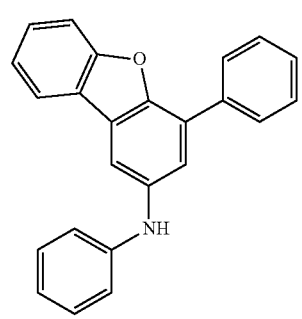

Sub2-92
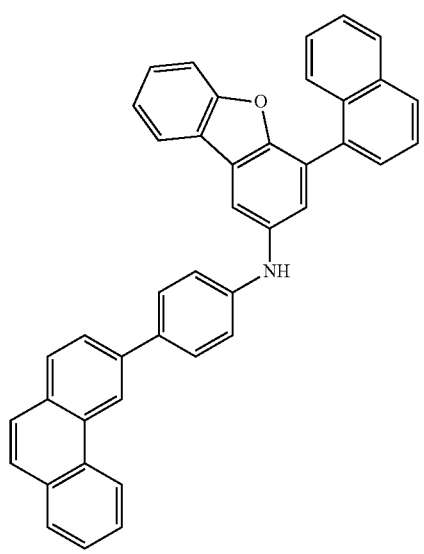
Sub2-93
Sub2-94
Sub2-95
Sub2-96
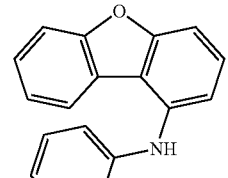
Sub2-97
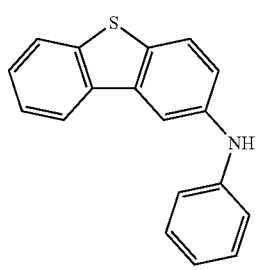
Sub3-1
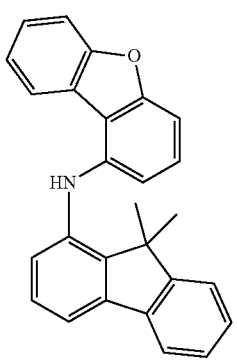
Sub3-2
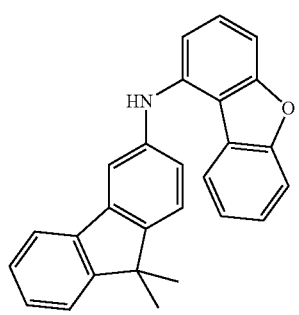
Sub3-3
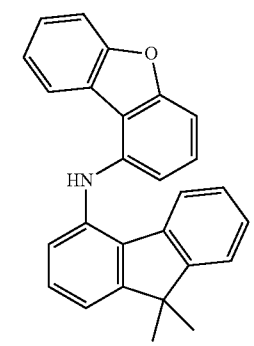

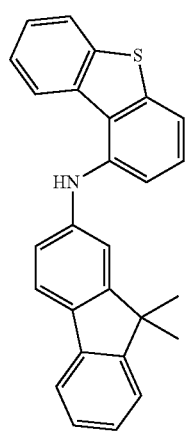 Sub3-4
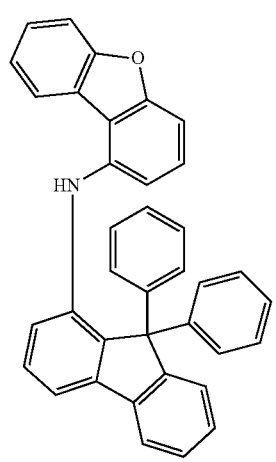 Sub3-5
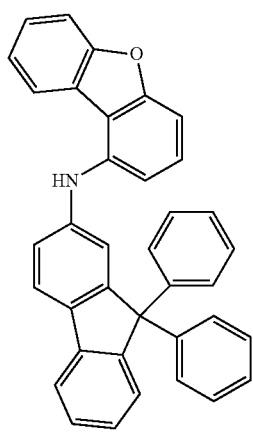 Sub3-6
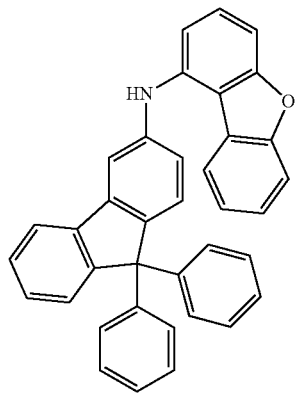 Sub3-7
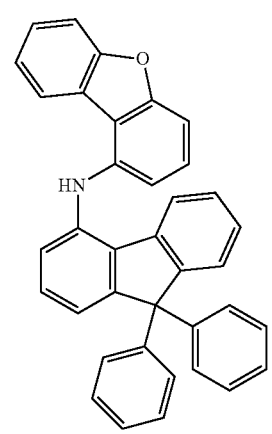 Sub3-8
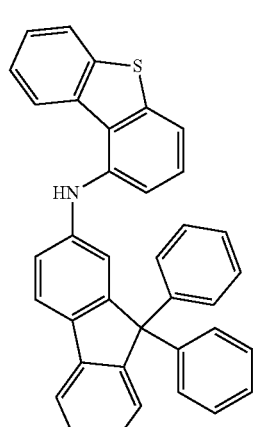 Sub3-9

Sub3-10
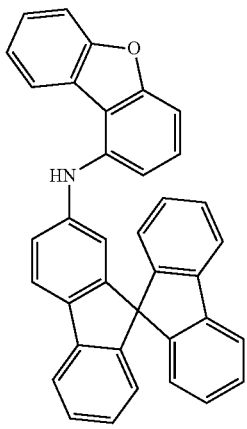
Sub3-11
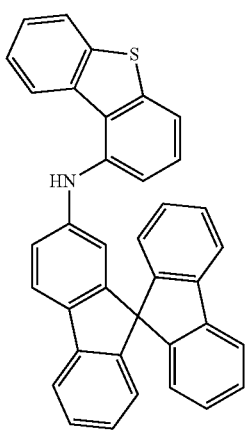
Sub3-12
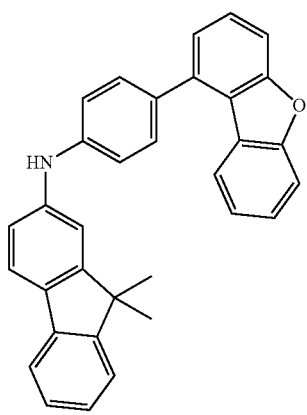
Sub3-13
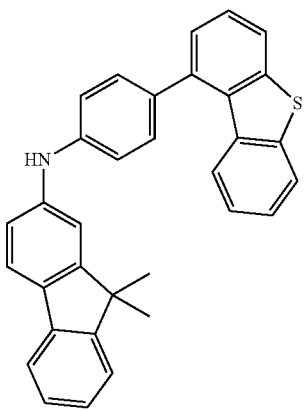
Sub3-14
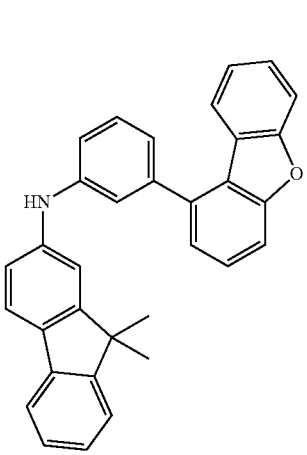
Sub3-15
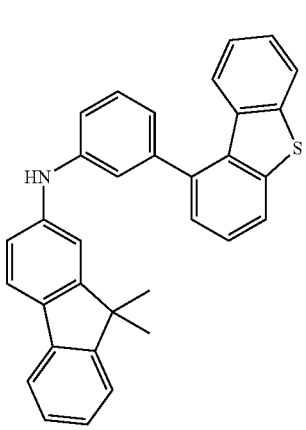

Sub3-16
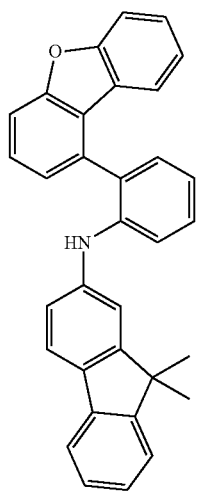
Sub3-17
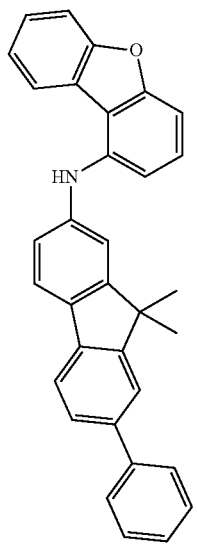
Sub3-18
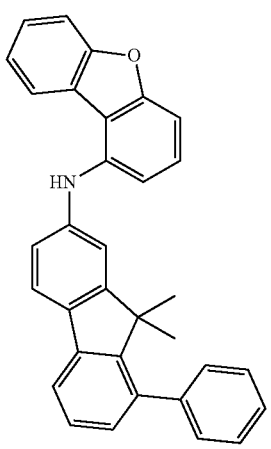
Sub3-19
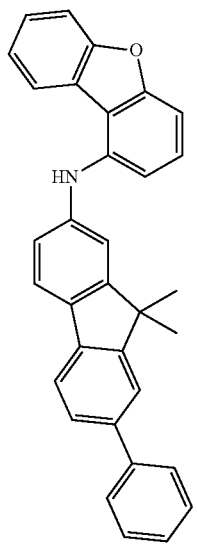
Sub3-20
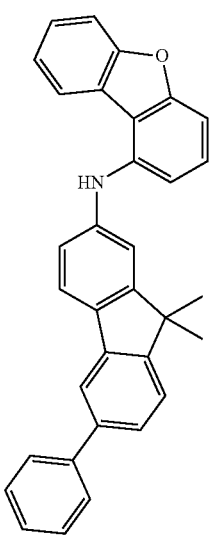
Sub3-21
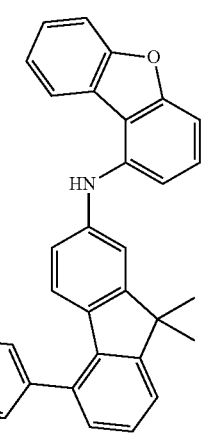

Sub3-22
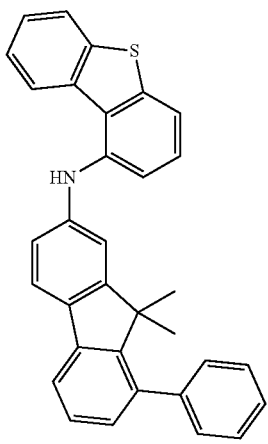
Sub3-23
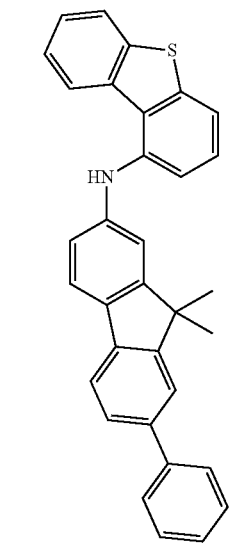
Sub3-24
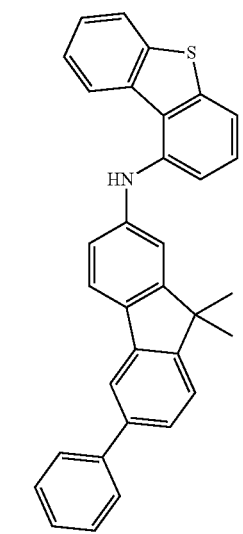
Sub3-25
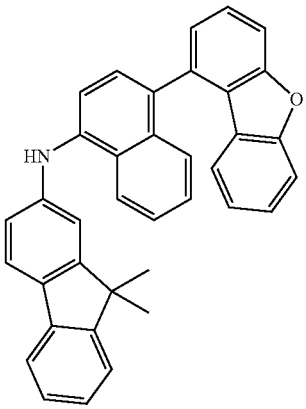
Sub3-26
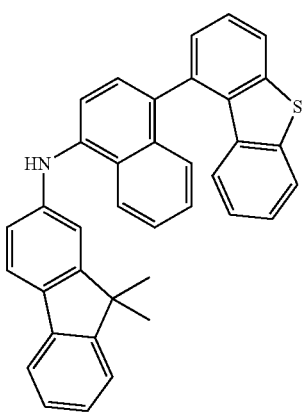
Sub3-27
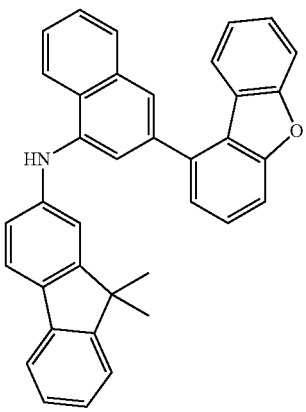
Sub3-28
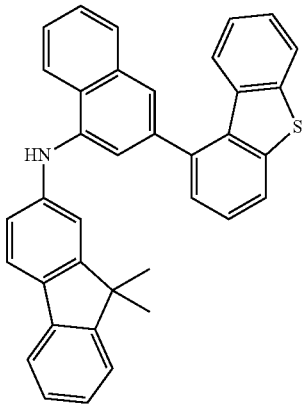

Sub3-29
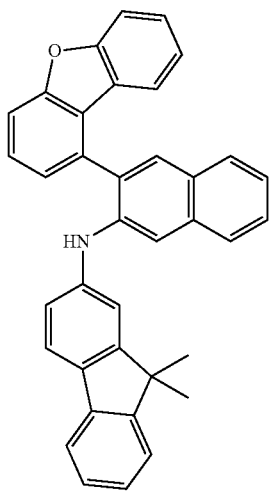
Sub3-32
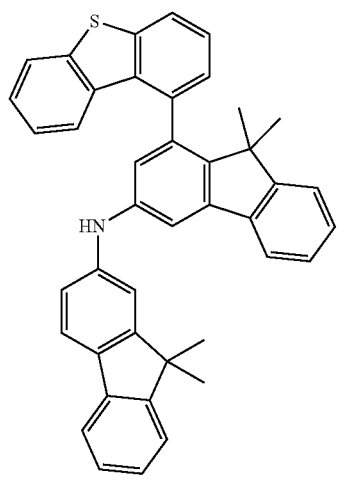
Sub3-30
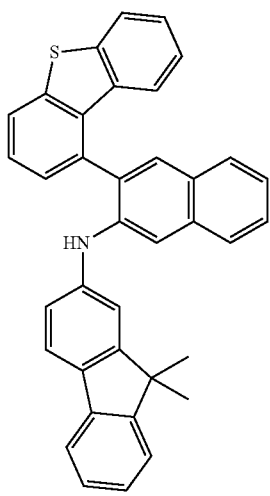
Sub3-33
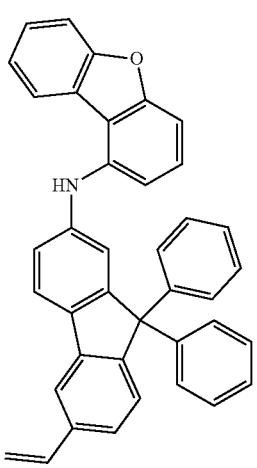
Sub3-31
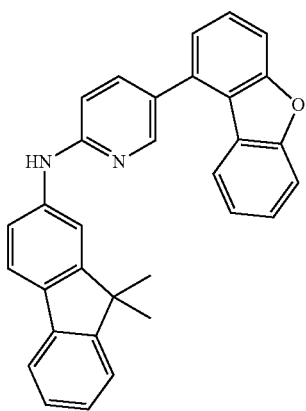
Sub3-34
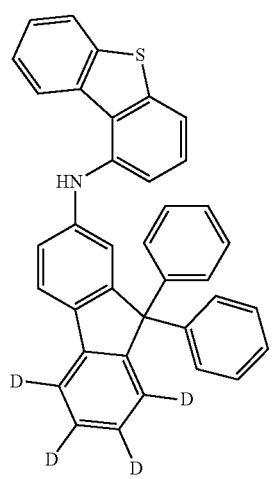

Sub3-35
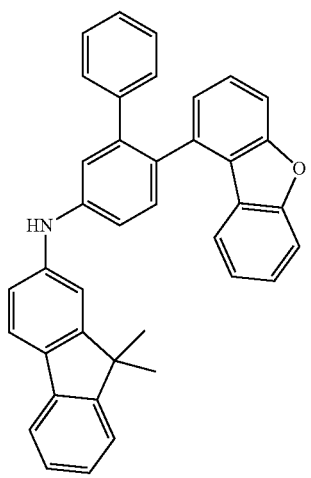
Sub3-36
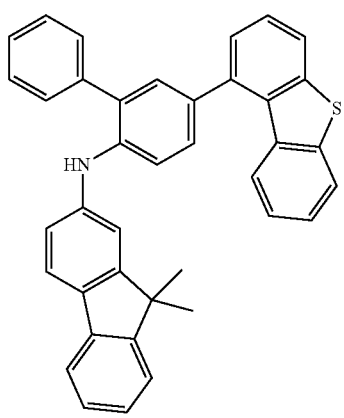
Sub3-37
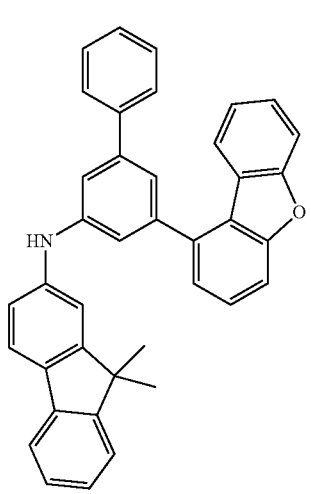
Sub3-38
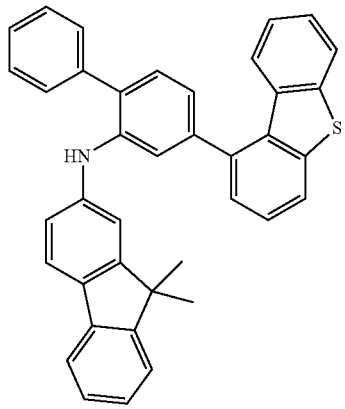
Sub3-39
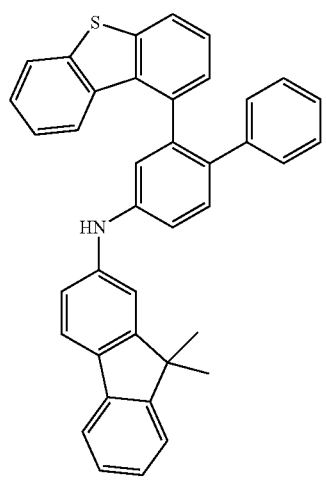
Sub3-40
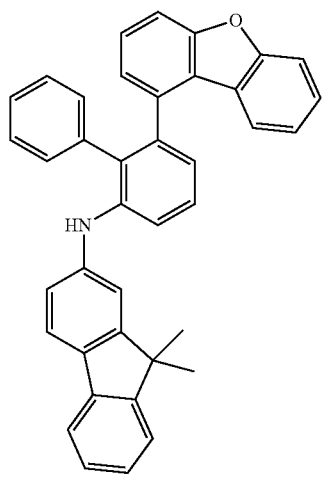

Sub3-41
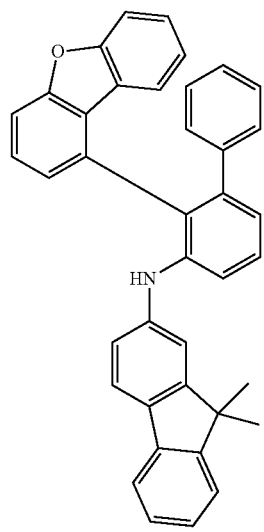
Sub3-42
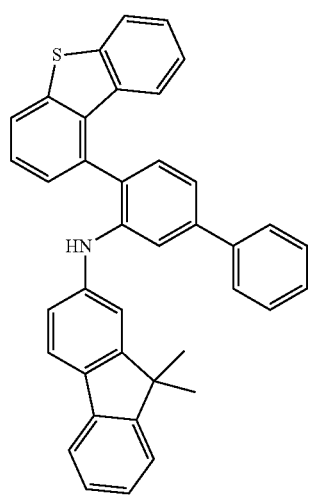
Sub3-43
Sub3-44
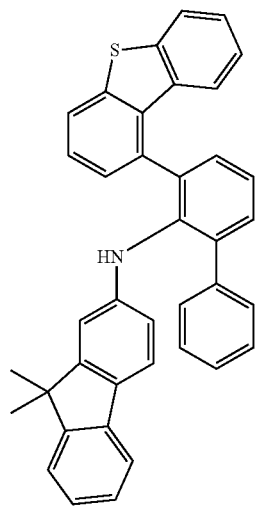
Sub3-45
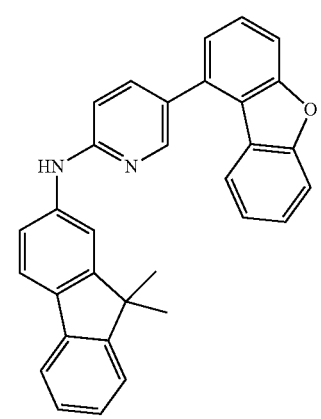
Sub3-46
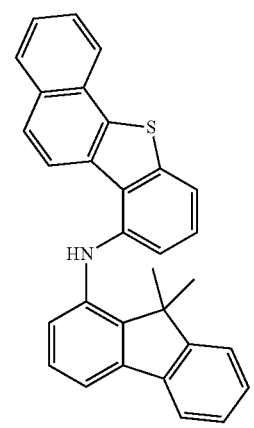

301
-continued
Sub3-47
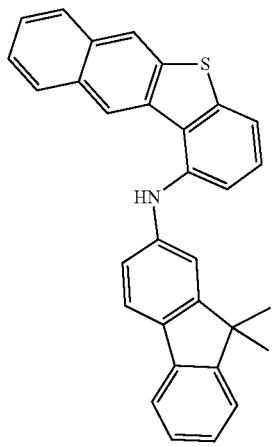
Sub3-48
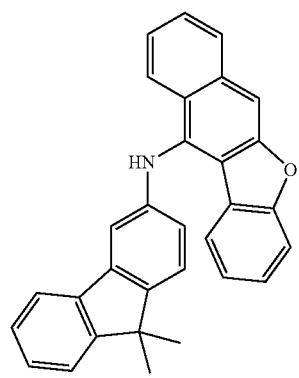
Sub3-49
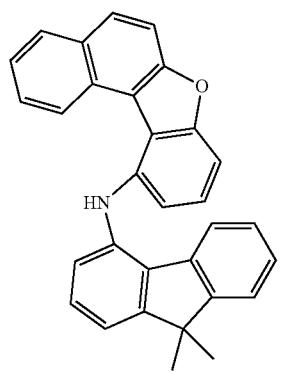
302
-continued
Sub3-50
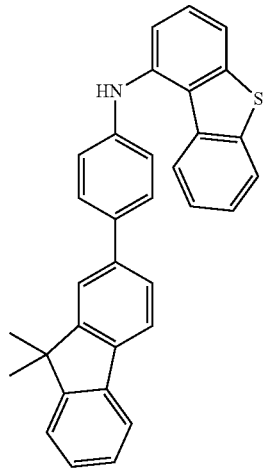
Sub3-51
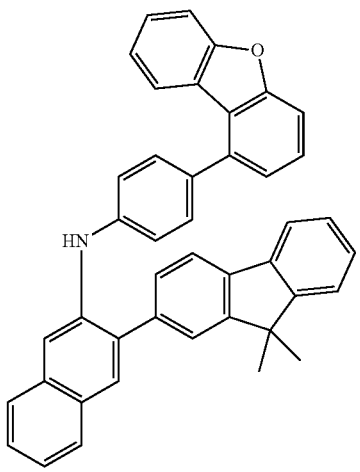
Sub3-52
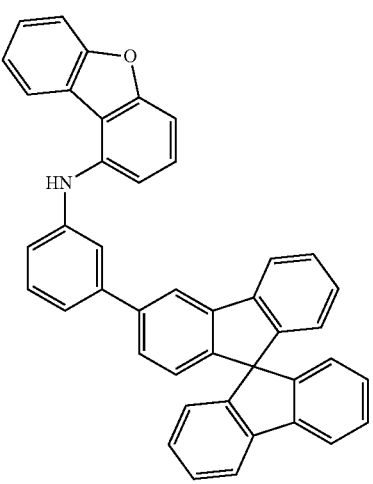

Sub3-53
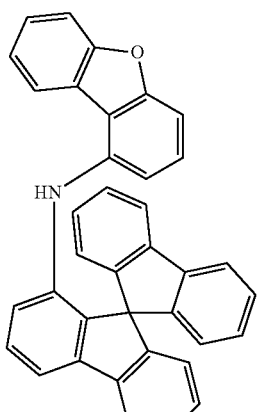
Sub3-56
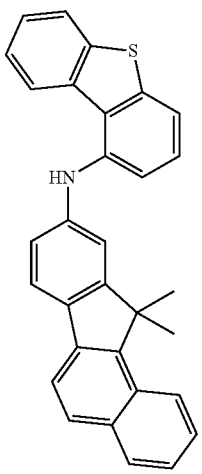
Sub3-54
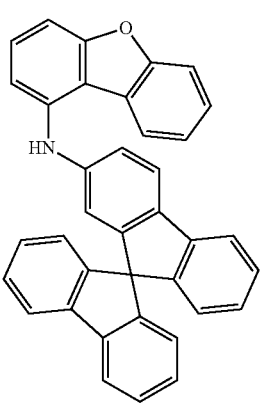
Sub3-57
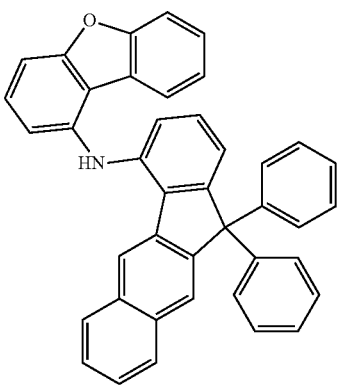
Sub3-55
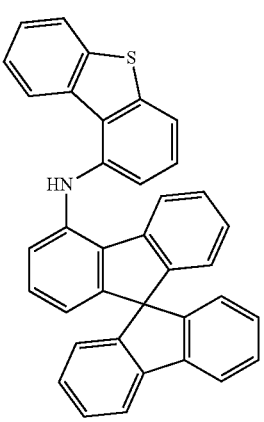
Sub4-1
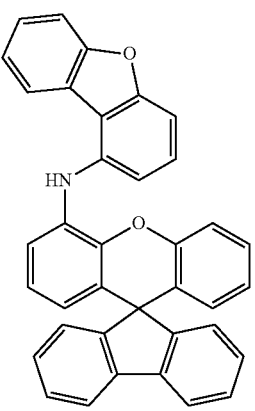

Sub4-2
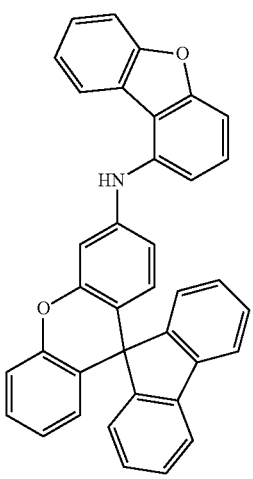
Sub4-3
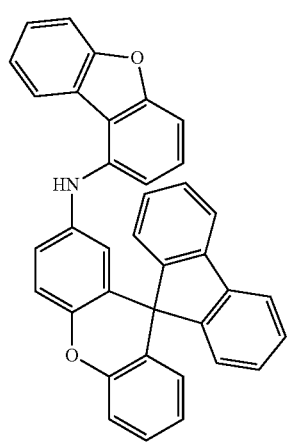
Sub4-4
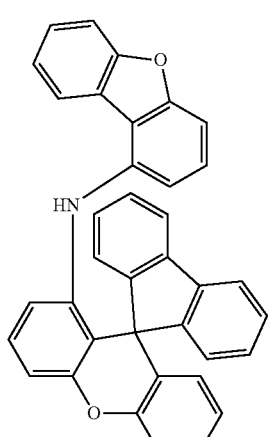
Sub4-5
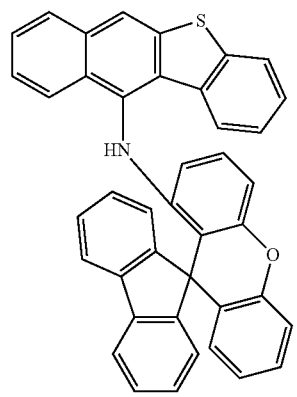
Sub4-6
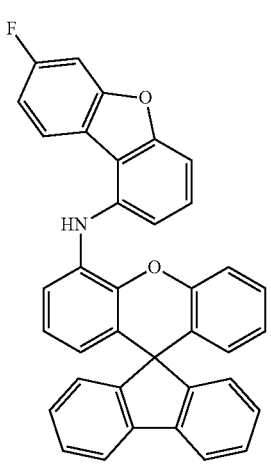
Sub4-7
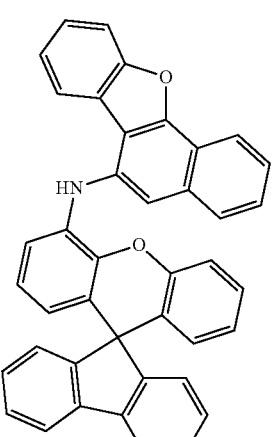

Sub4-8
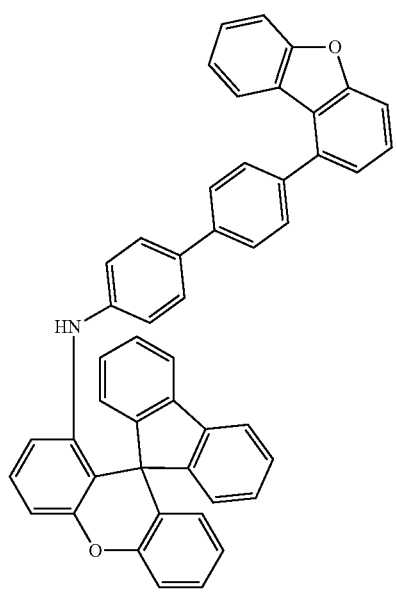
Sub4-9
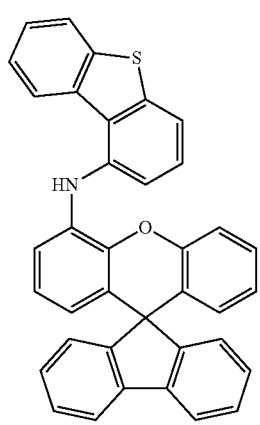
Sub4-10
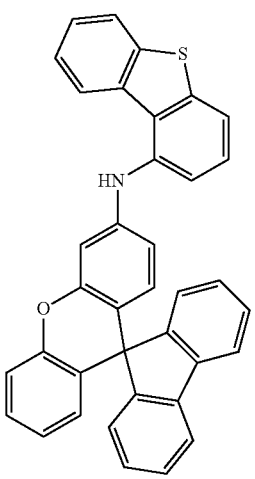
Sub4-11
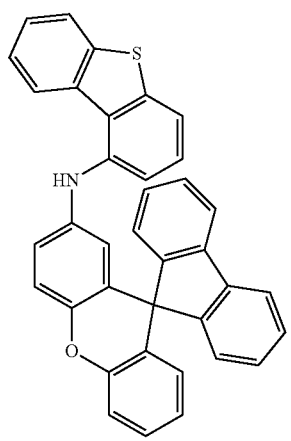
Sub4-12
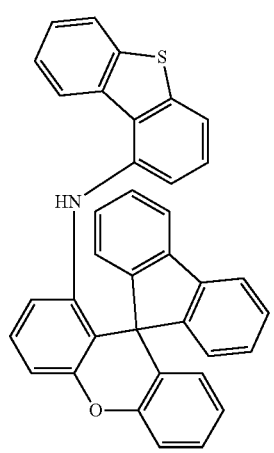
Sub4-13
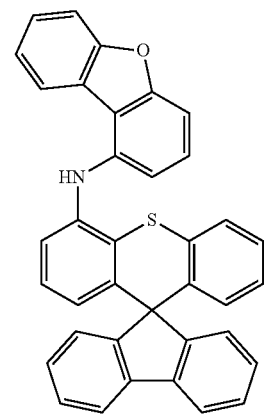

Sub4-14
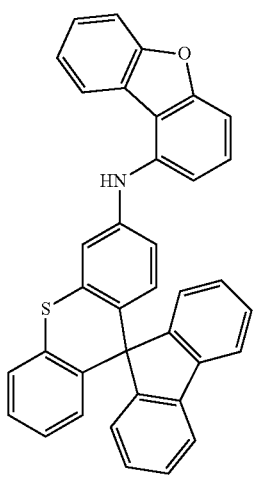
Sub4-15
Sub4-16
Sub4-17
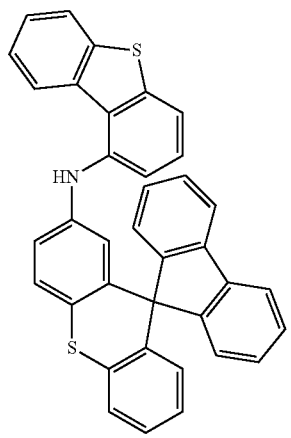
Sub4-18
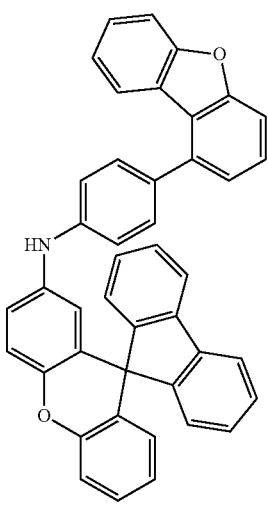
Sub4-19
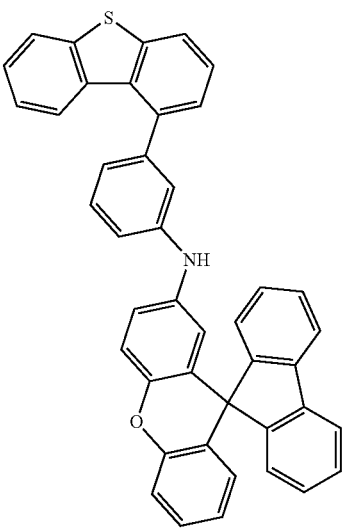

Sub4-20
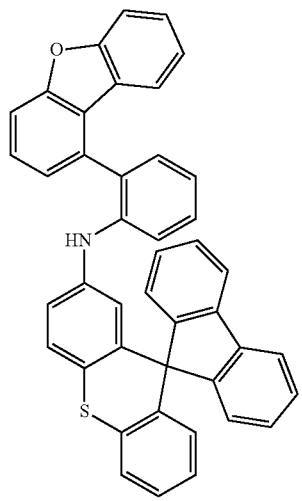
Sub4-21
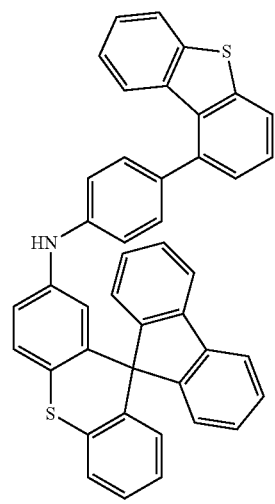
Sub4-22
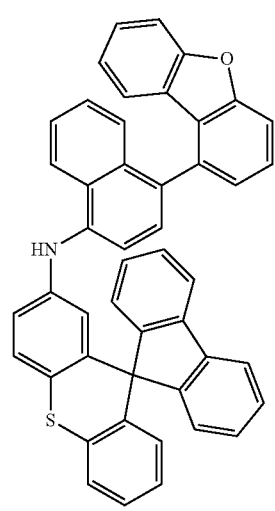
Sub4-23
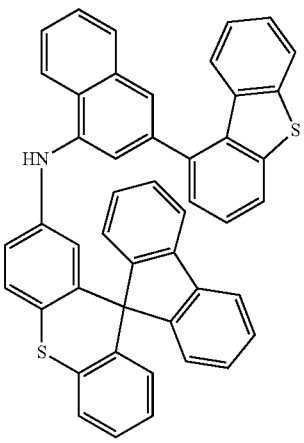
Sub4-24
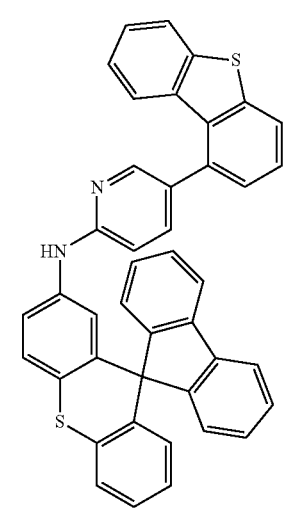
Sub4-25

Sub4-26
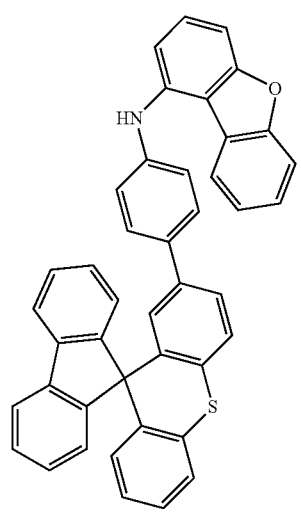
Sub4-27
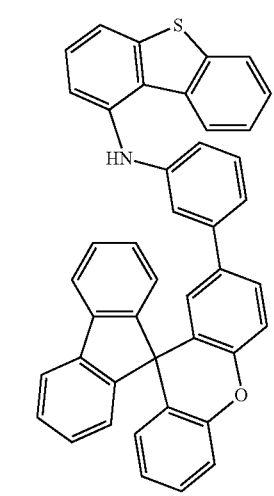
Sub4-28
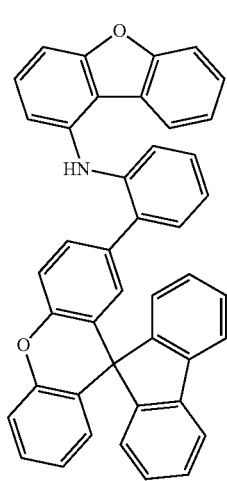
Sub4-29
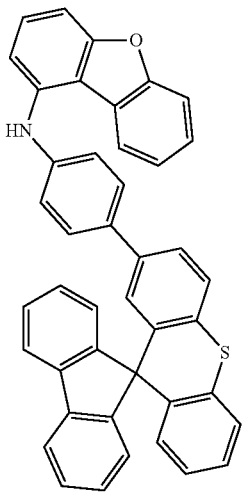
Sub4-30
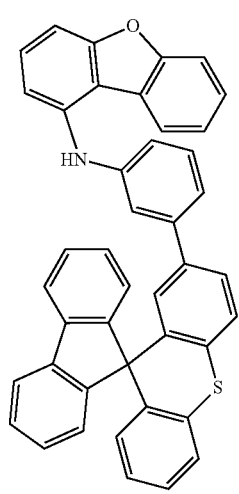
Sub4-31
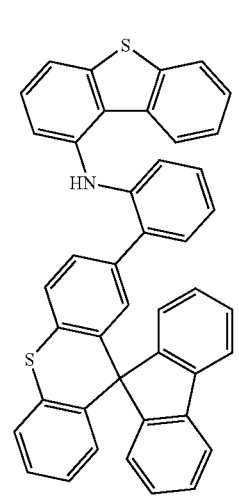

Sub4-32
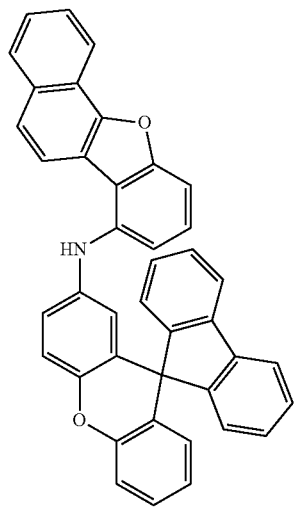
Sub4-33
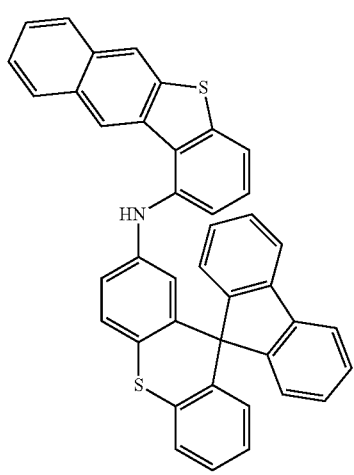
Sub4-34
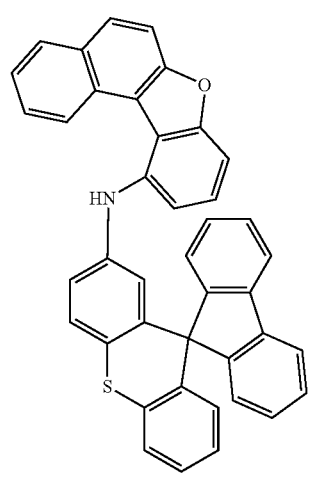
Sub4-35
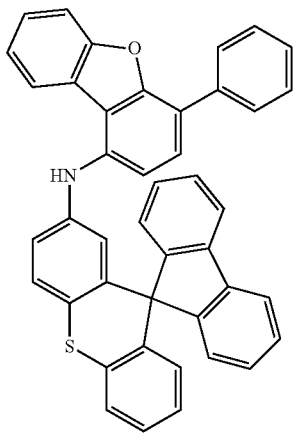
Sub4-36
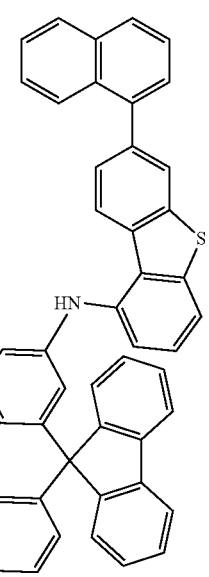
Sub4-37
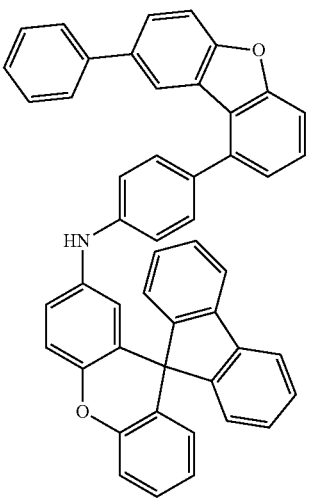

-continued
Sub4-38
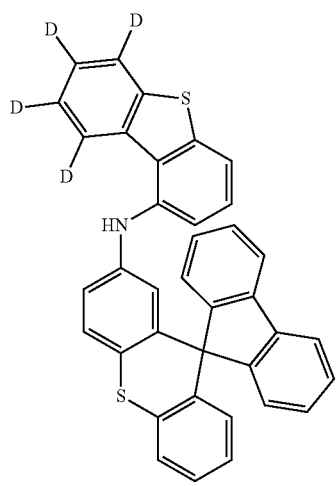
Sub4-39
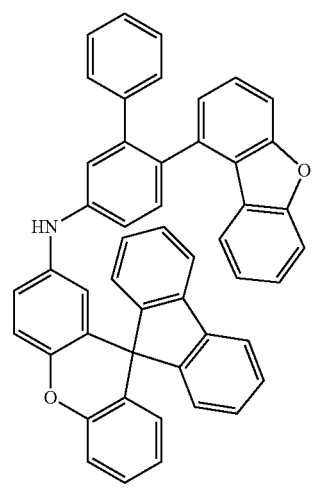
Sub4-40
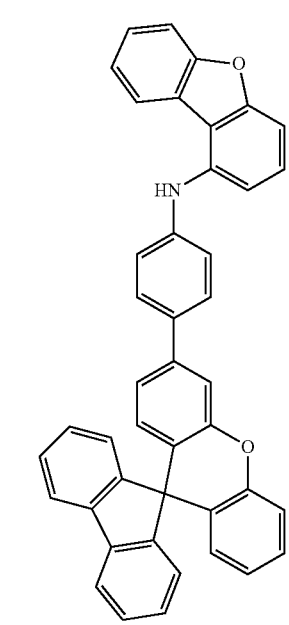
-continued
Sub4-41
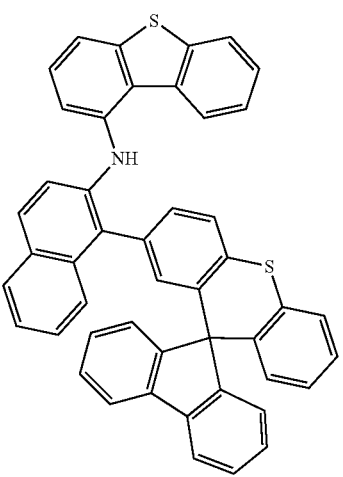
Sub4-42
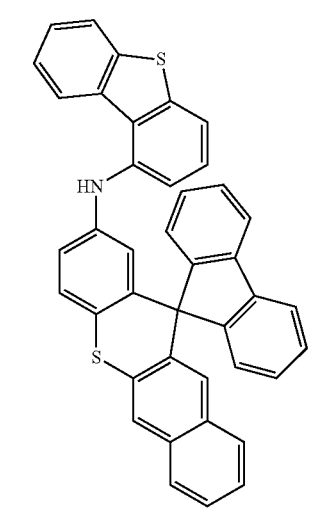
Sub4-43
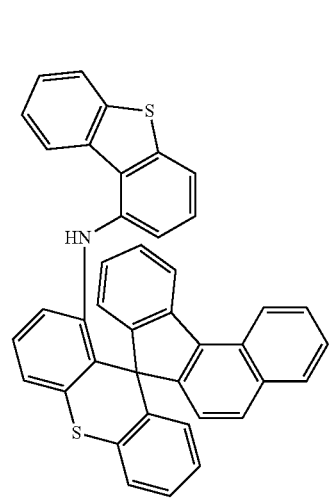

Sub4-44
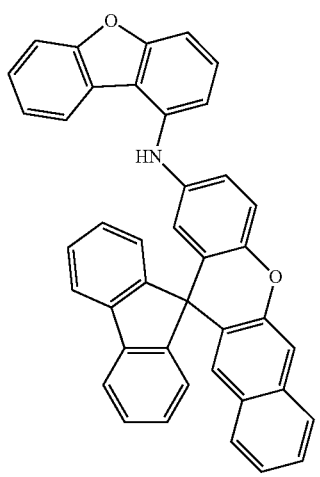
Sub4-45
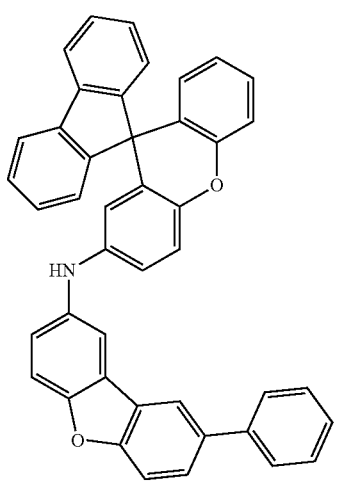
Sub4-46
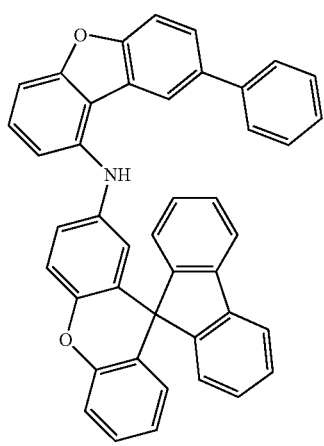
Sub4-47
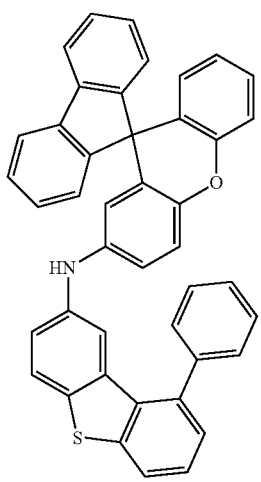
Sub4-48
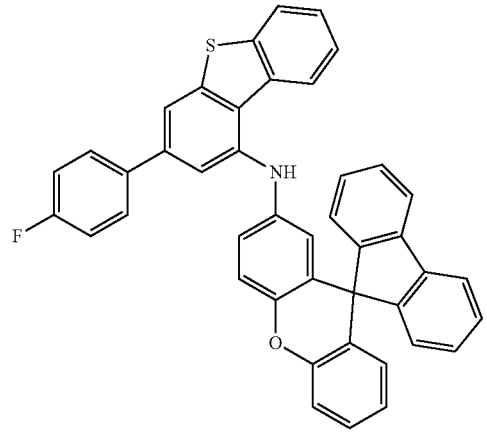
Sub4-49
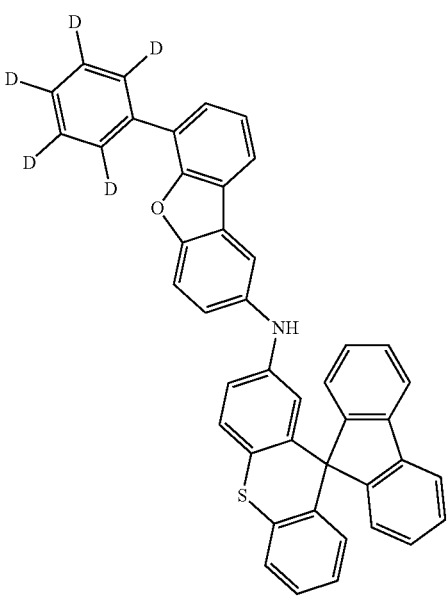

Sub4-50
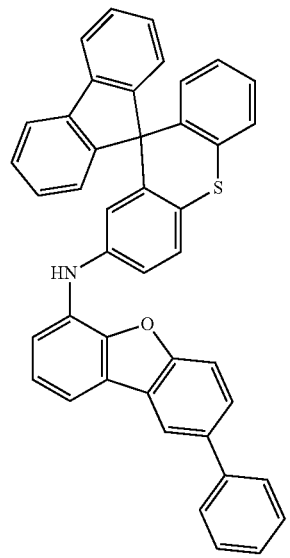
Sub4-51
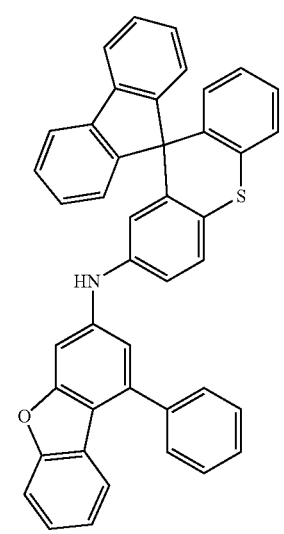
Sub4-52
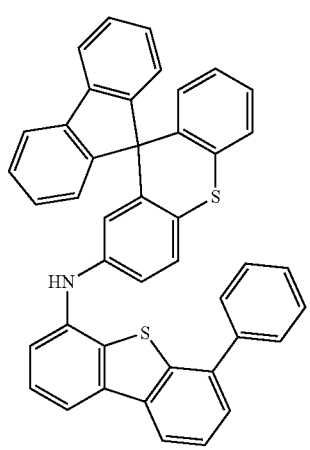
Sub4-53
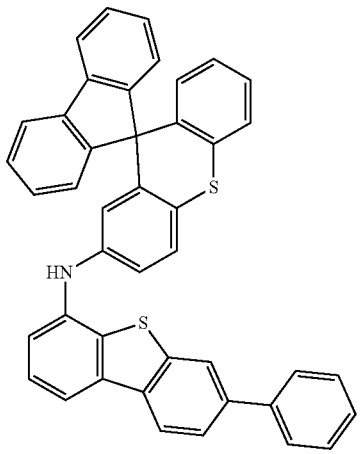
Sub4-54
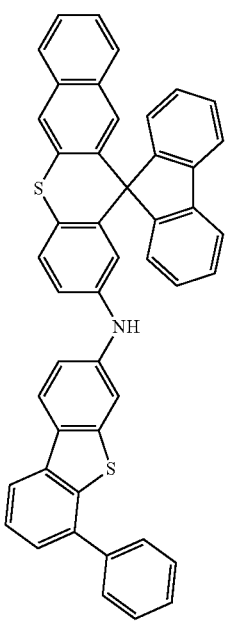
Sub4-55
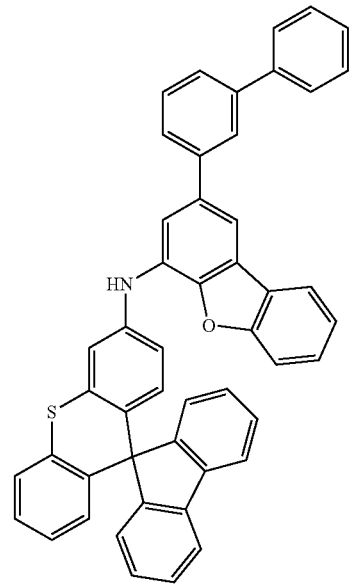

-continued
Sub4-56
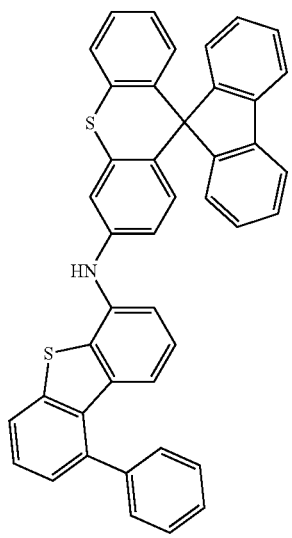
Sub4-58
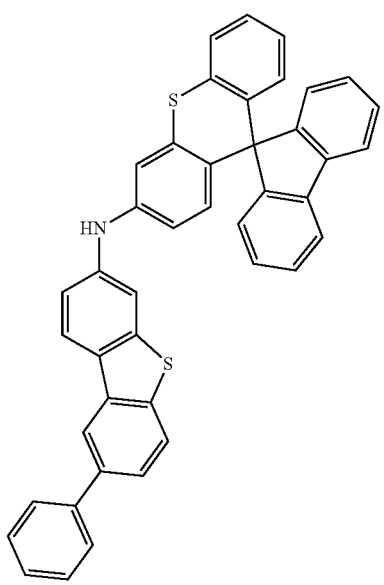
Sub4-59
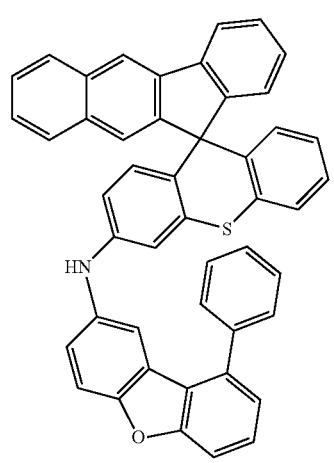
Sub4-57
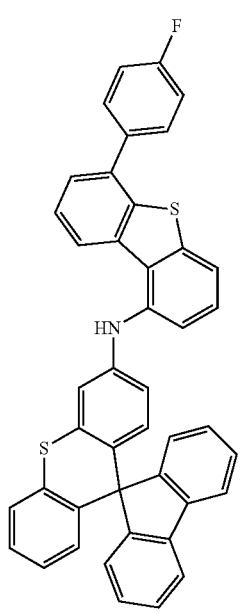
Sub4-60
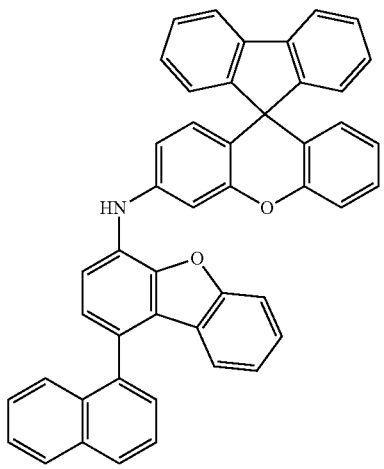

Sub4-61
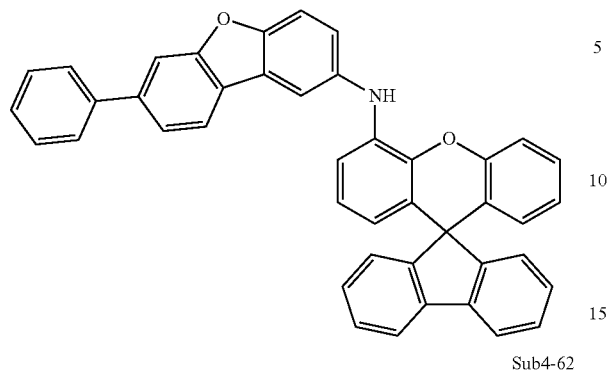
Sub4-62
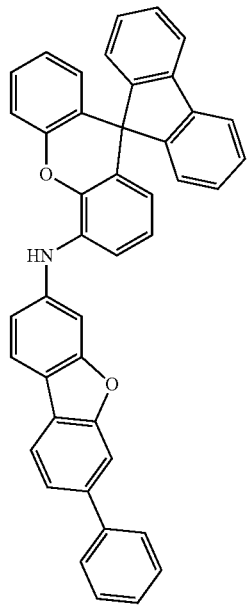
Sub4-63
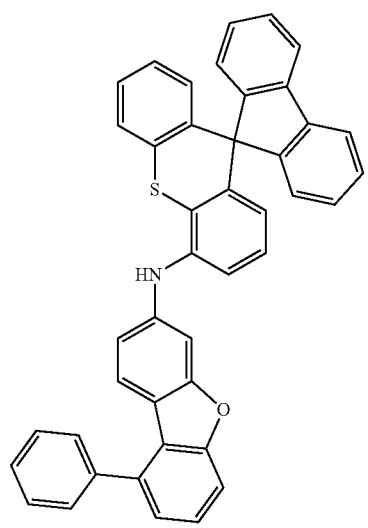
Sub4-64
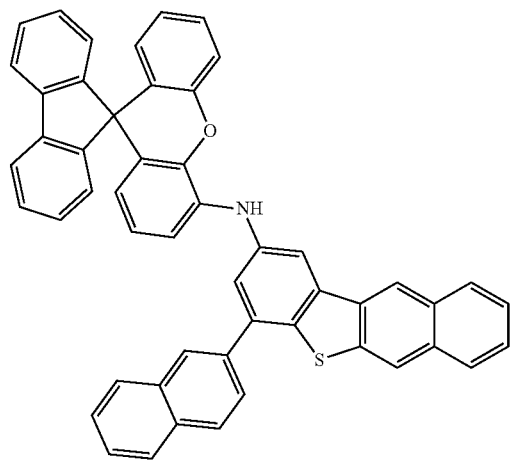
Sub5-1
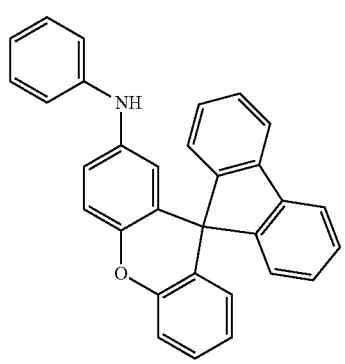
Sub5-2
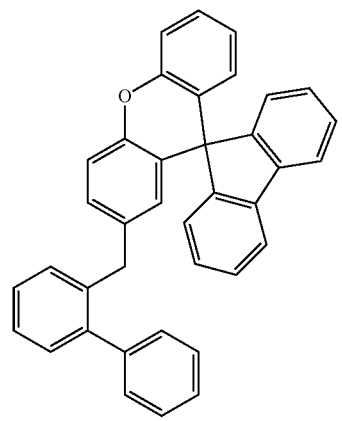
Sub5-3
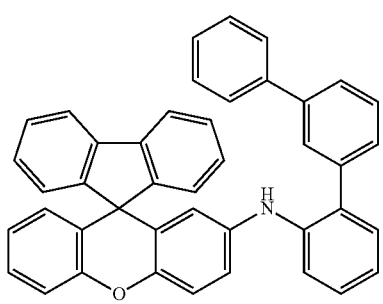

327
-continued
Sub5-4
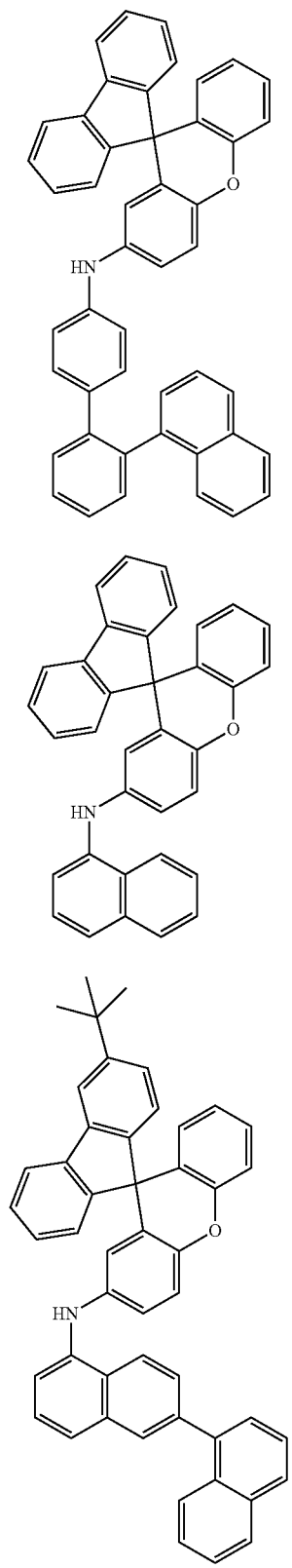
Sub5-5
Sub5-6
328
-continued
Sub5-7
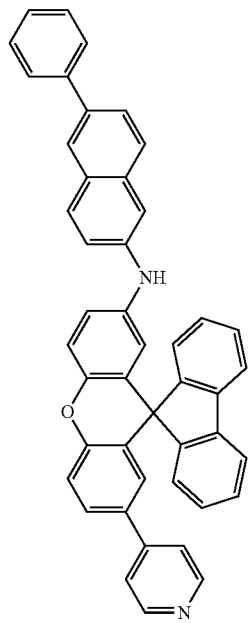
Sub5-8
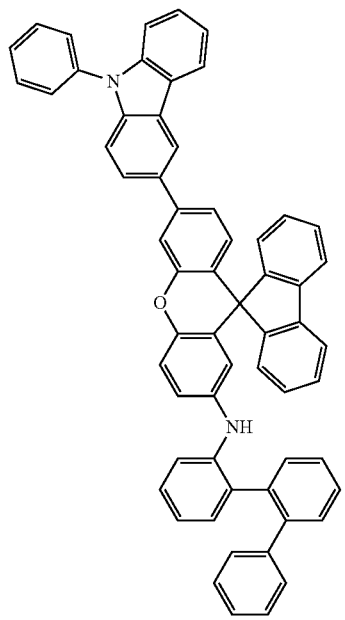
Sub5-9
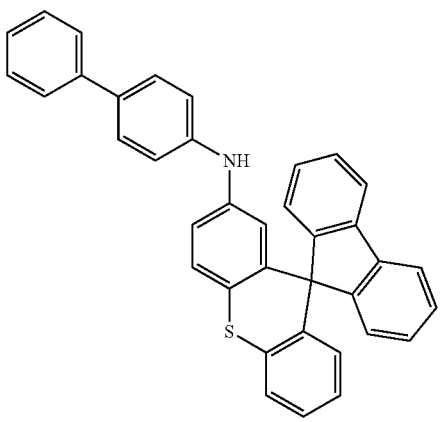

-continued
Sub5-10
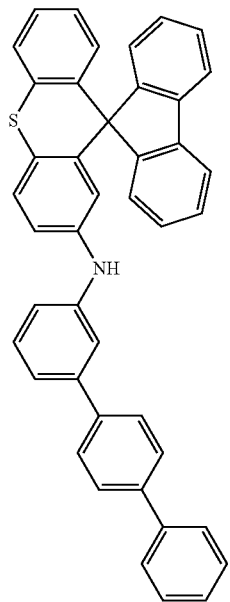
Sub5-11
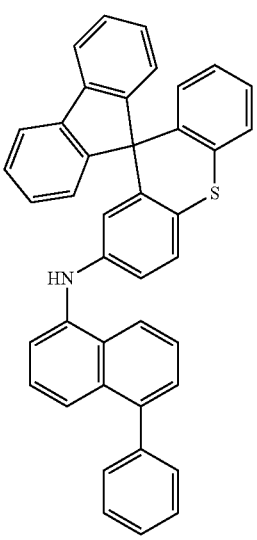
-continued
Sub5-12
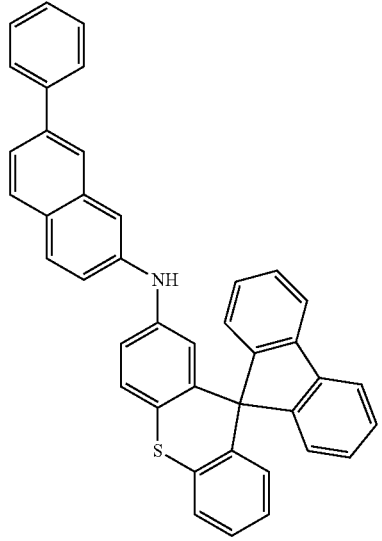
Sub5-13
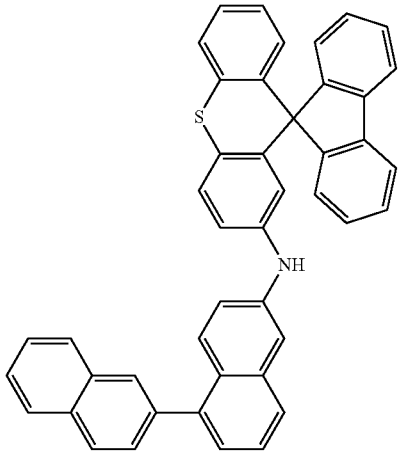
Sub5-14
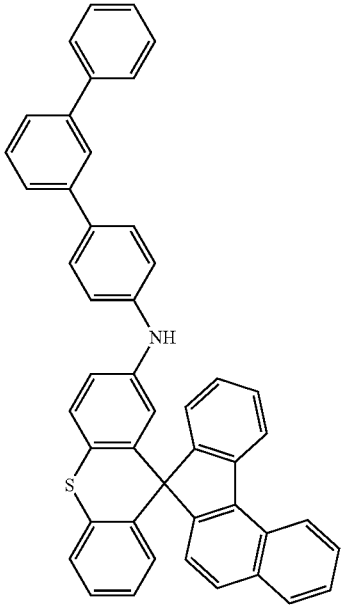

-continued
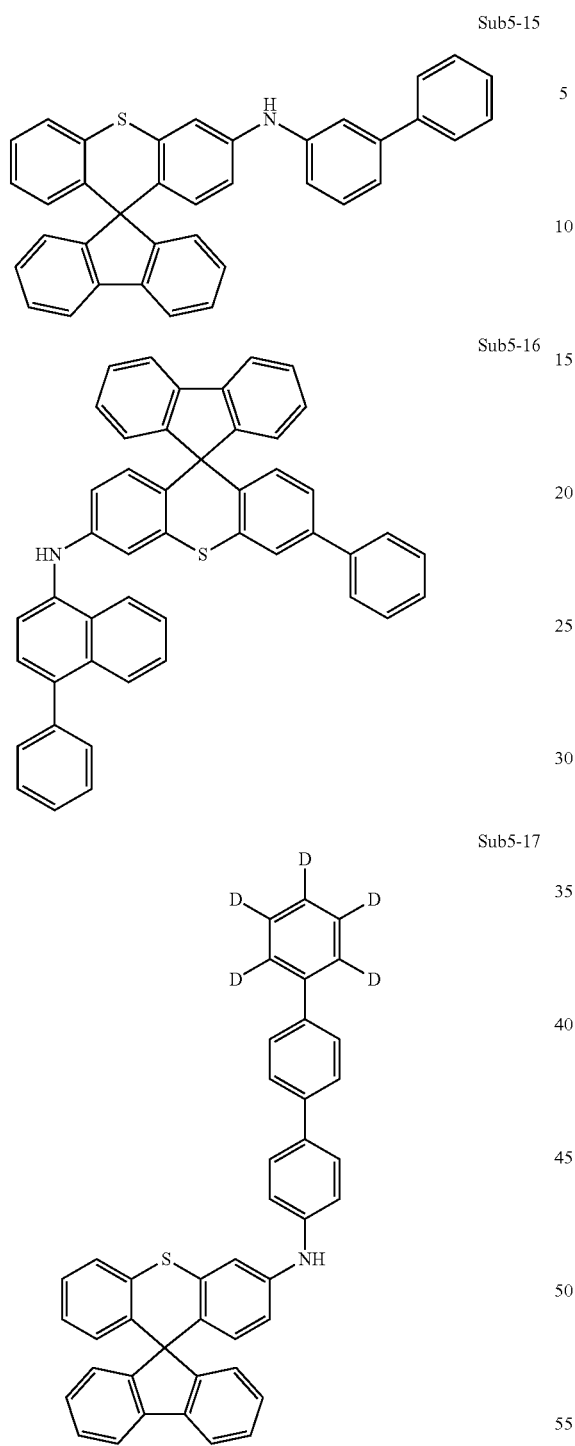
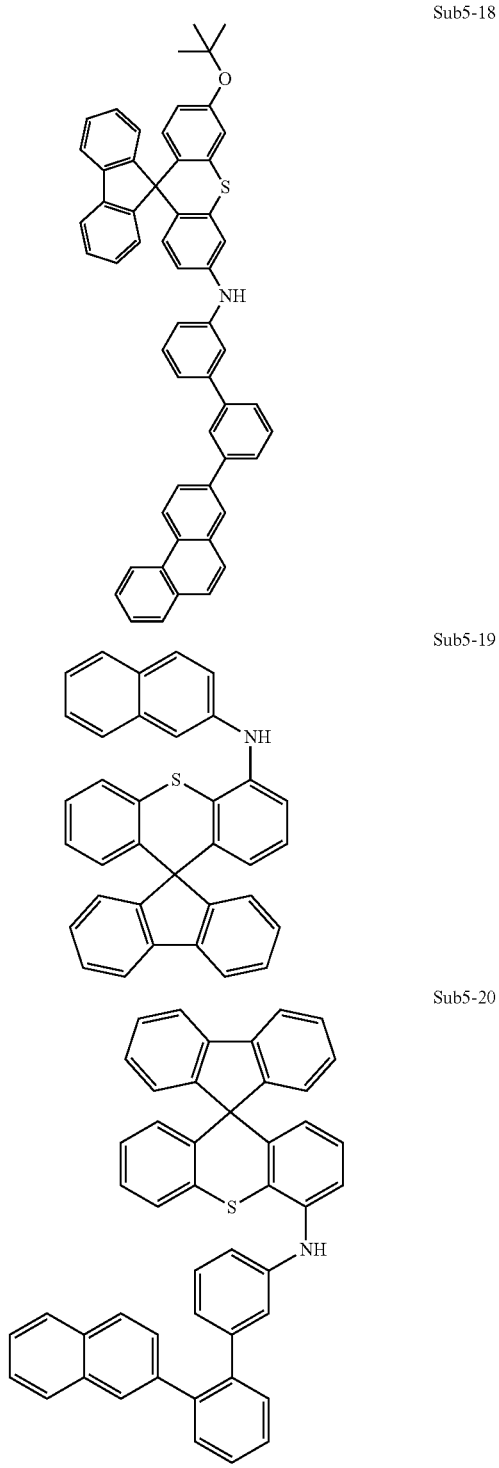
TABLE 2
| compound | FD-MS | compound | FD-MS |
|---|---|---|---|
| Sub2-1 | m/z = 335.13($C_{24}H_{17}NO$ = 335.41) | Sub2-2 | m/z = 427.19($C_{31}H_{25}NO$ = 427.55) |
| Sub2-3 | m/z = 561.21($C_{42}H_{27}NO$ = 561.68) | Sub2-4 | m/z = 461.18($C_{34}H_{23}NO$ = 461.56) |
| Sub2-5 | m/z = 461.18($C_{34}H_{23}NO$ = 461.56) | Sub2-6 | m/z = 435.16($C_{24}H_{17}NO$ = 435.53) |
| Sub2-7 | m/z = 335.13($C_{24}H_{17}NO$ = 335.41) | Sub2-8 | m/z = 335.13($C_{32}H_{21}NO$ = 335.41) |
| Sub2-9 | m/z = 527.22($C_{39}H_{29}NO$ = 527.67) | Sub2-10 | m/z = 511.19($C_{38}H_{25}NO$ = 511.62) |

TABLE 2-continued

| compound | FD-MS | compound | FD-MS |
| --- | --- | --- | --- |
| Sub2-11 | m/z = 487.19($C_{36}H_{25}NO$ = 487.60) | Sub2-12 | m/z = 537.21($C_{40}H_{27}NO$ = 537.66) |
| Sub2-13 | m/z = 435.16($C_{32}H_{21}NO$ = 435.53) | Sub2-14 | m/z = 336.13($C_{23}H_{16}N_2O$ = 336.39) |
| Sub2-15 | m/z = 452.15($C_{31}H_{20}N_2O_2$ = 452.51) | Sub2-16 | m/z = 500.19($C_{36}H_{24}N_2O$ = 500.60) |
| Sub2-17 | m/z = 465.20($C_{34}H_{19}D_4NO$ = 465.59) | Sub2-18 | m/z = 482.11($C_{31}H_{18}N_2O_2S$ = 482.56) |
| Sub2-19 | m/z = 567.17($C_{40}H_{25}NOS$ = 567.71) | Sub2-20 | m/z = 351.11($C_{24}H_{17}NS$ = 351.47) |
| Sub2-21 | m/z = 475.14($C_{34}H_{21}NS$ = 475.61) | Sub2-22 | m/z = 477.16($C_{34}H_{23}NS$ = 477.63) |
| Sub2-23 | m/z = 577.19($C_{42}H_{27}NS$ = 577.75) | Sub2-24 | m/z = 477.16($C_{34}H_{23}NS$ = 477.63) |
| Sub2-25 | m/z = 467.17($C_{33}H_{25}NS$ = 467.63) | Sub2-26 | m/z = 427.14($C_{30}H_{21}NS$ = 427.57) |
| Sub2-27 | m/z = 441.12($C_{30}H_{19}NOS$ = 441.55) | Sub2-28 | m/z = 427.14($C_{30}H_{21}NS$ = 427.57) |
| Sub2-29 | m/z = 457.10($C_{30}H_{19}NS_2$ = 457.61) | Sub2-30 | m/z = 527.17($C_{38}H_{25}NS$ = 527.69) |
| Sub2-31 | m/z = 517.15($C_{36}H_{23}NOS$ = 517.65) | Sub2-32 | m/z = 352.10($C_{23}H_{16}N_2S$ = 352.46) |
| Sub2-33 | m/z = 451.14($C_{32}H_{21}NS$ = 451.59) | Sub2-34 | m/z = 553.19($C_{40}H_{27}NS$ = 553.72) |
| Sub2-35 | m/z = 503.17($C_{36}H_{25}NS$ = 503.66) | Sub2-36 | m/z = 451.14($C_{32}H_{21}NS$ = 451.59) |
| Sub2-37 | m/z = 592.20($C_{42}H_{28}N_2S$ = 592.76) | Sub2-38 | m/z = 583.14($C_{40}H_{25}NS_2$ = 583.77) |
| Sub2-39 | m/z = 385.15($C_{28}H_{19}NO$ = 385.47) | Sub2-40 | m/z = 352.10($C_{23}H_{16}N_2S$ = 352.46) |
| Sub2-41 | m/z = 401.12($C_{28}H_{19}NS$ = 401.53) | Sub2-42 | m/z = 477.16($C_{34}H_{23}NS$ = 477.63) |
| Sub2-43 | m/z = 507.11($C_{34}H_{21}NS_2$ = 507.67) | Sub2-44 | m/z = 553.19($C_{40}H_{27}NS$ = 553.72) |
| Sub2-45 | m/z = 527.17($C_{38}H_{25}NS$ = 527.69) | Sub2-46 | m/z = 517.15($C_{36}H_{23}NOS$ = 517.65) |
| Sub2-47 | m/z = 498.09($C_{31}H_{18}N_2OS_2$ = 498.62) | Sub2-48 | m/z = 427.14($C_{30}H_{21}NS$ = 427.57) |
| Sub2-49 | m/z = 468.13($C_{31}H_{20}N_2OS$ = 468.57) | Sub2-50 | m/z = 385.15($C_{28}H_{19}NO$ = 385.47) |
| Sub2-51 | m/z = 441.12($C_{30}H_{19}NOS$ = 441.55) | Sub2-52 | m/z = 367.14($C_{25}H_{21}NS$ = 367.51) |
| Sub2-53 | m/z = 577.24($C_{43}H_{31}NO$ = 577.73) | Sub2-54 | m/z = 351.16($C_{25}H_{21}NO$ = 351.45) |
| Sub2-55 | m/z = 435.16($C_{32}H_{21}NO$ = 435.53) | Sub2-56 | m/z = 451.19($C_{33}H_{25}NO$ = 451.57) |
| Sub2-57 | m/z = 427.19($C_{31}H_{25}NO$ = 427.55) | Sub2-58 | m/z = 441.12($C_{30}H_{19}NOS$ = 441.55) |
| Sub2-59 | m/z = 477.21($C_{35}H_{27}NO$ = 477.61) | Sub2-60 | m/z = 528.22($C_{38}H_{28}N_2O$ = 528.66) |
| Sub2-61 | m/z = 375.13($C_{26}H_{17}NO_2$ = 375.43) | Sub2-62 | m/z = 609.25($C_{44}H_{35}NS$ = 609.83) |
| Sub2-63 | m/z = 533.18($C_{37}H_{27}NOS$ = 533.69) | Sub2-64 | m/z = 507.17($C_{35}H_{25}NOS$ = 507.65) |
| Sub2-65 | m/z = 572.16($C_{38}H_{24}N_2O_2S$ = 572.68) | Sub2-66 | m/z = 391.10($C_{25}H_{17}NOS$ = 391.49) |
| Sub2-67 | m/z = 724.25($C_{51}H_{36}N_2OS$ = 724.92) | Sub2-68 | m/z = 527.22($C_{39}H_{29}NO$ = 527.67) |
| Sub2-69 | m/z = 441.12($C_{30}H_{19}NOS$ = 441.55) | Sub2-70 | m/z = 493.19($C_{35}H_{27}NS$ = 493.67) |
| Sub2-71 | m/z = 467.17($C_{33}H_{25}NS$ = 467.63) | Sub2-72 | m/z = 556.18($C_{38}H_{24}N_2O_3$ = 556.62) |
| Sub2-73 | m/z = 475.16($C_{34}H_{21}NO_2$ = 475.55) | Sub2-74 | m/z = 567.22($C_{41}H_{29}NO_2$ = 567.69) |
| Sub2-75 | m/z = 627.26($C_{47}H_{33}NO$ = 627.79) | Sub2-76 | m/z = 527.22($C_{39}H_{29}NO$ = 527.67) |
| Sub2-77 | m/z = 335.13($C_{24}H_{17}NO$ = 335.41) | Sub2-78 | m/z = 467.17($C_{33}H_{25}NS$ = 467.63) |
| Sub2-79 | m/z = 501.17($C_{36}H_{23}NO_2$ = 501.59) | Sub2-80 | m/z = 351.11($C_{24}H_{17}NS$ = 351.47) |
| Sub2-81 | m/z = 351.11($C_{24}H_{17}NS$ = 351.47) | Sub2-82 | m/z = 516.17($C_{36}H_{24}N_2S$ = 516.66) |
| Sub2-83 | m/z = 708.31($C_{52}H_{40}N_2O$ = 708.91) | Sub2-84 | m/z = 401.12($C_{28}H_{19}NS$ = 401.53) |
| Sub2-85 | m/z = 401.12($C_{28}H_{19}NS$ = 401.53) | Sub2-86 | m/z = 351.11($C_{24}H_{17}NS$ = 351.47) |
| Sub2-87 | m/z = 518.18($C_{36}H_{26}N_2S$ = 518.68) | Sub2-88 | m/z = 427.14($C_{30}H_{21}NS$ = 427.57) |
| Sub2-89 | m/z = 461.18($C_{34}H_{23}NO$ = 461.56) | Sub2-90 | m/z = 461.18($C_{34}H_{23}NO$ = 461.56) |
| Sub2-91 | m/z = 335.13($C_{24}H_{17}NO$ = 335.41) | Sub2-92 | m/z = 561.21($C_{42}H_{27}NO$ = 561.68) |
| Sub2-93 | m/z = 461.18($C_{34}H_{23}NO$ = 461.56) | Sub2-94 | m/z = 353.12($C_{24}H_{16}FNO$ = 353.40) |
| Sub2-95 | m/z = 391.19($C_{28}H_{25}NO$ = 391.51) | Sub2-96 | m/z = 259.10($C_{18}H_{13}NO$ = 259.31) |
| Sub2-97 | m/z = 275.08($C_{18}H_{13}NS$ = 275.37) | | |
| Sub3-1 | m/z = 375.16($C_{27}H_{21}NO$ = 375.47) | Sub3-2 | m/z = 375.16($C_{27}H_{21}NO$ = 375.47) |
| Sub3-3 | m/z = 375.16($C_{27}H_{21}NO$ = 375.47) | Sub3-4 | m/z = 391.14($C_{27}H_{21}NS$ = 391.53) |
| Sub3-5 | m/z = 499.19($C_{37}H_{25}NO$ = 499.61) | Sub3-6 | m/z = 499.19($C_{37}H_{25}NO$ = 499.61) |
| Sub3-7 | m/z = 499.19($C_{37}H_{25}NO$ = 499.61) | Sub3-8 | m/z = 499.19($C_{37}H_{25}NO$ = 499.61) |
| Sub3-9 | m/z = 515.17($C_{37}H_{25}NS$ = 515.67) | Sub3-10 | m/z = 497.18($C_{37}H_{23}NO$ = 497.60) |
| Sub3-11 | m/z = 513.16($C_{37}H_{23}NS$ = 513.66) | Sub3-12 | m/z = 451.19($C_{33}H_{25}NO$ = 451.57) |
| Sub3-13 | m/z = 467.17($C_{33}H_{25}NS$ = 467.63) | Sub3-14 | m/z = 451.19($C_{33}H_{25}NO$ = 451.57) |
| Sub3-15 | m/z = 467.17($C_{33}H_{25}NS$ = 467.63) | Sub3-16 | m/z = 451.19($C_{33}H_{25}NO$ = 451.57) |
| Sub3-17 | m/z = 467.17($C_{33}H_{25}NS$ = 467.63) | Sub3-18 | m/z = 451.19($C_{33}H_{25}NO$ = 451.57) |
| Sub3-19 | m/z = 451.19($C_{33}H_{25}NO$ = 451.57) | Sub3-20 | m/z = 451.19($C_{33}H_{25}NO$ = 451.57) |
| Sub3-21 | m/z = 451.19($C_{33}H_{25}NO$ = 451.57) | Sub3-22 | m/z = 467.17($C_{33}H_{25}NS$ = 467.63) |
| Sub3-23 | m/z = 467.17($C_{33}H_{25}NS$ = 467.63) | Sub3-24 | m/z = 467.17($C_{33}H_{25}NS$ = 467.63) |
| Sub3-25 | m/z = 501.21($C_{37}H_{27}NO$ = 501.63) | Sub3-26 | m/z = 517.19($C_{37}H_{27}NS$ = 517.69) |
| Sub3-27 | m/z = 501.21($C_{37}H_{27}NO$ = 501.63) | Sub3-28 | m/z = 517.19($C_{37}H_{27}NS$ = 517.69) |
| Sub3-29 | m/z = 501.21($C_{37}H_{27}NO$ = 501.63) | Sub3-30 | m/z = 517.19($C_{37}H_{27}NS$ = 517.69) |
| Sub3-31 | m/z = 452.19($C_{32}H_{24}N_2O$ = 452.56) | Sub3-32 | m/z = 583.23($C_{42}H_{33}NS$ = 583.79) |
| Sub3-33 | m/z = 525.21($C_{39}H_{27}NS$ = 525.65) | Sub3-34 | m/z = 519.20($C_{37}H_{21}D_4NS$ = 519.70) |
| Sub3-35 | m/z = 527.22($C_{39}H_{29}NO$ = 527.67) | Sub3-36 | m/z = 543.20($C_{39}H_{29}NS$ = 543.73) |
| Sub3-37 | m/z = 527.22($C_{39}H_{29}NO$ = 527.67) | Sub3-38 | m/z = 543.20($C_{39}H_{29}NS$ = 543.73) |
| Sub3-39 | m/z = 543.20($C_{39}H_{29}NS$ = 543.73) | Sub3-40 | m/z = 527.22($C_{39}H_{29}NO$ = 527.67) |
| Sub3-41 | m/z = 527.22($C_{39}H_{29}NO$ = 527.67) | Sub3-42 | m/z = 527.22($C_{39}H_{29}NO$ = 527.67) |
| Sub3-43 | m/z = 543.20($C_{39}H_{29}NS$ = 543.73) | Sub3-44 | m/z = 543.20($C_{39}H_{29}NS$ = 543.73) |
| Sub3-45 | m/z = 452.19($C_{32}H_{24}N_2O$ = 452.56) | Sub3-46 | m/z = 441.16($C_{31}H_{23}NS$ = 441.59) |
| Sub3-47 | m/z = 441.16($C_{31}H_{23}NS$ = 441.59) | Sub3-48 | m/z = 425.18($C_{31}H_{23}NO$ = 425.53) |
| Sub3-49 | m/z = 425.18($C_{31}H_{23}NO$ = 425.53) | Sub3-50 | m/z = 467.17($C_{33}H_{25}NS$ = 467.63) |
| Sub3-51 | m/z = 577.24($C_{43}H_{31}NO$ = 577.73) | Sub3-52 | m/z = 573.21($C_{43}H_{27}NO$ = 573.70) |
| Sub3-53 | m/z = 497.18($C_{37}H_{23}NO$ = 497.60) | Sub3-54 | m/z = 497.18($C_{37}H_{23}NO$ = 497.60) |
| Sub3-55 | m/z = 513.16($C_{37}H_{23}NS$ = 513.66) | Sub3-56 | m/z = 441.16($C_{31}H_{23}NS$ = 441.59) |
| Sub3-57 | m/z = 549.21($C_{41}H_{27}NO$ = 549.67) | | |
| Sub4-1 | m/z = 513.17($C_{37}H_{23}NO_2$ = 513.60) | Sub4-2 | m/z = 513.17($C_{37}H_{23}NO_2$ = 513.60) |
| Sub4-3 | m/z = 513.17($C_{37}H_{23}NO_2$ = 513.60) | Sub4-4 | m/z = 513.17($C_{37}H_{23}NO_2$ = 513.60) |
| Sub4-5 | m/z = 579.17($C_{41}H_{25}NOS$ = 579.72) | Sub4-6 | m/z = 531.16($C_{37}H_{22}FNO_2$ = 531.59) |
| Sub4-7 | m/z = 563.19($C_{41}H_{25}NO_2$ = 563.66) | Sub4-8 | m/z = 665.24($C_{49}H_{31}NO_2$ = 665.79) |
| Sub4-9 | m/z = 529.15($C_{37}H_{23}NOS$ = 529.66) | Sub4-10 | m/z = 529.15($C_{37}H_{23}NOS$ = 529.66) |

TABLE 2-continued

| compound | FD-MS | compound | FD-MS |
|---|---|---|---|
| Sub4-11 | m/z = 529.15($C_{37}H_{23}NOS$ = 529.66) | Sub4-12 | m/z = 529.15($C_{37}H_{23}NOS$ = 529.66) |
| Sub4-13 | m/z = 529.15($C_{37}H_{23}NOS$ = 529.66) | Sub4-14 | m/z = 529.15($C_{37}H_{23}NOS$ = 529.66) |
| Sub4-15 | m/z = 529.15($C_{37}H_{23}NOS$ = 529.66) | Sub4-16 | m/z = 529.15($C_{37}H_{23}NOS$ = 529.66) |
| Sub4-17 | m/z = 545.13($C_{37}H_{23}NS_2$ = 545.72) | Sub4-18 | m/z = 589.20($C_{43}H_{27}NO_2$ = 589.69) |
| Sub4-19 | m/z = 605.18($C_{43}H_{27}NOS$ = 605.76) | Sub4-20 | m/z = 605.18($C_{43}H_{27}NOS$ = 605.76) |
| Sub4-21 | m/z = 621.16($C_{43}H_{27}NS_2$ = 621.82) | Sub4-22 | m/z = 655.20($C_{47}H_{29}NOS$ = 655.82) |
| Sub4-23 | m/z = 671.17($C_{47}H_{29}NS_2$ = 671.88) | Sub4-24 | m/z = 606.18($C_{42}H_{26}N_2OS$ = 606.74) |
| Sub4-25 | m/z = 622.15($C_{42}H_{26}N_2S_2$ = 622.80) | Sub4-26 | m/z = 589.20($C_{43}H_{27}NO_2$ = 589.69) |
| Sub4-27 | m/z = 605.18($C_{43}H_{27}NOS$ = 605.76) | Sub4-28 | m/z = 589.20($C_{43}H_{27}NO_2$ = 589.69) |
| Sub4-29 | m/z = 605.18($C_{43}H_{27}NOS$ = 605.76) | Sub4-30 | m/z = 605.18($C_{43}H_{27}NOS$ = 605.76) |
| Sub4-31 | m/z = 621.16($C_{43}H_{27}NS_2$ = 621.82) | Sub4-32 | m/z = 563.19($C_{41}H_{25}NO_2$ = 563.66) |
| Sub4-33 | m/z = 595.14($C_{41}H_{25}NS_2$ = 595.78) | Sub4-34 | m/z = 579.17($C_{41}H_{25}NOS$ = 579.72) |
| Sub4-35 | m/z = 605.18($C_{43}H_{27}NOS$ = 605.76) | Sub4-36 | m/z = 671.17($C_{47}H_{29}NS_2$ = 671.88) |
| Sub4-37 | m/z = 665.24($C_{49}H_{31}NO_2$ = 665.79) | Sub4-38 | m/z = 549.15($C_{37}H_{19}D_4NS_2$ = 549.74) |
| Sub4-39 | m/z = 665.24($C_{49}H_{31}NO_2$ = 665.79) | Sub4-40 | m/z = 589.20($C_{43}H_{27}NO_2$ = 589.69) |
| Sub4-41 | m/z = 671.17($C_{47}H_{29}NS_2$ = 671.88) | Sub4-42 | m/z = 595.14($C_{41}H_{25}NS_2$ = 595.78) |
| Sub4-43 | m/z = 595.14($C_{41}H_{25}NS_2$ = 595.78) | Sub4-44 | m/z = 563.19($C_{41}H_{25}NO_2$ = 563.66) |
| Sub4-45 | m/z = 589.2($C_{43}H_{27}NO_2$ = 589.69) | Sub4-46 | m/z = 589.2($C_{43}H_{27}NO_2$ = 589.69) |
| Sub4-47 | m/z = 605.18($C_{43}H_{27}NOS$ = 605.76) | Sub4-48 | m/z = 623.17($C_{43}H_{26}FNOS$ = 623.75) |
| Sub4-49 | m/z = 610.21 ($C_{43}H_{22}D_5NOS$ = 610.79) | Sub4-50 | m/z = 605.18($C_{43}H_{27}NOS$ = 605.76) |
| Sub4-51 | m/z = 605.18($C_{43}H_{27}NOS$ = 605.76) | Sub4-52 | m/z = 621.16($C_{43}H_{27}NS_2$ = 621.82) |
| Sub4-53 | m/z = 621.16($C_{43}H_{27}NS_2$ = 621.82) | Sub4-54 | m/z = 671.17($C_{47}H_{29}NS_2$ = 671.88) |
| Sub4-55 | m/z = 681.21 ($C_{49}H_{31}NOS$ = 681.85) | Sub4-56 | m/z = 621.16($C_{43}H_{27}NS_2$ = 621.82) |
| Sub4-57 | m/z = 639.15($C_{43}H_{26}FNS_2$ = 639.81) | Sub4-58 | m/z = 621.16($C_{43}H_{27}NS_2$ = 621.82) |
| Sub4-59 | m/z = 655.2($C_{47}H_{29}NOS$ = 655.82) | Sub4-60 | m/z = 639.22($C_{47}H_{29}NO_2$ = 639.75) |
| Sub4-61 | m/z = 589.2($C_{43}H_{27}NO2$ = 589.69) | Sub4-62 | m/z = 589.2($C_{43}H_{27}NO_2$ = 589.69) |
| Sub4-63 | m/z = 605.18($C_{43}H_{27}NOS$ = 605.76) | Sub4-64 | m/z = 705.21($C_{51}H_{31}NOS$ = 705.88) |
| Sub5-1 | m/z = 423.16($C_{31}H_{21}NO$ = 423.52) | Sub5-2 | m/z = 499.19($C_{37}H_{25}NO$ = 499.61) |
| Sub5-3 | m/z = 575.22($C_{43}H_{29}NO$ = 575.71) | Sub5-4 | m/z = 625.24($C_{47}H_{31}NO$ = 625.77) |
| Sub5-5 | m/z = 473.18($C_{35}H_{23}NO$ = 473.58) | Sub5-6 | m/z = 655.29($C_{49}H_{37}NO$ = 655.84) |
| Sub5-7 | m/z = 626.24($C_{46}H_{30}N_2O$ = 626.76) | Sub5-8 | m/z = 816.31($C_{61}H_{40}N_2O$ = 817) |
| Sub5-9 | m/z = 515.17($C_{37}H_{25}NS$ = 515.67) | Sub5-10 | m/z = 591.2($C_{43}H_{29}NS$ = 591.77) |
| Sub5-11 | m/z = 565.19($C_{41}H_{27}NS$ = 565.73) | Sub5-12 | m/z = 565.19($C_{41}H_{27}NS$ = 565.73) |
| Sub5-13 | m/z = 615.2($C_{45}H_{29}NS$ = 615.79) | Sub5-14 | m/z = 641.22($C_{47}H_{31}NS$ = 641.83) |
| Sub5-15 | m/z = 515.17($C_{37}H_{25}NS$ = 515.67) | Sub5-16 | m/z = 641.22($C_{47}H_{31}NS$ = 641.83) |
| Sub5-17 | m/z = 596.23($C_{43}H_{24}D_5NS$ = 596.8) | Sub5-18 | m/z = 763.29($C_{55}H_{41}NOS$ = 764) |
| Sub5-19 | m/z = 489.16($C_{35}H_{23}NS$ = 489.64) | Sub5-20 | m/z = 641.22($C_{47}H_{31}NS$ = 641.83) |

III. Synthesis of Final Product

1. Synthesis Example of P-1

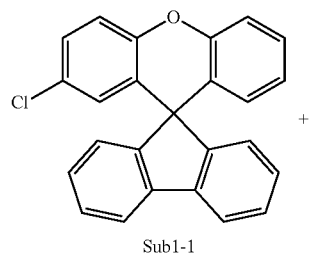

Sub1-1

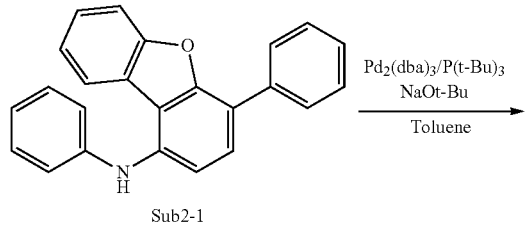

Sub2-1

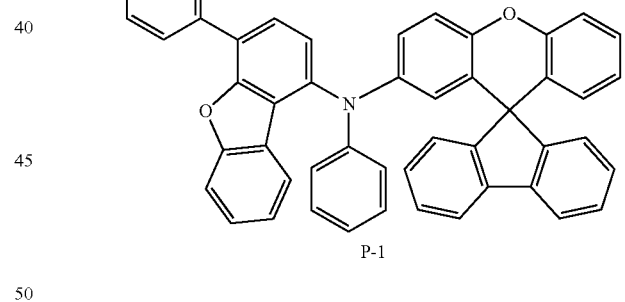

P-1

Sub1-1 (20 g, 54.5 mmol) was dissolved in a round bottom flask with Toluene (400 mL) and Sub2-1 (18.3 g, 54.5 mmol), $Pd_2(dba)_3$ (1.5 g, 1.64 mmol), P(t-Bu)$_3$ (50 wt % Sol.) (1.3 mL, 3.3 mmol), NaOt-Bu (15.7 g, 163.6 mmol) were added and stirred at 80° C. When the reaction was completed, the solvent was removed, extracted with $CH_2Cl_2$ and water, the organic layer was dried over $MgSO_4$, concentrated, and the resulting compound was purified by silica gel column and sublimation to obtain 29.8 g (82% yield) of the product.

2. Synthesis Example of P-73
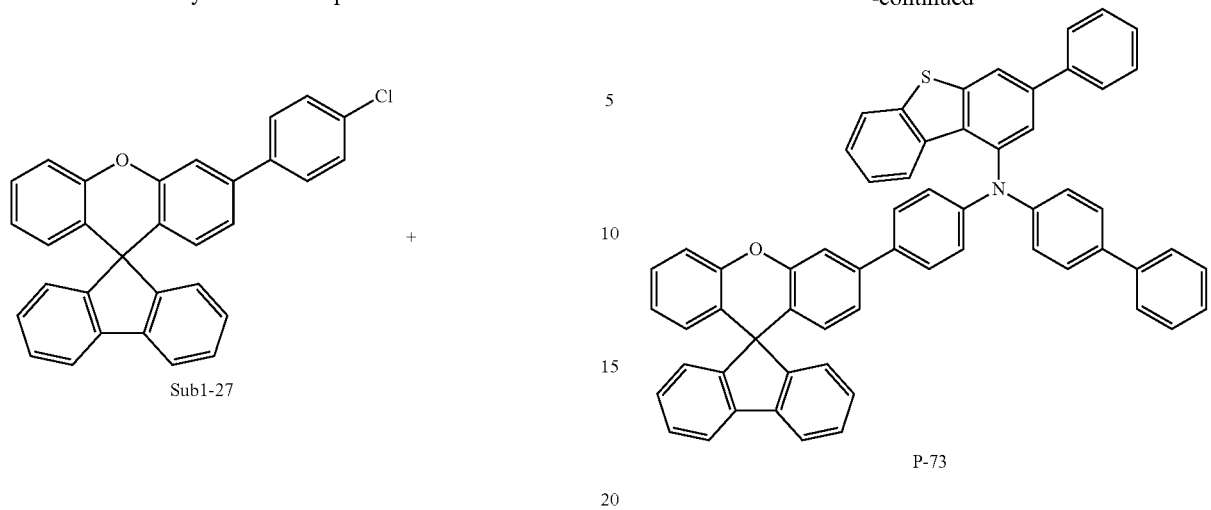
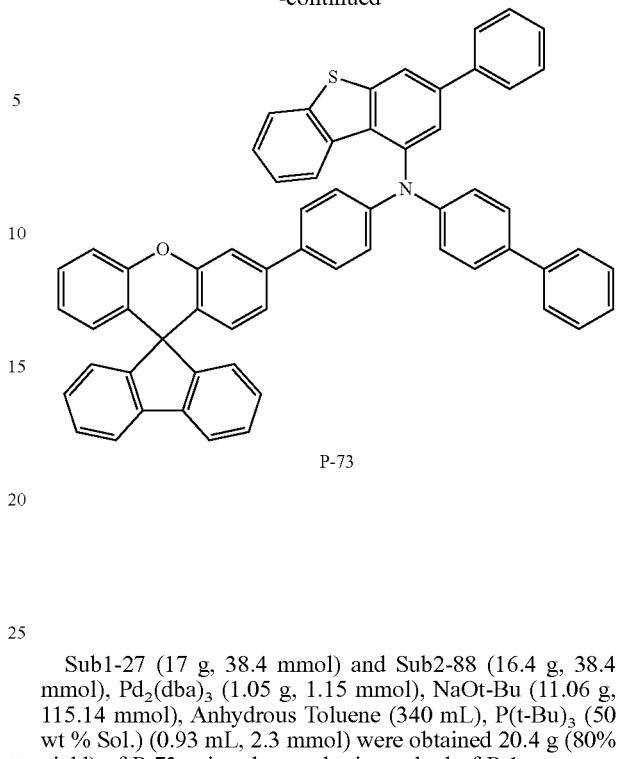
Sub1-27 (17 g, 38.4 mmol) and Sub2-88 (16.4 g, 38.4 mmol), Pd$_2$(dba)$_3$ (1.05 g, 1.15 mmol), NaOt-Bu (11.06 g, 115.14 mmol), Anhydrous Toluene (340 mL), P(t-Bu)$_3$ (50 wt % Sol.) (0.93 mL, 2.3 mmol) were obtained 20.4 g (80% yield) of P-73 using the synthesis method of P-1.
3. Synthesis Example of P-113
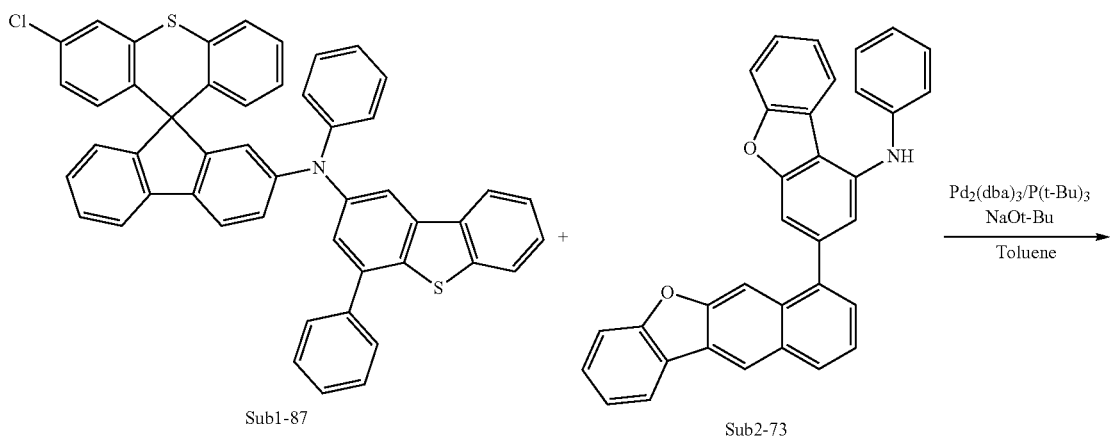

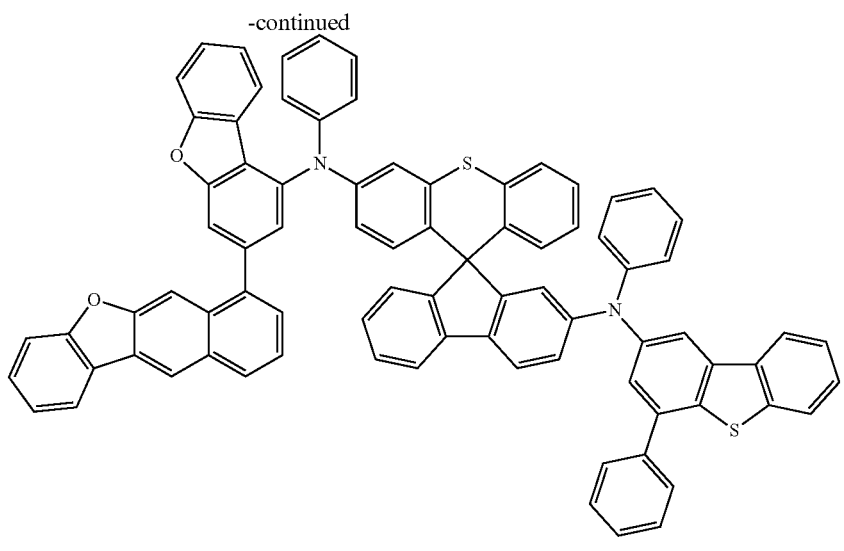
P-113
Sub1-87 (12 g, 16.4 mmol) and Sub2-73 (7.8 g, 16.4 mmol), Pd₂(dba)₃ (0.45 g, 0.5 mmol), NaOt-Bu (4.7 g, 49.2 mmol), anhydrous Toluene (240 mL), P(t-Bu)₃ (50 wt % Sol.) (0.2 mL, 0.98 mmol) were obtained 14.2 g (74% yield) of P-113 using the synthesis method of P-1.
4. Synthesis Example of P-121
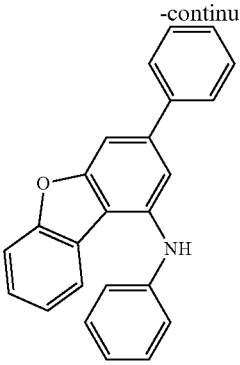
Sub2-77
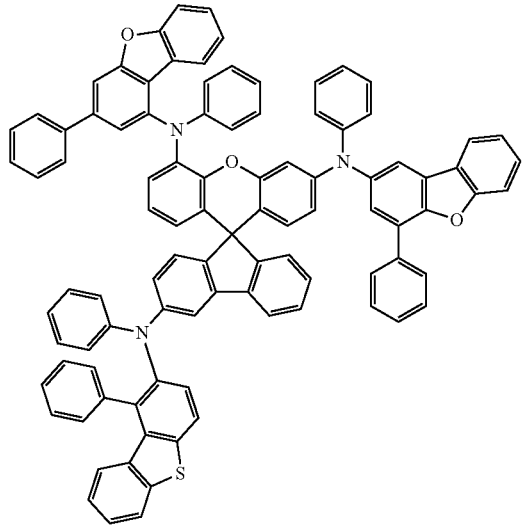
P-121
Sub1-105 (12 g, 11.4 mmol) and Sub2-77 (3.8 g, 11.4 mmol), Pd₂(dba)₃ (0.3 g, 0.34 mmol), NaOt-Bu (3.3 g, 34.3 mmol), anhydrous Toluene (240 mL), P(t-Bu)₃ (50 wt % Sol.) (0.3 mL, 0.7 mmol) were obtained 11.7 g (76% yield) of P-121 using the synthesis method of P-1.

5. Synthesis Example of P-139

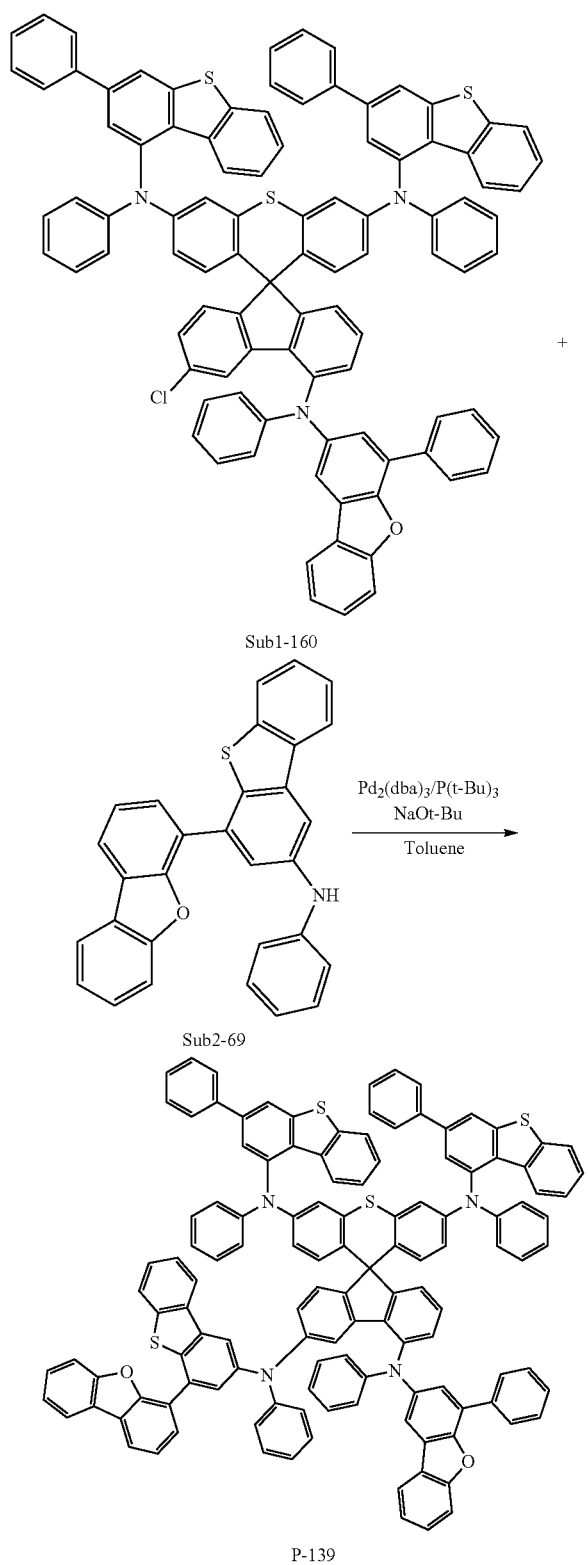

Sub1-160 (9 g, 7.8 mmol) and Sub2-69 (3.5 g, 7.8 mmol), Pd₂(dba)₃ (0.2 g, 0.23 mmol), NaOt-Bu (2.3 g, 23.5 mmol), anhydrous Toluene (180 mL), P(t-Bu)₃ (50 wt % Sol.) (0.2 mL, 0.5 mmol) were obtained 10.9 g (73% yield) of P-139 using the synthesis method of P-1.

6. Synthesis Example of P 1-2

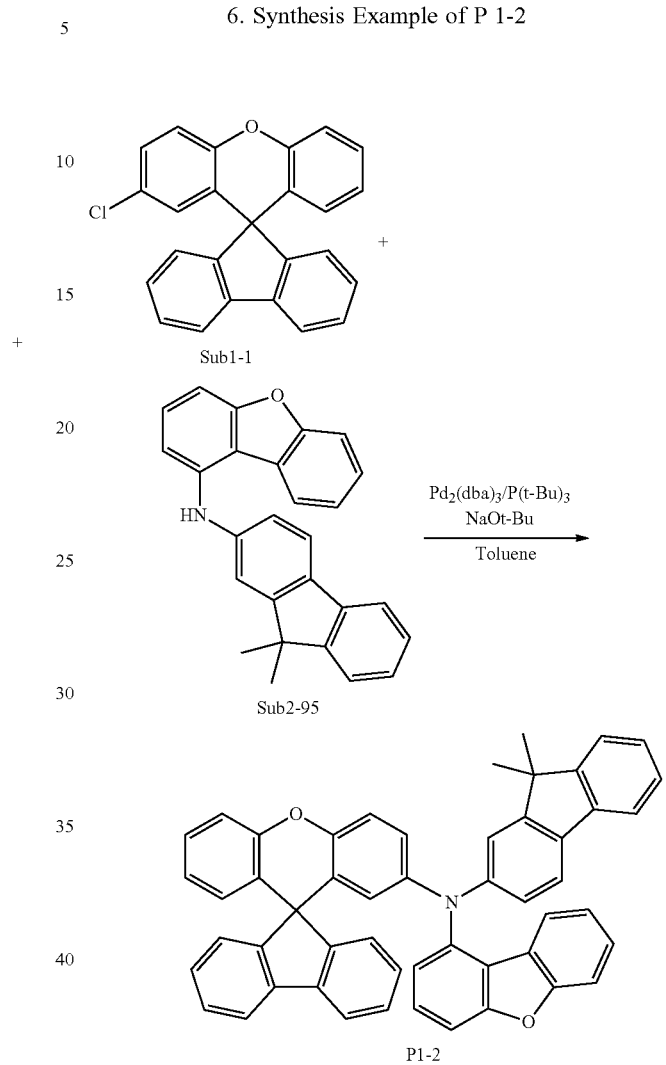

Sub1-1 (15 g, 40.9 mmol) and Sub2-95 (16.0 g, 40.9 mmol), Pd₂(dba)₃ (1.12 g, 1.2 mmol), NaOt-Bu (11.8 g, 122.7 mmol), anhydrous Toluene (300 mL), P(t-Bu)₃ (50 wt % Sol.) (1.00 mL, 2.5 mmol) were obtained 24.2 g (84% yield) of P1-2 using the synthesis method of P-1.

7. Synthesis Example of P 1-13

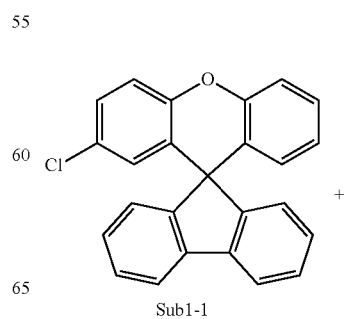

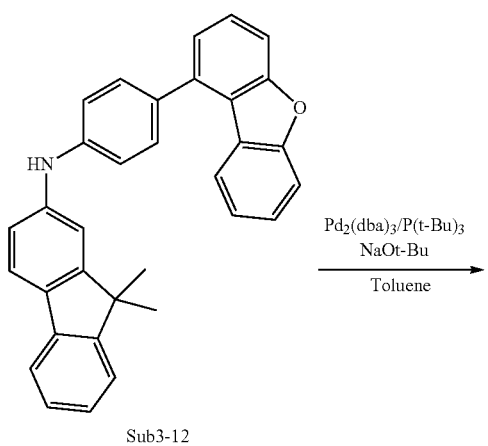

Sub3-12

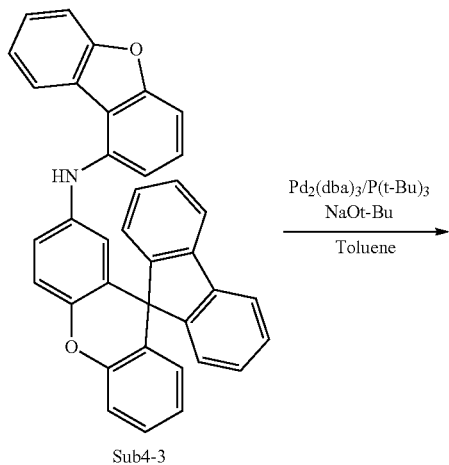

Sub4-3

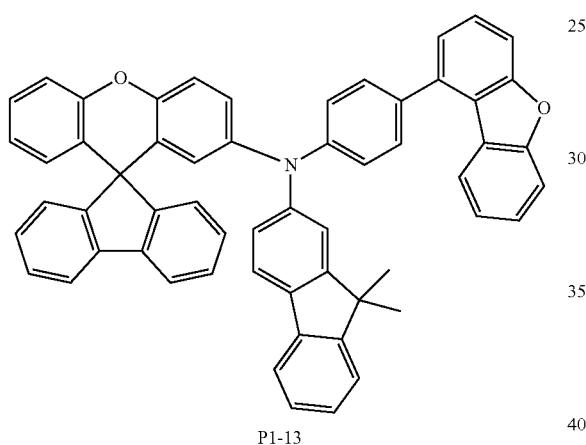

P1-13

Sub1-1 (10.2 g, 27.8 mmol) and Sub3-12 (12.6 g, 27.8 mmol), Pd₂(dba)₃ (0.8 g, 0.76 mmol), NaOt-Bu (8.0 g, 83.4 mmol), anhydrous Toluene (210 mL), P(t-Bu)₃ (50 wt % Sol.) (0.7 mL, 1.7 mmol) were obtained 17.6 g (81% yield) of P1-13 using the synthesis method of P-1.

8. Synthesis Example of P 2-3

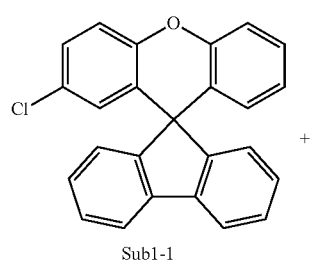

Sub1-1

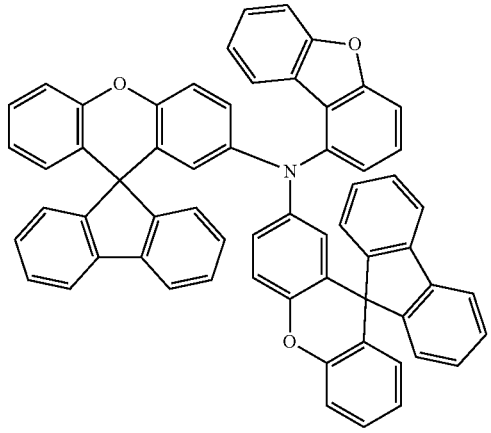

P2-3

Sub1-1 (9.5 g, 25.9 mmol) and Sub4-3 (13.3 g, 25.9 mmol), Pd₂(dba)₃ (0.7 g, 0.8 mmol), NaOt-Bu (7.5 g, 77.7 mmol), anhydrous Toluene (200 mL), P(t-Bu)₃ (50 wt % Sol.) (0.6 mL, 0.8 mmol) were obtained 18.1 g (83% yield) of P2-3 using the synthesis method of P-1.

9. Synthesis Example of P3-3

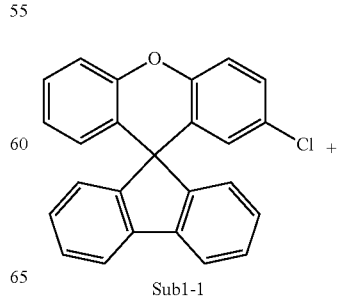

Sub1-1

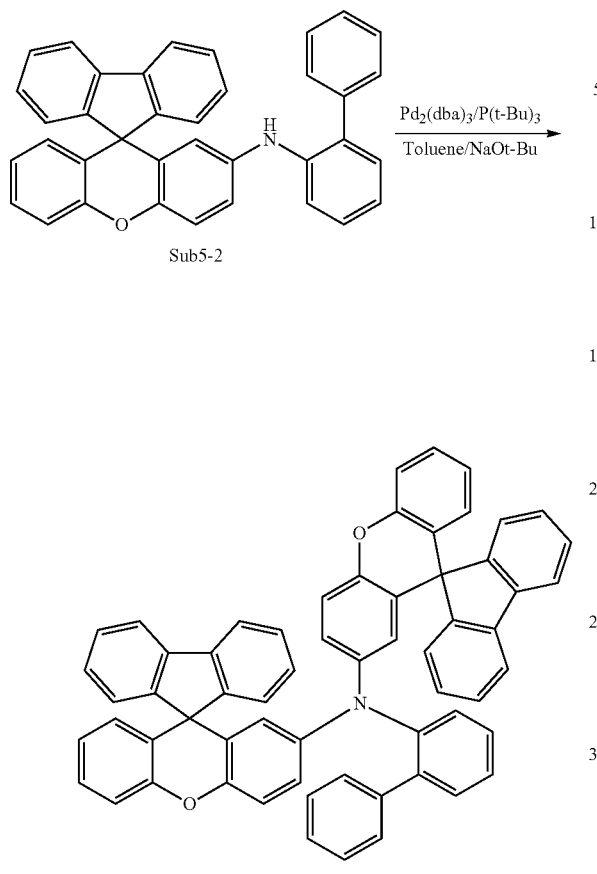

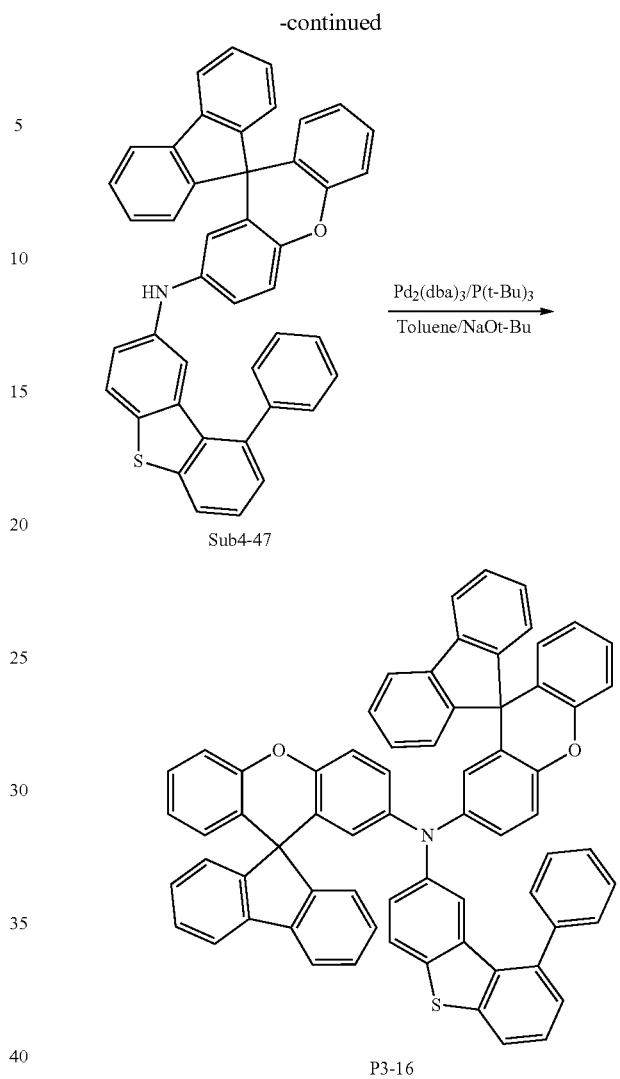

Sub1-1 (10.2 g, 27.8 mmol), Sub5-2 (13.9 g, 27.8 mmol), Pd$_2$(dba)$_3$ (1.27 g, 1.39 mmol), NaOt-Bu (8.02 g, 83.4 mmol), anhydrous toluene (204 mL), P(t-Bu)$_3$ (50 wt % Sol.) (1.13 mL, 2.78 mmol) were obtained by using the synthesis method of P-1 to obtain 17.1 g (yield 74%) of P3-3.

10. Synthesis Example of P3-16

Sub1-1 (9.10 g, 24.81 mmol), Sub4-47 (15.03 g, 24.81 mmol), Pd$_2$(dba)$_3$ (1.14 g, 1.24 mmol), NaOt-Bu (7.15 g, 74.42 mmol), anhydrous toluene (182 mL), P(t-Bu)$_3$ (50 wt % Sol.) (1.00 mL, 2.48 mmol) were obtained by using the synthesis method of P-1 to obtain 18.8 g (yield 81%) of P3-16.

11. Synthesis Example of P3-23

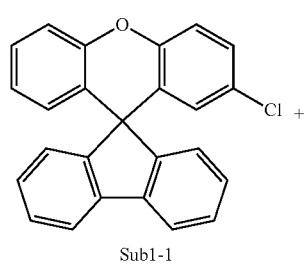

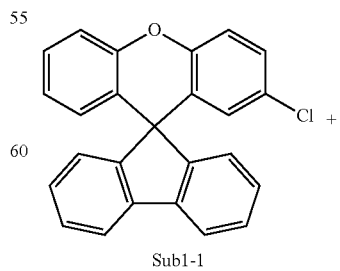

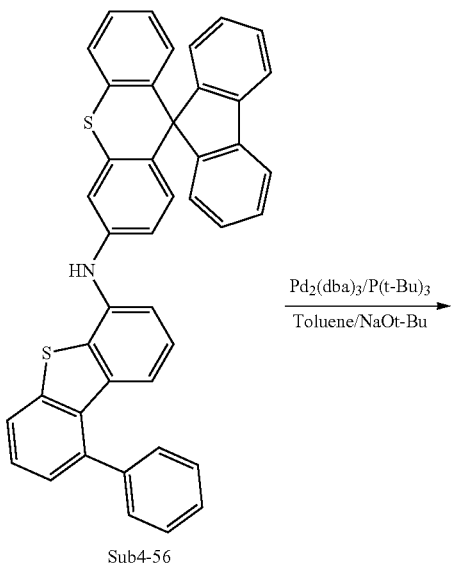

Sub4-56

Pd$_2$(dba)$_3$/P(t-Bu)$_3$
Toluene/NaOt-Bu
→

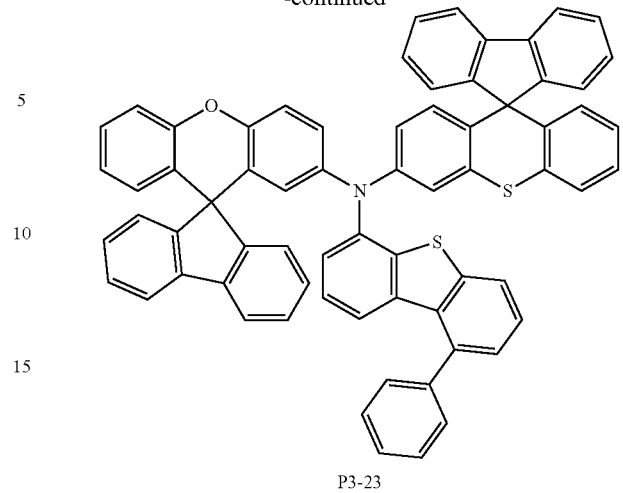

P3-23

Sub1-1 (8.56 g, 23.33 mmol), Sub4-56 (14.51 g, 23.33 mmol), Pd$_2$(dba)$_3$ (1.07 g, 1.17 mmol), NaOt-Bu (6.73 g, 70.0 mmol), anhydrous Toluene (171 mL), P(t-Bu)$_3$ (50 wt % Sol.) (0.94 mL, 2.33 mmol) were obtained by using the synthesis method of P-1 to obtain 16.9 g (yield 76%) of P3-23.

Meanwhile, FD-MS values of P-1 to P-139, P1-1 to P1-86, P2-1 to P2-55 and P3-1 to P3-40, the compounds of the present invention prepared according to the synthesis example as described above are shown in Table 3:

TABLE 3

| Compound | FD-MS | compound | FD-MS |
|---|---|---|---|
| P-1 | m/z = 665.24(C$_{49}$H$_{31}$NO$_2$ = 665.79) | P-2 | m/z = 791.28(C$_{59}$H$_{37}$NO$_2$ = 791.95) |
| P-3 | m/z = 891.31(C$_{67}$H$_{41}$NO$_2$ = 892.07) | P-4 | m/z = 741.27(C$_{55}$H$_{35}$NO$_2$ = 741.89) |
| P-5 | m/z = 791.28(C$_{59}$H$_{37}$NO$_2$ = 791.95) | P-6 | m/z = 665.24(C$_{49}$H$_{31}$NO$_2$ = 665.79) |
| P-7 | m/z = 665.24(C$_{49}$H$_{31}$NO$_2$ = 665.79) | P-8 | m/z = 665.24(C$_{49}$H$_{31}$NO$_2$ = 665.79) |
| P-9 | m/z = 665.24(C$_{49}$H$_{31}$NO$_2$ = 665.79) | P-10 | m/z = 857.33(C$_{64}$H$_{43}$NO$_2$ = 858.05) |
| P-11 | m/z = 841.30(C$_{63}$H$_{39}$NO$_2$ = 842.01) | P-12 | m/z = 817.30(C$_{61}$H$_{39}$NO$_2$ = 817.99) |
| P-13 | m/z = 867.31(C$_{65}$H$_{41}$NO$_2$ = 868.05) | P-14 | m/z = 833.30(C$_{60}$H$_{39}$N$_3$O$_2$ = 833.99) |
| P-15 | m/z = 666.23(C$_{48}$H$_{30}$N$_2$O$_2$ = 666.78) | P-16 | m/z = 782.26(C$_{56}$H$_{34}$N$_2$O$_3$ = 782.90) |
| P-17 | m/z = 830.29(C$_{61}$H$_{38}$N$_2$O$_2$ = 830.99) | P-18 | m/z = 795.31(C$_{59}$H$_{33}$D$_4$NO$_2$ = 795.97) |
| P-19 | m/z = 812.21(C$_{56}$H$_{32}$N$_2$O$_3$S = 812.94) | P-20 | m/z = 897.27(C$_{65}$H$_{39}$NO$_2$S = 898.09) |
| P-21 | m/z = 681.21(C$_{49}$H$_{31}$NOS = 681.85) | P-22 | m/z = 807.26(C$_{59}$H$_{37}$NOS = 808.01) |
| P-23 | m/z = 907.29(C$_{67}$H$_{41}$NOS = 908.13) | P-24 | m/z = 807.26(C$_{59}$H$_{37}$NOS = 808.01) |
| P-25 | m/z = 805.24(C$_{59}$H$_{35}$NOS = 806.00) | P-26 | m/z = 797.28(C$_{58}$H$_{39}$NOS = 798.02) |
| P-27 | m/z = 757.24(C$_{55}$H$_{35}$NOS = 757.95) | P-28 | m/z = 771.22(C$_{55}$H$_{33}$NO$_2$S = 771.93) |
| P-29 | m/z = 757.24(C$_{55}$H$_{35}$NOS = 757.95) | P-30 | m/z = 787.20(C$_{55}$H$_{33}$NOS$_2$ = 788.00) |
| P-31 | m/z = 857.28(C$_{63}$H$_{39}$NOS = 858.07) | P-32 | m/z = 833.28(C$_{61}$H$_{39}$NOS = 834.05) |
| P-33 | m/z = 883.29(C$_{65}$H$_{41}$NOS = 884.11) | P-34 | m/z = 781.24(C$_{57}$H$_{35}$NOS = 781.97) |
| P-35 | m/z = 682.21(C$_{48}$H$_{30}$N$_2$OS = 682.84) | P-36 | m/z = 681.21(C$_{49}$H$_{31}$NOS = 681.85) |
| P-37 | m/z = 807.26(C$_{59}$H$_{37}$NOS = 808.01) | P-38 | m/z = 907.29(C$_{67}$H$_{41}$NOS = 908.13) |
| P-39 | m/z = 807.26(C$_{59}$H$_{37}$NOS = 808.01) | P-40 | m/z = 807.26(C$_{59}$H$_{37}$NOS = 808.01) |
| P-41 | m/z = 681.21(C$_{49}$H$_{31}$NOS = 681.85) | P-42 | m/z = 681.21(C$_{49}$H$_{31}$NOS = 681.85) |
| P-43 | m/z = 681.21(C$_{49}$H$_{31}$NOS = 681.85) | P-44 | m/z = 681.21(C$_{49}$H$_{31}$NOS = 681.85) |
| P-45 | m/z = 873.31(C$_{64}$H$_{43}$NOS = 874.11) | P-46 | m/z = 857.28(C$_{63}$H$_{39}$NOS = 858.07) |
| P-47 | m/z = 833.28(C$_{61}$H$_{39}$NOS = 834.05) | P-48 | m/z = 883.29(C$_{65}$H$_{41}$NOS = 884.11) |
| P-49 | m/z = 781.24(C$_{57}$H$_{35}$NOS = 781.97) | P-50 | m/z = 682.21(C$_{48}$H$_{30}$N$_2$OS = 682.84) |
| P-51 | m/z = 798.23(C$_{56}$H$_{34}$N$_2$O$_2$S = 798.96) | P-52 | m/z = 846.27(C$_{61}$H$_{38}$N$_2$OS = 847.05) |
| P-53 | m/z = 811.28(C$_{59}$H$_{33}$D$_4$NOS = 812.04) | P-54 | m/z = 828.19(C$_{56}$H$_{32}$N$_2$O$_2$S$_2$ = 829.00) |
| P-55 | m/z = 863.23(C$_{61}$H$_{37}$NOS$_2$ = 864.09) | P-56 | m/z = 823.24(C$_{59}$H$_{37}$NS$_2$ = 824.07) |
| P-57 | m/z = 863.23(C$_{61}$H$_{37}$NOS$_2$ = 864.09) | P-58 | m/z = 929.22(C$_{65}$H$_{39}$NS$_3$ = 930.21) |
| P-59 | m/z = 938.28(C$_{67}$H$_{42}$N$_2$S$_2$ = 939.21) | P-60 | m/z = 797.22(C$_{57}$H$_{35}$NS$_2$ = 798.03) |
| P-61 | m/z = 813.25(C$_{58}$H$_{39}$NS$_2$ = 814.08) | P-62 | m/z = 773.22(C$_{55}$H$_{35}$NS$_2$ = 774.01) |
| P-63 | m/z = 747.21(C$_{53}$H$_{33}$NS$_2$ = 747.97) | P-64 | m/z = 823.24(C$_{59}$H$_{37}$NS$_2$ = 824.07) |
| P-65 | m/z = 853.19(C$_{59}$H$_{35}$NS$_3$ = 854.12) | P-66 | m/z = 923.27(C$_{67}$H$_{41}$NS$_2$ = 924.19) |
| P-67 | m/z = 949.28(C$_{69}$H$_{43}$NS$_2$ = 950.23) | P-68 | m/z = 781.24(C$_{57}$H$_{35}$NOS = 781.97) |
| P-69 | m/z = 847.24(C$_{61}$H$_{37}$NS$_2$ = 848.09) | P-70 | m/z = 698.19(C$_{48}$H$_{30}$N$_2$S$_2$ = 698.90) |
| P-71 | m/z = 874.27(C$_{62}$H$_{38}$N$_2$O$_2$S = 875.06) | P-72 | m/z = 872.29(C$_{63}$H$_{40}$N$_2$OS = 873.09) |
| P-73 | m/z = 833.28(C$_{61}$H$_{39}$NOS = 834.05) | P-74 | m/z = 970.21(C$_{66}$H$_{38}$N$_2$OS$_3$ = 971.22) |
| P-75 | m/z = 1055.33(C$_{76}$H$_{49}$NOS$_2$ = 1056.35) | P-76 | m/z = 741.27(C$_{55}$H$_{35}$NO$_2$ = 741.89) |
| P-77 | m/z = 883.29(C$_{65}$H$_{41}$NOS = 884.11) | P-78 | m/z = 931.31(C$_{69}$H$_{41}$NO$_3$ = 932.09) |

TABLE 3-continued

| Compound | FD-MS | compound | FD-MS |
|---|---|---|---|
| P-79 | m/z = 868.31($C_{64}H_{40}N_2O_2$ = 869.04) | P-80 | m/z = 841.30($C_{63}H_{39}NO_2$ = 842.01) |
| P-81 | m/z = 922.32($C_{67}H_{42}N_2O_3$ = 923.08) | P-82 | m/z = 1124.40($C_{83}H_{52}N_2O_3$ = 1125.34) |
| P-83 | m/z = 1164.43($C_{86}H_{56}N_2O_3$ = 1165.41) | P-84 | m/z = 1124.40($C_{83}H_{52}N_2O_3$ = 1125.34) |
| P-85 | m/z = 1014.33($C_{73}H_{46}N_2O_2S$ = 1015.24) | P-86 | m/z = 1154.35($C_{83}H_{50}N_2O_3S$ = 1155.38) |
| P-87 | m/z = 1115.41($C_{81}H_{53}N_3O_3$ = 1116.33) | P-88 | m/z = 1140.43($C_{84}H_{56}N_2O_3$ = 1141.38) |
| P-89 | m/z = 1104.34($C_{79}H_{48}N_2O_3S$ = 1105.32) | P-90 | m/z = 1074.38($C_{79}H_{50}N_2O_3$ = 1075.28) |
| P-91 | m/z = 1038.38($C_{76}H_{50}N_2O_3$ = 1039.25) | P-92 | m/z = 1235.38($C_{87}H_{53}N_3O_4S$ = 1236.46) |
| P-93 | m/z = 1154.35($C_{83}H_{50}N_2O_3S$ = 1155.38) | P-94 | m/z = 1196.40($C_{86}H_{56}N_2O_3S$ = 1197.47) |
| P-95 | m/z = 1296.43($C_{94}H_{60}N_2O_3S$ = 1297.59) | P-96 | m/z = 1232.38($C_{89}H_{56}N_2OS_2$ = 1233.56) |
| P-97 | m/z = 1196.35($C_{85}H_{52}N_2O_2S_2$ = 1197.48) | P-98 | m/z = 1154.35($C_{83}H_{50}N_2O_3S$ = 1155.38) |
| P-99 | m/z = 1443.45($C_{102}H_{65}N_3O_3S_2$ = 1444.78) | P-100 | m/z = 1190.44($C_{88}H_{58}N_2O_3$ = 1191.44) |
| P-101 | m/z = 938.30($C_{67}H_{42}N_2O_2S$ = 939.15) | P-102 | m/z = 1140.37($C_{83}H_{52}N_2O_2S$ = 1141.40) |
| P-103 | m/z = 1180.41($C_{86}H_{56}N_2O_2S$ = 1181.47) | P-104 | m/z = 1216.41($C_{89}H_{56}N_2O_2S$ = 1217.50) |
| P-105 | m/z = 1030.31($C_{73}H_{46}N_2O_2S$ = 1031.30) | P-106 | m/z = 1170.33($C_{83}H_{50}N_2O_2S_2$ = 1171.45) |
| P-107 | m/z = 1131.39($C_{81}H_{53}N_3O_2S$ = 1132.39) | P-108 | m/z = 1188.36($C_{84}H_{56}N_2S_3$ = 1189.57) |
| P-109 | m/z = 1120.32($C_{79}H_{48}N_2O_2S_2$ = 1121.39) | P-110 | m/z = 1090.36($C_{79}H_{50}N_2O_2S$ = 1091.34) |
| P-111 | m/z = 1070.34($C_{76}H_{50}N_2OS_2$ = 1071.37) | P-112 | m/z = 1251.35($C_{87}H_{53}N_3O_3S_2$ = 1252.52) |
| P-113 | m/z = 1170.33($C_{83}H_{50}N_2O_2S_2$ = 1171.45) | P-114 | m/z = 1246.42($C_{90}H_{58}N_2O_3S$ = 1247.53) |
| P-115 | m/z = 1346.45($C_{98}H_{62}N_2O_3S$ = 1347.65) | P-116 | m/z = 1216.41($C_{89}H_{56}N_2O_2S$ = 1217.50) |
| P-117 | m/z = 1271.39($C_{91}H_{57}N_3OS_2$ = 1272.60) | P-118 | m/z = 1170.33($C_{83}H_{50}N_2O_2S_2$ = 1171.45) |
| P-119 | m/z = 1459.42($C_{102}H_{65}N_3O_2S_3$ = 1460.84) | P-120 | m/z = 1206.42($C_{88}H_{58}N_2O_3S$ = 1207.50) |
| P-121 | m/z = 1347.44($C_{97}H_{61}N_3O_3S$ = 1348.63) | P-122 | m/z = 1579.48($C_{113}H_{69}N_3O_3S_2$ = 1580.93) |
| P-123 | m/z = 1705.58($C_{124}H_{79}N_3O_4S$ = 1707.07) | P-124 | m/z = 1489.47($C_{107}H_{67}N_3O_2S_2$ = 1490.85) |
| P-125 | m/z = 1453.43($C_{103}H_{63}N_3O_3S_2$ = 1454.78) | P-126 | m/z = 1619.51($C_{116}H_{73}N_3O_3S_2$ = 1621.00) |
| P-127 | m/z = 1456.42($C_{102}H_{64}N_4OS_3$ = 1457.84) | P-128 | m/z = 1565.50($C_{113}H_{71}N_3O_2S_2$ = 1566.95) |
| P-129 | m/z = 1528.48($C_{109}H_{68}N_4O_2S_2$ = 1529.89) | P-130 | m/z = 1519.42($C_{107}H_{65}N_3O_2S_3$ = 1520.90) |
| P-131 | m/z = 1826.61($C_{131}H_{86}N_4O_3S_2$ = 1828.27) | P-132 | m/z = 1555.51($C_{112}H_{73}N_3O_2S_2$ = 1556.96) |
| P-133 | m/z = 1439.45($C_{103}H_{65}N_3O_2S_2$ = 1440.79) | P-134 | m/z = 1595.46($C_{113}H_{69}N_3O_2S_3$ = 1596.99) |
| P-135 | m/z = 1721.56($C_{124}H_{79}N_3O_2S_2$ = 1723.13) | P-136 | m/z = 1571.44($C_{111}H_{69}N_3S_4$ = 1573.03) |
| P-137 | m/z = 1898.71($C_{133}H_{102}N_4O_3S_3$ = 1900.48) | P-138 | m/z = 1812.54($C_{129}H_{80}N_4O_2S_3$ = 1814.27) |
| P-139 | m/z = 1914.69($C_{133}H_{102}N_4O_2S_4$ = 1916.55) | | |
| P1-1 | m/z = 705.27($C_{52}H_{35}NO_2$ = 705.86) | P1-2 | m/z = 705.27($C_{52}H_{35}NO_2$ = 705.86) |
| P1-3 | m/z = 705.27($C_{52}H_{35}NO_2$ = 705.86) | P1-4 | m/z = 705.27($C_{52}H_{35}NO_2$ = 705.86) |
| P1-5 | m/z = 721.24($C_{52}H_{35}NOS$ = 721.92) | P1-6 | m/z = 829.30($C_{62}H_{39}NO_2$ = 830.00) |
| P1-7 | m/z = 829.30($C_{62}H_{39}NO_2$ = 830.00) | P1-8 | m/z = 829.30($C_{62}H_{39}NO_2$ = 830.00) |
| P1-9 | m/z = 829.30($C_{62}H_{39}NO_2$ = 830.00) | P1-10 | m/z = 845.28($C_{62}H_{39}NOS$ = 846.06) |
| P1-11 | m/z = 827.28($C_{62}H_{37}NO_2$ = 827.98) | P1-12 | m/z = 843.26($C_{62}H_{37}NOS$ = 844.04) |
| P1-13 | m/z = 781.30($C_{58}H_{39}NO_2$ = 781.96) | P1-14 | m/z = 797.28($C_{58}H_{39}NOS$ = 798.02) |
| P1-15 | m/z = 781.30($C_{58}H_{39}NO_2$ = 781.96) | P1-16 | m/z = 797.28($C_{58}H_{39}NOS$ = 798.02) |
| P1-17 | m/z = 781.30($C_{58}H_{39}NO_2$ = 781.96) | P1-18 | m/z = 797.28($C_{58}H_{39}NOS$ = 798.02) |
| P1-19 | m/z = 781.30($C_{58}H_{39}NO_2$ = 781.96) | P1-20 | m/z = 781.30($C_{58}H_{39}NO_2$ = 781.96) |
| P1-21 | m/z = 781.30($C_{58}H_{39}NO_2$ = 781.96) | P1-22 | m/z = 781.30($C_{58}H_{39}NO_2$ = 781.96) |
| P1-23 | m/z = 797.28($C_{58}H_{39}NOS$ = 798.02) | P1-24 | m/z = 797.28($C_{58}H_{39}NOS$ = 798.02) |
| P1-25 | m/z = 797.28($C_{58}H_{39}NOS$ = 798.02) | P1-26 | m/z = 831.31($C_{62}H_{41}NO_2$ = 832.02) |
| P1-27 | m/z = 847.29($C_{62}H_{41}NOS$ = 848.08) | P1-28 | m/z = 831.31($C_{62}H_{41}NO_2$ = 832.02) |
| P1-29 | m/z = 847.29($C_{62}H_{41}NOS$ = 848.08) | P1-30 | m/z = 831.31($C_{62}H_{41}NO_2$ = 832.02) |
| P1-31 | m/z = 847.29($C_{62}H_{41}NOS$ = 848.08) | P1-32 | m/z = 782.29($C_{57}H_{38}N_2O_2$ = 782.94) |
| P1-33 | m/z = 913.34($C_{67}H_{47}NOS$ = 914.18) | P1-34 | m/z = 855.31($C_{64}H_{41}NO_2$ = 856.04) |
| P1-35 | m/z = 849.30($C_{62}H_{35}D_4NOS$ = 850.08) | P1-36 | m/z = 857.33($C_{64}H_{43}NO_2$ = 858.05) |
| P1-37 | m/z = 873.31($C_{64}H_{43}NOS$ = 874.11) | P1-38 | m/z = 857.33($C_{64}H_{43}NO_2$ = 858.05) |
| P1-39 | m/z = 873.31($C_{64}H_{43}NOS$ = 874.11) | P1-40 | m/z = 873.31($C_{64}H_{43}NOS$ = 874.11) |
| P1-41 | m/z = 857.33($C_{64}H_{43}NO_2$ = 858.05) | P1-42 | m/z = 857.33($C_{64}H_{43}NO_2$ = 858.05) |
| P1-43 | m/z = 857.33($C_{64}H_{43}NO_2$ = 858.05) | P1-44 | m/z = 873.31($C_{64}H_{43}NOS$ = 874.11) |
| P1-45 | m/z = 873.31($C_{64}H_{43}NOS$ = 874.11) | P1-46 | m/z = 797.28($C_{58}H_{39}NOS$ = 798.02) |
| P1-47 | m/z = 721.24($C_{52}H_{35}NOS$ = 721.92) | P1-48 | m/z = 721.24($C_{52}H_{35}NOS$ = 721.92) |
| P1-49 | m/z = 721.24($C_{52}H_{35}NOS$ = 721.92) | P1-50 | m/z = 737.22($C_{52}H_{35}NS_2$ = 737.98) |
| P1-51 | m/z = 845.28($C_{62}H_{39}NOS$ = 846.06) | P1-52 | m/z = 861.25($C_{62}H_{39}NS_2$ = 862.12) |
| P1-53 | m/z = 861.25($C_{62}H_{39}NS_2$ = 862.12) | P1-54 | m/z = 861.25($C_{62}H_{39}NS_2$ = 862.12) |
| P1-55 | m/z = 861.25($C_{62}H_{39}NS_2$ = 862.12) | P1-56 | m/z = 921.28($C_{66}H_{39}N_3OS$ = 922.12) |
| P1-57 | m/z = 859.24($C_{62}H_{37}NS_2$ = 860.11) | P1-58 | m/z = 797.28($C_{58}H_{39}NOS$ = 798.02) |
| P1-59 | m/z = 813.25($C_{58}H_{39}NS_2$ = 814.08) | P1-60 | m/z = 797.28($C_{58}H_{39}NOS$ = 798.02) |
| P1-61 | m/z = 813.25($C_{58}H_{39}NS_2$ = 814.08) | P1-62 | m/z = 797.28($C_{58}H_{39}NOS$ = 798.02) |
| P1-63 | m/z = 813.25($C_{58}H_{39}NS_2$ = 814.08) | P1-64 | m/z = 797.28($C_{58}H_{39}NOS$ = 798.02) |
| P1-65 | m/z = 813.25($C_{58}H_{39}NS_2$ = 814.08) | P1-66 | m/z = 847.29($C_{62}H_{41}NOS$ = 848.08) |
| P1-67 | m/z = 863.27($C_{62}H_{41}NS_2$ = 864.14) | P1-68 | m/z = 847.29($C_{62}H_{41}NOS$ = 848.08) |
| P1-69 | m/z = 863.27($C_{62}H_{41}NS_2$ = 864.14) | P1-70 | m/z = 847.29($C_{62}H_{41}NOS$ = 848.08) |
| P1-71 | m/z = 863.27($C_{62}H_{41}NS_2$ = 864.14) | P1-72 | m/z = 798.27($C_{57}H_{38}N_2OS$ = 799.00) |
| P1-73 | m/z = 797.28($C_{58}H_{39}NOS$ = 798.02) | P1-74 | m/z = 787.24($C_{56}H_{37}NS_2$ = 788.04) |
| P1-75 | m/z = 787.24($C_{56}H_{37}NS_2$ = 788.04) | P1-76 | m/z = 771.26($C_{56}H_{37}NOS$ = 771.98) |
| P1-77 | m/z = 771.26($C_{56}H_{37}NOS$ = 771.98) | P1-78 | m/z = 813.25($C_{58}H_{39}NS_2$ = 814.08) |

TABLE 3-continued

| Compound | FD-MS | compound | FD-MS |
|---|---|---|---|
| P1-79 | m/z = 907.35($C_{68}H_{45}NO_2$ = 908.11) | P1-80 | m/z = 903.31($C_{68}H_{41}NO_2$ = 904.08) |
| P1-81 | m/z = 827.28($C_{62}H_{37}NO_2$ = 827.98) | P1-82 | m/z = 843.26($C_{62}H_{37}NOS$ = 844.04) |
| P1-83 | m/z = 843.26($C_{62}H_{37}NOS$ = 844.04) | P1-84 | m/z = 787.24($C_{56}H_{37}NS_2$ = 788.04) |
| P1-85 | m/z = 879.31($C_{66}H_{41}NO_2$ = 880.06) | P1-86 | m/z = 781.30($C_{58}H_{39}NO_2$ = 781.96) |
| P2-1 | m/z = 843.28($C_{62}H_{37}NO_3$ = 843.98) | P2-2 | m/z = 843.28($C_{62}H_{37}NO_3$ = 843.98) |
| P2-3 | m/z = 843.28($C_{62}H_{37}NO_3$ = 843.98) | P2-4 | m/z = 843.28($C_{62}H_{37}NO_3$ = 843.98) |
| P2-5 | m/z = 909.27($C_{66}H_{39}NO_2S$ = 910.10) | P2-6 | m/z = 861.27($C_{62}H_{36}FNO_3$ = 861.97) |
| P2-7 | m/z = 893.29($C_{66}H_{39}NO_3$ = 894.04) | P2-8 | m/z = 995.34($C_{74}H_{45}NO_3$ = 996.18) |
| P2-9 | m/z = 859.25($C_{62}H_{37}NO_2S$ = 860.04) | P2-10 | m/z = 859.25($C_{62}H_{37}NO_2S$ = 860.04) |
| P2-11 | m/z = 859.25($C_{62}H_{37}NO_2S$ = 860.04) | P2-12 | m/z = 859.25($C_{62}H_{37}NO_2S$ = 860.04) |
| P2-13 | m/z = 859.25($C_{62}H_{37}NO_2S$ = 860.04) | P2-14 | m/z = 859.25($C_{62}H_{37}NO_2S$ = 860.04) |
| P2-15 | m/z = 859.25($C_{62}H_{37}NO_2S$ = 860.04) | P2-16 | m/z = 859.25($C_{62}H_{37}NO_2S$ = 860.04) |
| P2-17 | m/z = 875.23($C_{62}H_{37}NOS_2$ = 876.10) | P2-18 | m/z = 875.23($C_{62}H_{37}NOS_2$ = 876.1) |
| P2-19 | m/z = 891.21($C_{62}H_{37}NS_3$ = 892.17) | P2-20 | m/z = 919.31($C_{68}H_{41}NO_3$ = 920.08) |
| P2-21 | m/z = 935.29($C_{68}H_{41}NO_2S$ = 936.14) | P2-22 | m/z = 951.26($C_{68}H_{41}NOS_2$ = 952.20) |
| P2-23 | m/z = 967.24($C_{68}H_{41}NS_3$ = 968.26) | P2-24 | m/z = 985.30($C_{72}H_{43}NO_2S$ = 986.20) |
| P2-25 | m/z = 1001.28($C_{72}H_{43}NOS_2$ = 1002.26) | P2-26 | m/z = 952.26($C_{67}H_{40}N_2OS_2$ = 953.19) |
| P2-27 | m/z = 952.26($C_{67}H_{40}N_2OS_2$ = 953.19) | P2-28 | m/z = 919.31($C_{68}H_{41}NO_3$ = 920.08) |
| P2-29 | m/z = 935.29($C_{68}H_{41}NO_2S$ = 936.14) | P2-30 | m/z = 919.31($C_{68}H_{41}NO_3$ = 920.08) |
| P2-31 | m/z = 935.29($C_{68}H_{41}NO_2S$ = 936.14) | P2-32 | m/z = 935.29($C_{68}H_{41}NO_2S$ = 936.14) |
| P2-33 | m/z = 967.24($C_{68}H_{41}NS_3$ = 968.26) | P2-34 | m/z = 900.23($C_{63}H_{36}N_2OS_2$ = 901.11) |
| P2-35 | m/z = 901.25($C_{64}H_{39}NOS_2$ = 902.14) | P2-36 | m/z = 893.29($C_{66}H_{39}NO_3$ = 894.04) |
| P2-37 | m/z = 941.22($C_{66}H_{39}NS_3$ = 942.23) | P2-38 | m/z = 909.27($C_{66}H_{39}NO_2S$ = 910.10) |
| P2-39 | m/z = 919.31($C_{68}H_{41}NO_3$ = 920.08) | P2-40 | m/z = 941.22($C_{66}H_{39}NS_3$ = 942.23) |
| P2-41 | m/z = 909.27($C_{66}H_{39}NO_2S$ = 910.1) | P2-42 | m/z = 893.29($C_{66}H_{39}NO_3$ = 894.04) |
| P2-43 | m/z = 941.22($C_{66}H_{39}NS_3$ = 942.23) | P2-44 | m/z = 909.27($C_{66}H_{39}NO_2S$ = 910.10) |
| P2-45 | m/z = 893.29($C_{66}H_{39}NO_3$ = 894.04) | P2-46 | m/z = 951.26($C_{68}H_{41}NOS_2$ = 952.2) |
| P2-47 | m/z = 1017.26($C_{72}H_{43}NS_3$ = 1018.32) | P2-48 | m/z = 995.34($C_{74}H_{45}NO_3$ = 996.18) |
| P2-49 | m/z = 895.23($C_{62}H_{33}D_4NS_3$ = 896.19) | P2-50 | m/z = 995.34($C_{74}H_{45}NO_3$ = 996.18) |
| P2-51 | m/z = 995.34($C_{74}H_{45}NO_3$ = 996.18) | P2-52 | m/z = 1093.29($C_{78}H_{47}NS_3$ = 1094.42) |
| P2-53 | m/z = 975.26($C_{70}H_{41}NOS_2$ = 976.22) | P2-54 | m/z = 991.24($C_{70}H_{41}NS_3$ = 992.29) |
| P2-55 | m/z = 943.31($C_{70}H_{41}NO_3$ = 944.10) | | |
| P3-1 | m/z = 753.27($C_{56}H_{35}NO_2$ = 753.9) | P3-2 | m/z = 845.28($C_{62}H_{39}NOS$ = 846.06) |
| P3-3 | m/z = 829.3($C_{62}H_{39}NO_2$ = 830) | P3-4 | m/z = 803.28($C_{60}H_{37}NO_2$ = 803.96) |
| P3-5 | m/z = 911.27($C_{66}H_{41}NS_2$ = 912.18) | P3-6 | m/z = 985.39($C_{74}H_{51}NO_2$ = 986.23) |
| P3-7 | m/z = 995.32($C_{74}H_{45}NOS$ = 996.24) | P3-8 | m/z = 956.34($C_{71}H_{44}N_2O_2$ = 957.15) |
| P3-9 | m/z = 945.31 ($C_{70}H_{43}NOS$ = 946.18) | P3-10 | m/z = 971.32($C_{72}H_{45}NOS$ = 972.22) |
| P3-11 | m/z = 921.31($C_{68}H_{43}NOS$ = 922.16) | P3-12 | m/z = 905.33($C_{68}H_{43}NO_2$ = 906.1) |
| P3-13 | m/z = 955.35($C_{72}H_{45}NO_2$ = 956.16) | P3-14 | m/z = 1146.42($C_{86}H_{54}N_2O_2$ = 1147.39) |
| P3-15 | m/z = 940.32($C_{68}H_{36}D_5NO_2S$ = 941.17) | P3-16 | m/z = 935.29($C_{68}H_{41}NO_2S$ = 936.14) |
| P3-17 | m/z = 919.31($C_{68}H_{41}NO_3$ = 920.08) | P3-18 | m/z = 919.31($C_{68}H_{41}NO_3$ = 920.08) |
| P3-19 | m/z = 1017.26($C_{72}H_{43}NS_3$ = 1018.32) | P3-20 | m/z = 951.26($C_{68}H_{41}NOS_2$ = 952.2) |
| P3-21 | m/z = 967.24($C_{68}H_{41}NS_3$ = 968.26) | P3-22 | m/z = 951.26($C_{68}H_{41}NOS_2$ = 952.2) |
| P3-23 | m/z = 951.26($C_{68}H_{41}NOS_2$ = 952.2) | P3-24 | m/z = 951.26($C_{68}H_{41}NOS_2$ = 952.2) |
| P3-25 | m/z = 953.28($C_{68}H_{40}FNOS$ = 954.13) | P3-26 | m/z = 861.25($C_{62}H_{39}NS_2$ = 862.12) |
| P3-27 | m/z = 971.32($C_{72}H_{45}NOS$ = 972.22) | P3-28 | m/z = 942.32($C_{68}H_{38}D_5NS_2$ = 943.25) |
| P3-29 | m/z = 11 09.37($C_{80}H_{55}NOS_2$ = 1110.45) | P3-30 | m/z = 969.25($C_{68}H_{40}FNOS_2$ = 970.19) |
| P3-31 | m/z = 967.24($C_{68}H_{41}NS_3$ = 968.26) | P3-32 | m/z = 967.24($C_{72}H_{43}NO_3$ = 970.14) |
| P3-33 | m/z = 1103.33($C_{80}H_{49}NOS_2$ = 1104.4) | P3-34 | m/z = 1001.28($C_{72}H_{43}NOS_2$ = 1002.26) |
| P3-35 | m/z = 835.24($C_{60}H_{37}NS_2$ = 836.08) | P3-36 | m/z = 1047.35($C_{78}H_{49}NOS$ = 1048.32) |
| P3-37 | m/z = 1027.31($C_{74}H_{45}NO_3S$ = 1028.24) | P3-38 | m/z = 991.35($C_{72}H_{49}NO_2S$ = 992.25) |
| P3-39 | m/z = 919.31($C_{68}H_{41}NO_3$ = 920.08) | P3-40 | m/z = 1051.29($C_{76}H_{45}NOS_2$ = 1052.32) |

Evaluation of Manufacture of Organic Electronic element

[Example 1] Red Organic Light Emitting Diode (Emitting Auxiliary Layer)

An organic light emitting diode was manufactured according to a conventional method using the compound of the present invention as an emitting auxiliary layer material. First, a hole injection layer was formed by vacuum depositing 4,4',4"-Tris[2-naphthyl(phenyl)amino]triphenylamine (hereinafter, 2-TNATA) to a thickness of 60 nm on an ITO layer (anode) formed on a glass substrate, and a hole transport layer was formed by vacuum deposition of N,N'-bis(1-naphthalenyl)-N,N'-bis-phenyl-(1,1'-biphenyl)-4,4'-diamine (hereinafter, NPB) to a thickness of 60 nm on the hole injection layer. Subsequently, compound PA-1 was vacuum-deposited to a thickness of 20 nm on the hole transport layer to form an emission auxiliary layer, 4,4'-N,N'-dicarbazole-biphenyl (hereinafter, CBP) was used as a host material and bis-(1-phenylisoquinolyl)iridium(III) acetylacetonate (hereinafter, (piq)2Ir(acac)) was used as a dopant material on the emitting auxiliary layer, doped at a weight ratio of 95:5, and vacuum deposited to a thickness of 30 nm to form an emitting layer.

Subsequently, (1,1'-biphenyl-4-olato)bis(2-methyl-8-quinolinolato)aluminum (hereinafter, BAIq) was vacuum deposited to a thickness of 10 nm on the emitting layer to form a hole blocking layer, an electron transport layer was formed by vacuum depositing tris-(8-hydroxyquinoline)aluminum (hereinafter, Alq3) to a thickness of 40 nm on the hole blocking layer. Thereafter, an electron injection layer was formed by depositing LiF, an alkali metal halide, to a thickness of 0.2 nm, then, Al was deposited to a thickness of 150 nm to form a cathode, thereby manufacturing an organic light emitting diode.

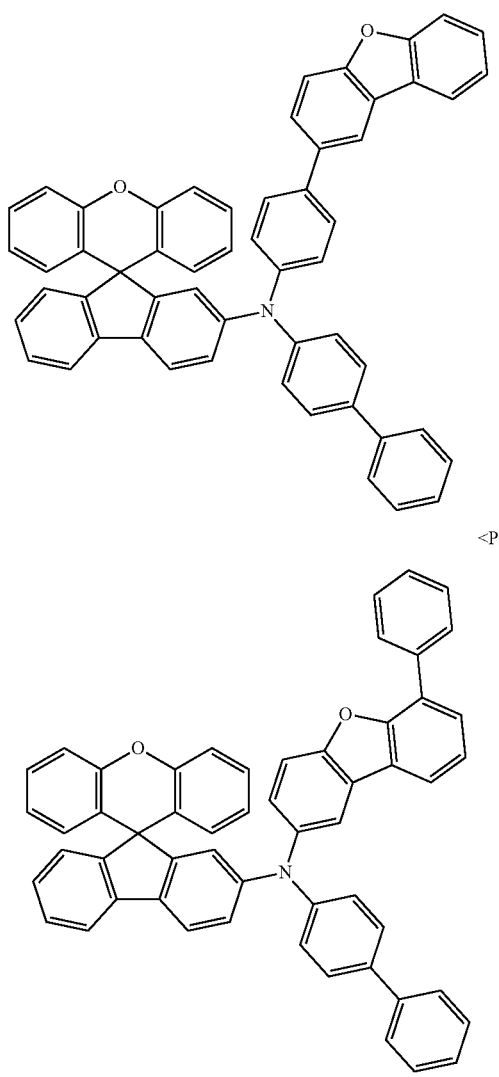

<PA-1>

<PA-2>

[Example 2] to [Example 21] Red Organic Light Emitting Diode (Emitting Auxiliary Layer)

An organic light emitting diode was manufactured in the same manner as in Example 1, except that the compound PA-2 and the compound of the present invention described in Table 4 below were used instead of the compound PA-1 as the emitting auxiliary layer material.

Comparative Example 1

An organic light emitting diode was manufactured in the same manner as in Example 1, except that the comparative example 1 below were used instead of the compound PA-1 as the emitting auxiliary layer material.

Comparative Example 1

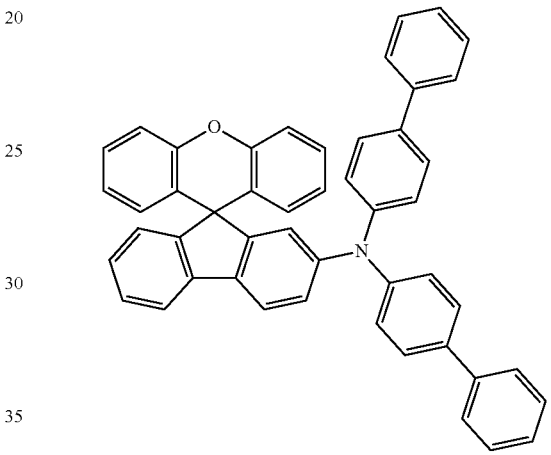

Electroluminescence (EL) characteristics were measured by PR-650 of photoresearch company by applying a forward bias direct current voltage to the organic light emitting diodes prepared according to Examples 1 to 21 and Comparative Example 1 of the present invention, T95 life was measured through a life measurement equipment manufactured by McScience at a luminance of 2500 cd/m², and the measurement results are shown in Table 4 below.

TABLE 4

| | compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| comparative example(1) | Comparative compound 1 | 6.3 | 26.6 | 2500.0 | 9.4 | 75.6 | 0.64 | 0.31 |
| example(1) | PA-1 | 6.0 | 21.9 | 2500.0 | 11.4 | 98.3 | 0.63 | 0.35 |
| example(2) | PA-2 | 5.6 | 18.1 | 2500.0 | 13.8 | 110.5 | 0.61 | 0.31 |
| example(3) | P-1 | 4.8 | 11.1 | 2500.0 | 22.6 | 116.4 | 0.64 | 0.30 |
| example(4) | P-4 | 4.9 | 10.3 | 2500.0 | 24.3 | 112.7 | 0.63 | 0.31 |
| example(5) | P-12 | 4.8 | 9.7 | 2500.0 | 25.7 | 118.3 | 0.62 | 0.30 |
| example(6) | P-14 | 4.9 | 9.7 | 2500.0 | 25.9 | 117.2 | 0.61 | 0.31 |
| example(7) | P-22 | 4.8 | 9.7 | 2500.0 | 25.7 | 119.0 | 0.64 | 0.30 |
| example(8) | P-30 | 5.0 | 10.7 | 2500.0 | 23.5 | 113.4 | 0.65 | 0.35 |

TABLE 4-continued

|  | compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| example(9) | P-37 | 4.9 | 10.8 | 2500.0 | 23.2 | 116.9 | 0.62 | 0.33 |
| example(10) | P-57 | 5.2 | 10.9 | 2500.0 | 22.9 | 112.0 | 0.64 | 0.32 |
| example(11) | P-59 | 5.2 | 9.7 | 2500.0 | 25.9 | 115.4 | 0.61 | 0.30 |
| example(12) | P-68 | 5.2 | 10.6 | 2500.0 | 23.6 | 114.7 | 0.64 | 0.30 |
| example(13) | P-77 | 5.1 | 10.3 | 2500.0 | 24.4 | 119.5 | 0.61 | 0.30 |
| example(14) | P-81 | 5.0 | 11.6 | 2500.0 | 21.6 | 122.8 | 0.62 | 0.30 |
| example(15) | P-82 | 5.2 | 11.9 | 2500.0 | 21.1 | 120.7 | 0.63 | 0.30 |
| example(16) | P-94 | 5.1 | 11.5 | 2500.0 | 21.8 | 120.9 | 0.65 | 0.32 |
| example(17) | P-109 | 5.0 | 11.6 | 2500.0 | 21.5 | 120.8 | 0.63 | 0.35 |
| example(18) | P-115 | 5.2 | 11.1 | 2500.0 | 22.6 | 123.9 | 0.62 | 0.31 |
| example(19) | P-124 | 5.3 | 12.0 | 2500.0 | 20.8 | 124.1 | 0.60 | 0.34 |
| example(20) | P-136 | 5.3 | 12.3 | 2500.0 | 20.3 | 126.7 | 0.63 | 0.34 |
| example(21) | P-138 | 5.3 | 12.4 | 2500.0 | 20.2 | 127.3 | 0.64 | 0.35 |

As can be seen from the results in Table 4, when a red organic light emitting diode is manufactured using the material for an organic light emitting diode of the present invention as a phosphorescent host material, compared to the case of using the compound PA-1, the compound PA-2, and the comparative compound 1, the driving voltage of the organic light emitting diode could be lowered and the efficiency and lifespan were significantly improved.

In detail, the comparative compound and the compound of the present invention are the same in that they contain a xanthene core and an amine substituent, the device result of compound PA-1 substituted with dibenzofuran was improved compared to Comparative Compound 1 in which a simple aryl group was substituted with the substituent of the amine group, and the device result of compound PA-2 with more secondary substituents bonded was more improved. Also, the compound PA-2 and the compound of the present invention differ in the bonding position of the secondary substituent of the amine substituent, dibenzofuran or dibenzothiophene. In other words, it was confirmed that the compound of the present invention, in which an amine group and a secondary substituent group are bonded to the same ring in dibenzofuran or dibenzothiophene, exhibits more improved device performance than compound PA-2.

This result shows that the difference in hole mobility is large depending on the bonding position of the substituent, and this difference in mobility affects the overall device.

By using the compound of the present invention as an emitting auxiliary layer, the HOMO or LUMO energy level of the compound of the present invention has an appropriate value between the hole transport layer and the emitting layer, as a result, holes and electrons achieve a charge balance, and light emission occurs inside the emitting layer rather than at the interface of the hole transport layer, maximizing efficiency and lifespan.

Meanwhile, comparing the results of the embodiments of the present invention, it can be seen that there are differences in driving voltage and luminous efficiency according to the bonding position and type of the secondary substituent, and different lifespan results are produced depending on the number of substitutions of amino groups in the central core.

In conclusion, the physical properties of the compound such as hole characteristics, light efficiency characteristics, energy level (LUMO, HOMO level, T1 level), hole injection & mobility characteristics, and electron blocking characteristics vary depending on the substituent, resulting in completely different device results.

[Example 22] Green Organic Light Emitting Diode (Emitting Auxiliary Layer)

2-TNATA was vacuum-deposited to a thickness of 60 nm on the ITO layer (anode) formed on the glass substrate to form a hole injection layer, and then NPB was vacuum-deposited to a thickness of 60 nm on the hole injection layer to form a hole transport layer. Subsequently, the following compound PA-3 was vacuum-deposited to a thickness of 20 nm on the hole transport layer to form an emitting auxiliary layer, and on the emitting auxiliary layer, CBP was used as a host material and tris(2-phenylpyridine)-iridium (hereinafter, Ir(ppy)₃) was used as a dopant material, doped at a weight ratio of 95:5, and vacuum deposited to a thickness of 30 nm to form an emitting layer. Then, BAlq was vacuum-deposited to a thickness of 10 nm on the emitting layer to form a hole blocking layer, Alq3 was vacuum deposited on the hole blocking layer to a thickness of 40 nm on the hole blocking layer to form an electron transport layer. Thereafter, an electron injection layer was formed by depositing LiF, an alkali metal halide, to a thickness of 0.2 nm, and subsequently, Al was deposited to a thickness of 150 nm to form a cathode, thereby manufacturing an organic light emitting diode.

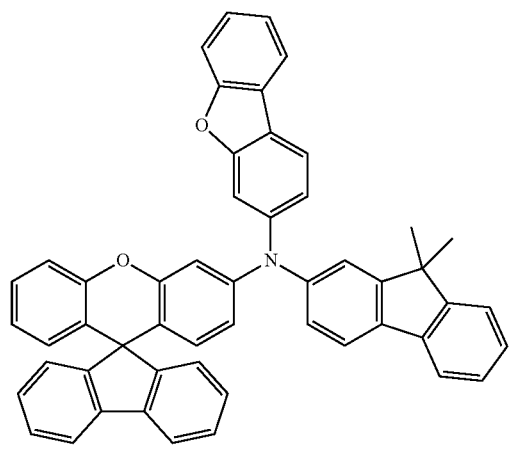

<PA-3>

[Example 23] to [Example 35] Green Organic Light Emitting Diode (Emitting Auxiliary Layer)

An organic light emitting diode was manufactured in the same manner as in Example 22, except that the compound of the present invention described in Table 5 below was used instead of the compound PA-3 as the emitting auxiliary layer material.

[Comparative Example 2] and [Comparative Example 3]

An organic light emitting diode was manufactured in the same manner as in Example 22, except that Comparative Compound 2 and Comparative Compound 3 were used, respectively, instead of the compound PA-3 as the emitting auxiliary layer material. [Comparative example 2] [Comparative example 3]

[Comparative example 2]

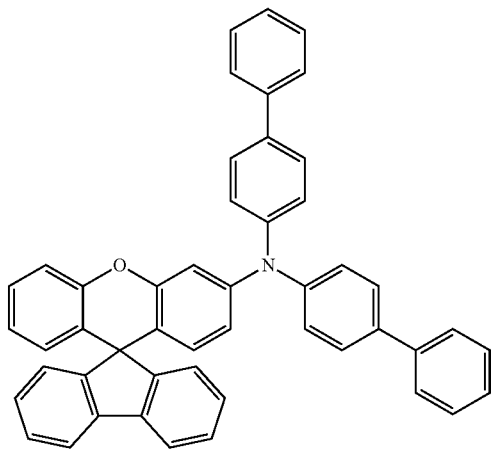

[Comparative example 3]

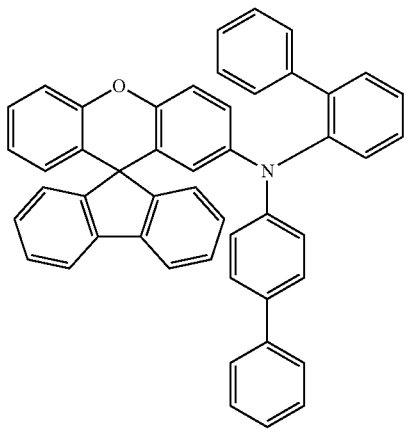

Electroluminescence (EL) characteristics were measured by PR-650 of photoresearch company by applying a forward bias direct current voltage to the organic light emitting diode prepared according to Examples 22 to 35 and Comparative Example 2 to 3 of the present invention, T95 life was measured through a life measurement equipment manufactured by McScience at a luminance of 5000 cd/m², and the measurement results are shown in Table 5 below.

TABLE 5

| | compound | Voltage (V) | Current Density (mA/cm²) | Brightness (cd/m²) | Efficiency (cd/A) | Lifetime T(95) | CIE x | y |
|---|---|---|---|---|---|---|---|---|
| comparative example (2) | comparative compound 2 | 6.3 | 36.2 | 5000.0 | 13.8 | 75.6 | 0.30 | 0.61 |
| comparative example (3) | comparative compound 3 | 6.1 | 25.6 | 5000.0 | 19.5 | 75.9 | 0.30 | 0.60 |
| example(22) | PA-3 | 5.6 | 24.5 | 5000.0 | 20.4 | 103.3 | 0.32 | 0.65 |
| example(23) | P1-2 | 5.0 | 10.1 | 5000.0 | 49.7 | 139.6 | 0.32 | 0.62 |
| example(24) | P1-5 | 5.2 | 12.7 | 5000.0 | 39.4 | 129.3 | 0.32 | 0.61 |
| example(25) | P1-6 | 5.1 | 11.7 | 5000.0 | 42.9 | 135.6 | 0.33 | 0.60 |
| example(26) | P1-12 | 5.2 | 12.6 | 5000.0 | 39.6 | 130.5 | 0.31 | 0.64 |
| example(27) | P1-20 | 5.2 | 12.4 | 5000.0 | 40.2 | 129.5 | 0.33 | 0.61 |
| example(28) | P1-44 | 5.1 | 11.4 | 5000.0 | 43.9 | 137.0 | 0.31 | 0.60 |
| example(29) | P1-50 | 5.1 | 12.6 | 5000.0 | 39.5 | 129.7 | 0.30 | 0.62 |
| example(30) | P1-55 | 5.1 | 10.6 | 5000.0 | 47.2 | 137.3 | 0.31 | 0.64 |
| example(31) | P1-73 | 5.0 | 12.1 | 5000.0 | 41.2 | 136.2 | 0.33 | 0.61 |
| example(32) | P1-77 | 5.3 | 11.3 | 5000.0 | 44.3 | 129.7 | 0.35 | 0.61 |
| example(33) | P1-78 | 5.0 | 11.9 | 5000.0 | 42.2 | 132.6 | 0.32 | 0.61 |
| example(34) | P1-84 | 5.3 | 13.8 | 5000.0 | 36.2 | 127.3 | 0.33 | 0.62 |
| example(35) | P1-85 | 5.3 | 14.1 | 5000.0 | 35.5 | 127.6 | 0.32 | 0.63 |

As can be seen from the results in Table 5, when a green organic light emitting diode is manufactured using the material for an organic light emitting diode of the present invention as an emitting auxiliary layer material, compared to the case of using the comparative compound 2, the comparative compound 3, the compound PA-3, and the driving voltage of the organic light emitting diode could be lowered and the efficiency and lifespan were significantly improved.

Specifically, in the case of a comparative compound, the device results using Comparative Compound 3 with arylamine bonded at the 2 position of the xanthene core, compared to Comparative Compound 2 with arylamine bonded at the 3 position of the xanthene core, improved efficiency. Also, it can be seen that the device result of the compound PA-3 in which a heterocyclic compound such as dibenzofuran is bonded as a substituent of an amine group is improved as a whole.

The compound of the present invention is a compound characterized in that an amine group is bonded to 2 position of the xanthene core, and dibenzofuran or 1 substituted dibenzothiophene is bonded as a substituent of the amine group bonded to the core, it can be seen that the device results of Examples 23 to 35 made of the compounds of the present invention having such characteristics are remarkably excellent.

These results can be explained by the HOMO values of Comparative Compound 2, Comparative Compound 3, Compound PA-3, and the present compound. Referring to Table 6 below, it can be seen that the HOMO value of Comparative Compound 3 in which an amine group is bonded at the 2 position of the core is higher than Comparative Compound 2 in which an amine group is bonded at the 3 position of the core. Also, it can be seen that the HOMO value of Compound P-14 of the present invention in which the amine group is bonded to the 2 position of the core and 1 substituted dibenzofuran is bonded as a substituent of the bonded amine group is the highest, compared to the compound PA-3 in which an amine group is bonded to the 3 position of the core and 3 substituted dibenzofuran is bonded as a substituent of the bonded amine group.

TABLE 6

|  | comparative compound 2 | comparative compound 3 | PA-3 | P-14 |
|---|---|---|---|---|
| HOMO (eV) | −4.956 | −4.808 | −4.844 | −4.781 |

That is, it is shown that the compound of the present invention facilitates hole injection compared to the comparative compounds, thereby improving hole mobility, thereby improving the driving voltage, efficiency, and lifespan of the entire element.

In conclusion, even if the core is the same compound, the physical properties of the compound such as hole characteristics, light efficiency characteristics, energy level (LUMO, HOMO level, T1 level), hole injection & mobility characteristics, and electron blocking characteristics vary depending on the bonding position of the substituent, resulting in completely different element results.

[Example 36] Green Organic Light Emitting Diode (Emitting Auxiliary Layer)

2-TNATA was vacuum-deposited to a thickness of 60 nm on the ITO layer (anode) formed on the glass substrate to form a hole injection layer, and then NPB was vacuum-deposited to a thickness of 60 nm on the hole injection layer to form a hole transport layer. Then, after vacuum deposition of the compound P 2-1 of the present invention to a thickness of 20 nm on the hole transport layer to form an emitting auxiliary layer, and on the emitting auxiliary layer, CBP was used as a host material and tris(2-phenylpyridine)-iridium (hereinafter, Ir(ppy)$_3$) was used as a dopant material, doped at a weight ratio of 95:5, and vacuum deposited to a thickness of 30 nm to form an emitting layer. Subsequently, BAlq was vacuum deposited to a thickness of 10 nm on the emitting layer to form a hole blocking layer, Bis(10-hydroxybenzo[h]quinolinato)beryllium (hereinafter, BeBq2) was vacuum deposited to a thickness of 40 nm on the hole blocking layer to form an electron transport layer.

Thereafter, an electron injection layer was formed by depositing LiF, an alkali metal halide, to a thickness of 0.2 nm, and subsequently, Al was deposited to a thickness of 150 nm to form a cathode, thereby manufacturing an organic light emitting diode.

[Example 37] to [Example 47] Green Organic Light Emitting Diode (Emitting Auxiliary Layer)

An organic light emitting diode was manufactured in the same manner as in Example 36, except that the compound of the present invention described in Table 7 below was used instead of the compound P2-1 as the emitting auxiliary layer material.

[Comparative Example 4] to [Comparative Example 6]

An organic light emitting diode was manufactured in the same manner as in Example 36, except that Comparative Compound 2 and Comparative Compound 4 were used, respectively, instead of the compound P2-1 as the emitting auxiliary layer material.

[Comparative example 2]

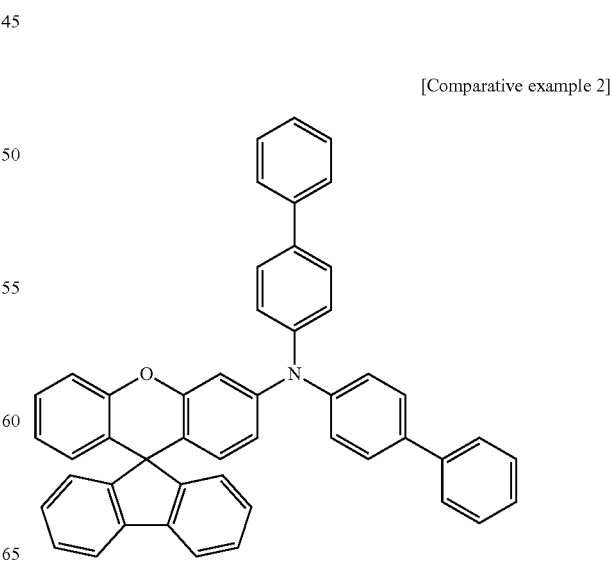

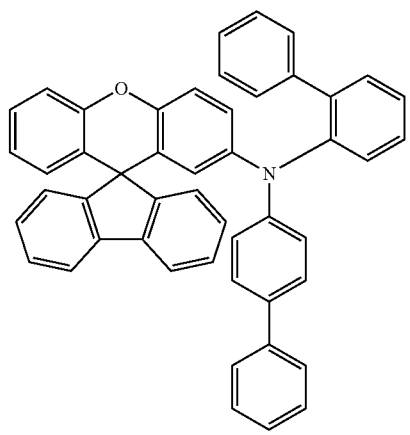

[Comparative example 3]

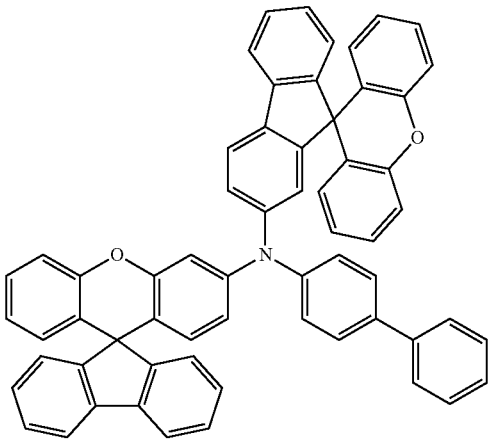

[Comparative example 4]

Electroluminescence (EL) characteristics were measured by PR-650 of photoresearch company by applying a forward bias direct current voltage to the organic light emitting diode prepared according to Examples 36 to 47 and Comparative Example 4 to 6 of the present invention, T95 life was measured through a life measurement equipment manufactured by McScience at a luminance of 5000 cd/m$^2$, and the measurement results are shown in Table 7 below.

TABLE 7

|  | compound | Voltage (V) | Current Density (mA/cm$^2$) | Brightness (cd/m$^2$) | Efficiency (cd/A) | Lifetime T(95) | CIE x | y |
|---|---|---|---|---|---|---|---|---|
| comparative example (4) | comparative compound 2 | 6.5 | 33.1 | 5000.0 | 15.1 | 80.4 | 0.32 | 0.64 |
| comparative example (5) | comparative compound 3 | 6.3 | 24.9 | 5000.0 | 20.1 | 88.6 | 0.30 | 0.64 |
| comparative example (6) | comparative compound 4 | 5.9 | 19.3 | 5000.0 | 25.9 | 105.7 | 0.32 | 0.63 |
| example(36) | P2-1 | 5.1 | 10.6 | 5000.0 | 47.2 | 133.2 | 0.33 | 0.60 |
| example(37) | P2-3 | 5.1 | 10.3 | 5000.0 | 48.4 | 135.1 | 0.33 | 0.61 |
| example(38) | P2-7 | 5.3 | 11.2 | 5000.0 | 44.5 | 128.7 | 0.34 | 0.60 |
| example(39) | P2-12 | 5.2 | 10.7 | 5000.0 | 46.7 | 122.6 | 0.30 | 0.62 |
| example(40) | P2-14 | 5.1 | 11.3 | 5000.0 | 44.2 | 127.1 | 0.32 | 0.60 |
| example(41) | P2-22 | 5.1 | 11.2 | 5000.0 | 44.7 | 122.5 | 0.30 | 0.62 |
| example(42) | P2-28 | 5.2 | 10.8 | 5000.0 | 46.4 | 132.5 | 0.34 | 0.65 |
| example(43) | P2-37 | 5.4 | 12.8 | 5000.0 | 39.0 | 120.2 | 0.34 | 0.60 |
| example(44) | P2-39 | 5.3 | 12.7 | 5000.0 | 39.3 | 131.5 | 0.32 | 0.64 |
| example(45) | P2-40 | 5.4 | 12.9 | 5000.0 | 38.8 | 120.8 | 0.34 | 0.61 |
| example(46) | P2-46 | 5.3 | 11.1 | 5000.0 | 45.0 | 124.2 | 0.31 | 0.62 |
| example(47) | P2-50 | 5.2 | 12.2 | 5000.0 | 41.0 | 126.6 | 0.31 | 0.62 |

As can be seen from the results in Table 7, when a green organic light emitting diode is manufactured using the material for an organic light emitting diode of the present invention as an emitting auxiliary layer material, compared to the comparative compound 4 to 6, and the driving voltage of the organic light emitting diode could be lowered and the efficiency and lifespan were significantly improved.

First, the device result using Comparative Compound 3 with arylamine bonded at the 2 position of the xanthene core was slightly improved than Comparative Compound 2 with arylamine bonded at the 3 position of the xanthene core, and the device result of Comparative Compound 4 in which one more xanthene was bonded as a substituent of the amine group was improved compared to Comparative Examples 4 and 5.

The compound of the present invention is a compound characterized in that an amine group is bonded to 2 position of the xanthene core, and as a substituent of the amine group bonded to the core, one is bonded with 1 position of the dibenzofuran or dibenzothiophene, and the other is bonded with xanthene one more, and it can be seen that the device results of Examples 36 to 47 made of the compounds of the present invention having such characteristics are remarkably excellent.

This is as described in Table 5 above, it is suggested that the compounds of the present invention having a substituent at a specific bonding site may have significantly different chemical and physical properties from those of the Comparative Example compounds, thereby leading to improved device results.

Additionally, referring to Table 8 below, which lists the HOMO values of Comparative Compound 4 and the compound of the present invention, it can be seen that the HOMO value of Compound P 2-3 of the present invention, in which an amine group is bonded to the 2 position of the core, and one more xanthene is bonded at the same time as 1 position of dibenzofuran as a substituent of the bonded amine group, is higher than that of Comparative Compound 4.

TABLE 8

|  | Comparative compound 4 | P2-3 |
|---|---|---|
| HOMO (eV) | −4.856 | −4.788 |

That is, it is judged that the compound of the present invention can more efficiently transport holes in the hole transport layer, as a result, it is believed that the charge balance of holes and electrons in the emitting layer is increased, thereby improving the driving voltage, efficiency, and lifespan of the entire device.

In the case of the emitting auxiliary layer, it is necessary to grasp the correlation between the hole transport layer and the emitting layer (host), even if a similar core is used, it will be very difficult for a person skilled in the art to infer the characteristics exhibited in the emitting auxiliary layer in which the compound of the present invention is used.

In addition, the device characteristics in which the compound of the present invention was applied to only one of the emitting auxiliary layers were described in the result of evaluation of manufacture of the element above, but it may be applied to a case where a hole transport layer or both a hole transport layer and an emitting auxiliary layer are formed by using the compound of the present invention.

[Example 48] Green Organic Light Emitting Diode (Emitting Auxiliary Layer)

First, on an ITO layer(anode) formed on a glass substrate, 2-TNATA was vacuum-deposited to a thickness of 60 nm to form a hole injection layer, and NPB as a hole transport compound on the hole injection layer was vacuum-deposited to a thickness of 60 nm to form a hole transport layer. Subsequently, after vacuum deposition of the compound P3-1 of the present invention to a thickness of 20 nm on the hole transport layer to form a first emitting auxiliary layer, a second emitting auxiliary layer was formed by vacuum depositing PA-5 to a thickness of 5 nm on the first emitting auxiliary layer. Then, CBP was used as a host material on the second emitting auxiliary layer, and Ir(ppy)$_3$ was used as a dopant material and doped at a weight ratio of 95:5 to form an emitting layer by vacuum deposition to a thickness of 30 nm on the emitting auxiliary layer. Next, BAlq was vacuum-deposited to a thickness of 5 nm on the emission layer to form a hole blocking layer, and BeBq2 was vacuum-deposited to a thickness of 40 nm on the hole blocking layer to form an electron transport layer.

Thereafter, the electron injection layer is formed by depositing LiF, an alkali metal halide, to a thickness of 0.2 nm on the electron transport layer, and then Al is deposited on the electron injection layer to a thickness of 150 nm to form a cathode to form an organic electroluminescent device.

[Example 49] to [Example 58]

An organic electroluminescent device was manufactured in the same manner as in Example 48, except that the compound of the present invention described in Table 9 was used as the material of the first emitting auxiliary layer or the second emitting auxiliary layer.

Example 7

An organic electroluminescent device was manufactured in the same manner as in Example 48, except that Comparative Compound 4 was used as both the first emitting auxiliary layer and the second emitting auxiliary layer material.

Example 8

An organic electroluminescent device was manufactured in the same manner as in Example 48, except that Comparative Compound 4 was used instead of Compound P3-1 of the present invention as the first emitting auxiliary layer material.

Example 9

An organic electroluminescent device was manufactured in the same manner as in Example 48, except that PA-4 was used instead of the compound P3-1 of the present invention as the first emitting auxiliary layer material, and Comparative Compound 4 was used instead of PA-5 as the second emitting auxiliary layer material.

<Comparative compound 4>

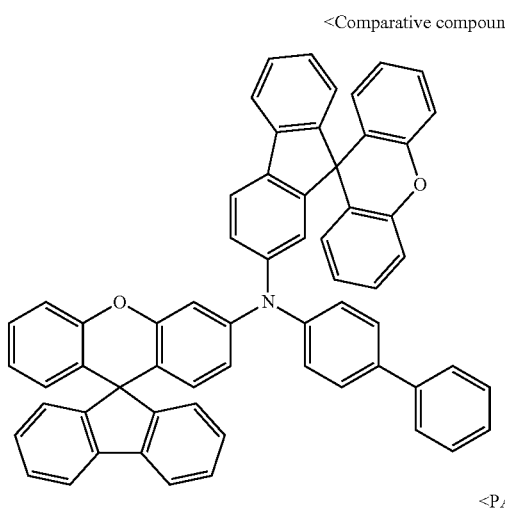

<PA-4>

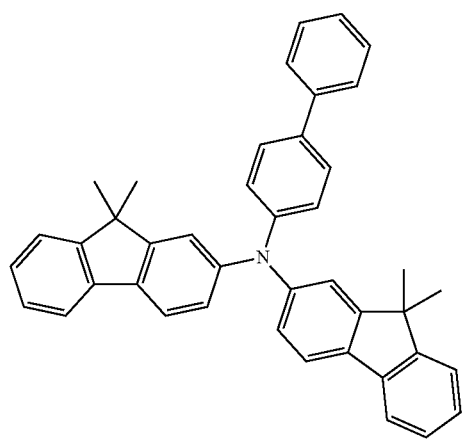

<PA-5>

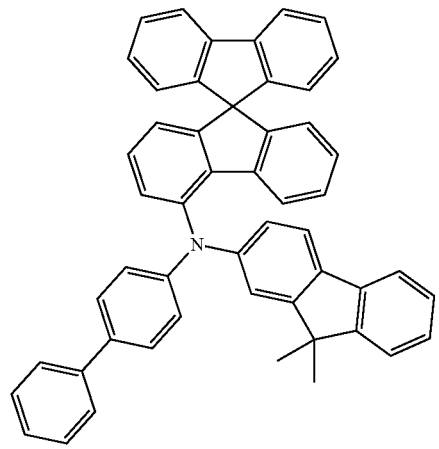

To the OLED prepared according to Examples 48 to 58 and Comparative Examples 7 to 9 of the present invention, a forward bias direct current voltage was applied, and electroluminescent (EL) properties were measured using PR-650 of Photoresearch Co., and T95 life was measured using a life measuring apparatus manufactured by McScience Inc. with a reference luminance of 5000 cd/m². In the following table 9, the manufacture of a device and the results of evaluation are shown.

TABLE 9

| | $1^{st}$ emitting auxiliary layer | $2^{nd}$ emitting auxiliary layer | Voltage | Current Density (mA/cm²) | Brightness (cd/m²) | Efficiency (cd/A) | T(95) |
|---|---|---|---|---|---|---|---|
| comparative example(7) | comparative compound 4 | comparative compound 4 | 6.1 | 20.7 | 5000.0 | 24.2 | 96.1 |
| comparative example(8) | comparative compound 4 | PA-5 | 6.2 | 19.2 | 5000.0 | 26.1 | 108.9 |
| comparative example(9) | PA-4 | comparative compound 4 | 5.7 | 20.0 | 5000.0 | 25.0 | 98.5 |
| example(48) | P3-1 | PA-5 | 5.1 | 10.9 | 5000.0 | 46.0 | 131.3 |
| example(49) | P3-3 | PA-5 | 5.1 | 10.6 | 5000.0 | 47.3 | 137.0 |
| example(50) | P3-16 | PA-5 | 4.8 | 11.1 | 5000.0 | 45.1 | 141.2 |
| example(51) | P3-18 | PA-5 | 4.9 | 11.6 | 5000.0 | 43.1 | 136.4 |
| example(52) | P3-24 | PA-5 | 5.0 | 11.8 | 5000.0 | 42.3 | 130.6 |
| example(53) | PA-4 | P3-27 | 5.2 | 11.5 | 5000.0 | 43.4 | 135.7 |
| example(54) | PA-4 | P3-38 | 5.3 | 11.2 | 5000.0 | 44.6 | 136.8 |
| example(55) | P3-3 | P3-3 | 5.2 | 12.1 | 5000.0 | 41.2 | 128.8 |
| example(56) | P3-16 | P3-16 | 5.1 | 13.0 | 5000.0 | 38.4 | 134.7 |
| example(57) | P3-18 | P3-18 | 5.1 | 14.0 | 5000.0 | 35.6 | 133.1 |
| example(58) | P3-38 | P3-38 | 5.4 | 12.3 | 5000.0 | 40.5 | 120.4 |

As can be seen in Table 9, when a green organic light emitting diode is manufactured using the material for an organic electronic element of the present invention as an emitting auxiliary layer material, compared to Comparative Examples 7 to 9 using the comparative compound, the driving voltage of the organic electric element may be lowered, as well as efficiency and lifespan may be improved.

First, compared to Comparative Compound 4, the device results of Examples 48 to 58 using the compound of the present invention were remarkably superior. Comparing Comparative Compound 4 and the compound of the present invention, Comparative Compound 4 and the compound of the present invention have the same point that 2 xanthene cores are bonded to the amine group, but in the compound of the present invention, the amine group is bound only to xanthene, whereas the comparative compound 4 has a structure in which one amine group is bound to xanthene and the other is bound to fluorene.

In this case, the chemical and physical properties may be remarkably different depending on the substituent at the specific bonding site, and thus the device result may be different.

Table 10 below shows the HOMO and T1 values of Comparative Compound 4 and P3-3 and P3-16, compounds of the present invention.

TABLE 10

|  | compound 4 | P3-3 | P3-16 |
|---|---|---|---|
| HOMO (eV) | −4.856 | −4.742 | −4.669 |
| T1 (eV) | 2.654 | 3.001 | 2.762 |

As can be seen in Table 10, in the case of the compound of the present invention, it can be seen that HOMO is higher than that of Comparative Compound 4, and T1 is also increased. Accordingly, as the HOMO increases, hole characteristics increase, and hole injection occurs rapidly. As a result, it is determined that the mobility of holes is improved and the driving voltage is decreased. Also, since the high T1 prevents electrons from being injected from the host to the hole transport layer, the overall efficiency and lifespan of the device seems to be improved.

In other words, the compound of the present invention facilitates hole injection compared to Comparative Compound 4, resulting in excellent hole mobility, and due to the high T1, electrons are further blocked, thereby increasing the charge balance of the holes and electrons in the emitting layer, which is believed to improve the performance of the entire device.

In conclusion, even if the core is the same compound, the properties of the compound such as hole characteristics, light efficiency characteristics, energy level (LUMO, HOMO level, T1 level), hole injection & mobility characteristics, and electron blocking characteristics vary depending on the bonding position of the substituent, and this suggests that a completely different device result may be derived.

In the case of an emitting auxiliary layer, it is necessary to grasp the correlation between the hole transport layer and the emitting layer (host), therefore even if a similar core is used, it will be very difficult for a person skilled in the art to infer the characteristics exhibited in the emitting auxiliary layer in which the compound of the present invention is used.

In addition, in the evaluation results of the device fabrication described above, the device characteristics in which the compound of the present invention is applied only to the emitting auxiliary layer have been described, but the compound of the present invention may be applied to the hole transport layer or both the hole transport layer and the emitting auxiliary layer may be used.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment.

The scope of the present invention shall be construed on the basis of the accompanying claims, and it shall be construed that all of the technical ideas included within the scope equivalent to the claims belong to the present invention.

BRIEF DESCRIPTION OF THE DRAWINGS

| 100, 200, 300: organic electronic element | 110: the first electrode |
|---|---|
| 120: hole injection layer | 130: hole transport layer |
| 140: emitting layer | 150: electron transport layer |
| 160: electron injection layer | 170: second electrode |
| 180: light efficiency enhancing Layer | 210: buffer layer |
| 220: emitting-auxiliary layer | 320: first hole injection layer |
| 330: first hole transport layer | 340: first emitting layer |
| 350: first electron transport layer | 360: first charge generation layer |
| 361: second charge generation layer | 420: second hole injection layer |
| 430: second hole transport layer | 440: second emitting layer |
| 450: second electron transport layer | CGL: charge generation layer |
| ST1: first stack | ST2: second stack |

What is claimed is:
1. A compound represented by Formula 7:

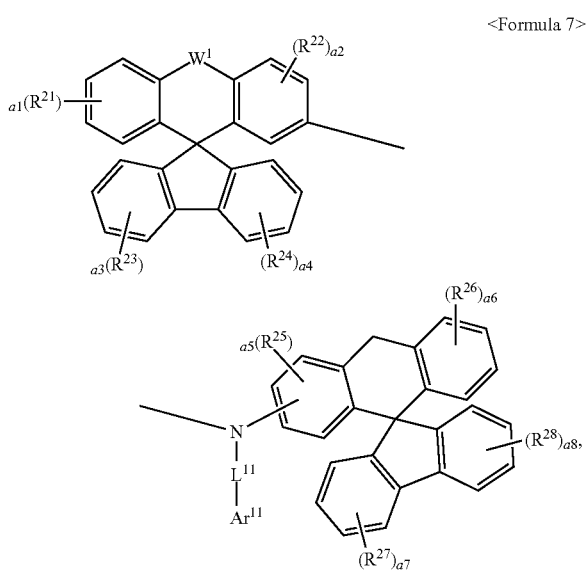

<Formula 7> wherein:
1) $R^{21}$, $R^{22}$, $R^{23}$, $R^{24}$, $R^{25}$, $R^{26}$, $R^{27}$ and $R^{28}$ are each independently selected from the group consisting of hydrogen; deuterium; halogen; cyano; nitro; a $C_6$-$C_{60}$ aryl group; a fluorenyl group; a $C_2$-$C_{60}$ heterocyclic group including at least one heteroatom selected from the group consisting of O, N, S, Si or P; a fused ring group of a $C_3$-$C_{60}$ aliphatic ring and a $C_6$-$C_{60}$ aromatic ring; a $C_1$-$C_{60}$ alkyl group; a $C_2$-$C_{60}$ alkenyl group; a $C_2$-$C_{60}$ alkynyl group; a $C_1$-$C_{60}$ alkoxy group; and a $C_6$-$C_{60}$ aryloxy group, and where they are plural, adjacent $R^{21}$s, adjacent $R^{22}$s, adjacent $R^{23}$s, adjacent $R^{24}$s, adjacent $R^{25}$s, adjacent $R^{26}$s, adjacent $R^{27}$s, or adjacent $R^{28}$s are optionally bonded to each other to form a ring, 2) $W^1$ and $W^2$ are each independently O or S, 3) $L^{11}$ is a single bond; a $C_6$-$C_{60}$ arylene group; a fluorenylene group; a $C_2$-$C_{60}$ heterocyclic group containing at least one hetero atom of O, N, S, Si and P; a fused ring group of a $C_3$-$C_{60}$ aliphatic ring and a $C_6$-$C_{60}$ aromatic ring, 4) $Ar^{11}$ is a $C_6$-$C_{60}$ aryl group, 5) a1, a3, a4, a6, a7 and a8 are each independently an integer of 0 to 4; and a2 and a5 are each independently an integer of 0 to 3, wherein the aryl group, arylene group, heterocyclic group, fluorenyl group, fluorenylene group, aliphatic ring group, fused ring group, alkyl group, alkenyl group, alkynyl group, alkoxyl group and aryloxy group may be substituted with one or more substituents selected from the group consisting of deuterium; halogen; a silane group; a siloxane group; a boron group; a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group; a $C_3$-$C_{20}$ cycloalkyl group; a $C_7$-$C_{20}$ arylalkyl group and a $C_8$-$C_{20}$ arylalkenyl group, wherein the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

2. The compound of claim 1, wherein Formula 7 is represented by one of Formulas 7-1 to 7-3:

<Formula 7-1>

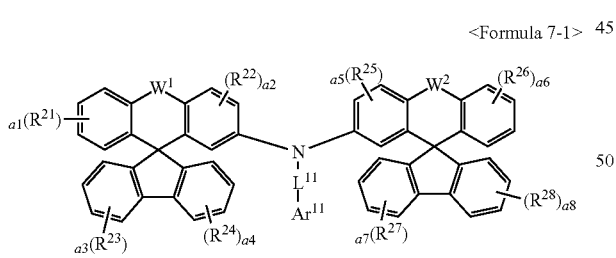

<Formula 7-1>

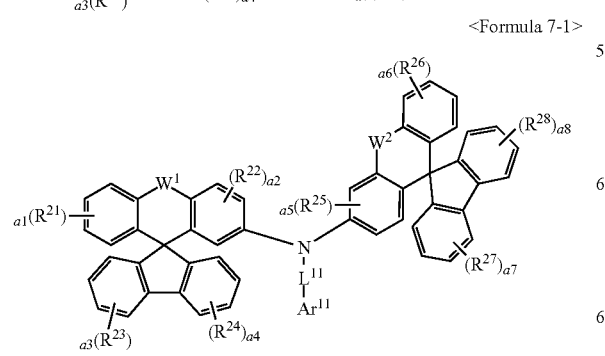

<Formula 7-3>

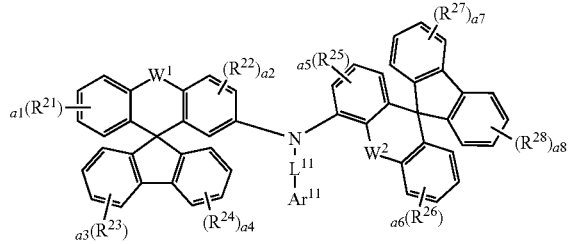

wherein $R^{21}$, $R^{22}$, $R^{23}$, $R^{24}$, $R^{25}$, $R^{26}$, $R^{27}$ and $R^{28}$, $W^1$, $W^2$, $L^{11}$, $Ar^{11}$, and a1, a2, a3, a4, a5, a6, a7 and a8 are the same as defined in claim 1.

3. The compound of claim 1, wherein $L^{11}$ is represented by one of Formulas a-1 to a-5:

<Formula a-1>

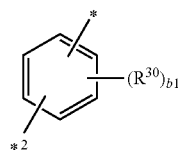

<Formula a-2>

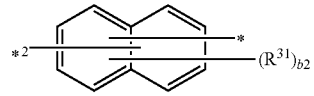

<Formula a-3>

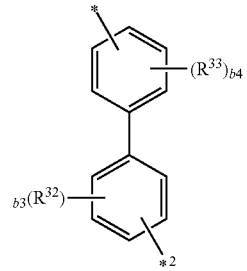

<Formula a-4>

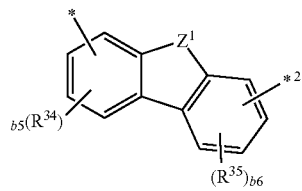

<Formula a-5>

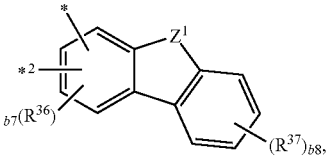

wherein:
1) $R^{30}$, $R^{31}$, $R^{32}$, $R^{33}$, $R^{34}$, $R^{35}$, $R^{36}$ and $R^{37}$ are the same as the definition of $R^{21}$ in claim 1,
2) b1, b3, b4 and b8 are each independently an integer of 0 to 4; b2 is an integer of 0 to 6; b5 and b6 are each independently an integer of 0 to 3; and b7 is an integer of 0 to 2,
3) $Z^1$ is O or S,
4) * means a position bonded to N (nitrogen) in Formula 7, and *2 means a position bonded to $Ar^{11}$ in Formula 7.

4. The compound of claim 1, wherein Formula 7 is represented by Formula 7-4 or Formula 7-5:

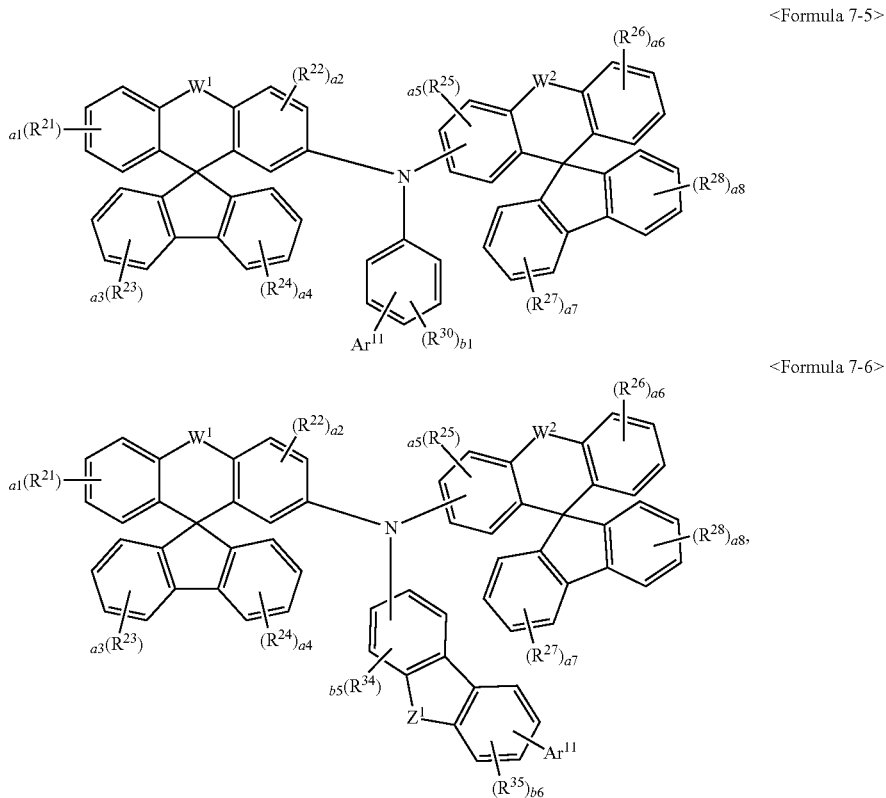

wherein:
1) $R^{21}$, $R^{22}$, $R^{23}$, $R^{24}$, $R^{25}$, $R^{26}$, $R^{27}$ and $R^{28}$ are the same as defined in claim 1,
2) $R^{30}$, $R^{34}$ and $R^{35}$ are the same as the definition of $R^{21}$ in claim 1,
3) $W^1$, $W^2$, $L^{11}$, $Ar^{11}$, a1, a2, a3, a4, a5, a6, a7 and a8 are the same as defined in claim 1,
4) b1 is an integer of 0 to 4; and b5 and b6 are each independently an integer of 0 to 3, and
5) $Z^1$ is O or S.

5. The compound of claim 1, wherein Formula 7 is represented by Formula 7-6:

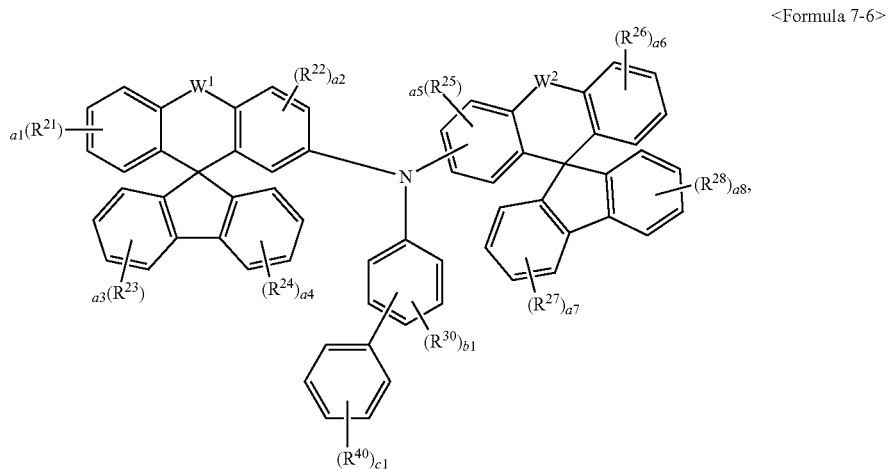

wherein:
1) $R^{21}$, $R^{22}$, $R^{23}$, $R^{24}$, $R^{25}$, $R^{26}$, $R^{27}$ and $R^{28}$, a1, a2, a3, a4, a5, a6, a7 and a8, $W^1$ and $W^2$ are the same as defined in claim 1,
2) $R^{30}$ and $R^{40}$ is the same as the definition of $R^{21}$ in claim 1,
3) b1 is an integer of 0 to 4, and
4) c1 is an integer of 0 to 5.

6. The compound of claim 1, wherein Formula 7 is represented by Formula 7-7:

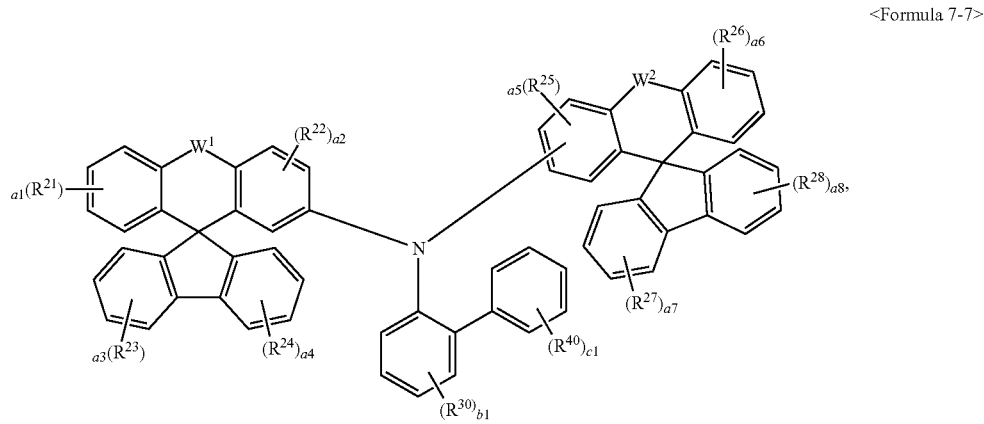

<Formula 7-7> wherein:
1) $R^{21}$, $R^{22}$, $R^{23}$, $R^{24}$, $R^{25}$, $R^{26}$, $R^{27}$ and $R^{28}$, a1, a2, a3, a4, a5, a6, a7 and a8, $W^1$ and $W^2$ are the same as defined in claim 1,
2) $R^{30}$ and $R^{40}$ is the same as the definition of $R^{21}$ in claim 1,
3) b1 is an integer of 0 to 4,
4) c1 is an integer of 0 to 5.

7. The compound of claim 1, selected from the group consisting of compounds P2-46, P2-47, and P3-1 to P3-40:

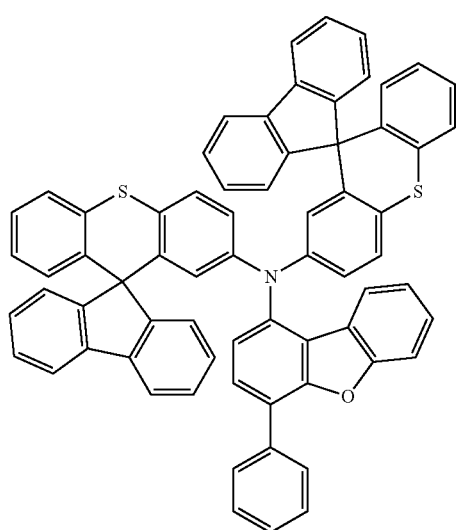

P2-46

-continued

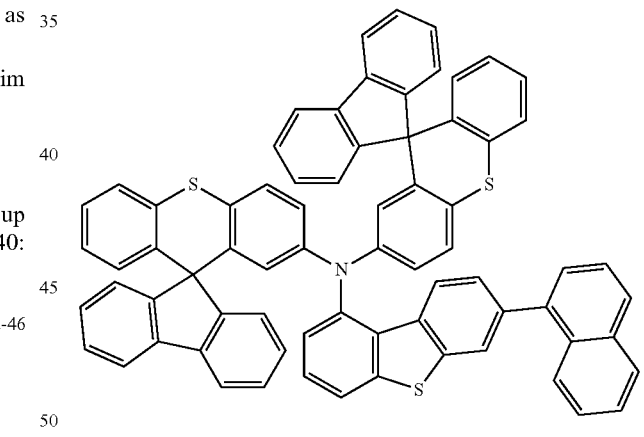

P2-47

P3-1

P3-2
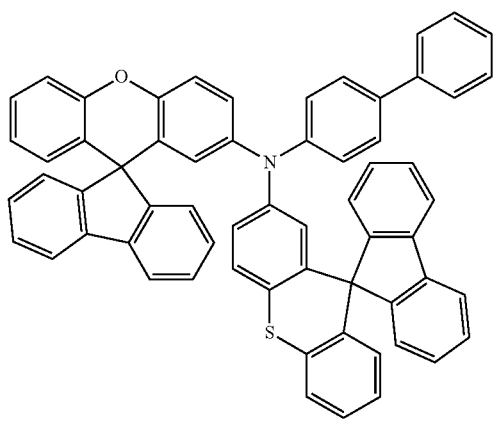
P3-3
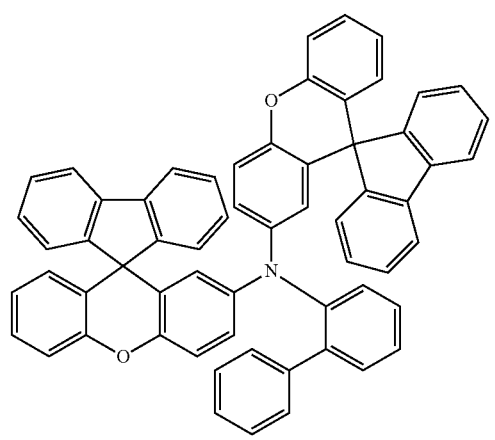
P3-4
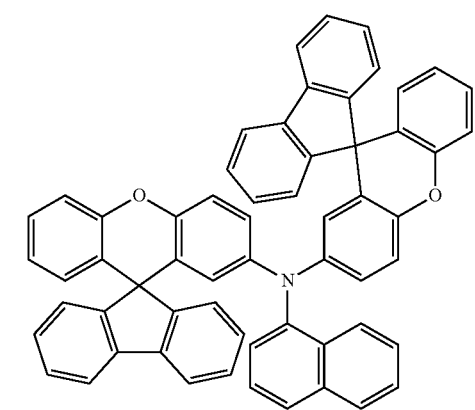
P3-5
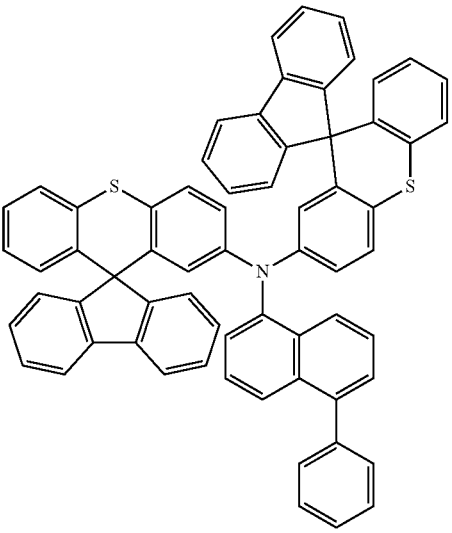
P3-6
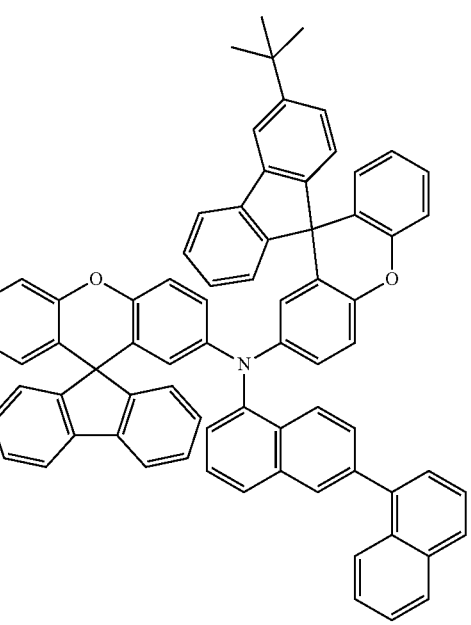

P3-7
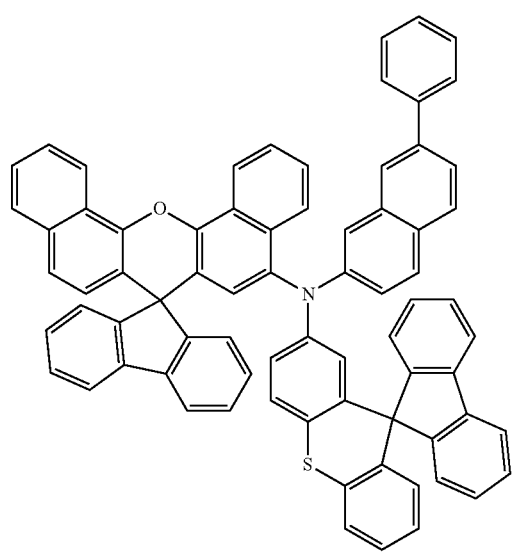
P3-10
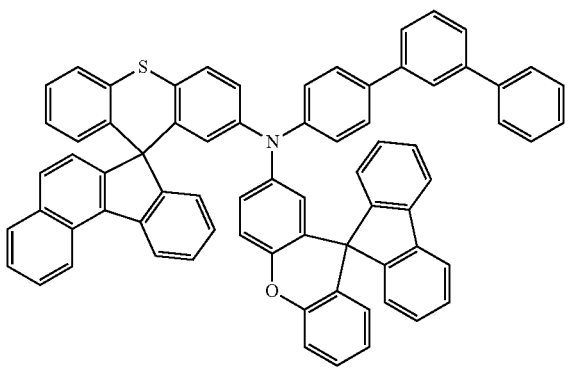
P3-8
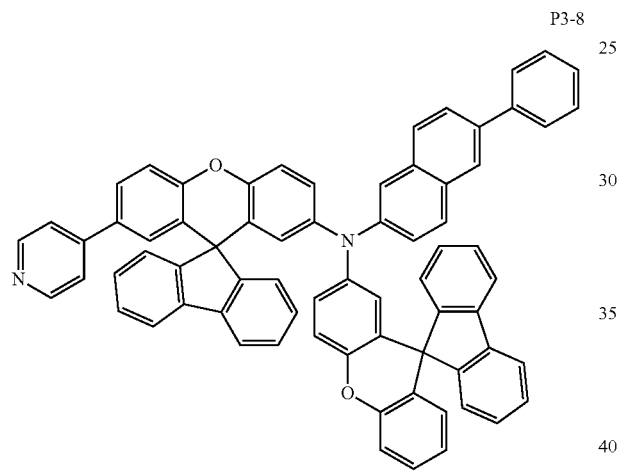
P3-11
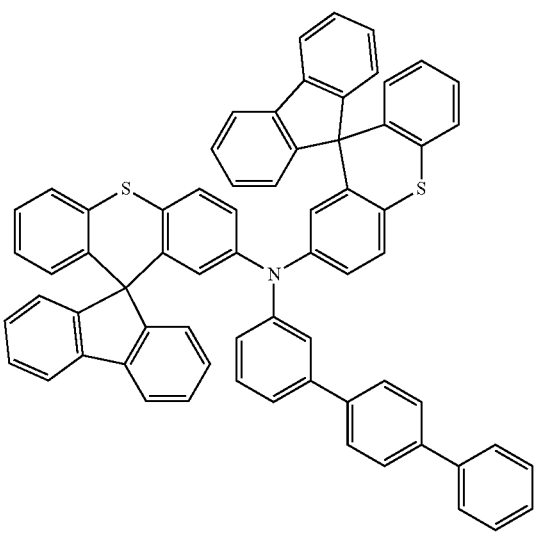
P3-9
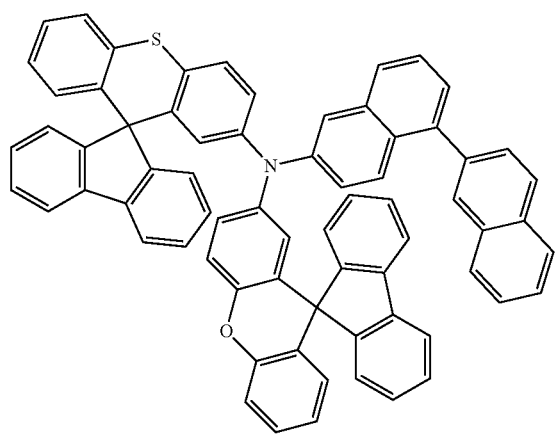
P3-12
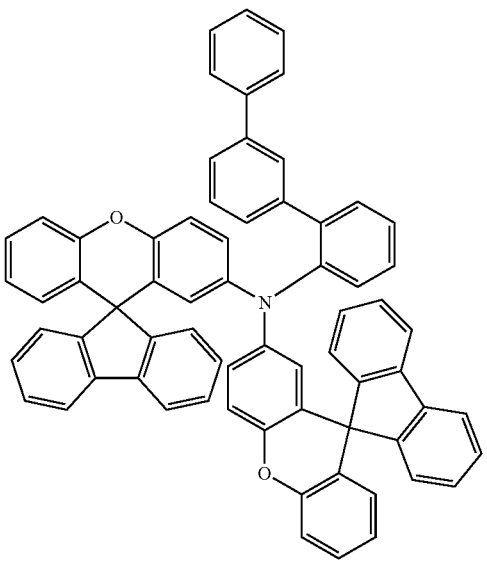

P3-13
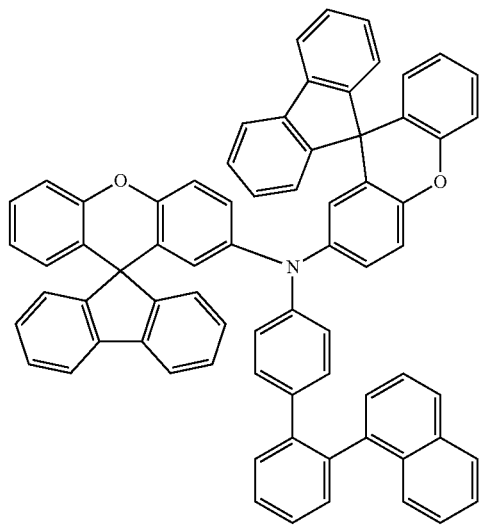
P3-14
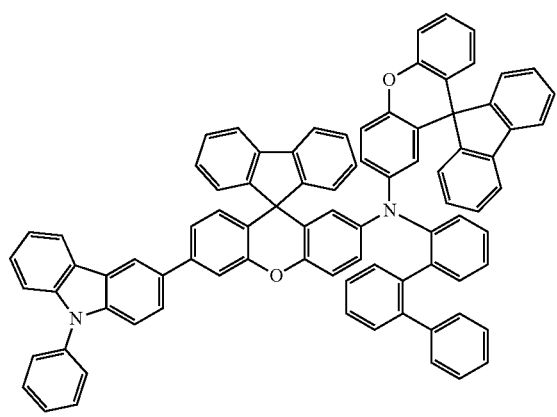
P3-15
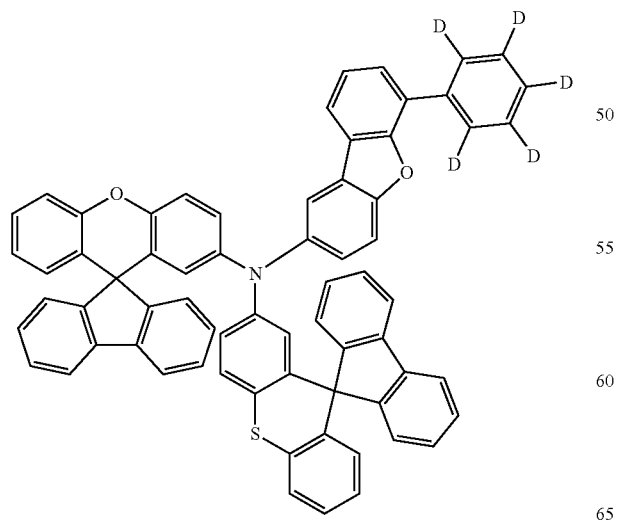
P3-16
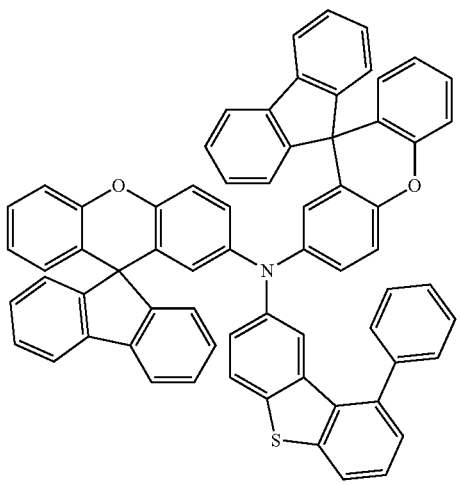
P3-17
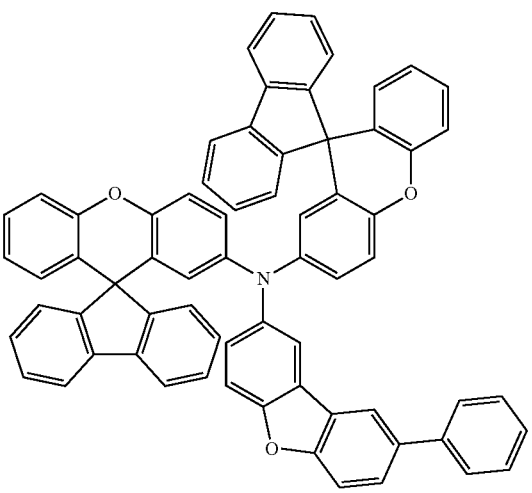
P3-18
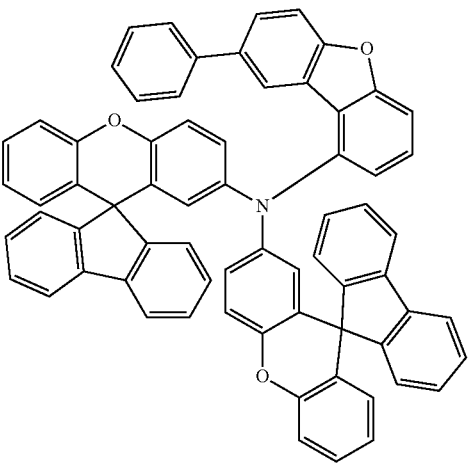

P3-19
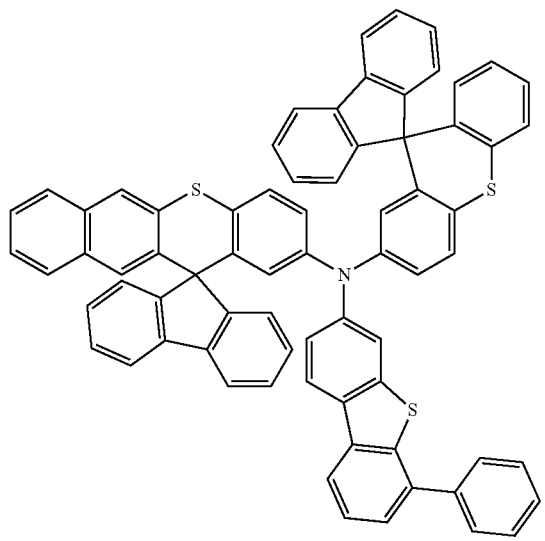
P3-20
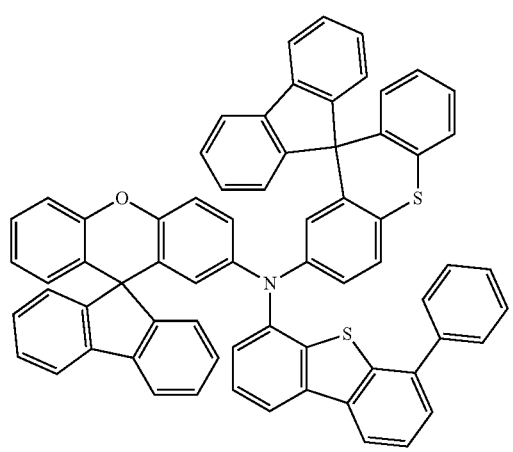
P3-21
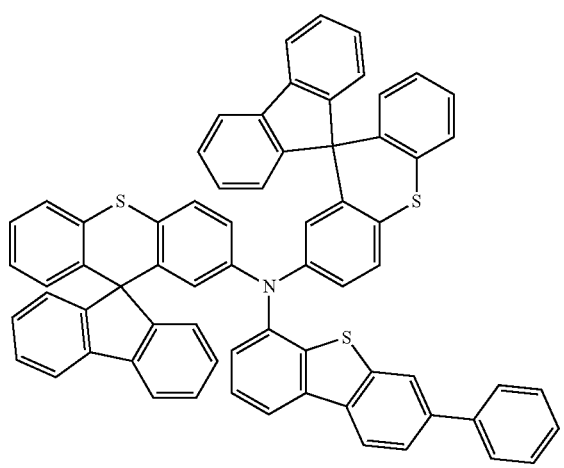
P3-22
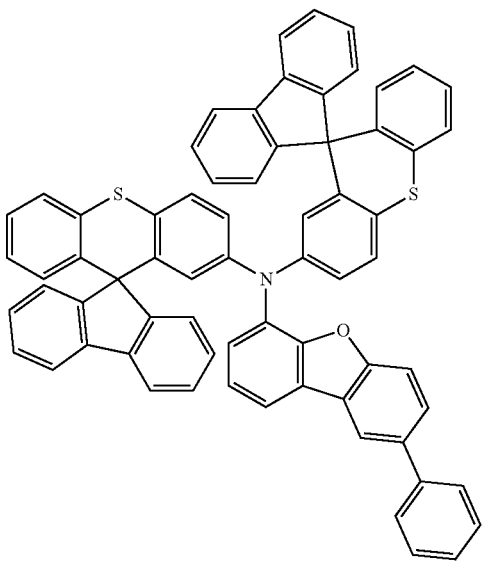
P3-23
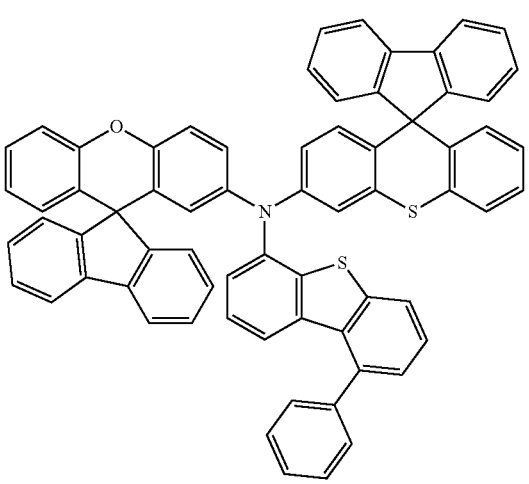
P3-24
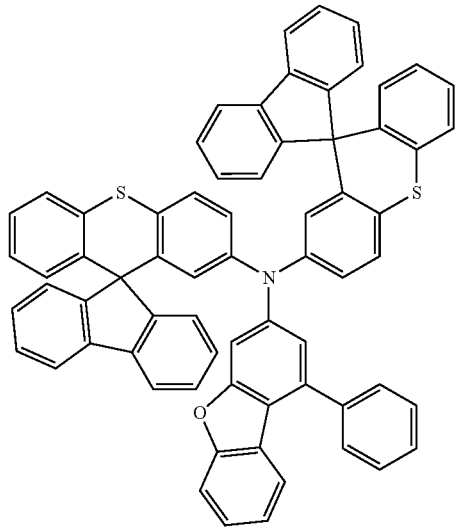

P3-25
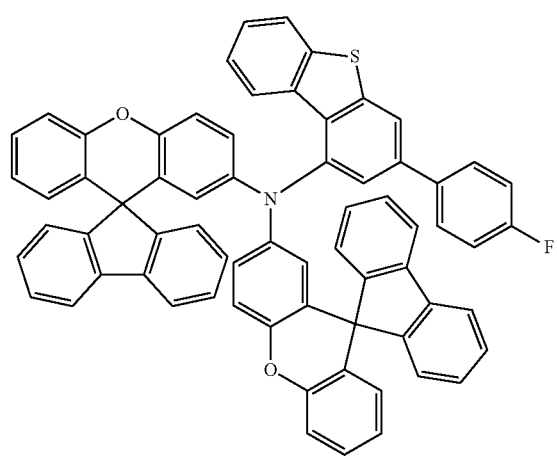
P3-26
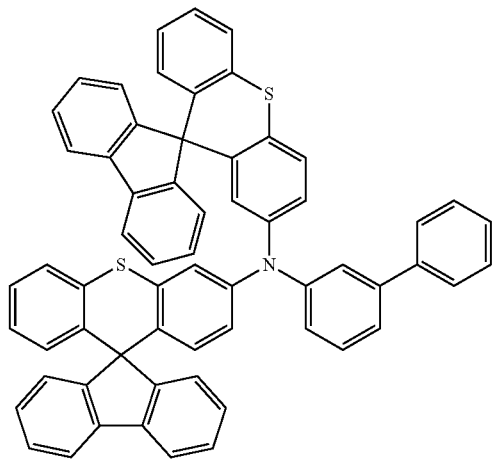
P3-27
P3-28
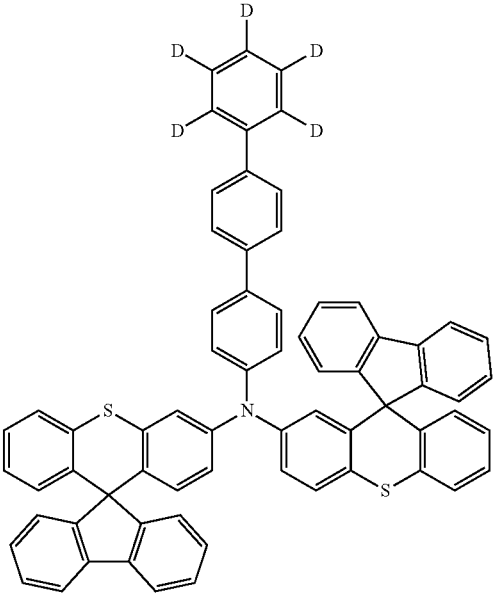
P3-29
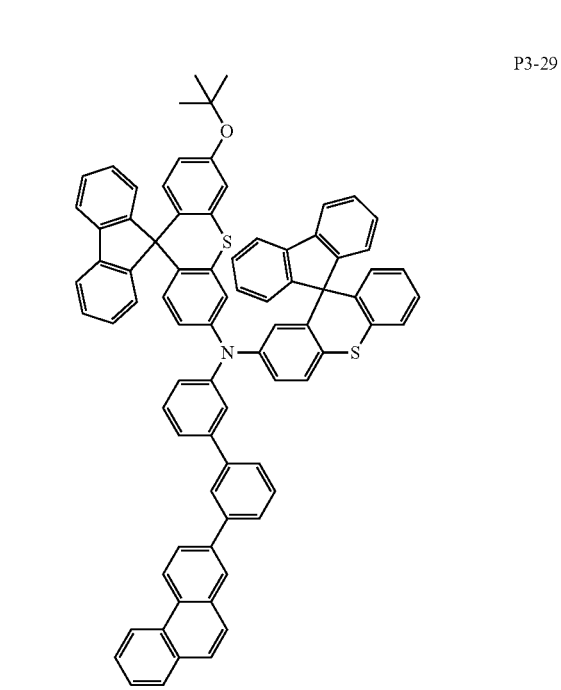

P3-30
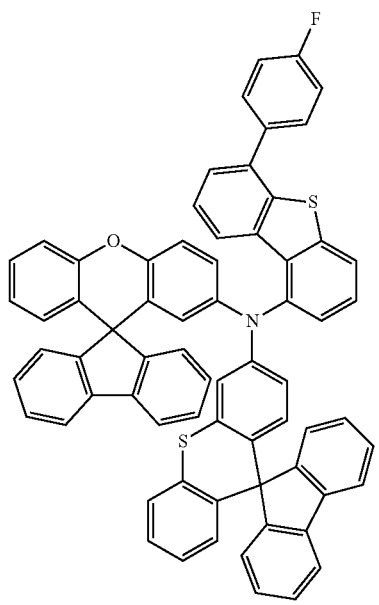
P3-31
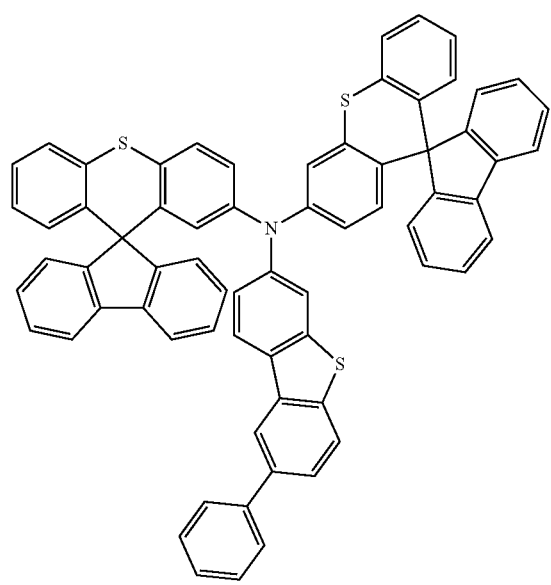
P3-32
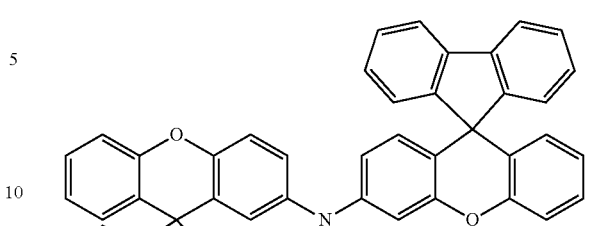
P3-33
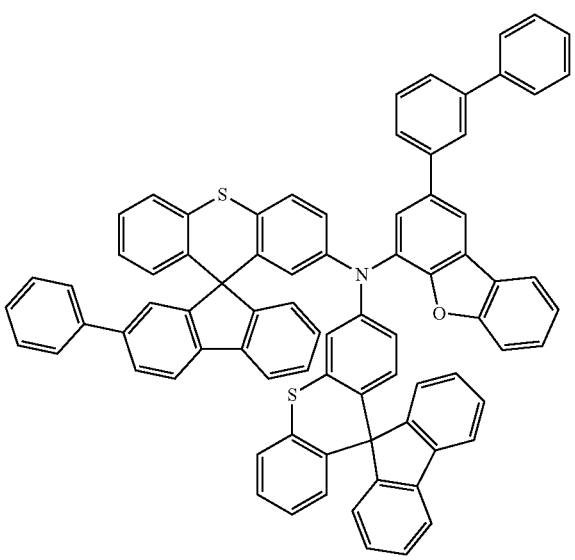
P3-34
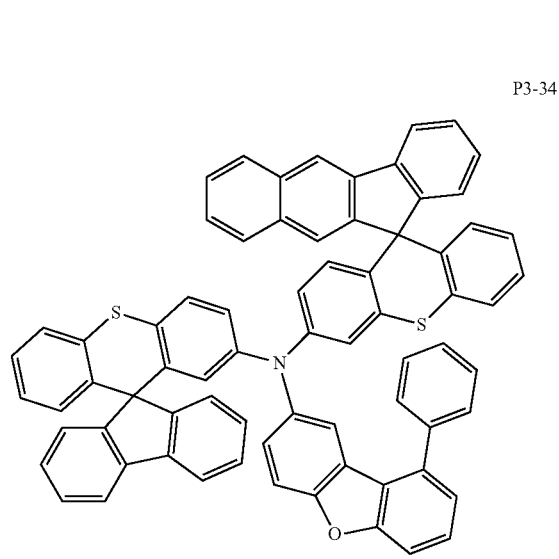

P3-35
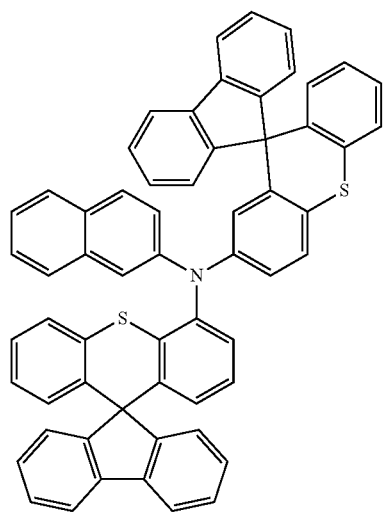
P3-38
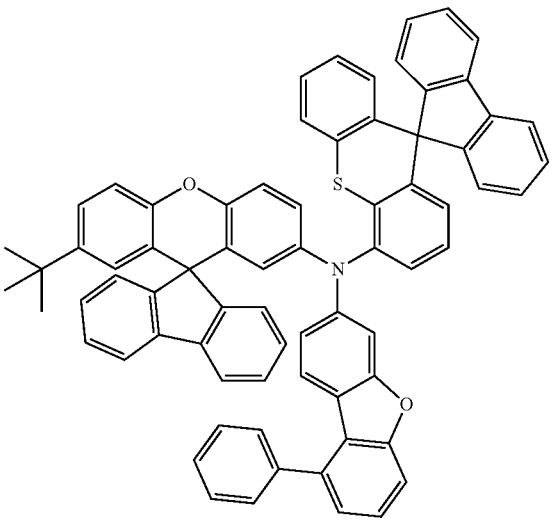
P3-36
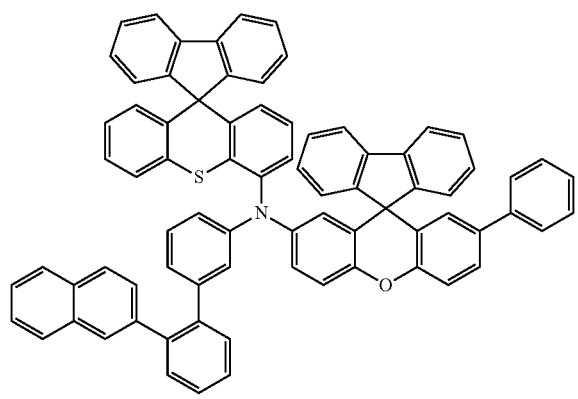
P3-39
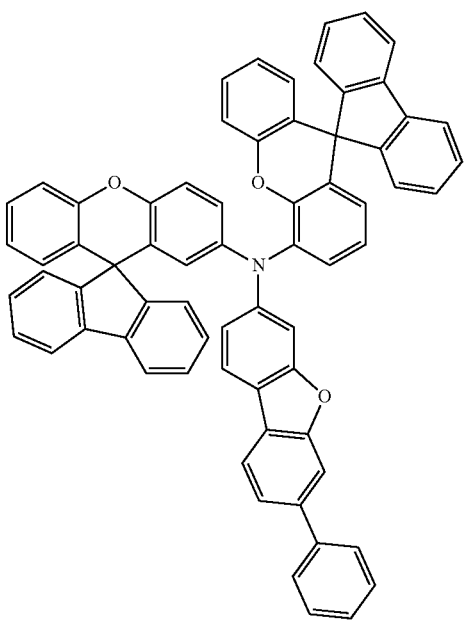
P3-37
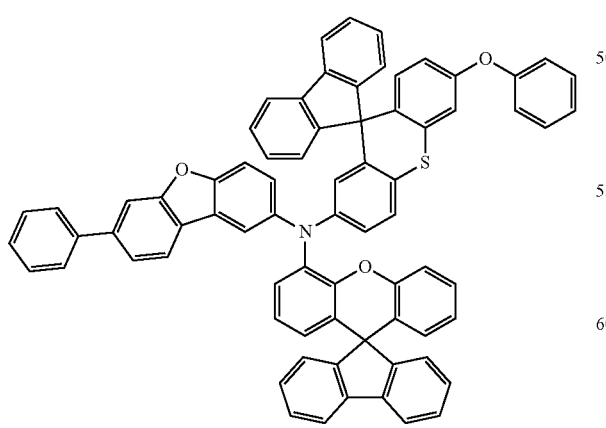
P3-40
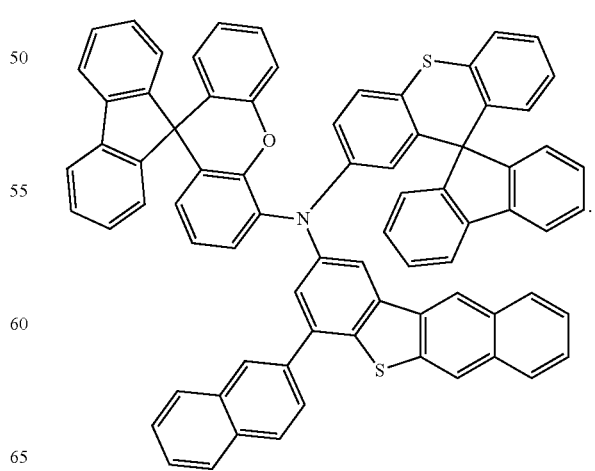

8. An organic electronic element comprising a first electrode, a second electrode, and an organic material layer formed between the first and the second electrodes, wherein the organic material layer comprises a compound represented by Formula 7 of claim 1.

9. The organic electronic element of claim 8, wherein the organic material layer comprises at least one of a hole injection layer, a hole transport layer, an emitting auxiliary layer, an emitting layer, an electron transport auxiliary layer, an electron transport layer, and an electron injection layer.

10. The organic electronic element of claim 8, wherein the organic material layer comprises an emitting auxiliary layer.

11. The organic electronic element of claim 8, wherein the organic material layer comprises an emitting layer, a hole transport layer formed between the anode and the emitting layer, and a plurality of emitting auxiliary layers formed between the hole transport layer and the emitting layer, and at least one of the plurality of emitting auxiliary layers comprises the compound represented by Formula 7.

12. The organic electronic element of claim 11, wherein the plurality of emitting auxiliary layers comprises a first emitting auxiliary layer adjacent to the hole transport layer and a second emitting auxiliary layer adjacent to the emitting layer.

13. The organic electronic element of claim 12, wherein the first emitting auxiliary layer comprises the compound represented by Formula 7.

14. The organic electronic element of claim 12, wherein the second emitting auxiliary layer comprises the compound represented by Formula 7.

15. The organic electronic element of claim 8, further comprising a light efficiency enhancing layer formed on at least one surface of the anode and the cathode opposite to the organic material layer.

16. The organic electronic element of claim 8, wherein the organic material layer comprises at least 2 stacks of layers each including a hole transport layer, an emitting layer, and an electron transport layer sequentially formed on the anode.

17. The organic electronic element of claim 16, wherein the organic material layer further comprises a charge generation layer formed between the at least 2 stacks of layers.

18. An electronic device comprising: a display device including the organic electric element of claim 8; and a control unit for driving the display device.

19. The compound of claim 18, wherein the organic electronic element is at least one of an OLED, an organic solar cell, an organic photo conductor, an organic transistor and an element for monochromic or white illumination.

* * * * *

UNITED STATES PATENT AND TRADEMARK OFFICE
CERTIFICATE OF CORRECTION

PATENT NO. : 11,997,923 B2  Page 1 of 2
APPLICATION NO. : 17/343622
DATED : May 28, 2024
INVENTOR(S) : Kim et al.

It is certified that error appears in the above-identified patent and that said Letters Patent is hereby corrected as shown below:

In the Claims

Column 368, Claim 1, Formula 7:

Please delete "
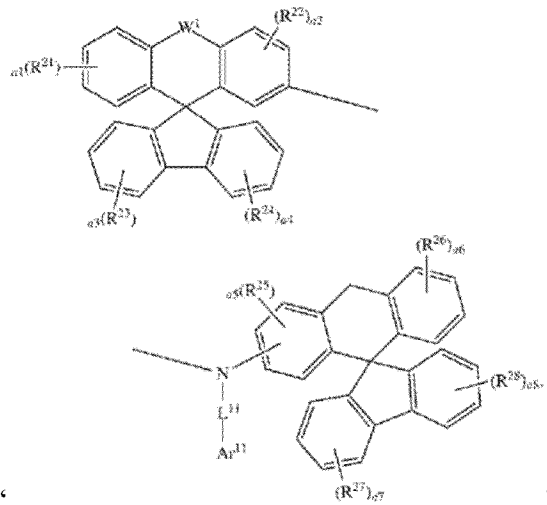
"

And replace with --
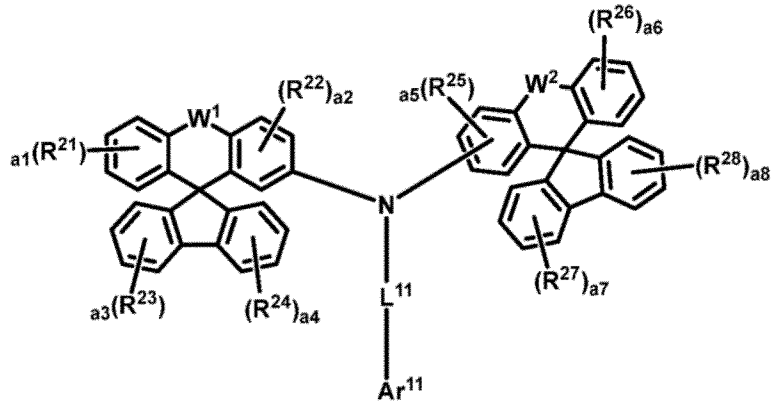
--

Signed and Sealed this
Sixteenth Day of July, 2024

*Katherine Kelly Vidal*
Katherine Kelly Vidal
*Director of the United States Patent and Trademark Office*

CERTIFICATE OF CORRECTION (continued)
U.S. Pat. No. 11,997,923 B2

Column 378, Claim 7, Formula P3-11:

Please delete " 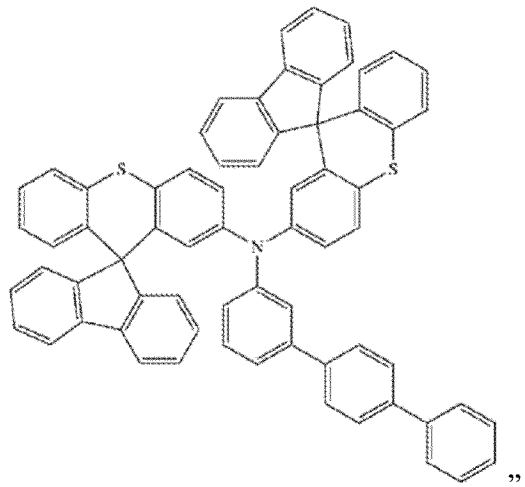 "

And replace with -- 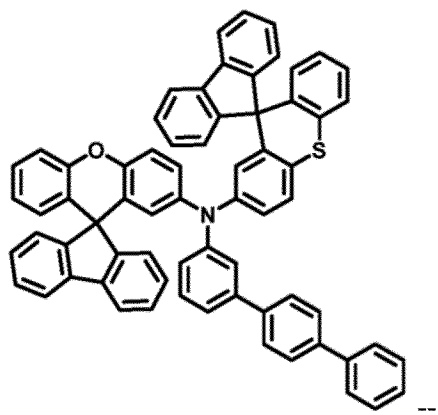 --